US011426409B2

(12) United States Patent
Doebele

(10) Patent No.: US 11,426,409 B2
(45) Date of Patent: Aug. 30, 2022

(54) COMPOUNDS, COMPOSITIONS AND METHODS FOR TREATING OR PREVENTING HER-DRIVEN DRUG-RESISTANT CANCERS

(71) Applicant: The Regents of the University of Colorado, Denver, CO (US)

(72) Inventor: Robert C. Doebele, Denver, CO (US)

(73) Assignee: The Regents of the University of Colorado, Denver, CO (US)

( * ) Notice: Subject to any disclaimer, the term of this patent is extended or adjusted under 35 U.S.C. 154(b) by 10 days.

(21) Appl. No.: 16/644,208

(22) PCT Filed: Sep. 7, 2018

(86) PCT No.: PCT/US2018/049842
§ 371 (c)(1),
(2) Date: Mar. 4, 2020

(87) PCT Pub. No.: WO2019/051155
PCT Pub. Date: Mar. 14, 2019

(65) Prior Publication Data
US 2020/0268759 A1    Aug. 27, 2020

Related U.S. Application Data

(60) Provisional application No. 62/712,531, filed on Jul. 31, 2018, provisional application No. 62/556,121, filed on Sep. 8, 2017.

(51) Int. Cl.
*A61K 31/519* (2006.01)
*A61P 35/00* (2006.01)
*A61K 45/06* (2006.01)

(52) U.S. Cl.
CPC ............ *A61K 31/519* (2013.01); *A61K 45/06* (2013.01); *A61P 35/00* (2018.01)

(58) Field of Classification Search
CPC .............................. A61K 31/517; A61P 35/00
See application file for complete search history.

(56) References Cited

U.S. PATENT DOCUMENTS

| | | |
|---|---|---|
| 5,007,790 A | 4/1991 | Shell |
| 5,582,837 A | 12/1996 | Shell |
| 5,972,389 A | 10/1999 | Shell et al. |
| 6,340,475 B2 | 1/2002 | Shell et al. |
| 6,451,808 B1 | 9/2002 | Cowles |
| 6,488,962 B1 | 12/2002 | Berner et al. |
| 2003/0039688 A1 | 2/2003 | Shell et al. |
| 2003/0044466 A1 | 3/2003 | Markey et al. |
| 2003/0104053 A1 | 6/2003 | Gusler et al. |
| 2003/0104062 A1 | 6/2003 | Berner et al. |
| 2003/0147952 A1 | 8/2003 | Lim et al. |
| 2011/0224205 A1* | 9/2011 | Chen ...................... A61K 31/12 514/234.5 |
| 2012/0077811 A1 | 3/2012 | Smaill et al. |
| 2012/0202832 A1* | 8/2012 | Smaill .................... A61P 35/00 514/264.11 |
| 2015/0057798 A1* | 2/2015 | Meissner ............... B25J 9/1638 700/250 |
| 2020/0316071 A1* | 10/2020 | Robichaux ......... A61K 31/7088 |

FOREIGN PATENT DOCUMENTS

| | | |
|---|---|---|
| WO | WO 90/11757 A1 | 10/1990 |
| WO | WO 97/47285 A1 | 12/1997 |
| WO | WO 98/11879 A1 | 3/1998 |
| WO | WO 98/55107 A1 | 12/1998 |
| WO | WO 01/32217 A2 | 5/2001 |
| WO | WO 01/97783 A1 | 12/2001 |
| WO | WO 02/32416 A2 | 4/2002 |
| WO | WO 02/96404 A1 | 12/2002 |
| WO | WO 03/35029 A1 | 5/2003 |
| WO | WO 03/35039 A1 | 5/2003 |
| WO | WO 03/35040 A1 | 5/2003 |
| WO | WO 03/35041 A1 | 5/2003 |
| WO | WO 2010/104406 A1 | 9/2010 |
| WO | WO 2011/028135 A1 | 3/2011 |
| WO | WO 2016/090174 A1 | 6/2016 |

OTHER PUBLICATIONS

Yasuda (Science Translation Medicine vol. 5 216ra177216ra177 published 2013), (Year: 2013).*
Estrada-Bernal, A. et al. (2018) "Abstract A157: Antitumor activity of tarloxotinib, a hypoxia-activated EGFR TKI, in patient-derived lung cancer cell lines harboring EGFR exon 20 insertions" Mol Cancer Ther, 17 (1 Supplement):A157; DOI: 10.1158/1535-7163. TARG-17-A157.
Arcila, M.E. et al. (2013) "EGFR Exon 20 Insertion Mutations in Lung Adenocarcinomas: Prevalence, Molecular Heterogeneity, and Clinicopathologic Characteristics" Mol Cancer Ther, 12:220-229.
Barretina, J. et al. (2012) "The Cancer Cell Line Encyclopedia enables predictive modelling of anticancer drug sensitivity" Nature, 483(7391): 603-607.
Bellmunt, J. et al. (2015) "HER2 as a target in invasive urothelial carcinoma" Cancer Med, 4:844-852.
Bhandari, V. et al. (Feb. 2019) "Molecular landmarks of tumor hypoxia across cancer types" Nature Genetics, 51(2), 308-318. https://doi.org/10.1038/s41588-018-0318-2.
Bonneville, R. et al. (2017) "Landscape of Microsatellite Instability Across 39 Cancer Types" JCO Precis Oncol. PO.17.00073. doi: 10.1200/PO.17.00073. Epub Oct. 3, 2017, 15 pages.
Bose, R. et al. (2013) "Activating HER2 Mutations in HER2 Gene Amplification Negative Breast Cancer" Cancer Discov, 3:224-237.
Campbell, J.D. et al. (2016) "Distinct patterns of somatic genome alterations in lung adenocarcinomas and squamous cell carcinomas" Nature Genetics, 48(6):607-616. HHS Public Access Author Manuscript; available in PMC Nov. 9, 2016, 29 pages.
The Cancer Genome Atlas Research Network (2014) "Comprehensive molecular profiling of lung adenocarcinoma" Nature, 511:543-550.

(Continued)

*Primary Examiner* — Theodore R. Howell
*Assistant Examiner* — George W Kosturko
(74) *Attorney, Agent, or Firm* — Snell & Wilmer L.L.P.

(57) ABSTRACT

The present invention includes methods of treating or preventing HER-driven drug-resistant cancers. In certain embodiments, the cancer comprises lung cancer.

13 Claims, 30 Drawing Sheets
Specification includes a Sequence Listing.

(56) References Cited

OTHER PUBLICATIONS

Cancer Genome Project and Collaborative Group (2004) "Intragenic ERBB2 kinase mutations in tumours" Nature, 431:525-526.
Chmielecki, J. et al. (2015) "Oncogenic Alterations in ERBB2/HER2 Represent Potential Therapeutic Targets Across Tumors From Diverse Anatomic Sites of Origin" Oncologist, 20:7-12.
Chou, A. et al. (2013) "Clinical and molecular characterization of HER2 amplified-pancreatic cancer" Genome Med, 5:78. Retrieved from: http://genomemedicine.com/content/5/8/78, 11 pages.
Chou, T-C. and P. Talalay (1984) "Quantitative Analysis of Dose-Effect Relationships: The Combined Effects of Multiple Drugs or Enzyme Inhibitors" Adv Enzyme Regul, 22:27-55.
Das, K. et al. (2014) "Mutually exclusive FGFR2, HER2, and KRAS gene amplifications in gastric cancer revealed by multicolour FISH" Cancer Lett, 353:167-175.
Database Cbioportal, Lung Adenocarcinoma (TCGA, PanCancer Atlas) [online]. Retrieved from: https://www.cbioportal.org/study/summary?id=laml_tcga_pan_can_atlas_2018; retrieved on Oct. 5, 2020, 1 printed page.
Database Cbioportal, Lung Adenocarcinoma (Broad, Cell 2012) [online]. Retrieved from: https://www.cbioportal.org/study/summary?id=luad_broad; retrieved on Oct. 5, 2020, 1 printed page.
Database Cbioportal, Lung Adenocarcinoma (MSKCC, Science 2015) [online]. Retrieved from: https://www.cbioportal.org/study/summary?id=luad_mskcc_2015; retrieved on Oct. 5, 2020, 1 printed page.
Database Cbioportal, Lung Adenocarcinoma (TCGA, Firehose Legacy) [online]. Retrieved from: https://www.cbioportal.org/study/summary?id=luad_tcga; retrieved on Oct. 5, 2020, 1 printed page.
Database Cbioportal, Non-Small Cell Cancer (MSKCC, Cancer Discov 2017) [online]. Retrieved from: https://www.cbioportal.org/study/summary?id=lung_msk_2017; retrieved on Oct. 5, 2020, 1 printed page.
Database Cbioportal, Non-Small Cell Lung Cancer (MSKCC, J Clin Oncol 2018) [online]. Retrieved from: https://www.cbioportal.org/study/summary?id=nsclc_pd1_msk_2018; retrieved on Oct. 5, 2020, 1 printed page.
Database Cbioportal, Non-Small Cell Lung Cancer (University of Turin, Lung Cancer 2017) [online]. Retrieved from: https://www.cbioportal.org/study/summary?id=nsclc_unito_2016; retrieved on Oct. 5, 2020, 1 printed page.
Database Cbioportal, Pan-Lung Cancer (TCGA, Nat Genet 2016) [online]. Retrieved from: https://www.cbioportal.org/study/summary?id=nsclc_tcga_broad_2016; retrieved on Oct. 5, 2020, 1 printed page.
Dhanasekaran, S.M. et al. (2014) "Transcriptome meta-analysis of lung cancer reveals recurrent aberrations in NRG1 and Hippo pathway genes" Nat Commun, 5:5893; DOI: 10.1038/ncomms6893, 12 pages.
Ding, L. et al. (2018) "Perspective on Oncogenic Processes at the End of the Beginning of Cancer Genomics" Cell, 173(2):305-320. HHS Public Access Author Manuscript; available in PMC Apr. 5, 2019, 42 pages.
Drilon, A. et al. (2018) "Response to ERBB3-Directed Targeted Therapy in NRG1-Rearranged Cancers" Cancer Discov, 8:686-695.
Elamin, Y. et al. (2017) "Preliminary Results of a Phase II Study of Poziotinib in EGFR Exon 20 Mutant Advanced NSCLC" J Thor Oncol, 20(8 Suppl):S1536.
Ellrott, K. et al. (2018) "Scalable Open Science Approach for Mutation Calling of Tumor Exomes Using Multiple Genomic Pipelines" Cell Systems, 6(3):271-281. HHS Public Access Author Manuscript; avalable in PMC Mar. 28, 2019, 36 pages.
Fernandez-Cuesta, L. et al. (2014) "CD74-NRG1 Fusions in Lung Adenocarcinoma" Cancer Discov, 4:415-422.
Gao, J. et al. (2013) "Integrative Analysis of Complex Cancer Genomics and Clinical Profiles Using the cBioPortal" Sci Signal, 6(239):pl1, DOI: 10.1126/scisignal.2004088, 20 pages.

Gao, Q. et al. (2018) "Driver Fusions and Their Implications in the Development and Treatment of Human Cancers" Cell Reports, 23:227-238.
Gonzaga, I.M. et al. (2012) "Alterations in epidermal growth factor receptors 1 and 2 in esophageal squamous cell carcinomas" BMC Cancer, 12:569 [online]. Retrieved from: http://www.biomedcentral.com/1471-2407/12/569, 10 printed pages.
Gordon, M.A. et al. (2013) "Assessment of HER2 gene amplification in adenocarcinomas of the stomach or gastroesophageal junction in the INT-0116/SWOG9008 clinical trial" Ann Oncol, 24:1754-1761.
Greulich, H. et al. (2012) "Functional analysis of receptor tyrosine kinase mutations in lung cancer identifies oncogenic extracellular domain mutations of ERBB2" Proc Natl Acad Sci USA. 109:14476-14481.
Guo, T. et al. (2016) "Characterization of functionally active gene fusions in human papillomavirus related oropharyngeal squamous cell carcinoma" Int J Cancer, 139:373-382.
Heining, C. et al. (2018) "NRG1 Fusions in KRAS Wild-Type Pancreatic Cancer" Cancer Discov, 8(9):1087-1095.
Hellmann, M.D. et al. (2018) "Genomic Features of Response to Combination Immunotherapy in Patients with Advanced Non-Small-Cell Lung Cancer" Cancer Cell, 33(5):843-852.
Hoadley, K.A. et al. (2018) "Cell-of-Origin Patterns Dominate the Molecular Classification of 10,000 Tumors from 33 Types of Cancer" Cell, 173(2):291-304.
Holford, N.H.G. and L.B. Scheiner (1981) "Understanding the Dose-Effect Relationship: Clinical Application of Pharmacokinetic-Pharmacodynamic Models" Clinical Pharmacokinetics, 6:429-453.
Imielinski, M. et al. (2012) "Mapping the hallmarks of lung adenocarcinoma with massively parallel sequencing" Cell, 150(6):1107-1120.
Jaiswal, B.S. et al. (2013) "Oncogenic ERBB3 Mutations in Human Cancers" Cancer Cell, 23:603-617.
Jones, M.R. et al. (2017) "Successful targeting of the NRG1 pathway indicates novel treatment strategy for metastatic cancer" Ann Oncol, 28:3092-3097.
Jordan, E.J. et al. (2017) "Prospective Comprehensive Molecular Characterization of Lung Adenocarcinomas for Efficient Patient Matching to Approved and Emerging Therapies" Cancer Discovery, 7(6):596-609.
Jung, Y. et al. (2015) "VAMP2-NRG1 Fusion Gene is a Novel Oncogenic Driver of Non-Small-Cell Lung Adenocarcinoma" J Thor Oncol, 10:1107-1111.
Kavuri, S.M. et al. (2015) "HER2 Activating Mutations Are Targets for Colorectal Cancer Treatment" Cancer Discov, 5:832-841.
Kloth, M. et al. (2016) "Activating ERBB2/HER2 mutations indicate susceptibility to pan-HER inhibitors in Lynch and Lynch-like colorectal cancer" Gut, 65:1296-1305.
Lebeau, A. et al. (2001) "HER-2/neu Analysis in Archival Tissue Samples of Human Breast Cancer: Comparison of Immunohistochemistry and Fluorescence In Situ Hybridization" J Clin Oncol, 19(2):354-363.
Li, B.T. et al. (2016) "HER2 Amplification and HER2 Mutation Are Distinct Molecular Targets in Lung Cancers" J Thorac Oncol, 11:414-419.
Liu, J. et al. (2018) "An Integrated TCGA Pan-Cancer Clinical Data Resource to Drive High-Quality Survival Outcome Analytics" Cell, 173(2):400-416. HHS Public Access Author Manuscript; avalable in PMC Apr. 5, 2019, 42 pages.
Loewe, S. and H. Muischnek (1926) "Über Kombinationswirkungen. I. Mitteilung: Hilfsmittel der Fragestellung" Arch Exp Pathol Pharmacol, 114:313-326 (German, with machine translation).
Morrison, C. et al. (2006) "HER-2 Is an Independent Prognostic Factor in Endometrial Cancer: Association With Outcome in a Large Cohort of Surgically Staged Patients" J Clin Oncol, 24:2376-2385.
Naidoo, J. et al. (2015) "Epidermal Growth Factor Receptor Exon 20 Insertions in Advanced Lung Adenocarcinomas: Clinical Outcomes and Response to Erlotinib" Cancer, 121(18):3212-3220.
Nakaoku, T. et al. (2014) "Druggable Oncogene Fusions in Invasive Mucinous Lung Adenocarcinoma" Clin Cancer Res, 20(12):3087-3093.

(56) References Cited

OTHER PUBLICATIONS

Nardi, V. et al. (2013) "Detection of Novel Actionable Genetic Changes in Salivary Duct Carcinoma Helps Direct Patient Treatment" Clin Cancer Res, 19:480-490.

Ou, S-H. I. et al. (2017) "HER2 Transmembrane Domain (TMD) Mutations (V659/G660) That Stabilize Homo- and Heterodimerization Are Rare Oncogenic Drivers in Lung Adenocarcinoma That Respond to Afatinib" J Thorne Oncol, 12:446-457.

Poore, G. D. et al. (2020) "Microbiome analyses of blood and tissues suggest cancer diagnostic approach" Nature, 579(7800):567-574.

Rizvi, N.A. et al. (2015) "Mutational landscape determines sensitivity to PD-1 blockade in non-small cell lung cancer" Science, 348(6230):124-128.

Ross, J.S. et al. (2013) "Relapsed Classic E-Cadherin (CDH1)-Mutated Invasive Lobular Breast Cancer Shows a High Frequency of HER2 (ERBB2) Gene Mutations" Clin Cancer Res, 19:2668-2676.

Ross, J.S. et al. (2014) "A High Frequency of Activating Extracellular Domain ERBB2 (HER2) Mutation in Micropapillary Urothelial Carcinoma" Clin Cancer Res, 20:68-75.

Sanchez-Vega, F. et al. (2018) "Oncogenic Signaling Pathways in The Cancer Genome Atlas" Cell, 173(2):321-337.

Shigematsu, H. et al. (2005) "Somatic Mutations of the HER2 Kinase Domain in Lung Adenocarcinomas" Cancer Res, 65:1642-1646.

Shrotriya, R.C. (Jan. 2017) Spectrum Pharmaceuticals. Investor Presentation [online]. Retrieved from the internet: <URL: https://www.stlc.gov/Archives/edgar/data/831547/000083154717000002/sppicorporatepresentaf74.htm>, 28 printed pages.

Slomovitz, B.M. et al. (2004) "Her-2/neu Overexpression and Amplification in Uterine Papillary Serous Carcinoma" J Clin Oncol, 22:3126-3132.

Takeda, M. et al. (2018) "Clinical characteristics of non-small cell lung cancer harboring mutations in exon 20 of EGFR or HER2" Oncotarget, 9(30):21132-21140.

Tallarida, R.J. and R.B. Raffa (1996) "Testing for synergism over a range of fixed ration drug combinations: replacing the isobologram" Life Sci, 58:23-28.

Taylor, A.M. et al. (2018) "Genomic and Functional Approaches to Understanding Cancer Aneuploidy" Cancer Cell, 33(4):676-689.

Tuefferd, M. et al. (2007) "HER2 Status in Ovarian Carcinomas: A Multicenter GINECO Study of 320 Patients" PLoS ONE, 2(11):e1138, 8 pages.

Vavalà, T. et al. (2017) "Precision medicine in age-specific non-small-cell-lung-cancer patients: Integrating biomolecular results into clinical practice—A new approach to improve personalized translational research" Lung Cancer, 107:84-90. https://doi.org/10.1016/j.lungcan.2016.05.021.

Verma, S. et al. (2018) "Structural investigations on mechanism of lapatinib resistance caused by HER-2 mutants" PLoS ONE, 13(2):e0190942.

Wang, S.E. et al. (2006) "HER2 kinase domain mutation results in constitutive phosphorylation and activation of HER2 and EGFR and resistance to EGFR tyrosine kinase inhibitors" Cancer Cell, 10:25-38.

Wang, X-Z. et al. (1999) "γ-heregulin is the product of a chromosomal translocation fusing the DOC4 and HGL/NRG1 genes in the MDA-MB-175 breast cancer cell line" Oncogene, 18:5718-5721.

Williams, M.D. et al. (2010) "Genetic and Expression Analysis of HER-2 and EGFR Genes in Salivary Duct Carcinoma: Empirical and Therapeutic Significance" Clin Cancer Res, 16:2266-2274.

Wilson, T.R. et al. (2011) "Neuregulin-1-Mediated Autocrine Signaling Underlies Sensitivity to HER2 Kinase Inhibitors in a Subset of Human Cancers" Cancer Cell, 20:158-172.

Xia, D. et al. (2017) "KIF13B-NRG1 Gene Fusion and KRAS Amplification in a Case of Natural Progression of Lung Cancer" Int J Surg Pathol, 25:238-240.

Xu, X. et al. (2017) "HER2 Reactivation through Acquisition of the HER2 L755S Mutation as a Mechamsm of Acquired Resistance to HER2-targeted Therapy in HER2$^+$ Breast Cancer" Clin Cancer Res, 23:5123-5134.

Yasuda, H. et al. (2013) "Structural, Biochemical, and Clinical Characterization of Epidermal Growth Factor Receptor (EGFR) Exon 20 Insertion Mutations in Lung Cancer" Sci Transl Med, 5(216):216ra177; DOI: 10.1126/scitranslmed.3007205, 10 pages.

Yu, D-H. et al. (2015) "Oncogenic HER2 fusions in gastric cancer" J Transl Med, 13:116, DOI 10.1186/s12967-015-0476-2, 13 pages.

Yun, S. et al. (2018) "Clinical significance of overexpression of NRG1 and its receptors, HER3 and HER4, in gastric cancer patients" Gastric Cancer, 21:225-236.

Zuo, W-J. et al. (2016) "Dual Characteristics of Novel HER2 Kinase Domain Mutations in Response to HER2-Targeted Therapies in Human Breast Cancer" Clin Cancer Res, 22:4859-4869.

\* cited by examiner

FIG. 6C

|         | PC9   | H3255  | A549    |
|---------|-------|--------|---------|
| afatinib | 0.336 | 0.0002 | 4,545   |
| TH4000E | 0.08  | 0.4637 | 2,098   |
| TH4000  | 18    | 5.6    | >10,000 |
| gefitinib | 30  | 0.562  | >10,000 |

FIG. 9B

| Study of origin | ERBB2 Genetic Alteration | Study of origin | ERBB2 Genetic Alteration | Study of origin | ERBB2 Genetic Alteration | Study of origin | ERBB2 Genetic Alteration |
|---|---|---|---|---|---|---|---|
| n | f | n | f | p | f | p | a |
| l | f | n | f | p | f | p | a |
| p | f, a | n | f | p | f | l | a |
| n | f, a | n | f | m | f | p | a |
| n | f, a | n | f | l | f | m | a |
| o | f, a | o | f | p | f | p | a |
| n | f, a | n | f | p | f | m | a |
| p | f, a | n | f | l | f | l | a |
| n | f, b | n | f | p | g | p | a |
| n | f, b | p | f | j | a | p | c |
| n | f, d | p | f | j | a | n | c |
| p | f, d | p | f | p | a | n | c |
| n | f, c | p | f | n | a | n | c |
| p | f | p | f | n | a | o | c |
| j | f | p | f | n | a | n | c |
| j | f | m | f | n | a | n | c |
| p | f | l | f | n | a | n | c |
| j | f | p | f | n | a | n | c |
| p | f | m | f | n | a | o | c |
| p | f | l | f | n | a | m | c |
| n | f | p | f | o | a | l | c |
| n | f | m | f | n | a | p | c |
| n | f | l | f | n | a | i | d |
| n | f | p | f | n | a | j | d |
| n | f | p | f | n | a | p | d |
| n | f | p | f | n | a | n | d |
| n | f | l | f | n | a | o | d |
| n | f | p | f | n | a | m | d |
| o | f | m | f | o | a | | |
| n | f | l | f | o | a | | |
| n | f | p | f | l | a | | |
| n | f | m | f | p | a | | |
| n | f | l | f | m | a | | |
| n | f | p | f | l | a | | |

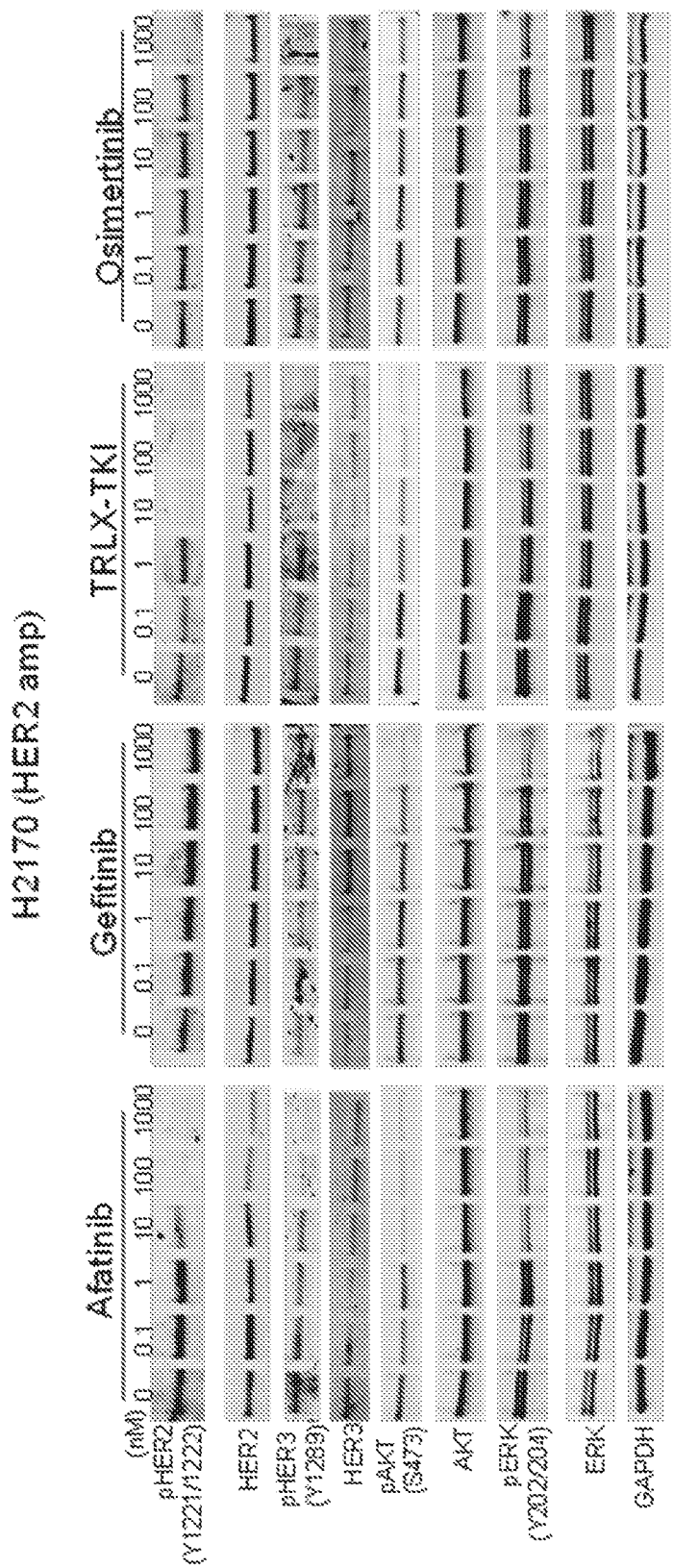

TRLX administration

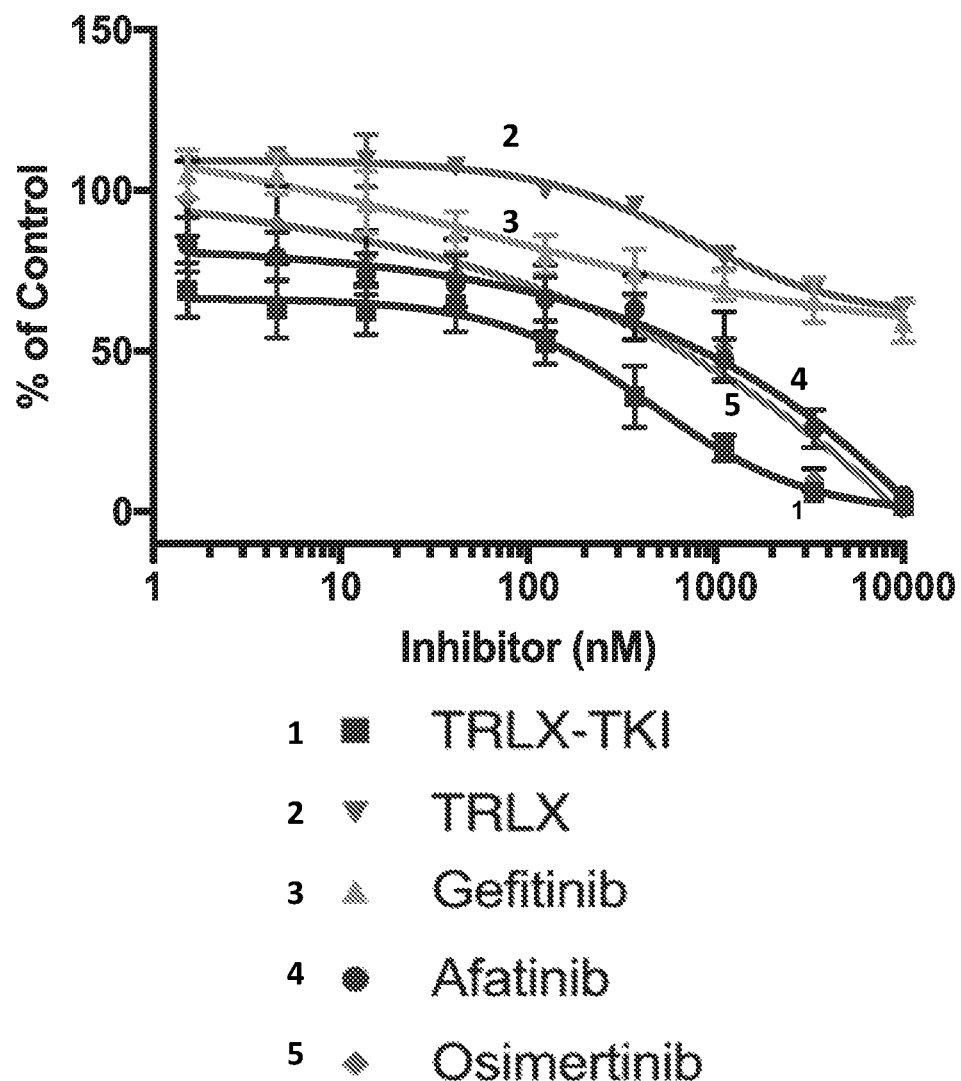

COMPOUNDS, COMPOSITIONS AND METHODS FOR TREATING OR PREVENTING HER-DRIVEN DRUG-RESISTANT CANCERS

This application is a U.S. National Phase Application, filed under 35 U.S.C. 371, of International Application No. PCT/US2018/049842, filed on Sep. 7, 2018, which claims priority under 35 U.S.C. § 119(e) to U.S. Provisional Application Nos. 62/556,121, filed Sep. 8, 2017, and 62/712,531, filed Jul. 31, 2018, all of which disclosures are hereby incorporated by reference in their entireties.

SEQUENCE LISTING

The present specification is being filed with a computer readable form (CRF) copy of the Sequence Listing. The CRF entitled 373330_7084WO1_ST25.txt, which was created on Sep. 6, 2018 and is 451 KBytes in size, is incorporated herein by reference in its entirety.

BACKGROUND OF THE INVENTION

The ErbB family of receptors is a subfamily of four closely related receptor tyrosine kinases: epidermal growth factor receptor or EGFR (ErbB-1; or HER1 in humans), HER2/c-neu (ErbB-2), HER3 (ErbB-3) and HER4 (ErbB-4).

EGFR is the cell-surface receptor for members of the epidermal growth factor family (EGF family) of extracellular protein ligands. Mutations that lead to EGFR overexpression (upregulation) or overactivity have been associated with a number of cancers, including squamous-cell carcinoma of the lung (80% of cases), anal cancers, glioblastoma (50% of cases), and epithelial tumors of the head and neck (80-100% of cases). These somatic mutations involving EGFR lead to its constant activation, which produces uncontrolled cell division. In a non-limiting example, in glioblastoma, a more or less specific mutation of EGFR, called EGFRvIII, is often observed. Mutations, amplifications, or misregulations of EGFR or family members are implicated in about 30% of all epithelial cancers.

The identification of EGFR as an oncogene has led to the development of anticancer therapeutics directed against EGFR (called "EGFR tyrosine kinase inhibitors"), including gefitinib, erlotinib, afatinib, osimertinib, and icotinib for lung cancer. Cetuximab, panitumumab, necitumumab, zalutumumab, nimotuzumab and matuzumab are examples of monoclonal antibody EGFR inhibitors. Gefitinib, erlotinib, afatinib, dacomitinib, osimertinib, and lapatinib (mixed EGFR and ERBB2 inhibitor) are examples of small molecule EGFR kinase inhibitors.

Unfortunately, many patients develop resistance of the existent EGFR inhibitors. Non-limiting sources of resistance are the EGFR T790M Mutation, HER2 and MET oncogenes, transformation to small cell lung cancer (SCLC), epithelial to mesenchymal transition (EMT), nd fusions including those involving BRAF, NTRK1, RET, ALK, and/or ROS1. Options to combat resistance are limited, with only osimertinib being approved to treat EGFR T790M. While in frame deletions in exon 19 of EGFR and the L858R substitution in exon 21 of EGFR are sensitive to EGFR inhibitors (such as erlotinib, gefitinib, and afatinib), other mutations, such as in frame insertions in EGFR exon 20, demonstrate intrinsic resistance to these inhibitors. Other rare mutations in EGFR, such as G719X (exon 18) and L861Q (exon 21), have variable response to EGFR inhibitors. That said, the major reason why it is difficult to target these mutations is due to the undesirable on-target inhibition of WT EGFR in normal tissues.

There is thus a need in the art to identify compounds and methods that can be used to treat or prevent HER-driven drug-resistant cancers. In certain embodiments, the compounds and methods can be used to treat or prevent EGFR-driven, HER2-driven, and/or NGR1-driven drug-resistant cancers. The present application addresses and meets these needs.

BRIEF SUMMARY OF THE INVENTION

The application provides a method of treating or preventing a HER-driven drug-resistant cancer in a subject in need thereof. In certain embodiments, the method comprises providing tumor cells of the subject. In other embodiments, the method comprises detecting presence or absence of an EGFR exon 20 insertion mutation in the provided tumor cells. In yet other embodiments, the method comprises predicting the subject as being likely to be responsive to treatment by (2E)-4-{[4-(3-bromo-4-chloroanilino)pyrido[3,4-d]pyrimidin-6-yl]amino}-N,N-dimethyl-N-[(1-methyl-4-nitro-1H-imidazol-5-yl)methyl]-4-oxo-2-buten-1-ammonium bromide (Compound A) and/or (2E)-N-[4-(3-bromo-4-chloroanilino)pyrido[3,4-d]pyrimidin-6-yl]-4-(dimethylamino)-2-butenamide) (Compound B), if the EGFR exon 20 insertion mutation is detected. In yet other embodiments, the method comprises administering a therapeutically effective amount of at least one compound selected from the group consisting of Compound A and Compound B, or a salt or a solvate thereof.

The application further provides a method of treating a HER-driven drug-resistant cancer in a subject with cancer, where an EGFR exon 20 insertion mutation is detected in tumor cells of the subject. In certain embodiments, the method comprises administering a therapeutically effective amount of at least one compound selected from the group consisting of Compound A and Compound B, or a salt or a solvate thereof.

The application further provides a method of predicting the responsiveness of a subject with a HER-driven drug-resistant cancer to treatment with at least one compound selected from the group consisting of Compound A and Compound B. In certain embodiments, the method comprises providing tumor cells of the subject. In other embodiments, the method comprises detecting presence or absence of an EGFR exon 20 insertion mutation in the provided tumor cells of the subject. In yet other embodiments, the method comprises predicting the subject as being likely to be responsive to a treatment with the at least one compound if the EGFR exon 20 insertion mutation is detected in the provided tumor cells of the subject.

The application further provides a method of predicting the responsiveness of a subject with a HER-driven drug-resistant cancer to treatment with at least one compound selected from the group consisting of Compound A and Compound B. In certain embodiments, the method comprises detecting presence or absence of an EGFR exon 20 insertion mutation in a sample of tumor cells from the subject. In other embodiments, the subject is likely to be responsive to the treatment with the at least one compound if the EGFR exon 20 insertion mutation is detected in the sample of tumor cells from the subject.

The application further provides a method of identifying a subject with cancer who is likely to be responsive to treatment with at least one compound selected from the group consisting of Compound A and Compound B. In certain embodiments, the method comprises providing tumor cells of the subject. In other embodiments, the method comprises detecting presence or absence of an EGFR exon 20 insertion mutation in the provided tumor cells. In yet other embodiments, the method comprises identifying the subject as being likely to be responsive to treatment with the at least one compound if the EGFR exon 20 insertion mutation is detected in the provided tumor cells.

In certain embodiments, the HER-driven cancer comprises an EGFR-driven cancer.

In certain embodiments, the EGFR-driven cancer comprises lung cancer.

In certain embodiments, the lung cancer comprises non-small cell lung cancer (NSCLC).

In certain embodiments, the mutation comprises at least one selected from the group consisting of A763_Y764insFQEA, A763_Y764insFQQA, A767_V769dupASV, D770_N771insGL, D770_N771insGT, D770_N771insNPG, D770_N771insSVD, E762Q_insFQEA, H773_V774insH, H773_V774insH, H773_V774insNPH, M766_A767insAI, M766_A767insASV, N771_H773dupNPH, P772_H773insYNP, P772_V774insPHV, S768_770dupSVD, V769_D770insASV, Y764_V765insHH, delD770insGY, and delL747_P753insS.

In certain embodiments, the cancer comprises at least one ERBB2 gene fusion selected from the group consisting of ZNF207-HER2, MDK-HER2, NOS2-HER2, ERBB2-GRB7, ERBB2-CTTN, ERBB2-PPP1R1B, and ERBB2-PSMB3.

In certain embodiments, the cancer comprises at least one ERBB2 mutation selected from the group consisting of G309A/E; S310F/Y; V659E/D; G660D; K753E; L755P/S; Del755-759; L768S; D769H/Y; V773L; A775_G776insYVMA; G776V/L, Cins; V777L; P780Ins; P780_Y781insGSP; V842I; L866M; and R896C.

In certain embodiments, the cancer comprises at least one NRG1 gene fusion selected from the group consisting of DOC4-NRG1; CD74-NRG1; SLC3A2-NRG1; RBPMS-NRG1; WRN-NRG1; SDC4-NRG1; RAB2IL1-NRG1; VAMP2-NRG1; KIF13B-NRG1; ATP1B1-NRG1; CDH6-NRG1; APP-NRG1; AKAP13-NRG1; THBS1-NRG1; PDE7A-NRG1; THAP7-NRG1; SMAD4-NRG1; RAB3IL1-NRG1; NRG1-PMEPA1; and NRG1-STMN2.

In certain embodiments, the cancer comprises at least one ERBB3 mutation selected from the group consisting of V104M; A232V; P262H; G284R; T389K; Q809R; S846I; and E928G.

In certain embodiments, the cancer comprises at least one ERBB4 fusion selected from the group consisting of EZR-ERBB4; IKZF2-ERBB4; and BGALT-ERBB4.

In certain embodiments, the cancer is resistant to at least one agent selected from the group consisting of osimertinib, gefitinib, afatinib, and erlotinib.

In certain embodiments, the method further comprises administering at least one additional agent, or a salt or solvate thereof, that treats or prevents the cancer. In other embodiments, the at least one compound and the at least one additional agent are co-administered to the subject. In yet other embodiments, the at least one compound and the at least one additional agent are coformulated.

In certain embodiments, the at least one compound is administered by at least one route selected from the group consisting of inhalational, oral, nasal, rectal, parenteral, sublingual, transdermal, transmucosal, intravesical, intrapulmonary, intraduodenal, intragastrical, intrathecal, epidural, intrapleural, intraperitoneal, intratracheal, otic, intraocular, subcutaneous, intramuscular, intradermal, intraarterial, intravenous, intrabronchial, inhalation, and topical. In other embodiments, the at least one compound is administered orally. In yet other embodiments, the at least one compound is administered parenterally.

In certain embodiments, the subject is a mammal. In other embodiments, the mammal is a human. In yet other embodiments, the subject is in need of treatment thereof. In yet other embodiments, the subject is a human in need of treatment thereof.

BRIEF DESCRIPTION OF THE DRAWINGS

The following detailed description of specific embodiments of the disclosure will be better understood when read in conjunction with the appended drawings. For the purpose of illustrating the disclosure, specific embodiments are shown in the drawings. It should be understood, however, that the disclosure is not limited to the precise arrangements and instrumentalities of the embodiments shown in the drawings.

FIG. 3A is a schematic illustration to the EGFR kinase domain and certain oncogenic mutations thereof. exon 20_ins EGFR mutations are the third most common activating mutations in EGFR. Affected patients have poor response to first and second generation EGFR-TKIs (ORR-10%). FIG. 3B is a schematic representation of an EGFR protein domain, as well as localization of exon 20 insertions identified in patient derived cell lines generated in the present study. Three patient derived cell lines were isolated and propagated from pleural fluid; each of the cell lines presented a different EGFR exon 20 insertion mutation.

FIG. 6C comprises a table summarizing IC$_{50}$ values of proliferation experiments. Values are expressed in nanomolar concentration. The data show that RN-4000E inhibits proliferation of cell lines harboring EGFR exon 20 insertion mutations. See also Table 5 for IC$_{50}$ values of proliferation experiments.

FIG. 7A: 1×10$^6$ cells were injected in each flank of nude mice. Once tumors reached 200 mm$^3$, mice were randomly separated and treated with afatinib (6 mg/Kg, daily, PO), cetuximab (40 mg/Kg, Q3d, IP), tarloxotinib (48 mg/Kg, Qwx4, IP) and vehicle for four weeks. Tumor volume was measured two times a week. FIG. 7B: Tarloxotinib is active in PDX models of EGFR exon 20 insertion that have been permitted to grow to a large size (average size of about 573 mm$^3$) before initiating treatment.

FIGS. 9A-9C comprise a series of images and a table depicting data compiled from the cBioPortal (accessed Jun. 14, 2018; Gao, et al., 2013, Sci. Signal. 6(239):pl1). FIG. 9A illustrates that ERBB2 is mutated or amplified in NSCLC. FIG. 9B comprises a table illustrating presence of ERBB2 gene amplification, missense mutations, indels, and gene fusions in NSCLC cohorts. Legend for genetic alteration: a, In-Frame Mutation (putative driver); b, Missense Mutation (putative driver); c, Missense Mutation (unknown significance); d, Truncating Mutation (unknown significance), e, Fusion; f, Amplification; g, Deep Deletion; h, No Alterations. Legend for study of origin: i, Genetic Characterization of NSCLC young adult patients (University of Turin, Lung Cancer 2016); j, Lung Adenocarcinoma (Broad, Cell 2012); k, Lung Adenocarcinoma (MSKCC, 2015); l, Lung Adenocarcinoma (TCGA, PanCancer Atlas); m, Lung Adenocarcinoma (TCGA, Provisional); n, MSK-IMPACT Clinical Sequencing Cohort for Non-Small Cell Cancer (MSK, Cancer Discovery 2017); o, Non-Small Cell Lung Cancer (MSK, JCO 2018); p, Pan-Lung Cancer (TCGA, Nat Genetics 2016). FIG. 9C illustrates a lollipop diagram highlighting recurrent mutations in NSCLC samples.

FIGS. 10A-10C comprise a series of gel images illustrating the finding that TRLX-TKI (RN-4000E) inhibits HER2 and HER3 phosphorylation and downstream signaling in AKT in cell lines harboring HER2 gene amplification (H2170 and Calu-3) or HER2 exon 20 insertion mutation (H1781). Cells were treated with the indicated doses of afatinib, gefitinib, osimertinib, TRLX-TKI (RN-4000E; active drug) for 2 hours under normoxic conditions, lysed and analyzed by immunoblot. Blots are representatives of three independent experiments.

FIGS. 16A-16B comprise a series of graphs illustrating dose response curves of cell viability of EGFR exon 20 insertion mutation patient derived cell lines (CUTO-14, CUTO-17, CUTO-18). Cells were treated with TRLX-TKI, TRLX (pro-drug), gefitinib, afatinib, and osimertinib. As demonstrated herein, TRLX-TKI inhibits proliferation of cell lines harboring EGFR exon 20 insertion mutations.

DETAILED DESCRIPTION OF THE INVENTION

Figure 1:
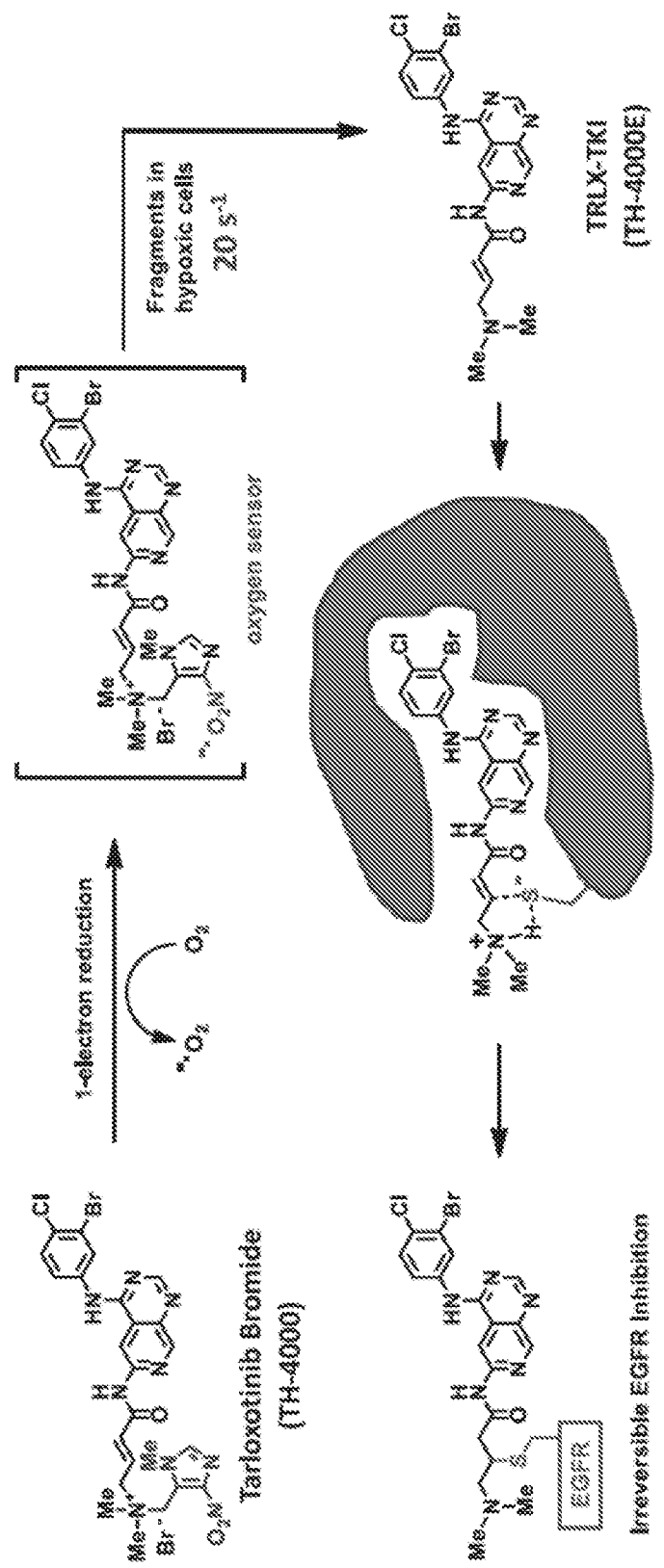
FIG. 1 is a schematic illustration of the mechanism of activation of Compound A (tarloxotinib or TRLX, indicated as RN-4000) to Compound B (tarloxotinib-TKI or TRLX-TKI, indicated as RN-4000E), and subsequent irreversible inhibition of EGFR by Compound B.

The present disclosure relates in part to the discovery that certain nitromethylaryl quaternary ammonium salts (also referred to as NMQ prodrugs) can be used as small molecule EGFR inhibitors to treat or prevent certain HER-driven drug-resistant cancers. In certain embodiments, a small molecule EGFR inhibitor (RN-4000; also known as "(E)-4-((4-((3-bromo-4-chlorophenyl)amino)pyrido[3,4-d]pyrimidin-6-yl)amino)-N,N-dimethyl-N-((1-methyl-4-nitro-1H-imidazol-5-yl)methyl)-4-oxobut-2-en-1-aminium salt (bromide)"; also referred to herein as "(2E)-4-{[4-(3-bromo-4-chloroanilino)pyrido[3,4-d]pyrimidin-6-yl]amino}-N,N-dimethyl-N-[(1-methyl-4-nitro-1H-imidazol-5-yl)methyl]-4-oxo-2-buten-1-ammonium bromide"; also referred to herein as Compound A, RN-4000, TRLX, or tarloxotinib; FIG. 1) and/or its active metabolite (RN-4000E; also known as "(E)-N-(4-((3-bromo-4-chlorophenyl)amino)pyrido[3,4-d]pyrimidin-6-yl)-4-(dimethylamino)but-2-enamide"; also referred to herein as "(2E)-N-[4-(3-bromo-4-chloroanilino)pyrido[3,4-d]pyrimidin-6-yl]-4-(dimethylamino)-2-butenamide"); also referred to herein as Compound B; FIG. 1) are used to treat or prevent certain HER-driven drug-resistant cancers. In certain embodiments, the cancer is EGFR-driven.

It will be understood by one of ordinary skill in the art that recitation of Compound A herein also includes the corresponding cation ((E)-4-((4-((3-bromo-4-chlorophenyl)amino)pyrido [3,4-d]pyrimidin-6-yl)amino)-N,N-dimethyl-N-((1-methyl-4-nitro-1H-imidazol-5-yl)methyl)-4-oxobut-2-en-1-aminium), as well as any salt of such cation, such as but not limited to the bromide salt. It will be further understood by one of ordinary skill in the art that Compound A may exist as a cation or salt, for example, a bromide salt, as depicted below.

Structures of Compound A and Compound B are provided below:

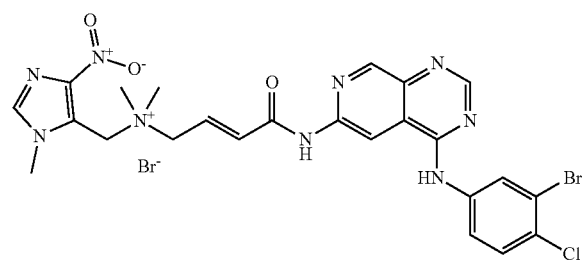

Compound A, RN-4000, TH-4000, TRLX, or tarloxotinib

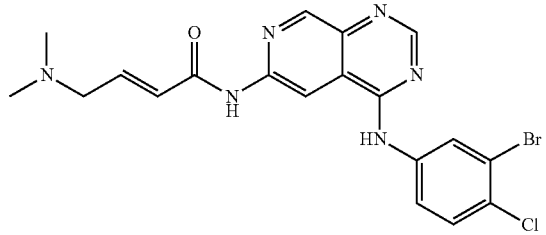

Compound B, RN-4000E, TH-4000E, or TRLX-TKI

The disclosure further contemplates the use of other NMQ prodrugs and/or small molecule EGFR inhibitors, including any other small molecule analogues of Compound A and/or Compound B, to treat or prevent certain HER-driven drug-resistant cancers. Such NMQ prodrugs and/or small molecule EGFR inhibitors include, but are not limited to those disclosed in WO2010104406, WO2011028135, US20120077811, and US20120202832, each of which is incorporated herein by reference in its entirety.

For example, the disclosure contemplates NMQ prodrugs of quaternary nitrogen salt compounds of Formula I:

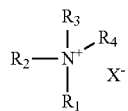

(I)

wherein in (I):

X is any negatively charged counterion (anion);

$R_1$ is a group of the formula —$(CH_2)_n$Tr, where Tr is an aromatic nitroheterocycle or an aromatic nitrocarbocycle and —$(CH_2)_n$Tr acts as a reductively-activated fragmenting trigger ("reductive trigger"); and n is an integer ranging from 0 to 6;

$R_2$, $R_3$ and $R_4$ are each independently an aliphatic or an aromatic group of a tertiary amine kinase inhibitor $(R_2)(R_3)(R_4)N$, or two of $R_2$, $R_3$, and $R_4$ may form an aliphatic or aromatic heterocyclic amine ring of a kinase inhibitor, or one of $R_2$, $R_3$ and $R_4$ may be absent and two of $R_2$, $R_3$ and $R_4$ form an aromatic heterocyclic amine ring of a kinase inhibitor.

In certain embodiments, the compounds are of Formula II:

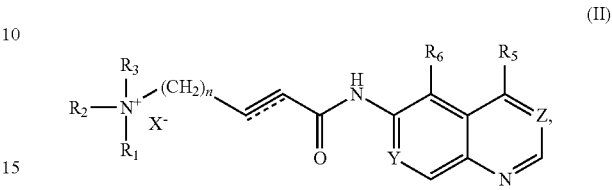

(II)

wherein:

X is any negatively charged counterion (anion);

Y is N or C—$R_7$, where $R_7$ is selected from the group consisting of H, $C_1$-$C_6$ alkyl, $C_1$-$C_6$ alkoxy, and a group of the one of the following Formulas IIIa, IIIb, and IIIc:

(IIIa)

(IIIb)

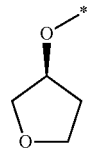

(IIIc)

wherein

* is the point of attachment;

T is selected from the group consisting of O, NH, N($C_1$-$C_6$ alkyl), and a direct link (null);

m is an integer ranging from 0 to 6;

U is selected from the group consisting of $OR_{10}$, $CF_3$, $OCF_3$, CN, $NR_{11}R_{12}$, pyrrolidinyl, piperidinyl, piperazinyl, N1-methylpiperazinyl, morpholinyl, $CON(R_{13})(R_{14})$, $SO_2N(R_{15})(R_{16})$, $N(R_{17})COR_{18}$, $N(R_{19})SO_2R_{20}$, $COR_{21}$, $SOR_{22}$, $SO_2R_{23}$, and $COOR_{24}$; and $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$ are independently selected from the group consisting of H and $C_1$-$C_6$ alkyl;

Z is N or C—CN;

n is an integer ranging from 0 to 6;

$R_1$ is a group of the formula $(CH_2)_p$Tr, wherein Tr is an aromatic nitroheterocycle or aromatic nitrocarbocycle and —$(CH_2)_p$Tr acts as a reductive trigger; and p is an integer ranging from 0 to 6;

$R_2$ and $R_3$ are independently selected from the group consisting of $C_1$-$C_6$ alkyl, cyclopropyl, cyclobutyl, cyclopentyl, cyclohexyl, $CH_2CH_2OH$, and $CH_2CH_2O(C_1$-$C_6$ alkyl); or $R_2$ and $R_3$ may together form a non-aromatic carbocyclic ring or non-aromatic heterocyclic ring containing at least one heteroatom;

$R_5$ is selected from the group consisting of an aniline, an indole, an indoline, an amine, an aminoindole, and an aminoindazole, each of which may be optionally substituted with one or more substituents selected from the group consisting of H, $C_1$-$C_6$ alkyl, $C_2$-$C_6$ alkenyl, $C_2$-$C_6$ alkynyl, $C_1$-$C_6$ alkoxy, F, Cl, Br, I, CN, $CH_2F$, $CHF_2$, $CF_3$, OH, $NH_2$, $NO_2$, $NH(C_1$-$C_6$ alkyl), $N(C_1$-$C_6$ alkyl)$_2$, $CONH_2$, $CO(C_1$-$C_6$ alkyl), $SO_2NH_2$, and $SO_2(C_1$-$C_6$ alkyl); and $R_6$ is selected from the group consisting of H, $C_1$-$C_6$ alkyl, $C_1$-$C_6$ alkoxy, $NH(C_1$-$C_6$ alkyl), $N(C_1$-$C_6$ alkyl)$_2$, and a group of the following Formula IV:

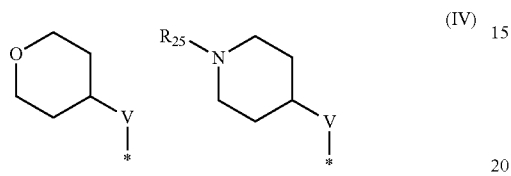

(IV)

wherein:
* is the point of attachment;
V is selected from the group consisting of $(CH_2)_k$, O, NH, and $N(C_1$-$C_6$ alkyl);
k is an integer ranging from 0 to 6, and
$R_{25}$ is selected from the group consisting of H and $C_1$-$C_6$ alkyl.

In certain embodiments, X is selected from the group consisting of halide (e.g., fluoride, chloride, bromide, iodide), methanesulfonate, trifluoromethanesulfonate, acetate, trifluoroacetate, tosylate, lactate, citrate, and formate. In certain embodiments, X is a halide. In certain embodiments, X is selected from the group consisting of fluoride, chloride, bromide, and iodide.

In certain embodiments, $R_1$ is a group of one of the following Formulas Va-Vq:

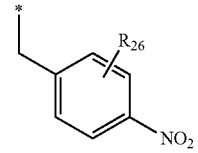

a

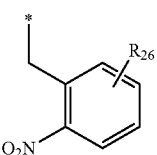

b

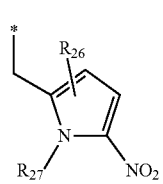

c

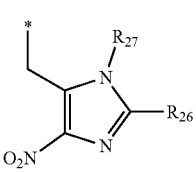

d

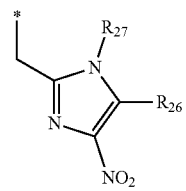

e

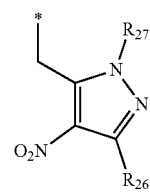

f

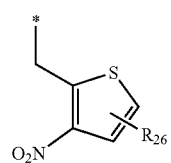

g

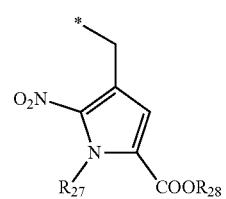

h

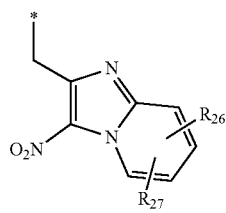

i

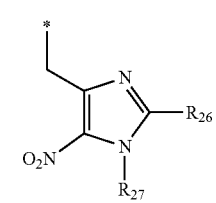

j

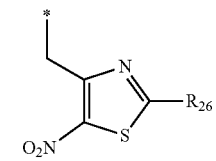

k

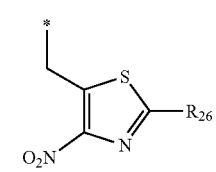

l

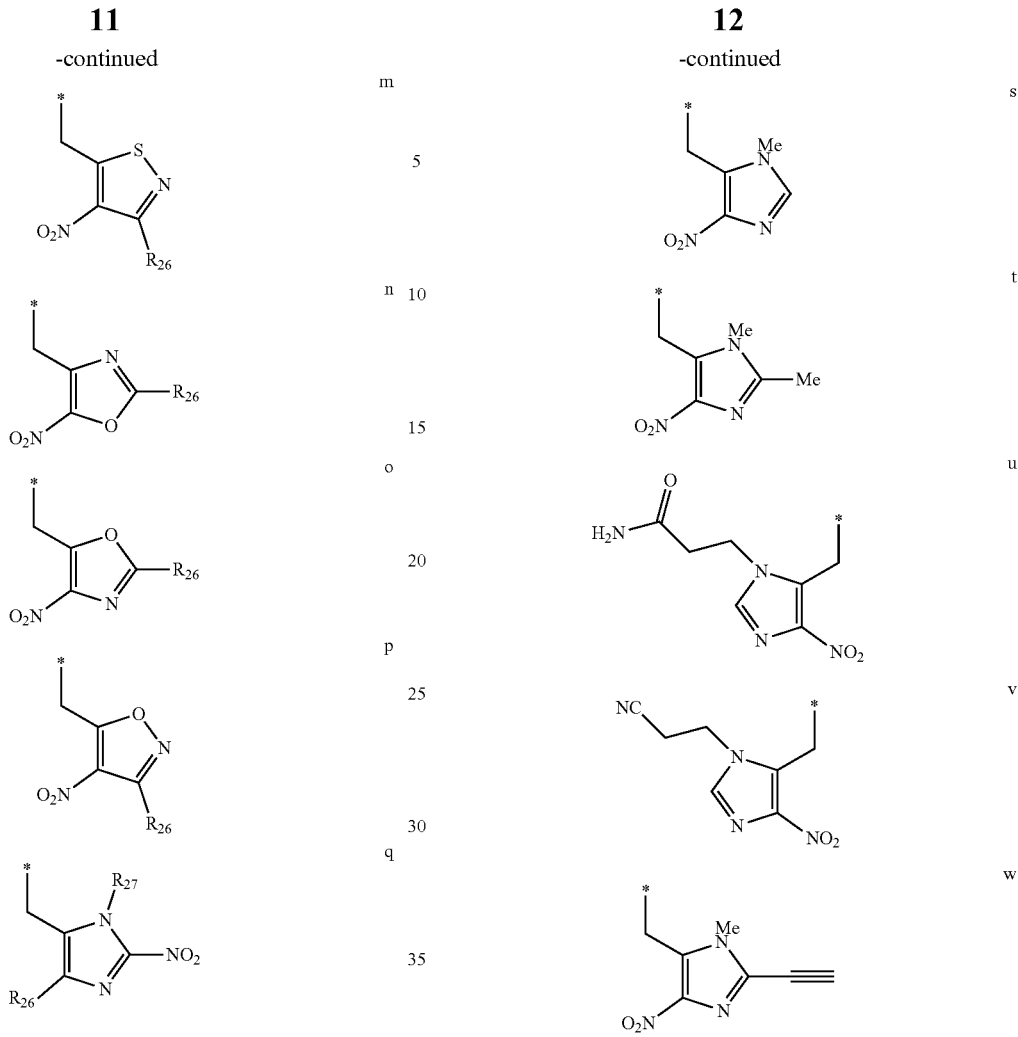

wherein:
 * is the point of attachment to the quaternary nitrogen of a compound of Formula II;

R$_{26}$ is selected from the group consisting of H, C$_1$-C$_6$ alkyl, C$_1$-C$_6$ alkoxy, C$_2$-C$_6$ alkenyl, C$_2$-C$_6$ alkynyl, CF$_3$, OCF$_3$, F, Cl, Br, I, NO$_2$, CN, COOH, COO(C1-C6 alkyl), CONH$_2$, CONH(C$_1$-C$_6$ alkyl), CON(C$_1$-C$_6$ alkyl)$_2$, CO(C$_1$-C$_6$ alkyl), SO$_2$NH$_2$, SO$_2$NH(C$_1$-C$_6$ alkyl), SO$_2$N(C$_1$-C$_6$ alkyl)$_2$, SO$_2$(C$_1$-C$_6$ alkyl), and a group of Formula IIIa, as defined above, wherein * is the point of attachment to a group of Formula V;

R$_{27}$ is selected from the group consisting of H, C$_1$-C$_6$ alkyl, and a group of Formula IIIa, as defined above, wherein * is the point of attachment to a group of Formula V; and R$_{28}$ is selected from the group consisting of H and C$_1$-C$_6$ alkyl.

In certain embodiments, R$_1$ is a group of one of the following Formulas Vr-Vae:

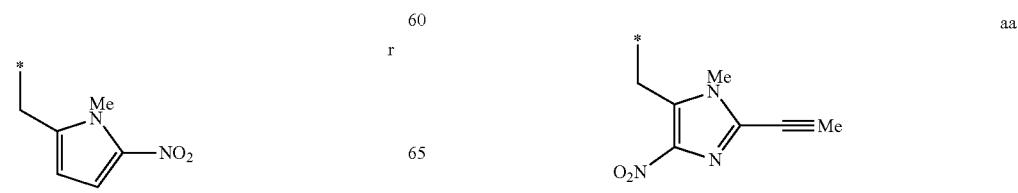

-continued

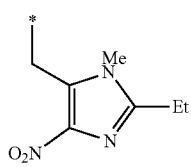

ab

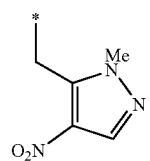

ac

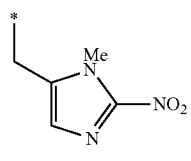

ad

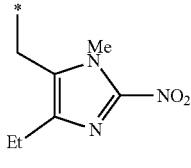

ae

In certain embodiments, $R_1$ is a group of Formula Vc, wherein $R_{26}$ is H and $R_{27}$ is $CH_3$.

In certain embodiments, $R_1$ is a group of Formula Vd, where $R_{26}$ is selected from the group consisting of H, $C_1$-$C_6$ alkyl (e.g., methyl), $C_1$-$C_6$ alkoxy (e.g., $OCH_3$), $C_2$-$C_6$ alkynyl (e.g., ethynyl), $CONH_2$, CONHMe, $CF_3$, $OCF_3$, Br, $NO_2$, and CN, and $R_{27}$ is selected from the group consisting of $CH_3$, $CH_2CH_2CONH_2$, and $CH_2CH_2CN$.

In certain embodiments, $R_1$ is a group of Formula Vd,

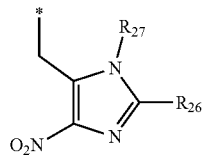

(Vd)

wherein * is a point of attachment, $R_{26}$ is selected from the group consisting of H and $C_1$-$C_3$ alkyl, and $R_{27}$ is selected from the group consisting of H and $C_1$-$C_6$ alkyl. In certain embodiments, $R_{26}$ is selected from the group consisting of H, methyl, ethyl, trifluoromethyl, —CN, —$CONH_2$, and propyn-1-yl, and $R_{27}$ is $C_1$-$C_6$ alkyl.

In certain embodiments, $R_{26}$ is H and $R_{27}$ is $C_1$-$C_3$ alkyl (e.g., methyl).

In certain embodiments, $R_1$ is a group of Formula Vd, wherein $R_{26}$ is 1-propynyl and $R_{27}$ is $CH_3$.

In certain embodiments, $R_1$ is a group of Formula Vq, where $R_{26}$ is selected from the group consisting of H, $C_1$-$C_6$ alkyl (e.g., methyl or ethyl) and $C_1$-$C_6$ alkoxy (e.g., $OCH_3$), and $R_{27}$ is $CH_3$.

In certain embodiments, $R_1$ is a group of any one of Formulas $Vd^{(1)}$-$Vd^{(7)}$:

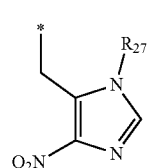

$(Vd^{(1)})$

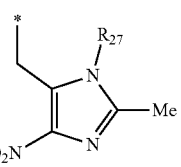

$(Vd^{(2)})$

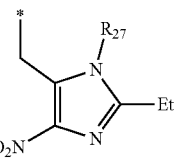

$(Vd^{(3)})$

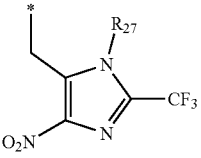

$(Vd^{(4)})$

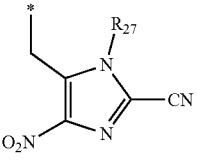

$(Vd^{(5)})$

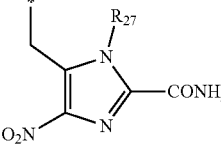

$(Vd^{(6)})$

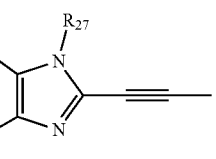

$(Vd^{(7)})$

In certain embodiments, $R_{27}$ is selected from the group consisting of methyl, ethyl and propyl. In certain embodiments $R_{27}$ is methyl.

In certain embodiments, $R_2$ and $R_3$ form a ring selected from the group consisting of pyrrolidinium, piperidinium, piperazinium, N1-methylpiperazinium, and morpholinium.

In certain embodiments, $R_5$ is a group of one of the following Formulas VIa-VIg:

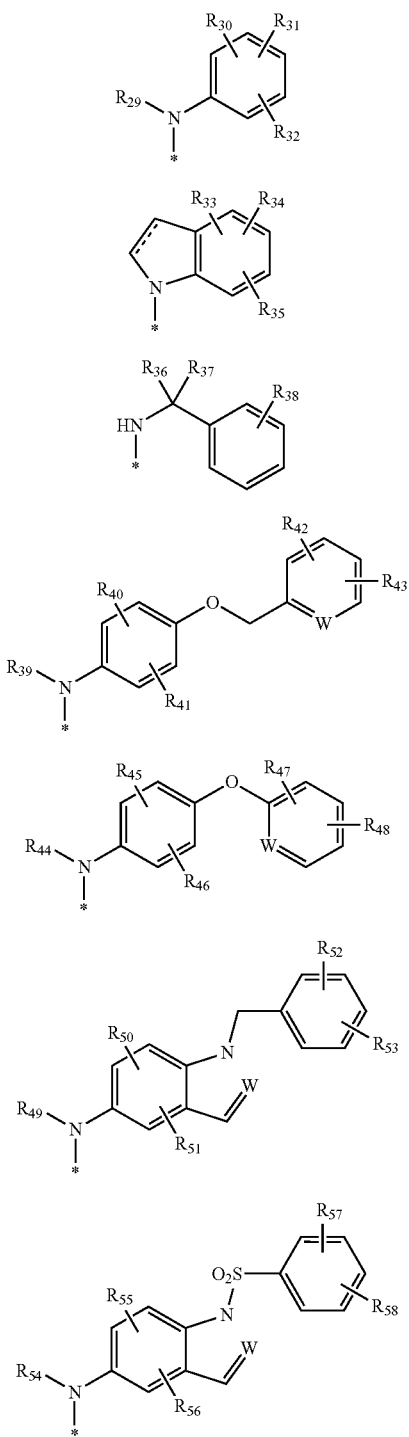

alkyl), N($C_1$-$C_6$ alkyl)$_2$, CONH$_2$, CO($C_1$-$C_6$ alkyl), SO$_2$NH$_2$, and SO$_2$($C_1$-$C_6$ alkyl); and W is N or C—H.

In certain embodiments, Y is N, Z is N or C—CN; and $R_1$ is selected from the following:

(a) a group of Formula Vc, where $R_{26}$ is H and $R_{27}$ is CH$_3$;

(b) a group of Formula Vd, where (i) $R_{26}$ is selected from the group consisting of H, $C_1$-$C_6$ alkyl (e.g., methyl), $C_1$-$C_6$ alkoxy (e.g., OCH$_3$), $C_2$-$C_6$ alkynyl (e.g., ethynyl), CF$_3$, OCF$_3$, Br, NO$_2$, and CN, and $R_{27}$ is selected from the group consisting of CH$_3$, CH$_2$CH$_2$CONH$_2$, and CH$_2$CH$_2$CN; or (ii) $R_{26}$ is 1-propynyl and $R_{27}$ is CH$_3$;

(c) a group of Formula Vf, where $R_{26}$ is H and $R_{27}$ is CH$_3$; and (d) a group of Formula Vq, where $R_{26}$ is selected from the group consisting of H, $C_1$-$C_6$ alkyl (e.g., methyl and ethyl) and $C_1$-$C_6$ alkoxy (e.g., OCH$_3$), and $R_{27}$ is CH$_3$; wherein:

$R_2$ and $R_3$ are independently selected from the group consisting of $C_1$-$C_6$ alkyl, or together form a ring selected from the group consisting of pyrrolidinium, piperidinium, piperazinium, N1-methylpiperazinium, and morpholinium; and $R_5$ is selected from the following:

(a) a group of Formula VIa, where * is the point of attachment, $R_{29}$ is H, and $R_{30}$, $R_{31}$, $R_{32}$ are independently selected from the group consisting of H, $C_1$-$C_6$ alkyl, $C_2$-$C_6$ alkenyl, $C_2$-$C_6$ alkynyl, $C_1$-$C_6$ alkoxy, F, Cl, Br, I, CN, CH$_2$F, CHF$_2$, CF$_3$, OH, NH$_2$, NO$_2$, NH($C_1$-$C_6$ alkyl), and N($C_1$-$C_6$ alkyl)$_2$;

(b) a group of Formula VId, where * is the point of attachment, $R_{39}$ is H, and $R_{40}$ and $R_{41}$ are independently selected from the group consisting of H, $C_1$-$C_6$ alkyl, $C_2$-$C_6$ alkenyl, $C_2$-$C_6$ alkynyl, $C_1$-$C_6$ alkoxy, F, Cl, Br, I, CN, CH$_2$F, CHF$_2$, CF$_3$, OH, NH$_2$, NO$_2$, NH($C_1$-$C_6$ alkyl), and N($C_1$-$C_6$ alkyl)$_2$; $R_{42}$ and $R_{43}$ are independently selected from the group consisting of H, $C_1$-$C_6$ alkyl, $C_2$-$C_6$ alkenyl, $C_2$-$C_6$ alkynyl, $C_1$-$C_6$ alkoxy, F, Cl, Br, I, CN, CH$_2$F, CHF$_2$, CF$_3$, OH, NH$_2$, NO$_2$, NH($C_1$-$C_6$ alkyl), and N($C_1$-$C_6$ alkyl)$_2$; and W is N or C—H; and (c) a group of Formula VIf, where * is the point of attachment, $R_{49}$ is H, and $R_{50}$ and $R_{51}$ are independently selected from the group consisting of H and F; $R_{52}$ and $R_{53}$ are independently selected from the group consisting of H, $C_1$-$C_6$ alkyl, F, Cl, Br, I, CH$_2$F, CHF$_2$, and CF$_3$; W is N or C—H; $R_6$ is H; X is any negatively charged counterion; and n=1 or 2.

In certain embodiments, Y is C—H or C—($C_1$-$C_6$ alkoxy), Z is N or C—CN; and $R_1$ is selected from the following:

(a) a group of Formula Vc, where $R_{26}$ is H, and $R_{27}$ is CH$_3$;

(b) a group of Formula Vd, where $R_{26}$ is selected from the group consisting of H, $C_1$-$C_6$ alkyl, $C_1$-$C_6$ alkoxy, $C_2$-$C_6$ alkynyl, CF$_3$, OCF$_3$, Br, NO$_2$, and CN, and $R_{27}$ is selected from the group consisting of CH$_3$, CH$_2$CH$_2$CONH$_2$, and CH$_2$CH$_2$CN; or $R_{26}$ is 1-propynyl and $R_{27}$ is CH$_3$;

(c) a group of Formula Vf, where $R_{26}$ is H and $R_{27}$ is CH$_3$; and (d) a group of Formula Vq, where $R_{26}$ is selected from the group consisting of H, $C_1$-$C_6$ alkyl (e.g., methyl and ethyl), and $C_1$-$C_6$ alkoxy (e.g., OCH$_3$), and $R_{27}$ is CH$_3$;

$R_2$ and $R_3$ are independently selected from the group consisting of $C_1$-$C_6$ alkyl, or together form a ring selected from pyrrolidinium, piperidinium, piperazinium, N1-methylpiperazinium, and morpholinium;

wherein:

* is the point of attachment;

$R_{29}$, $R_{36}$, $R_{37}$, $R_{39}$, $R_{44}$, $R_{49}$ and $R_{54}$, are independently selected from the group consisting of H and $C_1$-$C_6$ alkyl;

$R_{30}$, $R_{31}$, $R_{32}$, $R_{33}$, $R_{34}$, $R_{35}$, $R_{38}$, $R_{40}$, $R_{41}$, $R_{42}$, $R_{43}$, $R_{45}$, $R_{46}$, $R_{47}$, $R_{48}$, $R_{50}$, $R_{51}$, $R_{52}$, $R_{53}$, $R_{55}$, $R_{56}$, $R_{57}$ and $R_{58}$ are independently selected from the group consisting of H, $C_1$-$C_6$ alkyl, $C_2$-$C_6$ alkenyl, $C_2$-$C_6$ alkynyl, $C_1$-$C_6$ alkoxy, F, Cl, Br, I, CN, CH$_2$F, CHF$_2$, CF$_3$, OH, NH$_2$, NO$_2$, NH($C_1$-$C_6$ $R_5$ is selected from the following:

(a) a group of Formula VIa, where * is the point of attachment; $R_{29}$ is H; and $R_{30}$, $R_{31}$, $R_{32}$ are independently selected from the group consisting of H, $C_1$-$C_6$ alkyl, $C_2$-$C_6$ alkenyl, $C_2$-$C_6$ alkynyl, $C_1$-$C_6$ alkoxy, F, Cl, Br, I, CN, $CH_2F$, $CHF_2$, $CF_3$, OH, $NH_2$, $NO_2$, $NH(C_1$-$C_6$ alkyl), and $N(C_1$-$C_6$ alkyl$)_2$;

(b) a group of Formula VId, where * is the point of attachment; $R_{39}$ is H; and $R_{40}$ and $R_{41}$ are independently selected from the group consisting of H, $C_1$-$C_6$ alkyl, $C_2$-$C_6$ alkenyl, $C_2$-$C_6$ alkynyl, $C_1$-$C_6$ alkoxy, F, Cl, Br, I, CN, $CH_2F$, $CHF_2$, $CF_3$, OH, $NH_2$, $NO_2$, $NH(C_1$-$C_6$ alkyl), and $N(C_1$-$C_6$ alkyl$)_2$; $R_{42}$ and $R_{43}$ are independently selected from the group consisting of H, $C_1$-$C_6$ alkyl, $C_2$-$C_6$ alkenyl, $C_2$-$C_6$ alkynyl, $C_1$-$C_6$ alkoxy, F, Cl, Br, I, CN, $CH_2F$, $CHF_2$, $CF_3$, OH, $NH_2$, $NO_2$, $NH(C_1$-$C_6$ alkyl), and $N(C_1$-$C_6$ alkyl$)_2$; and W is N or C—H; and (c) a group of Formula VIf, where * is the point of attachment; $R_{49}$ is H; and $R_{50}$ and $R_{51}$ are independently selected from the group consisting of H and F; $R_{52}$ and $R_{53}$ are independently selected from the group consisting of H, $C_1$-$C_6$ alkyl, F, Cl, Br, I, $CH_2F$, $CHF_2$, and $CF_3$; and W is N or C—H;

$R_6$ is H;

X is any negatively charged counterion (anion); and n=1 or 2.

In certain embodiments, Y is C—$R_7$, where $R_7$ is a group of Formula IIIb; Z is N or C—CN; $R_1$ is selected from the following:

(a) a group of Formula Vc, where $R_{26}$ is H, and $R_{27}$ is $CH_3$;

(b) a group of Formula Vd, where $R_{26}$ is selected from the group consisting of H, $C_1$-$C_6$ alkyl, $C_1$-$C_6$ alkoxy, $C_2$-$C_6$ alkynyl, $CF_3$, $OCF_3$, Br, $NO_2$, and CN, and $R_{27}$ is selected from the group consisting of $CH_3$, $CH_2CH_2CONH_2$, and $CH_2CH_2CN$; or $R_{26}$ is 1-propynyl; and $R_{27}$ is $CH_3$;

(c) a group of Formula Vf, where $R_{26}$ is H and $R_{27}$ is $CH_3$; and (d) a group of Formula Vq, where $R_{26}$ is selected from the group consisting of H, $C_1$-$C_6$ alkyl (e.g., methyl and ethyl) and $C_1$-$C_6$ alkoxy (e.g., $OCH_3$); and $R_{27}$ is $CH_3$;

$R_2$ and $R_3$ are independently selected from $C_1$-$C_6$ alkyl, or together form a ring selected from the group consisting of pyrrolidinium, piperidinium, piperazinium, N1-methylpiperazinium, and morpholinium;

$R_5$ is selected from the following:

(a) a group of Formula VIa, where * is the point of attachment to a compound of Formula II; $R_{29}$ is H; and $R_{30}$, $R_{31}$, $R_{32}$ are independently selected from the group consisting of H, $C_1$-$C_6$ alkyl, $C_2$-$C_6$ alkenyl, $C_2$-$C_6$ alkynyl, $C_1$-$C_6$ alkoxy, F, Cl, Br, I, CN, $CH_2F$, $CHF_2$, $CF_3$, OH, $NH_2$, $NO_2$, $NH(C_1$-$C_6$ alkyl), and $N(C_1$-$C_6$ alkyl$)_2$;

(b) a group of Formula VId, where * is the point of attachment to a compound of Formula II; $R_{39}$ is H; and $R_{40}$ and $R_{41}$ are independently selected from the group consisting of H, $C_1$-$C_6$ alkyl, $C_2$-$C_6$ alkenyl, $C_2$-$C_6$ alkynyl, $C_1$-$C_6$ alkoxy, F, Cl, Br, I, CN, $CH_2F$, $CHF_2$, $CF_3$, OH, $NH_2$, $NO_2$, $NH(C_1$-$C_6$ alkyl), and $N(C_1$-$C_6$ alkyl$)_2$; $R_{42}$ and $R_{43}$ are independently selected from the group consisting of H, $C_1$-$C_6$ alkyl, $C_2$-$C_6$ alkenyl, $C_2$-$C_6$ alkynyl, $C_1$-$C_6$ alkoxy, F, Cl, Br, I, CN, $CH_2F$, $CHF_2$, $CF_3$, OH, $NH_2$, $NO_2$, $NH(C_1$-$C_6$ alkyl), and $N(C_1$-$C_6$ alkyl$)_2$; and W is N or C—H; and (c) a group of Formula VIf, where * is the point of attachment to a compound of Formula II; $R_{49}$ is H; and $R_{50}$ and $R_{51}$ are independently selected from the group consisting of H or F; $R_{52}$ and $R_{53}$ are independently selected from the group consisting of H, $C_1$-$C_6$ alkyl, F, Cl, Br, I, $CH_2F$, $CHF_2$, and $CF_3$; and W is N or C—H;

$R_6$ is H;

X is any negatively charged counterion; and n=1 or 2.

In certain embodiments, the compounds are of Formula VII:

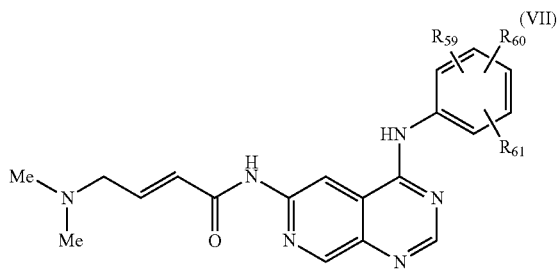

(VII)

wherein either:

(1) $R_{59}$ is H, and one of the following applies: (a) $R_{60}$ is (3-chlorobenzyl)oxy- and $R_{61}$ is chloro; (b) $R_{60}$ and $R_{61}$, together with the carbon atoms to which they are attached, form 1-(3-fluorobenzyl)-1H-pyrazole; (c) $R_{60}$ is 2-pyridinylmethoxy and $R_{61}$ is chloro; (d) $R_{60}$ and $R_{61}$ are both chloro; (e) $R_{60}$ is chloro and $R_{61}$ is bromo; (f) $R_{60}$ and $R_{61}$ are both bromo; (g) $R_{60}$ is fluoro and $R_{61}$ is ethynyl; (h) $R_{60}$ is chloro and $R_{61}$ is ethynyl; (i) $R_{60}$ is bromo and $R_{61}$ is ethynyl; (j) other than when $R_{60}$ is in the 3-position in combination with $R_{61}$ in the 4-position, $R_{60}$ is bromo and $R_{61}$ is fluoro; (k) $R_{60}$ is 2-pyridinylmethoxy and $R_{61}$ is fluoro; or (l) $R_{60}$ is 2-pyridinylmethoxy and $R_{61}$ is bromo; or (2) at least one of $R_{59}$, $R_{60}$ and $R_{61}$ is selected from the group consisting of benzyloxy, 3-chlorobenzyloxy, and 2-pyridinylmethoxy, and when at least one of $R_{59}$, $R_{60}$ and $R_{61}$ is not benzyloxy, 3-chlorobenzyloxy or 2-pyridinylmethoxy, each of the others is independently selected from the group consisting of H, halogen, and $C_2$-$C_4$ alkynyl, with the proviso that when one of $R_{59}$, $R_{60}$ and $R_{61}$ is benzyloxy or 2-pyridinylmethoxy, the other two of $R_{59}$, $R_{60}$ and $R_{61}$ are not H; or (3) two of $R_{59}$, $R_{60}$ and $R_{61}$, together with the carbon atoms to which they are attached, form 1-(3-fluorobenzyl)-1H-pyrazole, and the other is selected from the group consisting of H, halogen, and $C_2$-$C_4$ alkynyl.

In certain embodiments, the compound of Formula VII is a compound according to Formula VIII:

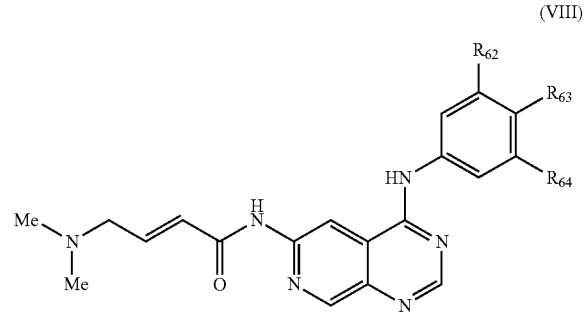

(VIII)

wherein $R_{62}$ is H, and either (a) $R_{63}$ is (3-chlorobenzyl)oxy- and $R_{64}$ is chloro; (b) $R_{63}$ and $R_{64}$, together with the carbon atoms to which they are attached, form 1-(3-fluorobenzyl)-

1H-pyrazole; (c) $R_{63}$ is 2-pyridinylmethoxy and $R_{64}$ is chloro; (d) $R_{63}$ and $R_{64}$ are both chloro; (e) $R_{63}$ is chloro and $R_{64}$ is bromo; (f) $R_{63}$ is bromo and $R_{64}$ is chloro; (g) $R_{63}$ and $R_{64}$ are both bromo; (h) $R_{63}$ is fluoro and $R_{64}$ is ethynyl; (i) $R_{63}$ is chloro and $R_{64}$ is ethynyl; (j) $R_{63}$ is bromo and $R_{64}$ is ethynyl; (k) $R_{63}$ is bromo and $R_{64}$ is fluoro; (l) $R_{63}$ is 2-pyridinylmethoxy and $R_{64}$ is fluoro; or (m) $R_{63}$ is 2-pyridinylmethoxy and $R_{64}$ is bromo.

In certain embodiments, the compound of Formula VII is selected from the group consisting of:

(2E)-N-(4-{3-chloro-4-[(3-chlorobenzyl)oxy]anilino}pyrido[3,4-d]pyrimidin-6-yl)-4-(dimethylamino)-2-butenamide (1), (2E)-4-(dimethylamino)-N-(4-{[1-(3-fluorobenzyl)-1H-indazol-5-yl]amino}pyrido[3,4-d]pyrimidin-6-yl)-2-butenamide (2), (2E)-N-{4-[3-chloro-4-(2-pyridinylmethoxy)anilino]pyrido[3,4-d]pyrimidin-6-yl}-4-(dimethylamino)-2-butenamide (3), (2E)-N-[4-(3,4-dichloroanilino)pyrido[3,4-d]pyrimidin-6-yl]-4-(dimethylamino)-2-butenamide (4), (2E)-N-[4-(3-bromo-4-chloroanilino)pyrido[3,4-d]pyrimidin-6-yl]-4-(dimethylamino)-2-butenamide (5), (2E)-N-[4-(4-bromo-3-chloroanilino)pyrido[3,4-d]pyrimidin-6-yl]-4-(dimethylamino)-2-butenamide (6), (2E)-N-[4-(3,4-dibromoanilino)pyrido[3,4-d]pyrimidin-6-yl]-4-(dimethylamino)-2-butenamide (7), (2E)-4-(dimethylamino)-N-[4-(3-ethynyl-4-fluoroanilino)pyrido[3,4-d]pyrimidin-6-yl]-2-butenamide (8), (2E)-N-[4-(4-chloro-3-ethynylanilino)pyrido[3,4-d]pyrimidin-6-yl]-4-(dimethylamino)-2-butenamide (9), (2E)-N-[4-(4-bromo-3-ethynylanilino)pyrido[3,4-d]pyrimidin-6-yl]-4-(dimethylamino)-2-butenamide (10), (2E)-N-[4-(4-bromo-3-fluoroanilino)pyrido[3,4-d]pyrimidin-6-yl]-4-(dimethylamino)-2-butenamide (11), (2E)-4-(dimethylamino)-N-{4-[3-fluoro-4-(2-pyridinylmethoxy)anilino]pyrido[3,4-d]pyrimidin-6-yl}-2-butenamide (89) and (2E)-N-{4-[3-bromo-4-(2-pyridinylmethoxy)anilino]pyrido[3,4-d]pyrimidin-6-yl}-4-(dimethylamino)-2-butenamide (90);

or a salt, solvate, or a salt thereof.

The structures of compounds provided in the list above are depicted below:

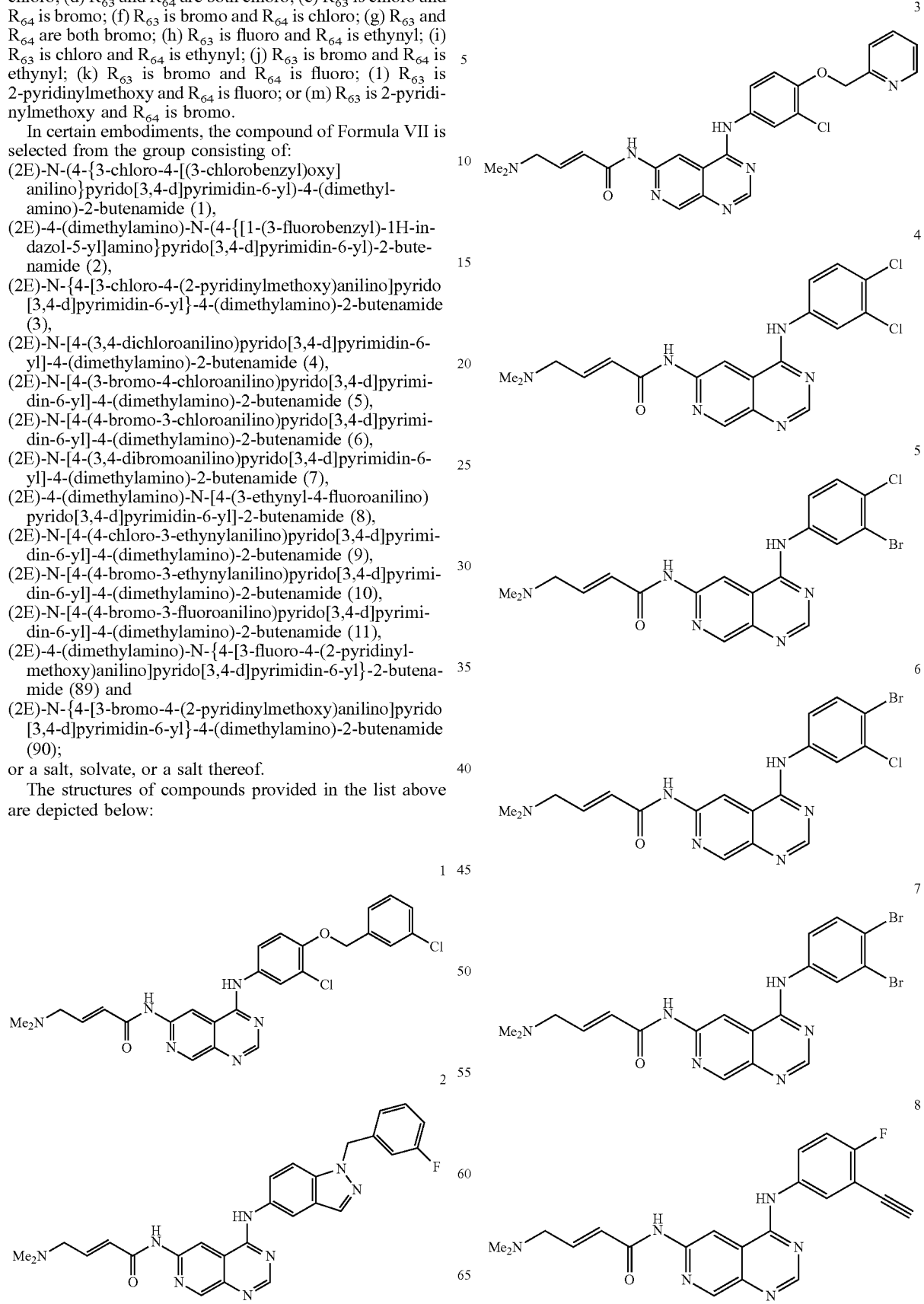

-continued

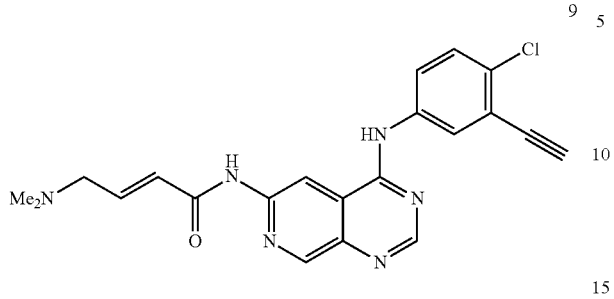

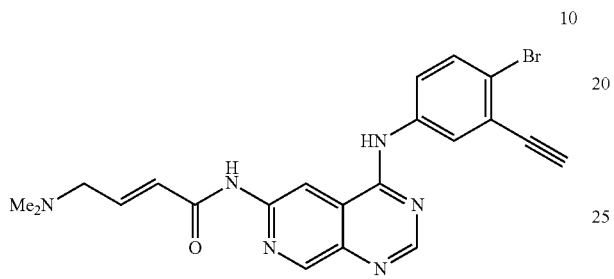

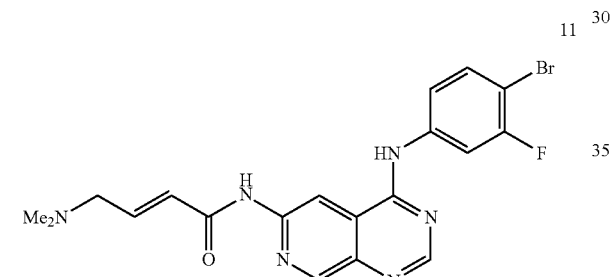

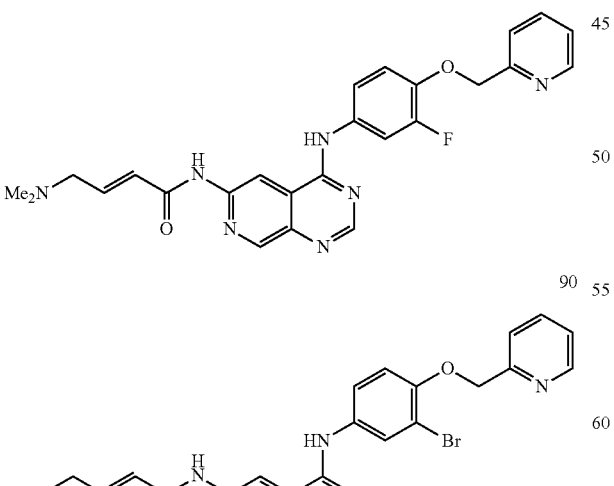

In certain embodiments, the compounds are of Formula IX:

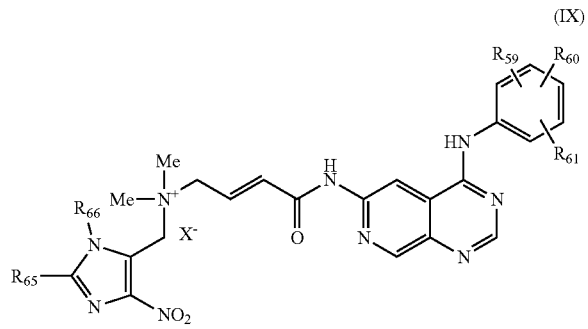

(IX)

wherein X is any negatively charged counterion, $R_{59}$, $R_{60}$ and $R_{61}$ are as defined for Formula VII, $R_{65}$ is selected from the group consisting of H, methyl, ethyl, trifluoromethyl, —CN, —CONH$_2$, and propyn-1-yl, and $R_{66}$ is $C_1$-$C_6$ alkyl.

In certain embodiments, the compounds are of Formula X:

(X)

wherein X is any negatively charged counterion, $R_{59}$, $R_{60}$ and $R_{61}$ are as defined for Formula VII and $R_{67}$ is selected from the group consisting of H, methyl, ethyl, trifluoromethyl, —CN, —CONH$_2$, and propyn-1-yl.

In certain embodiments, the compounds are of Formula XI:

(XI)

wherein X is any negatively charged counterion, $R_{62}$, $R_{63}$ and $R_{64}$ are as defined for Formula VIII and $R_{68}$ is selected from the group consisting of H, methyl, ethyl, trifluoromethyl, —CN, —CONH$_2$, and propyn-1-yl.

In certain embodiments, X is selected from the group consisting of halide (e.g., fluoride, chloride, bromide, iodide), methanesulfonate, trifluoromethanesulfonate, acetate, trifluoroacetate, tosylate, lactate, citrate and formate.

In certain embodiments, the compounds are selected from the group consisting of:

(2E)-4-[(4-{3-chloro-4-[(3-chlorobenzyl)oxy]anilino}pyrido[3,4-d]pyrimidin-6-yl)amino]-N,N-dimethyl-N-[(1-methyl-4-nitro-1H-imidazol-5-yl)methyl]-4-oxo-2-buten-1-ammonium bromide (12), (2E)-4-[(4-{[1-(3-fluorobenzyl)-1H-indazol-5-yl]amino}pyrido[3,4-d]pyrimidin-6-yl)amino]-N,N-dimethyl-N-[(1-methyl-4-nitro-1H-imidazol-5-yl)methyl]-4-oxo-2-buten-1-ammonium bromide (13), (2E)-N-[(1,2-dimethyl-4-nitro-1H-imidazol-5-yl)methyl]-4-[(4-{[1-(3-fluorobenzyl)-1H-indazol-5-yl]amino}pyrido[3,4-d]pyrimidin-6-yl)amino]-N,N-dimethyl-4-oxo-2-buten-1-ammonium bromide (14), (2E)-4-({4-[3-chloro-4-(2-pyridinylmethoxy)anilino]pyrido[3,4-d]pyrimidin-6-yl}amino)-N,N-dimethyl-N-[(1-methyl-4-nitro-1H-imidazol-5-yl)methyl]-4-oxo-2-buten-1-ammonium bromide (15), (2E)-4-{[4-(3,4-dichloroanilino)pyrido[3,4-d]pyrimidin-6-yl]amino}-N,N-dimethyl-N-[(1-methyl-4-nitro-1H-imidazol-5-yl)methyl]-4-oxo-2-buten-1-ammonium bromide (16), (2E)-4-{[4-(3-bromo-4-chloroanilino)pyrido[3,4-d]pyrimidin-6-yl]amino}-N,N-dimethyl-N-[(1-methyl-4-nitro-1H-imidazol-5-yl)methyl]-4-oxo-2-buten-1-ammonium bromide (17), (2E)-4-{[4-(4-bromo-3-chloroanilino)pyrido[3,4-d]pyrimidin-6-yl]amino}-N,N-dimethyl-N-[(1-methyl-4-nitro-1H-imidazol-5-yl)methyl]-4-oxo-2-buten-1-ammonium bromide (18), (2E)-4-{[4-(3,4-dibromoanilino)pyrido[3,4-d]pyrimidin-6-yl]amino}-N,N-dimethyl-N-[(1-methyl-4-nitro-1H-imidazol-5-yl)methyl]-4-oxo-2-buten-1-ammonium bromide (19), (2E)-4-{[4-(3-ethynyl-4-fluoroanilino)pyrido[3,4-d]pyrimidin-6-yl]amino}-N,N-dimethyl-N-[(1-methyl-4-nitro-1H-imidazol-5-yl)methyl]-4-oxo-2-buten-1-ammonium bromide (20), (2E)-4-{[4-(4-chloro-3-ethynylanilino)pyrido[3,4-d]pyrimidin-6-yl]amino}-N,N-dimethyl-N-[(1-methyl-4-nitro-1H-imidazol-5-yl)methyl]-4-oxo-2-buten-1-ammonium bromide (21), (2E)-4-[(4-{3-chloro-4-[(3-chlorobenzyl)oxy]anilino}pyrido[3,4-d]pyrimidin-6-yl)amino]-N-[(1,2-dimethyl-4-nitro-1H-imidazol-5-yl)methyl]-N,N-dimethyl-4-oxo-2-buten-1-ammonium bromide (22), (2E)-4-[(4-{3-chloro-4-[(3-chlorobenzyl)oxy]anilino}pyrido[3,4-d]pyrimidin-6-yl)amino]-N-[(2-ethyl-1-methyl-4-nitro-1H-imidazol-5-yl)methyl]-N,N-dimethyl-4-oxo-2-buten-1-ammonium bromide (23), (2E)-4-[(4-{3-chloro-4-[(3-chlorobenzyl)oxy]anilino}pyrido[3,4-d]pyrimidin-6-yl)amino]-N,N-dimethyl-N-{[1-methyl-4-nitro-2-(trifluoromethyl)-1H-imidazol-5-yl]methyl}-4-oxo-2-buten-1-ammonium bromide (24), (2E)-4-[(4-{3-chloro-4-[(3-chlorobenzyl)oxy]anilino}pyrido[3,4-d]pyrimidin-6-yl)amino]-N-[(2-cyano-1-methyl-4-nitro-1H-imidazol-5-yl)methyl]-N,N-dimethyl-4-oxo-2-buten-1-ammonium bromide (25), (2E)-N-{[2-(aminocarbonyl)-1-methyl-4-nitro-1H-imidazol-5-yl]methyl}-4-[(4-{3-chloro-4-[(3-chlorobenzyl)oxy]anilino}pyrido[3,4-d]pyrimidin-6-yl)amino]-N,N-dimethyl-4-oxo-2-buten-1-ammonium bromide (26), (2E)-4-[(4-{3-chloro-4-[(3-chlorobenzyl)oxy]anilino}pyrido[3,4-d]pyrimidin-6-yl)amino]-N,N-dimethyl-N-{[1-methyl-4-nitro-2-(1-propynyl)-1H-imidazol-5-yl]methyl}-4-oxo-2-buten-1-ammonium bromide (27), (2E)-N-[(2-ethyl-1-methyl-4-nitro-1H-imidazol-5-yl)methyl]-4-[(4-{[1-(3-fluorobenzyl)-1H-indazol-5-yl]amino}pyrido[3,4-d]pyrimidin-6-yl)amino]-N,N-dimethyl-4-oxo-2-buten-1-ammonium bromide (28), (2E)-4-[(4-{[1-(3-fluorobenzyl)-1H-indazol-5-yl]amino}pyrido[3,4-d]pyrimidin-6-yl)amino]-N,N-dimethyl-N-{[1-methyl-4-nitro-2-(trifluoromethyl)-1H-imidazol-5-yl]methyl}-4-oxo-2-buten-1-ammonium bromide (29), (2E)-N-[(2-cyano-1-methyl-4-nitro-1H-imidazol-5-yl)methyl]-4-[(4-{[1-(3-fluorobenzyl)-1H-indazol-5-yl]amino}pyrido[3,4-d]pyrimidin-6-yl)amino]-N,N-dimethyl-4-oxo-2-buten-1-ammonium bromide (30), (2E)-N-{[2-(aminocarbonyl)-1-methyl-4-nitro-1H-imidazol-5-yl]methyl}-4-[(4-{[1-(3-fluorobenzyl)-1H-indazol-5-yl]amino}pyrido[3,4-d]pyrimidin-6-yl)amino]-N,N-dimethyl-4-oxo-2-buten-1-ammonium bromide (31), (2E)-4-[(4-{[1-(3-fluorobenzyl)-1H-indazol-5-yl]amino}pyrido[3,4-d]pyrimidin-6-yl)amino]-N,N-dimethyl-N-{[1-methyl-4-nitro-2-(1-propynyl)-1H-imidazol-5-yl]methyl}-4-oxo-2-buten-1-ammonium bromide (32), (2E)-4-({4-[3-chloro-4-(2-pyridinylmethoxy)anilino]pyrido[3,4-d]pyrimidin-6-yl}amino)-N-[(1,2-dimethyl-4-nitro-1H-imidazol-5-yl)methyl]-N,N-dimethyl-4-oxo-2-buten-1-ammonium bromide (33), (2E)-4-({4-[3-chloro-4-(2-pyridinylmethoxy)anilino]pyrido[3,4-d]pyrimidin-6-yl}amino)-N-[(2-ethyl-1-methyl-4-nitro-1H-imidazol-5-yl)methyl]-N,N-dimethyl-4-oxo-2-buten-1-ammonium bromide (34), (2E)-4-({4-[3-chloro-4-(2-pyridinylmethoxy)anilino]pyrido[3,4-d]pyrimidin-6-yl}amino)-N,N-dimethyl-N-{[1-methyl-4-nitro-2-(trifluoromethyl)-1H-imidazol-5-yl]methyl}-4-oxo-2-buten-1-ammonium bromide (35), (2E)-4-({4-[3-chloro-4-(2-pyridinylmethoxy)anilino]pyrido[3,4-d]pyrimidin-6-yl}amino)-N-[(2-cyano-1-methyl-4-nitro-1H-imidazol-5-yl)methyl]-N,N-dimethyl-4-oxo-2-buten-1-ammonium bromide (36), (2E)-N-{[2-(aminocarbonyl)-1-methyl-4-nitro-1H-imidazol-5-yl]methyl}-4-({4-[3-chloro-4-(2-pyridinylmethoxy)anilino]pyrido[3,4-d]pyrimidin-6-yl}amino)-N,N-dimethyl-4-oxo-2-buten-1-ammonium bromide (37), (2E)-4-({4-[3-chloro-4-(2-pyridinylmethoxy)anilino]pyrido[3,4-d]pyrimidin-6-yl}amino)-N,N-dimethyl-N-{[1-methyl-4-nitro-2-(1-propynyl)-1H-imidazol-5-yl]methyl}-4-oxo-2-buten-1-ammonium bromide (38), (2E)-4-{[4-(3,4-dichloroanilino)pyrido[3,4-d]pyrimidin-6-yl]amino}-N-[(1,2-dimethyl-4-nitro-1H-imidazol-5-yl)methyl]-N,N-dimethyl-4-oxo-2-buten-1-ammonium bromide (39), (2E)-4-{[4-(3,4-dichloroanilino)pyrido[3,4-d]pyrimidin-6-yl]amino}-N-[(2-ethyl-1-methyl-4-nitro-1H-imidazol-5-yl)methyl]-N,N-dimethyl-4-oxo-2-buten-1-ammonium bromide (40), (2E)-4-{[4-(3,4-dichloroanilino)pyrido[3,4-d]pyrimidin-6-yl]amino}-N,N-dimethyl-N-{[1-methyl-4-nitro-2-(trifluoromethyl)-1H-imidazol-5-yl]methyl}-4-oxo-2-buten-1-ammonium bromide (41), (2E)-N-[(2-cyano-1-methyl-4-nitro-1H-imidazol-5-yl)methyl]-4-{[4-(3,4-dichloroanilino)pyrido[3,4-d]pyrimidin-6-yl]amino}-N,N-dimethyl-4-oxo-2-buten-1-ammonium bromide (42), (2E)-N-{[2-(aminocarbonyl)-1-methyl-4-nitro-1H-imidazol-5-yl]methyl}-4-{[4-(3,4-dichloroanilino)pyrido[3,4-d]pyrimidin-6-yl]amino}-N,N-dimethyl-4-oxo-2-buten-1-ammonium bromide (43), (2E)-4-{[4-(3,4-dichloroanilino)pyrido[3,4-d]pyrimidin-6-yl]amino}-N,N-dimethyl-N-{[1-methyl-4-nitro-2-(1-propynyl)-1H-imidazol-5-yl]methyl}-4-oxo-2-buten-1-ammonium bromide (44), (2E)-4-{[4-(3-bromo-4-chloroanilino)pyrido[3,4-d]pyrimidin-6-yl]amino}-N-[(1,2-dimethyl-4-nitro-1H-imidazol-5-yl)methyl]-N,N-dimethyl-4-oxo-2-buten-1-ammonium bromide (45), (2E)-4-{[4-(3-bromo-4-chloroanilino)pyrido[3,4-d]pyrimidin-6-yl]amino}-N-[(2-ethyl-1-methyl-4-nitro-1H-imidazol-5-yl)methyl]-N,N-dimethyl-4-oxo-2-buten-1-ammonium bromide (46), (2E)-4-{[4-(3-bromo-4-chloroanilino)pyrido[3,4-d]pyrimidin-6-yl]amino}-N,N-dimethyl-N-{[1-methyl-4-nitro-2-(trifluoromethyl)-1H-imidazol-5-yl]methyl}-4-oxo-2-buten-1-ammonium bromide (47), (2E)-4-{[4-(3-bromo-4-chloroanilino)pyrido[3,4-d]pyrimidin-6-yl]amino}-N-[(2-cyano-1-methyl-4-nitro-1H-imidazol-5-yl)methyl]-N,N-dimethyl-4-oxo-2-buten-1-ammonium bromide (48), (2E)-N-{[2-(aminocarbonyl)-1-methyl-4-nitro-1H-imidazol-5-yl]methyl}-4-{[4-(3-bromo-4-chloroanilino)pyrido[3,4-d]pyrimidin-6-yl]amino}-N,N-dimethyl-4-oxo-2-buten-1-ammonium bromide (49), (2E)-4-{[4-(3-bromo-4-chloroanilino)pyrido[3,4-d]pyrimidin-6-yl]amino}-N,N-dimethyl-N-{[1-methyl-4-nitro-2-(1-propynyl)-1H-imidazol-5-yl]methyl}-4-oxo-2-buten-1-ammonium bromide (50), (2E)-4-{[4-(4-bromo-3-chloroanilino)pyrido[3,4-d]pyrimidin-6-yl]amino}-N-[(1,2-dimethyl-4-nitro-1H-imidazol-5-yl)methyl]-N,N-dimethyl-4-oxo-2-buten-1-ammonium bromide (51), (2E)-4-{[4-(4-bromo-3-chloroanilino)pyrido[3,4-d]pyrimidin-6-yl]amino}-N-[(2-ethyl-1-methyl-4-nitro-1H-imidazol-5-yl)methyl]-N,N-dimethyl-4-oxo-2-buten-1-ammonium bromide (52), (2E)-4-{[4-(4-bromo-3-chloroanilino)pyrido[3,4-d]pyrimidin-6-yl]amino}-N,N-dimethyl-N-{[1-methyl-4-nitro-2-(trifluoromethyl)-1H-imidazol-5-yl]methyl}-4-oxo-2-buten-1-ammonium bromide (53), (2E)-4-{[4-(4-bromo-3-chloroanilino)pyrido[3,4-d]pyrimidin-6-yl]amino}-N-[(2-cyano-1-methyl-4-nitro-1H-imidazol-5-yl)methyl]-N,N-dimethyl-4-oxo-2-buten-1-ammonium bromide (54), (2E)-N-{[2-(aminocarbonyl)-1-methyl-4-nitro-1H-imidazol-5-yl]methyl}-4-{[4-(4-bromo-3-chloroanilino)pyrido[3,4-d]pyrimidin-6-yl]amino}-N,N-dimethyl-4-oxo-2-buten-1-ammonium bromide (55), (2E)-4-{[4-(4-bromo-3-chloroanilino)pyrido[3,4-d]pyrimidin-6-yl]amino}-N,N-dimethyl-N-{[1-methyl-4-nitro-2-(1-propynyl)-1H-imidazol-5-yl]methyl}-4-oxo-2-buten-1-ammonium bromide (56), (2E)-4-{[4-(3,4-dibromoanilino)pyrido[3,4-d]pyrimidin-6-yl]amino}-N-[(1,2-dimethyl-4-nitro-1H-imidazol-5-yl)methyl]-N,N-dimethyl-4-oxo-2-buten-1-ammonium bromide (57), (2E)-4-{[4-(3,4-dibromoanilino)pyrido[3,4-d]pyrimidin-6-yl]amino}-N-[(2-ethyl-1-methyl-4-nitro-1H-imidazol-5-yl)methyl]-N,N-dimethyl-4-oxo-2-buten-1-ammonium bromide (58), (2E)-4-{[4-(3,4-dibromoanilino)pyrido[3,4-d]pyrimidin-6-yl]amino}-N,N-dimethyl-N-{[1-methyl-4-nitro-2-(trifluoromethyl)-1H-imidazol-5-yl]methyl}-4-oxo-2-buten-1-ammonium bromide (59), (2E)-N-[(2-cyano-1-methyl-4-nitro-1H-imidazol-5-yl)methyl]-4-{[4-(3,4-dibromoanilino)pyrido[3,4-d]pyrimidin-6-yl]amino}-N,N-dimethyl-4-oxo-2-buten-1-ammonium bromide (60), (2E)-N-{[2-(aminocarbonyl)-1-methyl-4-nitro-1H-imidazol-5-yl]methyl}-4-{[4-(3,4-dibromoanilino)pyrido[3,4-d]pyrimidin-6-yl]amino}-N,N-dimethyl-4-oxo-2-buten-1-ammonium bromide (61), (2E)-4-{[4-(3,4-dibromoanilino)pyrido[3,4-d]pyrimidin-6-yl]amino}-N,N-dimethyl-N-{[1-methyl-4-nitro-2-(1-propynyl)-1H-imidazol-5-yl]methyl}-4-oxo-2-buten-1-ammonium bromide (62), (2E)-N-[(1,2-dimethyl-4-nitro-1H-imidazol-5-yl)methyl]-4-{[4-(3-ethynyl-4-fluoroanilino)pyrido[3,4-d]pyrimidin-6-yl]amino}-N,N-dimethyl-4-oxo-2-buten-1-ammonium bromide (63), (2E)-N-[(2-ethyl-1-methyl-4-nitro-1H-imidazol-5-yl)methyl]-4-{[4-(3-ethynyl-4-fluoroanilino)pyrido[3,4-d]pyrimidin-6-yl]amino}-N,N-dimethyl-4-oxo-2-buten-1-ammonium bromide (64), (2E)-4-{[4-(3-ethynyl-4-fluoroanilino)pyrido[3,4-d]pyrimidin-6-yl]amino}-N,N-dimethyl-N-{[1-methyl-4-nitro-2-(trifluoromethyl)-1H-imidazol-5-yl]methyl}-4-oxo-2-buten-1-ammonium bromide (65), (2E)-N-[(2-cyano-1-methyl-4-nitro-1H-imidazol-5-yl)methyl]-4-{[4-(3-ethynyl-4-fluoroanilino)pyrido[3,4-d]pyrimidin-6-yl]amino}-N,N-dimethyl-4-oxo-2-buten-1-ammonium bromide (66), (2E)-N-{[2-(aminocarbonyl)-1-methyl-4-nitro-1H-imidazol-5-yl]methyl}-4-{[4-(3-ethynyl-4-fluoroanilino)pyrido[3,4-d]pyrimidin-6-yl]amino}-N,N-dimethyl-4-oxo-2-buten-1-ammonium bromide (67), (2E)-4-{[4-(3-ethynyl-4-fluoroanilino)pyrido[3,4-d]pyrimidin-6-yl]amino}-N,N-dimethyl-N-{[1-methyl-4-nitro-2-(1-propynyl)-1H-imidazol-5-yl]methyl}-4-oxo-2-buten-1-ammonium bromide (68), (2E)-4-{[4-(4-chloro-3-ethynylanilino)pyrido[3,4-d]pyrimidin-6-yl]amino}-N-[(1,2-dimethyl-4-nitro-1H-imidazol-5-yl)methyl]-N,N-dimethyl-4-oxo-2-buten-1-ammonium bromide (69), (2E)-4-{[4-(4-chloro-3-ethynylanilino)pyrido[3,4-d]pyrimidin-6-yl]amino}-N-[(2-ethyl-1-methyl-4-nitro-1H-imidazol-5-yl)methyl]-N,N-dimethyl-4-oxo-2-buten-1-ammonium bromide (70), (2E)-4-{[4-(4-chloro-3-ethynylanilino)pyrido[3,4-d]pyrimidin-6-yl]amino}-N,N-dimethyl-N-{[1-methyl-4-nitro-2-(trifluoromethyl)-1H-imidazol-5-yl]methyl}-4-oxo-2-buten-1-ammonium bromide (71), (2E)-4-{[4-(4-chloro-3-ethynylanilino)pyrido[3,4-d]pyrimidin-6-yl]amino}-N-[(2-cyano-1-methyl-4-nitro-1H-imidazol-5-yl)methyl]-N,N-dimethyl-4-oxo-2-buten-1-ammonium bromide (72), (2E)-N-{[2-(aminocarbonyl)-1-methyl-4-nitro-1H-imidazol-5-yl]methyl}-4-{[4-(4-chloro-3-ethynylanilino)pyrido[3,4-d]pyrimidin-6-yl]amino}-N,N-dimethyl-4-oxo-2-buten-1-ammonium bromide (73), (2E)-4-{[4-(4-chloro-3-ethynylanilino)pyrido[3,4-d]pyrimidin-6-yl]amino}-N,N-dimethyl-N-{[1-methyl-4-nitro-2-(1-propynyl)-1H-imidazol-5-yl]methyl}-4-oxo-2-buten-1-ammonium bromide (74), (2E)-4-{[4-(4-bromo-3-ethynylanilino)pyrido[3,4-d]pyrimidin-6-yl]amino}-N,N-dimethyl-N-[(1-methyl-4-nitro-1H-imidazol-5-yl)methyl]-4-oxo-2-buten-1-ammonium bromide (75), (2E)-4-{[4-(4-bromo-3-ethynylanilino)pyrido[3,4-d]pyrimidin-6-yl]amino}-N-[(1,2-dimethyl-4-nitro-1H-imidazol-5-yl)methyl]-N,N-dimethyl-4-oxo-2-buten-1-ammonium bromide (76), (2E)-4-{[4-(4-bromo-3-ethynylanilino)pyrido[3,4-d]pyrimidin-6-yl]amino}-N-[(2-ethyl-1-methyl-4-nitro-1H-imidazol-5-yl)methyl]-N,N-dimethyl-4-oxo-2-buten-1-ammonium bromide (77), (2E)-4-{[4-(4-bromo-3-ethynylanilino)pyrido[3,4-d]pyrimidin-6-yl]amino}-N,N-dimethyl-N-{[1-methyl-4-nitro-2-(trifluoromethyl)-1H-imidazol-5-yl]methyl}-4-oxo-2-buten-1-ammonium bromide (78), (2E)-4-{[4-(4-bromo-3-ethynylanilino)pyrido[3,4-d]pyrimidin-6-yl]amino}-N-[(2-cyano-1-methyl-4-nitro-1H-imidazol-5-yl)methyl]-N,N-dimethyl-4-oxo-2-buten-1-ammonium bromide (79), (2E)-N-{[2-(aminocarbonyl)-1-methyl-4-nitro-1H-imidazol-5-yl]methyl}-4-{[4-(4-bromo-3-ethynylanilino)pyrido[3,4-d]pyrimidin-6-yl]amino}-N,N-dimethyl-4-oxo-2-buten-1-ammonium bromide (80), (2E)-4-{[4-(4-bromo-3-ethynylanilino)pyrido[3,4-d]pyrimidin-6-yl]amino}-N,N-dimethyl-N-{[1-methyl-4-nitro-2-(1-propynyl)-1H-imidazol-5-yl]methyl}-4-oxo-2-buten-1-ammonium bromide (81), (2E)-4-{[4-(4-bromo-3-fluoroanilino)pyrido[3,4-d]pyrimidin-6-yl]amino}-N,N-dimethyl-N-[(1-methyl-4-nitro-1H-imidazol-5-yl)methyl]-4-oxo-2-buten-1-ammonium bromide (82), (2E)-4-{[4-(4-bromo-3-fluoroanilino)pyrido[3,4-d]pyrimidin-6-yl]amino}-N-[(1,2-dimethyl-4-nitro-1H-imidazol-5-yl)methyl]-N,N-dimethyl-4-oxo-2-buten-1-ammonium bromide (83), (2E)-4-{[4-(4-bromo-3-fluoroanilino)pyrido[3,4-d]pyrimidin-6-yl]amino}-N-[(2-ethyl-1-methyl-4-nitro-1H-imidazol-5-yl)methyl]-N,N-dimethyl-4-oxo-2-buten-1-ammonium bromide (84), (2E)-4-{[4-(4-bromo-3-fluoroanilino)pyrido[3,4-d]pyrimidin-6-yl]amino}-N,N-dimethyl-N-{[1-methyl-4-nitro-2-(trifluoromethyl)-1H-imidazol-5-yl]methyl}-4-oxo-2-buten-1-ammonium bromide (85), (2E)-4-{[4-(4-bromo-3-fluoroanilino)pyrido[3,4-d]pyrimidin-6-yl]amino}-N-[(2-cyano-1-methyl-4-nitro-1H-imidazol-5-yl)methyl]-N,N-dimethyl-4-oxo-2-buten-1-ammonium bromide (86), (2E)-N-{[2-(aminocarbonyl)-1-methyl-4-nitro-1H-imidazol-5-yl]methyl}-4-{[4-(4-bromo-3-fluoroanilino)pyrido[3,4-d]pyrimidin-6-yl]amino}-N,N-dimethyl-4-oxo-2-buten-1-ammonium bromide (87), (2E)-4-{[4-(4-bromo-3-fluoroanilino)pyrido[3,4-d]pyrimidin-6-yl]amino}-N,N-dimethyl-N-{[1-methyl-4-nitro-2-(1-propynyl)-1H-imidazol-5-yl]methyl}-4-oxo-2-buten-1-ammonium bromide (88), (2E)-4-({4-[3-fluoro-4-(2-pyridinylmethoxy)anilino]pyrido[3,4-d]pyrimidin-6-yl}amino)-N,N-dimethyl-N-[(1-methyl-4-nitro-1H-imidazol-5-yl)methyl]-4-oxo-2-buten-1-ammonium bromide (91), (2E)-N-[(1,2-dimethyl-4-nitro-1H-imidazol-5-yl)methyl]-4-({4-[3-fluoro-4-(2-pyridinylmethoxy)anilino]pyrido[3,4-d]pyrimidin-6-yl}amino)-N,N-dimethyl-4-oxo-2-buten-1-ammonium bromide (92), (2E)-N-[(2-ethyl-1-methyl-4-nitro-1H-imidazol-5-yl)methyl]-4-({4-[3-fluoro-4-(2-pyridinylmethoxy)anilino]pyrido[3,4-d]pyrimidin-6-yl}amino)-N,N-dimethyl-4-oxo-2-buten-1-ammonium bromide (93), (2E)-4-({4-[3-fluoro-4-(2-pyridinylmethoxy)anilino]pyrido[3,4-d]pyrimidin-6-yl}amino)-N,N-dimethyl-N-{[1-methyl-4-nitro-2-(trifluoromethyl)-1H-imidazol-5-yl]methyl}-4-oxo-2-buten-1-ammonium bromide (94), (2E)-N-[(2-cyano-1-methyl-4-nitro-1H-imidazol-5-yl)methyl]-4-({4-[3-fluoro-4-(2-pyridinylmethoxy)anilino]pyrido[3,4-d]pyrimidin-6-yl}amino)-N,N-dimethyl-4-oxo-2-buten-1-ammonium bromide (95), (2E)-N-{[2-(aminocarbonyl)-1-methyl-4-nitro-1H-imidazol-5-yl]methyl}-4-({4-[3-fluoro-4-(2-pyridinylmethoxy)anilino]pyrido[3,4-d]pyrimidin-6-yl}amino)-N,N-dimethyl-4-oxo-2-buten-1-ammonium bromide (96), (2E)-4-({4-[3-fluoro-4-(2-pyridinylmethoxy)anilino]pyrido[3,4-d]pyrimidin-6-yl}amino)-N,N-dimethyl-N-{[1-methyl-4-nitro-2-(1-propynyl)-1H-imidazol-5-yl]methyl}-4-oxo-2-buten-1-ammonium bromide (97), (2E)-4-({4-[3-bromo-4-(2-pyridinylmethoxy)anilino]pyrido[3,4-d]pyrimidin-6-yl}amino)-N,N-dimethyl-N-[(1-methyl-4-nitro-1H-imidazol-5-yl)methyl]-4-oxo-2-buten-1-ammonium bromide (98), (2E)-4-({4-[3-bromo-4-(2-pyridinylmethoxy)anilino]pyrido[3,4-d]pyrimidin-6-yl}amino)-N-[(1,2-dimethyl-4-nitro-1H-imidazol-5-yl)methyl]-N,N-dimethyl-4-oxo-2-buten-1-ammonium bromide (99), (2E)-4-({4-[3-bromo-4-(2-pyridinylmethoxy)anilino]pyrido[3,4-d]pyrimidin-6-yl}amino)-N-[(2-ethyl-1-methyl-4-nitro-1H-imidazol-5-yl)methyl]-N,N-dimethyl-4-oxo-2-buten-1-ammonium bromide (100), (2E)-4-({4-[3-bromo-4-(2-pyridinylmethoxy)anilino]pyrido[3,4-d]pyrimidin-6-yl}amino)-N,N-dimethyl-N-{[1-methyl-4-nitro-2-(trifluoromethyl)-1H-imidazol-5-yl]methyl}-4-oxo-2-buten-1-ammonium bromide (101), (2E)-4-({4-[3-bromo-4-(2-pyridinylmethoxy)anilino]pyrido[3,4-d]pyrimidin-6-yl}amino)-N-[(2-cyano-1-methyl-4-nitro-1H-imidazol-5-yl)methyl]-N,N-dimethyl-4-oxo-2-buten-1-ammonium bromide (102), (2E)-N-{[2-(aminocarbonyl)-1-methyl-4-nitro-1H-imidazol-5-yl]methyl}-4-({4-[3-bromo-4-(2-pyridinylmethoxy)anilino]pyrido[3,4-d]pyrimidin-6-yl}amino)-N,N-dimethyl-4-oxo-2-buten-1-ammonium bromide (103) and (2E)-4-({4-[3-bromo-4-(2-pyridinylmethoxy)anilino]pyrido[3,4-d]pyrimidin-6-yl}amino)-N,N-dimethyl-N-{[1-methyl-4-nitro-2-(1-propynyl)-1H-imidazol-5-yl]methyl}-4-oxo-2-buten-1-ammonium bromide (104); or any other salt thereof (e.g., the listed counterion is exchanged for any other counterion, which in certain embodiments is a pharmaceutically acceptable counterion, of same polarity—negative or positive), or any solvate thereof.

The structures of the compounds provided in the list above are depicted below:

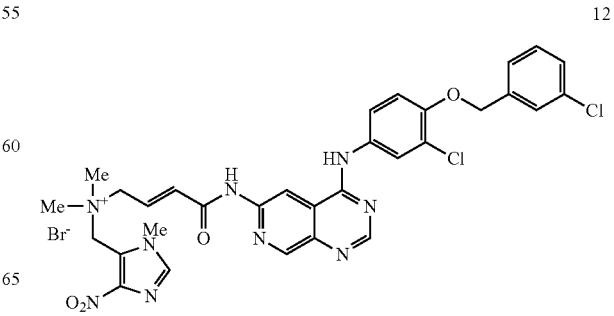

12

-continued
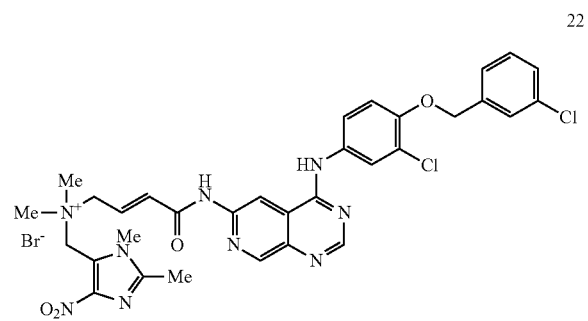
22
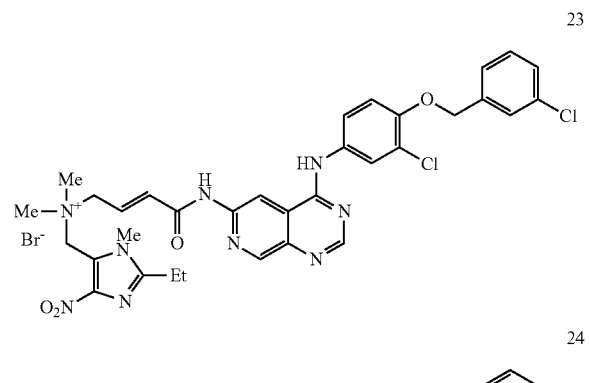
23
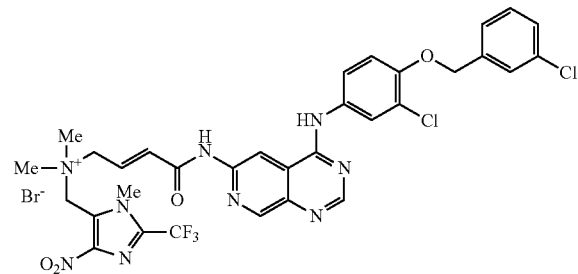
24
25
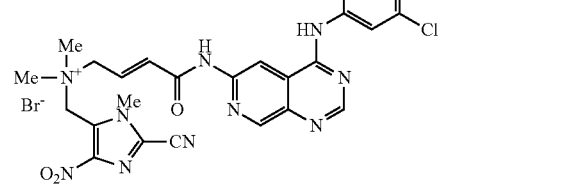
26
-continued
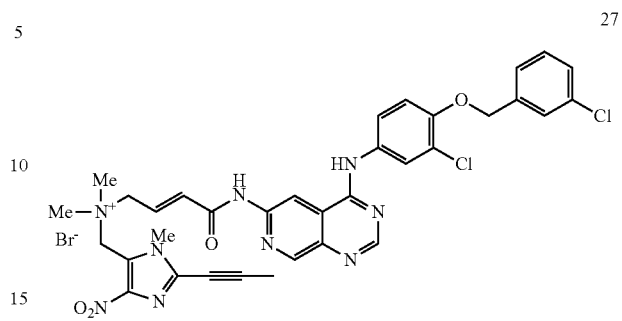
27
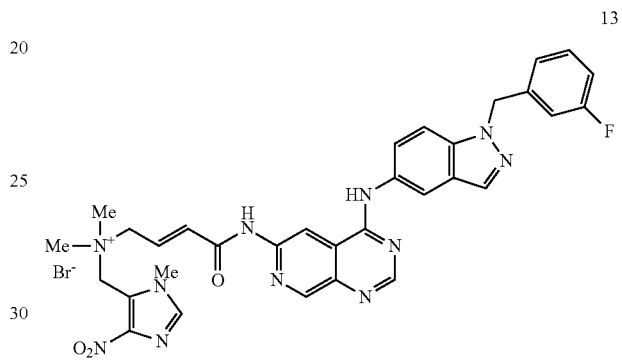
13
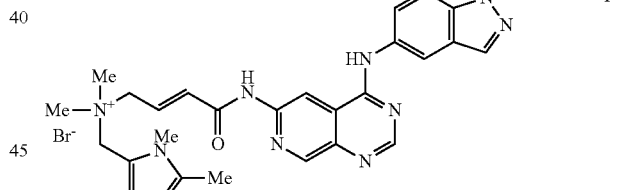
14
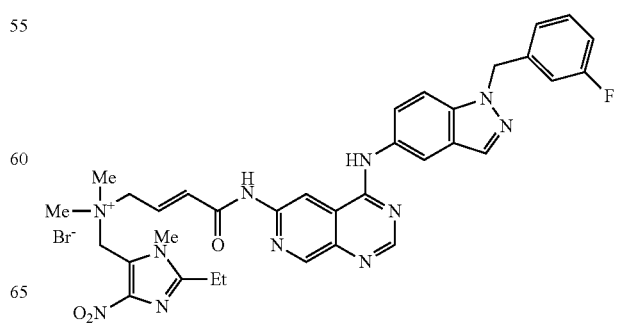
28

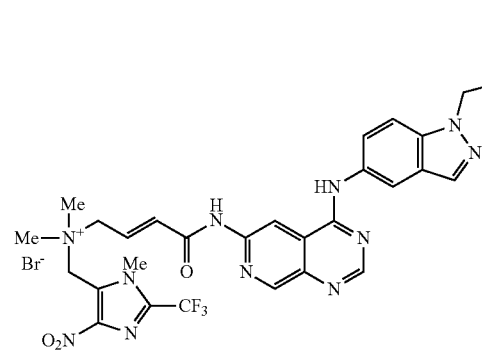
29
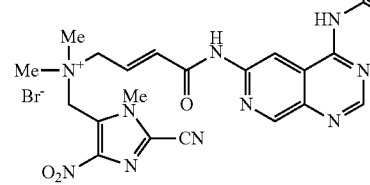
30
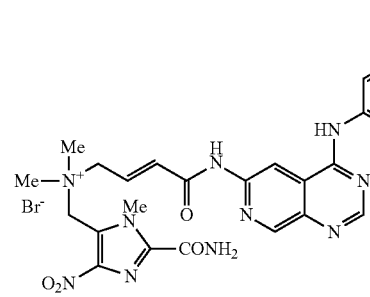
31
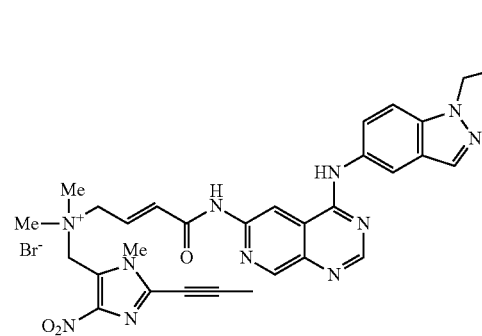
32
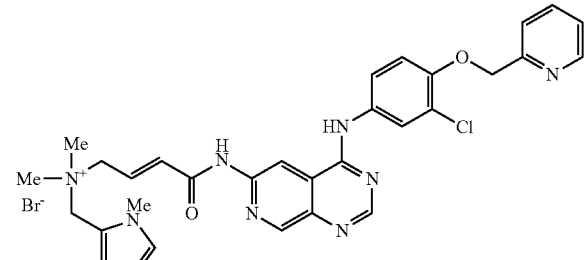
15
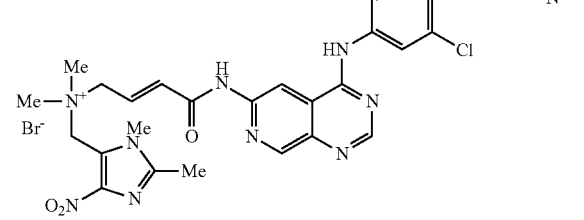
33
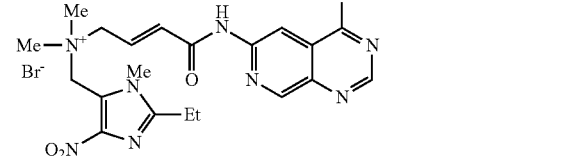
34
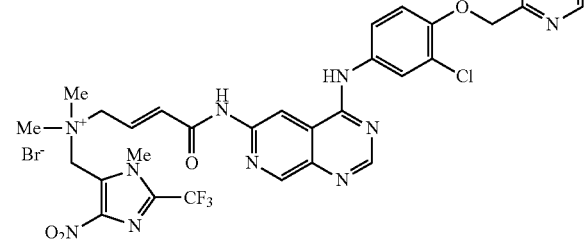
35
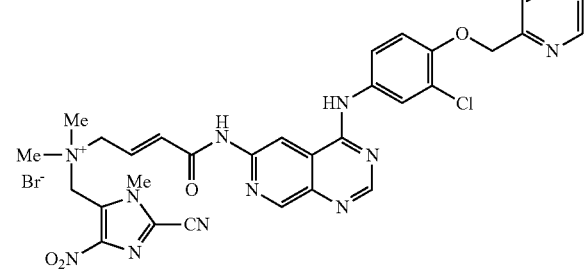
36

-continued
37
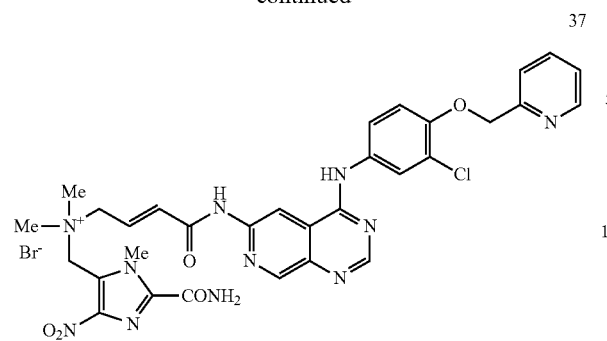
38
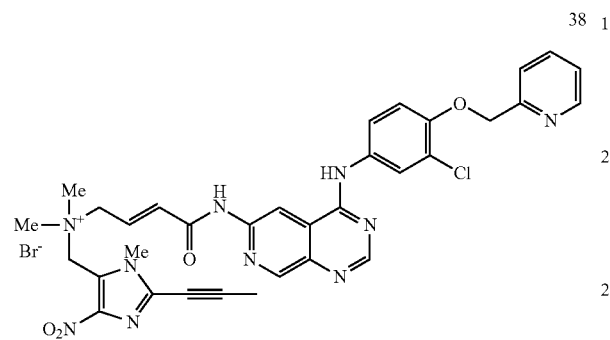
16
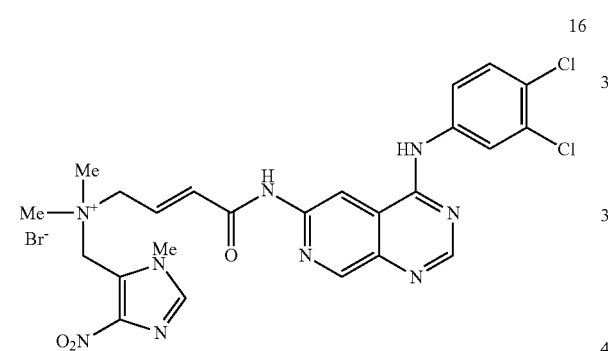
39
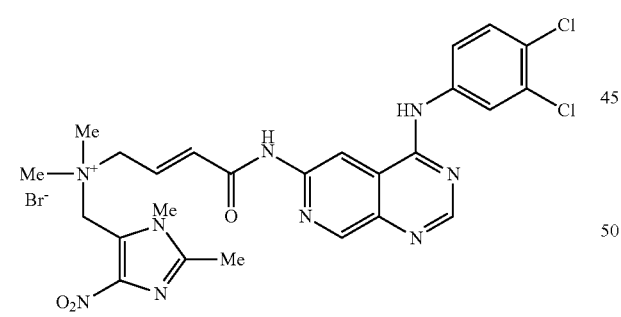
40
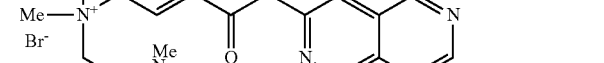
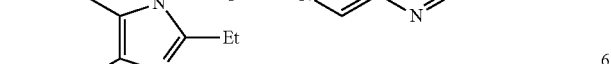
-continued
41
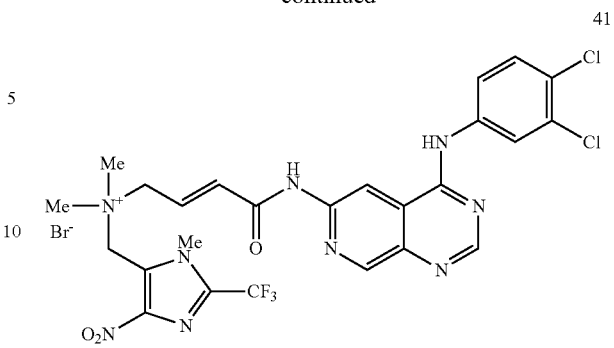
42
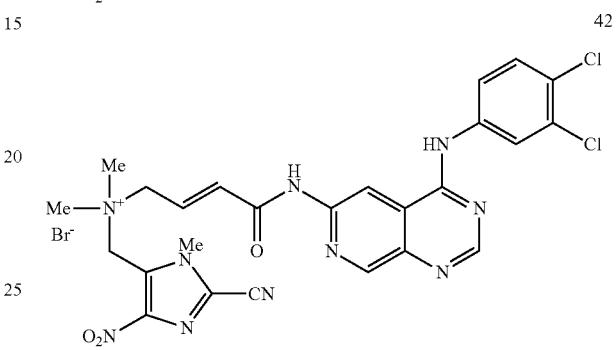
43
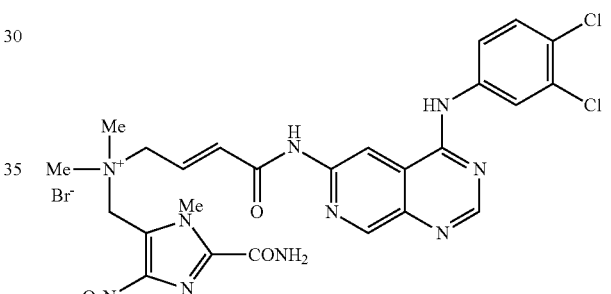
44
17

45
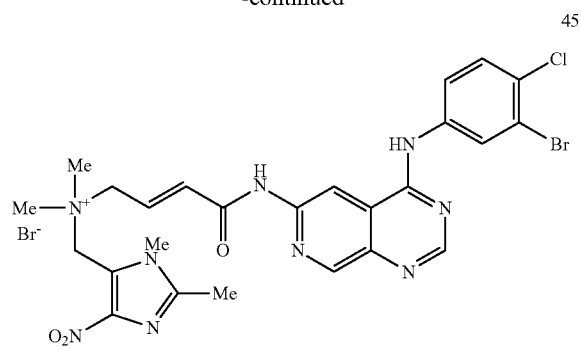
46
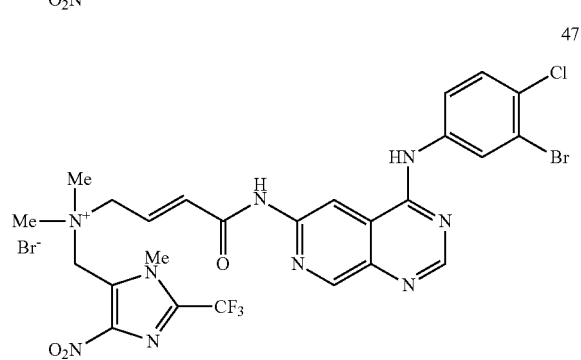
47
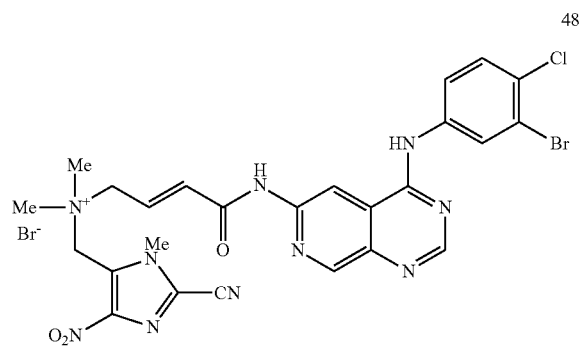
48
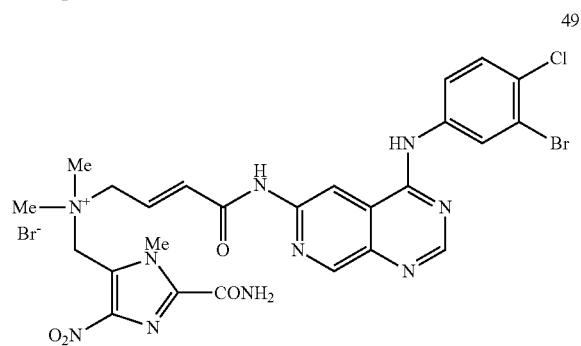
49
50
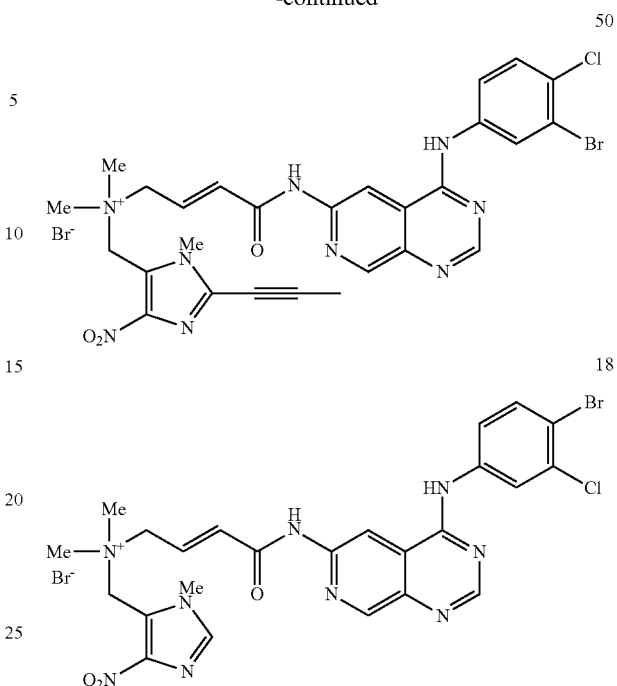
18
51
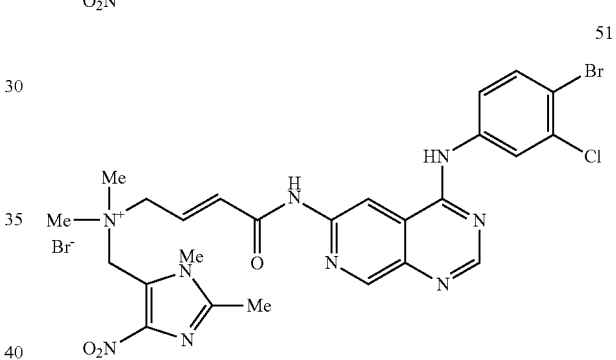
52
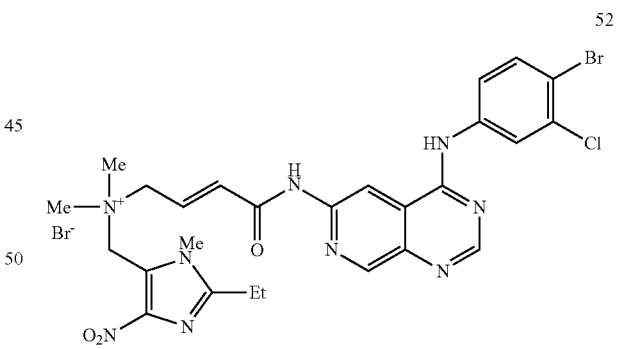
53
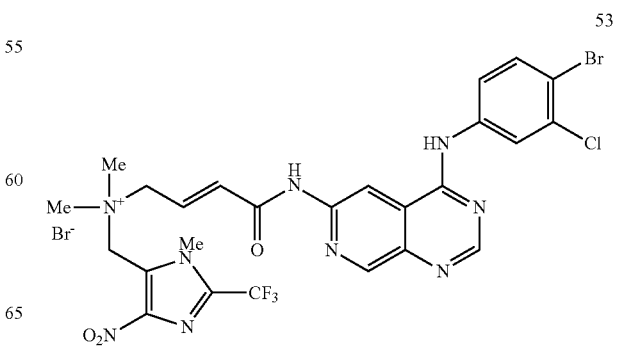

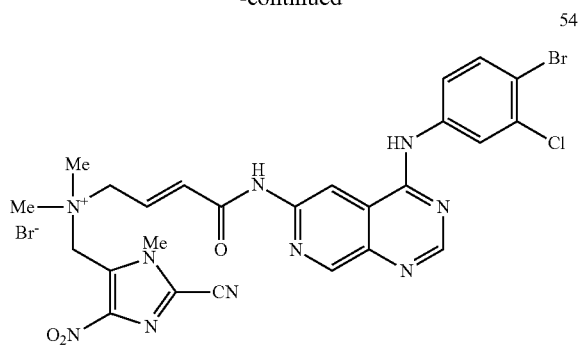
54
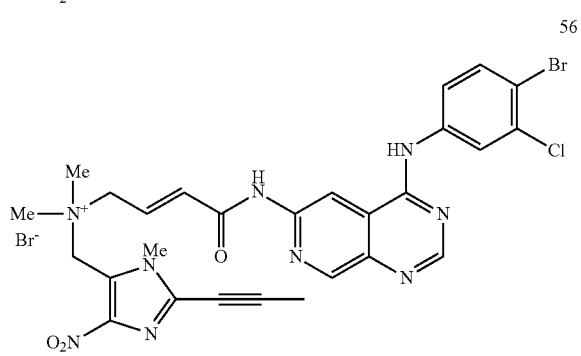
55
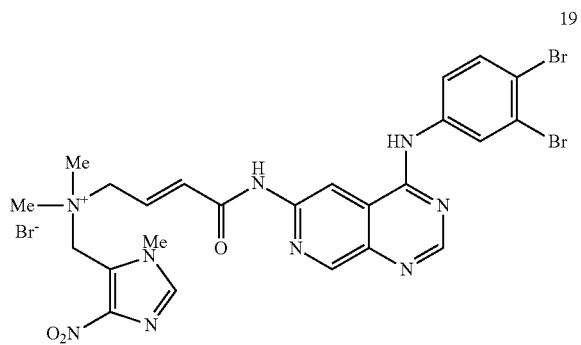
56
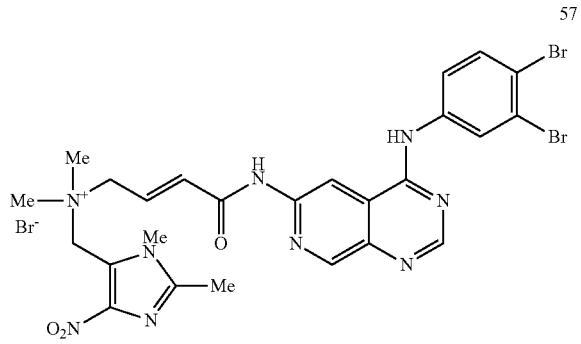
19
57
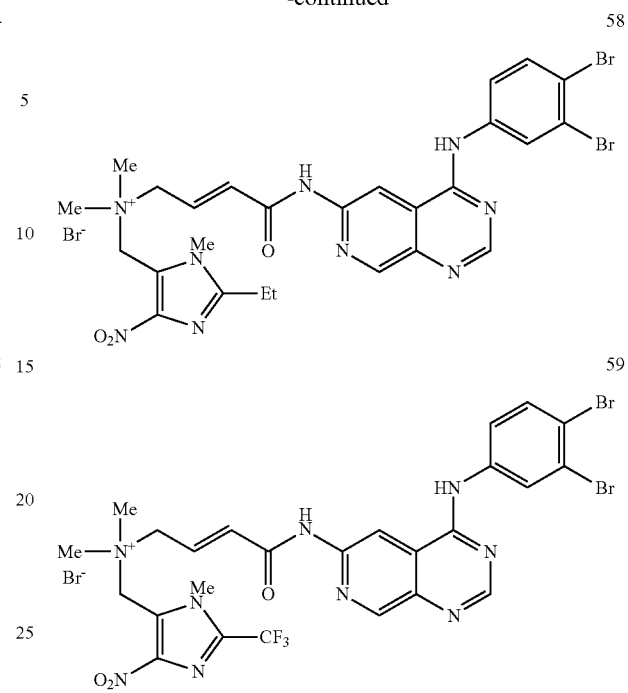
58
59
60
61
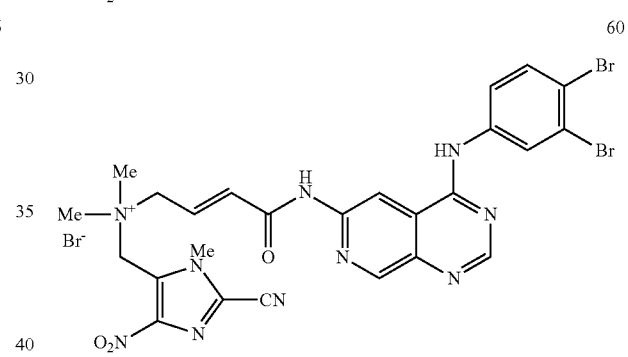
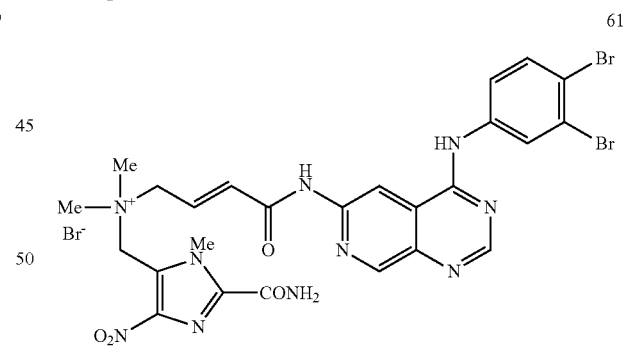
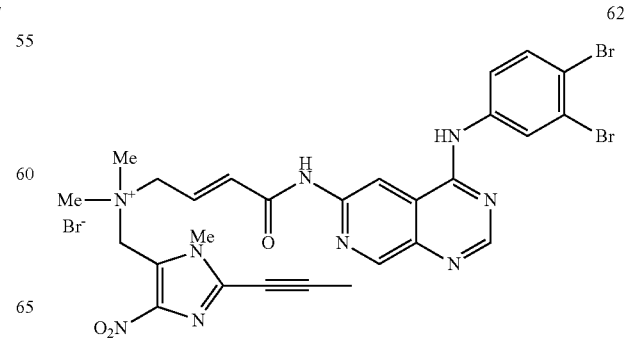
62

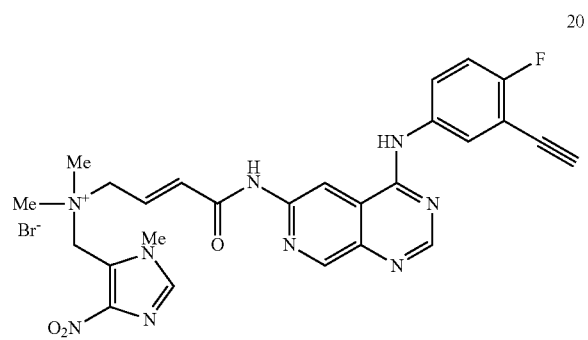
20
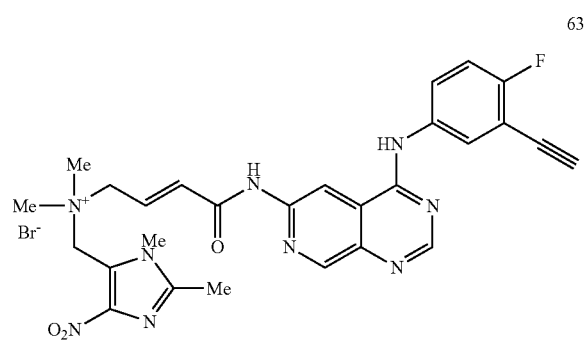
63
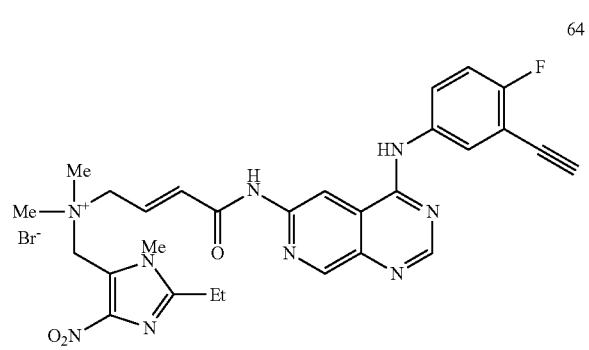
64
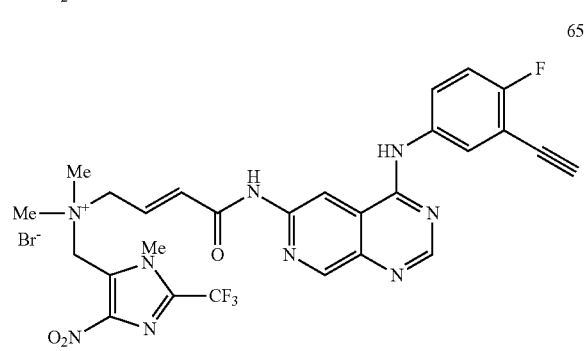
65
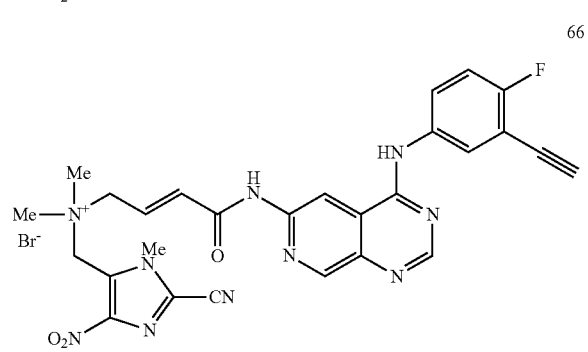
66
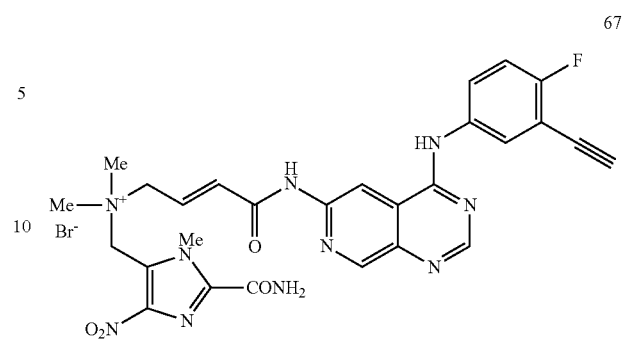
67
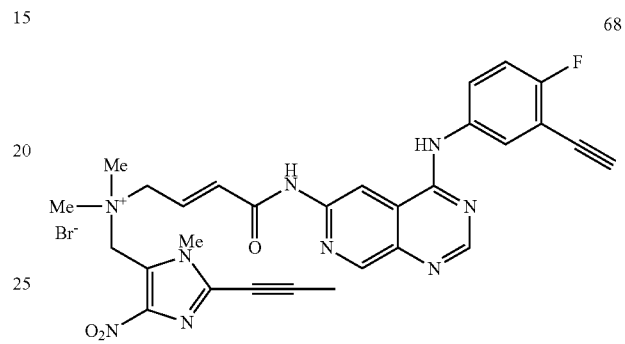
68
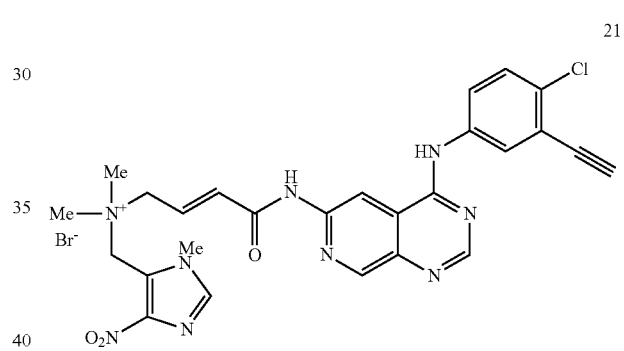
21
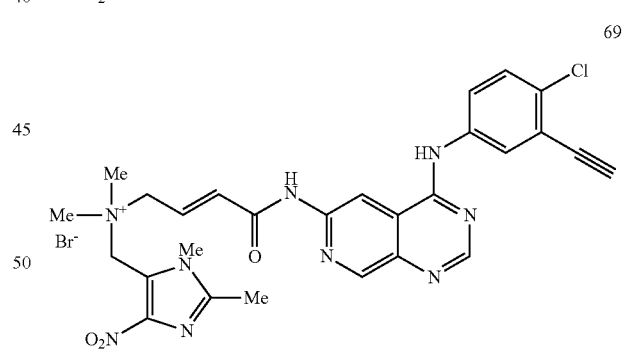
69
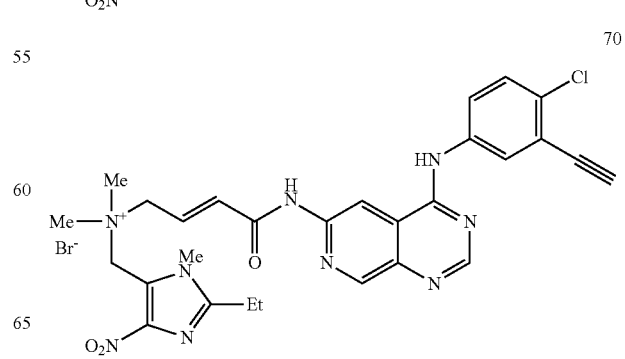
70

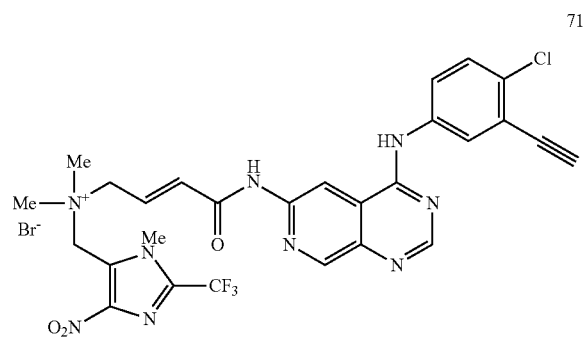
71
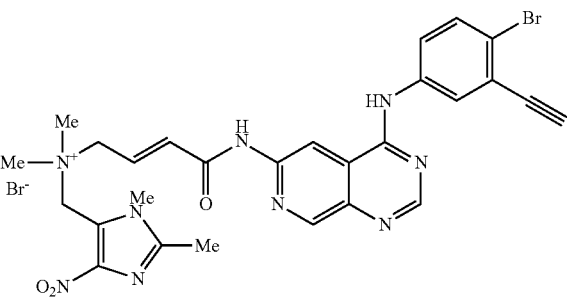
76
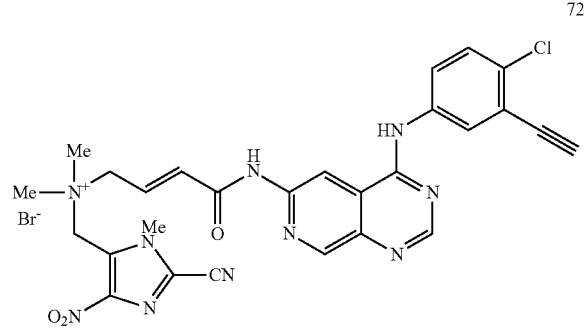
72
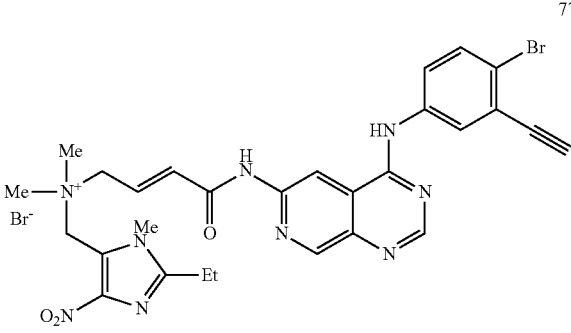
77
73
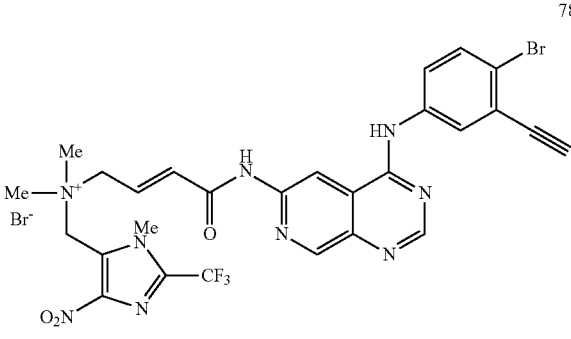
78
74
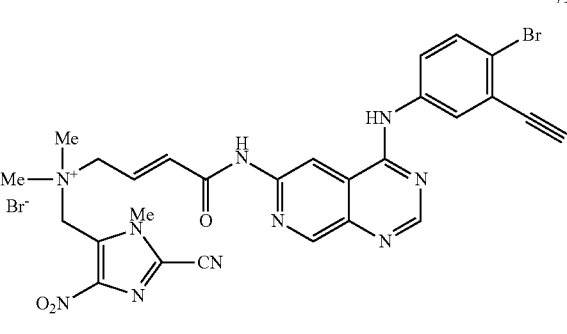
79
75
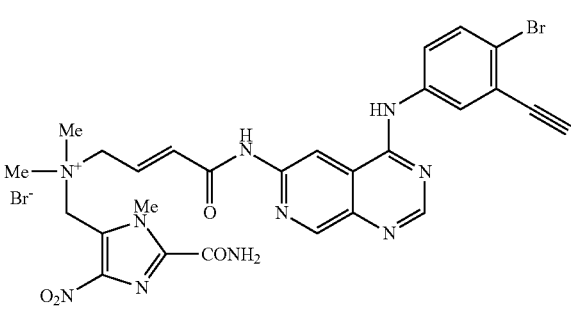
80

81
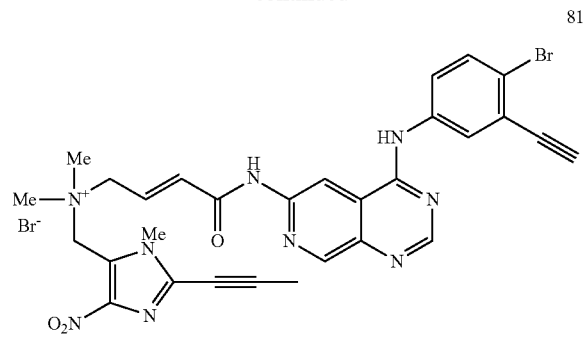
82
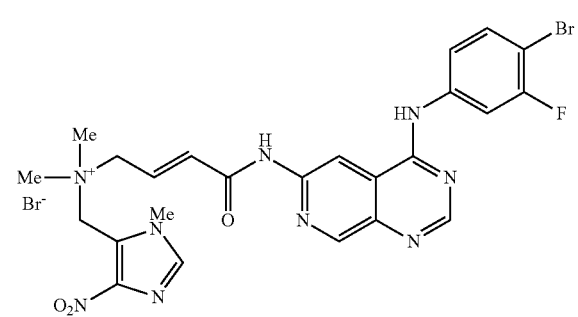
83
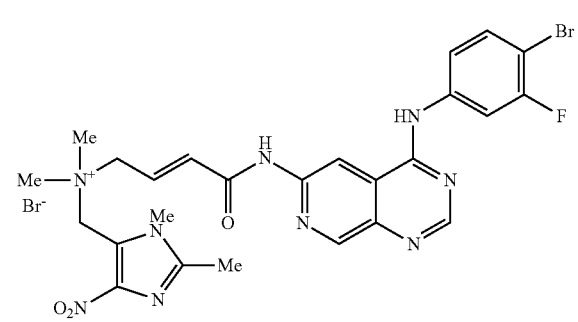
84
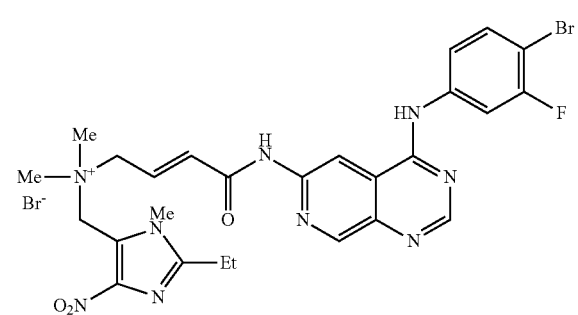
85
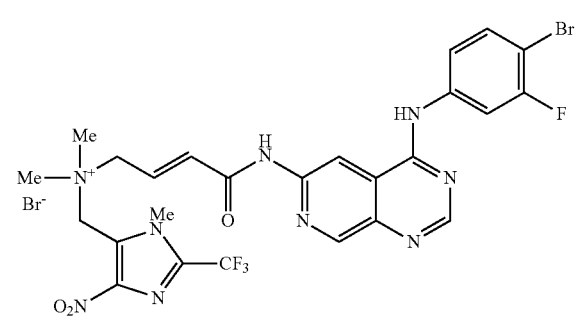
86
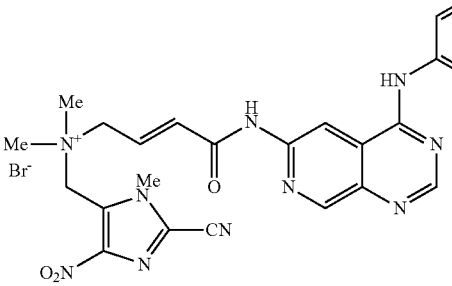
87
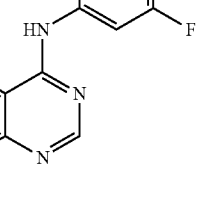
88
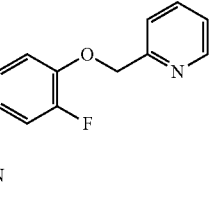
91
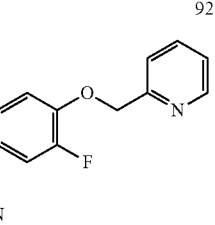
92

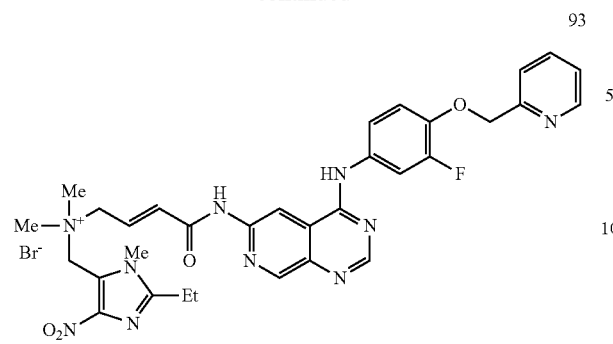
93
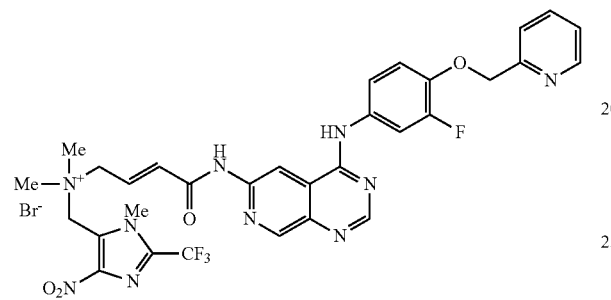
94
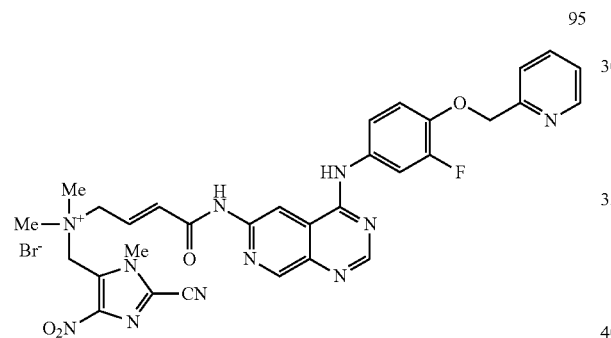
95
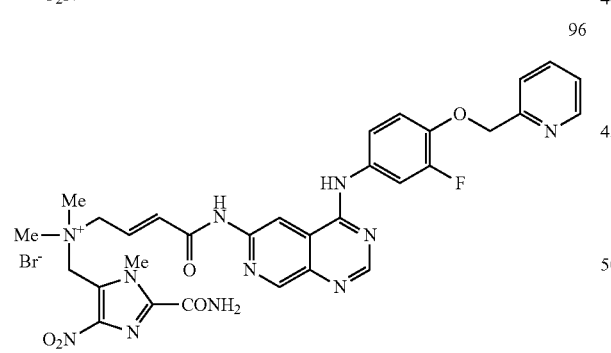
96
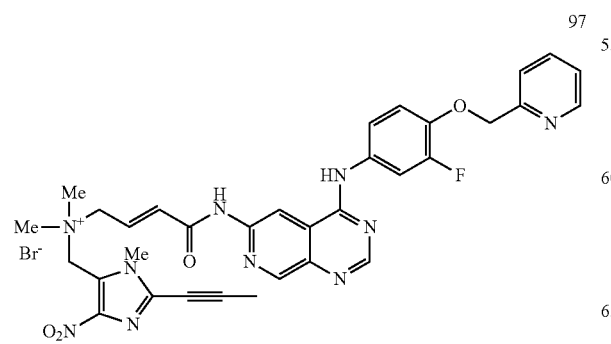
97
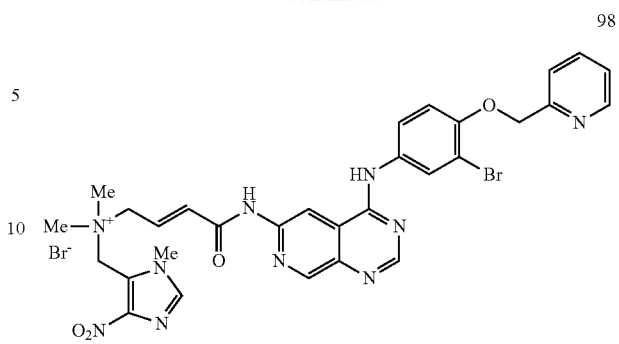
98
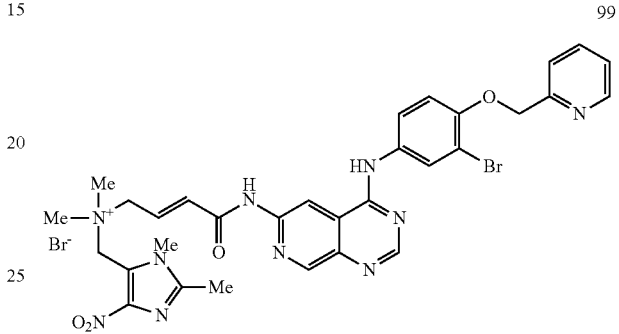
99
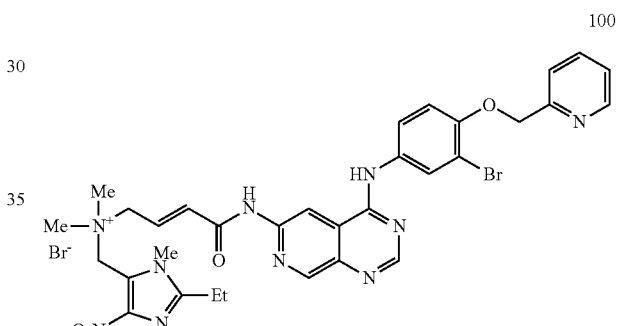
100
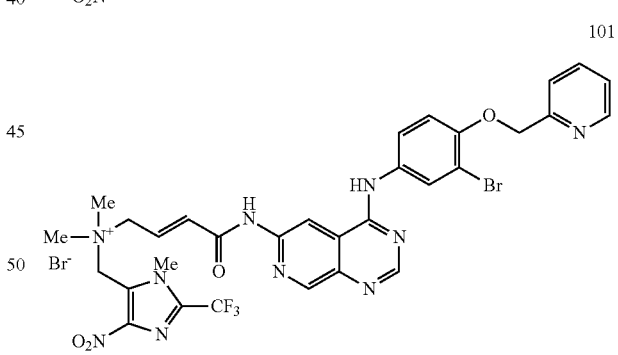
101
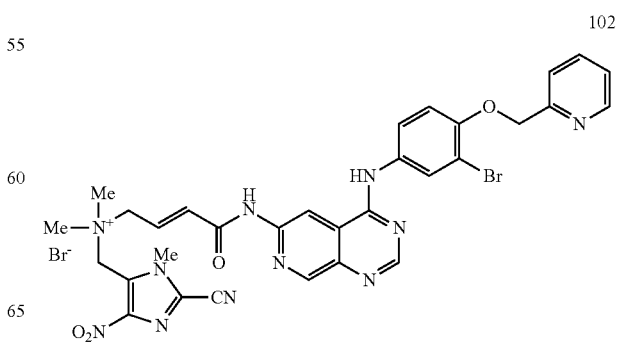
102

-continued

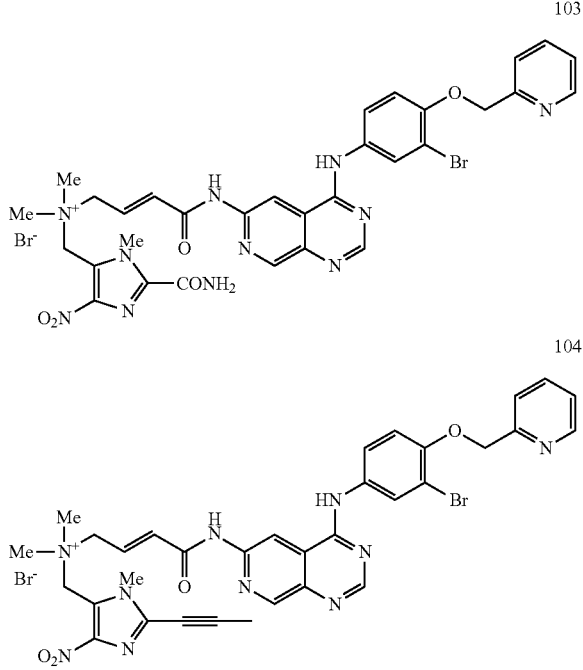

103

104

In certain embodiments, the compounds are selected from the group consisting of.
(2E)-4-{[4-(3-bromoanilino)-6-quinazolinyl]amino}-N,N-dimethyl-N-(4-nitro-benzyl)-4-oxo-2-buten-1-ammonium bromide;
(2E)-4-{[4-(3-bromoanilino)-6-quinazolinyl]amino}-N,N-dimethyl-N-(2-nitro-benzyl)-4-oxo-2-buten-1-ammonium bromide;
(2E)-4-{[4-(3-bromoanilino)-6-quinazolinyl]amino}-N,N-dimethyl-N-[(1-methyl-5-nitro-1H-pyrrol-2-yl)methyl]-4-oxo-2-buten-1-ammonium bromide;
(2E)-4-{[4-(3-bromoanilino)-6-quinazolinyl]amino}-N,N-dimethyl-N-[(1-methyl-4-nitro-1H-imidazol-5-yl)methyl]-4-oxo-2-buten-1-ammonium bromide;
(2E)-4-{[4-(3-bromoanilino)-6-quinazolinyl]amino}-N,N-dimethyl-N-[(1-methyl-4-nitro-1H-imidazol-2-yl)methyl]-4-oxo-2-buten-1-ammonium bromide;
(2E)-4-{[4-(3-bromoanilino)-6-quinazolinyl]amino}-N,N-dimethyl-N-[(1-methyl-4-nitro-1H-pyrazol-5-yl)methyl]-4-oxo-2-buten-1-ammonium bromide;
(2E)-4-{[4-(3-bromoanilino)-6-quinazolinyl]amino}-N,N-dimethyl-N-[(3-nitroimidazo[1,2-a]pyridin-2-yl)methyl]-4-oxo-2-buten-1-ammonium bromide;
1-((2E)-4-{[4-(3-bromoanilino)-6-quinazolinyl]amino}-4-oxo-2-butenyl)-[4-(1-methyl-4-nitro-1H-imidazol-5-yl)methyl]piperidinium bromide;
4-((2E)-4-{[4-(3-bromoanilino)-6-quinazolinyl]amino}-4-oxo-2-butenyl)-4-[-(1-methyl-4-nitro-1H-imidazol-5-yl)methyl]morpholin-4-ium formate
(2E)-4-{[4-(3-chloro-4-fluoroanilino)-7-methoxy-6-quinazolinyl]amino}-N,N-dimethyl-N-[(1-methyl-4-nitro-1H-imidazol-5-yl)methyl]-4-oxo-2-buten-1-ammonium bromide;
(2E)-4-{[4-(3-bromo-4-fluoroanilino)-6-quinazolinyl]amino}-N,N-dimethyl-N-[(1-methyl-4-nitro-1H-imidazol-5-yl)methyl]-4-oxo-2-buten-1-ammonium bromide;
(2E)-4-{[4-(4-fluoro-3-methoxyanilino)pyrido[3,4-d]pyrimidin-6-yl]amino}-N,N-dimethyl-N-[(1-methyl-4-nitro-1H-imidazol-5-yl) methyl]-4-oxo-2-buten-1-ammonium bromide;
(2E)-4-{[4-(3-bromo-4-fluoroanilino)pyrido[3,4-d]pyrimidin-6-yl]amino}-N,-N-dimethyl-N-[(1-methyl-4-nitro-1H-imidazol-5-yl)methyl]-4-oxo-2-buten-1-ammonium bromide;
(2E)-4-{[4-(3-bromo-4-fluoroanilino)pyrido[3,4-d]pyrimidin-6-yl]amino}-N-[(1,2-dimethyl-4-nitro-1H-imidazol-5-yl)methyl]N,N-dimethyl-4-oxo-2-buten-1-ammonium bromide;
(2E)-4-{[4-(3-bromo-4-fluoroanilino)pyrido[3,4-d]pyrimidin-6-yl]amino}-N-[(2-methoxy-1-methyl-4-nitro-1H-imidazol-5-yl)methyl]-N,N-dimethyl-4-oxo-2-buten-1-ammonium bromide;
(2E)-4-{[4-(3-bromo-4-fluoroanilino)pyrido[3,4-d]pyrimidin-6-yl]amino}-N-[(2-ethynyl-1-methyl-4-nitro-1H-imidazol-5-yl)methyl]-N,N-dimethyl-4-oxo-2-buten-1-ammonium bromide;
(2E)-4-{[4-(3-bromo-4-fluoroanilino)pyrido[3,4-d]pyrimidin-6-yl]amino}-N,-N-dimethyl-N-{[1-methyl-4-nitro-2-(trifluoromethyl)-1H-imidazol-5-yl]methy-l}-4-oxo-2-buten-1-ammonium bromide;
(2E)-N-{[1-(3-amino-3-oxopropyl)-4-nitro-1H-imidazol-5-yl]methyl}-4-{[4-(-3-bromo-4-fluoroanilino)pyrido[3,4-d]pyrimidin-6-yl]amino}-N,N-dimethyl-4-oxo-2-buten-1-ammonium bromide;
(2E)-4-{[4-(3-bromo-4-fluoroanilino)pyrido[3,4-d]pyrimidin-6-yl]amino}-N-[(2-cyano-1-methyl-4-nitro-1H-imidazol-5-yl)methyl]-N,N-dimethyl-4-oxo-2-buten-1-ammonium bromide;
(2E)-4-{[4-(3-bromo-4-fluoroanilino)pyrido[3,4-d]pyrimidin-6-yl]amino}-N-[(2-cyano-1-methyl-4-nitro-1H-imidazol-5-yl)methyl]-N,N-dimethyl-4-oxo-2-buten-1-ammonium trifluoroacetate;
(2E)-4-{[4-(3-bromo-4-fluoroanilino)pyrido[3,4-d]pyrimidin-6-yl]amino}-N-{[1-(2-cyanoethyl)-4-nitro-1H-imidazol-5-yl]methyl}-N,N-dimethyl-4-oxo-2-buten-1-ammonium bromide;
(2E)-4-({4-[4-fluoro-3-(trifluoromethyl)anilino]pyrido[3,4-d]pyrimidin-6-yl}amino)-N,N-dimethyl-N-[(1-methyl-4-nitro-1H-imidazol-5-yl)methyl]-4-oxo-2-buten-1-ammonium bromide;
(2E)-N-[(1,2-dimethyl-4-nitro-1H-imidazol-5-yl)methyl]-4-({4-[4-fluoro-3-(trifluoromethyl)anilino]pyrido[3,4-d]pyrimidin-6-yl}amino)-N,N-dimethyl-4-oxo-2-buten-1-ammonium bromide;
(2E)-4-({4-[4-fluoro-3-(trifluoromethyl)anilino]pyrido[3,4-d]pyrimidin-6-yl}amino)-N-[(2-methoxy-1-methyl-4-nitro-1H-imidazol-5-yl)methyl]-N,N-dimethyl-4-oxo-2-buten-1-ammonium bromide;
(2E)-N-[(2-ethynyl-1-methyl-4-nitro-1H-imidazol-5-yl)methyl]-4-({4-[4-fluoro-3-(trifluoromethyl)anilino]pyrido[3,4-d]pyrimidin-6-yl}amino)-N,N-dimethyl-4-oxo-2-buten-1-ammonium bromide;
(2E)-4-({4-[4-fluoro-3-(trifluoromethyl)anilino]pyrido[3,4-d]pyrimidin-6-yl}amino)-N,N-dimethyl-N-[1-methyl-4-nitro-2-(trifluoromethyl)-1H-imidazo-1-{5-yl]methyl}-4-oxo-2-buten-1-ammonium bromide;
(2E)-N-{[1-(3-amino-3-oxopropyl)-4-nitro-1H-imidazol-5-yl]methyl}-4-(1-[4-{4-fluoro-3-(trifluoromethyl)anilino}pyrido[3,4-d]pyrimidin-6-yl}amino)-N,N-dimethyl-4-oxo-2-buten-1-ammonium bromide;
(2E)-N-[(2-cyano-1-methyl-4-nitro-1H-imidazol-5-yl)methyl]-4-({4-[4-fluoro-3-(trifluoromethyl)anilino]pyrido[3,4-d]pyrimidin-6-yl}amino)-N,N-dimethyl-4-oxo-2-buten-1-ammonium bromide;
(2E)-N-{[1-(2-cyanoethyl)-4-nitro-1H-imidazol-5-yl]methyl}-4-({4-[4-fluoro-3-(trifluoromethyl)anilino]

pyrido[3,4-d]pyrimidin-6-yl}amino)-N,N-dimethyl-4-oxo-2-buten-1-ammonium bromide;

(2E)-4-{[4-(3-ethynylanilino)pyrido[3,4-d]pyrimidin-6-yl]amino}-N,N-dimet-hyl-N-[(1-methyl-4-nitro-1H-imidazol-5-yl)methyl]-4-oxo-2-buten-1-ammonium bromide;

(2E)-N-[(1,2-dimethyl-4-nitro-1H-imidazol-5-yl)methyl]-4-{[4-(3-ethynylanilino)pyrido[3,4-d]pyrimidin-6-yl]amino}-N,N-dimethyl-4-oxo-2-buten-1-ammonium bromide;

(2E)-4-{[4-(3-ethynylanilino)pyrido[3,4-d]pyrimidin-6-yl]amino}-N-[(2-methoxy-1-methyl-4-nitro-1H-imidazol-5-yl)methyl]-N,N-dimethyl-4-oxo-2-buten-1-ammonium bromide;

(2E)-4-{[4-(3-ethynylanilino)pyrido[3,4-d]pyrimidin-6-yl]amino}-N-[(2-ethynyl-1-methyl-4-nitro-1H-imidazol-5-yl)methyl]-N,N-dimethyl-4-oxo-2-buten-1-ammonium bromide;

(2E)-4-{[4-(3-ethynylanilino)pyrido[3,4-d]pyrimidin-6-yl]amino}-N,N-dimethyl-N-{[1-methyl-4-nitro-2-(trifluoromethyl)-1H-imidazol-5-yl]methyl}-4-oxo-2-buten-1-ammonium bromide;

(2E)-N-{[1-(3-amino-3-oxopropyl)-4-nitro-1H-imidazol-5-yl]methyl}-4-{[4-(-3-ethynylanilino)pyrido[3,4-d]pyrimidin-6-yl]amino}-N,N-dimethyl-4-oxo-2-buten-1-ammonium bromide;

(2E)-N-[(2-cyano-1-methyl-4-nitro-1H-imidazol-5-yl)methyl]-4-{[4-(3-ethynylanilino)pyrido[3,4-d]pyrimidin-6-yl]amino}-N,N-dimethyl-4-oxo-2-buten-1-ammonium bromide;

(2E)-N-{[1-(2-cyanoethyl)-4-nitro-1H-imidazol-5-yl]methyl}-4-{[4-(3-ethynylanilino)pyrido[3,4-d]pyrimidin-6-yl]amino}-N,N-dimethyl-4-oxo-2-buten-1-ammonium bromide;

(2E)-4-({4-(3-chloro-4-fluoroanilino)-7-[(3S)-tetrahydro-3-furanyloxy]-6-quinazolinyl}amino)-N,N-dimethyl-N-[(1-methyl-4-nitro-1H-imidazol-5-yl)methyl]-4-oxo-2-buten-1-ammonium trifluoroacetate;

(2E)-4-({4-[3-chloro-4-(2-pyridinylmethoxy)anilino]-3-cyano-7-ethoxy-6-quinolinyl}amino)-N,N-dimethyl-N-[(1-methyl-4-nitro-1H-imidazol-5-yl)methyl]-4-oxo-2-buten-1-ammonium trifluoroacetate;

(2E)-4-{[4-(3-chloro-4-fluoroanilino)-3-cyano-7-ethoxy-6-quinolinyl]amino-}-N,N-dimethyl-N-[(1-methyl-4-nitro-1H-imidazol-5-yl)methyl]-4-oxo-2-buten-1-ammonium bromide;

2-(4-{[6-(2,6-dichlorophenyl)-8-methyl-7-oxo-7,8-dihydropyrido[2,3-d]pyrimidin-2-yl]amino}phenoxy)-N,N-diethyl-N-[(1-methyl-4-nitro-1H-imidazol-5-yl)methyl]ethanammonium bromide;

2-(4-{[6-(2,6-dichlorophenyl)-8-methyl-7-oxo-7,8-dihydropyrido[2,3-d]pyrimidin-2-yl]amino}phenoxy)-N-[(1,2-dimethyl-4-nitro-1H-imidazol-5-yl)methyl-]N,N-diethylethanammonium bromide;

4-{[6-(2,6-dichlorophenyl)-8-methyl-7-oxo-7,8-dihydropyrido[2,3-d]pyrimidin-2-yl]amino}-1-[(1-methyl-4-nitro-1H-imidazol-5-yl)methyl]pyridinium bromide;

1-[2-(4-{[6-(2,6-dichlorophenyl)-8-methyl-7-oxo-7,8-dihydropyrido[2,3-d]pyrimidin-2-yl]amino}phenoxy)ethyl]-1-[(1-methyl-4-nitro-1H-imidazol-5-yl) methyl]piperidinium bromide;

N,N-diethyl-2-[({5-[(Z)-(5-fluoro-2-oxo-1,2-dihydro-3H-indol-3-ylidene)methyl]-2,4-dimethyl-1H-pyrrol-3-yl}carbonyl)amino]-N-[(1-methyl-4-nitro-1H-imidazol-5-yl)methyl]ethanammonium trifluoroacetate;

N-[(1,2-dimethyl-4-nitro-1H-imidazol-5-yl)methyl]-N,N-diethyl-2-[({5-[(Z)-(5-fluoro-2-oxo-1,2-dihydro-3H-indol-3-ylidene)methyl]2,4-dimethyl-1H-pyrrol-3-yl}carbonyl)amino]ethanammonium bromide;

4-({[4-(4-bromo-2-fluoroanilino)-6-methoxy-7-quinazolinyl]oxy}methyl)-1-m-ethyl-1-[(1-methyl-4-nitro-1H-imidazol-5-yl)methyl]piperidinium trifluoroacetate;

(2E)-4-{[4-(3-bromo-4-fluoroanilino)pyrido[3,4-d]pyrimidin-6-yl]amino}-N-[(2-ethyl-1-methyl-4-nitro-1H-imidazol-5-yl)methyl]-N,N-dimethyl-4-oxo-2-buten-1-ammonium bromide;

(2E)-4-{[4-(3-bromo-4-fluoroanilino)pyrido[3,4-d]pyrimidin-6-yl]amino}-N,-N-dimethyl-N-{[1-methyl-4-nitro-2-(1-propynyl)-1H-imidazol-5-yl]methyl}-4-oxo-2-buten-1-ammonium bromide;

(2E)-4-{[4-(3-bromo-4-fluoroanilino)pyrido[3,4-d]pyrimidin-6-yl]amino}-N,-N-dimethyl-N-[(1-methyl-2-nitro-1H-imidazol-5-yl)methyl]-4-oxo-2-buten-1-ammonium bromide;

(2E)-4-{[4-(3-bromo-4-fluoroanilino)pyrido[3,4-d]pyrimidin-6-yl]amino}-N-[(4-ethyl-1-methyl-2-nitro-1H-imidazol-5-yl)methyl]-N,N-dimethyl-4-oxo-2-buten-1-ammonium bromide; and (2E)-N-[(2-ethyl-1-methyl-4-nitro-1H-imidazol-5-yl)methyl]-4-{[4-(3-ethynylanilino)pyrido[3,4-d]pyrimidin-6-yl]amino}-N,N-dimethyl-4-oxo-2-buten-1 ammonium bromide.

In certain embodiments, the cancer comprises lung cancer. In other embodiments, the lung cancer comprises non-small cell lung cancer. In yet other embodiments, the cancer comprises gastric cancer. In yet other embodiments, the cancer comprises breast cancer. In yet other embodiments, the cancer comprises head and neck squamous cell carcinoma (HNSCC). In yet other embodiments, the cancer comprises gastric/gastroesophageal (GE) junction cancer. In yet other embodiments, the cancer comprises esophageal cancer. In yet other embodiments, the cancer comprises salivary cancer. In yet other embodiments, the cancer comprises ovarian cancer. In yet other embodiments, the cancer comprises endometrial cancer. In yet other embodiments, the cancer comprises uterine cancer. In yet other embodiments, the cancer comprises pancreatic cancer.

In certain embodiments, the cancer is selected from the group of lung cancer, gastric cancer, breast cancer, HNSCC, GE junction cancer, esophageal cancer, salivary cancer, ovarian cancer, endometrial cancer, uterine cancer, prostate cancer, pancreatic cancer, colon cancer, glioblastoma, mesothelioma, and adenocarcinoma.

In certain embodiments, the cancer is non-small cell lung cancer.

In certain embodiments, the cancer comprises an EGFR exon insertion mutation.

In certain embodiments, the cancer comprises an EGFR exon 20 insertion mutation. In certain embodiments, the EGFR exon 20 insertion mutation includes a mutation such as but not limited to any of the mutations described in Yasuda, et al., 2013, Sci. Transl. Med. 5(216):216ra177; doi:10.1126/scitranslmed.3007205, and Arcila, et al., 2013, Mol. Cancer Ther. 12:220; each of which is incorporated herein in its entirety by reference.

In certain embodiments, the EGFR exon 20 insertion mutation comprises A763_Y764insFQEA. In other embodiments, the EGFR exon 20 insertion mutation comprises A763_Y764insFQQA. In yet other embodiments, the EGFR exon 20 insertion mutation comprises A767_V769dupASV. In yet other embodiments, the EGFR exon 20 insertion mutation comprises D770_N771insGL. In yet other embodiments, the EGFR exon 20 insertion mutation comprises D770_N771insGT. In yet other embodiments, the EGFR exon 20 insertion mutation comprises D770_N771insNPG. In yet other embodiments, the EGFR exon 20 insertion mutation comprises D770_N771insSVD. In yet other embodiments, the EGFR exon 20 insertion mutation comprises E762Q_insFQEA. In yet other embodiments, the EGFR exon 20 insertion mutation comprises H773_V774insH. In yet other embodiments, the EGFR exon 20 insertion mutation comprises H773_V774insH. In yet other embodiments, the EGFR exon 20 insertion mutation comprises H773_V774insNPH. In yet other embodiments, the EGFR exon 20 insertion mutation comprises M766_A767insAI. In yet other embodiments, the EGFR exon 20 insertion mutation comprises M766_A767insASV. In yet other embodiments, the EGFR exon 20 insertion mutation comprises N771_H773dupNPH. In yet other embodiments, the EGFR exon 20 insertion mutation comprises P772_H773insYNP. In yet other embodiments, the EGFR exon 20 insertion mutation comprises P772_V774insPHV. In yet other embodiments, the EGFR exon 20 insertion mutation comprises S768_770dupSVD. In yet other embodiments, the EGFR exon 20 insertion mutation comprises V769_D770insASV. In yet other embodiments, the EGFR exon 20 insertion mutation comprises Y764_V765insHH. In yet other embodiments, the EGFR exon 20 insertion mutation comprises delD770insGY. In yet other embodiments, the EGFR exon 20 insertion mutation comprises delL747_P753insS.

In certain embodiments, the EGFR exon 20 insertion mutation comprises A767_V769dupASV (also referred to as A767_V769insASV). In other embodiments, the EGFR exon 20 insertion mutation comprises A763_Y764insFHEA, V769_D770insASV. In yet other embodiments, the EGFR exon 20 insertion mutation comprises D770_N771insSVD. In other embodiments, the EGFR exon 20 insertion mutation comprises A767_V769dupASV. In other embodiments, the EGFR exon 20 insertion mutation comprises N771_H773dupNPH. In yet other embodiments, the EGFR exon 20 insertion mutation comprises S768_770dupSVD.

In certain embodiments, the cancer comprises an ERBB2 gene fusion. In other embodiments, the ERBB2 gene fusion comprises ZNF207-HER2. In yet other embodiments, the ERBB2 gene fusion comprises MDK-HER2. In yet other embodiments, the ERBB2 gene fusion comprises NOS2-HER2. In yet other embodiments, the ERBB2 gene fusion comprises ERBB2-GRB7. In yet other embodiments, the ERBB2 gene fusion comprises ERBB2-CTTN. In yet other embodiments, the ERBB2 gene fusion comprises ERBB2-PPP1R1B. In yet other embodiments, the ERBB2 gene fusion comprises ERBB2-PSMB3.

In certain embodiments, the cancer comprises a ERBB2 mutation. In other embodiments, the ERBB2 mutation comprises G309A/E. In yet other embodiments, the ERBB2 mutation comprises S310F/Y. In yet other embodiments, the ERBB2 mutation comprises V659E/D. In yet other embodiments, the ERBB2 mutation comprises G660D. In yet other embodiments, the ERBB2 mutation comprises K753E. In yet other embodiments, the ERBB2 mutation comprises L755P/S. In yet other embodiments, the ERBB2 mutation comprises Del755-759. In yet other embodiments, the ERBB2 mutation comprises L768S. In yet other embodiments, the ERBB2 mutation comprises D769H/Y. In yet other embodiments, the ERBB2 mutation comprises V773L. In yet other embodiments, the ERBB2 mutation comprises A775_G776insYVMA. In yet other embodiments, the ERBB2 mutation comprises G776V/L, Cins. In yet other embodiments, the ERBB2 mutation comprises V777L. In yet other embodiments, the ERBB2 mutation comprises P780Ins. In yet other embodiments, the ERBB2 mutation comprises P780_Y781insGSP. In yet other embodiments, the ERBB2 mutation comprises V842I. In yet other embodiments, the ERBB2 mutation comprises L866M. In yet other embodiments, the ERBB2 mutation comprises R896C.

In certain embodiments, the cancer comprises a NRG1 gene fusion. In other embodiments, the NRG1 gene fusion comprises DOC4-NRG1. In yet other embodiments, the NRG1 gene fusion comprises CD74-NRG1. In yet other embodiments, the NRG1 gene fusion comprises SLC3A2-NRG1. In yet other embodiments, the NRG1 gene fusion comprises RBPMS-NRG1. In yet other embodiments, the NRG1 gene fusion comprises WRN-NRG1. In yet other embodiments, the NRG1 gene fusion comprises SDC4-NRG1. In yet other embodiments, the NRG1 gene fusion comprises RAB2IL1-NRG1. In yet other embodiments, the NRG1 gene fusion comprises VAMP2-NRG1. In yet other embodiments, the NRG1 gene fusion comprises KIF13B-NRG1. In yet other embodiments, the NRG1 gene fusion comprises ATP1B1-NRG1. In yet other embodiments, the NRG1 gene fusion comprises CDH6-NRG1. In yet other embodiments, the NRG1 gene fusion comprises APP-NRG1. In yet other embodiments, the NRG1 gene fusion comprises AKAP13-NRG1. In yet other embodiments, the NRG1 gene fusion comprises THBS1-NRG1. In yet other embodiments, the NRG1 gene fusion comprises PDE7A-NRG1. In yet other embodiments, the NRG1 gene fusion comprises THAP7-NRG1. In yet other embodiments, the NRG1 gene fusion comprises SMAD4-NRG1. In yet other embodiments, the NRG1 gene fusion comprises RAB3IL1-NRG1. In yet other embodiments, the NRG1 gene fusion comprises NRG1-PMEPA1. In yet other embodiments, the NRG1 gene fusion comprises NRG1-STMN2.

In certain embodiments, the cancer comprises an ERBB3 mutation. In other embodiments, the ERBB3 mutation comprises V104M. In yet other embodiments, the ERBB3 mutation comprises A232V. In yet other embodiments, the ERBB3 mutation comprises P262H. In yet other embodiments, the ERBB3 mutation comprises G284R. In yet other embodiments, the ERBB3 mutation comprises T389K. In yet other embodiments, the ERBB3 mutation comprises Q809R. In yet other embodiments, the ERBB3 mutation comprises S846I. In yet other embodiments, the ERBB3 mutation comprises E928G.

In certain embodiments, the cancer comprises an ERBB4 fusion. In other embodiments, the ERBB4 fusion comprises EZR-ERBB4. In yet other embodiments, the ERBB4 fusion comprises IKZF2-ERBB4. In yet other embodiments, the ERBB4 fusion comprises BGALT-ERBB4.

In certain embodiments, the cancer is resistant to at least one selected from the group consisting of osimertinib, gefitinib, afatinib, and erlotinib. In other embodiments, the cancer is resistant to osimertinib. In yet other embodiments, the cancer is resistant to gefitinib. In yet other embodiments, the cancer is resistant to afatinib. In yet other embodiments, the cancer is resistant to erlotinib.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present application, illustrative methods and materials are described.

As used herein, each of the following terms has the meaning associated with it in this section.

As used herein, the articles "a" and "an" are used to refer to one or to more than one (i.e., to at least one) of the grammatical object of the article. By way of example, "an element" means one element or more than one element.

As used herein, "about," when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the term "afatinib" refers to N-[4-[(3-Chloro-4-fluorophenyl)amino]-7-[[(3S)-tetrahydro-3-furanyl]oxy]-6-quinazolinyl]-4(dimethylamino)-2-butenamide, or a salt or solvate thereof.

A disease or disorder is "alleviated" if the severity of a symptom of the disease or disorder, the frequency with which such a symptom is experienced by a patient, or both, is reduced.

As used herein, the terms "alkyl", "alkenyl", "alkynyl" and "alkoxy" include both straight chain and branched chain groups, and unsubstituted and substituted groups. The optional substituents may include, without limitation, halogen, $C_1$-$C_6$ alkoxy, CN, OH, $NH_2$, $NO_2$, $NH(C_1$-$C_6$ alkyl), $N(C_1$-$C_6$ alkyl)$_2$, $CONH_2$, $CO(C_1$-$C_6$ alkyl), $SO_2NH_2$ and $SO_2(C_1$-$C_6$ alkyl).

As used herein, the term "aromatic nitroheterocycle" means an aromatic heterocyclic moiety substituted at any ring position by one or more nitro ($NO_2$) groups. The aromatic heterocyclic moiety may be a monocyclic or bicyclic ring containing 4 to 12 atoms of which at least one atom is chosen from the group consisting of nitrogen, sulphur or oxygen. The aromatic heterocyclic moiety may be carbon or nitrogen linked. The aromatic heterocyclic moiety may additionally be substituted by one or more additional substituents at any available ring carbon or heteroatom. The substituents may include, but are not limited to the groups as defined for $R_{26}$ in Formula V.

As used herein, the term "aromatic nitrocarbocycle" means a benzene moiety substituted at any position by one or more nitro ($NO_2$) groups. In addition, two adjacent ring carbon atoms may optionally be linked to form a fused carbocyclic or heterocyclic ring. The benzene moiety (and optional fused ring) may additionally be substituted by one or more additional substituents at any available carbon or heteroatom. The substituents may include, but are not limited to, the groups as defined for $R_{26}$ in Formula V.

In one aspect, the terms "co-administered" and "co-administration" as relating to a subject refer to administering to the subject a compound contemplated herein or salt thereof along with a compound that may also treat the disorders or diseases contemplated herein. In one embodiment, the co-administered compounds are administered separately, or in any kind of combination as part of a single therapeutic approach. The co-administered compound may be formulated in any kind of combinations as mixtures of solids and liquids under a variety of solid, gel, and liquid formulations, and as a solution.

As used herein, the term "composition" or "pharmaceutical composition" refers to a mixture of at least one compound contemplated herein with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, nasal, pulmonary and topical administration.

The term "container" includes any receptacle for holding the pharmaceutical composition or to add protection to manage stability and or water-uptake. For example, in one embodiment, the container is the packaging that contains the pharmaceutical composition such as liquid (solution and suspension), semisolid, lyophilized solid, solution and powder or lyophilized formulation present in dual chambers. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating, preventing, or reducing a breathing disorder in a patient.

The term "determining" as used herein generally refers to any form of measurement, and includes detecting the presence of a mutation, including, for example, an EGFR exon 20 insertion mutation in the tumor cells, as disclosed herein. The term "determining" includes both quantitative and/or qualitative determination. The mutation (e.g., EGFR exon 20 insertion mutation) may be determined by any suitable method known to those skilled in the art, including those as further disclosed herein.

A "disease" as used herein is a state of health of an animal wherein the animal cannot maintain homeostasis, and wherein if the disease is not ameliorated then the animal's health continues to deteriorate.

A "disorder" as used herein in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the terms "effective amount," "pharmaceutically effective amount" and "therapeutically effective amount" refer to a nontoxic but sufficient amount of a compound or agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation. A therapeutic benefit or improvement need not be complete ablation of any one, most or all symptoms, complications, consequences or underlying causes associated with the disorder or disease. Thus, in certain embodiments, a satisfactory endpoint is achieved when there is a transient, medium or long term, incremental improvement in a subject's condition, or a partial reduction in the occurrence, frequency, severity, progression, or duration, or inhibition or reversal, of one or more associated adverse symptoms or complications or consequences or underlying causes, worsening or progression (e.g., stabilizing one or more symptoms or complications of the condition, disorder or disease), of the disorder or disease, over a duration of time (hours, days, weeks, months, and so forth).

As used herein, the term "erlotinib" refers to N-(3-ethynylphenyl)-6,7-bis(2-methoxyethoxy)quinazolin-4-amine, or a salt or solvate thereof.

As used herein, the term "HER-driven cancer" refers to a cancer that is caused or promoted by a EGFR gene fusion, a EGFR kinase domain duplication, a ERBB2 gene fusion, a ERBB2 mutation, a NRG1 gene fusion, a ERBB3 mutation, and/or a ERBB4 fusion.

The HER-driven cancer may be indicated by the presence of a EGFR gene fusion, a EGFR kinase domain duplication, a ERBB2 gene fusion, a ERBB2 mutation, a NRG1 gene fusion, a ERBB3 mutation, and/or a ERBB4 fusion. The HER-driven cancer may be resistant to osimertinib, gefitinib, afatinib, and/or erlotinib, as described herein. The HER-driven cancer may also have an EGFR exon insertion mutation (e.g., an EGFR exon 20 insertion mutation), where the EGFR exon insertion mutation is indicated phenotypically, for example, by histopathology, imaging, tumor growth, DNA analysis, RNA analysis or other diagnostic means, as described herein.

"Instructional material," as that term is used herein, includes a publication, a recording, a diagram, or any other medium of expression that can be used to communicate the usefulness of a composition and/or compound contemplated herein in a kit. The instructional material of the kit may, for example, be affixed to a container that contains the compound and/or composition contemplated herein or be shipped together with a container that contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

As used herein, "likelihood", "likely to", and similar generally refers to an increase in the probability of an event. Thus, "likelihood", "likely to", and similar, when used in reference to responsiveness to cancer therapy, generally contemplates an increased probability that the individual will exhibit a reduction in the severity of cancer or the symptoms of cancer or the retardation or slowing of the cancer progression. The term "likelihood", "likely to", and similar, when used in reference to responsiveness to cancer therapy, can also generally mean the increase of indicators that may evidence an increase in cancer treatment.

As used herein, the term "osimertinib" refers to N-(2-{2-dimethylaminoethyl-methylamino}-4-methoxy-5-{[4-(1-methylindol-3-yl)pyrimidin-2-yl]amino}phenyl)prop-2-enamide, or a salt or solvate thereof.

The terms "patient," "subject" or "individual" are used interchangeably herein, and refer to any animal, or cells thereof whether in vitro or in situ, amenable to the methods described herein. In non-limiting embodiments, the patient is a human. In certain embodiments, the subject is a subject in need of treatment thereof. In other embodiments, the subject has a cancer comprising an EGFR mutation, for example, an EGFR insertion mutation. In yet other embodiments, the subject has EGFR exon 20 insertion mutation.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound disclosed herein or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including compounds disclosed herein, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of compounds disclosed herein, and are physiologically acceptable to the patient. Supplementary active compounds may also be incorporated into the compositions.

The "pharmaceutically acceptable carrier" may further include a pharmaceutically acceptable salt of the compounds disclosed herein. Other additional ingredients that may be included in the pharmaceutical compositions disclosed herein are known in the art and described, for example in Remington's Pharmaceutical Sciences (Genaro, Ed., Mack Publishing Co., 1985, Easton, Pa.), which is incorporated herein by reference.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof.

As used herein, the term "predict" can mean to determine or tell in advance. When used to "predict" the responsiveness to a treatment for example, the term "predict" can mean that the likelihood of the outcome of the cancer treatment can be determined at the outset, before the treatment has begun, or before the treatment period has progressed substantially. A predictive method may also be described as a prognostic method.

The term "prevent," "preventing" or "prevention," as used herein, means avoiding or delaying the onset of symptoms associated with a disease or condition in a subject that has not developed such symptoms at the time the administering of an agent or compound commences.

As used herein, the term "prodrug" refers to a compound that, after administration, is metabolized or otherwise converted to a biologically active or more active compound (or drug) with respect to at least one property. A prodrug, relative to the drug, is modified chemically in a manner that renders it, relative to the drug, less active or inactive, but the chemical modification is such that the corresponding drug is generated by metabolic or other biological processes after the prodrug is administered. A prodrug can have, relative to the active drug, altered metabolic stability or transport characteristics, fewer side effects or lower toxicity, or improved flavour (for example, see the reference Nogrady, 1985, Medicinal Chemistry A Biochemical Approach, Oxford University Press, New York, pages 388-392, incorporated herein by reference). A prodrug may be synthesized using reactants other than the corresponding drug.

As used herein, the phrase "providing tumor cells" refers to the step of obtaining cells of the individual (e.g. by way of biopsy or otherwise), and/or refers to the step of receiving a sample of tumor cells that has previously been obtained from the individual.

A "therapeutic" treatment is a treatment administered to a subject who exhibits signs of pathology, for the purpose of diminishing or eliminating those signs.

The term "responsiveness" or "responsive," when used in reference to a treatment, refers to the degree of effectiveness of the treatment in lessening or decreasing the symptoms of a disease, disorder, or condition being treated. For example, the term "increased responsiveness," when used in reference to a treatment of a cell or a subject, refers to an increase in the effectiveness in lessening or decreasing the symptoms of the disease when measured using any methods known in the art. In certain embodiments, the increase in the effectiveness is at least about 5%, at least about 10%, at least about 20%, at least about 30%, at least about 40%, or at least about 50%.

In certain embodiments, tumor cells comprise a "sample." In other embodiments, the sample comprises a biological sample and can be, for instance, a cell, a cell culture, a tissue, and/or a biological fluid. Suitably, the biological sample can comprise a tumor cell biopsy, a plurality of samples from a clinical trial, or the like. The sample can be a crude sample, or can be purified to various degrees prior to storage, processing, or measurement.

As used herein, the term "treatment" or "treating" is defined as the application or administration of a therapeutic agent, i.e., a compound disclosed herein (alone or in combination with another pharmaceutical agent), to a patient, or application or administration of a therapeutic agent to an isolated tissue or cell line from a patient (e.g., for diagnosis or ex vivo applications), who has a condition contemplated herein, a symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments may be specifically tailored or modified, based on knowledge obtained from the field of pharmacogenomics.

In certain embodiments, the term "treatment" or "treating" refers to an action that occurs while an individual is suffering from the specified cancer, which reduces the severity of the cancer or the symptoms of the cancer, and/or retards or slows the progression of the cancer. For instance, in certain embodiments, "treatment" or "treat" refers to a 5%, 10%, 25%, 50%, or 100% decrease in the rate of progress of a tumor. In other embodiments, "treatment" refers to a 5%, 10%, 25%, 50%, or 100% decrease in determined tumor burden (i.e., number of cancerous cells present in the individual, and/or the size of the tumor). In yet other embodiments, "treatment" refers to a 5%, 10%, 25%, 50%, or 100% decrease in any physical symptom(s) of a cancer. In yet other embodiments, "treatment" refers to a 5%, 10%, 25%, 50%, or 100% increase in the general health of the individual, as determined by any suitable means, such as cell counts, assay results, or other suitable means. As used herein, the cancer can be any cancer, including those contemplated herein, including, for example, a HER-driven drug-resistant cancer.

As used herein, the term "EGFR" or "ErbB1" or "ErbB-1" or "HER1" refers to epidermal growth factor receptor. The amino acid sequence for the human EGFR (isoform 1; canonical—UniProt ID P00533-1) is recited as SEQ ID NO:1.

The following non-limiting alternative isoforms of EGFR (as relating to the canonical isoform) are also contemplated: Isoform 2 (UniProt ID P00533-2), SEQ ID NO:2; Isoform 3 (UniProt ID P00533-3), SEQ ID NO:3; and Isoform 4 (UniProt ID P00533-4); SEQ ID NO:4.

The nucleotide sequence for the EGFR gene, complete cds, alternatively spliced, is recited as SEQ ID NO:5.

The nucleotide sequence for the EGFR exon 18 is recited as SEQ ID NO:6.

The nucleotide sequence for the EGFR exon 19 is recited as SEQ ID NO:7.

The nucleotide sequence for the EGFR exon 20 is recited as SEQ ID NO:8.

The nucleotide sequence for the EGFR exon 21 is recited as SEQ ID NO:9.

As used herein, the term "ErbB2" or "ErbB-2" or "HER2" or "HER-2" refers to receptor tyrosine-protein kinase erbB-2. The amino acid sequence for the human ErbB2 (isoform 1; canonical—UniProt ID P04626-1) is recited as SEQ ID NO:10.

The following non-limiting alternative isoforms of ErbB2 (as relating to the canonical isoform) are also contemplated: Isoform 2 (UniProt ID P04626-2), SEQ ID NO:11; Isoform 3 (UniProt ID P04626-3), SEQ ID NO:12; Isoform 4 (UniProt ID P04626-4), SEQ ID NO:13; Isoform 5 (UniProt ID P04626-5), SEQ ID NO:14; and Isoform 6 (UniProt ID P04626-6), SEQ ID NO:15.

As used herein, the term "ErbB3" or "ErbB-3" or "HER3" or "HER-3" refers to receptor tyrosine-protein kinase erbB-3. The amino acid sequence for the human ErbB3 (isoform 1; canonical—(UniProt ID P21860-1) is recited as SEQ ID NO:16.

The following non-limiting alternative isoforms of ErbB3 (as relating to the canonical isoform) are also contemplated: Isoform 2 (UniProt ID P21860-2), SEQ ID NO:17; Isoform 3 (UniProt ID P21860-3), SEQ ID NO:18; Isoform 4 (UniProt ID P21860-4), SEQ ID NO:19; and Isoform 5 (UniProt ID P21860-5), SEQ ID NO:20.

As used herein, the term "ErbB4" or "ErbB-4" or "HER4" or "HER-4" refers to receptor tyrosine-protein kinase erbB-4. The amino acid sequence for the human ErbB4 (isoform JM-A CYT-1; canonical—UniProt ID Q15303-1) is recited as SEQ ID NO:21.

The following non-limiting alternative isoforms of ErbB4 (as relating to the canonical isoform) are also contemplated: Isoform JM-B CYT-1 (UniProt ID Q15303-2), SEQ ID NO:22; Isoform JM-A CYT-2 (UniProt ID Q15303-3), SEQ ID NO:23; and Isoform JM-B CYT-2 (UniProt ID Q15303-4), SEQ ID NO:24.

As used herein, the term "NRG1" refers to pro-neuregulin-1. The amino acid sequence for the human NRG1 (isoform 1; canonical—UniProt ID Q02297-1) is recited as SEQ ID NO:25.

The following non-limiting alternative isoforms of NRG1 (as relating to the canonical isoform) are also contemplated: Isoform 2 (UniProt ID Q02297-2), SEQ ID NO:26; Isoform 3 (UniProt ID Q02297-3), SEQ ID NO:27; Isoform 4 (UniProt ID Q02297-4), SEQ ID NO:28; Isoform 6 (UniProt ID Q02297-6), SEQ ID NO:29; Isoform 7 (UniProt ID Q02297-7), SEQ ID NO:30; Isoform 8 (UniProt ID Q02297-8), SEQ ID NO:31; Isoform 9 (UniProt ID Q02297-9), SEQ ID NO:32; Isoform 10 (UniProt ID Q02297-10), SEQ ID NO:33; Isoform 11 (UniProt ID Q02297-11), SEQ ID NO:34; and Isoform 12 (UniProt ID Q02297-12), SEQ ID NO:35.

Throughout this disclosure, various aspects of the disclosure can be presented in a range format. It should be understood that the description in range format is merely for convenience and brevity and should not be construed as an inflexible limitation on the disclosure herein. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.1, 5.3, 5.5, and 6. Thus, for example, reference to a range of 90-100% includes 91-99%, 92-98%, 93-95%, 91-98%, 91-97%, 91-96%, 91-95%, 91-94%, 91-93%, and so forth. Reference to a range of 90-100% also includes 91%, 92%, 93%, 94%, 95%, 96%, 97%, etc., as well as 91.1%, 91.2%, 91.3%, 91.4%, 91.5%, etc., 92.1%, 92.2%, 92.3%, 92.4%, 92.5%, and so forth. A series of ranges are disclosed throughout this document. The use of a series of ranges includes combinations of the upper and lower ranges to provide another range. This construction applies regardless of the breadth of the range and in all contexts throughout this patent document. Thus, for example, reference to a series of ranges such as 5-10, 10-20, 20-30, 30-40, 40-50, 50-75, 75-100, 100-150, includes ranges such as 5-20, 5-30, 5-40, 5-50, 5-75, 5-100, 5-150, and 10-30, 10-40, 10-50, 10-75, 10-100, 10-150, and 20-40, 20-50, 20-75, 20-100, 20-150, and so forth. This applies regardless of the breadth of the range.

Compositions and Methods

Provided herein are compositions and methods using compound of Formula I, II, VII, VIII, IX, X and/or XI, as disclosed herein.

In certain embodiments, the compound is RN-4000 ["(E)-4-((4-((3-bromo-4-chlorophenyl)amino)pyrido[3,4-d]pyrimidin-6-yl)amino)-N,N-dimethyl-N-((1-methyl-4-nitro-1H-imidazol-5-yl)methyl)-4-oxobut-2-en-1-aminium salt (bromide)"; also referred to herein as "(2E)-4-{[4-(3-bromo-4-chloroanilino)pyrido[3,4-d]pyrimidin-6-yl]amino}-N,N-dimethyl-N-[(1-methyl-4-nitro-1H-imidazol-5-yl)methyl]-4-oxo-2-buten-1-ammonium bromide" Compound A], and/or RN-4000E ["(2E)-N-[4-(3-bromo-4-chloroanilino)pyrido[3,4-d]pyrimidin-6-yl]-4-(dimethylamino)-2-butenamide"; also referred to herein "(E)-N-(4-((3-bromo-4-chlorophenyl)amino)pyrido[3,4-d]pyrimidin-6-yl)-4-(dimethylamino) but-2-enamide"; Compound B].

In certain embodiments, the compounds of Formula I, II, VII, VIII, IX, X and/or XI, as disclosed herein, are part of a pharmaceutical composition, which optionally further comprises at least one additional agent that treats or prevents a HER-driven (such as, in a non-limiting example, an EGFR-driven) drug-resistant cancer.

In certain embodiments, Compound A and/or Compound B is part of a pharmaceutical composition, which optionally further comprises at least one additional agent that treats or prevents a HER-driven (such as, in a non-limiting example, an EGFR-driven) drug-resistant cancer.

Also provided herein is a method of treating or preventing HER-driven drug-resistant cancer in a subject. Further provided herein is a method of treating or preventing EGFR-driven drug-resistant cancer in a subject. In certain embodiments, the method comprises administering to the subject in need thereof a therapeutically effective amount of at least one compound contemplated herein, for example, a compound of Formula I, II, VII, VIII, IX, X and/or XI, as disclosed herein, including Compound A and/or Compound B, or a salt or solvate thereof. In other embodiments, the method comprises administering to the subject in need thereof a therapeutically effective amount of Compound A and/or Compound B, or a salt or solvate thereof HER-driven cancers include, but are limited to, cancers caused by a EGFR gene fusion, a EGFR kinase domain duplication, a ERBB2 gene fusion, a ERBB2 mutation, a NRG1 gene fusion, a ERBB3 mutation, and/or a ERBB4 fusion.

The oncogenic alterations involving a ERBB2 (HER2) proto-oncogene are illustrated in Table 1, and each of those alterations is contemplated herein.

TABLE 1

| ERBB2 gene amplification | ERBB2 gene fusions | ERBB2 mutations |
|---|---|---|
| Breast[1] | ZNF207-HER2[2] | G309A/E[3,4] |
| Lung[5,6] | MDK-HER2[2] | S310F/Y[4,7] |
| Gastric/GE Junction[8,9] | NOS2-HER2[2] | V659E/D[10] |
| Esophageal[11] | ERBB2-GRB7[12-14] | G660D[10] |
| Salivary[15,16] | ERBB2-CTTN[17] | K753E[18,19] |
| Ovarian[20] | ERBB2-PPP1R1B[17] | L755P/S[3,7,18,19,21-24] |
| Endometrial[25] | ERBB2-PSMB3[17] | Del755-759[3] |
| Uterine[26] | | L768S[18,19] |
| Pancreatic[27] | | D769H/Y[3] |
| | | V773L[18,19] |
| | | A775_G776insYVMA[24,28,29] |
| | | G776V/L, Cins[28] |
| | | V777L[3,7,21] |
| | | P780Ins[3] |
| | | P780_Y781insGSP[28] |
| | | V842I[3,7,22] |
| | | L866M[7] |
| | | R896C[3] |

References relating to Table 1:
[1]Lebeau, et al., 2001, J Clin Oncol 19: 354-63.
[2]Yu, et al., 2015, J Transl Med 13: 116, 2015.
[3]Bose, et al., 2013, Cancer Discov 3: 224-37.
[4]Greulich, et al., 2012, Proc Natl Acad Sci USA 109: 14476-81.
[5]Li, et al., 2016, J Thorac Oncol 11: 414-9.
[6]Cancer Genome Atlas Research N: Comprehensive molecular profiling of lung adenocarcinoma, 2014, Nature 511: 543-50.
[7]Kavuri, et al., 2015, Cancer Discov 5: 832-41.
[8]Gordon, et al., 2013, Ann Oncol 24: 1754-61.
[9]Das, et al., 2014, Cancer Lett 353: 167-75.
[10]Ou, et al., 2017, J Thorac Oncol 12: 446-457.
[11]Gonzaga, et al., 2012, BMC Cancer 12: 569.
[12]Ross, et al., 2013, Clin Cancer Res 19: 2668-76.
[13]Ross, et al., 2014, Clin Cancer Res 20: 68-75.
[14]Chmielecki, et al., 2015, Oncologist 20: 7-12.
[15]Nardi, et al., 2013, Clin Cancer Res 19: 480-90.
[16]Williams, et al., 2010, Clin Cancer Res 16: 2266-74.
[17]Gao, et al., 2018, Cell Rep 23: 227-238 e3.
[18]Zuo, et al., 2016, Clin Cancer Res 22: 4859-4869.
[19]Verma, et al., 2018, PLoS One 13: e0190942, 2018.

TABLE 1-continued

| ERBB2 gene amplification | ERBB2 gene fusions | ERBB2 mutations |
|---|---|---|

[20]Tuefferd, et al., 2007, PLoS One 2: e1138.
[21]Bellmunt, et al., 2015, Cancer Med 4: 844-52.
[22]Kloth, et al., 2016, Gut 65: 1296-305.
[23]Xu, et al., 2017, Clin Cancer Res 23: 5123-5134.
[24]Stephens, et al., 2004, Nature 431: 525-6.
[25]Morrison, et al., 2006, J Clin Oncol 24: 2376-85.
[26]Slomovitz, et al., 2004, J Clin Oncol 22: 3126-32.
[27]Chou, et al., 2013, Genome Med 5: 78.
[28]Shigematsu, et al., 2005, Cancer Res 65: 1642-6.
[29]Wang, et al., 2006, Cancer Cell 10: 25-38.

Neuregulin 1 (NRG1) encodes a growth factor ligand that binds to the human epidermal growth factor receptor 3 (HER3) encoded by the erb-b2 receptor tyrosine kinase 3 (ERBB3) gene and human epidermal growth factor receptor 4 (HER4) encoded by the erb-b2 receptor tyrosine kinase 4 (ERBB4). Binding of NRG1 to HER3 and HER4 can induce dimerization with other HER family members, including EGFR and HER3. Unlike EGFR, HER2, and HER4, the HER3 kinase domain is catalytically inactive but can activate EGFR or HER2 and thus can initiate oncogene signaling via its heterodimerization partner.

Gene fusions that contain sequences from NRG1 were initially discovered in a breast cancer cell line, MDA-MB-175 (Wang, et al., 1999, Oncogene 18:5718-21). Later CD74-NRG1 fusions were discovered in lung adenocarcinoma (Fernandez-Cuesta L, et al., 2014, Cancer Discov 4:415-22). NRG1 fusions have been identified in breast, NSCLC, cholangiocarcinoma, pancreatic cancer, and ovarian cancer (Wang, et al., 1999, Oncogene 18:5718-21; Fernandez-Cuesta L, et al., 2014, Cancer Discov 4:415-22; Dhanasekaran, et al., 2014, Nat Commun 5:5893; Heining, et al., 2018, Cancer Discov). NRG1 gene fusions have been demonstrated to be oncogenic by inducing overexpression the ligand Neuregulin 1 which induces heterodimerization of HER3 with HER2. Similarly, NRG1 overexpression by gene amplification or other mechanisms are be predicted to activate HER3:HER2 dimers. Tarloxotinib is a potent inhibitor of HER2 and thus inhibits proliferation of cancer cells that utilize HER3/HER2 signaling. Gene fusions involving the ERBB4 gene, similar to other fusions involving receptor tyrosine kinases, induce constitutive activation of HER4 and consequently activation of MAPK (Nakaoku, et al., 2014, Clin Cancer Res 20:3087-93). In certain embodiments, tarloxotinib inhibits HER4 oncogene-driven cancers. Currently there are no U.S. FDA approved (or other regulatory agencies) drugs for NRG1 fusions, NRG1 gene amplification, NRG1 overexpression, ERBB3 activation mutations, or ERBB4 fusions.

The oncogenic alterations involving a NRG1, ERBB3 (HER3) and ERBB4 (HER4) proto-oncogene are illustrated in Table 2, and each of those alterations is contemplated herein.

TABLE 2

| NRG1 gene amplification/ overexpression | NRG1 gene fusions | ERBB3 mutations | ERBB4 fusion |
|---|---|---|---|
| NSCLC[6,9] | DOC4-NRG1[4,9] | V104M[10] | EZR-ERBB4[8] |
| Gastric cancer[11] | CD74-NRG1[5,8,9] | A232V[10] | IKZF2-ERBB4[9] |
| Breast cancer[12] | SLC3A2-NRG1[8] | P262H[10] | BGALT-ERBB4[13] |
| HNSCC[12] | RBPMS-NRG1[6] | G284R[10] | |
| | WRN-NRG1[6] | T389K[10] | |
| | SDC4-NRG1[6,9] | Q809R[10] | |
| | RAB2IL1-NRG1[6] | S846I[10] | |
| | VAMP2-NRG1[14] | E928G[10] | |
| | KIF13B-NRG1[15] | | |
| | ATP1B1-NRG1[7,9,16] | | |
| | CDH6-NRG1[7] | | |
| | APP-NRG1[7] | | |
| | AKAP13-NRG1[9] | | |
| | THBS1-NRG1[9] | | |
| | PDE7A-NRG1[9] | | |
| | THAP7-NRG1[9] | | |
| | SMAD4-NRG1[9] | | |
| | RAB3IL1-NRG1[9] | | |
| | NRG1-PMEPA1[9] | | |
| | NRG1-STMN2[9] | | |

References relating to Table 2:
[4]Wang, et al., 1999, Oncogene 18: 5718-21.
[5]Fernandez-Cuesta, et al., 2014, Cancer Discov 4: 415-22.
[6]Dhanasekaran, et al., 2014, Nat Commun 5: 5893.
[7]Heining, et al., 2018, Cancer Discov.
[8]Nakaoku, et al., 2014, Clin Cancer Res 20: 3087-93.
[9]Drilon, et al., 2018, Cancer Discov 8: 686-695.
[10]Jaiswal, et al., 2013, Cancer Cell 23: 603-17.
[11]Yun, et al., 2018, Gastric Cancer 21: 225-236.
[12]Wilson, et al., 2011, Cancer Cell 20: 158-72.
[13]Guo, et al., 2016, Int J Cancer 139: 373-82.
[14]Jung, et al., 2015, J Thorac Oncol 10: 1107-11.
[15]Xia, et al., 2017, Int J Surg Pathol 25: 238-240.
[16]Jones, et al., 2017, Ann Oncol 28: 3092-3097.

The present application contemplates methods of treating a subject with cancer with the compounds contemplated herein, where an EGFR exon insertion mutation is present in the tumor cells of the subject. The present application also contemplates related uses of such methods.

In certain embodiments, the EGFR exon insertion mutation is an EGFR exon 20 insertion mutation. Cancers with an EGFR insertion mutation exhibit certain characteristics which indicate the presence of the mutation. For example, cancers with EGFR Exon 20 insertion mutations exhibit resistance and/or poor response to EGFR-TKIs such as osimertinib, gefitinib, afatinib, and erlotinib (see, e.g., Takeda et al., 2018, Oncotarget 9(30): 21132, incorporated herein by reference in its entirety). Accordingly, the present application further contemplates methods of treating a subject with cancer with the compounds contemplated herein, wherein the presence of an EGFR insertion mutation in the tumor cells of a subject is indicated by resistance and/or poor response to an oncology agent, such as an EGFR-TKI. An EGFR insertion mutation may also be indicated from a particular phenotype characteristic of the cancer, for example, histopathology, imaging, tumor growth, DNA analysis, RNA analysis, or other diagnostic means, and/or survival rate of the patient (see, e.g., Naidoo et al., 2015, Cancer 121(18): 3212, incorporated herein by reference in its entirety).

The present application further contemplates methods of treating a subject with cancer with the compounds contemplated herein, wherein the treatment is part of a maintenance therapy for subjects with recurring or refractory cancer. For example, the present application contemplates a method of treating a resistant or refractory cancer in a subject with the compounds disclosed herein. In certain embodiments, the treatment leads to a full response, remission, and/or complete cure in the subject with recurring or refractory cancer. In certain embodiments, the treatment maintains a stable disease, leads to a partial response (e.g., some tumor regression), or prevents the return of tumors that have fully regressed. In certain embodiments, the cancer has an EGFR exon insertion mutations. In certain embodiments, the EGFR exon insertion mutation is an EGFR exon 20 insertion mutation. The present application further contemplates methods of treating a subject with cancer with the compounds contemplated herein, where at least one fusion, duplication, or mutation selected from the group consisting of a EGFR gene fusion, a EGFR kinase domain duplication, a ERBB2 gene fusion, a ERBB2 mutation, a NRG1 gene fusion, a ERBB3 mutation, and a ERBB4 fusion is present in the tumor cells of the subject. The present application also contemplates related uses of such methods.

The present application further contemplates methods of treating or preventing a HER-driven drug-resistant cancer in a subject, the method comprising administering to the subject in need thereof a therapeutically effective amount of a compound contemplated herein, wherein at least one fusion, duplication, or mutation selected from the group consisting of a EGFR gene fusion, a EGFR kinase domain duplication, a ERBB2 gene fusion, a ERBB2 mutation, a NRG1 gene fusion, a ERBB3 mutation, and a ERBB4 fusion, is present in the tumor cells of the subject. The present application also contemplates related uses of such methods.

In certain embodiments, the compound of the methods and related uses disclosed herein is of a compound of Formula I, II, VII, VIII, IX, X, and/or XI. In certain embodiments, the compound is of Formula I, II, IX, X, and/or XI. In certain embodiments, the compound is of Formula VII and/or VIII. In certain embodiments, the compound is one of Compounds 12-88 and 91-104. In certain embodiments, the compound is one of Compounds 1-11, 89 and 90. In certain embodiments, the compound is Compound 17. In certain embodiments, the compound is Compound 5. In certain embodiments, the compound is Compound A. In certain embodiments, the compound is Compound B.

In one aspect, the present application provides a method of treating or preventing a HER-driven drug-resistant cancer in a subject, the method comprising administering to the subject in need thereof a therapeutically effective amount of at least one compound selected from the group consisting of (2E)-4-{[4-(3-bromo-4-chloroanilino)pyrido[3,4-d]pyrimidin-6-yl]amino}-N,N-dimethyl-N-[(1-methyl-4-nitro-1H-imidazol-5-yl)methyl]-4-oxo-2-buten-1-ammonium bromide (Compound A), and (2E)-N-[4-(3-bromo-4-chloroanilino)pyrido[3,4-d]pyrimidin-6-yl]-4-(dimethylamino)-2-butenamide (Compound B), or a salt or solvate thereof.

In another aspect, the present application provides a method of treating a HER-driven drug-resistant cancer in a subject with cancer, wherein an EGFR exon 20 insertion mutation is detected in tumor cells of the subject, wherein the method comprises administering a therapeutically effective amount of at least one compound selected from the group consisting of Compound A and Compound B, or a salt or a solvate thereof.

In another aspect, the present application provides a method of treating cancer in a subject with cancer. In other embodiments, the method comprises:
(a) providing tumor cells of the subject;
(b) detecting presence or absence of an EGFR exon 20 insertion mutation in provided tumor cells of the subject;
(c) predicting the subject as being likely to be responsive to treatment by a compound contemplated herein if the EGFR exon 20 insertion mutation is detected;
(d) administering a therapeutically effective amount of a compound contemplated herein to the subject.

In certain embodiments, the cancer is a HER-driven drug-resistant cancer.

In certain embodiments, the compound is Compound A. In certain embodiments, the compound is Compound B.

In another aspect, the present application provides a method of treating cancer in a subject with cancer. In other embodiments, the method comprises:
(a) detecting presence or absence of an EGFR exon 20 insertion mutation in tumor cells of the subject;
(b) predicting the subject as being likely to be responsive to treatment by a compound contemplated herein if the EGFR exon 20 insertion mutation is detected;
(c) administering a therapeutically effective amount of a compound contemplated herein to the subject.

In certain embodiments, the cancer is a HER-driven drug-resistant cancer.

In certain embodiments, the compound is Compound A. In certain embodiments, the compound is Compound B.

In yet another aspect, the present application provides a method of treating cancer in a subject with cancer, where an EGFR exon 20 insertion mutation is detected in tumor cells of the subject. In other embodiments, the method comprises administering a therapeutically effective amount of a compound contemplated herein to the subject. In yet other embodiments, the cancer is a HER-driven drug-resistant cancer. In yet other embodiments, the compound is Compound A or Compound B. In yet another aspect, the present application provides the use of a compound contemplated herein in the manufacture of a composition for the treatment of cancer in a subject with cancer, where an EGFR exon 20 insertion mutation is detected in the tumor cells of the subject. In other embodiments, the present application provides the use of a compound contemplated herein in the manufacture of a composition for the treatment of cancer in a subject with cancer, where an EGFR exon 20 insertion mutation is detected in a sample of tumor cells from the subject. In yet other embodiments, the cancer is a HER-driven drug-resistant cancer. In yet other embodiments, the compound is Compound A or Compound B.

In yet another aspect, the present application provides the use of a compound contemplated herein in the treatment of cancer in a subject with cancer, where an EGFR exon 20 insertion mutation is detected in tumor cells of the subject. In other embodiments, the present application provides the use of a compound contemplated herein in the treatment of cancer in a subject with cancer, where an EGFR exon 20 insertion mutation is detected in a sample of tumor cells of the subject. In yet other embodiments, the cancer is a HER-driven drug-resistant cancer. In yet other embodiments, the compound is Compound A or Compound B.

In yet another aspect, the present application provides a compound contemplated herein for use in the treatment of cancer in a subject with cancer, where an EGFR exon 20 insertion mutation is detected in tumor cells of the subject. In other embodiments, the present application provides a compound contemplated herein for use in the treatment of cancer in a subject with cancer, where an EGFR exon 20 insertion mutation is detected in a sample of tumor cells of the subject. In yet other embodiments, the cancer is a HER-driven drug-resistant cancer. In yet other embodiments, the compound is Compound A or Compound B.

In yet another aspect, the present application provides a compound contemplated herein for use in the treatment of cancer in a subject with cancer, comprising:

(a) providing tumor cells of the subject;
(b) detecting presence or absence of an EGFR exon 20 insertion mutation in the provided tumor cells of the subject; and
(c) administering a therapeutically effective amount of a compound contemplated herein to the subject if the EGFR exon 20 insertion mutation is detected.

In certain embodiments, the cancer is a HER-driven drug-resistant cancer.

In certain embodiments, the compound is Compound A. In certain embodiments, the compound is Compound B.

In yet another aspect, the present application provides a compound contemplated herein for use in the treatment of cancer in a subject with cancer. In certain embodiments, the method comprises:
(a) detecting presence or absence of an EGFR exon 20 insertion mutation in tumor cells of the subject; and
(b) administering a therapeutically effective amount of a compound contemplated herein to the subject if the EGFR exon 20 insertion mutation is detected in the provided tumor cells of the subject.

In certain embodiments, the cancer is a HER-driven drug-resistant cancer.

In certain embodiments, the compound is Compound A. In certain embodiments, the compound is Compound B.

In yet another aspect, the present application provides a method of treating cancer in a subject with cancer. In other embodiments, the method comprises:
(a) providing tumor cells of the subject;
(b) detecting presence or absence of at least one fusion, duplication, or mutation selected from the group consisting of a EGFR gene fusion, a EGFR kinase domain duplication, a ERBB2 gene fusion, a ERBB2 mutation, a NRG1 gene fusion, a ERBB3 mutation, and a ERBB4 fusion in provided tumor cells of the subject;
(c) predicting the subject as being likely to be responsive to treatment by a compound contemplated herein if the at least one fusion, duplication, or mutation is detected;
(d) administering a therapeutically effective amount of a compound contemplated herein to the subject.

In certain embodiments, the cancer is a HER-driven drug-resistant cancer.

In certain embodiments, the compound is Compound A. In certain embodiments, the compound is Compound B.

In another aspect, the present application provides a method of treating cancer in a subject with cancer. In other embodiments, the method comprises:
(a) detecting the presence of at least one fusion, duplication, or mutation selected from the group consisting of a EGFR gene fusion, a EGFR kinase domain duplication, a ERBB2 gene fusion, a ERBB2 mutation, a NRG1 gene fusion, a ERBB3 mutation, and a ERBB4 fusion in tumor cells of the subject;
(b) predicting the subject as being likely to be responsive to treatment by a compound contemplated herein if the at least one fusion, duplication, or mutation is detected;
(c) administering a therapeutically effective amount of a compound contemplated herein to the subject.

In certain embodiments, the cancer is a HER-driven drug-resistant cancer.

In certain embodiments, the compound is Compound A. In certain embodiments, the compound is Compound B.

In yet another aspect, the present application provides a method of treating cancer in a subject with cancer, where at least one fusion, duplication, or mutation selected from the group consisting of a EGFR gene fusion, a EGFR kinase domain duplication, a ERBB2 gene fusion, a ERBB2 muta-tion, a NRG1 gene fusion, a ERBB3 mutation, and a ERBB4 fusion is detected in tumor cells of the subject. In other embodiments, the method comprises administering a therapeutically effective amount of a compound contemplated herein to the subject. In yet other embodiments, the cancer is a HER-driven drug-resistant cancer. In yet other embodiments, the compound is Compound A or Compound B.

In yet another aspect, the present application provides the use of a compound contemplated herein in the manufacture of a composition for the treatment of cancer in a subject with cancer, where at least one fusion, duplication, or mutation selected from the group consisting of a EGFR gene fusion, a EGFR kinase domain duplication, a ERBB2 gene fusion, a ERBB2 mutation, a NRG1 gene fusion, a ERBB3 muta-tion, and a ERBB4 fusion is detected in the tumor cells of the subject. In other embodiments, the present application provides the use of a compound contemplated herein in the manufacture of a composition for the treatment of cancer in a subject with cancer, where at least one fusion, duplication, or mutation selected from the group consisting of a EGFR gene fusion, a EGFR kinase domain duplication, a ERBB2 gene fusion, a ERBB2 mutation, a NRG1 gene fusion, a ERBB3 mutation, and a ERBB4 fusion is detected in a sample of tumor cells from the subject. In yet other embodiments, the cancer is a HER-driven drug-resistant cancer. In yet other embodiments, the compound is Compound A or Compound B.

In yet another aspect, the present application provides the use of a compound contemplated herein in the treatment of cancer in a subject with cancer, where at least one fusion, duplication, or mutation selected from the group consisting of a EGFR gene fusion, a EGFR kinase domain duplication, a ERBB2 gene fusion, a ERBB2 mutation, a NRG1 gene fusion, a ERBB3 mutation, and a ERBB4 fusion is detected in tumor cells of the subject. In other embodiments, the present application provides the use of a compound contemplated herein in the treatment of cancer in a subject with cancer, where at least one fusion, duplication, or mutation selected from the group consisting of a EGFR gene fusion, a EGFR kinase domain duplication, a ERBB2 gene fusion, a ERBB2 mutation, a NRG1 gene fusion, a ERBB3 muta-tion, and a ERBB4 fusion is detected in a sample of tumor cells of the subject. In yet other embodiments, the cancer is a HER-driven drug-resistant cancer. In yet other embodiments, the compound is Compound A or Compound B.

In yet another aspect, the present application provides a compound contemplated herein for use in the treatment of cancer in a subject with cancer, where at least one fusion, duplication, or mutation selected from the group consisting of a EGFR gene fusion, a EGFR kinase domain duplication, a ERBB2 gene fusion, a ERBB2 mutation, a NRG1 gene fusion, a ERBB3 mutation, and a ERBB4 fusion is detected in tumor cells of the subject. In other embodiments, the present application provides a compound contemplated herein for use in the treatment of cancer in a subject with cancer, where at least one fusion, duplication, or mutation selected from the group consisting of a EGFR gene fusion, a EGFR kinase domain duplication, a ERBB2 gene fusion, a ERBB2 mutation, a NRG1 gene fusion, a ERBB3 muta-tion, and a ERBB4 fusion is detected in a sample of tumor cells of the subject. In yet other embodiments, the cancer is a HER-driven drug-resistant cancer. In yet other embodiments, the compound is Compound A or Compound B.

In yet another aspect, the present application provides a compound contemplated herein for use in the treatment of cancer in a subject with cancer, comprising:

(a) providing tumor cells of the subject;

(b) detecting presence or absence of at least one fusion, duplication, or mutation selected from the group consisting of a EGFR gene fusion, a EGFR kinase domain duplication, a ERBB2 gene fusion, a ERBB2 mutation, a NRG1 gene fusion, a ERBB3 mutation, and a ERBB4 fusion in the provided tumor cells of the subject; and (c) administering a therapeutically effective amount of a compound contemplated herein to the subject if the at least one fusion, duplication, or mutation is detected.

In certain embodiments, the cancer is a HER-driven drug-resistant cancer.

In certain embodiments, the compound is Compound A. In certain embodiments, the compound is Compound B.

In yet another aspect, the present application provides a compound contemplated herein for use in the treatment of cancer in a subject with cancer. In certain embodiments, the method comprises:

(a) detecting the presence of at least one fusion, duplication, or mutation selected from the group consisting of a EGFR gene fusion, a EGFR kinase domain duplication, a ERBB2 gene fusion, a ERBB2 mutation, a NRG1 gene fusion, a ERBB3 mutation, and a ERBB4 fusion in tumor cells of the subject; and (b) administering a therapeutically effective amount of a compound contemplated herein to the subject if the at least one fusion, duplication, or mutation is detected in the provided tumor cells of the subject.

In certain embodiments, the cancer is a HER-driven drug-resistant cancer.

In certain embodiments, the compound is Compound A. In certain embodiments, the compound is Compound B.

In certain embodiments, the subject is further administered at least one additional agent, or a salt or solvate thereof, that treats or prevents the drug-resistant cancer. Non-limiting examples of additional anti-proliferative agents contemplated include, but are not limited to, compounds listed on the cancer chemotherapy drug regimens in the 14$^{th}$ Edition of the Merck Index (2006), which is hereby incorporated by reference, such as asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, and vindesine. Additional anti-proliferative agents include other molecular targeted agents that modulate parallel pathways such as MEK 1/2 inhibitors, AKT inhibitors and mTOR inhibitors, monoclonal antibodies (such as Cetuximab), oxaliplatin, gemcitabine, gefinitib, taxotere, ara A, ara C, herceptin, BCNU, CCNU, DTIC, and actinomycin D. Still further anti-proliferative agents include but are not limited to those compounds acknowledged to be used in the treatment of neoplastic diseases in Goodman and Gilman's The Pharmacological Basis of Therapeutics (Eleventh Edition), editor Molinoff et al., publ. by McGraw-Hill, pages 1225-1287 (2006), which is hereby incorporated by reference, such as aminoglutethimide, L-asparaginase, azathioprine, 5-azacytidine cladribine, busulfan, diethylstilbestrol, 2″,2″-difluorodeoxycytidine, docetaxel, erythrohydroxynonyladenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, tenipdside, testosterone propionate, thiotepa, trimethylmelamine, uridine, and vinorelbine.

In certain embodiments, a compound of any one of Formulas I, II, VII, VIII, IX, X and/or XI, as disclosed herein, and at least one additional agent, are co-administered to the subject. In other embodiments, a compound of any one of Formulas I, II, VII, VIII, IX, X and/or XI, as disclosed herein, and at least one additional agent, are co-formulated.

In certain embodiments, Compound A or Compound B, and at least one additional agent, are co-administered to the subject. In other embodiments, Compound A or Compound B, and at least one additional agent, are co-formulated.

In certain embodiments, a compound of any one of Formulas I, II, VII, VIII, IX, X and/or XI, as disclosed herein, is administered by at least one route selected from the group consisting of inhalational, oral, nasal, rectal, parenteral, sublingual, transdermal, transmucosal, intravesical, intrapulmonary, intraduodenal, intragastrical, intrathecal, epidural, intrapleural, intraperitoneal, intratracheal, otic, intraocular, subcutaneous, intramuscular, intradermal, intraarterial, intravenous, intrabronchial, inhalation, and topical. In other embodiments, the subject is a mammal. In yet other embodiments, the mammal is a human. In certain embodiments, the subject is a human in need of treatment thereof.

In certain embodiments, Compound A or Compound B is administered by at least one route selected from the group consisting of inhalational, oral, nasal, rectal, parenteral, sublingual, transdermal, transmucosal, intravesical, intrapulmonary, intraduodenal, intragastrical, intrathecal, epidural, intrapleural, intraperitoneal, intratracheal, otic, intraocular, subcutaneous, intramuscular, intradermal, intraarterial, intravenous, intrabronchial, inhalation, and topical. In other embodiments, the subject is a mammal. In yet other embodiments, the mammal is a human. In certain embodiments, the subject is a human in need of treatment thereof.

Also provided herein is a kit comprising a compound of any one of Formulas I, II, VII, VIII, IX, X and/or XI, as disclosed herein, an applicator and instructional material for use thereof, wherein the instructional material comprises instructions for preventing or treating HER-driven drug-resistant cancers.

Further provided herein is a kit comprising Compound A or Compound B, an applicator and instructional material for use thereof, wherein the instructional material comprises instructions for preventing or treating HER-driven drug-resistant cancers.

Salts

The compounds described herein may form salts with acids, and such salts are included in the present application. In one embodiment, the salts are pharmaceutically acceptable salts. The term "salts" embraces addition salts of free acids that are useful within the methods disclosed herein. The term "pharmaceutically acceptable salt" refers to salts that possess toxicity profiles within a range that affords utility in pharmaceutical applications. Pharmaceutically unacceptable salts may nonetheless possess properties such as high crystallinity, which have utility in the practice of the present application, such as for example utility in process of synthesis, purification or formulation of compounds useful within the methods disclosed herein.

Suitable pharmaceutically acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric, galacturonic acid, glycerophosphonic acids and saccharin (e.g., saccharinate, saccharate). Salts may be comprised of a fraction of one, one or more than one molar equivalent of acid or base with respect to any compound contemplated herein.

Suitable pharmaceutically acceptable base addition salts of compounds contemplated herein include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

Predictive/Identification Methods

The present application also contemplates methods of predicting responsiveness of a subject with cancer to treatment with a compound contemplated herein.

In certain embodiments, the compound is of a compound of Formula I, II, VII, VIII, IX, X and/or XI. In certain embodiments, the compound is of Formula I, II, IX, X and/or XI. In certain embodiments, the compound is of Formula VII and/or VIII. In certain embodiments, the compound is one of Compounds 12-88 and 91-104. In certain embodiments, the compound is one of Compounds 1-11, 89 and 90. In certain embodiments, the compound is Compound 17. In certain embodiments, the compound is Compound 5. In certain embodiments, the compound is Compound A. In certain embodiments, the compound is Compound B.

In one aspect, the present application provides a method of predicting the responsiveness of a subject with cancer to treatment with a compound contemplated herein. In certain embodiments, the method comprises:
(a) providing tumor cells of the subject;
(b) detecting presence or absence of an EGFR exon 20 insertion mutation in the provided tumor cells of the subject;
(c) predicting the subject as being likely to be responsive to a treatment with a compound contemplated herein if the EGFR exon 20 insertion mutation is detected in the provided tumor cells of the subject.

In certain embodiments, the compound is Compound A. In certain embodiments, the compound is Compound B.

In another aspect, the present application provides a method of predicting the responsiveness of a subject with cancer to treatment with a compound contemplated herein. In certain embodiments, the method comprises:
(a) detecting presence or absence of an EGFR exon 20 insertion mutation in a sample from the subject, wherein the sample comprises tumor cells;
(b) predicting the subject as being likely to be responsive to a treatment with a compound contemplated herein if the EGFR exon 20 insertion mutation is detected in the sample from the subject.

In certain embodiments, the compound is Compound A. In certain embodiments, the compound is Compound B.

In yet another aspect, the present application provides a method of predicting the responsiveness of a subject with cancer to treatment with a compound contemplated herein. In certain embodiments, the method comprises:
(a) detecting presence or absence of an EGFR exon 20 insertion mutation in tumor cells of the subject; and
(b) predicting the subject as being likely to be responsive to treatment with a compound contemplated herein if an EGFR exon 20 insertion mutation is detected in the tumor cells of the subject.

In certain embodiments, the compound is Compound A. In certain embodiments, the compound is Compound B.

In yet another aspect, the present application provides a method of predicting the responsiveness of a subject with cancer to treatment with a compound contemplated herein. In certain embodiments, the method comprises:
(a) detecting presence or absence of an EGFR exon 20 insertion mutation in a sample of tumor cells from the subject; and
(b) predicting the subject as being likely to be responsive to treatment with a compound contemplated herein if the EGFR exon 20 insertion mutation is detected in the sample of tumor cells from the subject.

In certain embodiments, the compound is Compound A. In certain embodiments, the compound is Compound B.

In yet another aspect, the present application provides a method of predicting the responsiveness of a subject with cancer to treatment with a compound contemplated herein. In certain embodiments, the method comprises:
(a) providing tumor cells of the subject;
(b) detecting presence or absence of an EGFR exon 20 insertion mutation in the provided tumor cells of the subject;
wherein the subject is likely to be responsive to the treatment with a compound contemplated herein if the EGFR exon 20 insertion mutation is detected in the provided tumor cells of the subject.

In certain embodiments, the compound is Compound A. In certain embodiments, the compound is Compound B.

In yet another aspect, the present application provides a method of predicting the responsiveness of a subject with cancer to treatment with a compound contemplated herein. In certain embodiments, the method comprises detecting presence or absence of an EGFR exon 20 insertion mutation in tumor cells of the subject;
wherein the subject is likely to be responsive to the treatment with a compound contemplated herein if the EGFR exon 20 insertion mutation is detected in the tumor cells of the subject.

In certain embodiments, the compound is Compound A. In certain embodiments, the compound is Compound B.

In yet another aspect, the present application provides a method of predicting the responsiveness of a subject with cancer to treatment with a compound contemplated herein. In certain embodiments, the method comprises detecting presence or absence of an EGFR exon 20 insertion mutation in a sample of tumor cells from the subject;
wherein the subject is likely to be responsive to the treatment with a compound contemplated herein if the EGFR exon 20 insertion mutation is detected in the sample of tumor cells from the subject.

In certain embodiments, the compound is Compound A. In certain embodiments, the compound is Compound B.

In yet another aspect, the present application provides a method of predicting the responsiveness of a subject with cancer to treatment with a compound contemplated herein. In certain embodiments, the method comprises:

(a) providing tumor cells of the subject; and (b) detecting presence or absence of an EGFR exon 20 insertion mutation in the provided tumor cells of the subject;

wherein the presence of an EGFR exon 20 insertion mutation in the provided tumor cells of the subject correlates with an increased likelihood of responsiveness or an increased responsiveness of the subject to the treatment.

In certain embodiments, the compound is Compound A. In certain embodiments, the compound is Compound B.

In certain embodiments of the various methods provided herein, the prediction of the responsiveness of the subject with cancer to treatment by a compound contemplated herein is made by detecting the presence of an EGFR exon 20 insertion mutation in the tumor cells. In other embodiments, the method further comprises administration of a compound contemplated herein to the subject. In yet other embodiments, the method further comprises administration of a compound contemplated herein to the subject if the subject is predicted to be likely to be responsive to the treatment. In yet other embodiments, a compound contemplated herein is administered in an therapeutically effective amount.

The present application also contemplates methods of predicting whether a subject with cancer is likely to be responsive to treatment with a compound contemplated herein.

In one aspect, the present application provides a method of predicting whether a subject with cancer is likely to be responsive to treatment with a compound contemplated herein. In certain embodiments, the method comprises:

(a) providing tumor cells of the subject;

(b) detecting presence or absence of an EGFR exon 20 insertion mutation in the provided tumor cells of the subject;

(c) predicting the subject as being likely to be responsive to a treatment with a compound contemplated herein if the EGFR exon 20 insertion mutation is detected in the provided tumor cells of the subject.

In certain embodiments, the compound is Compound A. In certain embodiments, the compound is Compound B.

In another aspect, the present application provides a method of predicting whether a subject with cancer is likely to be responsive to treatment with a compound contemplated herein. In certain embodiments, the method comprises:

(a) detecting presence or absence of an EGFR exon 20 insertion mutation in a sample from the subject, wherein the sample comprises tumor cells;

(b) predicting the subject as being likely to be responsive to a treatment with a compound contemplated herein if the EGFR exon 20 insertion mutation is detected in the sample from the subject.

In certain embodiments, the compound is Compound A. In certain embodiments, the compound is Compound B.

In yet another aspect, the present application provides a method of predicting whether a subject with cancer is likely to be responsive to treatment with a compound contemplated herein. In certain embodiments, the method comprises:

(a) detecting presence or absence of an EGFR exon 20 insertion mutation in tumor cells of the subject; and (b) predicting the subject as being likely to be responsive to treatment with a compound contemplated herein if an EGFR exon 20 insertion mutation is detected in the tumor cells of the subject.

In certain embodiments, the compound is Compound A. In certain embodiments, the compound is Compound B.

In yet another aspect, the present application provides a method of predicting whether a subject with cancer is likely to be responsive to treatment with a compound contemplated herein. In certain embodiments, the method comprises:

(a) detecting presence or absence of an EGFR exon 20 insertion mutation in a sample of tumor cells from the subject; and (b) predicting the subject as being likely to be responsive to treatment with a compound contemplated herein if the EGFR exon 20 insertion mutation is detected in the sample of tumor cells from the subject.

In certain embodiments, the compound is Compound A. In certain embodiments, the compound is Compound B.

In yet another aspect, the present application provides a method of predicting whether a subject with cancer is likely to be responsive to treatment with a compound contemplated herein. In certain embodiments, the method comprises:

(a) providing tumor cells of the subject;

(b) detecting presence or absence of an EGFR exon 20 insertion mutation in the provided tumor cells;

wherein the subject is likely to be responsive to the treatment with a compound contemplated herein if the EGFR exon 20 insertion mutation is detected in the provided cells.

In certain embodiments, the compound is Compound A. In certain embodiments, the compound is Compound B.

In yet another aspect, the present application provides a method of predicting whether a subject with cancer is likely to be responsive to treatment with a compound contemplated herein. In certain embodiments, the method comprises detecting presence or absence of an EGFR exon 20 insertion mutation in tumor cells of the subject;

wherein the subject is likely to be responsive to the treatment with a compound contemplated herein if the EGFR exon 20 insertion mutation is detected.

In certain embodiments, the compound is Compound A. In certain embodiments, the compound is Compound B.

In another aspect, the present application provides a method of predicting whether a subject with cancer is likely to be responsive to treatment with a compound contemplated herein. In certain embodiments, the method comprises detecting presence or absence of an EGFR exon 20 insertion mutation in a sample of tumor cells from the subject;

wherein the subject is likely to be responsive to the treatment with a compound contemplated herein if the EGFR exon 20 insertion mutation is detected.

In certain embodiments, the compound is Compound A. In certain embodiments, the compound is Compound B.

In another aspect, the present application provides a method of predicting whether a subject with cancer is likely to be responsive to treatment with a compound contemplated herein. In certain embodiments, the method comprises:

(a) providing tumor cells of the subject; and (b) detecting presence or absence of an EGFR exon 20 insertion mutation in the tumor cells;

wherein the presence of the EGFR exon 20 insertion mutation correlates with an increased likelihood of responsiveness or an increased responsiveness of the subject to the treatment.

In certain embodiments, the compound is Compound A. In certain embodiments, the compound is Compound B.

In certain embodiments of the various methods provided herein, the prediction of whether a subject with cancer is likely to be responsive to treatment by a compound contemplated herein is made by detecting the presence of an EGFR exon 20 insertion mutation in the tumor cells. In other embodiments, the method further comprises administration of a compound contemplated herein to the subject. In yet other embodiments, the method further comprises administration of a compound contemplated herein to the subject if the subject is predicted to be likely to be responsive to the treatment. In yet other embodiments, a compound contemplated herein is administered in a therapeutically effective amount.

The present application also contemplates methods of identifying a subject with cancer who is likely to be responsive to treatment with a compound contemplated herein.

In one aspect, the present application provides a method of identifying a subject with cancer who is likely to be responsive to treatment with a compound contemplated herein. In certain embodiments, the method comprises:
(a) providing tumor cells of the subject;
(b) detecting presence or absence of an EGFR exon 20 insertion mutation in the provided tumor cells;
(c) identifying the subject as being likely to be responsive to treatment with a compound contemplated herein if the EGFR exon 20 insertion mutation is detected in the provided tumor cells.

In certain embodiments, the compound is Compound A. In certain embodiments, the compound is Compound B.

In another aspect, the present application provides a method of identifying a subject with cancer who is likely to be responsive to treatment with a compound contemplated herein. In certain embodiments, the method comprises:
(a) detecting presence or absence of an EGFR exon 20 insertion mutation in a sample from the subject, wherein the sample comprises tumor cells;
(b) identifying the subject as being likely to be responsive to a treatment with a compound contemplated herein if the EGFR exon 20 insertion mutation is detected in the sample from the subject.

In certain embodiments, the compound is Compound A. In certain embodiments, the compound is Compound B.

In yet another aspect, the present application provides a method of identifying a subject with cancer who is likely to be responsive to treatment with a compound contemplated herein. In certain embodiments, the method comprises:
(a) detecting presence or absence of an EGFR exon 20 insertion mutation in tumor cells of the subject; and
(b) identifying the subject as being likely to be responsive to a treatment with a compound contemplated herein if the EGFR exon 20 insertion mutation is detected in the tumor cells of the subject.

In certain embodiments, the compound is Compound A. In certain embodiments, the compound is Compound B.

In another aspect, the present application provides a method of identifying a subject with cancer who is likely to be responsive to treatment with a compound contemplated herein. In certain embodiments, the method comprises:
(a) detecting presence or absence of an EGFR exon 20 insertion mutation in a sample of tumor cells from the subject; and
(b) identifying the subject as being likely to be responsive to a treatment with a compound contemplated herein if the EGFR exon 20 insertion mutation is detected in the sample.

In certain embodiments, the compound is Compound A. In certain embodiments, the compound is Compound B.

In another aspect, the present application provides a method of identifying a subject with cancer who is likely to be responsive to treatment with a compound contemplated herein. In certain embodiments, the method comprises:
(a) providing tumor cells of the subject;
(b) detecting presence or absence of an EGFR exon 20 insertion mutation in the provided tumor cells;
wherein the subject is identified as likely to be responsive to the treatment with a compound contemplated herein if the EGFR exon 20 insertion mutation is detected in the provided tumor cells.

In certain embodiments, the compound is Compound A. In certain embodiments, the compound is Compound B.

In another aspect, the present application provides a method of identifying a subject with cancer who is likely to be responsive to treatment with a compound contemplated herein. In certain embodiments, the method comprises detecting presence or absence of an EGFR exon 20 insertion mutation in tumor cells of the subject;
wherein the subject is identified as likely to be responsive to the treatment with a compound contemplated herein if the EGFR exon 20 insertion mutation is detected in the tumor cells.

In certain embodiments, the compound is Compound A. In certain embodiments, the compound is Compound B.

In another aspect, the present application provides a method of identifying a subject with cancer who is likely to be responsive to treatment with a compound contemplated herein. In certain embodiments, the method comprises detecting presence or absence of an EGFR exon 20 insertion mutation in a sample of tumor cells from the subject;
wherein the subject is identified as likely to be responsive to the treatment with a compound contemplated herein if the EGFR exon 20 insertion mutation is detected in the sample.

In certain embodiments, the compound is Compound A. In certain embodiments, the compound is Compound B.

In another aspect, the present application provides a method of identifying a subject with cancer who is likely to be responsive to treatment with a compound contemplated herein. In certain embodiments, the method comprises:
(a) providing tumor cells of the subject; and
(b) detecting presence or absence of an EGFR exon 20 insertion mutation in the provided tumor cells;
wherein the presence of an EGFR exon 20 insertion mutation identifies the subject as likely to be responsive to the treatment with a compound contemplated herein.

In certain embodiments, the compound is Compound A. In certain embodiments, the compound is Compound B.

In certain embodiments of the various methods provided herein, the identification of a subject with cancer who is likely to be responsive to treatment by a compound contemplated herein is made by detecting the presence of an EGFR exon 20 insertion mutation in the tumor cells. In other embodiments, the method further comprises administration of a compound contemplated herein to the subject. In yet other embodiments, the method further comprises administration of a compound contemplated herein to the subject that is identified to be likely to be responsive to the treatment. In yet other embodiments, a compound contemplated herein is administered in a therapeutically effective amount.

In yet another aspect, provided herein is a method for determining whether a subject with cancer is sensitive to a treatment with a compound contemplated herein. In certain embodiments, the method comprises:
(a) providing tumor cells of the subject;
(b) detecting presence or absence of an EGFR exon 20 insertion mutation in the provided tumor cells;

(c) diagnosing the subject as being sensitive to the treatment with a compound contemplated herein if the EGFR exon 20 insertion mutation is detected in the provided tumor cells.

In certain embodiments, the compound is Compound A. In certain embodiments, the compound is Compound B.

In certain embodiments, the method further comprises administration of a compound contemplated herein to the subject. In other embodiments, the method further comprises administration of a compound contemplated herein to the subject if the subject is determined to be sensitive to the treatment. In yet other embodiments, a compound contemplated herein is administered in a therapeutically effective amount.

In yet another aspect, the present application provides a method of determining whether a subject with cancer is sensitive to treatment with a compound contemplated herein. In certain embodiments, the method comprises:
(a) providing tumor cells of the subject;
(b) detecting presence or absence of an EGFR exon 20 insertion mutation in the provided tumor cells;
(c) diagnosing the subject as being sensitive to treatment with a compound contemplated herein if the EGFR exon 20 insertion mutation is detected in the provided tumor cells.

In certain embodiments, the compound is Compound A. In certain embodiments, the compound is Compound B.

In certain embodiments, the method further comprises administration of a compound contemplated herein to the subject. In other embodiments, the method further comprises administration of a compound contemplated herein to the subject if the subject is determined to be sensitive to the treatment. In yet other embodiments, a compound contemplated herein is administered in a therapeutically effective amount.

In yet another aspect, the present application provides a method of determining whether a subject with cancer is sensitive to treatment with a compound contemplated herein. In certain embodiments, the method comprises:
(a) detecting presence or absence of an EGFR exon 20 insertion mutation in a sample from the subject, wherein the sample comprises tumor cells;
(b) diagnosing the subject as being sensitive to treatment with a compound contemplated herein if the EGFR exon 20 insertion mutation is detected in the sample.

In certain embodiments, the compound is Compound A. In certain embodiments, the compound is Compound B.

In one aspect, the present application provides a method of predicting the responsiveness of a subject with cancer to treatment with a compound contemplated herein. In certain embodiments, the method comprises:
(a) providing tumor cells of the subject;
(b) detecting presence or absence of at least one fusion, duplication, or mutation selected from the group consisting of a EGFR gene fusion, a EGFR kinase domain duplication, a ERBB2 gene fusion, a ERBB2 mutation, a NRG1 gene fusion, a ERBB3 mutation, and a ERBB4 fusion mutation in the provided tumor cells of the subject;
(c) predicting the subject as being likely to be responsive to a treatment with a compound contemplated herein if the at least one fusion, duplication, or mutation is detected in the provided tumor cells of the subject.

In certain embodiments, the compound is Compound A. In certain embodiments, the compound is Compound B.

In another aspect, the present application provides a method of predicting the responsiveness of a subject with cancer to treatment with a compound contemplated herein. In certain embodiments, the method comprises:
(a) detecting presence or absence of at least one fusion, duplication, or mutation selected from the group consisting of a EGFR gene fusion, a EGFR kinase domain duplication, a ERBB2 gene fusion, a ERBB2 mutation, a NRG1 gene fusion, a ERBB3 mutation, and a ERBB4 fusion mutation in a sample from the subject, wherein the sample comprises tumor cells;
(b) predicting the subject as being likely to be responsive to a treatment with a compound contemplated herein if the at least one fusion, duplication, or mutation is detected in the sample from the subject.

In certain embodiments, the compound is Compound A. In certain embodiments, the compound is Compound B.

In yet another aspect, the present application provides a method of predicting the responsiveness of a subject with cancer to treatment with a compound contemplated herein. In certain embodiments, the method comprises:
(a) detecting presence or absence of at least one fusion, duplication, or mutation selected from the group consisting of a EGFR gene fusion, a EGFR kinase domain duplication, a ERBB2 gene fusion, a ERBB2 mutation, a NRG1 gene fusion, a ERBB3 mutation, and a ERBB4 fusion in tumor cells of the subject; and
(b) predicting the subject as being likely to be responsive to treatment with a compound contemplated herein if the at least one fusion, duplication, or mutation is detected in the tumor cells of the subject.

In certain embodiments, the compound is Compound A. In certain embodiments, the compound is Compound B.

In yet another aspect, the present application provides a method of predicting the responsiveness of a subject with cancer to treatment with a compound contemplated herein. In certain embodiments, the method comprises:
(a) detecting presence or absence of at least one fusion, duplication, or mutation selected from the group consisting of a EGFR gene fusion, a EGFR kinase domain duplication, a ERBB2 gene fusion, a ERBB2 mutation, a NRG1 gene fusion, a ERBB3 mutation, and a ERBB4 fusion in a sample of tumor cells from the subject; and
(b) predicting the subject as being likely to be responsive to treatment with a compound contemplated herein if the at least one fusion, duplication, or mutation is detected in the sample of tumor cells from the subject.

In certain embodiments, the compound is Compound A. In certain embodiments, the compound is Compound B.

In yet another aspect, the present application provides a method of predicting the responsiveness of a subject with cancer to treatment with a compound contemplated herein. In certain embodiments, the method comprises:
(a) providing tumor cells of the subject;
(b) detecting presence or absence of at least one fusion, duplication, or mutation selected from the group consisting of a EGFR gene fusion, a EGFR kinase domain duplication, a ERBB2 gene fusion, a ERBB2 mutation, a NRG1 gene fusion, a ERBB3 mutation, and a ERBB4 fusion in the provided tumor cells of the subject;
wherein the subject is likely to be responsive to the treatment with a compound contemplated herein if the at least one fusion, duplication, or mutation is detected in the provided tumor cells of the subject.

In certain embodiments, the compound is Compound A. In certain embodiments, the compound is Compound B.

In yet another aspect, the present application provides a method of predicting the responsiveness of a subject with cancer to treatment with a compound contemplated herein.

In certain embodiments, the method comprises detecting presence or absence of at least one fusion, duplication, or mutation selected from the group consisting of a EGFR gene fusion, a EGFR kinase domain duplication, a ERBB2 gene fusion, a ERBB2 mutation, a NRG1 gene fusion, a ERBB3 mutation, and a ERBB4 fusion in tumor cells of the subject;

wherein the subject is likely to be responsive to the treatment with a compound contemplated herein if the at least one fusion, duplication, or mutation is detected in the tumor cells of the subject.

In certain embodiments, the compound is Compound A. In certain embodiments, the compound is Compound B.

In yet another aspect, the present application provides a method of predicting the responsiveness of a subject with cancer to treatment with a compound contemplated herein. In certain embodiments, the method comprises detecting presence or absence of at least one fusion, duplication, or mutation selected from the group consisting of a EGFR gene fusion, a EGFR kinase domain duplication, a ERBB2 gene fusion, a ERBB2 mutation, a NRG1 gene fusion, a ERBB3 mutation, and a ERBB4 fusion in a sample of tumor cells from the subject;

wherein the subject is likely to be responsive to the treatment with a compound contemplated herein if at least one fusion, duplication, or mutation is detected in the sample of tumor cells from the subject.

In certain embodiments, the compound is Compound A. In certain embodiments, the compound is Compound B.

In yet another aspect, the present application provides a method of predicting the responsiveness of a subject with cancer to treatment with a compound contemplated herein. In certain embodiments, the method comprises:

(a) providing tumor cells of the subject; and (b) detecting presence or absence of at least one fusion, duplication, or mutation selected from the group consisting of a EGFR gene fusion, a EGFR kinase domain duplication, a ERBB2 gene fusion, a ERBB2 mutation, a NRG1 gene fusion, a ERBB3 mutation, and a ERBB4 fusion in the provided tumor cells of the subject;

wherein the presence of the at least one fusion, duplication, or mutation in the provided tumor cells of the subject correlates with an increased likelihood of responsiveness or an increased responsiveness of the subject to the treatment.

In certain embodiments, the compound is Compound A. In certain embodiments, the compound is Compound B.

In certain embodiments of the various methods provided herein, the prediction of the responsiveness of the subject with cancer to treatment by a compound contemplated herein is made by detecting the presence of at least one fusion, duplication, or mutation selected from the group consisting of a EGFR gene fusion, a EGFR kinase domain duplication, a ERBB2 gene fusion, a ERBB2 mutation, a NRG1 gene fusion, a ERBB3 mutation, and a ERBB4 fusion in the tumor cells. In other embodiments, the method further comprises administration of a compound contemplated herein to the subject. In yet other embodiments, the method further comprises administration of a compound contemplated herein to the subject if the subject is predicted to be likely to be responsive to the treatment. In yet other embodiments, a compound contemplated herein is administered in an therapeutically effective amount.

The present application also contemplates methods of predicting whether a subject with cancer is likely to be responsive to treatment with a compound contemplated herein.

In one aspect, the present application provides a method of predicting whether a subject with cancer is likely to be responsive to treatment with a compound contemplated herein. In certain embodiments, the method comprises:

(a) providing tumor cells of the subject;

(b) detecting presence or absence of at least one fusion, duplication, or mutation selected from the group consisting of a EGFR gene fusion, a EGFR kinase domain duplication, a ERBB2 gene fusion, a ERBB2 mutation, a NRG1 gene fusion, a ERBB3 mutation, and a ERBB4 fusion in the provided tumor cells of the subject;

(c) predicting the subject as being likely to be responsive to a treatment with a compound contemplated herein if the at least one fusion, duplication, or mutation is detected in the provided tumor cells of the subject.

In certain embodiments, the compound is Compound A. In certain embodiments, the compound is Compound B.

In another aspect, the present application provides a method of predicting whether a subject with cancer is likely to be responsive to treatment with a compound contemplated herein. In certain embodiments, the method comprises:

(a) detecting presence or absence of at least one fusion, duplication, or mutation selected from the group consisting of a EGFR gene fusion, a EGFR kinase domain duplication, a ERBB2 gene fusion, a ERBB2 mutation, a NRG1 gene fusion, a ERBB3 mutation, and a ERBB4 fusion in a sample from the subject, wherein the sample comprises tumor cells;

(b) predicting the subject as being likely to be responsive to a treatment with a compound contemplated herein if the at least one fusion, duplication, or mutation is detected in the sample from the subject.

In certain embodiments, the compound is Compound A. In certain embodiments, the compound is Compound B.

In yet another aspect, the present application provides a method of predicting whether a subject with cancer is likely to be responsive to treatment with a compound contemplated herein. In certain embodiments, the method comprises:

(a) detecting presence or absence of at least one fusion, duplication, or mutation selected from the group consisting of a EGFR gene fusion, a EGFR kinase domain duplication, a ERBB2 gene fusion, a ERBB2 mutation, a NRG1 gene fusion, a ERBB3 mutation, and a ERBB4 fusion in tumor cells of the subject; and (b) predicting the subject as being likely to be responsive to treatment with a compound contemplated herein if the at least one fusion, duplication, or mutation is detected in the tumor cells of the subject.

In certain embodiments, the compound is Compound A. In certain embodiments, the compound is Compound B.

In yet another aspect, the present application provides a method of predicting whether a subject with cancer is likely to be responsive to treatment with a compound contemplated herein. In certain embodiments, the method comprises:

(a) detecting presence or absence of at least one fusion, duplication, or mutation selected from the group consisting of a EGFR gene fusion, a EGFR kinase domain duplication, a ERBB2 gene fusion, a ERBB2 mutation, a NRG1 gene fusion, a ERBB3 mutation, and a ERBB4 fusion in a sample of tumor cells from the subject; and (b) predicting the subject as being likely to be responsive to treatment with a compound contemplated herein if the at least one fusion, duplication, or mutation is detected in the sample of tumor cells from the subject.

In certain embodiments, the compound is Compound A. In certain embodiments, the compound is Compound B.

In yet another aspect, the present application provides a method of predicting whether a subject with cancer is likely to be responsive to treatment with a compound contemplated herein. In certain embodiments, the method comprises:

(a) providing tumor cells of the subject;

(b) detecting presence or absence of at least one fusion, duplication, or mutation selected from the group consisting of a EGFR gene fusion, a EGFR kinase domain duplication, a ERBB2 gene fusion, a ERBB2 mutation, a NRG1 gene fusion, a ERBB3 mutation, and a ERBB4 fusion in the provided tumor cells;

wherein the subject is likely to be responsive to the treatment with a compound contemplated herein if the at least one fusion, duplication, or mutation is detected in the provided cells.

In certain embodiments, the compound is Compound A. In certain embodiments, the compound is Compound B.

In yet another aspect, the present application provides a method of predicting whether a subject with cancer is likely to be responsive to treatment with a compound contemplated herein. In certain embodiments, the method comprises detecting presence or absence of at least one fusion, duplication, or mutation selected from the group consisting of a EGFR gene fusion, a EGFR kinase domain duplication, a ERBB2 gene fusion, a ERBB2 mutation, a NRG1 gene fusion, a ERBB3 mutation, and a ERBB4 fusion in tumor cells of the subject;

wherein the subject is likely to be responsive to the treatment with a compound contemplated herein if the at least one fusion, duplication, or mutation is detected.

In certain embodiments, the compound is of a compound of Formula I, II, VII, VIII, IX, X and/or XI. In certain embodiments, the compound is Compound A and/or Compound B.

In another aspect, the present application provides a method of predicting whether a subject with cancer is likely to be responsive to treatment with a compound contemplated herein. In certain embodiments, the method comprises detecting presence or absence of at least one fusion, duplication, or mutation selected from the group consisting of a EGFR gene fusion, a EGFR kinase domain duplication, a ERBB2 gene fusion, a ERBB2 mutation, a NRG1 gene fusion, a ERBB3 mutation, and a ERBB4 fusion in a sample of tumor cells from the subject;

wherein the subject is likely to be responsive to the treatment with a compound contemplated herein if the at least one fusion, duplication, or mutation is detected.

In certain embodiments, the compound is Compound A. In certain embodiments, the compound is Compound B.

In another aspect, the present application provides a method of predicting whether a subject with cancer is likely to be responsive to treatment with a compound contemplated herein.

In certain embodiments, the method comprises:

(a) providing tumor cells of the subject; and (b) detecting presence or absence of at least one fusion, duplication, or mutation selected from the group consisting of a EGFR gene fusion, a EGFR kinase domain duplication, a ERBB2 gene fusion, a ERBB2 mutation, a NRG1 gene fusion, a ERBB3 mutation, and a ERBB4 fusion in the tumor cells;

wherein the presence of the at least one fusion, duplication, or mutation correlates with an increased likelihood of responsiveness or an increased responsiveness of the subject to the treatment.

In certain embodiments, the compound is Compound A. In certain embodiments, the compound is Compound B.

In certain embodiments of the various methods provided herein, the prediction of whether a subject with cancer is likely to be responsive to treatment by a compound contemplated herein is made by detecting the presence of at least one fusion, duplication, or mutation selected from the group consisting of a EGFR gene fusion, a EGFR kinase domain duplication, a ERBB2 gene fusion, a ERBB2 mutation, a NRG1 gene fusion, a ERBB3 mutation, and a ERBB4 fusion in the tumor cells. In other embodiments, the method further comprises administration of a compound contemplated herein to the subject. In yet other embodiments, the method further comprises administration of a compound contemplated herein to the subject if the subject is predicted to be likely to be responsive to the treatment. In yet other embodiments, a compound contemplated herein is administered in a therapeutically effective amount.

The present application also contemplates methods of identifying a subject with cancer who is likely to be responsive to treatment with a compound contemplated herein.

In one aspect, the present application provides a method of identifying a subject with cancer who is likely to be responsive to treatment with a compound contemplated herein. In certain embodiments, the method comprises:

(a) providing tumor cells of the subject;

(b) detecting presence or absence of at least one fusion, duplication, or mutation selected from the group consisting of a EGFR gene fusion, a EGFR kinase domain duplication, a ERBB2 gene fusion, a ERBB2 mutation, a NRG1 gene fusion, a ERBB3 mutation, and a ERBB4 fusion in the provided tumor cells;

(c) identifying the subject as being likely to be responsive to treatment with a compound contemplated herein if the at least one fusion, duplication, or mutation is detected in the provided tumor cells.

In certain embodiments, the compound is Compound A. In certain embodiments, the compound is Compound B.

In another aspect, the present application provides a method of identifying a subject with cancer who is likely to be responsive to treatment with a compound contemplated herein. In certain embodiments, the method comprises:

(a) detecting presence or absence of at least one fusion, duplication, or mutation selected from the group consisting of a EGFR gene fusion, a EGFR kinase domain duplication, a ERBB2 gene fusion, a ERBB2 mutation, a NRG1 gene fusion, a ERBB3 mutation, and a ERBB4 fusion in a sample from the subject, wherein the sample comprises tumor cells;

(b) identifying the subject as being likely to be responsive to a treatment with a compound contemplated herein if the at least one fusion, duplication, or mutation is detected in the sample from the subject.

In certain embodiments, the compound is Compound A. In certain embodiments, the compound is Compound B.

In yet another aspect, the present application provides a method of identifying a subject with cancer who is likely to be responsive to treatment with a compound contemplated herein. In certain embodiments, the method comprises:

(a) detecting presence or absence of at least one fusion, duplication, or mutation selected from the group consisting of a EGFR gene fusion, a EGFR kinase domain duplication, a ERBB2 gene fusion, a ERBB2 mutation, a NRG1 gene fusion, a ERBB3 mutation, and a ERBB4 fusion in tumor cells of the subject; and (b) identifying the subject as being likely to be responsive to a treatment with a compound contemplated herein if the at least one fusion, duplication, or mutation is detected in the tumor cells of the subject.

In certain embodiments, the compound is Compound A. In certain embodiments, the compound is Compound B.

In another aspect, the present application provides a method of identifying a subject with cancer who is likely to be responsive to treatment with a compound contemplated herein. In certain embodiments, the method comprises:

(a) detecting presence or absence of at least one fusion, duplication, or mutation selected from the group consisting of a EGFR gene fusion, a EGFR kinase domain duplication, a ERBB2 gene fusion, a ERBB2 mutation, a NRG1 gene fusion, a ERBB3 mutation, and a ERBB4 fusion in a sample of tumor cells from the subject; and (b) identifying the subject as being likely to be responsive to a treatment with a compound contemplated herein if the at least one fusion, duplication, or mutation is detected in the sample.

In certain embodiments, the compound is Compound A. In certain embodiments, the compound is Compound B.

In another aspect, the present application provides a method of identifying a subject with cancer who is likely to be responsive to treatment with a compound contemplated herein. In certain embodiments, the method comprises:

(a) providing tumor cells of the subject;

(b) detecting presence or absence of at least one fusion, duplication, or mutation selected from the group consisting of a EGFR gene fusion, a EGFR kinase domain duplication, a ERBB2 gene fusion, a ERBB2 mutation, a NRG1 gene fusion, a ERBB3 mutation, and a ERBB4 fusion in the provided tumor cells;

wherein the subject is identified as likely to be responsive to the treatment with a compound contemplated herein if the at least one fusion, duplication, or mutation is detected in the provided tumor cells.

In certain embodiments, the compound is Compound A. In certain embodiments, the compound is Compound B.

In another aspect, the present application provides a method of identifying a subject with cancer who is likely to be responsive to treatment with a compound contemplated herein. In certain embodiments, the method comprises detecting presence or absence of at least one fusion, duplication, or mutation selected from the group consisting of a EGFR gene fusion, a EGFR kinase domain duplication, a ERBB2 gene fusion, a ERBB2 mutation, a NRG1 gene fusion, a ERBB3 mutation, and a ERBB4 fusion in tumor cells of the subject;

wherein the subject is identified as likely to be responsive to the treatment with a compound contemplated herein if the at least one fusion, duplication, or mutation is detected in the tumor cells.

In certain embodiments, the compound is Compound A. In certain embodiments, the compound is Compound B.

In another aspect, the present application provides a method of identifying a subject with cancer who is likely to be responsive to treatment with a compound contemplated herein. In certain embodiments, the method comprises detecting presence or absence of at least one fusion, duplication, or mutation selected from the group consisting of a EGFR gene fusion, a EGFR kinase domain duplication, a ERBB2 gene fusion, a ERBB2 mutation, a NRG1 gene fusion, a ERBB3 mutation, and a ERBB4 fusion in a sample of tumor cells from the subject;

wherein the subject is identified as likely to be responsive to the treatment with a compound contemplated herein if the at least one fusion, duplication, or mutation is detected in the sample.

In certain embodiments, the compound is Compound A. In certain embodiments, the compound is Compound B.

In another aspect, the present application provides a method of identifying a subject with cancer who is likely to be responsive to treatment with a compound contemplated herein. In certain embodiments, the method comprises:

(a) providing tumor cells of the subject; and (b) detecting presence or absence of at least one fusion, duplication, or mutation selected from the group consisting of a EGFR gene fusion, a EGFR kinase domain duplication, a ERBB2 gene fusion, a ERBB2 mutation, a NRG1 gene fusion, a ERBB3 mutation, and a ERBB4 fusion in the provided tumor cells;

wherein the presence of the at least one fusion, duplication, or mutation identifies the subject as likely to be responsive to the treatment with a compound contemplated herein.

In certain embodiments, the compound is Compound A. In certain embodiments, the compound is Compound B.

In certain embodiments of the various methods provided herein, the identification of a subject with cancer who is likely to be responsive to treatment by a compound contemplated herein is made by detecting the presence of at least one fusion, duplication, or mutation selected from the group consisting of a EGFR gene fusion, a EGFR kinase domain duplication, a ERBB2 gene fusion, a ERBB2 mutation, a NRG1 gene fusion, a ERBB3 mutation, and a ERBB4 fusion in the tumor cells. In other embodiments, the method further comprises administration of a compound contemplated herein to the subject. In yet other embodiments, the method further comprises administration of a compound contemplated herein to the subject that is identified to be likely to be responsive to the treatment. In yet other embodiments, a compound contemplated herein is administered in a therapeutically effective amount.

In yet another aspect, provided herein is a method for determining whether a subject with cancer is sensitive to a treatment with a compound contemplated herein. In certain embodiments, the method comprises:

(a) providing tumor cells of the subject;

(b) detecting presence or absence of at least one fusion, duplication, or mutation selected from the group consisting of a EGFR gene fusion, a EGFR kinase domain duplication, a ERBB2 gene fusion, a ERBB2 mutation, a NRG1 gene fusion, a ERBB3 mutation, and a ERBB4 fusion in the provided tumor cells;

(c) diagnosing the subject as being sensitive to the treatment with a compound contemplated herein if the at least one fusion, duplication, or mutation is detected in the provided tumor cells.

In certain embodiments, the compound is Compound A. In certain embodiments, the compound is Compound B.

In certain embodiments, the method further comprises administration of a compound contemplated herein to the subject. In other embodiments, the method further comprises administration of a compound contemplated herein to the subject if the subject is determined to be sensitive to the treatment. In yet other embodiments, a compound contemplated herein is administered in a therapeutically effective amount.

In yet another aspect, the present application provides a method of determining whether a subject with cancer is sensitive to treatment with a compound contemplated herein. In certain embodiments, the method comprises:

(a) providing tumor cells of the subject;

(b) detecting presence or absence of at least one fusion, duplication, or mutation selected from the group consisting of a EGFR gene fusion, a EGFR kinase domain duplication, a ERBB2 gene fusion, a ERBB2 mutation, a NRG1 gene fusion, a ERBB3 mutation, and a ERBB4 fusion in the provided tumor cells;

(c) diagnosing the subject as being sensitive to treatment to the treatment with a compound contemplated herein if the at least one fusion, duplication, or mutation is detected in the provided tumor cells.

In certain embodiments, the compound is Compound A. In certain embodiments, the compound is Compound B.

In certain embodiments, the method further comprises administration of a compound contemplated herein to the subject. In other embodiments, the method further comprises administration of a compound contemplated herein to the subject if the subject is determined to be sensitive to the treatment. In yet other embodiments, a compound contemplated herein is administered in a therapeutically effective amount.

In yet another aspect, the present application provides a method of determining whether a subject with cancer is sensitive to treatment with a compound contemplated herein. In certain embodiments, the method comprises:

(a) detecting presence or absence of at least one fusion, duplication, or mutation selected from the group consisting of a EGFR gene fusion, a EGFR kinase domain duplication, a ERBB2 gene fusion, a ERBB2 mutation, a NRG1 gene fusion, a ERBB3 mutation, and a ERBB4 fusion in a sample from the subject, wherein the sample comprises tumor cells;

b) diagnosing the subject as being sensitive to treatment to the treatment with a compound contemplated herein if the at least one fusion, duplication, or mutation is detected in the sample.

In certain embodiments, the compound is Compound A. In certain embodiments, the compound is Compound B.

In certain embodiments, the method further comprises administration of a compound contemplated herein to the subject. In other embodiments, the method further comprises administration of a compound contemplated herein to the subject if the subject is determined to be sensitive to the treatment. In yet other embodiments, a compound contemplated herein is administered in a therapeutically effective amount.

Combination and Concurrent Therapies

In one embodiment, the compounds contemplated herein are useful in the methods disclosed herein when used concurrently with at least one additional compound useful for preventing and/or treating diseases and/or disorders contemplated herein.

In one embodiment, the compounds contemplated herein are useful in the methods of present application in combination with at least one additional compound useful for preventing and/or treating diseases and/or disorders contemplated herein.

These additional compounds may comprise compounds of the present application or other compounds, such as commercially available compounds, known to treat, prevent, or reduce the symptoms of diseases and/or disorders contemplated herein. In certain embodiments, the combination of at least one compound contemplated herein or a salt thereof, and at least one additional compound useful for preventing and/or treating diseases and/or disorders contemplated herein, has additive, complementary or synergistic effects in the prevention and/or treatment of diseases and/or disorders contemplated herein.

In another non-limiting example, the compounds contemplated herein, or a salt or solvate thereof, can be used concurrently or in combination with one or more agents known to be useful in treating or preventing HER-driven (such as an EGFR-driven) drug-resistant cancer.

As used herein, combination of two or more compounds may refer to a composition wherein the individual compounds are physically mixed or wherein the individual compounds are physically separated. A combination therapy encompasses administering the components separately to produce the desired additive, complementary or synergistic effects.

In one embodiment, the compound and the agent are physically mixed in the composition. In another embodiment, the compound and the agent are physically separated in the composition.

A synergistic effect may be calculated, for example, using suitable methods such as, for example, the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326), the median-effect equation (Chou & Talalay, 1984, Adv. Enzyme Regul. 22: 27-55), and through the use of isobolograms (Tallarida & Raffa, 1996, Life Sci. 58: 23-28). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective amount. The therapeutic formulations may be administered to the subject either prior to or after the onset of a disease or disorder contemplated herein. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions contemplated herein to a patient, preferably a mammal, more preferably a human, may be carried out using known procedures, at dosages and for periods of time effective to treat a disease or disorder contemplated herein. An effective amount of the therapeutic compound necessary to achieve a therapeutic effect may vary according to factors such as the state of the disease or disorder in the patient; the age, sex, and weight of the patient; and the ability of the therapeutic compound to treat a disease or disorder contemplated herein. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound contemplated herein is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions disclosed herein may be varied so as to obtain an amount of the active ingredient that is effective to achieve the desired therapeutic response for a particular patient, composition, and mode of administration, without being toxic to the patient.

The therapeutically effective amount or dose of a compound contemplated herein n depends on the age, sex and weight of the patient, the current medical condition of the patient and the progression of a disease or disorder contemplated herein.

A medical doctor, e.g., physician or veterinarian, having ordinary skill in the art may readily determine and prescribe the effective amount of the pharmaceutical composition required. For example, the physician or veterinarian could start doses of the compounds contemplated herein employed in the pharmaceutical composition at levels lower than that required in order to achieve the desired therapeutic effect and gradually increase the dosage until the desired effect is achieved.

A suitable dose of a compound contemplated herein may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

Compounds contemplated herein for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 3050 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments there between.

In some embodiments, the dose of a compound contemplated herein is from about 1 mg and about 2,500 mg. In some embodiments, a dose of a compound contemplated herein used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the compositions contemplated herein are administered to the patient in dosages that range from one to five times per day or more. In another embodiment, the compositions contemplated herein are administered to the patient in range of dosages that include, but are not limited to, once every day, every two, days, every three days to once a week, and once every two weeks. It is readily apparent to one skilled in the art that the frequency of administration of the various combination compositions contemplated herein varies from individual to individual depending on many factors including, but not limited to, age, disease or disorder to be treated, gender, overall health, and other factors. Thus, the present application should not be construed to be limited to any particular dosage regime and the precise dosage and composition to be administered to any patient is determined by the attending physical taking all other factors about the patient into account.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the compound contemplated herein is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the disease or disorder, to a level at which the improved disease is retained. In one embodiment, patients require intermittent treatment on a long-term basis upon any recurrence of symptoms and/or infection.

The compounds for use in the method disclosed herein may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

In one embodiment, the compositions contemplated herein are formulated using one or more pharmaceutically acceptable excipients or carriers. In one embodiment, the pharmaceutical compositions contemplated herein comprise a therapeutically effective amount of a compound contemplated herein and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal and the like. In many cases, it is preferable to include isotonic agents, for example, sugars, sodium chloride, or polyalcohols such as mannitol and sorbitol, in the composition.

In one embodiment, the present application is directed to a packaged pharmaceutical composition comprising a container holding a therapeutically effective amount of a compound contemplated herein, alone or in combination with a second pharmaceutical agent; and instructions for using the compound to treat, prevent, or reduce one or more symptoms of a disease or disorder contemplated herein.

Formulations may be employed in admixtures with conventional excipients, i.e., pharmaceutically acceptable organic or inorganic carrier substances suitable for any suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., analgesic agents.

Routes of administration of any of the compositions contemplated herein include inhalational, oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, epidural, intrapleural, intraperitoneal, intratracheal, otic, intraocular, subcutaneous, intramuscular, intradermal, intra-arterial, intravenous, intrabronchial, inhalation, and topical administration.

Additional Administration Forms

Additional dosage forms contemplated herein include dosage forms as described in U.S. Pat. Nos. 6,340,475; 6,488,962; 6,451,808; 5,972,389; 5,582,837; and 5,007,790. Additional dosage forms contemplated herein also include dosage forms as described in U.S. Patent Applications Nos. 20030147952; 20030104062; 20030104053; 20030044466; 20030039688; and 20020051820. Further dosage forms contemplated herein include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In one embodiment, the formulations contemplated herein may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material that provides sustained release properties to the compounds. As such, the compounds for use in the methods disclosed herein may be administered in the form of microparticles, for example, by injection or in the form of wafers or discs by implantation.

In one embodiment, the compounds contemplated herein are administered to a patient, alone or in combination with another pharmaceutical agent, using a sustained release formulation.

The term delayed release is used herein in its conventional sense to refer to a drug formulation that provides for an initial release of the drug after some delay following drug administration and that may, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Those skilled in the art will recognize, or be able to ascertain using no more than routine experimentation, numerous equivalents to the specific procedures, embodiments, claims, and examples described herein. Such equivalents were considered to be within the scope of the present disclosure and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present disclosure. Moreover, all values that fall within these ranges, as well as the upper or lower limits of a range of values, are also contemplated by the present application.

The following examples further illustrate aspects of the present disclosure. However, they are in no way a limitation of the teachings or disclosure of the present disclosure as set forth herein.

EXAMPLES

Certain aspects of the application are now described with reference to the following Examples. These Examples are provided for the purpose of illustration only and the application should in no way be construed as being limited to these Examples, but rather should be construed to encompass any and all variations which become evident as a result of the teaching provided herein.

Example 1

Figure 2:
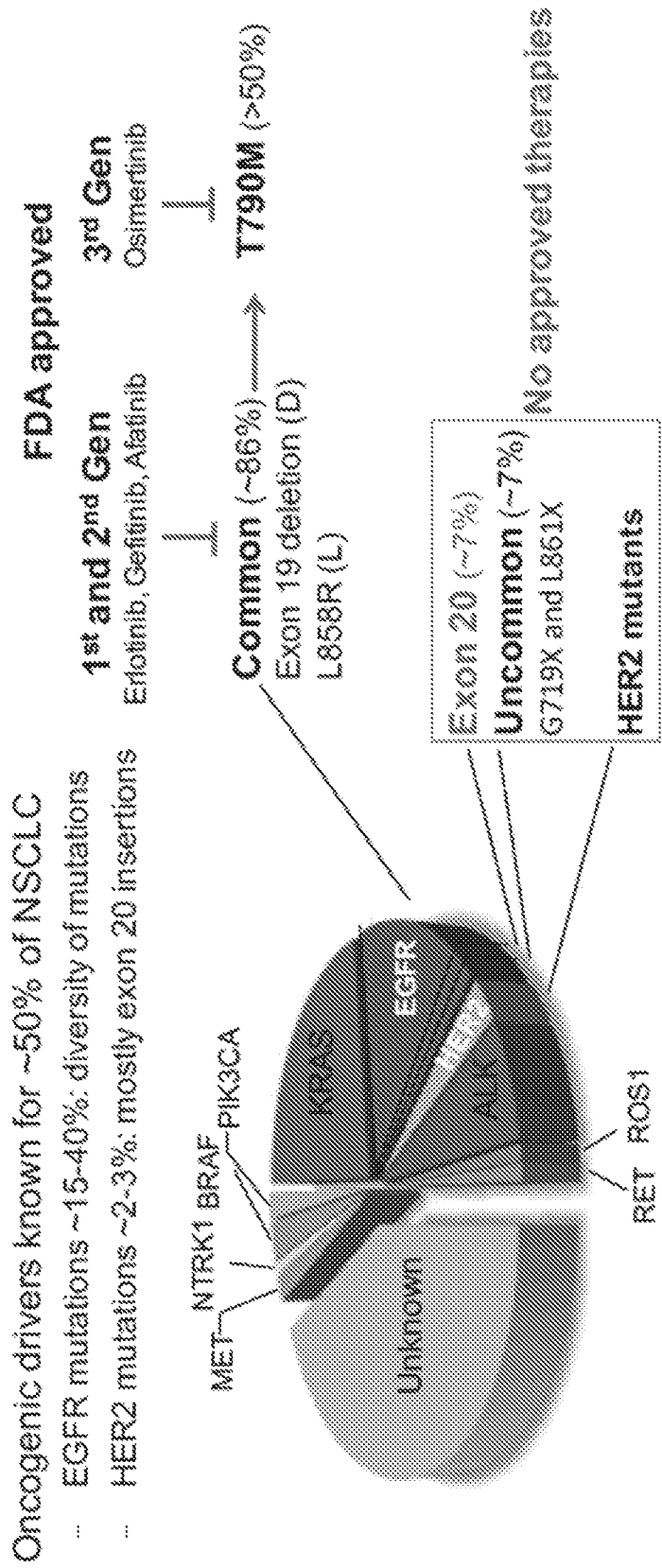
FIG. 2 is a schematic illustration of oncogenic mutations observed in non-small cell lung cancer (NSCLC) patients.
Figure 3A:
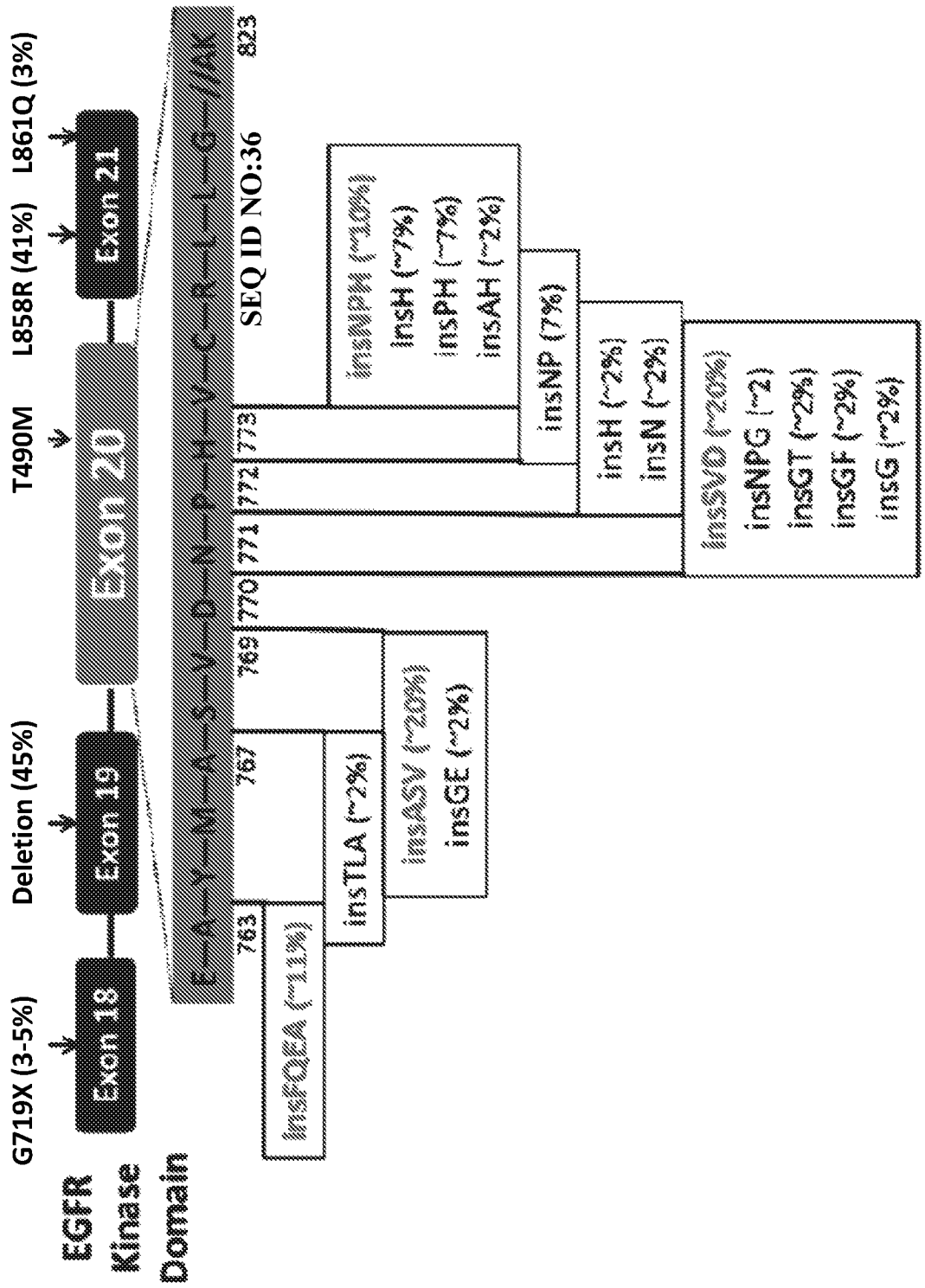
FIGS. 3A-3B illustrate certain non-limiting EGFR domains.
Figure 3B:
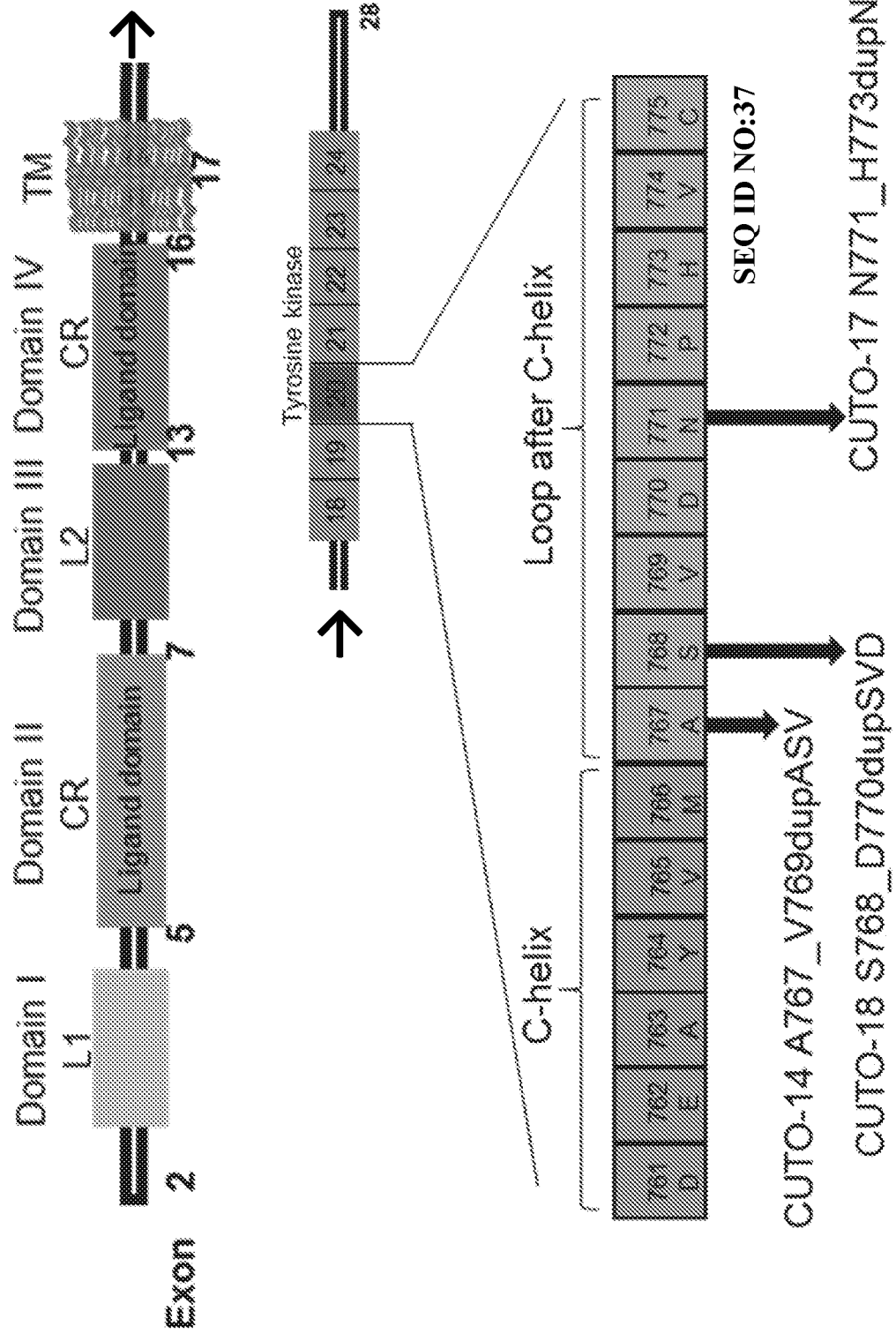

Tarloxotinib (TRLX or Compound A) is a hypoxia-activated EGFR/HER2/HER4 TKI prodrug that releases an irreversible EGFR/HER2 tyrosine kinase inhibitor (TRLX-TKI; in this case, Compound B) under pathophysiologically hypoxic conditions (FIG. 1). Non-small cell lung cancer (NSCLC) has been characterized as a hypoxic disease and approximately 15% of lung adenocarcinomas harbor EGFR mutations (FIG. 2). While most EGFR mutations predict for response to several FDA-approved tyrosine kinase inhibitors, in-frame insertions in exon 20 of EGFR are activating mutations in the tyrosine kinase domain that have significantly decreased sensitivity to EGFR inhibitors and currently have no approved targeted therapies (FIGS. 3A-3B).

Figure 4A:
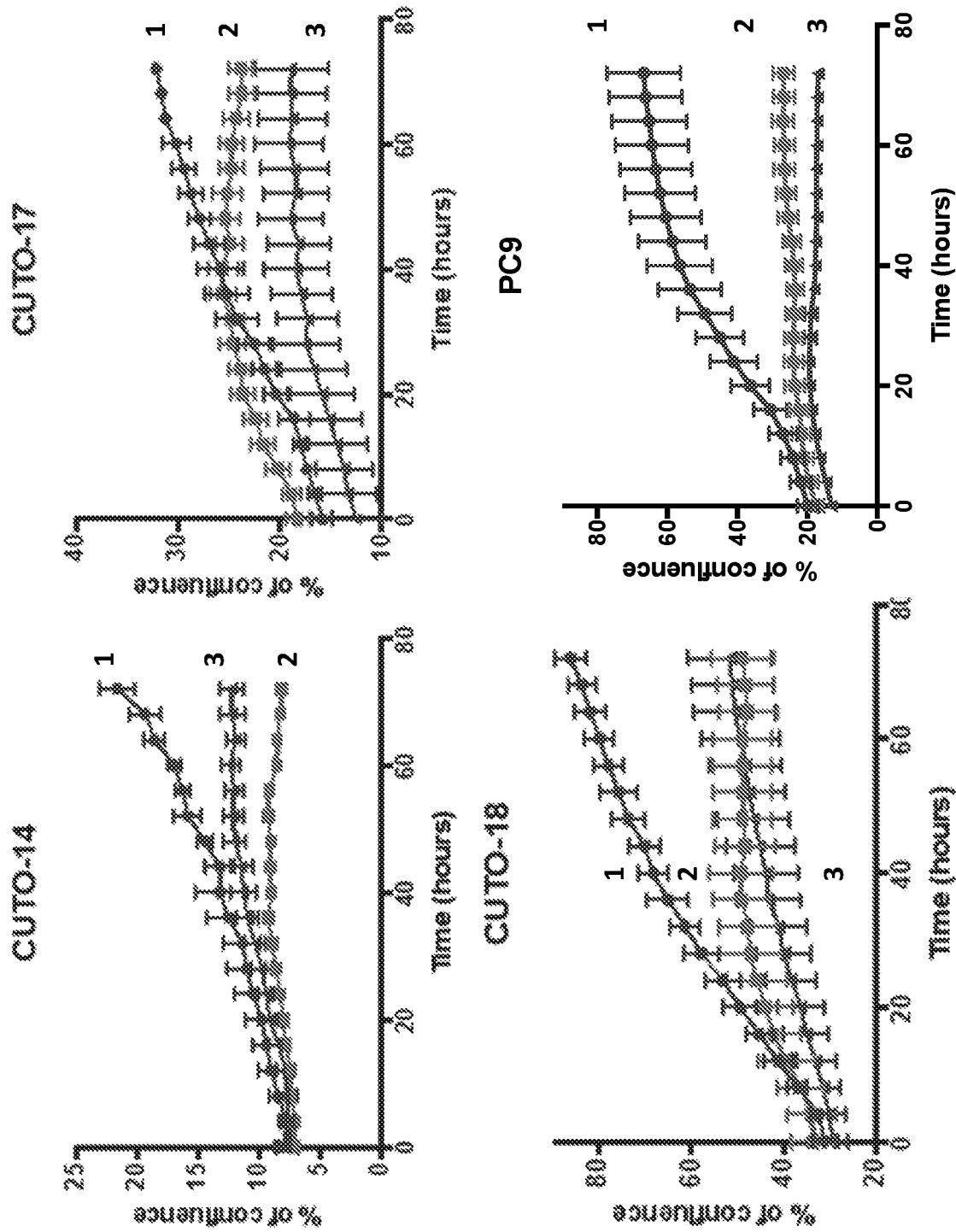
FIGS. 4A-4B comprise a series of graphs illustrating the finding that patient derived EGFR exon 20 insertion mutations cell lines depend on EGFR for proliferation. Cell lines were transduced with one of two different shEGFR (1212014 or 10329) or with non-targeted shRNA (NTC). Proliferation was monitored by IncuCyte live-cell imagining system continuously for 80 h. Cell growth was expressed as an increase in percentage of confluence. EGFR exon 20 insertion cell lines include CUTO-14, CUTO-17, CUTO-18. EGFR mutant cell lines known to be EGFR dependent include PC9 (EGFR del 19), and H3255 (L858R).
Figure 4B:
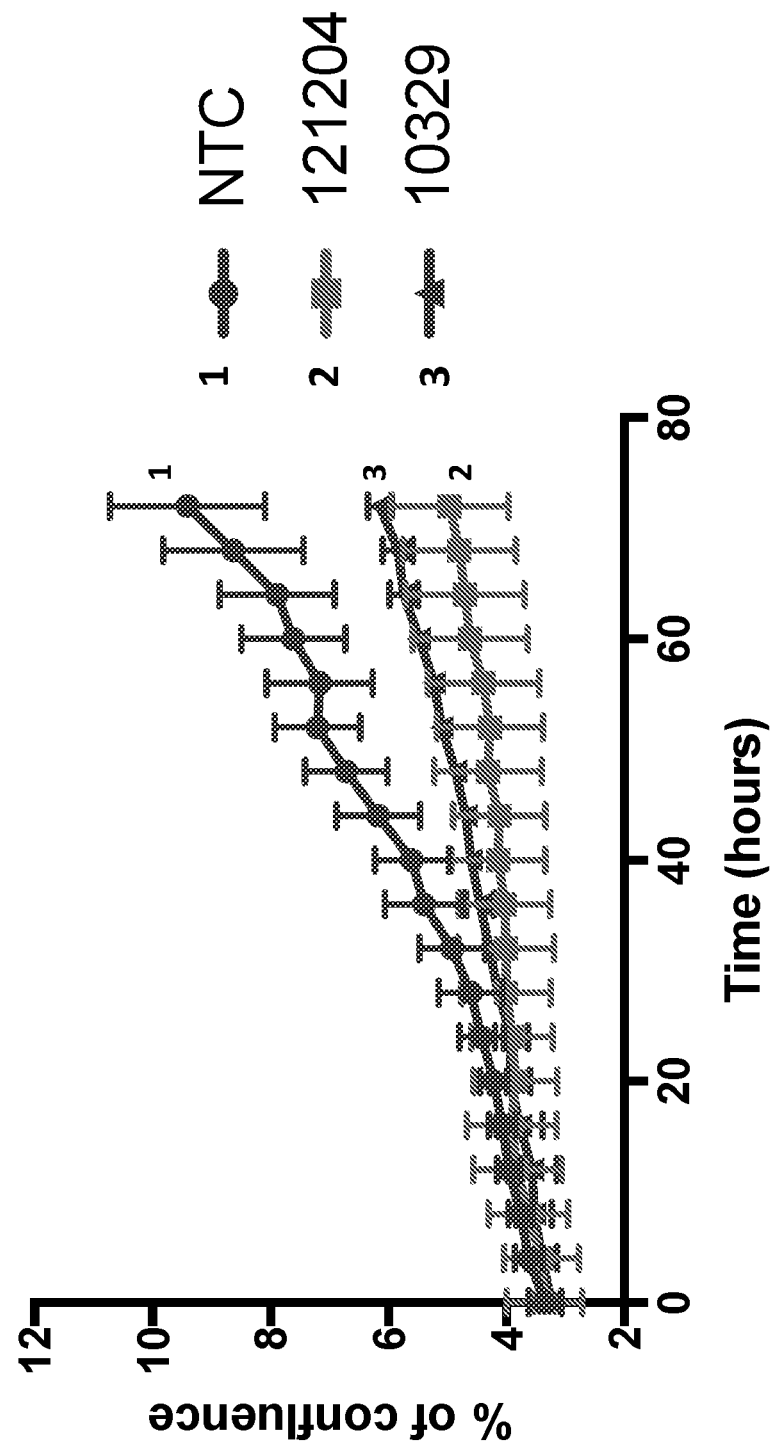

Three human lung adenocarcinoma cell lines with different EGFR exon20 insertions were derived and characterized, in order to accelerate development of targeted therapies for this mutation class (FIGS. 4A-4B). Cell lines were transduced with one of two different shEGFR (1212014 or 10329) or with non-targeted shRNA (NTC). Proliferation was monitored by IncuCyte live-cell imagining system continuously for 80 h. Cell growth was expressed as an increase in % confluence. EGFR exon 20 insertion cell lines: CUTO-14, CUTO-17, CUTO-18. (FIG. 4A) EGFR mutant cell lines known to be EGFR dependent: PC9 (EGFR del 19; FIG. 4A), and H3255 (L858R; FIG. 4B). Using these novel cell lines, tarloxotinib was evaluated as a therapeutic agent for tumors harboring this type of mutations. The three patient derived cell lines—CUTO14 (p.A767_V769dupASV), CUTO17 (p.N771_H773dupNPH), and CUTO18 (p.S768_770dupSVD)—were found to be dependent on EGFR for cell proliferation, using shRNA mediated knockdown. Thus, successful pharmacologic inhibition of EGFR in cancer cells harboring EGFR exon 20 insertion mutations has been proven to result in growth inhibition.

Figure 5A:
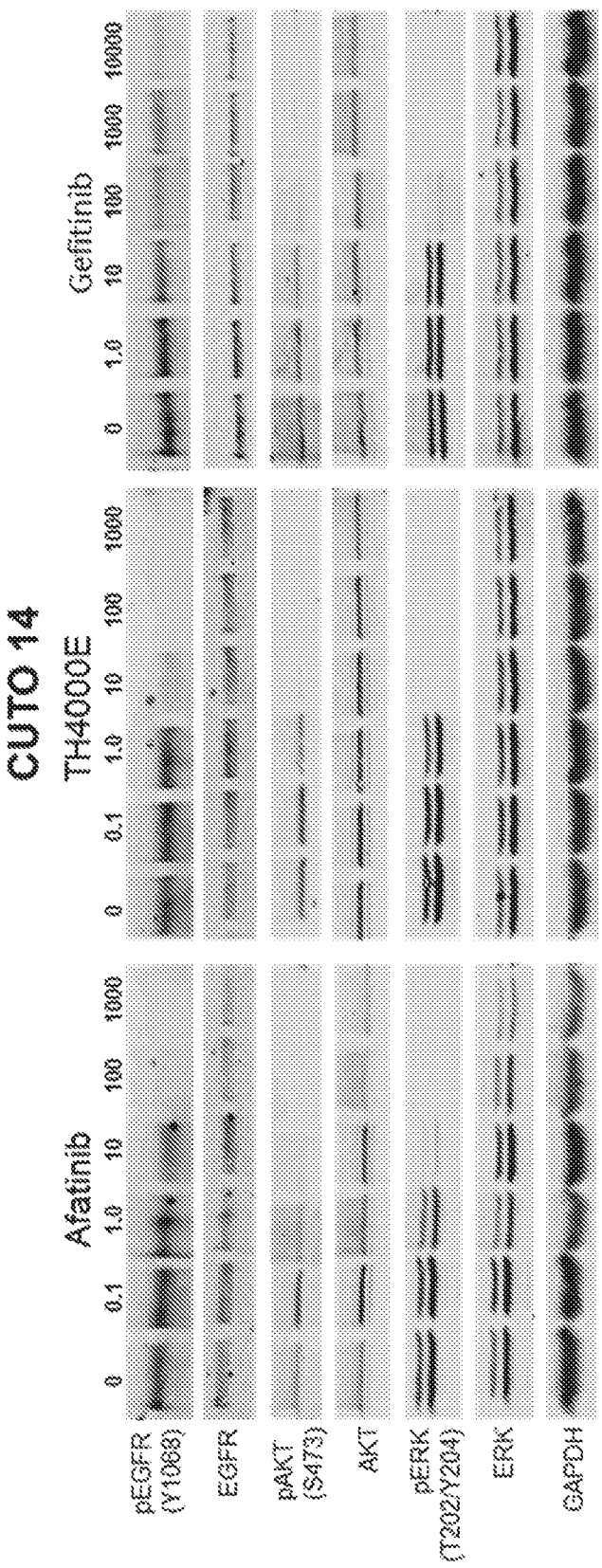
FIGS. 5A-5C comprise a series of gel images illustrating the finding that the active metabolite of tarloxotinib, RN-4000E, inhibits EGFR phosphorylation and downstream signaling in cell lines harboring EGFR exon 20 insertion mutation cell lines. Cells were treated with the indicated doses of afatinib, gefitinib, and RN-4000E (active drug) for 2 hours, lysed and analyzed by immunoblot. Blots are representatives of three independent experiments.
Figure 5B:
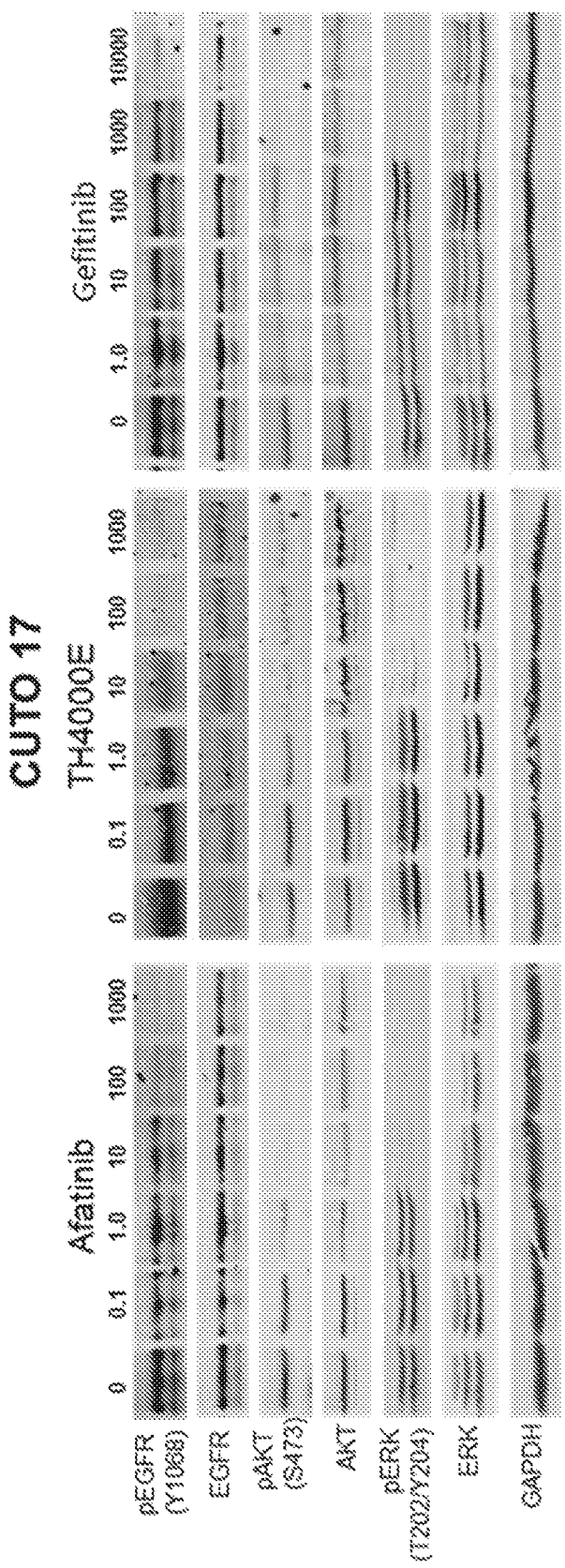
Figure 5C:
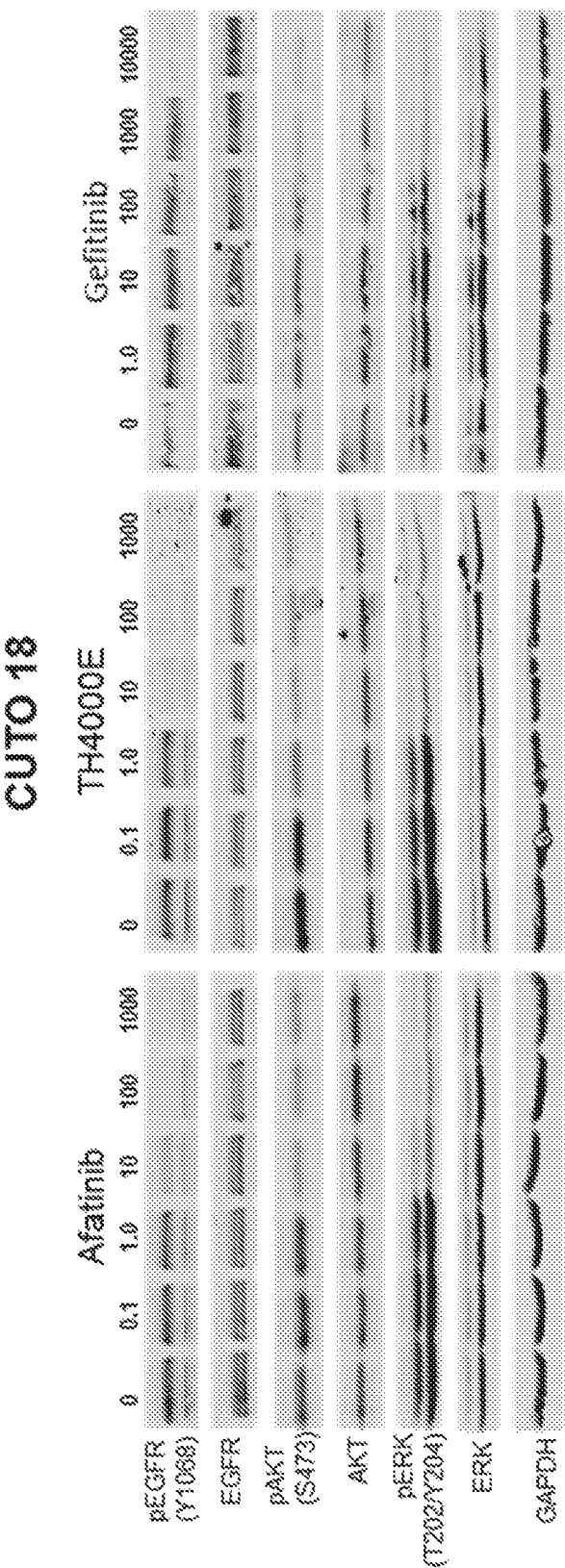
Figure 8A:
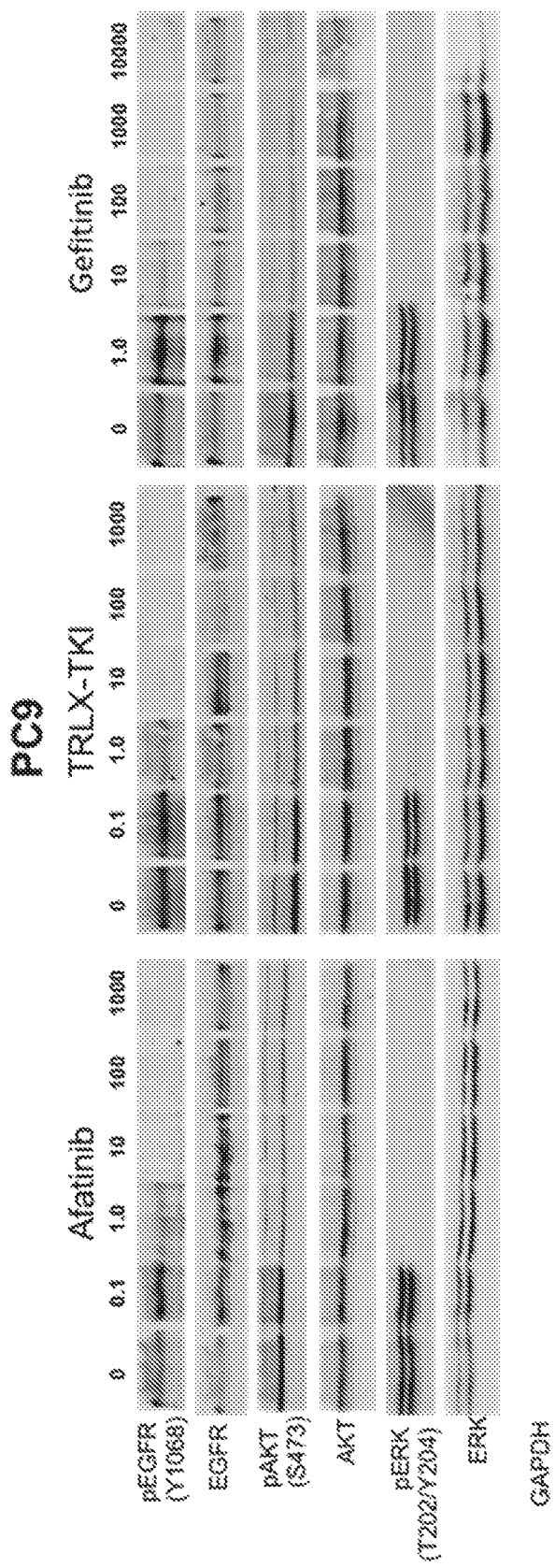
FIGS. 8A-8C comprise a series of gel images illustrating the finding that TRLX-TKI, also known as RN-4000E, has similar EGFR activity to afatinib in sensitizing EGFR mutation models.
Figure 8B:
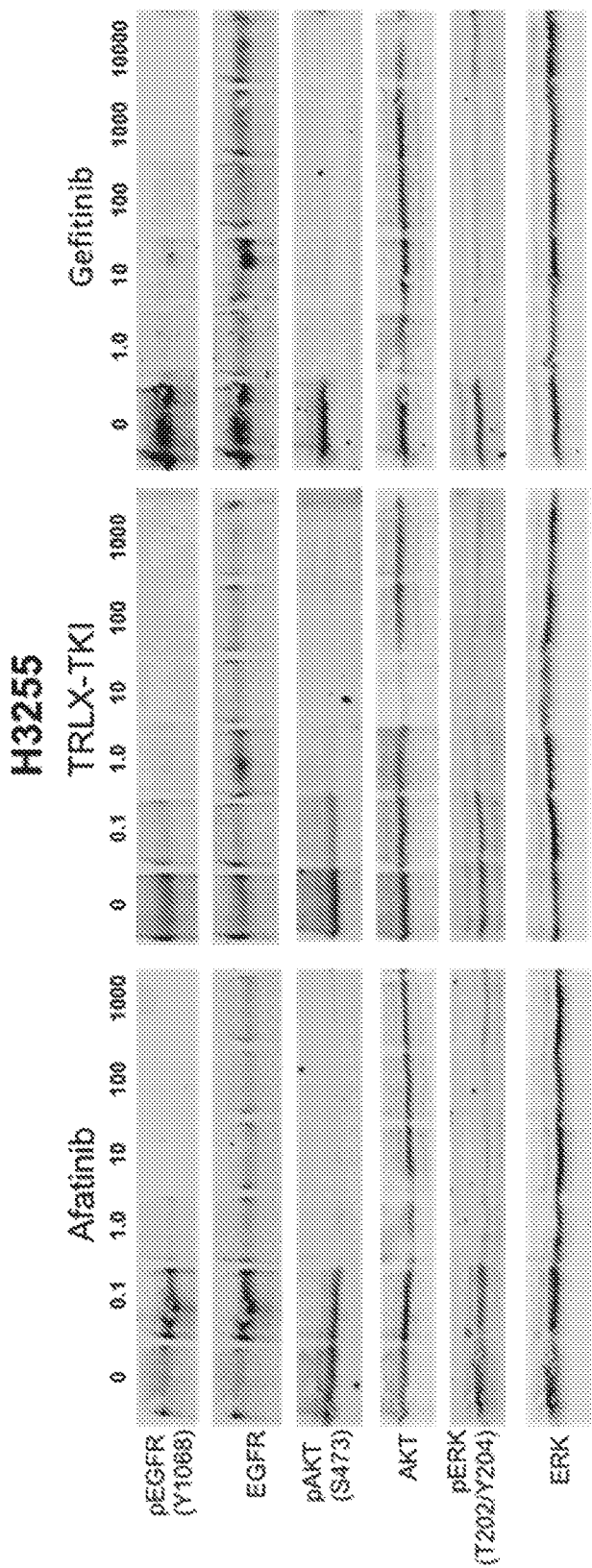
Figure 8C:
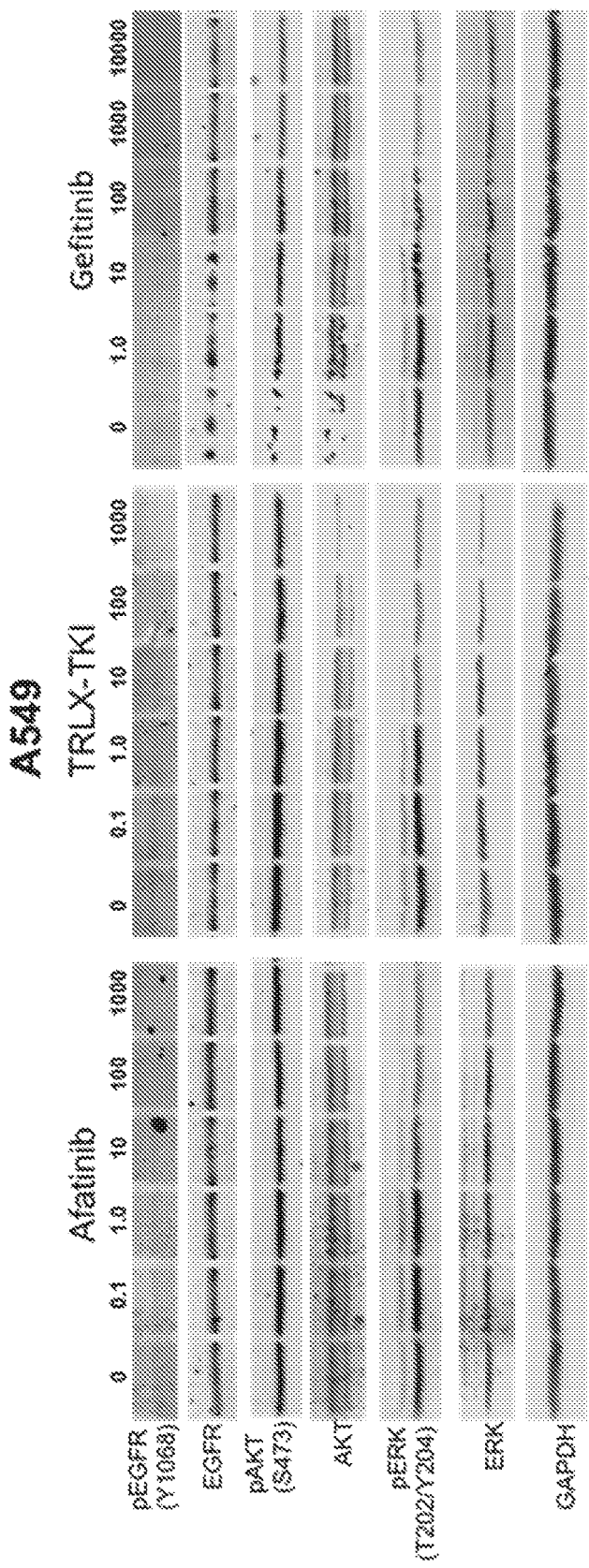

The active metabolite of tarloxotinib, RN-4000E, inhibits EGFR phosphorylation and downstream signaling in cell lines harboring EGFR exon 20 insertion mutation cell lines, as demonstrated in FIGS. 5A-5C. Cells were treated with the indicated doses (nM) of afatinib, gefitinib, and RN-4000E (TH4000E, active drug) for 2 hours, lysed and analyzed by immunoblot for phosphorylated EGFR (Y1068), total EGFR, phosphorylated AKT (S473), total AKT, phosphorylated ERK (T202/Y204), total ERK and GAPDH (loading control). Results demonstrate that RN-4000E inhibits pEGFR as well as downstream pAKT and pERK at ~10-100 nM. These data demonstrate the RN-4000E inhibits its intended target in these cancer cell lines harboring EGFR exon 20 insertions and further that inhibition of EGFR blocks critical downstream signaling pathways including MAPK and AKT. Blots are representatives of three independent experiments. Further evidence that that active metabolite of tarloxotinib, RN-4000E, has similar EGFR activity to afatinib in sensitizing EGFR mutation models (using PC9, H3255) but no effect in a KRAS mutation cell line that does not harbor an EGFR mutation (A549 cells) is provided in FIGS. 8A-8C. Cells were treated with the indicated doses (nM) of afatinib, gefitinib, and RN-4000E (TH4000E, active drug) for 2 hours, lysed and analyzed by immunoblot for phosphorylated EGFR (Y1068), total EGFR, phosphorylated AKT (S473), total AKT, phosphorylated ERK (T202/Y204), total ERK and GAPDH (loading control). Results demonstrate that RN-4000E inhibits pEGFR as well as downstream pAKT and pERK at ~0.1-10 nM in cancer cells harboring EGFR sensitizing mutations (PC9 and H3255). These data demonstrate the RN-4000E inhibits its intended target in these cancer cell lines harboring EGFR exon 20 insertions, and further that inhibition of EGFR blocks critical downstream signaling pathways including MAPK and AKT. pEGFR is not detectable in A549 cells and RN-4000E does not inhibit MAPK or AKT signaling even at does of 1000 nM, consistent with a lack of EGFR activation and dependence in this KRAS mutant cell line. Blots are representatives of three independent experiments.

The results showed that EGFR exon 20 insertion cell lines are resistant to gefitinib. However, treatment with afatinib or TRLX-TKI reduces cell proliferation and signaling in a similar manner.

Figure 6A:
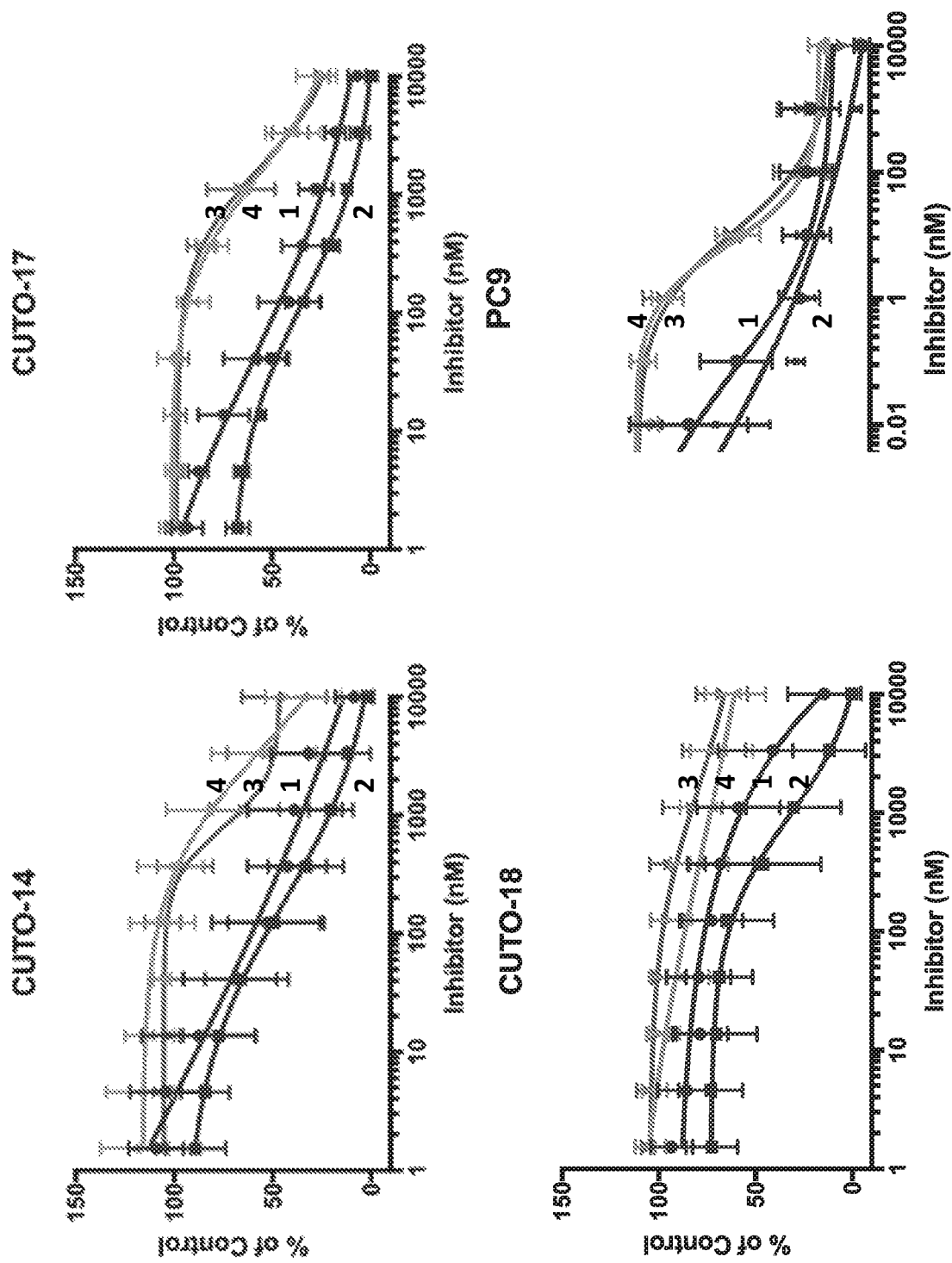
FIGS. 6A-6B comprise a series of graphs illustrating dose response curves of cell viability of EGFR exon 20 insertion mutation patient derived cell lines (CUTO-14, CUTO-17, CUTO-18), mutated EGFR (PC9, H3255) and wild type EGFR (A549). Cells were treated with afatinib, gefitinib, RN-4000 (pro-drug) and RN-4000E (effector drug) for 72 hours under normoxic conditions and analyzed by MTS. Experiments were done by triplicate, mean and ±SEM is plotted.
Figure 6B:
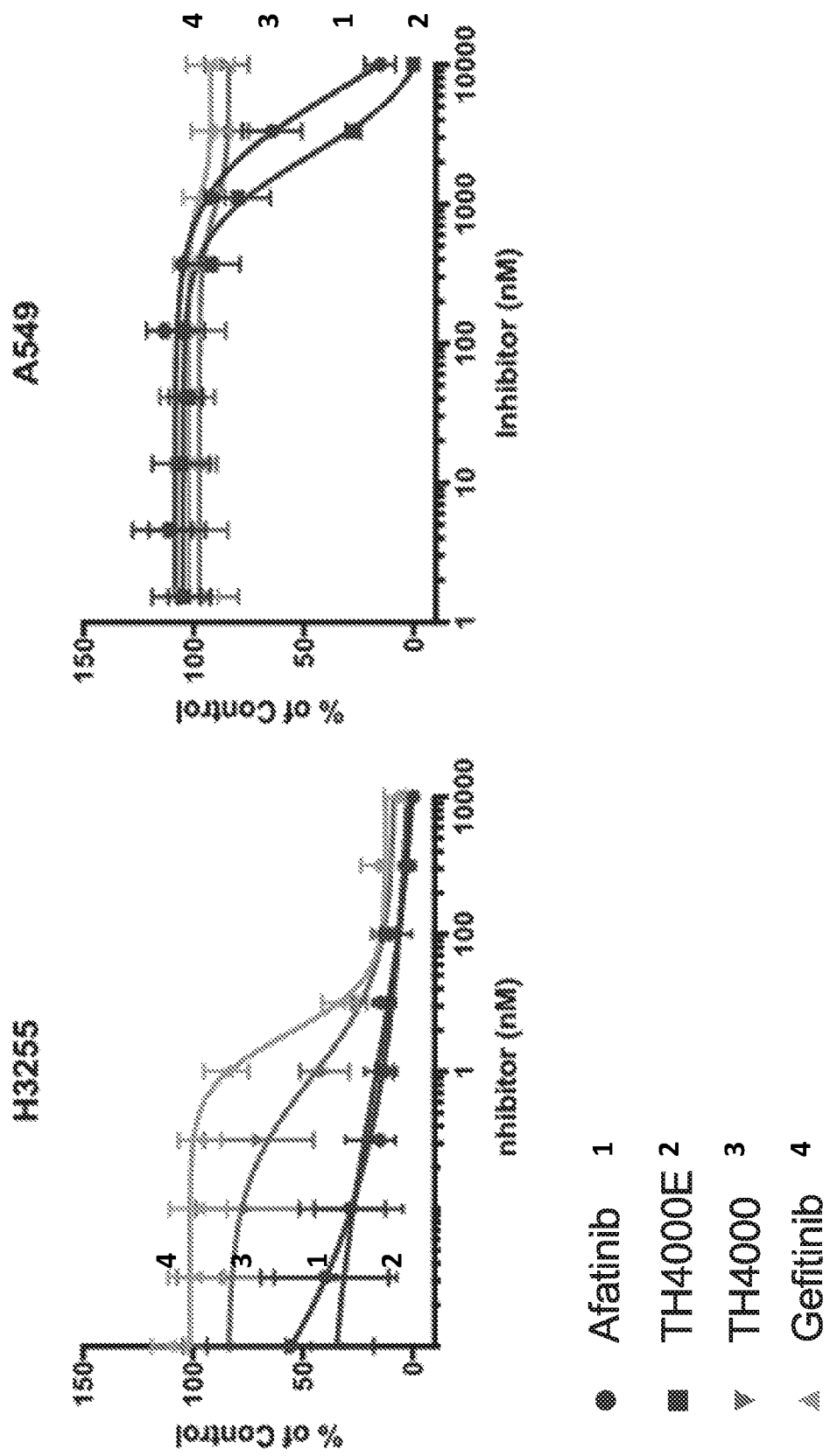

Further studies were performed to demonstrate that the active metabolite of tarloxotinib, RN-4000E, inhibits proliferation of cell lines harboring EGFR exon 20 insertion mutations (FIGS. 6A-6B). FIGS. 6A-6B illustrate dose response curves of cell viability of EGFR exon 20 insertion mutation patient derived cell lines (CUTO-14, CUTO-17, CUTO-18), mutated EGFR (PC9, H3255) and wild type EGFR (A549). Cells were treated with afatinib, gefitinib, RN-4000 (pro-drug) and RN-4000E (effector drug) for 72 hours under normoxic conditions and analyzed by MTS. Experiments were done by triplicate, mean and ±SEM is plotted. FIG. 6C comprises a table summarizing $IC_{50}$ values of proliferation experiments. Values are expressed in nanomolar concentration. The $IC_{50}$ values for the three cell lines were 203 nM, 89 nM and 709 nM for afatinib, and 208 nM, 33 nM and 345 nM for TRLX-TKI, respectively. The prodrug form of tarloxotinib has minimal effect on cell proliferation in these models, consistent with the necessity for hypoxia-induced activation (to TRLX-TKI).

Figure 7A:
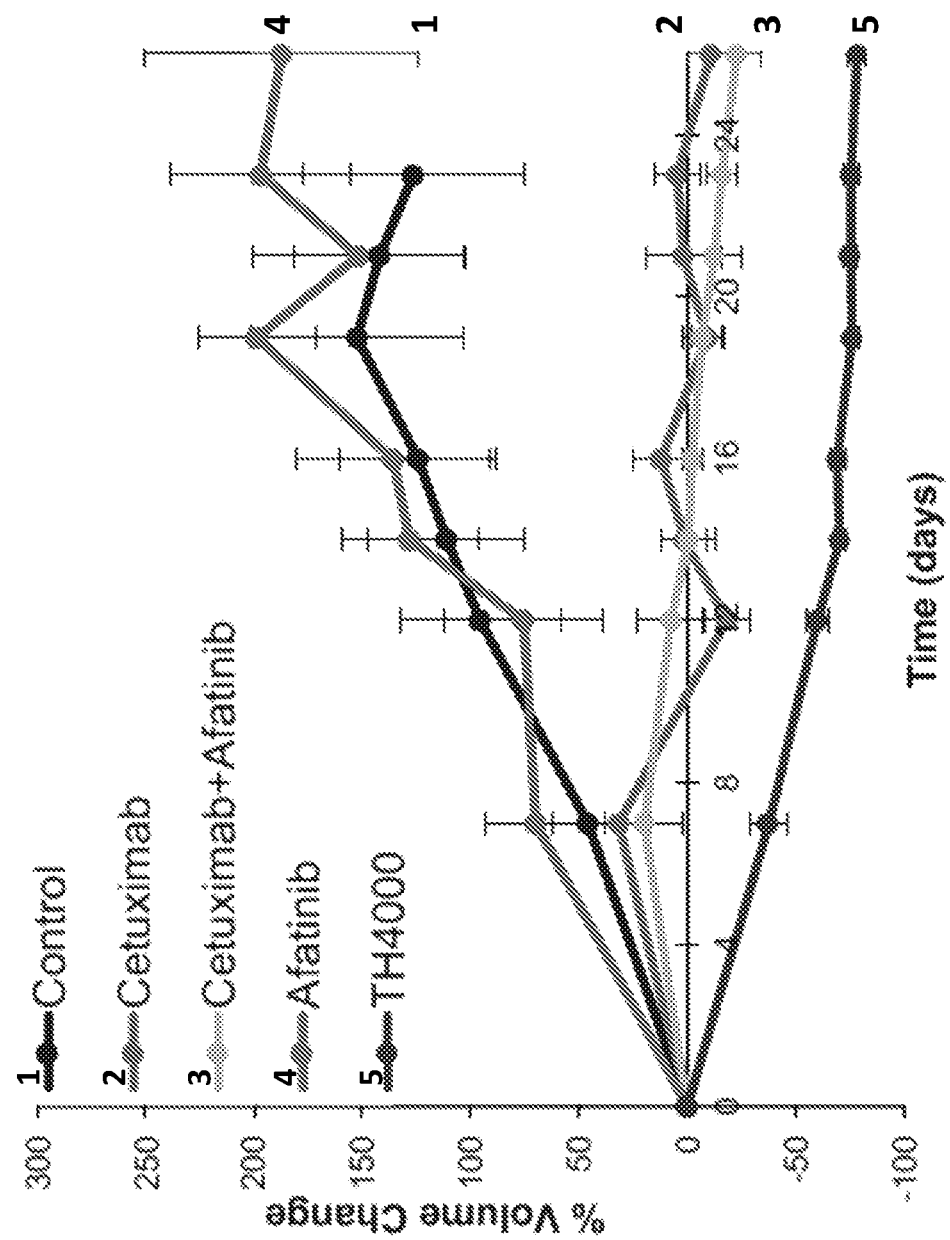
FIGS. 7A-7B comprise graphs illustrating the finding that tarloxotinib reduces tumor burden in CUTO-14 murine xenografts.
Figure 7B:
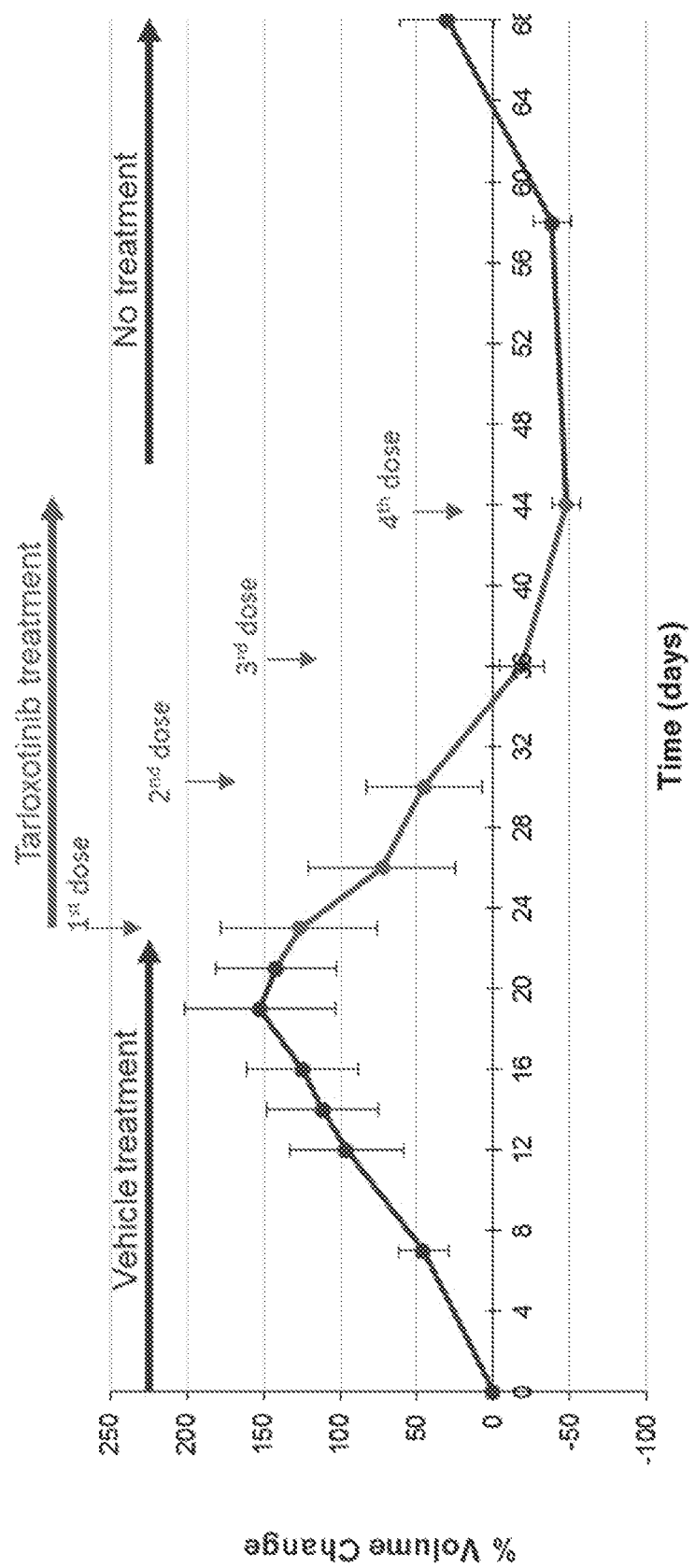

The effect of tarloxotinib was evaluated in vivo using murine xenograft models of CUTO14 (FIGS. 7A-7B). The data illustrated in FIG. 7A was obtained by injecting $1 \times 10^6$ cells in each flank of nude mice; once tumors reached 200 mm$^3$, mice were randomly separated and treated with afatinib (6 mg/Kg, daily, PO), cetuximab (40 mg/Kg, Q3d, IP), tarloxotinib (48 mg/Kg, Qwx4, IP) and vehicle for four weeks. Tumor volume was measured two times a week. After four weeks of treatment, afatinib did not alter tumor growth compared to untreated tumors, whereas treatment with tarloxotinib induced significant tumor regression. As demonstrated in FIG. 7B, tarloxotinib was active in PDX models of EGFR exon 20 insertion that were permitted to grow to a large size (average size of about 573 mm$^3$) before initiating treatment.

Figure 12:
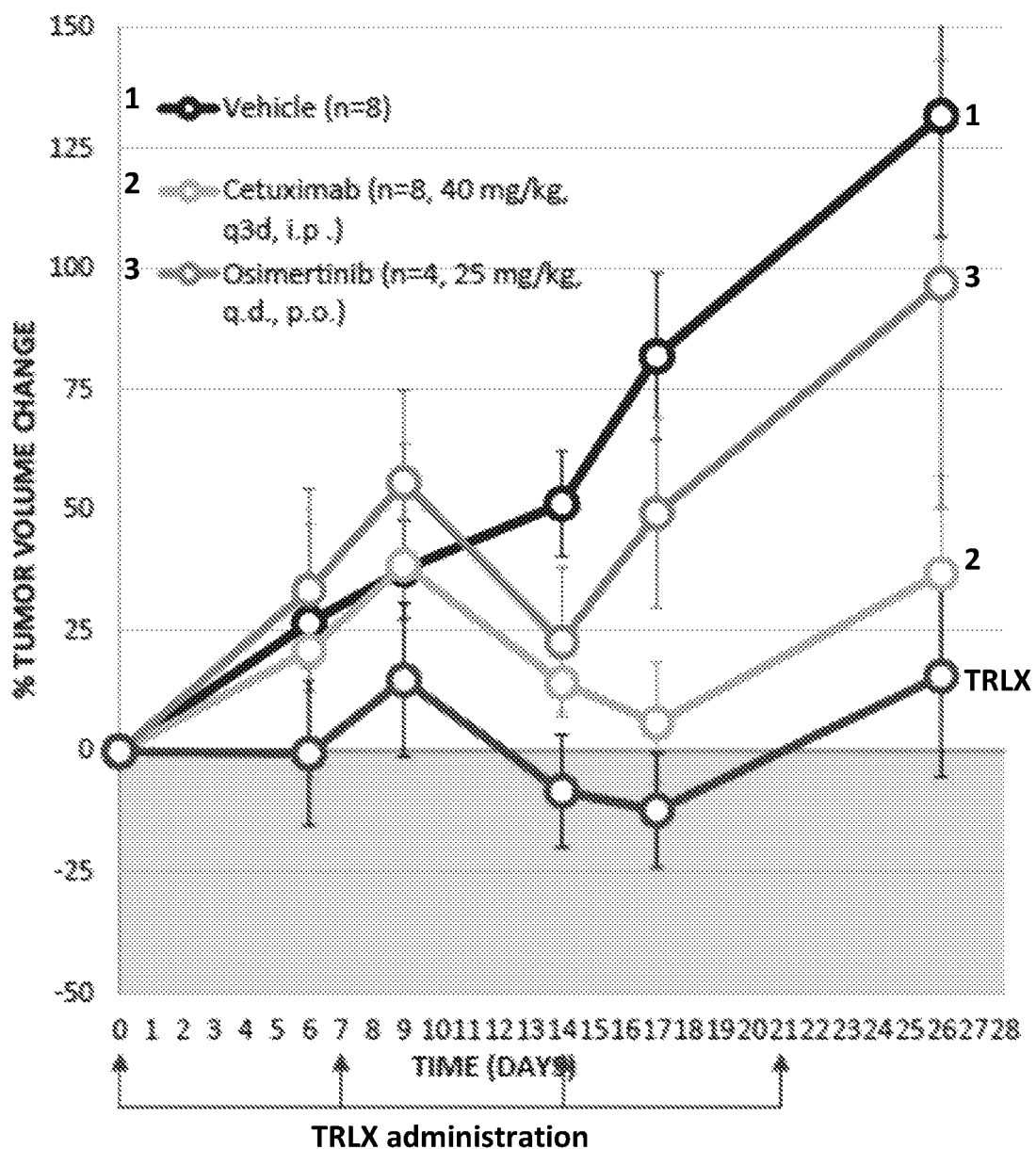
FIG. 12 comprises a graph illustrating the finding that tarloxotinib reduces tumor burden in CUTO-17 murine xenografts. 1×10$^6$ cells were injected in each flank of nude mice; once tumors reached 200 mm$^3$, mice were randomly separated and treated with cetuximab (40 mg/Kg, Q3d, IP), osimertinib (25 mg/kg, daily, PO), tarloxotinib (48 mg/Kg, Qwx4, IP) or vehicle for four weeks. Tumor volume was measured two times a week.

The effect of tarloxotinib was further evaluated in vivo using murine xenograft models of CUTO17 (FIG. 12). The data illustrated in FIG. 12 was obtained by injecting $1 \times 10^6$ cells in each flank of nude mice; once tumors reached 200 mm$^3$, mice were randomly separated and treated with cetuximab (40 mg/Kg, Q3d, IP), osimertinib (25 mg/kg, daily, PO), tarloxotinib (48 mg/Kg, Qwx4, IP) or vehicle for four weeks. Tumor volume was measure two times a week The in vivo data suggest that the activated TKI of tarloxotinib is accumulating to biologically active concentrations in tumors following cleavage of tarloxotinib under hypoxic conditions.

In summary, the EGFR exon 20 insertions cell lines represent novel models for the investigation of therapeutic strategies for this mutation class. These cell lines have the ability to develop tumors in vivo and show reduced sensitivity to current EGFR TKIs, mimicking the lack of response in patients with these mutations. As demonstrated herein, tarloxotinib can overcome intrinsic EGFR exon 20 mutation resistance to standard EGFR TKIs.

Example 2: Anti-Tumor Activity of Tarloxotinib in HER2 Driven Cell Lines

Figure 9A:
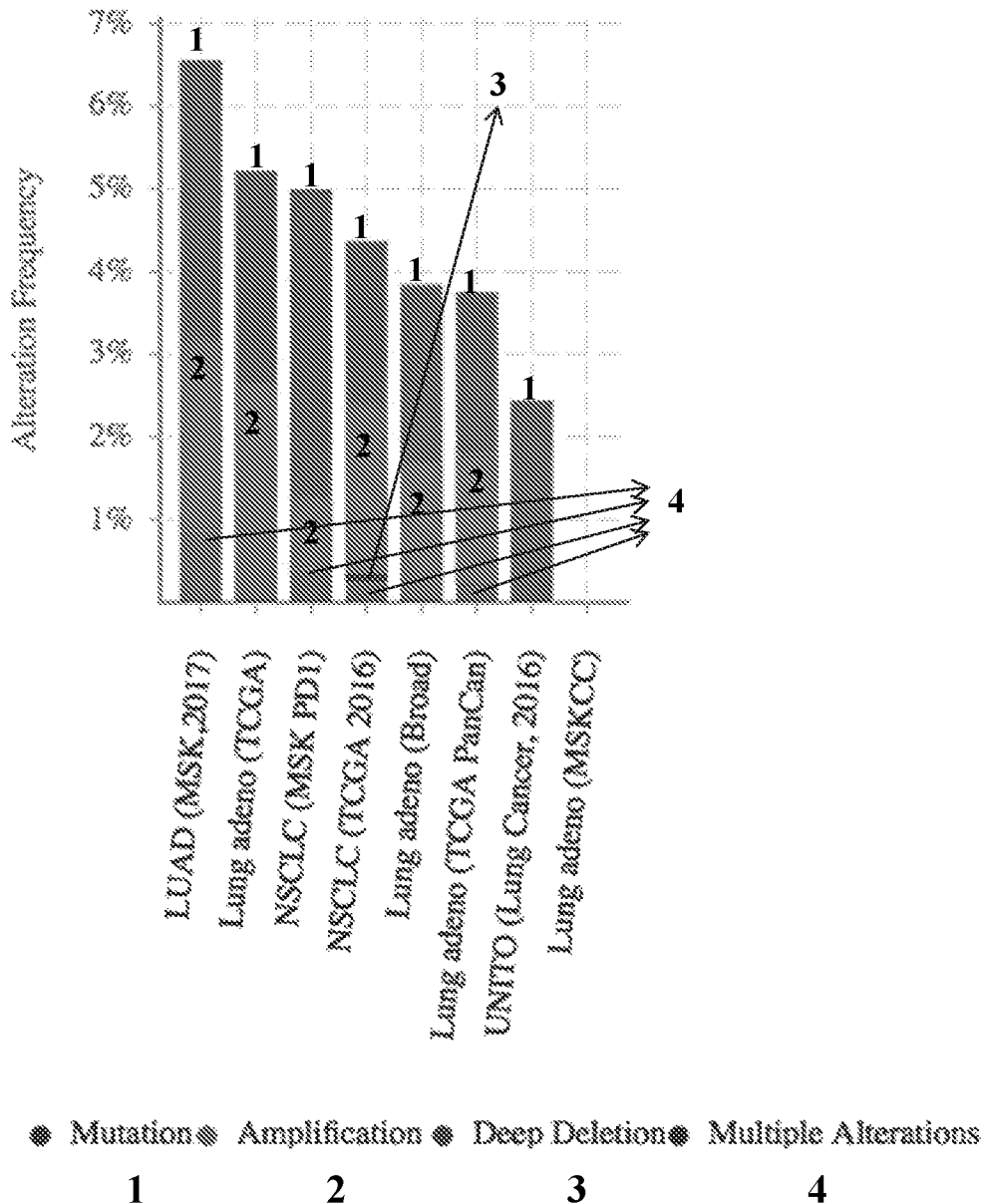
Figure 9C:
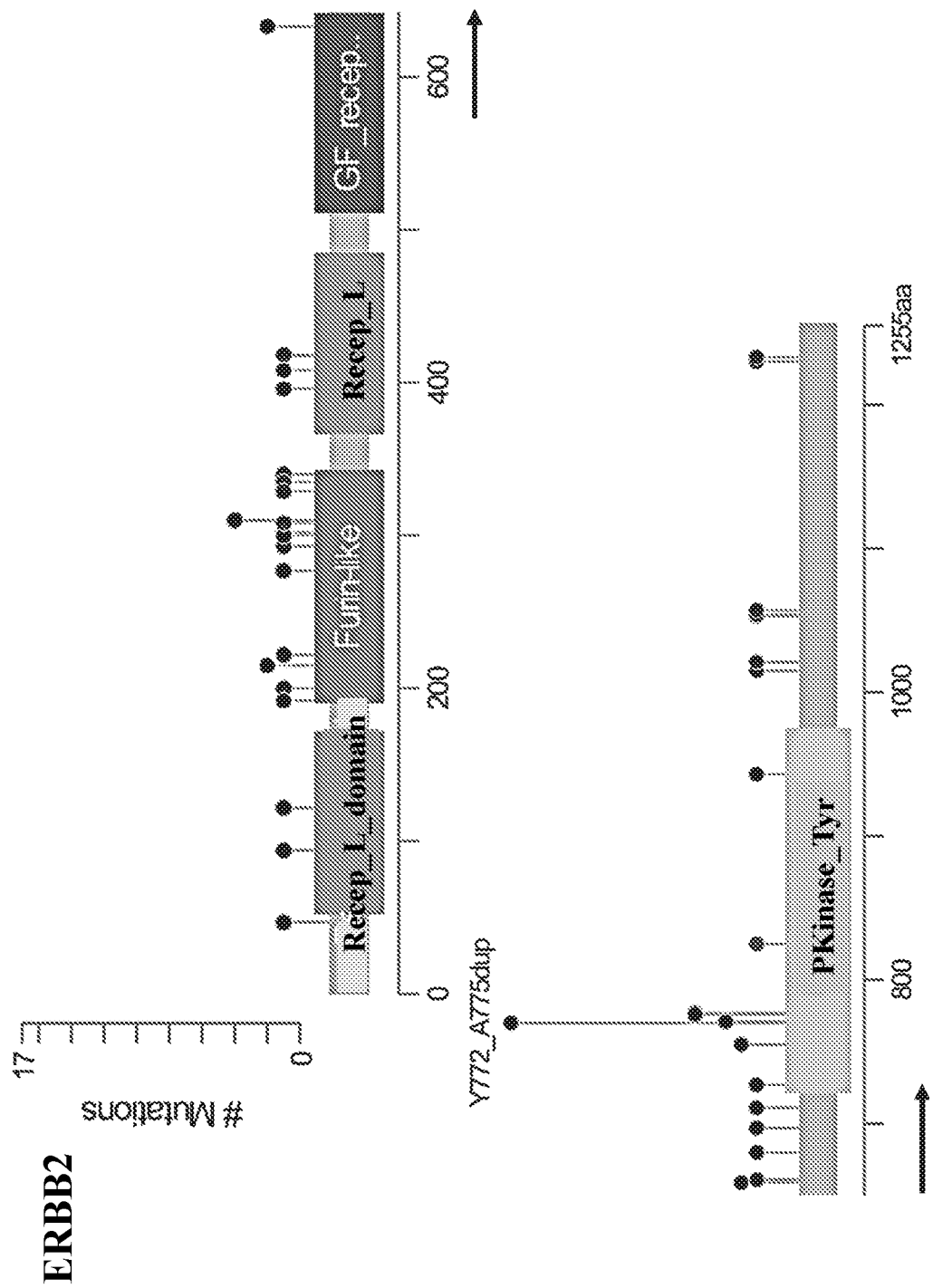

Lung adenocarcinoma is characterized by distinct subsets that can be classified by oncogene status. ERBB2 (HER2) gene amplification is present in ~3% and ERBB2 activating mutations in ~3% of the patients (FIGS. 9A-9C). FIGS. 9A-9B shows the type and frequency of ERBB2 alterations in the indicated lung cancer cohorts (data derived from www dot cbioportal dot org). FIG. 9C demonstrates the distribution of ERBB2 mutations identified in lung cancer across the ERBB2 gene (with key protein domains depicted by boxes) and also demonstrate the number of alterations identified at each corresponding amino acid position (www dot cbioportal dot org). Although HER2-directed therapies are available for breast and gastric cancer, the use of HER2-directed monoclonal antibodies and tyrosine kinase inhibitors (TKIs) have been disappointing in lung cancer.

Figure 10B:
Figure 10C:
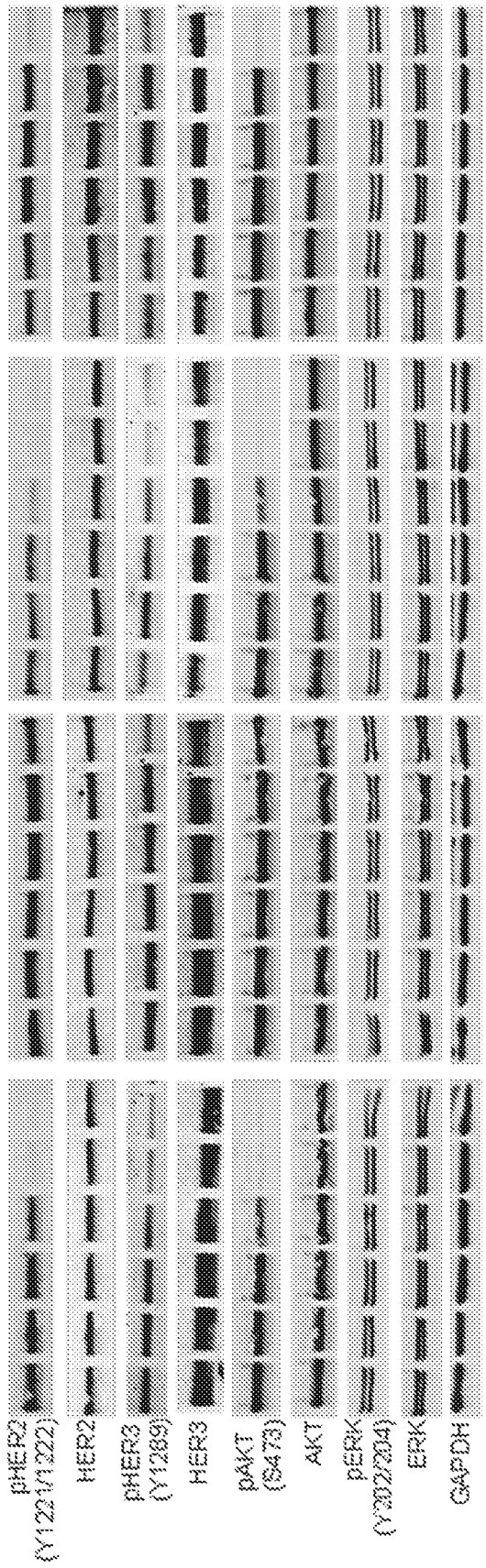

As illustrated in FIGS. 10A-10B, using MTS, proliferation of three HER2-driven cell lines (Calu-3 and H2071 with ERBB2 amplification; H1781 with ERBB2 p.G776>VC insertion mutation) treated with TRLX-TKI or TRLX or $1^{st}$, $2^{nd}$ or $3^{rd}$ generation EGFR/HER2 TKIs were evaluated. Cells were treated with the indicated doses of afatinib, gefitinib, osimertinib, TRLX-TKI (RN-4000E; active drug) for 2 hours under normoxic conditions, lysed, and analyzed by immunoblot. On-target and signaling effects elicited by TRLX-TKI were evaluated via immunoblots of pHER2, pHER3, pERK and pAKT. Using a nude mice xenograft model, effects of the TRLX prodrug with other TKIs on tumor growth were compared.

Figure 11:
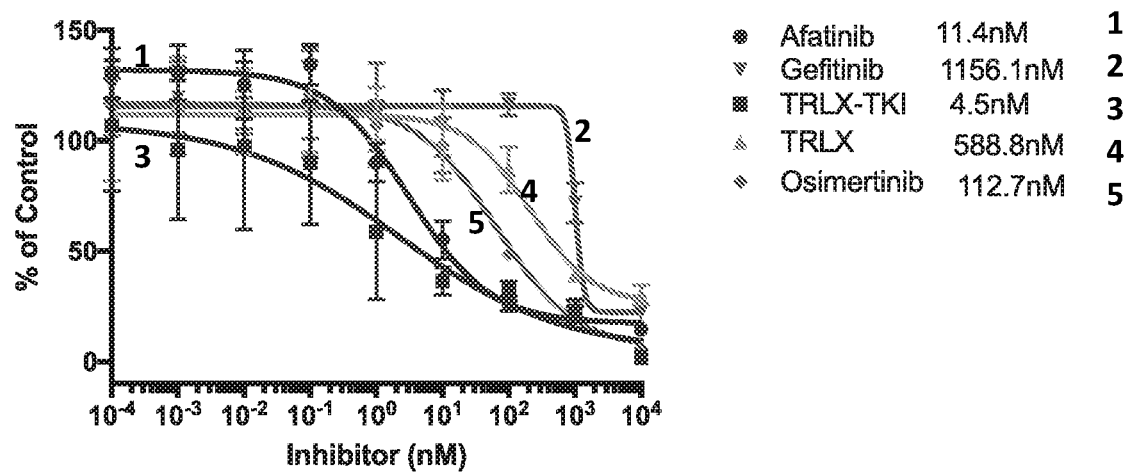
FIG. 11 comprises a series of graphs illustrating dose response curves of cell viability of the patient derived cell lines harboring HER2 gene amplification (H2170 and CALU-3) or a HER2 exon 20 insertion mutation (H1781). Cells were treated with afatinib, gefitinib, osimertinib, TRLX (RN-4000; pro-drug) and TRLX-TKI (RN-4000E; effector drug) for 72 hours under normoxic conditions and analyzed by MTS. Experiments were done by triplicate, mean and ±SEM is plotted. See Table 3 for IC$_{50}$ values of proliferation experiments. Values are expressed in nanomolar concentration. See Table 4 for fold difference in IC$_{50}$ between the prodrug (TRLX) and the active metabolite (TRLX-TKI) under normoxic conditions.
Figure 11:
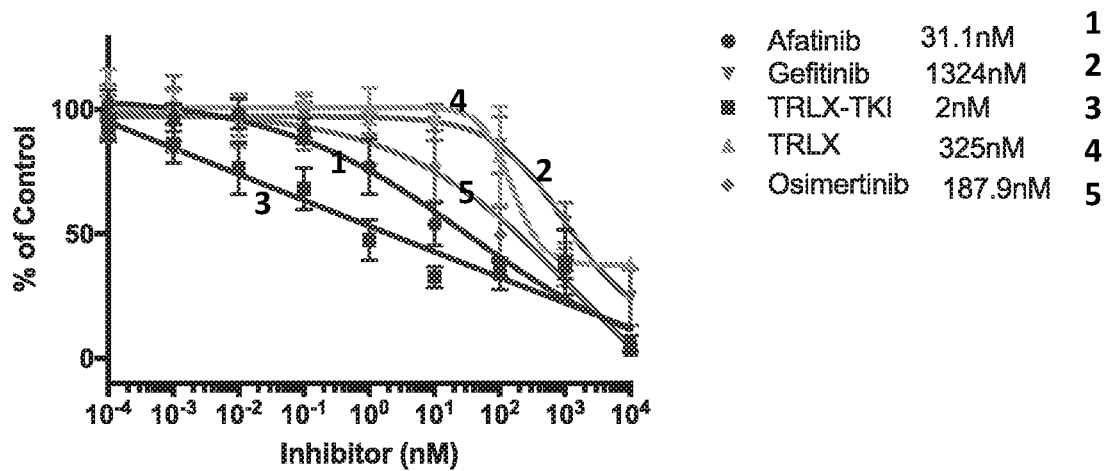
Figure 11:
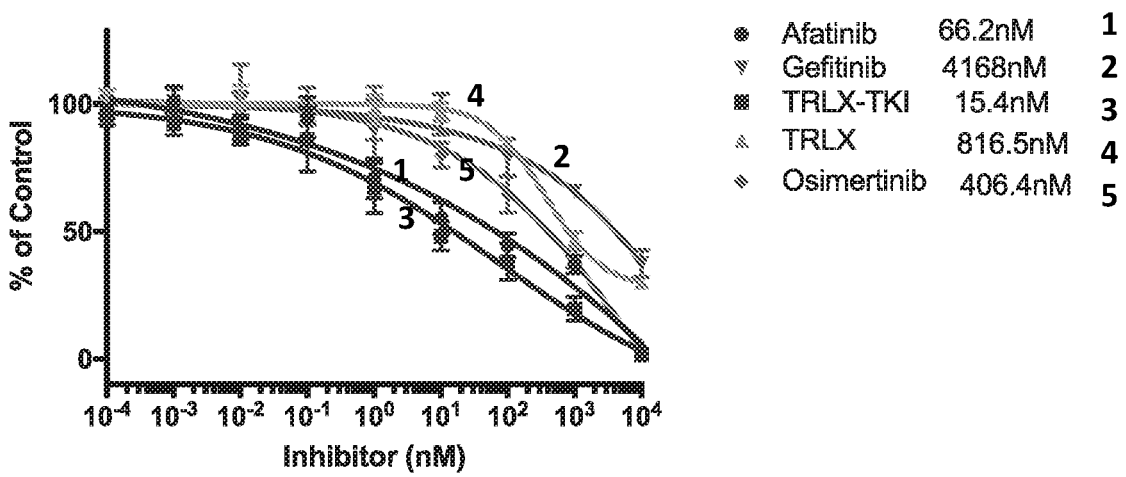

Further, dose response curves of cell viability of these patient derived cell lines, which harbor HER2 gene amplification (H2170 and CALU-3) or a HER2 exon 20 insertion mutation (H1781), were obtained (FIG. 11). Cells were treated with afatinib, gefitinib, osimertinib, TRLX (RN-4000; pro-drug) and TRLX-TKI (RN-4000E; effector drug) for 72 hours under normoxic conditions and analyzed by MTS. Experiments were done by triplicate. Table 3 further comprises a table summarizing $IC_{50}$ values of proliferation experiments. Values are expressed in nanomolar concentration. These data demonstrate that TRLX-TKI is the most potent inhibitor of cell proliferation in comparison to the other tyrosine kinase inhibitors tested for each of the 3 cancer cell lines bearing ERBB2 alterations. Table 4 comprises the fold difference in $IC_{50}$ between the prodrug (TRLX) and the active metabolite (TRLX-TKI) under normoxic conditions. The large fold difference in activity between RN-4000 (pro-drug) and RN-4000E (effector drug) demonstrates a key differentiating factor of RN-4000 compared to other tyrosine kinase inhibitors. RN-4000 has low activity against HER2, but the RN-4000E effector drug (produced in high concentrations at the tumor site by hypoxia) is potent against HER2.

TABLE 3

$IC_{50}$ of HER2 driven cell lines treated with EGFR/HER2 TKIs.

| Drug | H2170 | Calu-3 | H1781 |
|---|---|---|---|
| TRLX-TKI | 11.4 | 2 | 15.4 |
| TRLX | 588.8 | 325 | 816.5 |
| gefitinib | 1156.1 | 1324 | 4168 |
| afatinib | 11.4 | 31.1 | 66.2 |
| osimertinib | 112.7 | 187.9 | 406.4 |

TABLE 4

Fold difference in $IC_{50}$ between TRLX and TRLX-TKI under normoxic conditions.

| | H2170 | Calu-3 | H1781 |
|---|---|---|---|
| TRLX: TRLX-TKI ratio | 51.6 | 162.5 | 53.0 |

The results demonstrate that HER2-driven lung cancer cell lines show the highest sensitivity to TRLX-TKI whereas the TRLX prodrug is >50-fold less potent under normoxic conditions, consistent with the required mechanism of hypoxia for activation. Afatinib, which has poor activity in HER2 mutation positive NSCLC, was the next most potent drug in vitro, followed by osimertinib and gefitinib (Table 1). In immunoblot analyses, TRLX-TKI inhibits HER2 phosphorylation between 10-100 nM whereas afatinib inhibits pHER2 at 100 nM, consistent with the cell proliferation data. Notably, a concurrent reduction in pHER3 phosphorylation with TKI treatment was also observed. Analysis of downstream signaling pathways demonstrated that pERK was not inhibited by any of the TKIs, whereas AKT signaling was inhibited at similar doses to that of upstream HER2.

TRLX-TKI is a potent HER2 inhibitor in vitro that can inhibit HER2 (and HER3) phosphorylation at low nanomolar doses and with greater potency than currently approved TKIs for NSCLC. This activity was observed in cell lines harboring both amplified or mutant ERBB2. HER2-driven cells depend on the AKT pathway for survival whereas MAPK inhibition was not necessary to inhibit cell proliferation. Tarloxotinib represents a new therapeutic approach for NSCLC patients harboring ERBB2 gene alterations.

Example 3: Anti-Tumor Activity of Tarloxotinib in Cell Lines Harboring NRG1 Gene Amplification NRG1 overexpression by gene amplification or other mechanisms are be predicted to activate HER3:HER2 dimers. Currently there are no U.S. FDA approved (or other regulatory agencies) drugs for NRG1 gene amplification.

Figure 13:
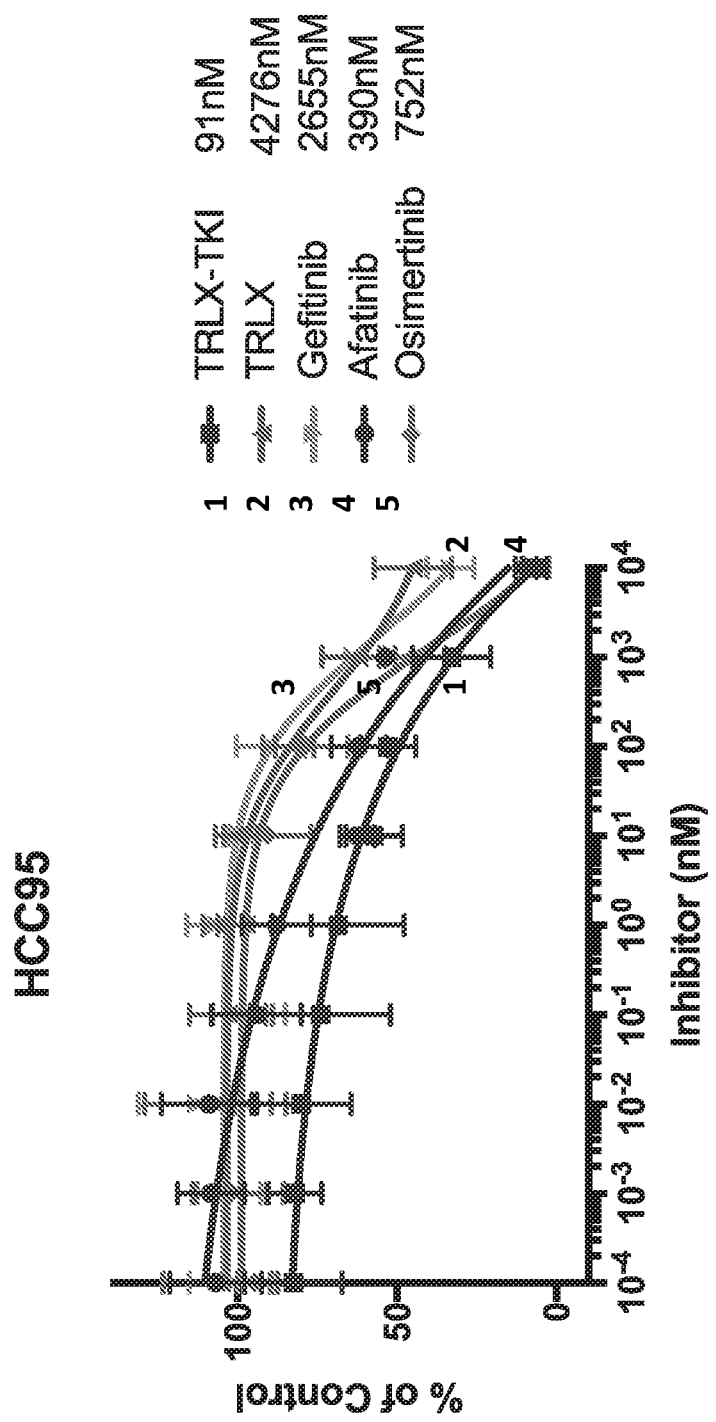
FIG. 13 comprises a graph illustrating dose response curves of cell viability of a patient derived cell line harboring NRG1 gene amplification (HCC95). Cells were treated with afatinib, gefitinib, osimertinib, TRLX (RN-4000; pro-drug) and TRLX-TKI (RN-4000E; effector drug) for 72 hours under normoxic conditions and analyzed by MTS. As demonstrated herein, TRLX-TKI (RN-4000E) inhibits proliferation of this cell line.
Figure 14:
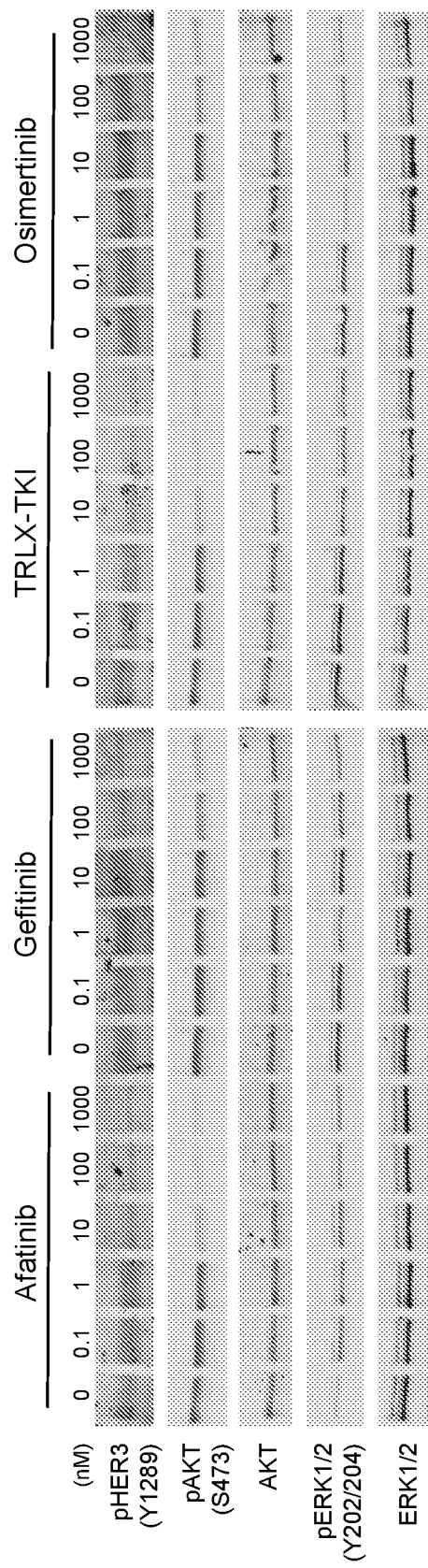
FIG. 14 comprises a series of gel images illustrating the finding that TRLX-TKI (RN-4000E) inhibits HER3 phosphorylation and downstream signaling in the HCC95 cell line harboring NRG1 gene amplification. Cells were treated with the indicated doses of afatinib, gefitinib, RN-4000E, and osimertinib (active drug) for 2 hours, lysed and analyzed by immunoblot. Blots are representatives of three independent experiments.

As demonstrated herein (FIGS. 13-14), the active metabolite of tarloxotinib, TRLX-TKI (RN-4000E), inhibits proliferation of a cell line harboring NRG1 gene amplification (in a non-limiting example, HCC95). FIG. 13 illustrates dose response curves of cell viability of this patient derived cell line. Cells were treated with afatinib, gefitinib, osimertinib, TRLX (RN-4000; pro-drug) and TRLX-TKI (RN-4000E; effector drug) for 72 hours under normoxic conditions and analyzed by MTS. The figure recites $IC_{50}$ values (in nanomolar) determined in the proliferation experiments. FIG. 14 comprises a series of gel images illustrating that RN-4000E inhibits HER3 phosphorylation and downstream signaling in the HCC95 cell line harboring NRG1 gene amplification. Cells were treated with the indicated doses of afatinib, gefitinib, RN-4000E, and osimertinib (active drug) for 2 hours, lysed and analyzed by immunoblot. Blots are representatives of three independent experiments.

Example 4: Anti-Tumor Activity of Tarloxotinib in Cell Lines Harboring NRG1 Gene Fusion Gene fusions that contain sequences from NRG1 have been identified in breast, lung adenocarcinoma, NSCLC, cholangiocarcinoma, pancreatic cancer, and ovarian cancer. NRG1 gene fusions have been demonstrated to be oncogenic by inducing overexpression the ligand Neuregulin 1 which induces heterodimerization of HER3 with HER2. Currently there are no U.S. FDA approved (or other regulatory agencies) drugs for NRG1 fusions.

Figure 15:
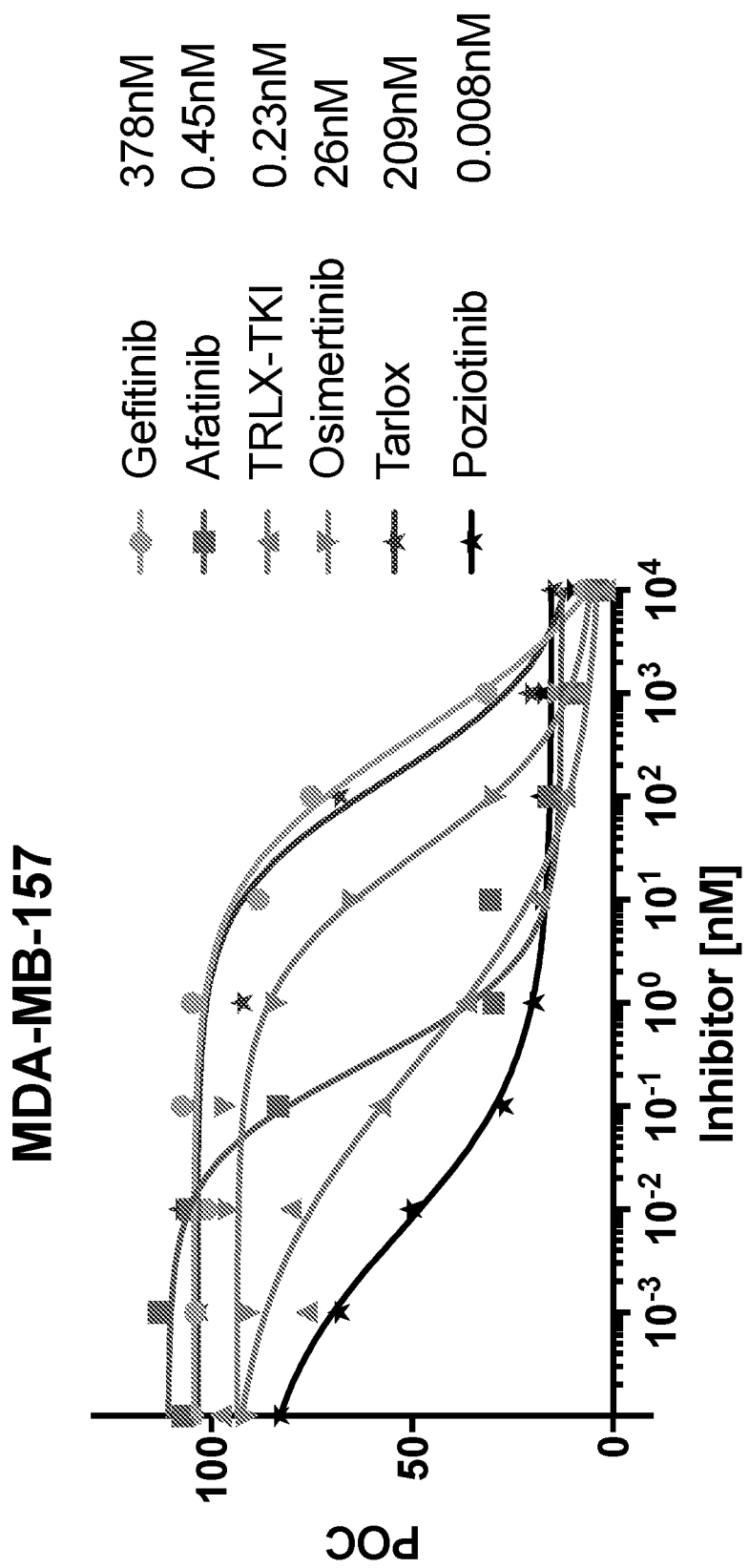
FIG. 15 comprises a graph illustrating the finding that TRLX-TKI (RN-4000E) inhibits proliferation of a breast cancer cell line harboring a DOC4-NRG1 gene fusion (MDA-MB-157). Dose response curves of cell viability of these patient derived cell lines. Cells were treated with gefitinib, afatinib, TRLX-TKI (RN-4000E; effector drug), osimertinib, TRLX (RN-4000; pro-drug) or poziotinib for 72 hours under normoxic conditions and analyzed by MTS.

As demonstrated herein (FIG. 15), the active metabolite of tarloxotinib, TRLX-TKI (RN-4000E), inhibits proliferation of a breast cancer cell line harboring a DOC4-NRG1 gene fusion (in a non-limiting example, MDA-MB-157). FIG. 15 illustrates dose response curves of cell viability of this cell line. Cells were treated with gefitinib, afatinib, TRLX-TKI (RN-4000E; effector drug), osimertinib, TRLX (RN-4000; pro-drug) or poziotinib for 72 hours under normoxic conditions and analyzed by MTS. The figure recites $IC_{50}$ values (in nanomolar) determined in the proliferation experiments.

Example 5: Anti-Tumor Activity of Tarloxotinib in Cell Lines Harboring EGFR Exon 20 Insertion Mutations Cancers with EGFR Exon 20 insertion mutations exhibit resistance and/or poor response to EGFR-TKIs such as osimertinib, gefitinib, afatinib, and erlotinib. Thus, there is great need to identify compounds that effectively treat and/or prevent such cancers.

Figure 16A:
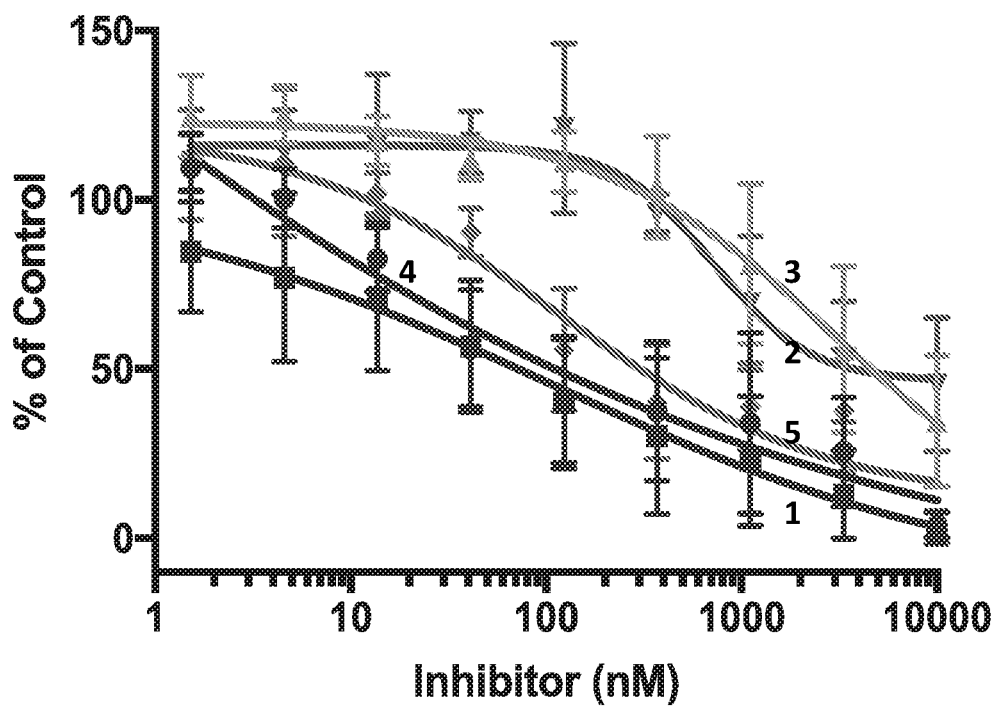
Figure 16A:
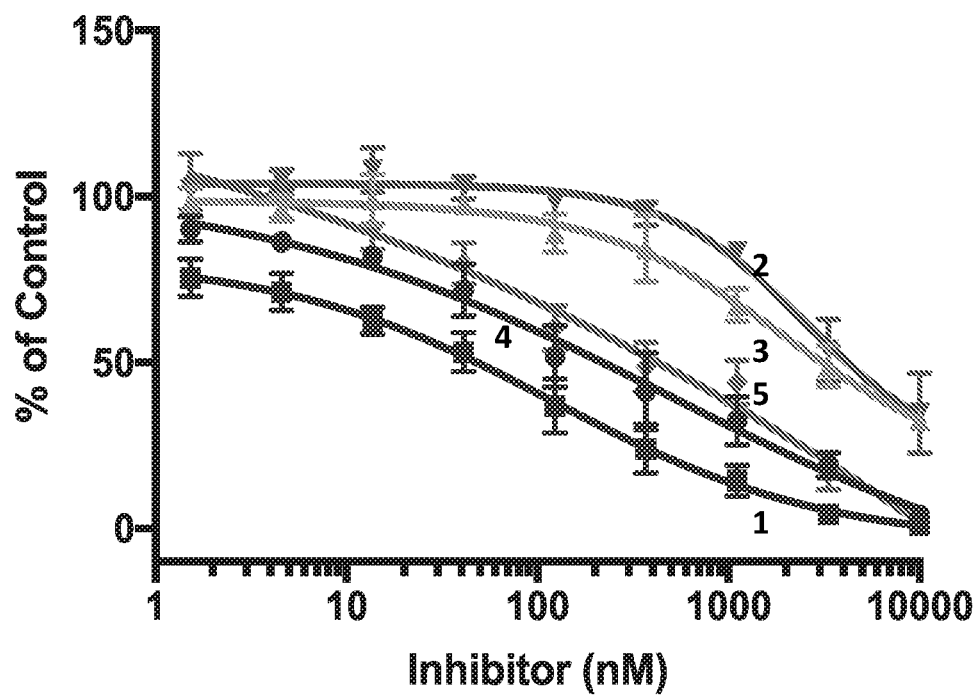

As demonstrated herein (FIGS. 16A-16B), the active metabolite of tarloxotinib, TRLX-TKI (RN-4000E), inhibits proliferation of cell lines harboring EGFR exon 20 insertion mutations. FIGS. 16A-16B illustrate dose response curves of cell viability of EGFR exon 20 insertion mutation patient derived cell lines (CUTO-14, CUTO-17, CUTO-18). Cells were treated with TRLX-TKI, TRLX (pro-drug), gefitinib, afatinib, or osimertinib for 72 hours under normoxic conditions and analyzed by MTS. Table 5 recites $IC_{50}$ values (in nanomolar) determined in the proliferation experiments illustrated in FIGS. 16A-16B. Table 6 comprises the fold difference in $IC_{50}$ between the prodrug (TRLX) and the active metabolite (TRLX-TKI) under normoxic conditions. The large fold difference in activity between RN-4000 (pro-drug) and RN-4000E (effector drug) demonstrates a key differentiating factor of RN-4000 compared to other tyrosine kinase inhibitors. RN-4000 has low activity against EGFR, but the RN-4000E effector drug (produced in high concentrations at the tumor site by hypoxia) is potent against EGFR.

TABLE 5

$IC_{50}$ (nM) of EGFR exon 20 driven cell lines treated with EGFR/HER2 TKIs

| Drug | CUTO-14 | CUTO-17 | CUTO-18 |
|---|---|---|---|
| TRLX-TKI | 72.2 | 48.1 | 158 |
| TRLX | 4645 | 3090 | >10000 |
| Gefitinib | 3741 | 4197 | >10000 |
| Afatinib | 111 | 220 | 841 |
| Osimertinib | 303 | 426 | 647 |

TABLE 6

Fold difference in $IC_{50}$ between TRLX and TRLX-TKI under normoxic conditions in EGFR exon 20 cell lines

| | CUTO-14 | CUTO-17 | CUTO-18 |
|---|---|---|---|
| TRLX: TRLX-TKI ratio | 64.3 | 64.2 | >60 |

The disclosures of each and every patent, patent application, and publication, as well as other references, GenBan citations and ATCC citations, cited herein are hereby incorporated herein by reference in their entirety. While the present disclosure has been made with reference to specific embodiments, it is apparent that other embodiments and variations of these specific embodiments may be devised by others skilled in the art without departing from the true spirit and scope of the present disclosure. The appended claims are intended to be construed to include all such embodiments and equivalent variations.

What is claimed:

1. A method of treating a HER-driven drug-resistant cancer in a subject in need thereof, the method comprising:
 (a) providing tumor cells of the subject;
 (b) detecting presence of an EGFR exon 20 insertion mutation in the provided tumor cells;
 (c) determining the subject as being likely to be responsive to treatment by (2E)-4-{[4-(3-bromo-4-chloroanilino)pyrido[3,4-d]pyrimidin-6-yl]amino}-N,N-dimethyl-N-[(1-methyl-4-nitro-1H-imidazol-5-yl)methyl]-4-oxo-2-buten-1-ammonium bromide (Compound A) and/or (2E)-N-[4-(3-bromo-4-chloroanilino)pyrido[3,4-d]pyrimidin-6-yl]-4-(dimethylamino)-2 butenamide) (Compound B); and
 d) administering to the subject in need thereof a therapeutically effective amount of at least one compound selected from the group consisting of Compound A and Compound B, or a salt or a solvate thereof,
 wherein the cancer comprises any one or more of:
  (i) at least one ERBB2 gene fusion selected from the group consisting of ZNF207-HER2, MDK-HER2, NOS2-HER2, ERBB2-GRB7, ERBB2-CTTN, ERBB2-PPP1R1B, and ERBB2-PSMB3;
  (ii) at least one NRGI gene fusion selected from the group consisting of DOC4-NRG1, CD74-NRG1, SLC3A2-NRG1, RBPMS-NRG1, WRN-NRG1, SDC4-NRG1, RAB2IL1-NRG1, VAMP2-NRG1, KIF13B-NRG1, ATP1B1NRG1, CDH6-NRG1, APP-NRG1, AKAP13-NRG1, THBS1-NRG1, PDE7A-NRG1, THAP7-NRG1, SMAD4-NRG1, RAB3IL1-NRG1, NRG1-PMEPA1, and NRG1-STMN2;
  (iii) at least one ERBB3 mutation selected from the group consisting of V104M, A232V, P262H, G284R, T389K, Q809R, S846I, and E928G; and
  (iv) at least one ERBB4 fusion selected from the group consisting of EZR-ERBB4, IKZF2-ERBB4, and BGALT-ERBB4.

2. The method of claim 1, wherein the HER-driven cancer comprises an EGFR-driven cancer.

3. The method of claim 2, wherein the EGFR-driven cancer comprises lung cancer.

4. The method of claim 3, wherein the lung cancer comprises non-small cell lung cancer (NSCLC).

5. The method of claim 1, wherein the mutation comprises at least one selected from the group consisting of A763_Y764insFQEA, A763_Y764insFQQA, A767_V769dupASV, D770_N77linsGL, D770_N77linsGT, D770_N77linsNPG, D770_N77linsSVD, E762Q_insFQEA, H773_V774insH, H773_V774insH, H773_V774insNPH, M766_A767insAI, M766_A767insASV, N771_H773dupNPH, P772_H773insYNP, P772_V774insPHV, S768_770dupSVD, V769_D770insASV, Y764_V765insHH, delD770insGY, and delL747_P753insS.

6. The method of claim 1, wherein the cancer is resistant to at least one agent selected from the group consisting of osimertinib, gefitinib, afatinib, anderlotinib.

7. The method of claim 1, further comprising administering at least one additional agent or a salt or solvate thereof, that treats the cancer.

8. The method of claim 7, wherein the at least one compound and the at least one additional agent are co-administered to the subject.

9. The method of claim 8, wherein the at least one compound and the at least one additional agent are coformulated.

10. The method of claim 1, wherein the at least one compound is administered by at least one route selected from the group consisting of, oral, nasal, rectal, parenteral, sublingual, transdermal, transmucosal, intravesical, intrapulmonary, intraduodenal, intragastrical, intrathecal, epidural, intrapleural, intraperitoneal, intratracheal, otic, intraocular, subcutaneous, intramuscular, intradermal, intraarterial, intravenous, intrabronchial, inhalation, and topical.

11. The method of claim 1, wherein the subject is a mammal.

12. The method of claim 11, wherein the mammal is a human.

13. The method of claim 12, wherein the human is in need of treatment thereof.

* * * * *

SEQUENCE LISTING

```
<160> NUMBER OF SEQ ID NOS: 37

<210> SEQ ID NO 1
<211> LENGTH: 1210
<212> TYPE: PRT
<213> ORGANISM: Homo sapiens
<220> FEATURE:
<221> NAME/KEY: misc_feature
<223> OTHER INFORMATION: human EGFR, Isoform 1 (canonical ; UniProt ID
      P00533-1)

<400> SEQUENCE: 1

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30
```

```
Gly Thr Ser Asn Lys Leu Thr Gln Leu Gly Thr Phe Glu Asp His Phe
             35                  40                  45

Leu Ser Leu Gln Arg Met Phe Asn Asn Cys Glu Val Val Leu Gly Asn
 50                  55                  60

Leu Glu Ile Thr Tyr Val Gln Arg Asn Tyr Asp Leu Ser Phe Leu Lys
 65                  70                  75                  80

Thr Ile Gln Glu Val Ala Gly Tyr Val Leu Ile Ala Leu Asn Thr Val
                 85                  90                  95

Glu Arg Ile Pro Leu Glu Asn Leu Gln Ile Ile Arg Gly Asn Met Tyr
                100                 105                 110

Tyr Glu Asn Ser Tyr Ala Leu Ala Val Leu Ser Asn Tyr Asp Ala Asn
            115                 120                 125

Lys Thr Gly Leu Lys Glu Leu Pro Met Arg Asn Leu Gln Glu Ile Leu
        130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
```

```
                450            455            460
    Gly Asn Lys Asn Leu Cys Tyr Ala Asn Thr Ile Asn Trp Lys Lys Leu
    465            470            475            480

Phe Gly Thr Ser Gly Gln Lys Thr Lys Ile Ile Ser Asn Arg Gly Glu
                    485            490            495

Asn Ser Cys Lys Ala Thr Gly Gln Val Cys His Ala Leu Cys Ser Pro
                500            505            510

Glu Gly Cys Trp Gly Pro Glu Pro Arg Asp Cys Val Ser Cys Arg Asn
            515            520            525

Val Ser Arg Gly Arg Glu Cys Val Asp Lys Cys Asn Leu Leu Glu Gly
        530            535            540

Glu Pro Arg Glu Phe Val Glu Asn Ser Glu Cys Ile Gln Cys His Pro
    545            550            555            560

Glu Cys Leu Pro Gln Ala Met Asn Ile Thr Cys Thr Gly Arg Gly Pro
                    565            570            575

Asp Asn Cys Ile Gln Cys Ala His Tyr Ile Asp Gly Pro His Cys Val
                580            585            590

Lys Thr Cys Pro Ala Gly Val Met Gly Glu Asn Asn Thr Leu Val Trp
            595            600            605

Lys Tyr Ala Asp Ala Gly His Val Cys His Leu Cys His Pro Asn Cys
        610            615            620

Thr Tyr Gly Cys Thr Gly Pro Gly Leu Glu Gly Cys Pro Thr Asn Gly
    625            630            635            640

Pro Lys Ile Pro Ser Ile Ala Thr Gly Met Val Gly Ala Leu Leu Leu
                    645            650            655

Leu Leu Val Val Ala Leu Gly Ile Gly Leu Phe Met Arg Arg Arg His
                660            665            670

Ile Val Arg Lys Arg Thr Leu Arg Arg Leu Leu Gln Glu Arg Glu Leu
            675            680            685

Val Glu Pro Leu Thr Pro Ser Gly Glu Ala Pro Asn Gln Ala Leu Leu
        690            695            700

Arg Ile Leu Lys Glu Thr Glu Phe Lys Lys Ile Lys Val Leu Gly Ser
    705            710            715            720

Gly Ala Phe Gly Thr Val Tyr Lys Gly Leu Trp Ile Pro Glu Gly Glu
                    725            730            735

Lys Val Lys Ile Pro Val Ala Ile Lys Glu Leu Arg Glu Ala Thr Ser
                740            745            750

Pro Lys Ala Asn Lys Glu Ile Leu Asp Glu Ala Tyr Val Met Ala Ser
            755            760            765

Val Asp Asn Pro His Val Cys Arg Leu Leu Gly Ile Cys Leu Thr Ser
        770            775            780

Thr Val Gln Leu Ile Thr Gln Leu Met Pro Phe Gly Cys Leu Leu Asp
    785            790            795            800

Tyr Val Arg Glu His Lys Asp Asn Ile Gly Ser Gln Tyr Leu Leu Asn
                    805            810            815

Trp Cys Val Gln Ile Ala Lys Gly Met Asn Tyr Leu Glu Asp Arg Arg
                820            825            830

Leu Val His Arg Asp Leu Ala Ala Arg Asn Val Leu Val Lys Thr Pro
            835            840            845

Gln His Val Lys Ile Thr Asp Phe Gly Leu Ala Lys Leu Leu Gly Ala
        850            855            860

Glu Glu Lys Glu Tyr His Ala Glu Gly Gly Lys Val Pro Ile Lys Trp
    865            870            875            880
```

Met Ala Leu Glu Ser Ile Leu His Arg Ile Tyr Thr His Gln Ser Asp
            885                 890                 895

Val Trp Ser Tyr Gly Val Thr Val Trp Glu Leu Met Thr Phe Gly Ser
        900                 905                 910

Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
    930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala Leu Met Asp Glu Glu Asp Met Asp
        995                 1000                1005

Asp Val Val Asp Ala Asp Glu Tyr Leu Ile Pro Gln Gln Gly Phe
    1010                1015                1020

Phe Ser Ser Pro Ser Thr Ser Arg Thr Pro Leu Leu Ser Ser Leu
    1025                1030                1035

Ser Ala Thr Ser Asn Asn Ser Thr Val Ala Cys Ile Asp Arg Asn
    1040                1045                1050

Gly Leu Gln Ser Cys Pro Ile Lys Glu Asp Ser Phe Leu Gln Arg
    1055                1060                1065

Tyr Ser Ser Asp Pro Thr Gly Ala Leu Thr Glu Asp Ser Ile Asp
    1070                1075                1080

Asp Thr Phe Leu Pro Val Pro Glu Tyr Ile Asn Gln Ser Val Pro
    1085                1090                1095

Lys Arg Pro Ala Gly Ser Val Gln Asn Pro Val Tyr His Asn Gln
    1100                1105                1110

Pro Leu Asn Pro Ala Pro Ser Arg Asp Pro His Tyr Gln Asp Pro
    1115                1120                1125

His Ser Thr Ala Val Gly Asn Pro Glu Tyr Leu Asn Thr Val Gln
    1130                1135                1140

Pro Thr Cys Val Asn Ser Thr Phe Asp Ser Pro Ala His Trp Ala
    1145                1150                1155

Gln Lys Gly Ser His Gln Ile Ser Leu Asp Asn Pro Asp Tyr Gln
    1160                1165                1170

Gln Asp Phe Phe Pro Lys Glu Ala Lys Pro Asn Gly Ile Phe Lys
    1175                1180                1185

Gly Ser Thr Ala Glu Asn Ala Glu Tyr Leu Arg Val Ala Pro Gln
    1190                1195                1200

Ser Ser Glu Phe Ile Gly Ala
    1205                1210

<210> SEQ ID NO 2
<211> LENGTH: 405
<212> TYPE: PRT
<213> ORGANISM: Homo sapiens
<220> FEATURE:
<221> NAME/KEY: misc_feature
<223> OTHER INFORMATION: human EGFR, Isoform 2 (UniProt ID P00533-2)

<400> SEQUENCE: 2

Met Arg Pro Ser Gly Thr Ala Gly Ala Ala Leu Leu Ala Leu Leu Ala

```
1               5                   10                  15
Ala Leu Cys Pro Ala Ser Arg Ala Leu Glu Glu Lys Lys Val Cys Gln
                20                  25                  30

Gly Thr Ser Asn Lys Leu Thr Gln Leu Gly Thr Phe Glu Asp His Phe
                35                  40                  45

Leu Ser Leu Gln Arg Met Phe Asn Asn Cys Glu Val Val Leu Gly Asn
                50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
                100                 105                 110

Tyr Glu Asn Ser Tyr Ala Leu Ala Val Leu Ser Asn Tyr Asp Ala Asn
                115                 120                 125

Lys Thr Gly Leu Lys Glu Leu Pro Met Arg Asn Leu Gln Glu Ile Leu
                130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
                180                 185                 190

Ser Cys Pro Asn Gly Ser Cys Trp Gly Ala Gly Glu Glu Asn Cys Gln
                195                 200                 205

Lys Leu Thr Lys Ile Ile Cys Ala Gln Gln Cys Ser Gly Arg Cys Arg
                210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
                260                 265                 270

Thr Thr Tyr Gln Met Asp Val Asn Pro Glu Gly Lys Tyr Ser Phe Gly
                275                 280                 285

Ala Thr Cys Val Lys Lys Cys Pro Arg Asn Tyr Val Val Thr Asp His
                290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
                340                 345                 350

Ala Thr Asn Ile Lys His Phe Lys Asn Cys Thr Ser Ile Ser Gly Asp
                355                 360                 365

Leu His Ile Leu Pro Val Ala Phe Arg Gly Asp Ser Phe Thr His Thr
                370                 375                 380

Pro Pro Leu Asp Pro Gln Glu Leu Asp Ile Leu Lys Thr Val Lys Glu
385                 390                 395                 400

Ile Thr Gly Leu Ser
                405

<210> SEQ ID NO 3
```

<211> LENGTH: 705
<212> TYPE: PRT
<213> ORGANISM: Homo sapiens
<220> FEATURE:
<221> NAME/KEY: misc_feature
<223> OTHER INFORMATION: human EGFR, Isoform 3 (UniProt ID P00533-3)

<400> SEQUENCE: 3

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
                20                  25                  30

Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
        50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
```

```
                        370                 375                 380
Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
                420                 425                 430

His Gly Gln Phe Ser Leu Ala Val Val Ser Leu Asn Ile Thr Ser Leu
                435                 440                 445

Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
                500                 505                 510

Glu Gly Cys Trp Gly Pro Glu Pro Arg Asp Cys Val Ser Cys Arg Asn
                515                 520                 525

Val Ser Arg Gly Arg Glu Cys Val Asp Lys Cys Asn Leu Leu Glu Gly
530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
                580                 585                 590

Lys Thr Cys Pro Ala Gly Val Met Gly Glu Asn Asn Thr Leu Val Trp
                595                 600                 605

Lys Tyr Ala Asp Ala Gly His Val Cys His Leu Cys His Pro Asn Cys
                610                 615                 620

Thr Tyr Gly Pro Gly Asn Glu Ser Leu Lys Ala Met Leu Phe Cys Leu
625                 630                 635                 640

Phe Lys Leu Ser Ser Cys Asn Gln Ser Asn Asp Gly Ser Val Ser His
                645                 650                 655

Gln Ser Gly Ser Pro Ala Ala Gln Glu Ser Cys Leu Gly Trp Ile Pro
                660                 665                 670

Ser Leu Leu Pro Ser Glu Phe Gln Leu Gly Trp Gly Gly Cys Ser His
                675                 680                 685

Leu His Ala Trp Pro Ser Ala Ser Val Ile Ile Thr Ala Ser Ser Cys
                690                 695                 700

His
705

<210> SEQ ID NO 4
<211> LENGTH: 628
<212> TYPE: PRT
<213> ORGANISM: Homo sapiens
<220> FEATURE:
<221> NAME/KEY: misc_feature
<223> OTHER INFORMATION: human EGFR, Isoform 4 (UniProt ID P00533-4)

<400> SEQUENCE: 4

Met Arg Pro Ser Gly Thr Ala Gly Ala Ala Leu Leu Ala Leu Leu Ala
1               5                   10                  15
```

```
Ala Leu Cys Pro Ala Ser Arg Ala Leu Glu Lys Lys Val Cys Gln
             20                  25                  30

Gly Thr Ser Asn Lys Leu Thr Gln Leu Gly Thr Phe Glu Asp His Phe
         35                  40                  45

Leu Ser Leu Gln Arg Met Phe Asn Asn Cys Glu Val Val Leu Gly Asn
 50                  55                  60

Leu Glu Ile Thr Tyr Val Gln Arg Asn Tyr Asp Leu Ser Phe Leu Lys
 65                  70                  75                  80

Thr Ile Gln Glu Val Ala Gly Tyr Val Leu Ile Ala Leu Asn Thr Val
                 85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
            115                 120                 125

Lys Thr Gly Leu Lys Glu Leu Pro Met Arg Asn Leu Gln Glu Ile Leu
        130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
```

```
                435                 440                 445
Gly Leu Arg Ser Leu Lys Glu Ile Ser Asp Gly Asp Val Ile Ile Ser
    450                 455                 460
Gly Asn Lys Asn Leu Cys Tyr Ala Asn Thr Ile Asn Trp Lys Lys Leu
465                 470                 475                 480
Phe Gly Thr Ser Gly Gln Lys Thr Lys Ile Ile Ser Asn Arg Gly Glu
                485                 490                 495
Asn Ser Cys Lys Ala Thr Gly Gln Val Cys His Ala Leu Cys Ser Pro
            500                 505                 510
Glu Gly Cys Trp Gly Pro Glu Pro Arg Asp Cys Val Ser Cys Arg Asn
        515                 520                 525
Val Ser Arg Gly Arg Glu Cys Val Asp Lys Cys Asn Leu Leu Glu Gly
    530                 535                 540
Glu Pro Arg Glu Phe Val Glu Asn Ser Glu Cys Ile Gln Cys His Pro
545                 550                 555                 560
Glu Cys Leu Pro Gln Ala Met Asn Ile Thr Cys Thr Gly Arg Gly Pro
                565                 570                 575
Asp Asn Cys Ile Gln Cys Ala His Tyr Ile Asp Gly Pro His Cys Val
            580                 585                 590
Lys Thr Cys Pro Ala Gly Val Met Gly Glu Asn Asn Thr Leu Val Trp
        595                 600                 605
Lys Tyr Ala Asp Ala Gly His Val Cys His Leu Cys His Pro Asn Cys
    610                 615                 620
Thr Tyr Gly Ser
625

<210> SEQ ID NO 5
<211> LENGTH: 197496
<212> TYPE: DNA
<213> ORGANISM: Homo sapiens
<220> FEATURE:
<221> NAME/KEY: misc_feature
<223> OTHER INFORMATION: EGFR gene, complete cds, alternatively spliced

<400> SEQUENCE: 5 ttcttttag cacagaataa caatccattg tccacatgta ccatggttta tttatccact       60
catccacatg aagacatctt agttgattct aagttaggga agttatgaat aaagctgtta      120
taaatattca tgagcagatt tatgtggaca acagtgttca actcatttgg gtaagtatca      180
aggagagaaa tcattggatc atatggtaag agtatgtaca cttttatagg aaactgctaa      240
gctgcattcc taagtggctg taccattgtg ccttcccatc agcaatgaat gagacttcct      300
attgttccac atcctcatca gaatttggtg ttgtcactga tctgaatttt ttccattgta      360
acagatgtgt agtggtatct cactgttgtt ttaatttgca atttcctaat gacatatgat      420
gttgaacatc tttttatatg cttacttgcc atcagtgtat cctctgatga ggtgtttgtg      480
tagggctttg gcccattttt aaatcaggtt atttatcctc ttattattaa cttttaagag      540
tttagttctt tgcatatttt ggataacaat cctttatcac atatttcttt tgcaaatttt      600
tctccagtat atggcttgtc ttcttctcct ggcattgtcc ttctcagagc agaagttttt      660
aattttaata aactccagct tataaattat ttatttcatg gattgtgcct ttggttttgt      720
acttaaaaag tcattgtcat acctaaggtc atctaggttt tctcctacgt tatctcctag      780
gtgttttata gttttgcatt ttacattat atgtatgatc agtttgagt taattttat       840 gaagtgtgta aggtttgtat ctacattcat ttttgcatg tggatgtcca tttgttccag      900
```

```
caatatttgt tgaaaagact atacttgctc tattgtattg tgtttctttt ttgtcaaaga    960
tcaattgact aaatttatgt gcgtcagttt ctgatctctc tggtccattg atatatttgt   1020
ctattcttc accaatacca catagtctag actactgtag ttgtatatgt cttgaagtca   1080
ggtagtgttg atcctccaat tttgttctcc aatattgagt tggctattgt gggtcttttg   1140
cttgcccata gaatcaatta gtcaatattt acaaaataac ttgctcgaac tttgactggg   1200
attaatctat aaatcaagtt gggaataagt gacattttga cattatggag tctttctgac   1260
catgaacaca aactattgat ccatttattt agttatttga tatcttcac cagagttttt   1320
ttgtttttt cttatagatc ttatacatat tttcttatat tcatacctca gtattccatt   1380
tcagggtgtt aatgtaaatg gtaatgtgtt tttaatttca aattcccta gttctttgct   1440
ggtatatagg aaagtgattg cttttgtat gttaacgttg tatcctgctc acttgctata   1500
actgcttatt agttccagga gctttttat tgtttctttt ggattttcta agagacaatt   1560
acattatcag tgaacaaaca cgatttattt cttccctccc aatcagtatt catttattt   1620
atttattgtg tgttattgca ttagctagga cttctaatac aatgttgaaa agcattggtg   1680
aaaggaaaca tccttgcttt gttcctgatt ttagctatag gttttgtag ctgttcttta   1740
ttaagttgag gatatccttc tctattctta gtttgctgag aatttttatc atgaataggt   1800
gtaggatttt gcctaatgtt ttcttctgta tctattgata tgatcatgta atttttcttt   1860
atctattgat atgatctgtt gatgtgatga actacattaa ttgagttttc aaatgttgaa   1920
ccagtcttgc atatctggaa taaatcggag ttggtcatca tgtataactt tgttacactt   1980
tgttgcattt gattttgtaa tattttcttg agaattttta catctatgtt cataaaagat   2040
atcggtctac agttttcttt cctttcttgt aatatctctg tctggttttg ctattaaggt   2100
aattctggct tcacaaaatt aattatggag tcttccctct acttctagtt tctggaagag   2160
attgtagaga atggatgtaa tttctttctt aaatgtttga cgaaaatcag cactgatctc   2220
atctgggctt ggtgctttct gttttggaag gttattaatt atttattcaa tttctatagt   2280
ggatataggc ctatattgat tggcaatttc ttcttgtatg acttttggta cattctattt   2340
caaggaattg gttcatttca tgtaggttgt taaattcgtg ggtatagctg ttcataatat   2400
tcatttatta tccttcaat gttcatgaga tcagtagtga tgttccttct ttcatttctg   2460
atattcataa tttgtgtatt ctctcttgt ttccttagcct ggtgagaggc ttataaatt   2520
tattgatttt ttgaagaatc acttttggt tttgctgatt tcttgctgg gattataggc   2580
gtgagccacc acactcttgc tcattttttc tattttgtt ttccacactt tttctgcctc   2640
tgtggatttt acacagcatt ttgtataatt cgatttcctc tttttagcat agcaattatt   2700
ttagtcttta acttttaaa atcagttgcc ctagattttt ttctcccaac attttgggag   2760
gccaagggga gaggatcact tcaagccagg agtttgagac cagcctgagc aacatagcaa   2820
ggcactatct atacaaacat aatttaaaa agtccaggca ttagctagga ctgtgcctgt   2880
agtcccagct actcaggagg ctgagatgag aagatcaccg gagcctagaa atttgaggct   2940
gcagtgggct gtgatcatgt cacttcactc ctgcctagaa gacagttaga ccctgcctct   3000
aaaataaaca agcaaataaa taaaagaaa ggaagaaaag aagagcaagg gcagcaaata   3060
gaaaatagta ataaatatgg tagctattaa tccaactatg tcaataatta ccttaaatgt   3120
tagtggtcta aatatactgc aatggactga atgtttatgt ctcctcaaaa tgtatatgat   3180
gaaatgtaag ctcccaaaat gatgttatca ggggagagtg ttttgggag gggattatgt   3240
catgagggtg gaggccttac aaatgggggtt agtgctataa aagagaccac agagagctgc   3300
```

```
cttggtcctt ctgccatgtg agggcactgt gaaattatgg ccatctatga agaagtgggc    3360
ccttattaga catcaaatct gcaaatacct tgatcttgaa tttcccagcc tccagaacta    3420
tgggaaataa atttctgttg tttacaagta aatcatttta tgttattttg ttacagaagc    3480
ccaaaaagat gaagacatac accagatcac tccattctct tcttgcttgc atggtttctg    3540
aggatacgtt ggatgtaatt ctaatattct ctataggtat tttctttatg gctcctctac    3600
aggtaaggtg ttttttccct ttggcttcat ttaagaattt ttcgttaacc tttgattttc    3660
tgaagtgtga atatgttatg cctaggtatc atttgtttgt ttgggttttc ttggcatata    3720
tcttcctgat gttctctgaa cttccagaat ctgtgatttg ttgtctgaca ttaatttgga    3780 ggaattttttg gtattattgc tttaaatatt gcttctgctc cttttctct ttctttgact    3840 tacagtattc ccattacatg taattatctc acagttcttg aaagttttgt tttgttcttt    3900
ttgttagtcg ttttctttc tgttttcag ttttggcagt ttctgtttac gtatcttcaa    3960
tctcagaaat tctttcctca agcatgttca gcccactaat gtgtacttca aaagtattct    4020
acatttcttt tacagtgttt ttgatctcta gaatttttaa attctttctt aaaactttca    4080
tctctcagga attcaagact agcctgggca acatagtgaa actctatctc tacaaaacat    4140
tagccaggta tggtgatgca tgcctgtagt cagagctact caggaggcta aggtgggagg    4200
atcacctgag cctgggaagt tgaggttgca gtgagccaag gtcacgccac tgcactctgg    4260
attgggcaac agagccagac cctgtctcaa aaaaagaaa aattccatgg ctctgcttac    4320
attatccatc tgatcttaca tgttgcctat tttttccatt aaaactccta gcctattaat    4380
catagttttt ttataattaa tactccgatg tgataatgtc ttagtccaat tactgtggtt    4440
ataacagaat gccacaaact gggtgattta taaacaaaag aagctgattt aggctgattt    4500
agaggctggg gagtccaaga gcttggtgct agcatctgat gagtgtcttc ttgcttcatc    4560
ataacatggg agagggcatc acgtgtgaag agagcttact cttataacat agccactccc    4620
acaagaatta acccaccgcc atgagagcca tgtgaattca ttcatgagga cagcgggtta    4680
agtttccaat atatggactt ttcggggaca cattcaaacc acagcagtta gttgtaacgt    4740
tcgtgtcatg tctcattctg gttctgatgc ttgtgcagtc tcttcaaact gcgtctttgc    4800
cttttagtgt gccttgcaat gtggaaatga tatactgggt aagaggagct gtagtaaaga    4860
ggcttctagt gacgtagtga caagctgtgg ggagagggag tgttgcacag tcctgccgca    4920
tgtcacagtc ttccagtgag cctgtgtccc tggactgtga acttcatgct gcttctcag    4980 cttccccagc cccttagatg gtacagaact gttggagggg ggtggagttg tatatttccc    5040
ttgctctggg taggtcaccc tctgataaaa caccaggtta ggcctctggt gaataatt    5100 ctcctgaggg cagaccttct attaataata gaatgttcca acctatttca aaatggttcc    5160
tcttctcctt ccactgccag aagcataatg agatttccc cctaatattc gtggtaagga    5220
cctagcagag ctccaggagg taacactctc aagtgtctca tactaccctg caccatgact    5280
gggctctgct ggagttctta atttgcagaa ctgcccacac tgagcctccc gcaatttctc    5340
aattacaggg caaactttcc cagccggcac tgggtccttg gaggtttctg tctgctggtt    5400
tcttcctctg gaggttgtgc ttctgtgttt gcctgtctct ccaatttggg gggcagtggt    5460
ttgcccaatg acctcaattc tctgaaagag ctaagaagag gtgttaattt ttcggtttgc    5520 tcagcttttct acttgttgct agaatggagc gccaatagtg cctcctatag tgacatgtaa    5580
ccctcaactc tagagatgat gaagcatact aatgacaaag gagaaatgct tcagcagttt    5640
```

```
tctgtcagca cattacccct tgaaaaagct gcttcttcca cattctgcaa gagatgggtc    5700
tcaactcaga gctcaaggca aatgacttcc ttcaaggaga aggaataaac agtctcagaa    5760
accatgaaag cctgccccca ggagtgtccc tgaacctcag caggggccac acttaccttg    5820
cagaaatagg tgaggcatgc tcctggtaca aaatcccaat ggtacagaag acaaattga    5880 aaaacaagtc tccctctaaa cccctgaccc cgagctacct agttctcctc cctagaggca    5940
aagctgttac cagattcttg tatctcctta acatatatcc ttagaagagc tgtcaagtga    6000
acacatgttt aagtgaaaac ctattttaga agtgcatttt cttaaggaac tttaggggttg    6060 gaaggaacct gtgtcagtcc ttaattcaca acctccatta gtacttattg ttcttgcaca    6120
aaaatctttc tcaaaaagc cctttccact ctgacatagc ttattctact tttacttagc    6180
tccaataact tataaaacat atttttgaaa gtctaaaatc tgccactatg ttttttttc    6240 ctaatcaatc tttactttga cctctaagcc agagaaaaca ggtggtcaaa tgccttttgc    6300
ctaagatgga acttagaata tttgaagacc tcagatcttc accctgccaa ataacgtgtt    6360
tctcctcccc tttcacagag catttggttt taggaaaattc agagccacat tccttataga    6420
caagactaaa ctcttattca acatactcag aaacttcttc taagaggata accactcatc    6480
agaggaaaaa agtttctcat gtacagctgg caaagggatg gaaccatctg tgttattaaa    6540
attgacagac gcttatgaga tttattaagg gaaatactag agtcttagta catacttgct    6600
aatatagcat acatgaaggc tttatctata attttttggg ccaagcagaa attttggtat    6660 tactcacccct aacaaattc caagacatta tgaaatagaa ttttaggtcc tgacatcacc    6720
atttgtctca ggttttgaag cgttgctgga caagaggggt aaaacacggc tctgccttgg    6780
attcaaagtt ggcctctcat actagcaagt ataccttggt atcctggtca cttctcccgg    6840
ccacagcatc acattgctat aaaaggcaga tacaagtatt aaccagctca caggttatca    6900
gataagctta gtctgaccaa tgcttaacac agcaactggg ccactattgt cattcctgtg    6960
gtggtggcac acacacccag cctctgtccg ggccatggtc taggaccacc ctccacagag    7020
gctgtgagct agagccctaa ctgtgcaggg ccctaactat gccaggctac ttatctctct    7080
taagaggact tcattagtgc ctgctcggcc atacagtttt ttacttacca agtaacacag    7140
ttatcagcac actccaggta ctagccaagg actacaaaat caacgtgaat gtcagctttt    7200
gtatcaaaag ctcaaaggag aaactcaaac tttacataga tgtcccatga agatgttcag    7260
caaacccatt cttctctgtt ccctggaatc catcccagta ttgtgctatg tgtgtgtcta    7320
gtaattcttt acaaaaagct ctgtttcttg tgatgctatc agatcacatt gaagaatata    7380
caagccgtac tatgaaggct gttgtctcat atagtcctaa cgtagtgaga actgatgttc    7440
ttacatgctg tcttttttggg cactcaaaga aattcctgta cagtcttaca aatcagttgt    7500
agcttaaatt gatttgtgtt gtgacttgta cacacaggtc acattccctt gacagaaaat    7560
atagtttaaa accaaatttg cagcccttgt taagtgaatg cacaggactt tattgtattc    7620
aggtctttta ttgtaagact cactcctgtc ttcatttat gttccactgt tgtgcttccc    7680
atttgccttt ctctagtttt gttttctgtg tttctacgga ctgctctcag cccaggtgtg    7740
caggaagcac acacatgcct gcagagcctt catggcctct gcattcaggg catgacttca    7800
acgcacagtg gctgtactga tttgttaaaa caaaggaaca gattacttct cctaattcac    7860
agggaagttc caggttgtgc gggcagtgag cagacctgtg tctgtctgcg cttgccctgg    7920 tgaaaaccc caccgttcag gctgcagggt gcgagaccca ggcacaaaca ttttgctgga    7980
tgaggaggaa agatgtaagg ttgctcccct tcagagacag caaagggcag gtctgtagct    8040
```

```
tcacttactt caggattgtg attttgaca gagccgagag atcagggttg ttgaaccagg    8100
cctgaaggtc ctagtgaatc tcgtgaagag aggaggggtc tggctgtaac atggacctag    8160
aggacatttt tactgcagga gaaggaacag tggggatggg gtggacttgc caaaggaata    8220
tagctcaagt tcctgcagcc caaaaaagct cagtttcttt tggccaaagc ttccgcgagt    8280
ttccctggca tttctcctgc gggagctaca ggggcagtgg gacacttagc ctctctaaaa    8340
gcacctccac ggctgtttgt gtcaagcctt tattccaaga gcttcacttt tgcgaagtaa    8400
tgtgcttcac acattggctt caaagtaccc atggctggtt gcaataaaca ttaaggaggc    8460
ctgtctctgc acccggagtt gggtgccctc atttcagatg atttcgaggg tgcttgacaa    8520
gatctgaagg accctcggac tttagagcac cacctcggac gcctggcacc cctgccgcgc    8580
gggcacggcg acctcctcag ctgccaggcc agcctctgat ccccgagagg gtcccgtagt    8640
gctgcagggg aggtggggac ccgaataaag gagcagtttc cccgtcggtg ccattatccg    8700
acgctggctc taaggctcgg ccagtctgtc taaagctggt acaagtttgc tttgtaaaac    8760
aaaagaaggg aaaggggggaa ggggaccctg gcacagattt ggctcgacct ggacataggc    8820
tgggcctgca agtccgcggg gacccgggtcc agaggggcag tgctgggaac gcccctctcg    8880
gaaattaact cctcagggca cccgctcccc tcccatgcgc cgccccactc ccgccggaga    8940
ctaggtcccg cggggccac cgctgtccac cgcctccggc ggccgctggc cttgggtccc    9000
cgctgctggt tctcctccct cctcctcgca ttctcctcct cctctgctcc tcccgatccc    9060
tcctccgccg cctggtccct cctcctcccg ccctgcctcc ccgcgcctcg gcccgcgcga    9120
gctagacgtc cgggcagccc ccggcgcagc gcggccgcag cagcctccgc cccccgcacg    9180
gtgtgagcgc ccgacgcggc cgaggcggcc ggagtcccga gctagccccg gcggccgccg    9240
ccgcccagac cggacgacag gccacctcgt cggcgtccgc ccgagtcccc gcctcgccgc    9300
caacgccaca accaccgcgc acggccccct gactccgtcc agtattgatc gggagagccg    9360
gagcgagctc ttcggggagc agcgatgcga ccctccggga cggccggggc agcgctcctg    9420
gcgctgctgg ctgcgctctg cccggcgagt cgggctctgg aggaaaagaa aggtaagggc    9480
gtgtctcgcc ggctcccgcg ccgccccggg atcgcgcccc ggaccccgca gcccgcccaa    9540
ccgcgcaccg gcgcaccggc tcggcgcccg cgccccgcc cgtcctttcc tgtttccttg    9600
agatcagctg cgccgccgac cgggaccgcg ggaggaacgg gacgtttcgt tcttcggccg    9660
ggagagtctg gggcgggcgg aggaggagac gcgtgggaca ccgggctgca ggccaggcgg    9720
ggaacggccg ccgggacctc cggcgccccg aaccgctccc aactttcttc cctcactttc    9780
cccgcccagc tgcgcaggat cggcgtcagt gggcgaaagc cgggtgctgg tgggcgcctg    9840
gggccggggt cccgcacgtg cgcccgcgc tgtcttccca gggcgcgacg gggtcctggc    9900
gcgcacccga ggggcgggcg ctgcccaccc gccgagactg cactgtttag gaagctgag    9960
gaaggaaccc aaaaatacag cctcccctcg accccgcgg acaggcggc tttctgagag   10020
gacctccccg cctccgccct ccgcgcaggt ctcaaactga agccggcgcc cgccagcctg   10080
gccccggccc ctctccaggt ccccgcgatc ctcgttcccc agtgtggagt cgcagcctcg   10140
acctgggagc tgggagaact cgtctaccac cacctgcggc tcccggggag gggtggtgct   10200
ggcggcggtt agtttcctcg ttggcaaaag gcaggtgggg tccgaccccg ccctttgggcg   10260
cagacccccgg ccgctcgcct cgccccggtgc gccctcgtct tgcctatcca agagtgcccc   10320
ccacctcccg gggaccccag ctccctcctg ggcgcccgcg ccgaaagccc caggctctcc   10380
```

```
ttcgatggcc gcctcgcgga gacgtccggg tctgctccac ctgcagccct tcggtcgcgc   10440
ctgggcttcg cggtggagcg ggacgcggct gtccggccac tgcagggggg gatcgcggga   10500
ctcttgagcg gaagccccgg aagcagagct catcctggcc aacaccatgg tgtttcaaaa   10560
tggggctcac agcaaacttc tcctcaaaac ccggagactt tctttcttgg atgtctcttt   10620
ttgctgtttg aagaatttga gccaaccaaa atattaaacc tgtcttacac acacacacac   10680
acacacacac acacacacac cggattgctg tccctggttc aagtgtgcca agtgtgcaga   10740
cagaacatga gcgagtctgg cttcgtgact accgaccata aacccacttg acagggaaa    10800 catgccttgg aaggtttaat tgcacaattc aaccttgag ctgcgcgggt tccaagagcc    10860
aggcccgtac ttgctgttga tgtcattggc ttggggagtt ggggtttggt gcccagcgcg   10920
gtcgttgggg gaggggcaag gcatagaaca gtggttccca gaccttgctg cacattggaa   10980
ttacctggga ttaaaaaaaa aaaaatcaaa acaaaaacca gtgtctggct cccgccccca   11040
gacattctga tttaattggc atggggcaag acctggactt gggattttt ttaatgctct    11100 tcatgtgatc tgttgggcag ccagatttgg ggatcactag acggaagaag gattgttaaa   11160
gtctccggag atgttacttg ccaatgctaa gagctctttg aggacatctg gaattgttac   11220
aatattgcca aatataggaa agagggaaaa ggtagagtgt gattccaata ataaaggatt   11280
ccgcttttca ttgaaggaac tggtggaaag gtttcttctc tgctgagcct gcaggcccgt   11340
cctgcctgcc tggggtgccc gggagacgcg ggcctgctcc ggagactgct gactgccggt   11400
cctgttagtc aggtgtcagc cctgtctctg ccgaagagac tcttctcttt atttttaaatt  11460 aaaccctcag agcaccacca aagcatcact tttctccctc cattggtgtt ctcattcttt   11520
gatgttactt gtttgaacac cactattagt agttggagat tgttcctga gaaaaatata    11580 aataccactt aatttgcctg tttgtcccgc attcactcaa aacagaatgc tcctgaagac   11640
aagagagaga gtaggagaac agacgctatt ccattacagt aacataaaag actggatttt   11700
caggggcaaa ttattaaaat aggagatgag ctcttttaac agaaatttgt ttaaggcctg   11760
tgtctatcaa attcagtgga ttttattcaa gatgcacttt gtttagtggg agttttgttt   11820
ggttctggga catgctaact tctagacttg ctgctcttag aggtaatgac tgccagacac   11880
catttcatga gtcctaatcc ccacattaag cataagaggt gcacactctc ctcctatggg   11940
ggaaactgag gtacgaagaa ctaaagtgac tttcccacag ctggtgggag gcagacggga   12000
aattcacacc aggggcttcc aactccagat ccctctctca acttccaaac tccactgcct   12060
tgtccgagtt ctggtttcag gagatccaaa tcaggtgtgt gcaaatgtct aatgtcagag   12120
ctggcaaggg gaaagggccc agggagccgg ctcatgacga tgagcctgtc tgaagcttca   12180
acgcgggctg tccggcagtc tgcattcctg ccgagttcct cagccctctg ttgggtcacc   12240
ttccatagag gcagcttagt cctcagttca gtgagcatgg agtggagact gcttgagggg   12300
tgctgagcaa agccctgcct cttacaggat gaaggtgctc tccagaaggg acactggaaa   12360
gtattccaag gcgagtcgaa ttcccaactg agggagcttt gtggaaataa gcccgcccag   12420
ccccacttct ggagacgttc ccattcagta ggtccgagct gtcttaaaga gaaaccaaag   12480
tggggatatt aatggtatcc aaagtgagat ctaccccacc ctccctcctc aaaggaggtc   12540
agatcaagaa agcccaagcc cggcctggca attgggacct tcttctcac tccagcccag    12600 ggtgaaggtg gacaagtcac tttgacccct caggcttctg agctgttgtt tctgaattca   12660
gtgaatattt actgagtgca tagaaatatgc tagatattct gggctaaagg ttgaaggggg   12720
ggtgagtttt aagggtttct gctcttgctt ccagattgct ttcaaatctg gaaaggacac   12780
```

```
cagtggtttg tgtgttagac ccacactgcc gtagcacaga atacaagaaa ctggctgaga   12840
gctccaatag gcttttaaca gtaatttctg gcttcacgta tttagtttca taactcatga   12900
tttttcaaaa acttctggtt tgaagacacc gattgccgaa agtccattgt gctgcataat   12960
tacacttggt ccacgtgaca gcactaacat gttctgaaat gttttttagaa gtagtctcag  13020
caaagatgaa ggattcctcc ctgtttgaaa agaaaatatt ctttgttttt tctttgatct   13080
aagctctaag actagcagct agcatctgaa acttttttga cgagagtgac aaaccaactc   13140
taatattaaa ggcaattgat gattatgggc actgaaggga aggtaacccc aggctggtgc   13200
cccggaatag ggatgggtca caatgttgag gacatttcgc ctgttgcaga acccacctgc   13260
aacacagtgt ggcccttgcc atgtgacttg tgtgtgtgcc tgtgtgtctg tgtgtgcgtg   13320
ttttaatttt gacttcataa gtactctagt tatgagctta tttaacattg gttttactaa  13380
ataggggtat gtgttgagaa aatttcaaag ttttagaata tggttcaccc acatgttgct   13440
tccctgtaaa tataattttt aaaccagat tctgggccgg gcatggtggc tcacctctat    13500
aatcccaaaa cgttgggagg ccgaggcagg cgaatcatga agccaggagt ttgagaccag   13560
gctgaccaac acggtgaaac ccagtctcta ctaaaaatac aaaaaaaatt agctgggcgt   13620
ggtggcaggt gcctgtaatc ccagctactc aggaggctga ggcaggagaa ttgcttgaac   13680
ccaggaggca gaggttgcag tgagccaaga tcgcaccatt gcactccagc ccgcgcgaca   13740
gtgtgagact ccatctcaaa aaaaaaaaa aaaaaacaga ttctgttcct cagatccatt    13800
ccatttttgt tttcctttat cacttatgga catttgaaat tatggtaata acattgtta    13860
gtctcagtta attattactg gtttattctt gaaccactaa tccatagaga atagagtgta   13920
aatcttaact tgttcctgta ggccatcccc attaaacatc atagtgtttt ctcattcgtt   13980
cttttttcgtt ttcctcctac aggaatgaat tttctaagaa aattccagca gttggctctt  14040
tggacgacat ctctagattg tcctccattg ggcccatagg cacaagctgg ccagtttgaa   14100
tttgggcaag aatccaggca ttggaactta ttcaaataac tagtttgcct gtaattttca   14160
cttttttcaga gtcatctgat aaagcttttct tgctacacat ttagatagat acactcaatc  14220
cagttgtcta gaaagttccc tgagccagct gggagcagga ggggtagttg gggccaggaa   14280
tattgggggt gtgtttactg agcccctaga aagtaagtgc tagatttgac atttcaatcc   14340
ctgaaggccc tgaagttcag tatcaaatga ctggtcctgt ggactgagca tctgtgaatt   14400
gcatatgctt agagtaaatt ttactcctac cagtttcagc agcttgcttt agcaagcagt   14460
atggaaacac taacatgggg gagtagaatt tctctctctg atccaagttt tatctcattc   14520
tggtgggttt tcaaggagag actcggagtc caagtgtcct ttctgaatat atctggaact   14580
tctcattaac aaaagactca agttataatt taggggacaa ggcacccaat gagaatgcct   14640
tgcaggcagc cctaagtaca cctgcaatta caccattact agcgcggcag cacacatggc   14700
cctgacttag tttaaataat tacgtaagtc aaccatgatt gtttgccctt tgcatagaag   14760
ggcaagtatt ggtacctgtt acaacttagg cttttttttc tttatgtttg agccatgatg   14820
agtgatttac actgttgcat ccatatgttg agatgtaaga ataaattaga cttggtaatt   14880
gcccttaagt gtctggaagt caactgggga aagagagcta gagataataa gtgtgaaaca   14940
atgtcacaga atcaatgacg gaactcttcc caggacaaag gatgacttt gagttcagtc    15000
tttgccttta attctacatg gggaggagag cacgttagc cacaaatgga agggattact    15060
catttgagct atttggttat atgattattt ccccagagaa taggatgtgc agggcattac   15120
```

-continued

```
acaagcagtg ccaatagcag caaagttctt gagagtgcta gtaattcaaa tggcaggaag    15180
agaaggaata aatggtaagg ctacctacag ttcacagaga gctccatcct cactgtggct    15240
ttggattttg tcctgtgtga aagagaagtg actgtgaact gacatgctgt gtttggtgtt    15300
ttagaaagat ggctgcagca gcggtttggg gaatggactg caggagtggc attggaaaca    15360
ggaaggttca tgactattgc cagagacaga ggatgaagca ggagcaagga agattcagga    15420
caggggactc cggggctgat caggaggcag aactggttga taagtatatg tagcagcata    15480
agaaagaaag aatcccagat tgacacccag gcttctcact tggaagcctg gatagatact    15540
gaatgcaatc acaaaggctg ggaagtcaat gggactgcag ggaagggaag ggaagggagg    15600
agaagaggaa gggcaggagg gtccaatatc aatattcagc ttttagatgt gttgagcttg    15660
aagtgctcag atgagaagt ccaggaggca gtagaatacg gtggtccaga gcacaggaga    15720
gcaatgtggc ttgagttgtc atttgctcac atatttccgt gtcagttact tgtcttagat    15780
cacagaacaa gttctcctct cacagtttcc tggctccacc tgtctcatgc tcaccgtcag    15840
catcgaaatt gagccacacc aggggttctg gataccagct tctctctagg tgaggctgct    15900
atagtcagca gctgattagt tgcagttatc agcaactggt aatataatat attgtgcata    15960
taagtgtacc agaagtcatg tttatatatt gctgcaaata ctcggaatgg ggatctcttg    16020
ttccctgctt aagaccacat cacattactt ggttttgtac gctagtggct gaaccaaaaa    16080
aagtaggaga tgatttttt tctttttct taaagcagta gcttttgaac cttgaccatg    16140 cttttctaacc agctgagggg cttttgaaaa agagggtgcc ttactgtgcc ccagaccagg    16200
acaatcagta tttctgggga atggagcctg cacacacac atttcttaaa gctcccttgg    16260
caattctgag gagtggatta catgttgtat gtagctcgta acgaaagaaa tcttgtcttt    16320 gctctcgac ccccatttct tactcatctc atgagctcct tcgagatcca gaaacagttg    16380
catatttcat tagtaaatca gttccagagt cacattttat ttcacaagtt agtccattaa    16440
aagtttcctg cagtgaggaa atagccagaa agaacactcc accctcctc ctttttataa    16500 ctatagggtc tggctcgaca gagcaggagc atcgccatct tggacaagcc cctcattcta    16560
aagttcacct taataaaaaa ctgcctaaat tcaaactgca tcagcctaat ggctaaggtc    16620
agcatgacca taaaccacaa ataacatctc caaccggaaa cattcgaaac tcctcctcga    16680
ccagagacat gctagtcccg agataacccc cctccagcag ggaagatgcc agtctcggga    16740
taacctctct ctggccggaa agatgcctgc cccaagataa acttgcctcc tcccagagat    16800
attccaaccc tgccataaaa cttctccctc aaacaggaac attccaaaat tctgataatc    16860
tccctcaccc taaaccaat atatactcct agtctgtaag agaaagcgct cttgaccaaa    16920
attcaccagg agtgcctccc aggttttaac taaagaaaac ctctctttaa ctgccaaaaa    16980
aaaaaaggga aaaaaaaag ctttctgcag tggctttcag cgggcccagc atggcagcag    17040
cacctgagaa cctgttggag atgcacactc ttggacccca ccctggcctc tgagtaagac    17100
actggaaggg caggccccgg tctgtgcaca caagtcctca gggagattct gactgatgca    17160
tgccagattt tgagaactgc tgatatactc caggcacatc gcatgctggg atctagatac    17220
accaagggaa caaataact gcacttgtcc tctgaggacc gacttacctt ttggaagggc    17280
tgagaaagag agacacatac aagatcactc cctgtaatgc aatgttttat aacagatgtg    17340
atttgggatt tcagtgggag cccaaaagag ggactgacta attcagcctc tgtgacaagg    17400
ggagtttctc agaaacagaa tgcttagctg ggcctccagg cacagggaca ggaatgagga    17460
aatacttgta ggccctgtgc tccttcagca aaaccctcag tttcttgtta tttttataaa    17520
```

```
tgcaaacatc ttattaaagt agatgctaag gcattagaat ttcctgcttt attttctaa    17580 atgaccatga ggaaacctgg aatgtcaaag ataaagtgca acacattctg catttaaaaa    17640
ttaaaatgat cctttttaaa agtagcaacc agatgtgaaa aattggactg gagtccaggt    17700
tatagttgat agctttaact ttctccccaa cagcaacagc acaattttcc ctaaaatgtg    17760
ttatgaataa gtaaaatgac tacttcacat cctttaactc ttcctacaga aatctaagag    17820
agaaatgaaa caaagtttg cacagttcta gacacgataa atacatgtga aatcacacaa    17880
ctcagaaaat gtcccttaaa ttaattgagc cattggtact tgtgaattag aagagacatc    17940
tatgttctga tccactgttg aaagctgtac aatgttacct atttatttgc agacatcctt    18000
tggaaacaaa taggtagatt tgcaacaaat aaagagtgga gtacagctgc tgacattacc    18060
ttgtatattc atgcctttat gtaaaaaaaa aaaaaaaat atatatatat atatatatat    18120
atatatatat atacacacac acacacatat ggaggtaaag accactgctt gctttgcagt    18180
tgttttaaga gcattcatga aggattttat tttataagca gaaatgtgat atctgacgat    18240
tttaccacta catgcttgca ggccagtgca cagcagatga cgtcatgatt gttttagcag    18300
tcctatcgtt ttacttatga tgtcattaca acccttttgct aaaatttctt tcctttactc    18360
caggttttgg ataaaattga tgcattgcac atagtctctc tgataagaca aactggcatt    18420
tgtatgtgaa aaactgtgca tgttttagtg tctctgctga tactcaaatt atccattatt    18480
ttagtgctgg aataaaaaca aaccacttag tgaatttgtg caggtcctta aggacaggca    18540
aaggtgtcct gagattttct gatcattgta taccaaattt tagaaacttt ttcaaaaaca    18600 ttttttaat ttcaaaaacc tggttttgtt tatttaccag caatcattga atacctgaaa    18660
gctttcagga gattttatta caatggtttc tattcactta caaaattatc tcctagttca    18720
ttctcataca ctgtaagcca ttgtaaatgc ttcaaattgt gccgaacaag ataaactaga    18780
caaactattt taagtttgtt ctagtgctaa cttgcaagat ctaatggctc caactagatt    18840
tttaaaataa agtatatttt aatatattat tagaaagtta agcaattatc tgtttatagg    18900
taacaaaaac cctggaaccc caatgtcaga tgtcatccac ttttgattaa gtccaaacat    18960
atgacagata aacaaaagat ggttggctgg gctcagtggc tcatgcctgt aatctcagca    19020
ctttcagagg ccgaggcggg cggatcacaa ggtcaggagt ttgagacttg cctgaccaac    19080
atggtgaaac ccgcctctac taaaaataca aaaaaaacag ctgggtgcgg tggcacgtgc    19140
ctgtagtccc agctactcag gaggctgagg caggagaatc acttaaacct ggaaggcagg    19200
ggttgcagtg agctgagatc acaccactac actccagcct aggcgacaga gcaagactca    19260
gtcaaaaaac aaaaaaaaag tggtcattgg agaattattg tgtcacctgt tgttttttaa    19320
tgtactaatt ttgagaggct tttaaataga gtgcactata gaactttttc ttggcttcaa    19380
tttgctacaa tgttaataga gaatcagaaa ccttatcctt atagatgttt cttgattttt    19440
ttaatttctg gtgacattta tgagtgagaa tagtgtattg ccctgttttc tttcttactc    19500
ccctttcttc ttccttcctt gctttctttc ttcttcccct ccttctttct cttcctcgct    19560 ccttctttt tacaagctgt tatgaattag ccttcacaga gaaagaaaaa ttttataaaa    19620
taactggaaa tgaaactttg caaggactg cagatgaaaa actttgtcaa atgactgtaa    19680
aaatatacta tataattttc aaaagttaga aagtaccaaa cacactcagt attcatggtt    19740
atacaagtat gcatacacat gtattgctcc ctgaaaagtg gtgttgttaa gggagttttt    19800
cttagtacgc ggcttaacat atttttttct gtaatttgtt gttagttata atggggagag    19860
```

```
aaaacaggtt agagtctccc ctctcagttt caccttccat aaaacagcta aactagacga    19920
tcgtcagact ccttccagct gaaaacatct gtaaaattaa aaacaaatct aaatgtatgc    19980
aagatatgta tttaaacatg ctggtaataa gtgtgctgtc cctataattt agatgctaaa    20040
acattgatgt cataataata acaacacctc gcatttgtac agcacctcat agtttacaca    20100
atgccttaac attcttctct ctcagcctcc tacaaccccca caggattggg atagctttcc    20160
agattgggag gtgagggacc caggctcaga gcgattctgc tgttgtccgt aatcaccagg    20220
ctggtgatca gtgggcactg ggtgctctcc tgctacacag cactgtctct caacatgcag    20280
gtcaaggtta cttattcctc cttcaagacg tcattgggtt ttttagctat ggatgcccca    20340
tcacttttag ttctatttgt gaatcaaagg ctaaataaag tattcctcaa aatttgttat    20400
acttctgtta ctaatgctta atgtccctca caatttctgt atatttctgt gtatttctgc    20460
tctgttttgg ttcctttccc aggtttcttt tttgttatga agtagttttt agactcaagt    20520
ctcttctgta tgtgttataa ctgcccattc cataagatac agggcagtga atttgtgagc    20580
cttgaaaata tttactttag aaatgagaag tatgactttt caacgttgtg tcatcaactt    20640
ctgtaaattt tccagaccta taaatacttg cagaaaaaaa atgaaaggag aaggcaactt    20700
gatttagcag ttgggtcagt tagcaatgcc tatggcaagc tgtagtaatt cccttacata    20760
gatttgtaag actcatttct atgatttaaa tgaaggcata cacttaacct ctttagggtg    20820
tgaaacagct tttacaaaaa gagacaaact taagaaacag tgtggccctc caagagtgtt    20880
cattttccat atcataccat ttgtaataag ctattctggc tgggatttac ttgcaagcat    20940
tggcttttaa gaagagatgg tttcacacat caaattattc acttggaggc actttctggg    21000
ttgaaggaat ggaatggaga gtgcggcagt gagtagatct ctcagtgacg gtgatgtgcc    21060
tctcccagaa gaaatttcaa aatgcagtgt tcatttttcct ccacaagaaa ggaagaaact    21120
gttttgttat tgtttattcc taacatagtg gaaactttttc agtactctgg cagaaatttc    21180
ccaaaagcaa ttttctattt catgattata aagtagcaaa ggaaaaagtc ctgcactcca    21240
gctgagcaat ggatctccag ttgttatcta ggtgctgcag gtttagagag gattgccagg    21300
agaacacatc gattttcag gcctgtgatg acgtatctct tgttaataa gtaaaccctt     21360
ccagtaaaca gacagttagt atattgattt cagggtggct ttagccactg aacctgtaag    21420
tcttgcaaag gttacttggg caaaagcatc attattttac cttcagtcaa caaaaatcta    21480
cctggccaag gcagaacaga aagttcagca atttgatgaa gtgggacaac atgaagaatc    21540
aggtgagttg cctacttttt cacttcactt tccacccttta gagattcttg tttagatgca    21600
gagtagtgac gtgcctggtg tcagggagag agttgaatga gaaaagtccc agaagggcag    21660
aagacttggg tgattatctg agtccatctt tccttatcac atgacagagt tcttgaagtc    21720
ttggctagga attctaggct tttagattct ttgggcaatg gctactaaat gttcataatg    21780
ttgctcagtt gcaaaaacaa gacattcaaa ctatagccag ggagataagt agtcacgaac    21840
tcaaggccta aattctgctg atggagccga tgagaattgg gtgctaaggc aaagagagtt    21900
gccaatatta tattcttcgg ggttttttgt ttttattcgc attttggaaa aggaaaatat    21960
tagcattcct ctgacttaat attgagaaga cattgggcac tctttttcct cccacacttg    22020
tcttctttca ctaggtgaca agggaagagg tagcatgagg tggtggtcac aggtgagagg    22080
ggctgttgtg agcacaggca tgttgactgc acattggtca cctagtagaa gttttgcagg    22140
cttggtgact tctgaacact gttttcaagg ttgatttta gttgagagaa cctctaggta    22200
ccacgtaatg ttattaacag tagtactgat ctcacaatcg ccctatgtcc cattcacaag    22260
```

```
atgttctgcc aagccataaa aggcccagtt aagtttaaga gaagtctcaa aagtaacaga   22320
tgataactaa ttaatacccca gtgattttga aatgtagaca tcaaacatac caattcagtg   22380
gtatcatcct tagaggcaga cagaggatga ttaaatcatt cagcccatct ctgtctgagg   22440
acgcagctta gcacagcatg gtggaggcta aatgggcctt aagggaaaaa atgatatctg   22500
aagatgcaat ttatttcaaa aagagtttgc tcccgtgaat tttcactctc tatgtagaac   22560
ggcaccagca cacactttc ctgagccttt gcatgtgtgg caggcagcgg cctggcatcc   22620
tggggaactg aatgaggacg cagatgaccc ggacgtgttc acagtttgac acatctgact   22680
cccagatcag ggacagctag ctttgctggc tggttaagtt gatgattcca tctttgcctg   22740
gttctctgac tgtctcatgc tttctgttat tactattttg cagcagatat ttctgctcat   22800 tttcaatca tatatgcatc ctggatggca tagagttgat tctcctaaca aatcagtgtc   22860
cctttgtatt ttttctggc cataagatag aatatatatg tcatttatta aaaatggaga   22920
aaatgttcag gagtttcttg actcagagag ggaaaaggga tactcagggc acttttcag   22980 ccaggaattt actacctttg cagggtaaag gggactcacc acgctggaag tcaaaataag   23040
ccaccagtgc caagtgttca aagcccttag aatcacaatg ctcttaaagc aaagtcttca   23100
acaatgcttg aaaacttcca ctggttctca gtatgtccaa aattgtcatg tctatgaatg   23160
attttctcaa tctgaaaatt tttatagcag gctaaagaat gagataggtc agtgtgattc   23220
tagaactaat cattaacatt caatagatga ctattttatt ctagaaaaag cagcaacttt   23280
ctatttactc tctattttga gggtaaattc tctgtaagta gaaaaagcaa aatgtggaca   23340
tgggactaac atatgaatat acaaagcaaa tgtaccgaaa aatcttaag acctgccttg   23400 tggtgttttt tgtttttgtt tgttttcatt aaagtgactt gttagcctct tgctccctgt   23460
gaagcacagg gaggtgacgt gatgtgcaca gggcagactc tgccatatgc cctggccttg   23520
aactcagggc cccctgggga ctgcagggga tgctggccat gctgagcaat gcctgtgggt   23580
gtcagtttcc tcatctgcag aatgagggta ggcctggtgc ttatttcata gggtcgcaga   23640
ggggattcag tgacagggtg gtgtagaggc tggagcgtgc cccatgtgtg cacgacagcc   23700
ttccaactag gggaggcggg cctgggctct caccagagag cctgtgttct ccatggctac   23760
atgactttgc cccagacgtc cttcccgtgg tctggaccct gggaagtcgc caagagccag   23820
acaggagaaa ggctccactt ggctctcctc tttggtgacc atcccttgcc tccatggcgg   23880
gactctcagg tgacatccca ccaaccctca ctttgcttcc ctggtgggtc tcactttccc   23940
tcaagagtgt tgctttttg tttcctgcat agtcctgggc cagttttgat aaccctcttc   24000
atttcacttc agaaaccctg atgatttctt cctgtgctct ttttaccttta ggacttttac   24060 tatgacgact gtgactggcc catttcttgt ttttttctc ttgctctgct ttctccccca   24120
tcatcactaa agcagacatg gcaatgatgg ccatgcacac tttccaaggg tccagctgta   24180
gatcttcatg gttccccagg tgcctggacc atcttgtgag gagggaggca aacacaccct   24240
gcctggagca cttggccctt tcggcaatgt tttggcttcc tcaagtgaga aagaatgga   24300 tttgtattcc ccctctgcat tattgttttt gttttgtttg tttgtttttgt tttgtattga   24360 gacagagtct cactttttc cccaggctgg agtgcagtgg cccgacctcg gctcactgca   24420
acctccacct tccgggttca agtgattctc ctgtctcagc ccctgagta gctgggacta   24480 caggtgcccg ccaccacacc tgactaattt ttgtatgttt tgtagagaca gggtttcacc   24540
atgttggcca ggtgcccatt attatttgat ctggaattaa ctgagctact gcaggaattg   24600
```

```
cttgattcac tgatgactgg tgttgagcca gtacacaccc acacccaagg actgtgactg    24660
tcttctgagg tccatcctca gaaattcctg tctcttcacc tagtgtgtaa taaggcctgc    24720
gcgtgttata tggaactgta aaaaatgcgc caaccatctg tccttcctct ttatctgatt    24780
acttatcatt gttctctaag ttgcaagtta atagactgat cataaattaa tgcatgctgg    24840
agacttgctg tttcctacta gcagcatata aaagttattt ttaaagttgt tttaaatctg    24900
tgagtaaaaa taaattgctt tgctgcaaga acaccaaac atggaaaagc taacggttca     24960
aagttaataa tttatcttat ggacatcact agtggcatag ttgctttaaa cagtgagagg    25020
atttaataga tatttgattt gcaagtggga tgaagggtgg tctaaccttt gtcctgtgtt    25080
taccttccat gagatcctag aggttgtaca gcacagtagt ggcatgtgac acacttgaga    25140
gtgcctgttc tgtttggaaa cctggaaact atgaagggaa gtggccttcg agcttaacac    25200
ataagacttg ggaggcaaaa cctttttattc tctttaaata ttcactttag gataagcatt    25260
tttttaggtg ttaggaacag ggaaaactgt gtggttagga aggaagaaag aagaaagtta    25320
actgttgtac attccctagg taatgttttt aagcattgtt attcactttc aaaacacatt    25380
ttatttattt ggacttaata ttttgatctt attttttcaa tttctttaa tttaacagac     25440 aggatgagtt ttttatagt tgtattactt agaaattata ctaaaaatgg ccgagtgtgg     25500
tggctcacac ctgtaatccc agcactttgg gaggccaagg caggtggatc acttggatca    25560
cttgaggttg ggagttcaag accagcctgg ccaacatagc aaaacccgt cttcactaaa     25620 aaaaaaaaac aaaaaaaaaa ctagccacgc atggtggcag gtgtgcctgt aaccctatct    25680
actagggaga ctgagacata gaatcactt gaatccagga agcagaggtt gcagtgagca     25740
gagattgcac cactgcactt cagcctgggt gacagagcaa gactctgtct cggaaaaaaa    25800
aaaaaaaaag gataaagaaa tcatactaaa aacaaaacag aatgctgacc accttataga    25860
aatagaaata gtggtttgct gtgatagcaa attttcttgt taacttttta tttttaaga    25920 attgcacatt cacaggaagt tgcaaaaaat ctactgggag gtcctatccc ccttccccca    25980
acctcctcca gtagtaacat cttagtagca aagttttgta tatttatttt gatatcatta    26040
tctaagtttg acatcattat ctaatattaa cctaagccaa aagcccacta ttttaattat    26100
ctagtgatgc agtgttatag aactcatagc cttttcacagc attatttgga agttaatttt    26160
cttaagtgaa atgttttttgg tcttaaggt ttggaggcca tggaggcatg aggagaaatg    26220
ggatgaggga gagagagcta agatagataa agacagagat ggggagatcc actgattcgt    26280
tgaacaaacc agatacttcc ttatagtttt tggattaact tacatgagct aagtttatat    26340
tctgttcaga tcacaagtgg tcaagtttgt gtgtgtgtgg ggggggggggg gtgggtgtgt    26400 gtgtgtacca ctctacccat cctatattta ttgtcctgta tttggtctgt tctgccttct    26460
ttattttcag gataggtgtc ctaaatgagg gtctttggaa agctggtgag gccatgttgc    26520
ccgtttcagg tgttccgtgc tcaaatgtat tcatttcttg aaaaattcag ggagtgcaca    26580
cttttgtaca ttttcctatg tgtatatgat accattatat aaatcttaaa aatatatatg    26640
gttcacctga atccccagcc atttggtaga gaagatagaa aacctacaga ggaggctaag    26700
attttattag aaaattcagc ttctcgacgg aggtattggc tttaaagtca aggcaatgca    26760
tctattcttt ctttttgatat aactagctaa aagatctctt aaattcaaag tggccctcat    26820
cttactgtta ctgcaattta ctcttaatta caaattatat aaaaataggt tttgaaaatac   26880 tgtagcgaca aagtaacata cctctgctcc attacacaga taaaacctct aaggaacacc    26940
tcctctctta acaggcatta accaactgca gaaactgcag aaggacaggg ctatttggga    27000
```

```
ataacacagc tcccttcctt gtctgttccc tcccattgtc aggcttctgt ggagccatat  27060
tcagagcaac atagggaggg ggaagagaaa atcaacccct tggtgaagga aagctcccaa  27120
ttcacagagc aaacatgggt actcttgttt gtgggagctc ccagggcctc ccagctcacc  27180
gagcattctg agccctgatc cttacactaa ttgtattatg caaccataaa tgatgtctgc  27240
tgtaccagcg gggacagttt attttaatag attggtataa cttggcagaa tcttatctgc  27300
atgtttcatc ttggattttt agctcaattc aactcaatag gcatgtgtca aatgtctact  27360
gcagactgag cactgaaaag ctgctgggta cagggttaca tggatagaaa cgtagcctc   27420 tgaccccaa ggagcctgta atccagatcc ccattctttc catcccattc tcccaagcaa  27480
gaatttacct aatgtggttt gcgagaattt aagagctgga aaggtggtca cgagaagccg  27540
gaatgggttc gctaaaatgt gtctatatga ttaagcataa cgtagctttg cagcactctt  27600
cacagcttcc tcagagcctt ccgcacgcgg tgtctcattt gaatacttgt gtgaggatag  27660
cctcataccc ctcagtgagc tcttcatgga gtgatgcagt agacagcaag cctcacactt  27720
ctatgctcac ggaagaccaa atttgccttg aaaaatcttt atagtctctt cacatttcta  27780
agttgacatc aaaaatcggt taccataaaa tcctaatagt tgaagagatg taatttcaat  27840
tatttggtaa acctgacctt cattgtcaaa gcaattagtc aactcagatt tactttctcc  27900
cagataatag attctgactt ctttttttct gattaaaaaa cttaacaccct tcctcaggag  27960 atctatctca gttctgaatg ctgattctaa ctaagaagga tatttggcta catgctggga  28020
agaggggtac tgaggcacgc cgcgattcca ctccagcatt tccagttagt cgggtgcctc  28080
tgcactcccg gtgttccggc gcccagttag ttgtgtactc tgggctgtcc ctatactgga  28140
gtcctaaaac acttacgact gcagataggg ggaggttttt caaaaccttg gtctgaaaag  28200
ccatagaagg gagataggaa agcggggggg tggagccaca gtacattcag gtggatccgt  28260
ttttggaaat agtacaaact ggaggtgaaa ccctggaaat tgatctgtcg ttcacatgct  28320
tcatgccgag tccttgtgga cccacagaga cacactcgcc ccagtttgaa ggctgctaac  28380
ttgattctga ggacaccagt gaggtggtag tgtgcaaatg atgtgtgagg aaactttgga  28440
ggagtctcac cctgcctgga gcacgtggcc cctaaaacag cgcagcctcc caaagacaga  28500
agatgtggac tagtgagaag ccaggtatgg tgactgctgc tggatgaagc ttgtcccacc  28560
agaggctcgc ttgtttcatt gagcacctac tgtgtgcttg tgggatgcaa acacacgtgt  28620
ggtccctgcc ctcaggttaa taggcagggg tggaacagtt atgaaactgc tctaaagtca  28680
ttttctcaaa ctgggagtga caaatgtatc cacttggaaa agattgagaa ttttataaga  28740
tttttaaatt tttgtttatt cacattgagg agaatctaaa ttcttttgaa cttatgtata  28800
gatttcacca ttttatagta ataaatcagt cctcctgtgt gtgtgtgtgt atgtgtgtgt  28860
gtgtgtatgt aaacctcacc ttgcaatatt attattttaa atagccactt gcatcttaag  28920
gaaattaaga ggacaaaaga aaagctgctg ttttgtatgt atccacatat ttaccagctg  28980
cttccctgcc ggcaggtgct ctggttctgc actgcctgtt gtcccttgcc tgaaaatggt  29040
tgcctccaat attttgctca gttttctgat tgtttacagt ggcagaggag ggtagatctg  29100
gtaccagtta gtaattgcca gaggtggaag tctgtggatg aaatttgtat aacatggaac  29160
gttagttcca cagttaatgc tactcaattg gaacccatgg aaattatttt ttggtgaaaa  29220
gggcccatgc gttatgaaat ttgagatcca tcactttaag tgaatgtagg ccctggatac  29280
agtgggagct cagaagagca aatcagttgg tcaccttgct caacgtattt tactaagggc  29340
```

| | | | | | |
|---|---|---|---|---|---|
| atcagtaagg | ctttctatga | cctgctcctt | caatgcttgg | ttgacatttg | gggagcaaag 29400 |
| ataaactaag | gattctaagt | tctgtcctgt | gatgctgtaa | ggggaatctc | aaacctctag 29460 |
| gtggaggagt | gcagagatga | ccaggatggt | ggaagcctgc | aggagagctg | aacacctgaa 29520 |
| gacacccagt | gggaagacca | ggacctttaa | cgcccatatc | tgctgctcaa | gactggcaga 29580 |
| gagaagaggg | tttgtgatga | gaaaaggtgg | tgaaaggcac | aaggaggcac | agagcatgtc 29640 |
| aggtcccata | tcccaaaagg | aatgtgcttg | ggtgagggag | agctcctcca | tggctggagg 29700 |
| cattcagaga | ccaggcagtc | gcttgtgggt | ttgtgattag | agtgaggttc | ttttataaag 29760 |
| ggagtgagaa | gagaaggtct | gtggatactt | gagtgtatcg | gtaattaaga | aataaattgt 29820 |
| gtacatccca | tttcttttcca | cattttcctg | ggctgtcaca | gtggctgcaa | agaaagcagt 29880 |
| ccgtgaactg | aactgtgatc | ccagacaggc | aagcacacca | ggaatctctt | ctcagctgtt 29940 |
| gataatgagg | gagcgctggg | gagagaaatg | gggtcctctt | tgagtttcct | ctgtgccgat 30000 |
| acctttctct | ttgttaaaac | agctaattaa | acactgaagc | agtatagctc | tcttactata 30060 |
| cactggtagt | catagttctc | ttactgttct | cttcactgac | agttctctta | ctatacactg 30120 |
| atggtgacgc | agaaattcag | aattccccgc | atgtgtcccg | gtttgaaagc | cactgtgctt 30180 |
| tgctgtggat | taggatcaga | cagttgagtc | ttgttccaac | aaggaaagtt | gcttattgga 30240 |
| aagttttgct | gcagggagcc | ttgagttctg | catcaggctt | ggaagtgggc | tctgtggagg 30300 |
| tcagaaggag | gatcccccac | ccgcagcctc | aagaaaaata | tgaaaagtgg | attatgcctc 30360 |
| tgtagctata | ttgcctataa | actttctgca | gaatgacagt | attcatatcc | tacatttttt 30420 |
| caaagcgata | ttaatcctga | gacctgcagc | taaagtcaag | tagaatttag | ggataattaa 30480 |
| taggaggaag | gtggggttgg | aagatctgca | tgattatagt | cctctgatat | aactggaaaa 30540 |
| ttctttccat | tagcaaggag | ctttggttaa | tataaaatgg | acagattaaa | cctaggcaat 30600 |
| ttatttact | cattgctgta | ttttatttc | agagctggtt | gaaaatatta | caaagtaata 30660 |
| ttttaaagtg | cttatctaaa | ctcttactct | gcattttatc | attgggttat | gaaatgactg 30720 |
| gggaaagact | tttcttgctt | ttatttctca | gtgtctactt | ataaacatgt | tttttgaact 30780 |
| actgttttg | tgacaacatg | cctttttccc | agaaaatctc | aggttaacat | taaataggca 30840 |
| ctggatgttt | atctgatctt | gtttatagaa | acacaagaaa | attttaacct | tgtatatact 30900 |
| ttactcaatt | aactaggtaa | gaggtcattg | aaacatttag | aattccactc | tacatttcaa 30960 |
| taattatcag | gtgaaagcta | ctgcatctac | atcagaagat | gtttgtaatt | tatttaagaa 31020 |
| taaaattagc | tatgcaagaa | atagtatgtg | gagtcctatg | tggaaatcac | agaaaccctg 31080 |
| acaacttgat | gatctttccg | caagctaaaa | atatcactct | ggatcacagc | agtagaggac 31140 |
| tctgtaaatt | taatctgtgt | gtctcctgta | aataagtgca | ttagcagtac | acaggtggtg 31200 |
| tcagagtcag | tgatgatgga | tagaaattct | acataaaatc | caggctcagt | ggctcatgcc 31260 |
| tttaatccca | gcactttggg | agtctgaggc | gggtggatca | cctgaggtca | ggagttcgag 31320 |
| accagcctgg | ccaacatggc | aaaaccctgt | ctctactaaa | aatacaaaaa | ttagctggat 31380 |
| gatggcacat | gcctgtaatc | ccagctattc | gggaggcgga | ggcaggagaa | tctcttgaac 31440 |
| ctgggaggta | gaggttgcag | tgagccgaga | tcacgccatt | gcactccagc | ctgggcaaaa 31500 |
| gagcgacact | ccatcgcaaa | aaaaaagaa | gtaagaagtt | ttacataaaa | acgtggagtg 31560 |
| agcccaaggt | gccatttatc | cagcccatac | acatcgtacc | atgtacagag | tggacaccag 31620 |
| ataaatacat | tgactgcatg | ccacaaacat | atatatgtag | gcaccgttgc | attcaaatac 31680 |
| acatctgcag | ccctaacaca | tctttatttg | ctaacgagca | tcaatgtatt | taaaaacaaa 31740 |

```
catgtttaaa ctagtgaatg attagattat aatgatctta attcataagt tttctcattg    31800
gcctttgta tacttcaatt gtaataccta gaaaaacagt tatgtccaaa ggagtgaata     31860
ggccttatct gaaacaggtg agcgtgacaa gtgttttctt acttatttta cttttcagat    31920
aattcatcct taaagtacat tagtttaaaa gtactgttta aggaaacagt acttggatta    31980
aaacttgaat cattgttaag gaaaactata ccttaacttc atgtaatcac aattaaacct    32040
cttcatatag aaggatctaa gaattttctg cagcattcac cagcaccaaa aagctcagag    32100
acatatattt ctttctctgt atatgtattt taaattcaag ttagtataaa ttgacaggca    32160
ggtcagagta atatatgatc ttctgagtcc cctagtaat taaaagaaat gattattttt     32220
gcatgaaata tgataaagtg atttaagtg cctgataaaa agtcttaacc atgacaacca     32280
ttaaagatta catcaaagaa aaataagttt gactttcatt taccttggaa acagctatta    32340
actggtaacc tcaagaaaca ccatgaagag tcagtttgct ccacacatgt cttgtaaaag    32400
tcaaataact ggtggttatc cagtaatgac aagaggtaga agttacatcc ttgctgtctg    32460
attgaacctt cccagagctg cacaaggct gggaagacca taggtgctaa atgaggaact     32520
acttaaagaa agaaaatgga atttcacgga caagaaaatc catgtccatt tggttctgtg    32580
acccacatcc tttgtatcct atgcttttt acacttggta catggttgca agattgcccc     32640
tgttttctac ttatagttcc atgcagcatg gatgtgggaa aaagtctcct ctgcaaaggg    32700
ggttaatgca ggtcactcta cgtatgtgca cgaggtcgtt ataaagctcg aaaatatggg    32760
ctcaccaacc aggtgatttt tttaattatc caaccagaag acataacata taggggaatc    32820
aaaagaaatc tctgagtaaa ataatgataa caggtcaaac tttgcggtcc cacgtgaggc    32880
tggagatgcg tattgtcttg actttgcatc tacaagttta acaaatgatg ctttctcagt    32940
ttacctctgg aaatggaaat tagcattgca aatgacttca tgaggaggta gaagctatct    33000
gtgaatttcc tttcgctgtg tttacgatag actctcacgt ctagatgtgt catgtattat    33060
gttaaattgg tatgtcttga agttataaag cacagccctc tataagtata tatattccac    33120
ctctttcaaa tcggatggta cctatccttc aaactgctat ttaatgactg tctgctatgt    33180
tcaaggcact gctctcaatg ttaatacttg atgagatcgg gcgcgttcaa ggtggcatgg    33240
ccgtagactc aatgttagta tctgaaatat ggcctacgag ctgagttgtg aatcaagtta    33300
atagattttc ggaatgttaa ggtctaaacc agtagctctt aactgagaca atcctgtcct    33360
catctcacct gggagacatc tggcaatgtt tggagaacct tttggttgtc acactggggc    33420
atctagtgag tagaggtcag ggatggtggt aaacaagttt ttttgtttgt ttgttttgtt    33480
tttgagacag agtctcactt tgtcacccag gctggagtgc agtggtgtga tctcagctca    33540
ctgcaacctc tgcctcctag gttcaagcaa ttcttatgcc tcagcctccc aagtagtagc    33600
tgggattaca ggtgtgcacc actacactca gctaattttt gcatttttag tagagacggg    33660
gttttgccat gttggctagg ttggtctcga actcctggcc tcaagagaac cgccccttc     33720
ttggcctccc aatatgccgg gattacaggt gtgagccacc gtgcccaggc taacattctt    33780
taatgcatag gacagccccc accatacaga ggaatcccca gcccagaatg ttaatagttc    33840
taaggttgag aaacccaagg ttaagccaag tcaacttatc tatcttcttt aaaattgcat    33900
aagaatgcag tcctgttctt cattcctctt gctttgcagt taatgatcct tgcctggac     33960
tttctaagtg cccagaagag caacagccag catgcaggat ggcattcctg accagttgca    34020
cttggcctag cattccaacc tcacctgcct cagcttgttc aacctgaaaa cctaccaagt    34080
```

```
gaaagcaaga gccacgtgaa gacgccttag ttatatgcac ccacccagac acttgctcag   34140
aaaggaatca gtggggccct ggccttagaa actggctcct tcactgctgt agaaacaaca   34200
taaatttaac ataaaacacg tgcttttctt ttttcttctt acttttcct gtcttggcaa    34260 tgcaaggatg ccattaggta aagaaatcct tcaccacact aatcctgcag agccagaaga   34320
gaaaccagct tgttctaacc cagctttgtc atggagagaa ggcagctgct ccagtctgaa   34380
ctattctttc ttttggtagc agcctgccca agggtgaaag tgtgtttaat agtttgaatt   34440
acacaagtga acagtaaatg tatgcctgtt tctgctttat gggactttga ataatgttg    34500 tttgtgccaa ggttttagat tactatacct aacaacctag aaaagaaat gaaaggaag    34560 ccttctgcca ggcagaggtc actacgggcc tggagctggg cacctgactc agcagctgcc   34620
cagatcccca gagctgagaa gtcaccatgc atttgtggtg cttcgagcga gttaccagag   34680
tcctggaaca gagcagcaca cctgcggggt gtccccttgg catttgggca gggcaggtga   34740
ccaagggtct tgttgaact gaagtccagc ttgaaaagca aatctggttg tgagctagag    34800
tccagtaaca cttgtttccc gccgccccc gcataactcg tgtgtcctaa aatcaataa     34860 tttcttgaac ttcagtcact tatgcctata agcgggcata caacaggggc acaataaatg   34920
tttgttaagt gaatgaattc tttcagaact agatgggatc ttagtccaac tctcttattt   34980
aacgaggtcc acagaggttc tgcgattgtc taagaaagaa ggctgtgttc atggcctttg   35040
ttgtttacgt ggccctgtga ttctcttggc tccgtgaaag tcctgatgca gacattccgg   35100
ccatctagaa aggcatgcag acaagccatc cagctggcat gatcctgagt ccagctttct   35160 ttaaagagc ttccaaaact gcttaagctt tgactgcaca aaacctgcat cacctccagt    35220
tgagaaactc aagagaataa gtaagttatg gagttggaga ccccagctta actactagtt   35280
ttaaaatagt gaaatcaaca ttttcaaatc tttgacttca ctaagattta ataaagttta   35340
ttaatcatat attatgagtt attgctctct ctttatgtct gtaatgcagt tgctcctctc   35400
tgtataaatt aataagtttt agagatccaa aatgagaatt ttaaaataaa ttacgtatat   35460
tttaatcaag tttaatttga ctatatccag ctaaacaatt gattgaactt cacttgcttt   35520
tctatgacag gttttttgtt cttagtaaaa gaccccagtt ttctcacttg tgaacagaag   35580
gggttagact tcatgacagc taaggttcct tccgtctcta acaaaagtgg cctgaagaga   35640
ggcttctaga ctatactcac ggtgggttct tgggacctca gagtcagctc catcacttaa   35700
gtggctgtgt gattgagtgg agacacctca atctcttgt gcctcagttt cctcacctgt    35760
cgagtgtcaa catgatggca cctaaagctg ttgagacttc agaaaggtaa tgtgtgaaaa   35820
gtgaaaagtg cctggcatcc aggaagtact caataaatac caactatttt attgctgcag   35880
ctgttcttat agatgtgatt tctagaacat tgccttctaa tagggtagcc atgggccaca   35940
attgttggct gttcggtgtt tcacatatgg ttagtccaaa ctaagatgtg ttgtgagtct   36000
caaatacaca ctggattgtg aagacttagg acaaggaaaa caatgttaat aaaatctcat   36060
tgataacttt taaattaatt acatgttgaa atgaaaatat ttgggacata ttgagttaaa   36120
taaaacagga gattaatttc ttctgttct ttctactttt tttattagtg tggctactca    36180
aaaatgtgac attatgtatg catctcgtat tacatttcta ttggacagca gcgctctaga   36240
cagtactatg ggtagtatct gtggggaggt tctcagaaac atgtcgcatg ctcttttaga   36300
acctaaaagt attcctagtc tcctctactt ccagcccttg gctcttgggc tcagtctttt   36360 ttactttgc ggctgtgttt ctctgaaggc ttggcattag tagattgaaa agaataacca    36420
tctagggaaa tgtgaattca gtttcttct gacattctgc tctctacaag gggatattat    36480
```

```
gtacacataa acctacttcc aaaataatga agtgaggcct aattccttac tcttcagaga    36540
gcccactgtg gaagtgtcac tgaccttgtg tatgggctgc ccttcatggc tctgggagtc    36600
attataaagg gcagcatttg gcgtggtgcg tcctaagcca gtgtttctcg gctctgttcc    36660
ttagacatgt gttagtgtta atagatgttc ttggaaaaaa aaaaaaaaaa cagcattctg    36720
aggtcaaaca tgctcagaaa gcttggaatc tgcactacgc ttctcgtaca catttcatat    36780
taaagatttt ggaaagtcct gcaatacaga gccctgtcta atattgccac aacccacaat    36840
tgctcaaatg taaatagatt tgagtttatt cacattcaga tcacctctta aggcccacc     36900 tcccaatgct gtcacaatgg caattagatt tccacatgag ttttggaagg gacattcaga    36960
ccacagcagg ggaaagcagg gtacttgctg ctttgcaagt gtgtccacat ctaattaata    37020
gtacagttct tactcttggt gtgtccggtg atattaaaaa ttaatgtgcc ttatttagat    37080
aagtaacata aaaatcacaa aatgtatgcc ttagatttat atgtatttat aactagtcta    37140
tttcctgaaa acagttgaga caccttgtaa aagttaccgg tacgataggg ccattccaac    37200
aaagctgtaa agtggtgata acacagtcat aaagaagagg agatagctct gggagaaaag    37260
gtggcccaga aaccagctct gagcctcatg gctgcaggca aggtctgcag gttcctggtc    37320
ctgattgcag gccatttgct gccttgagtg gtggttacac aaggccagcc ctggggtat    37380 cacccagaac acctagtaca cgaatttcag tttagaggac gaagcattac tggagtattg    37440
ttatgcagga aaactttttc ctaaaaatgc cctgaaaaga gagtagccta atgcattcaa    37500
tcaaaatgtt tttaagtgga aaacatattg tgtgtacttg atctggcctg ctgcttttaa    37560
aagattaaaa ctgggactgg gcatggtggc tcacacctgt aatcccagca ctttgggagg    37620
cagaggcagg tggatcacct gaggtcaaga gttggagacc agcctgacca agatggtgaa    37680
accccatgcc tactaaaaat gcaaaaagtt agccaggctt ggtggcgcat gccggtaatc    37740
ccagctagtt gaggggctga ggcaggggaa tcacttgaac ctgggagccg gaggttgcag    37800
tgagctgaga tcgcatcatt gtactccagc ctgggcaaca agagtgaaac tccatctcga    37860
aaacaaacaa acaaacaaaa aaacactggg gccaaagaac tctgtgtgct gtatcaccta    37920
accacatttc atgacacggc tagagaagaa tcatgcaaat aaaaatttcc aacatgttcg    37980
taaactggga aagtatttca ctggggagtg agcagaaaag taatactata acctctatat    38040
ctagacaaat gtgaattcag tttcacatat aaatatataa gtgaaaaaat atataaatat    38100
aaataatatg aaataatggt tatctcacca cttttctacat cttttgtgaa tattttatag    38160
tgctcaaata tattagtgca ctagtatatg tacattacat taaataacta atcatttatt    38220
aggaggatgt gcttgttttt tgctaataaa gatgataata aaaaaatcct tagaccccc     38280 ctcggtttgt tttcagttag gaattaggga tatttataag aatatcttta aatgacacat    38340
gccttgctct gggacgaggc atctgcatgg gtgacacata tgtgttgtgt gtacaggctc    38400
ccagcatttc cagggccctg ctcagaatgt aggccttact gattcttaca gagttacaag    38460
cgctggtgag gttggcgaag tttaggtaaa cacagctggg aatgccccat ggcctctggg    38520
tgactttgga catcactgaa ctttacccctt agagatgcat acctgcatct tttttaccct    38580
gatagggcct tccatgatgc tttcaaagtg ttttttgtctg cttttcggtt aatagacttt    38640
cacagtagcc aattgaatat attggttaaa tgcatctctt tatacacaga ctggattcaa    38700
actgaggttg tgtctctccc tggctgtgtg acgtttggga tgatccaagt gtcagattac    38760
tcaacttcaa aatgaggaca gagcctttcc cttctagggc tgccaggaac attgaatgag    38820
```

| | | | | | |
|---|---|---|---|---|---|
| agagtgctgg | cagcttagta | caggtgttca | ttgctcttgt | atggtactgt ctgtggcacg | 38880 |
| gctagataaa | atacagtagc | cactgattca | aatttcaact | gaggagtaaa ataaactgaa | 38940 |
| taacttagaa | aagttttctt | cttttgaatg | actctaagaa | tttaaggagc atgtgagtgt | 39000 |
| tgatggctct | aaaagggtaa | cagagcccaa | ctagctcagt | tctcagcatg aaaatagtca | 39060 |
| tatggcacag | actcagtgga | gtgggtgcac | ttcaataact | ggaagcacag atgccctaca | 39120 |
| gcagcatcaa | agatggcact | ctaaactact | ttcaatcctt | aaaataaat ggaaacgcac | 39180 |
| atttagtatg | catatgacaa | cacgaaggac | ttcgattttg | ctgatgcaat acagttttac | 39240 |
| aggattttt | atactcaaat | tagtaaaatt | ctgtattgca | tccaaattat aaattataat | 39300 |
| atcatctaga | ttggacatag | gaataacgac | cactggtatc | tgcccagaaa gctctaccgc | 39360 |
| ctgtttataa | gctcctgcag | gagacacaaa | aagaagagaa | tttgaatata acttgaaatg | 39420 |
| accgtaatct | cctgccccaa | ctcatttcat | taccaaaccg | cctctttctt cattatttct | 39480 |
| cctgaagcac | aaatctatag | agaactcagc | tgccagtctc | tcccactgca ctcagcagtg | 39540 |
| aaagggttag | gcctaggctt | tcaaacaga | ccagtgcttg | tatcagccct aaacatctc | 39600 |
| tggagaagga | aatgggatcc | ttcttggta | attcatttt | gacagttggg gattaggtgt | 39660 |
| tctgtatctg | gggggccttg | ctgtcttctc | tcctcctcct | cccactgcag accctctcct | 39720 |
| cccctcccct | ctccagctct | ctgatgactg | cttcatgctc | cttccacctg aggactgcca | 39780 |
| gcacagccta | ttgcaggaac | agccaatgag | gggctggctg | tgctctttta tttataaaat | 39840 |
| tataaactca | agcaaaatct | agactatgtg | tccccaagat | cagaggagca caaatcccctt | 39900 |
| gcttacagat | tgcatggggg | gcacattctt | taaaattggt | ccctgatcta gactctagcc | 39960 |
| tgagaatcat | ctttaagttc | agaatttcca | ctcatgacct | cacatctgtg ggctcccaca | 40020 |
| ttgtcttcca | aaacacacat | ggcatctggc | atcaccttca | cccccaccct cagagcctca | 40080 |
| tctccctgca | ggtagatagt | caaggcaacc | tcttcactct | tctgccaagc ctcctctcct | 40140 |
| cagctcttcc | cttcctctct | cttttgaaa | atatttttaa | ttgtggcaaa atatacacaa | 40200 |
| cataaaattt | accatcttaa | tcatgtataa | aagtggagtt | cagtggcatt aaatacattc | 40260 |
| acgttgttct | atagccataa | acaccattca | tctccagagc | tcctttcatc ttgcaaagct | 40320 |
| gaaactctgt | ccccattaag | caatggctct | gttttcctcc | gttccccag ccctggcca | 40380 |
| ccatcctcag | ttttctgtct | ctgtgagttt | gattactcta | agcacctctt ataagtggat | 40440 |
| catacaatgt | atctgtcttt | ttgtgactgg | cttgtttcac | tttccataat gtcttcaagg | 40500 |
| ttcatccacg | ttgcagcata | tggcagaaca | tctgtccatt | tccaggctga atggtactct | 40560 |
| tttgtacgtg | tggaccacat | ttcatttatc | cattcatcca | cgggagggca cttgggttgc | 40620 |
| ttctgctttt | tagctattgt | gaataacgct | gctatgaaca | tagctgtatg cctttgtctt | 40680 |
| ttaaagccca | aatctgatca | agtcactccc | cagcttaaaa | ccttcactg ctccccagca | 40740 |
| gtgggataaa | ggccagtctc | ccctgtaggt | ctctcccgcc | agccctgctc agtcttcttg | 40800 |
| cttgtcatcc | ttggctaggc | cttgcattgc | catagccctc | tgcctctgtt cacgctctct | 40860 |
| catcttggag | catgagcctt | ccatcatctc | taccagatga | actctcattt cttctttcaa | 40920 |
| aaaataaaaa | acccaaaaaa | cccagagatc | ccaactgtcc | tggtgtctgc atagtctgca | 40980 |
| gcacacgccc | cctccatggc | ccttcctcca | taagcagaat | cactcctcac tgttcctgca | 41040 |
| gcacctcctg | tgtgcccaca | cagctgtcct | gcggtgggct | gtgtgtgtga gtgtgccccc | 41100 |
| tctaggacct | gagctccttc | tggagggtgg | gcacagcatc | cattcattct gggaatcctg | 41160 |
| gtcggcacca | tgctagaact | tctgcaagtg | agtgcctttg | gtgctggccc atgggagagc | 41220 |

```
tgttggtaag gcatactttt gcagattcca gttgctgctg aggttgttgc tctttgcaca   41280
agtttcttct agtcaccagt gaagtgacat gtgtggcagg catggcccag ggaggctttt   41340
tcataaagaa gaggttgaat ctttggggct gtggtttgaa tatgtccctc aagcttatgt   41400
gttgaaaact taatcccaaa tgcaatagtg ttaggaggtg gggcctaatc acaggtgatt   41460
aggtcataag gctctgccct catggatggc ttaacatgtt tagtgaggca gtgggttagc   41520
tattgtgaga gtgggcttgt tagaaaattg agtgcagccc cctcttgctt gctggctacc   41580
atgctctctt gcttttctgc cttctgccgt ggggtgacac agcaagaaga ccctccccag   41640
atgctggcac catgccctgg gactttccag ccttcagaac cacgagccag acaaatttct   41700
tttctttata aattacccag tctgtggtat tctgttatag aaacacaaaa tggactaaga   41760
caatcttctt tcatcaagtt agggtaccaa cctttaaaga ctgccagtcc aaggttaaag   41820 gaaactttc aagagcagtc caaacatgat ctggccctca gctactctcc agggtcatgc   41880
caccctatca cccactggct cacacagacg ctgaccactg cttagtttct caaactgaag   41940
ttttcctcct cagagctttt gcaaaacctt ttctttgcct ggaaaactcc ccccacaaat   42000
ctttagttgt aggttccttc tcatcttgca gaattattag tttgctcttc aaatagtctc   42060
tccagctaga ctatcaactc caggagggca gagttcttct tcgcttcctt cacccatgtg   42120
cccactgagt ccagaactgt atagcagttt gattgaaaaa atccacaggg tggaggatga   42180
gaggaccctg gatcccagcc tcacagcctc ttacttcacc tgtgtgattt tggtcaagtc   42240
ctttattctt cctgggcttt agttttccct tatctaaaat atgagaaaag ttcccctctc   42300
ctgggtattc tgggagactc atgtaaaagg cactgagcca gtgcagcaca tctatgacca   42360
ggaagggtca gcttcctgcc ttgcatgaga cacacattcc cttcttcatg cacagttatt   42420
catgagttaa atatgtattg agaagtgggt tctcaggaga tgatgcatcc acagcattgt   42480
ttgtatgcct ctgtctttga tgtccctgcc tgagtcgccc actttagagc ccttctgttc   42540
ttcagaaacc agacttttct ttcaatagtt tcagtaatca atcgatcaat caatcaacca   42600
atcaacagtg ataataatca tgagtgagcc cctgcccgtg ctggctgtgt cctgctgaag   42660
gcacactaag tgctgccctt cccagaagcc tcaggaagct tgcgaagctc aggtgcatgg   42720
atgcctggtg gaatgaggaa gggatgcagc caggtagaga aatgccctgc catcacttgc   42780
atcagcatct gtgaagagct ggccaggctt ttgctcacag tggttgacac agtcaaggag   42840
caagggcccc gtaggagagg ggagtcaagg gctccgggtg ggaatggagc tgggggctga   42900
tgctggcttc tggagcactg taatgtgact gagaaaggtg aaggagccgt tctgaaaaag   42960
aagaaggcag gagctcgcac agctcttgac tcatcttgac ttctttttcc tgcttcatcc   43020
aagcaggtcg actctctcgt gatctcagag acagagtgaa gtcatgagtg ggaggggagc   43080
acagaaaata agaccttgat tcccagcatt gggagactcc ctgctcccct gagtctcgga   43140
aaatagcacc cttcaaatgt tttagggatc cagatttgat gaagagatgt tattttggct   43200
tttagattct taggagagat ttgtctttct caggtcagga agaaaatgct gcccgctgca   43260
cattcttcgg gacagactct tttaattatt actagtttaa tgtatgtttt gcttagttaa   43320
ggaaaacccc tgtggtttct tgacgtgctt cagtattcta actcacagct gattcagttc   43380 aggggctgg ggagatgtcc tcgacctctg gaaggaggg tgcatctcta gaaataaggc   43440
taagtatgcc actgacactg tctgcataaa cgtgtgtgat ctcaggtcca aaggatgggg   43500
cctggtctaa gccagggacg tgggaaatca ttttcctgtg gcaacttgtg aagaccattc   43560
```

```
tgtgaccttg gtgtctctgg gccttctctt agattttcta agttggctag tcagtggagc   43620
tgccatccct cctttgccca tgttctactc ccagagttcc tccaagaaat tgcggagcaa   43680
tgcctgtttc atgagagctg agtttgctgt gtcttccact tagaaacaac actgtggacc   43740
aggaggacac acagctccca gggccatcac cacacaaagt gaaggctggt gaatccgagg   43800
cttctagccc ttgccgggcc aggcccgcag cactccgctc cccaacccag ccgctgcttt   43860
gtcgcaggaa cctcagcagg gcagggtgtt tcctaggagg acatccgatt cccagccatt   43920
cctttcagtg aatcacctga gctcacattc ttttttcttt tattttttgaa gctcttagcc   43980 aatctgcttc gcgatgaacc agttttgctt gaagcagaca aacccgattg tcaggagaca   44040
gtgatgattt cttcagtctc tgaggaagag ttttcatttt ccccaattcg caaaaaaagt   44100
caggtccctc cctccctccc tctccgtaga atatttttcca tgtgtgttaa caatggctga   44160
gcgtggtaga tgccaggaat ttctgtcaac cctcaaagag gaaagccctg cctaatggtc   44220
tgcccgttct tgttcactcc ctgccccagg ctcccccaccc gccttctttc tggaaggtat   44280
aaaggctcct gcttatacct ggcactgcac gcttcgctcc ctctgatctc ctgactgtca   44340
tgcccagtgt ctcagcctat cattctacct ctaactcgac cttgagtgac cttgagcaag   44400
tttctcagga ttccacctcc aagtcactct ccctttggga tatgcagcac taagttaagc   44460
ttgcctggaa aacatcactt gaagctggaa accactttt aacacagcgg gaaaagctat   44520
ttgttcagac aggagtgggg tgggtctggg cagagcactg ctctaacttg gccatgccgt   44580
ggcagcagct cctttaatgc cactttttcc tggcgcgccc gcggggcctg gagctcagaa   44640
agaggggaac gctcccctcgt ctctcaacag ttgctccaga caggtcagca aacatggaat   44700
tcagaatgtt cattaaacac tggctgtgtc ttttgtgttc aaaagcaaga cactctctct   44760
gaaccatggc cccacagaga gtgcagaatg tgtgaaacct gccgggaagg tctgaccccc   44820
ttgcggggca gtgggcagca ccgtgcctcc gttcacacca ctcacatggc tgtgcctctg   44880
cttccttctg gcatggctgc ttcttcctca ggtctcaacc atctcccctca gatgctcttt   44940 cccatgtttg tggctacagg tccccgtgac ctgcagaggc agagcactca ccagcagccc   45000
agcctcgttg cgcacccatg tttgcatttg caggccctag aaccactcca agctccgtgt   45060
ggcgagatgc accctcctgc ccttcactgg ggagctgccc tcctgttcac agcggcacct   45120
gagtcacaca tctggagcca tcctggactg cctcattttcc ccgatggggg gtttccctga   45180
cttcatccat cctgtctttt gggtccccat aataactgac atgggtcggc ccgtaccagc   45240
ccctgtgaga agggctttaa ctgccttccc accccctgct catcttagag tctctctata   45300
gtgctgctga aagaatctct aaatcagtgg ttctcaacct cagccgcaca ttgagaatca   45360
cctgggaccc ttaaaaaaat cttaactctt ggtccaagaa ttctattaca atcggtctgg   45420
gatggggccc tacaggtatt ttttttaaagc tctccagttg gtaatgcata gctagagttg   45480
agtatcgctg ttctaacgtg cagatctggt catgttacca gccttttagg tggtcttctt   45540
tggctttctc tatctaaagt tcaaaaccga acatgtgcgc attcagtgca cccatttca   45600 actgtgcatt aacacattca gcccaccagc aagatttatg aaccattttc tgctgttgta   45660
tataacatat catatgcata atggcatagg ttattgtttt cttcaaaata tatgagatgt   45720
gagtccttct acgaactgac tcacactgat tgcccaactt cctctctcga ggtctcatcc   45780
tctttccctg cagccgtctc cctcttgcac gcacacacac acacacacac cacacacaca   45840
cacacaccac acacaccagg gtcgatgcca tctaccctgg acttcatctt gaactccttc   45900
gagtgtgagt cattactcct ttgtgcacct ctgctttctc ttctcaagat gttcacctgc   45960
```

```
ttgaggtcag ttccttgagc gtcttccact tgccatgttc accacagtgc tcaacatgcc   46020
tgaatgcatg gatggcgact tctcagatcc tcagtctcct catctgggta ataaggcatt   46080
gggttggcgg gtccatctgg tttcttccag ctctgagagt gcatttgctc tgtgattcat   46140
tcgttccaca acacttcacc aattaaagag agggtacaaa aggtgaacat ccttggctcc   46200
cagcagatgc tcctcaaaac ctgaaaaatc agataggtga gggaagattg aatgaaaggc   46260
ctcttatgat tctgcagcaa ttttggtggt ttaagaactc tatggaaaaa tcatcagtat   46320
ttctggaatt gaagtaaaat ggatagtgag cctctgtgta tgtgaaggcc cgcatctgga   46380
acatgaaaga acctgtctga tgtgttctag tcaggaaagc aggtagccaa tactatttat   46440
agaatttaca gaaactgaag attttgtttc tactgatttt caaaatagta ttatgtctga   46500 ttttttttcct cagaaatata cttcctgctc ttctcaacaa actcatttga aaatatgatt   46560
agaacatgat agaatcttac tcatttgcca actgcggttc ccatttcaca tattgttaga   46620
attctgcatg gtggctttgc cctttaacca ctaactgata aatgatgtag ttagctttta   46680
aatgtgtgga aaaatataat ttcaggttca accataggtc agaagtacac gtgttttgtt   46740
agtctatttg tctctcagtc atctcatgga aaattctcag cttttggtat ggaaataatt   46800
ttcttgaagg caatatttgt tgagtgactg acggaatgaa aaacgccagt tgcgtaagtg   46860
tgaaaaagat ctgggtgttt tcattggatc caaattccac atgagccaac aacagcgtgg   46920
tgtggaggct ggagcacatt aataagaaca gtgtcctaaa ttcaggaggt aatgctctgc   46980
ccatgccctg tgcagctcag acggtgtgtg cagtgcagta tgtaacccag ggcacatttc   47040
aggggcccac agggagctgc agcttgtaag gtggagtgca gccaacagag cagagagtca   47100
gaatccccgc agagtggttg aaggcacaag gatgcgcagc aaggaagaca gacttatagg   47160
tggtgcgact gccatcctct ggtactgaag gtgctatcat ggagggaggg aagtagattg   47220
accctcctgg ctccagagta cggaactcag acaaacggtc agaagcttac agggaggcca   47280
attttggatc aactttaaga agaattttttt aaaagctaga gcaatcctaa aatggaattt   47340
gctctttata aagttgcgaa tgcctcaccc tggaattgct taagcaaagt tgggacgggc   47400
agttgtgagt aatctccttt ccaatccata cccgcaatca ccagaaacgt ggacttccct   47460
gacactgagc acctcttaat taagcatctc ataagtgaac aaaacccagc ccttcaaaga   47520 agtcactta tttatgtgtg gtctgcagc ttggatttct tgataatgtt aaataaaact   47580
ccatctactc ttccacaaac acttcaagaa acctaagact tttggccaga gtaacaccga   47640
ggtttgagag aaaggatatg tgtgtgagag gtgtggtttc attagaacat attatttgac   47700
ttcatgttga atcaacactt ttgtgcaaaa tgcagtttta ccagcctctt tccttgtttt   47760
ggtcacataa tttaacttaa cattctcggt acttgatttt ctaacataaa atgggattga   47820
gaggggaatt ttgaagttcc catggtctgt cctctacatt ctgacagctc attatctctg   47880
cggtattgtt ctcacattta agtgaggtta gcggaggcag aggcctctca ggcctgaaga   47940
tagcctctgt tttcagggaa atactagact gtgagatctg tgacactgaa gcactaagtt   48000
catctcacaa aagcaacgtg ctcttttttaa atggttgatc aaagttactt tcaaaaggaa   48060
gtgttagttt ttgttattag ccgaaacaag agctgcttta atgtagtata tttaaaatca   48120
tatctcaatt aagatgttat tcaaatacta tttgacccac caatctcatt actggatata   48180
tacccaaagg aatagaaatc attctattat aaaaacacat ggctgggcac agtggctcac   48240
gcctgtaatc ccagcatttt gggaggccga ggcgggtgga tcacgaggtc aggagttcaa   48300
```

```
gaccagcctg gccaagatgg tgaaacctca tctctactaa aaatacaaaa attagccagg   48360
cgcggtggca ggcacctgta atcccagcta ctcggaaggc tgaggcagga aaattgcttg   48420
aacgcgggag gcggagtttg cagtgaacag agatgaagcc actgcacttt agcctaggtg   48480
acagagcgag actctgtctc aaaaaaaaaa aaagaaccac ttgcatatac actattcaca   48540
atagcaaaga cgtggaatca acctaaatgc ccatcggtga tagactgcat aaagaaaatg   48600
tggtacatat ataccacgaa atactatgca gccataaaaa agaacaagat catgtccttt   48660
gcggggacat ggatggaact gcaggtcatt atccttagca aacgaataag aaaagaaaac   48720
aaaataccgc atgttatcac ttataagtgg gaggtaaatg atgagaacac aaggatacac   48780
tggggcctac ttgagggtag agggttgaag ggagagaagc agaaaaaata actattgggg   48840
tactaggctt agtaccaggg tgacaaaata atctgtacaa caaactacta tgacacaagt   48900
ttacctgttt aacatacctg cacatgtacc cctgaactta aaaaaatttt taaaaagatg   48960
ctatgcaata aaattctcaa ttaagaattt aacttggtaa atgttcattt aatgatctaa   49020
aaatatgtgt ctggatggct ctagcaaaaa aataaataat aagtttctca gagatggtaa   49080
ggctgaaata aatggggaaa aatctgaatt gtaatccttt ttctgttgga cctggtgttg   49140
gggtttcaca cttgtgggtg aatgtgggcc tcctgtgagc accagcacaa aagactaaac   49200
tgaacaaaag attaaatgtc acctctaaaa ttctgtgcaa caagacttcc agccacagaa   49260
tgtgcaactc agatttccaa gtaaaaacac accaggaagc agatcttaga tctctgttat   49320
ctccttggca ccagctggta ttcatcctca atgctagcta gagttgaaat aaagagtgaa   49380
agaactttct cttttattac ttaataaact tccttttttg agctgtttta ggcttacaga   49440
aaaattgagt ggcagtttca gggagttcca gcacggcccc tgtttctttc tcatggtccc   49500
tgcaggtttc ccctattatt aacgtctgtc attagcatgg cacatttgtt acaattaatg   49560
agccaatatt gatacattat tcactaaagc ccacaggttg cgttaggggt cattcttggt   49620
ggtgtacgtt cttcaggtct ggacaaatct ataatgacat gcattcacca ttactatatc   49680
acgcagagtc gtctcctggc cctacaagtc ccctccttcc ccacctgctc actcctcctt   49740
cccaccctcc ccaaactgtg gcaaccattt aacttttgac tgaatggatt tattcttatt   49800
ctgccttatt gtatgtacac catattttaa taagataaaa taatagtcta tagtagactt   49860
ctgtaaatac tcaatgaata aatacttgca tgaatgcagg aaaaatcaat cagtcttgca   49920
ggatttctta tgcgttacat cgtccttata agaaagcagt cattctcacc gagatgtgct   49980
gagcagatac tggacatgtt ctgacccaga taagggctgg gtggaagtag ggctggagac   50040
acagagaccc agtgccaact tccaggacct cggaagaact gaaggcagag aggtcctctc   50100
agtgtggact gggcctctgc tggcagccac cagcgggcac agagctgatg tgtgttatgc   50160
cacgtgggga aaacctacag acgattctga gaaaggctca cagggacacc ctctgcccct   50220
aaaagaacaa tttaactcta atttatttct gtcactctgc attttctgac ctttcccaag   50280
tgtacagttt tatatgcatt taactgccaa attgtcatgt gagattatat ggttatattt   50340
cattaatata ttctagtttg ttcagctgtt cttactgggt gaatttgtgt ggtttcctga   50400 cattttgtt tttagtagtg cctcagtagt tttatacata attacgtttc ccttctggat   50460
tatttcctta gtatctagtt caagaagtga aatcgctgga ttcttgtggt aaattttga   50520 atttcacagt ataatgctga ttttctcaaa gtctcacatt ctaagaaagt ataatgaggc   50580
aaaacaaaca acaaacatct taagttgatt ttttcctagc atcttttcct tccatctttg   50640
cttgtagaat ctagactatt tcatgaaccc aagatataat cagtatcctt cttcagtatg   50700
```

```
gccaaagtga gtttctcatt attttacctc cccttcagga aatgactttt catcttgtgt   50760
tttgggagcc atagatggtt ctgggcagga aactggcttt ggatagaccc agcatgtaga   50820
tggctatttg gccttgctcc cagtataacg atgcagttcc ctgtgaaagg gtatgagtag   50880
gttttggggc tctggatacc gtgtggcctg aagagacaag ggctcaatgc caactctgcc   50940
tgtttccaac tgtgtaacca tgtgagcgtc aaaaatcatg gacgtgctct ggttaacact   51000
gagtgggagc tcaacaaatt attatttta attgttactt ggacatggcc aagttgacta   51060
cactttatgt tctgctacct gccagtctga aagtgacgcc acagaaggtg aaccgcatgt   51120
tgggagatgc tcctcatctg cttaaatgag gtgcaaacac agcccatgcg cctgctcttc   51180
atgactgtat ctgtaccagc aatatttgta ttggcaaatc acatgcccca gtgggaacta   51240
cttaagggga attcaatgga tttcattcct tttatgtaat tggccactta gtaatagacg   51300
tgtaggtctc ttgtgtggat aaggattctg cctttatgt aagatatgtg ttgcaattca   51360
gctttcaggt cccagccccg ggaaggctcc aggccttcac aaactggccc acccacgaga   51420
aggaaagcaa ttgtccaaat gtgggtagct tttcttccca ctgttgtcag ctgcttccaa   51480
ttagccccca tatacataat cccagtttgt gtctgtatca gtacaattct cccatgtcaa   51540
tgtgaatttt aagccacaga gggaaagggg acagagaata tgctttcatt cagctctcct   51600
cgtctcacac ctcttgccct gcatgcattt ctttgctctg attaaacgag cattttataa   51660
gccacatttg ctgtgtgaaa ggcaaagtct tccctcccac ggatgacggt ctccagggat   51720
gtgtgtgtgt gtgtgtgtgt gtgtgtgtgt gtgtgagaa gagagagaga gagagagaga   51780
ctgtaaacat atatctctgt gaaacttcat tttccatatg tgaattttg gaaccgagac   51840
aaatggaact tagctaaaag atgggaaagg tagactgact ctgacttaat ctacttaacc   51900
taccaggcaa tttataactt gatggcctaa tttttgcagc acccagaagc aagcctgttt   51960
cagcacggca aaggctcagc tgctaagtgg gcagcattgt tggaggtgag cagcttaggc   52020
tgactgttca tcaaaggacc aagcgcttga ggttcgctca tcgctggagg ccagagtggg   52080
gagggccatt taactgctca aggccatgga actctactgt cagtttcagg gaaatttggg   52140
accctggagc acaaaccaaa actccaatta accaggagag gaactcgatc cccaggagat   52200
aagtgaagag taagaagtct atctttagaa acaagagatg tccaaggcta gaaagatggg   52260
gaaggagggt ggaactgttc tggaagtggg tctcaatctc agcaccagca gctctcaaga   52320
ctttctagag aaggaaactt catttctgaa ttaaaattag tcttcaatga catggcaggg   52380
atttcggcac actctcttgc gtcataggcc actgtgttgg aggcaggagt gttggctttg   52440
gaggcataga gattaaaatt agagtaacac gtgagcactg aaaaggttaa acagtagaga   52500
catggaggac tcccgacccc catgtacccc tttcttaacc ctttaattaa gatcacagcc   52560
ctagaaatag cttgcaaaat aattaactac tgatcattta taccttagtg cttctgtgag   52620
catgttttct ctttcattgc tgctcatctg catggaaaaa tgtgcatggg tttctgaata   52680
taactccatg gtgcttgctt ccattatatt tgtgccattt ggatcataac tgataagcaa   52740
ccaaagagtc ccatattact gcacgttccc atcgctattt tatgtgaagg tggtcctggg   52800
ggctgttctg aattctcagt ttccttttt cccctcccca gttctttgaa aatatcagaa   52860
acggacttgt ggcatctttg aaaagctact aaaatgtgc tgctgtgctc tgaacttgaa   52920
aatgtgcttt taatacaaag tttgtgcagc ccttgctgct catacgagat gaatcttacc   52980
atgtggtgga tgcccgtctc atgccaggca ctgtgctcta agcccattgg tttatttcag   53040
```

```
tgcttgaaat tggctttcga gagaggcacc acggttccct ttttacagga gaggaaacac   53100
cagaggatca gagatggaga gtctttctcc acaaactcac agaccccaaa ggcaagctca   53160
gggttgtcag cttccaaagt ctgcctgctc caggacctca tgttgcatct ccattctctt   53220
cactgagggt caaatggaaa gaacacatgg gggtcaagtt tcagaaaata agagaaatga   53280
agaaatatgt gcccggaagc aagaacgacc gacctcatta aactggctcc cttcacctcc   53340
tctcacatct ttttctgcct tttggccaag ttttctctcc cccgcatttc ctccttgatc   53400
tcgtttgaat cctcttccct ggtgaagtca tttaggttca ggctcttatt ttactttggt   53460
ccataattta gatcgaacca catgtgctga tgtgattgaa acgatgtgga attctctgga   53520
cagagataga attatggagg ggttagtgtg tgtgtttaag attaaaagac caggtgtatg   53580
ggaggaaata taatgaacaa aaatagtat tttaaatgaa tactaaactt gcactcatgg   53640
aaaaagttct cttcccatga ggttctcgca aagcatttta ccatcagcac acgcagtttt   53700
tctcagtttt ctgagatggg gccatcttga atccaacaga caacacacag catcagccag   53760
actaacacaa aggacgtcat gggcatggac gtaaatactg gtgtcaacac taggtctgca   53820
cctcgagagg agtggagcaa aaggatggag tggcagatga aggtatgctg ttcagaaagg   53880
aggcagaaat gaaggaaga ccatcagtgc gctccacagc ttgaggaccg tcctggaggg   53940
caaatgccag ctgctcactt ctgaaaagaa aaattccagt gaaatgagta cagtcattct   54000
taggattact cacttgatac tgtgtatgtc tcttcttggc ttctcatctc cacacaaaac   54060
cctcaggtgg taaaaatcta attaaaaaaa ttatataaag tcttgtagat ttattagcct   54120
gaacataata gattttttt aagcacgtta agtcttccat ggactaaaag aaaacttgta   54180
aacctaagag aacctctatt tttgatatac aaaataatac atttccttaa actatgatct   54240
tgatactaga atttttaatta aaaaatacct gcagtttata tgcaaagtta tagattaatg   54300
cttaaaaata ggttgtatgt agtatccaca ggtcatgttt gactgtcaaa tagatgtaat   54360
tttaattcat aataattgtg tcgtgttctt ccccactaga agccaattat gcaagcttca   54420
ccattcacac atggaaaata atttaatgga gtactcattg caatttcact tatccagaat   54480
tggctgttgt tctcagagca gcttgtgttg ccttgttaag gagaatatgt tagtatccag   54540
acatccagaa aggatccttt actgtttcag agtccatttt ccccacttt gaaatacaca   54600 cacaaacacc cattcatgca aaccaaacag agattgtaaa gtgattccac tgacattat   54660 gcacttcttt tttctctttg gttcttcaaa ctctcagtca gtgcgcattt actcttaatt   54720
tagatacggt ttaaacctaa ttagaaacca gaagctcttg tatttccaca aaggattatg   54780
acagccccaa gaaaagatag tgaaaccatt atataacaag ataaaggctt cttaacaata   54840
caaggatgga ttttctcatt gatcttagcc ttctgaattt tagaaattgc catttcaaag   54900
tctaaaacaa aggaaaatca gggaataaaa gaatggtaag tagacacaaa cctactggct   54960
ccatcatttc tgttttagca aataacctgc cacatatacc aatagcccaa gagatgggca   55020
tgtccctgca tttcctggtc aaggtgacaa cactgcgtcc tcctggaaga ggtctgccac   55080
tcaccatacc acaaaccaaa tataataaaa tcagaaggca cactatagtg aattttttag   55140
aggcatgtat tgaaaagcat ctcaaaaagc attctcgaag cttccagaag tcaactcaag   55200
ttatctgaaa agtgacactt tgatgattg ctcgcttaat actgggagag ccagatgaag   55260
attcctcccc acttcctcag atgtgcaact ctgaatttc ttagtgttac tggagattcc   55320
tgctgcattc tgggccttta atgcataaac actgagatgt tctaaggaaa ttactcccta   55380
gggaggagag gggtggacga ggagtaagct ttgctggtga ctcatgcgct gtgtggaaac   55440
```

```
tccctgcaca agtgagctgc gcagggtgag tctaaagggt taatgcactt tcaaaagcct   55500
ctaatttgtt attccagaag agtaatttac tcactagaag tatctgggtg gctactaaca   55560
catttgtgtc tttaaaaaga tcagttttat tttaagatta aaatatataaa gcaagagctg   55620 gaaagtcact aaaaactgac agccagtttc ccattttcaa gagtatttat taaaaggttc   55680
tggttgcaga aggaataaga aatggcttga gatcatgaca cagtgaatca tgttgtaaac   55740
atgttagcta tggctgtgaa ttcaaccagc gatgagttca agcgtcccca gaaggtgttg   55800
ggggaattag ggacatggct gtgtttcccc agagaaaagt ggccatttta ctttccctct   55860
tcactaacat gcttttgaca tgcatggcag agctgaaggc aaggggaagg ggacaacata   55920
gtaagtgact aagtggcttt tttttttttt tttttgccaa gtgaagctga gtcatatggc   55980
ctctgtcatt ccaaaactat tctctacggc tgcattcctt tcgctcttgc cttcctttag   56040
aaccctggag aaggcctcct gaagcctggc cctattatgt atcctgacaa agataaactt   56100
ttccaaaaag ctgcatgttg tttctagcac agttttttcct cgcagtgact acgtgatgaa   56160
agtaccatgc agaggaggtg tctgactgag gcgttcgtgg tgtgtgacag agtcccctgc   56220
acaggacagc cgcactcccc tcttgcgtcc tttcctccca tgtttgcaaa gcctcttttcc   56280 ctgtcagcag ggggtgttct ggcagttgac atttctgaaa actacagcct acatttttaa   56340
aaaatccagt aagtgaaaac taaaaaatta ataccgtggt cataatagtg tggcatttga   56400
taactaatga ggcactgtcg tgccagctat tattttcaga catttacagt ccttttttaa   56460
atacaaagaa atatttggtg tgaaatgttc cccgggagct ggtgcaagca gaggcgacag   56520
ggcaagggag cttgggttgt agcctcgaat tcctccggcc agggctaccg tcagcctgcg   56580
gcacacaagt aaatcaaata taaaaccaaa atttctgtaa gcaaatcagt ttctaactca   56640
ctgtaacgaa ttatctttcg cacatcacag aggcatctct tttcactgtc gagtttggtt   56700
tgcttggtta caaaagggc agttcaaaag ctttggttgc tattgtgaaa gtcagctgaa   56760
ttccttccac cgtgctgggg tggggtgggg ttcacgcagg ttctcttttg tcaccagggg   56820
tgctgtggat tcacaagtaa gcaagaggct cctcaggtca agcctctggc tgctccctga   56880
ggtcagctgc ctagcttctc ctcctctgag atagacggga acaaagtctt tgatgtgtgc   56940
atttctcaag cttgacaatg atacagctac ataaaaaccc atgatttcat atagatattc   57000
caaaacgtaa aagtaaaacca tgcatccaca gagacatgga attacagaac tggatgctga   57060
gctggtcact tgggaggcag gcgtccttgc cattggttta tgcctcagcc ccaccatgca   57120
gtggctggcc aggtgaccta ggccagtcct gcatcctcgg ctcctcacct gcctggtggg   57180
acagtgacat ctctcctgca gcactgctgt cagggtgagg gaggtagggc gcagtttcag   57240
aaaaccattg ggctgcacct gcgtgagcac agctgcagga gcaaaagtca gaaaggtcag   57300
caaaggattt caggagcaaa ggtcagaaga aaccctcaag gtggttgtgt ctgcaggaaa   57360
gtgctgtcgt ctcctgcaat gctttcaaga ctattcagaa gcacagtgtg aagggagagc   57420
cggagcccat ggggaaatga ctccagagtg ttccacgtgt tggaaggcat ctgttggaaa   57480
acggacattc aagcaaatag ttgcctgcat agacaacgca gaatgactgg gaaagcccca   57540
acaagttacc tactggtaaa tgaggtgaga agcttaaagt gagaacccca ttgctgcctc   57600
tttttcactt taaaaacatt taagttttga attatggtaa aatacacgta agatttacta   57660
ctgtaaccat tttaagtgt acggttcagt agtgttaagt atattcacat tgctaaggaa   57720
ccaatctgct acttttgttt attaattttt tcctgagggg aaatattttt aaattttaaa   57780
```

```
atatttaatt gacaaataaa aattgtgtat attcaaggtg tagaacatga tttcatatgc    57840
acgtacattg tatactcatt accacaatca aagaaattaa cacatccaac ccacccatag    57900
ttgccattgt gtgtgcgcgg atgtgcgtgt atgtgtgtgt atgtgtgcac gtgtgcgcct    57960
gtgtgtgtct gtgtgtctct gtgtatacgt gtgtgtacat gtgtgtacgt gtgtgttcct    58020
gtgtatgtgt gtctgcgcac gtgtgtatgc atgtatatgg gtatgtgtgt acgtgtgtac    58080
gtgtgtgtgc atgtgtgtat atgtgtgtct gtgggcacag gtgtgcctgt gtgtatgtgt    58140
atatgtgtat gtgtgtacat gtatgtacgc gtgtgcatac gtgtgtgtgt gtgcacaggt    58200
gtgtatgtgt gtgcctgtgt gtgtgtgtgc atgtgtggtg gggacactaa aaatctctca    58260
tcaccttttt agtcaaaaga acagttgttt tggtttggct cttctgtttt aaaatatcag    58320
aacaataata atttcccaca gacaaaatcc tcaatcctca ccatccttct atttcctata    58380
ttcatcataa acttcatgct tgatgttgaa attgttttct gaaaatagag aatacaaaga    58440
ggagatttta aaatgtcagt ggcagcccca cactccttt taatcttatt tcctgatatc     58500
ttgagtttac ttggacgtag agttttcctt gactatggtt atttctggta gtagcagctc    58560
cagattaggc aatggttttc ttcagagata gcttagagtg agccccagaa caaggtcaat    58620
gcgaagattg cttgtgtctg cgtgtccagg gcacagtgat cctcatcact agccgggggg    58680
ctccgtgagg atctgctcct ggtcgtttct gttctgtatc ttctctgcag cccttactga    58740
agccgttacc aactggcaca attcaattcc tactgtaccc atcatgcaca gatggctgaa    58800
gtattgagaa cgctccagtg accgggaggc aatagtctgt ccacatctaa gaacacactt    58860
ggaataacct tagagaagag agagagagag agaatgcatg gttagtaggt tatcaaactc    58920
ctatgacttt tcacaggaaa agccctcatc cacaccaact ttaggaatgt gtagaaagaa    58980
gggtcaggga caggggtgag tggtgggcag agcagttgga gggcacaggg aaaaggcatc    59040
tggtcatgta tttggagtag gaggtcttgc tttactattg aattgcaggg acactttggg    59100
aacagtgttc acttctttt gcaaccattt cttcagagaa aagtcatgat actcaagtct     59160
tcttacaaag cagtttgagg ctttgagtac cagactgatt acagagatga gtatgaagca    59220
ttattgtagt atttttaagt gaaattcact aaatgcaaat aaacctagca aatgctctat    59280
ggttaatttt tttctaaaat tcagataatt aagacaattc attctcctga aactgctgtt    59340
catgtaaaaa ggaattttat cgaggtggcc cttgagtgcc aaacagcctg tcctcagctg    59400
caaaatgagt cgttgatgat cctccagcaa gggatacttt ttagctcgtg tggtgattgc    59460
tgcacacggg atatgtgcag caagtatctg ctgagctaat aataaacagc ctcagacaga    59520
aagacagtgg gcacaaggtc atgcttaaaa agacccctg ttctactgca tcccagctcc     59580
ccaccatggg gcctcacagg ccctggtgac caagcacatc agacctggtt cttgctcagt    59640
cctgggagcc acagaaccca gcacgtactt taccccaag accagactcc agcttggctt     59700
ttgtcctcct ctccaggatt ggtgacctcc taggtcgtga agctgtgatg agcaaagaca    59760
cactcctctc cattctccca acttcaggtc cctttgacag tgtcagcagg catttaaata    59820
gcagaccacc cacagcaggg ctggtagatg cagtgaactc aggaagatgc ctgcatagac    59880
tctagtgtta aagacagaat ccttacaagg aaccccata gttacctaac tgctgtctcc     59940
agtggtcata gaagtgtgat aacccactaa tcatcattct ctgtctctct gtctttctca    60000
tacacactta cacacacata cacacaacct tgttgcttaa ttttcagaga gtctactttc    60060
agaaaagcct tcaggaatac atcatgtaca aaactgagaa attacctgaa gtatctttaa    60120
atttagtaaa aagttgcatt gttttttgaa catcacactt gaaaagtaca tgaatacaaa    60180
```

| | |
|---|---|
| catacttagg aaaaaaagct ttaattaatt taaaaaggag aacaatgcta tatgctgtat | 60240 |
| cccacctttc tctgaatgtt acattttctc ccctatccca ggctgcatct aagaaaactc | 60300 |
| agagggaata tgctatctat cttttccgag caatgaaagc tctgggtttt ttccttgctt | 60360 |
| ttcagggcac aatacttctc tttcttcctg gttagacagg ataagttctg agtcccctgg | 60420 |
| tatcatcagc ttacttcttc tctgttaaat attcacaaaa aatcactaac tttcatgcct | 60480 |
| cagcaaacct ccactgccta aaatatagtg aggtcattca tcttcggaca aattgcccca | 60540 |
| actacggtgg gaaagaacc aatgtgttgg actatttatc taattttgt ttagttcggg | 60600 |
| gatacaaata aatgcataga tacatacaaa catgcgtaca taatagcagc agcagcctgt | 60660 |
| gaaacattga caagacctgg agttggaaga ggactttgcc atcctccagt ccaacagttg | 60720 |
| cctgtcacag attagacgac tgggatgtgc gcaggcgatt atttgcaaac ggccctgagt | 60780 |
| cccccagttt atgtcttaat tcgcagccag ggctgattgt agaagcaaat ttgcaaacat | 60840 |
| gtgcaagaag aaatcacaca tcctagagct tggatttcct cgtttcttgc tatttctatc | 60900 |
| cgtagacaga accattgctg agctgttaaa tttgtctcct tcccctatac cagtcttgaa | 60960 |
| aaaggaaagg aagtggagca aagaaaaaga aattaataaa gccggcagat cctaggagaa | 61020 |
| tcttatttaa tccaagcttt gtaaagtttt gctttattcc atggcaacat gggtatacac | 61080 |
| atcccaccgg ctgtttcagt ggctcagagc aggtaaggcc tgtgccaaac gccgctagca | 61140 |
| ggaggaacaa cgtggagaca gccccagagg tggaacgttg gcccttctgt ggctccggtg | 61200 |
| tctcaggacc tccctaaagc ccagccctga cactgagcaa gtttccacca ctgttaggaa | 61260 |
| gaagtagaaa ggaatttgga gggttggtgt tactgttcaa gagctggaag gcttctgccc | 61320 |
| ccattcccat tccattaatt gcgtgaggta gagaactcat agaagatagg aacacatatg | 61380 |
| ctgatttcca aaattgcctt tgtatatttt cacgtgaaga ctttaggggc aaaagaaaag | 61440 |
| aagcaagcat tttgaatatg tgtttcaatt tgccttctgt tatataaaat tgtatttgc | 61500 |
| ctattctttt ttcattattc ggaaccttca agaaataaat taagttctct caaaaatgtg | 61560 |
| ttttttgaaa agaggactaa aacagatggc ctggctgtgt taaacacagg gaccagacca | 61620 |
| gcacccacct ctccacctgc cctgccttca ctggcagaat tgtgatccat catgttctct | 61680 |
| gttcaatgtc atcatccctt tcagagcatg ggtctcttcc tttctaggca gtcttaccag | 61740 |
| gatgcatggg tgtgcctgcg taggcacacg cacagctccc aaggactcta aaaaagata | 61800 |
| ttttctgct tatatactaa taatatgtta gagatttatg tttcaaatta gtacagaatc | 61860 |
| acatggttct ctccaaatta tatttgagag agaaagaata gaacaaaatt tattttacaa | 61920 |
| aaatactcag tacatttagg gcatatacaa agatgttcca gaatgtagct tatctctttta | 61980 |
| aagacaatta acacagtttc tgggcaaggc aaggcaaaat attcagtaac ttagcaacac | 62040 |
| caacagaaga cagccaatat tgcagcacat ttttctcttg gattgggtca gagagtactg | 62100 |
| cagagaaaat ggagtagaga gacctgaaat actttcgcac acactgtggt cagtgcagcg | 62160 |
| tccactgtgt gccacagtaa tactagaaac tccctggtta ggccttggaa tccagctctc | 62220 |
| atttcgtatg tgacctgcag ggaagtaagt taaatgcaca cgtttatca agttcaaatg | 62280 |
| caaacttaat tttaaatgta tgcaacatca gtttaagcgt tgtagctatt actagcaatt | 62340 |
| gtacctatta ctagtctgta ctctgcacaa cttttggagta tactgcctac tcaaggtgga | 62400 |
| ttttagagct ctatttgtgg cattatatca cggacaaaag cacgttcatc agagtcagag | 62460 |
| gaatgtggtg caaatcccag ctgtcccact taccagctgt gggacttgag taagctcctg | 62520 |

| | |
|---|---|
| aagcagctgc acctgcattt tctggtgggc accatggagc tgtcagcagt gcttttcctca | 62580 |
| gagggctgcg ggctggatga ggtttgctgg tgcatgtgaa gtgtcaatca ttgctctcat | 62640 |
| gagtggtgat gctgatgccg ttcccttttt tagggaagtg attttcccct acaaagttac | 62700 |
| caacagtttc atgttggccc attttttctat taattgtttc cactaatagg accaacagtg | 62760 |
| gtagtcccat cattttatta ctgcttgtcg tagcacaagc agttgcttca ttgtgtttag | 62820 |
| ataaatattg acggctgctt ttaacagtct gctgttttgt ctccttttga ggtccttaaa | 62880 |
| gtaatcctta aaaagatagt gcagatggaa agatgtctgg agtcagtgaa cctgccttct | 62940 |
| ttcctgtgtg cttgtcagtt tctaaaatgc catacacaaa ggactttcat gatttctttt | 63000 |
| taggtacatg attacagttc aattcacttc actgtctgga aaatttcctt ataatcagga | 63060 |
| tgaaatttct catgttagcc tttcacattt cactactttt agataaggaa ttctcaggct | 63120 |
| ttgctatatc tgactgctct tggaggctga gcttttggct aactacctga ctactttgtc | 63180 |
| gtttctcttc ccttggaatg aagcaaatat ctaacttctc actcattgtt tctgctattt | 63240 |
| taccatttag tcatctgtga ttttttctaaa tactgaaaga cttccctcaa ttcaaactat | 63300 |
| gtgccggatc aaggaaaggg cagttggata ttgcagacag catagtgcaa ttgtgaagag | 63360 |
| tgtctgctta ccagccacgc tgccttgcac aagttatcaa gcctctcaac ccacttcctc | 63420 |
| aatctgtaaa ataggtatga gtgtaggacc ttcccagggg attttttttgt gactatagaa | 63480 |
| tgattctcag aagactttca ggcagtatgt gggtgaggca catgctggaa aggcttctgc | 63540 |
| aggtgcagtg atcaatgctt ttctcagtgt gtacatccca taatacagac acgttaccag | 63600 |
| aaactcccta gccaggactt tgattgcagc tcacattttg tatatggccc atagggaaat | 63660 |
| gaagtgtgta ttttttataa agttcaagtg ttaacttaat ttggaattta ctatcaaatc | 63720 |
| tcagttgtta tgggcatttta tagctattaa tacttcgtcc catgtgtccc atgaggaaac | 63780 |
| caaggaacag aaattaaagt tcttctggaa gtcccctgaa tctcgttcct gttcttttgc | 63840 |
| accctgttaa ttcatagag acattcacag ctcttctgac cttatcagcg ttaaggaaaa | 63900 |
| cagaaaacca gcgtgctatt tgttctgtcc cttagtcaag ccttctcaac atatattttt | 63960 |
| cttccaagat tttgcatgtg cacagggatg cctatcctct acaagaaaca cattttaggc | 64020 |
| aaattataat taaaatgctg tttacatctc ttcaccttta gaatttaaag aatgatcatt | 64080 |
| tcttagattg catctcagac acacccttcc cctagtctgg agagggcgag gcccatgggt | 64140 |
| actgcaaaca gcctgacgtt gtcaggggcg gtctcaacgg ctcattcacc acatctgcct | 64200 |
| cgcgaaggct aagccatgtg ctgttacccc tgctgcgctc tggctcattc taaggtacac | 64260 |
| gctattaacc ttgtgagaaa acaaagaggc cagccccacc cttcctgctc actctgagtc | 64320 |
| acggtgaaaa tgtttcagga tctcgggttc gaccatgagt cctgtccagg tccaggagga | 64380 |
| aattcggaag gaccacatgt tcactctgag atcccacttt catttccctc ctggttgagc | 64440 |
| agcattaata ctctggctag atttaaattc tggctttctc cagttagaac tgaaagttat | 64500 |
| gacaatgtaa tcaaaataga atgtgggttt acagctggcc ccctggcctg gtttgtgaac | 64560 |
| ataaaacaga acagaaagt gtaagtggtg acatcatatt ctctcattca atgtgaaagg | 64620 |
| ccaccgaagt ctttccagaa ttattttga gaataatatg aattttaaa aaatacctaa | 64680 |
| ttattttaaa tatcgtcttg cttgctcccc aaatacctac tgttttcaac ttggatatac | 64740 |
| gacatgatta agaatatct aatatttggg aatgcatact ttaaccttat aaactaccac | 64800 |
| tgtaaataga cagactcatt aaagtgaaag gacattttaa atcaattagt aagcaaatca | 64860 |
| attaggtggc aaagacaaga ttattttcc ttatggtagt tgaagaataa tgcttaacct | 64920 |

```
gtcattctaa ttaccaagca cggtgttctc tttggaagat catttcaaca aaacattatt   64980
ttcatccaga atttgaacct tgagattgca tggtatttta gaaatctatt ttagaaatct   65040
ttggcaaagg ttactattaa acaatcaca ttcatggaaa atcagtataa gagcaactaa    65100
aataactcac aataccagta aaatcacttt gtcatcttct taagactttt aaagagcatt   65160
tgtaagtaac tgaatagaag gccaaagggt gtgtaggtag cccagaccat cagtgggcag   65220
ccagggccag ggcaggggcc acggttgcag cctgcattct tctaaagggc agagcaaatt   65280
aaagttgaag caggagctaa aaaaaaaaaa aaaaatgttt caagaattc caccaaccag    65340 aggatactac ctaggacagt ttgggcctaa cttatctgtg aaggcctcca gcttcctcca   65400
caccggtggc cacttttcat tcactctgaa cccttctttg tatggaggtc attttattaa   65460
ttgagctgtg accaacatga cagaatttcc tgttttaggg cttttataat atagatagtt   65520
tatatctaat ttcagaatat attcactggg gaatggactt agcaaccact accacaacaa   65580
tgcaacaatg tgttttggaa caaatttacc aatctgaatt tcccctaga ttaggtcaca    65640 ggaacattgc agctgatgta cagctatgtt cctcctgaaa cttggagaca catcctcttg   65700
agctgggtta taatgggcca cccaaagctc gagttcctgt aatggataca ctcaggcagc   65760
agaacctacc accgtagtga ggacagcacc cagagccctc agaggccatc acaagtgcac   65820
cacagctgcc ttctctggca cgctcagagc tacacagtgt actctgggat tggaactctt   65880
tatttttttt tcagttgatt tgtaaataag attgcacaaa aatccatgca catcaactct   65940
ccaaatcaga atttgctgag ctaaaaagag cattaaatta tgatgggctgg ctttcaaggg   66000 gtggggtgc aatagtggaa ctctgcacaa cagttcttta caaagagaca agcaagcaca    66060
tcgcgtggaa atttccattc aactggaaat gtccaagcct gtttacctca attaattgtc   66120
cttgttcact tgtccagcct agcaattgtc cattagtaat ttgttataaa tgagacattt   66180
ggtattaaag catctctttg ggatactggt atggtttatt ataacattct gttagtagtg   66240
ttgtacaagc ttgagatgta ttaatacgaa atccaagctg catgagggct ttatttttca   66300
agcctacacc ttgctgaaat tctgaattaa aatatgattc tcagtacaaa tgaataaatc   66360
aacagaaatg gtaacgcatg tcaaatattc ttaaaaccca agaaagcctt gtaacttcct   66420
tcaatctaat gggaaatgca ggcaaataca agactgatgt ccttgagttt tattatcaag   66480
actcaagggc accagtaaaa tctagtttca ttggttggaa aaaaaatcct gataagcact   66540
gttaggcata ttaactttaa tgattacaat ttttaggaca ctctgtggcc tagacttaga   66600
aacacaacta atgtccagaa aaagattcct cttttattc catcatctga taggcctatt    66660
tttacacata cacaccaacc aaaagtagcc aagcaaacaa acaacatac tcacacccct     66720 tcgcctatta tcatctaggt gattttcaat gctcattgca atgaaaccta cttattgtgc    66780
atggcaccca cccccactga ggaatactgt agtttctttc cctttgaact tcattagtag   66840
agcacatggt tcattcactc ctgaagagtt cttcgtatgt cagaatatat atactacaac    66900
ataatttcca tcagagctct gaccacccgc ttatctattt tcataatgcc tgccactcca   66960
tcattagctg ttgtcatgta ggctatcaat aaatatatga caaataaaac agttagggaa   67020
tgagggaaat tgactagcag ccaaagacct aagccatcct ctgcttggac attagaaaac   67080
tgagttcact acagtcataa gatacacaaa ggcagaatgt aagccataca aaaatccatg   67140
tcaatcccaa tatgtgagta caactattga acaccatgta ctaatggatg agttggtaaa   67200
tcattcaatg tcttcatgag gtcaattaca gattattatt tagaccccaa agattccaaa   67260
```

```
gatggtattt cggtcagatc ttcatccttt gtaagcctag cagaaaatat ggcagtttta    67320
ttgactacta ttctttgctg ggtgtggtat ttttaaactg agacatcagt gtgcctagca    67380
cagggcctca agcacacaga aaaattcctt gataataatt aaataaaatt tcagcaaaaa    67440
atatcatctt aaggctgtga aattatcttc ctgtgtggct aaaatagtga ataaaattca    67500
gcgcaatata aatcatagta caatttcatc actaaatttt ctgatcttga tcttgtcatt    67560
ttacattgga agtaaaaatg tgtcctcctt tttttctctg acagtgaaaa gtgtgtgtgt    67620
gttgtgtgcc cttttgcaca ccctgcctca cacttgctgg tctaattcct tccagcatga    67680
ttatgatata attaaatgac agaaatgttt acttccaagt ggaactaagc cagggtaact    67740
cagggtaggg cagctgcttg caccgaaaga ccaagactgc tagagaacta ggaaacaggc    67800
ggtgcaagaa ctccaggctc tcatggaaga gcgggaggct tctatgggc tgcagaaact    67860 cttggtgct tggggaaaaa atgggttaaa tgctcttaaa aaagaaacct gggagaggta     67920
gtttccagat gcaggcccgt cttttctttt aaacagaggc agctccgaag agctggacat    67980
tgaaccctga gcaggaactg gaggccgtca gcgcagcttt gtttggcgag cggagctttg    68040
caagggtgta atgctgcacc agggagacgc tatctgcagg gaccggtgac gccgtgggtg    68100
tggaggggga ggcagtggct ggccctcttg gggtaaggta cgcccaggaa cagtttagaa    68160
taacgtgcgc gagtcaaagg gaagaagaag ctcctgcaga ccttctgggc actgtgcagg    68220
gtttgctcct gtccaccgtg ccgtgttcct gtcctgggt atttgggtgt gtggcgtgtg     68280
gggaggggag aaggagcaag gcggcaggga ggggatgagg accaccctgt ccatgggaca    68340
ggccctgggc cccgcacaca ccccaagccc cgcgtcccgc gtcctcactg tcctgggaca    68400
ccccccaccc caccccaccg ccacagccca gagcggtgcc aggaagccgc ctcgacgcag    68460
ccgtatcttg aggctccagc cccatcccca gggtaccacg ccacgtagag acactatttt    68520
tcacttcgtg tttgtcactc ctaaagcatg tgtgctagct gcaccaaccc tgggatgcct    68580
cggtgcatag ggtttatgtg cgtcctcctc cttccctctg agctggtccc ccgtggggaa    68640
ctgctgccca gactgacctg cgtccttccg cacgtgcagg aaaatgtcca cgtgcacttg    68700
tcagggtggg ggccacacgg gcaccaccac tgatcatctg tgggatcgag ttactgccca    68760
tgcagatccc acgtgcaggg cccagtcgct ttggtgagag agtggacgct gtggtgactc    68820
cacggtctgt ggctgtgctc aggaggacag agagggaca tcctgagatg gtttgggcag     68880
cccgcggatc ctgtgcatgt ccccagagcg tccactttct ccatggagca gtggagtggc    68940
gttgctgaga cagaaagttc aggttctcca ctccccatgc agcccccact cccctgtctc    69000
cggccaggca cgcgtctggg gtggagactc ccggtgcccg gggccctcca gacctctttc    69060
cccaccccag ggagcaggcg ggtacttcta ttccgtttgg cttcagaagg gaaaagagaa    69120
cgtaagttca gggagttctc gtccattcct ctcccgtggg ccgggcaggc agcagggaca    69180
gccttcagga gccaggaggg gctcgagctg cgaggccctg gaatgaggca ggcatgggct    69240
gaggctggag ggaaagcccc gctaaggctg ggcggggcg gaaaacttta ccaccagggg     69300
actcgagatg gggaaggaaa ggtcagaaga ggagaggcca ggcacggggt gtgggcggcc    69360
tgcagagctg gagcaggtgc tccgcccaga gccaggcatg cacactcaga gtaggtggcc    69420
tgtgcagcgg ggaagagggg cgggtcggcg tgctgctgaa gatgcaggag ctgcggcctg    69480
ctctgtgcgt gctgaaggtg tggtgagaag cacttacaaa aagaaatgga ctgtgttagg    69540
attgcacatt ttactttgtt tctcccaaat acgtgttctt tgaatttttt tccttccagg    69600
gccaggactg gagtgatggt tgagacaggc acgcactggg tcttgtctgc atttacattt    69660
```

```
tgagattttg ttcagcatgg attttatggc gttttttgt ttgtttgttt gttcgttttc    69720
aaaatactgc acggtttatc gtgaagacag ggtcctttgc tgccgtctta agttttgggc    69780
ccaagaacgt gccccaccct aggcccgggc ctgctggctt catagctctc atcattccca    69840
cggaacctta agacctgagg acagaaagga aggaaacaag cccagtagtc cgtgaaaatc    69900
cagggtcccg ccactccagg tgtctgcagc agagctgaac acacgtaggc tcttgccagg    69960
aggggcattt gtatgtgctg agcattcctt atattctcaa tatgacgcct ttgaaagatc    70020
tgtggtttgc aaatatttac tctcagtcca taacttatct ttccaacctc ttaccaggct    70080
cttttgctga ataaaagttt taaattttga agtctaatat atttttaatt tttttatttt    70140
atggatcata cttttgtgt caggtttgag aagtctgcac caaagtatgt cctgtggttt    70200
tcccttaggt catcttcaac aagtttcata gtatttgtt tagatgtaaa tctgtggccc    70260
attttgagtt agttttgca caagagttga ggtcaaggtt cttttttgc ctgtgatgtt    70320 cagtggctct ggcaccattt gttgaaaaca tgatagccaa tgtcaagact taatagttat    70380
aataatcagg agcttttgtt tcttttgtt ttgtttttag taactgccag tcactgcttg    70440
tggtatacat acacaatgga atactattca gtcttaaaaa aaaaaaaga aggaaatcct    70500 gtcatttgca tacctggagg acattatgtt aagtgaaata agccaggcac caaagaaaa    70560 acattgcatg atctcactcc ttcatggaat ctaaaaaatt gtattcagag aagcagagag    70620
tggaatggtg gttaccaggg gctgggaagg tgtgagcttg gggagatttg gtgaaggac    70680 atagaatctc agttagacag gaggaataag ttaaagagat ctattgcaca tcatggtaac    70740
tgtagttagt gacaatgtat tgtatacatg aaaattgcta agagagtaga ttttaagtgt    70800
tctcaccaca ccaaaaaaag gtatgtgcag taatacagtc attaattagc ttgatgtagc    70860
cattccacaa tggatacata tatcaaaaca tcatgttgta taccataaat atatactgtc    70920
tctttatgta aatttaaaaa taagataaaa taaatgttat tcacttgtcg tggatgtggt    70980
ggggacaggt gtgggatagc cctccctgta caactaggac ccagggtga tctagtgaca    71040 ctagccattt atcaggacgt atgggtgcca gtcaggatga taaagcttcc ttttggccac    71100
tatactactt agaaatgccc tgcaaaaggt gcacatcaaa gattgaaagc tcaatcctgg    71160
attttaagtg cttcaaaagt gcacttaatt gccacatttt tgtcaaacat tttcccaggt    71220 agtattttc ctcatgtaaa acaacagcaa tttaatttga acagaaagca ttttgaaaca    71280 tactttggc agggttcctt gcagatcaga atggaaatga ttaacagggc aattatcaat    71340
catggacttt tggcggcaga aggaactgta ttgtttggta cagtctgggc cagggccaca    71400
caccgtaacg gagatactct attctgtgga cggttggagg gggctgtgct gagcagggta    71460
actgcatctt ttcctagact gttcacactg ctgccacgaa ggagtcttgt ttagactgga    71520
cctggctttc ttcttcgcaa tgagtgttgc agactcccga caaaggccag gtggtaaagt    71580
gtggtgtctg tgagcgagag cctgagatgc ctgagctgac ctgtcctcag ccacctgcca    71640
tcgtgcagag gtgagagcag cccctgaatt ctgcccctcg gtctctccat agctaaagca    71700
aaaccatcct tccgtgctcc caggacaagc aggctattac caaatcaccc actaaccctg    71760
ggcgaggagg ggccatcact gcacaattca tcagtgtctg tgacaggaag agattgtttt    71820
agactggttt tttttttttt atttgcaagc ttttttctct ctccaaaacg tgctgtcagt    71880
gtgttctaat ttactctgta aggaattctg gagctaatca taggctcaca aaaagcagca    71940
caggaaagtt tcccagataa catctatttc agtggctttc aaacattttt gaccttacca    72000
```

| | | | | | |
|---|---|---|---|---|---|
| aagtaagaaa | tacattttaa | tatcatggca | cacatacagc | tgtatctaaa | ctttcataat | 72060 |
| actgccttta | cgatatcact | ctgatattgt | ctattctttt | ctgtttattt | ttcttttttgt | 72120 |
| tccttgttat | gctggttgtg | acccactcca | gtgatttcac | aatgcaggct | gggtggtgtc | 72180 |
| ccacagtttg | aaatcccaat | ctagggcctt | cctctcactg | tacaaagtag | gtaactgggg | 72240 |
| acattagtgg | atcagtgatc | aaaccaaagt | tatttgatct | taccaagtga | tatcaggatg | 72300 |
| agaaagctgt | tagagtgtca | gatatgtgaa | ggaacttggg | tcattcctga | tacctcaaag | 72360 |
| agaaaaaagg | tagtccttga | acacctccta | cttgtaaagg | atgcacaatc | ctacatgccc | 72420 |
| ctccctttcc | tttcctcccc | tctgtacccc | acccctgccc | acatttttctt | cataagcagc | 72480 |
| tttggtgttt | tggcttgttt | gtttcccttg | tctcctacct | gtgactttat | agccttttgg | 72540 |
| agactcacag | caatagttgt | atttaaactc | agtgggtggc | atccaaggct | aaaaaggaga | 72600 |
| ttgcctagac | acaaaaccac | ccaagggaga | aagcaggaca | gcatcttact | atgattgttt | 72660 |
| cttgtttctt | cctgtctcat | aaggattatt | acccagggtt | ttcattttttt | tcatttcatg | 72720 |
| gttcattttttc | gctccagtgt | agacatacaa | tagaccactc | gtccctgtgg | ctccgggcag | 72780 |
| cagcctcatc | tgagaccctc | ctgagacatc | tcgtgcaggg | cagccgtagt | gtgtggcttc | 72840 |
| cccagggctg | ctctaacaga | tcaccatcct | tgccatggct | taagaagctg | cagatttatt | 72900 |
| tgcttacagc | tctggaagcc | agaagtccaa | aatcaaggtg | tcagtagagt | ctctctctct | 72960 |
| gaaacctgct | gaggatgatg | cccctggcct | ctccccagcc | tctggtgttc | ccagcagccc | 73020 |
| ttggcattcc | ttgccttgta | gatgcaaaac | tccgatctcc | acctctatcc | tcacagtgag | 73080 |
| ttctcctgca | tgtctgtctc | tgtgccttca | cattcctctc | tgtgtgtctg | tgtttccatc | 73140 |
| tccttatgag | gacacccatc | actgaatcag | ggcccactct | ataccagtaa | gacctcatttt | 73200 |
| caactccatt | acatcttcaa | aaaccccatt | ctcaaataag | gttacttcac | aagtgctgga | 73260 |
| ggttaggact | tgaacatacc | ttattgaaca | atccaactga | tgacacatag | taatttatgc | 73320 |
| actcgttctt | ggagacgttg | actttatttta | gtagcattaa | ccatggcaat | gtcaccagca | 73380 |
| tcgctgacag | cctgaagcat | atgatctcca | gaatgtattt | caatcatcat | gttcacttcc | 73440 |
| ttggtattct | ttagacaata | actcagcctt | gaactccagt | aaagggtttc | cctgggattt | 73500 |
| tcttcttgac | tcactccact | gtggcctccc | tcatccagga | ctgtaacaga | cgcctgacgt | 73560 |
| cagtggtcta | gacctctctg | ctgaatgtca | tctttggtga | atgtcttatg | agaaaacaca | 73620 |
| tggttggtca | ctcttagaag | ggcatgaaag | cctgtctgca | gtataaccaa | aacaggcaca | 73680 |
| tggcgaggca | cactgtgcgc | atgtgtgtac | aattaatatc | atggttttaa | attattttca | 73740 |
| ggccaagggg | agatctttgc | tgcatctact | gaagaaagcg | aatcttttttc | ttcctgaaaa | 73800 |
| aaaatggcta | cttattagtc | gaatttgtgt | tttaaaaata | tgtgaactaa | tataatgcag | 73860 |
| acatgcatta | atgtttaaat | atactggaag | ttttttggtaa | aatgaaaccc | attgtctctg | 73920 |
| ttgattactt | tgatgagtca | agaagtaaca | tcctgggaat | gattggccag | tttaaatgag | 73980 |
| tgcctcaggt | ttttggaata | caagaaatca | agaggaaggg | attagaacat | ataggttagc | 74040 |
| aagattggga | tcctaaaata | cagacccaaa | tgaatggaac | aaaatcaggg | aatttattaa | 74100 |
| taacagggtc | aaggccaaat | cagtaacaaa | tatcctgagt | ggaagaaagg | tggtttaaca | 74160 |
| aatgccccta | tgaaagatag | agattggctt | accatgatga | gatgtaagcc | caagttatga | 74220 |
| ggttggcaca | caaaaccaca | aatgtcatag | cttaaaacaa | cacacacttc | ttatctctgt | 74280 |
| ttctgtgggt | cagggtctgg | gttctcaggg | actcacaaag | tatgttttca | tctgagctc | 74340 |
| caggtcctct | tccaggctca | taagggttct | tggcagaatt | cagtttcttg | aggctgtagg | 74400 |

```
actgaggtcc tggctcctag aggccaccct ctccataagc agttcttagc atggccgcct    74460
gcttctccag gcccagtggg aaagcatgtg cctccaggag ggctcagtcc attcttcatg    74520
gcttttacct ggttaagtca ggcccactca ggataacttc attttgtatt aaatcaaaac    74580
cagctgattt gggatgttaa ttacatctgc acaacttcaa ctttgccata taacctaacc    74640
atgggactga tatttatcat gcatttgggt caagttgcat taagagatat aataaagctg    74700
gacaagcttc tgttgattag aagagttcag ttacaaggct acacttggga ggaatgttta    74760
caaactggaa tggtcagagg atggggaaga cacttgagaa aagtcaagtg acggatgaag    74820
gcaaatgtgg atatttatct gggagaaaac taagaggagt tataatagct gtcttcaaat    74880
atttaaaggg cttttattag gaagaggaat ttggcatatt ggattttgcc ttcagagaag    74940
tggagtcctg agatgctctt agccattcat tccagcctcc agggctcacc tgctgtcttc    75000
tgtccaggtt ctcggtagca gggcagtaca gccccatccg tgatcttcca tagtcaggca    75060
tattgtcaca ctcagtgagc ggagagtcaa ccggaggaa ggcacagttt ctctggaatg    75120
acctacggaa tggtacgctc aaatgcaaat tctccttccc ttccccagtc cttgtccttc    75180
agatggtaat ttaggagctg aaggtcaggg caccagcagc cttggaagc ctacaggaca    75240
acagtcagcc tggctagaaa aaaaaacaat gtcacaggca tgttgtgttt aatcacatga    75300
aggatatttg cattgttttc caactgatgc cagcagacac attgtcagtg gtatcatgcc    75360
tggggtatca gagttgacat tgggttgccc cttctctgag gcattcatgt aaatccttt    75420
aagtttataa aacctccatg tggctcctgc atgcttcatc atttgcatgt gtctcttttt    75480
ccaggggagg cagcatgggg agcaggatgc tggtgggctc caggtgcaga gagcagggtg    75540
ggcgtcagac cccaggtcca ctgtgcacgc cctcttgtag agcccgttcc gttgtccatg    75600
agatgaggag tgttcttatc tctaaagtat tatcatgaaa acctaacaat gtagaaagac    75660
taaagcacat gggtggtgct tcataaatag tatttctccc actttctgaa aactcctgct    75720
gaagtaactg cacaagaatc cttgaacatt tagaattctg gttttagcca taccataaag    75780
tcagtagtgc gtggtggaat tctgctaacg aaaattgcga aggatcaagg cagagtacag    75840
agctggtgtg tagcgggtac cttctgtctg ctggcactag gtattttaca cattaaatca    75900
gctcgttctc acatcagctc ttttaaaaat aaggaaatga ggagccacag tggcccaact    75960
gatgcagtgg cagaagtaga atttgagctt gtgcagatgt gcctccgtgt tttgtctcct    76020
gagcatgctg ccccaagttt gacaatacca agatttgtac tggaacattc cctcccatcc    76080
ccaccccta gaagcccctc ttcctccctt agatttgaca catagtttga aaccactatt    76140
aactaccta tgagagccac tgtttgtgaa gtgctgacta tgtgccaggt cccgtgccgt    76200
gcaatttttg tgaattatct cgtgtctaca gtgcctcaca atttctctgc tcaataccto    76260
catgttactg ccgaggaaag ggaagctcag agagagtaag taatttgctc gagttaaaga    76320
gctggccagg acagccaggg gcttgcaccc cggagccttc atccactaca ctgtcagctg    76380
gtatctcaac cagccattac aggctgtaaa aaaattatat aagatagtct atggtaatgc    76440
agaaaagtga ggttattttg ctcccttttcc ctttgaagaa aaaagccctg gaaagacata    76500
tcacttgagt atgggaaaaa atgaagctgt ggcttttctg tgagtcaatt ctttcctggc    76560
agcttcttgg aataagacca agtatagcag cagagttttc tgttttaatt tgagctgcag    76620
ggtgactttt tttcttctat gctttcatct ctctgtggct tcttttgcct cgttaatttc    76680
atgccctgcc caggcgggct actgtgctgc ccagtcaccc gggtctgggg cggccaccgc    76740
```

```
tggccagcag gcaggccctc cagaggcaga ggtggccacg cttaggtcgc tcccgctgtg    76800
gaggcggcac acttgggtgg cagcacagct gtgatgtggc ggcagctggc agccccatgg    76860
gaaagatgtg tgaagtgtgg ggtttgacga cccatgggag aacagacttt cttcctcttc    76920
ttgttttccc ttcaaagccg tgagtcaacc tcaaattctc tgtcttttt ctccaccccc     76980 tcgtgcctct ctccctcacg ctctgcatct ctcattgcaa gcttgcattt ttttgcacac    77040
aacactatct taatatttct cttttctgca ggcaggaaat gagaagtcat ttttcagggt    77100
cattcaggaa gtcatccaga gttataatgg cccattatct actggtcaga gtttacttag    77160
gctttcacta cttccactgc ccacttgaaa cagggaaaaa tattttcccc ccgcgctgtg    77220
agtgtgctat ttagagctga ccacaagcgg ggggaagaga ggatggctcg gatgctgcat    77280
ttccactgag aacacaaggc tggcaaagct tgtctgctgc ccagcaagca cttcaggctc    77340
acaccatttt aggttcactt taagtagttt ctcaattgtt aaaaaaaaaa caaaaaaaaa    77400
aaaacctgta ctctgaggat atgcttataa tcccatagct aacccagaat tcttagaga    77460 actgatcaac atcagcagtg gcacttactg aaaatgcaca ttctcaggcc ctgcgtaggg    77520
cctactgagt tagaatatta gagagcaggt ctcagaaaca ttctatccgg cagtcttatt    77580
ctatgcaccc gaagggataa gagccatgct ttcatgaaac atgggttgtg tgtaaaatgt    77640 ttaaaggta tggcaaaatg tgtttgattg gcaccaagga tttctggttc ctcctagaat     77700
cattaatcaa actttgaagg agaaataaga gagtcggcat tttcttgcac attctttgtg    77760
atgttgtgat gagttggaaa cttcccgatt gggtttatta gagcatgaac acccaggcac    77820
ccagcttcta gccagccctg tcaggcagag tctcctcgaa gatgtggaaa ggactgacca    77880
acagctgagg cctacaggaa cctgagcagg caaggggaga ggcaccccgg aaccaggagc    77940
aatggccttc ccaccctccc tcgtcctctc ctcttctcct tttggagttg caggccacag    78000
aaaggaagtg acatgagtca ctttgggcct tcttaattcc ttcatcaaag gcagcacagg    78060
tgtgtatgtg tgttggtggc taattgaggt aggcccacag aggagataac agatggacat    78120
actatttcct ttcttccatt ctgatataat tcagggtata aacacacaca cacacacaca    78180
cacacattct cacttctttg gcatctacca cacctgcccc agtgcccatt tctctcccac    78240
ctgaataaaa agcccccaca aagcctgagg tacatggaaa ggagcagtgg tctggctccc    78300
aggagtgtga gaagcagcca tgttttcaga ggctgtattc cacttggact tggccctacg    78360
ctgaaggtag gagcggatgg gggaggcccc cttcgcacaa agagccccat gaaagagtgc    78420
acagtccagt ctataaaaca gacgcagaaa atgtgtgtag gacttcttcc tgaaaaagag    78480
cgtggtgcgt ccagtacctc catgttcatg gaacttccca gtctgcagtt tacccttttg    78540
tgcaactccc ttttggtaaa gccctggtca cacttctggt tgttcagatt atacagggat    78600
aattccagag tgattttaaa gtcaactgcc aggcatccgc acttgcaaat tagatgcctg    78660
gcacatgctt gtgttaaggt aataattcat tacaatacaa attacagggg agttcctctg    78720
ggcatgcgac ctttcccgtc atttggcttt ccctgtgatt atcaggggag cttccatcgt    78780
gctgctaatg ggaccttaac catgtgtcaa cccatggctg taatgctgac actgtttttct   78840 ttctggaata aaaggccttc gcaattgaaa ccaaaatgtt atccaactca gtcctgtccc    78900
tttgacgatg aaaacatcaa gttctggaga ctggccatcc agcctccctg cctcatctcc    78960
cacgccctcc atcattttt gtctctactt acttatttat ttggctgtat tttacgtaca     79020
tcatgcaaaa atattcctct ttgtaaaaag tataatgatt tcaggaaatt agagggtaaa    79080
aagcaagaac catgctttca ctccactgtc aagagttgtg gaagaatcct tccagcattt    79140
```

```
tttctgtgta ttttacatac atacaaatat atgtacaaat aaaggtcgat catttaggtt   79200
ttgtttatat ttttgtatat atgagcttat gtcattcata catattgttt tgcctcttgc   79260
ttttttttaa cttaattta ctttgcttga gagcttttg aactgaagta cgtgtaagtc    79320
agcctatgca tgtaatggct ccctcatctt ctgtgaggct gtcactaaaa aggggattta   79380
gcttgttctg ggctttgcag cccgtacact gggcactgtt catacgtact tctctgtgca   79440
cgcaaaggag ggcttgctag ggaggcctgg cagagggtgc cattcaaata ggattttcaa   79500
tggaggaatt tttaaatttt cagttatttg aataagtttt aatatatatc cagaacccca   79560
aatcatcaag tttgttttct tccacatctg tccttccatt tctgaactat tttaaggcca   79620
gtcatgtctc atccaagaaa tcccatcctt tcacacaaca ctatctccgt ttcatggtta   79680
tgaatctcta aaagcatgat ttttaaaaca taatcacaat gctgtcatcg aacttaaaaa   79740
ttagccataa atctcttatg ttacccaaca accagcctac tgacacatct ccagttgtct   79800
caaaaatgtg ttttccattg tggtttgtct gaaacatgat ccaaaagtca gacccacctc   79860
tcacctttcc ctaacctgcc ggagcccatg tttctttcca gccaggcttg gagaccacca   79920
cacgggattt gcttcttggg gcctccctct aaccagctat gcaggatgcc ctctttcctg   79980
tcaatacaag ctgctcaaag gactcattca gttcaaattc acctatgtga gcctaggtga   80040
tgctacttat ttatttattt atttatttat ttatttattt atttatttat tttgagatgg   80100
agtctcactc tgttgcccag gctggagttc agtggcataa tctgggctca ctgcaagctc   80160
tgcctcccgg gttcaagtga ttctcctgcc tcagcctcct cagtagctga gattacaggc   80220
acgtgccacc acgcccagct aattttata gttttagtag agacagggtt tcaccatgtt   80280
ggtcaggttg gtctcaaact cctgacctcg tgatccaccc acctcggctt cccaaagtgc   80340
ttcatgtttt caggagctgt acgtgcattt ttagttttga tgaccaggtc cttttctgt    80400 tttttaaaga acttcaaatg atctccaggg tacacagcgc ttgtgtgctg atgaaaaagc   80460
tggcagtaca aaggccacca gccaaggtca cacagccaaa aagcccctga cctcgggccc   80520
cttcccagac cctgggtctt ttgctgccac atgaatcttc ttcaaggtcc tatgtgtaga   80580
ttttcttgac ttggccatat tatttaggat tcagatataa taacaaaata gatgttaaag   80640
cataacatga aggcatttaa aagggtagaa agcacatgat ttactaaaac cataaatctt   80700
atgacctgaa agtttcacct aatctcttaa aaaataccgt actaaaccct gattgaaaat   80760
cagagctcag acatacagcc tgagatgcca aaaaatggcc aggcttgtct gttgagaaag   80820
ccatatgtaa ctaactgttt ggaaattcaa aatatatctt atcatttaa aaacatcttt   80880 cttctaaaga caatcatctt ggcttcagga atgaggctag taaaaagtga aatactccta   80940
cttgtggaag aaatcctcat tttaaccatg aagaactgaa aaatgcattc tgatgttgat   81000
ggacccaacc tatatttggg tattttatga tgtacacaat atactttgt atatgagatt    81060 gttattaaat gtgactttgc ttttcaaga catacaatgt tcctccgggg gtcaggcact   81120
gtgtttagca ctttgtcctg acctcatctg acttctcagc tgtccctgag aggtaccagt   81180
gtgcaagatc gctgagttgg caagtgatag tgacaatatt ttcaccccaa tttctaattt   81240
aaagaccccg atttctagtt ttgttttgta ttggatttgc acaatttcac gttctgaaag   81300
aggatgccct caactttgca aaatgggcct tttgaatgaa aaggatcagt catgtcagga   81360
aaagcgctac aatgatgaaa tatgataaat aagtcagtct ttcatctgta attatctact   81420
atggggtaaa aagtgatgaa aactaccatc ttgaaaggtt ctggtgatag tggttcctaa   81480
```

```
tgcagtgaaa gatgtgtaag tcaaagattt gtaaccagcc agggaatgag aggcgaagcc    81540
atagctggtg gcgggggcca catctgggtg tggggaggcc acagttgggt tgggggtggg    81600
gcctgcagtt atccacaccc ctcccacctc ccttcgacag tacaggcttc ctggttacct    81660
tccagagagt aaggccaggg agagttgaat aagttgagaa atgtcatgtc gaagctattg    81720
gtggaaagag ttccattaat tgacaataca agtccctact acattctaaa atctggtcct    81780
gactagtggc aagccgggcc caggagtagc acttaaacaa tggcaggctt gtgttgctgg    81840
caggatactt cagcctcaga ggagctgtgt gcagctgggg agactcacac tcagaggatt    81900
tcaaagcaga gggcatctcg tagagcaact tatccaaacc ctgacccact gtaaacacac    81960
acacacacac acacacacac acacacacac acacacaccc tgagagagag aaagagagag    82020
agataactaa agagagagaa ctaaagtttg gcaaaataat acatgctcta atgaaggttt    82080
attaatgatt aatctactcc tagcatttcc tagtccactc tatctcctta aaaaaaaatt    82140
ctggttgcag cccactaact tgattgtaca gctgcttaat ggatagcagg ctgtaatttt    82200
cagagaactg tttaatgcgg gctacctctg ttcttccatg ctgcttgtgg ttcctgctct    82260
gctcaggaca gaatggggag gaaaacaggc tctgcggcac aatattggca agtgaaattt    82320
tgtaaaccgg ccctcccttc cttttgcatt tggtctgaaa attcaattag atgctgagtc    82380
ctacaatgta tttgagaagc ccaggagtgc cctagaggat gagactgggt ggctccctgt    82440
caggttgaac atttgcctta attactttgg caagatttgc atcagtggta ttagtccctg    82500
cctcacttgg aggcctgcac ttaagtggcc acattcaggc tccaatttcc tggtgatttc    82560
atagtgtagg gcacttgcaa tcaaaactag gcttaaagcc caaccctctt acattttacc    82620 caccccccaca aatgcagcaa ataaaatgac tctgattttc attccctaga cctcttttct    82680
atatttatta cattattgtt aagacagttt ttgaagaaag ctgtttttatt taacaaaata    82740 gctttatgga atcaacttca tatatcttct ccgccagatc aaaacaagct cgtagtatta    82800
gatgtcaccg agcaccatga caggcagatg aacatcatcc ctgtgcccgg ctaatgatag    82860
ctcggcctgc cccggcgtca gccgctcctg gcagggccag cgggcggtgt gggaccggca    82920
ccgtatctcc agcaattcgc agataacaaa tatggttctg atgatgttac taaagatctg    82980
tccctttcaa gattggatta gacattagga atttggaggg cttttttattg ctagcatttt    83040 taagaataac caattagagt attgattcta aagtctgaaa gccacatgga cagagttcat    83100
gtaattggct actttatgtg cctcttccta gattgccctg cattttcaaa acaagagcct    83160 ttctattttta atcaaaagaa tccagaatga aatgaggctt tgaaaactca gcctatgttt    83220
gtcttgattt ccttaactga catctagaag aaaatatgag ctcaggggtc cgctgggttc    83280
cttccagcgc ctaagcctgt aagctcttcc tgctggaacc aagctttaaa tgcacttgtc    83340
agtcatgtcc catgagaata gatactgcct tccatgtttt tttgttctga tttccgtgtt    83400
tgaaatgatg aaaatcattt ttctgtgctt tttaaaaatg gaattgcttt tgtgttggga    83460
attgtgctgt tcatttttac tctacctcgt tttggaatca ctaatgtggc caatttatag    83520
ccaaaaatca gtatcgtaga gtgagcaatg aatggcatgg tgactgtgtg agcgaattca    83580
tgccctccct ccccaccgct cgcccgcgct ctcagtcctc agtgatggta aacagaatga    83640
ggaccttctc ccgaccgtga tgcgcctcag ccctacttcc cttgtccttt cctatcataa    83700
aatcttcttt catagaaatg gtcatttctg ttcatatctg tggactgtaa ataacaagga    83760
agtcattttt gaggtgaaaa ctgcacttag actcattcca attttgatgg aaactttag    83820 ctggtggatg gcattttgtt ttgtcttagt tttgcaagga gttatcttaa tttagggaga    83880
```

```
tgaaactagt ctgtgatccg aggtctcact tccatacatt tctctcgggc agtgtggctg   83940
cctgaatcat gcctggatgc cacaggtgct tagccagctg gtcctgtcgt aactgtcact   84000
ggtagctcag ggagtgcaga ggtgccagca gacactatga aattggcctc gtaaagcatc   84060
agttatgttg tgatggtggc aaagctgcag gcgagatggg aagtgcagcc actgagaact   84120
cacagtagag cgtgtgtaac gtaaaaagat gaaacccatt gtacacagct gtgtactgcc   84180
tccttgaagt caaatttccc ccattaccaa ggaaaagttt tttctgaagg gggctgcttg   84240
acaggatgac atctggtgat atcatttatt cctttggaaa tcaatctgtg gaagtgagtt   84300
tccactgact gatgaggaga aaaatgaatt ggcttcaccc agcatccagc ttcttatcct   84360
gggagagata gctcttggtc tgtcatccac gcagctgcct ggtgcaagag ccaagtttgt   84420
gcagcctgca gagcactctt cctgagctgt gggctgccag gtcgggggc aggggggcc    84480 tcactgtgca gcctcctgcc acccactgat catctgggga gactggccta tcctgtcagg   84540
agacgcagtt gcccagacgt tttcaagggc ctaagatgta ggcagttgat ccacagattt   84600
ttggagagtc cttgagttgg agattacagg tgacctcaga ggagggagtg agaacatctg   84660
ggtcatgggt ttctactagg agtccacagt gaaaacaaga agaggaattt acgacaagac   84720
agtccagcaa cttcctttct aacttctcct ttcacatatg ctggatactc caagactttg   84780
catttacatg gacatcacag atccactttg agagaagtag ggtaaaaaga aataaataca   84840
tagtgcttta ggtgtatttc tatacatctt aattgatatg ggattacatt ttcacttgtg   84900
tttactgtac agactctaga cagatcctgc tcttttgcag gtaaaacaaa tatttcttaa   84960
aacctagaaa gacccaaaac aatttaacag aaacattttg gaccattttg gaccttggca   85020
gttaggcccc agtgcagcag cggcaaccat aaacctctcc ataggtgctg aacccaggtg   85080
atccctggca ccggcagcct tatgtcaggg ctctcttatc gctggttttt atttctccta   85140
ataaaagtga ttaaaagatt catcttttaa agaaagcaag gacacagagg tggattctcc   85200
ctgacgctag cacagctcat gcccaagcca ctcctgcagg gctctggtct aagtgcaaaa   85260
gctggaaaag ctgcaggtcc cgcaagacac agagcaaccc tgcaagccag gtcaccttcc   85320
ctcttctctg ctgtccgact ggccctccac catgtgacat tcaaaagctc aagttactta   85380
acctctcaaa actcagcatc cttttctgta cagtggggaa gatactggac tgttgtgagg   85440
attaagtgag gagagtggcc caatgaggtt gacagttatt actgtcattg tcattatttg   85500
ccttctcaca ggcaggcgtg ccacagtcat tttactgaag ctgcttcagt gggtcctgaa   85560
ttaggccctg tcctttggga gagacagtcc tggttcaaca cacagctccc tgcccagggc   85620
agcttgggag tgtgggccag tttcgccttt agaaccacaa ttctctgata tgtgcaatga   85680
gagaattaat tatagactca aaggattgca tgcagacaca cacagataca aacacataca   85740
cacaacacac agagttacac acagacatgc tcacaataca cagaaataca cacagacaca   85800
cgcacacagc acacagagat acacacagac acacacacac acacacacag acatacgcac   85860
agatgggcac acacagagac acactcacag agacacacag atacacacag gcacacacac   85920
agagagacat acacacagcc cacagggata cacacagaca cacagagaca tacctacaac   85980
acacagagat acacacagtc acacacagag agacatacat acaatacaca gagatacaca   86040
cagagacaca gatacagaca cagacagaca tacacacaga cacgggcaca cacagagaca   86100
cacagacaca cacaggcaca cacgtgcaga taagtaata ttagctagtt caggaggaga    86160
aagagataaa gataaagtaa tattagctag ttcaggagga gtgaaagaag ccttgttttt   86220
```

```
ctccactttt tatagaagag aaagtgaaga ttcgatttga ggtgagttca gcacaaaagc    86280
gtatcccagg ccctctggct ccaactgcag ccctttctac ctcattccca gaccccacct    86340 aagcctttc  tcttcaaaat cttctcaggc acactgatac acatacctca gatttttaat    86400
tctccggttg tgttcaccag gtgcttggtc atgattaaga attccgtgat gtgtacccca    86460 tgtgttaaa  tttgctgctg agttaacttt gtggcggcct gtggactaga cctctgcaca    86520
tgcaatgcag aacggcaggg ccagatttga aatcctgcta tcttttcggc tgccttgtaa    86580
aaataacatc aggcgatggg gatacgatgc cagaggtcac ctgtgataag ttctgtttat    86640
ggccatttta cttctaggaa gacaggaagt gtcaggatct cagggatcta ggaagccaaa    86700 atgttttcc  actctgaaat aaagtgactg accaggagtt cccggccacg cagccctgtg    86760
ggaactgccg cacggccact tttatgaagt ggacacgtgt tggtcccact gaaaagaaac    86820
tccccaccca tggctccctc acgctgcagc agaggccctg ccacagcacc tgtcagcccc    86880
tgccagcttg caggggcgca ggcgcagagc ggtttgtgcc cttgctggag ccagggaagg    86940
gcacagggtc cctcctggag tcatgggagg tgcagccgag gttctatatt aaaatacaga    87000
ggctagcaca tgtgcttggg gaatgcagct acagtagtgg aatgaaagtg ctgtccgttc    87060
cttacccccc cagctcctca cctgtcctcc acacgcatat ccctggctcc cttttcctag    87120
taaggagact gaattgaaat tgtggcttgc ccgaggctgc atacctgtgc tctttctgaa    87180
gcccaagtca ctggctctag aattctaacc tgtgaggaag ccactgagga tgtttgtcaa    87240
aatacatatt tctgtgcctt gccccagttc cacggcccag gaatctgcag ttttcacaag    87300 caccccagg  tgattctggt ggtgtctttg cacttcttca aggcagtact gcctggaacg    87360
cagaatccca gcctcctcta tcctccttgc ctaatggcct ggatgctctc agatctacag    87420
gggaagggaa ggtcacacag tcatcgcaat agtaacctca gctgataaat cctcccccat    87480
aaaacttatt ccccagtgtt ttttaatagg aaacaataaa actgtaacca gcccaaatat    87540
ccatcaaaga gaaaatggag aagtaaatca tcgcacattc acctggacca gatctattgt    87600
aaagccaata atactgaagc cccttccaag gccctgggag tcctaacagt gcactggcag    87660
tgtctataat ttatattatg aaatttgcat aaggaaaaca ttttgtctca tttgtgcaat    87720
ttctccttct aaatatacgt gtcactttgt acctgatttc tataagaccc aggacctaca    87780
aaccctgtgt ctgcccctgc agccaccag  ggaaggactg cacagcagca agacagattg    87840
ccatggagca tgttgtgccc aactagggac agcgcagata gattctgtaa tttgcctaac    87900
aatgtctata ggatgatccc atttgtcaaa aaaaaaaag  aactgggctt tattgatgtc    87960
acctaaatgc acctaaactt ctttttttgcc ccatgctctt ctgtactctt gatctttccc    88020
caaattttta aaacatgac  actcattccc ttattttcc  tacttagaaa agtgtagatg    88080
gttttatcat aggaagttca aaaaaattaa aatataatga aaaatactca aatagtgcct    88140
cacaacagta actactgcta acataaataa aatccatatt tcctctcata cagaccccag    88200
agttgctttg cctgacagtg tagttgatgg agaaaataat ctttatcctt agcctccatc    88260
tggttgcaga ccataaagac agggaaaaaa tgagggtgtt ggtagcttcg ttagaaactg    88320
aaagctcact gattttttca aaacctaaat agcctgtgtt tctccaaata actaatttgc    88380
agccttcggc agccaggact ggcagggatg gggctagggg gactggggag aactgctctc    88440
tcctgagggt ggtctgaccc gacagcacgc atgaccttcc cacagtcagg aactgctcag    88500
agacgtgatg gcaactccat agaatgaaat actcttcagc cagtaaaatg tatttttgga    88560
taaatatttg ctttaaaaaa ctttactata tgttgttaaa tgaaaaaaaa accttaaggc    88620
```

```
atcagaaatt atgtgcagta aaatctcact tttgtaaata aatatacctg tttactacgt   88680
atgcataaaa agaatcctga gaaatataag tactgtatgc atattgttgt taagtatttt   88740
ttctgtttgc ttatctataa ttctaatttt gcttcaaaga acaagttact ccggcaatat   88800
aaaaataaaa taactaattt gtcttgtcat caaacagata gtaagaacag gcaaacctgg   88860
ccctccacac tgccagcctt ttgtgattca aggcttcagt ttcctccact tgttaaaaag   88920
attcaacaaa gtagttgaaa tagtatgtga accagtaaac cctaaaaggt gtccagtgtt   88980
gtctgtgagc taattaagtg atttgattct gactccccga gtcttctgat ttcgaagcag   89040
tggggagtca gacaggagcc tcaggtggcc tctcctgaga ggccctggaa agtgatgaga   89100
acctggcctc tggcagctct tcataaacgt ccatgttttc cctctactct ctcactcttt   89160
tcccagggcc tcaaacagaa gatgaaaatc aatttctaaa acagccctct gtgtgctctc   89220
tcgtatctct cctttcaca catcgtggtg gtggctttct ctgtgttcct ctgttgattc   89280
agtctctgga attaacggat caggattcca tgcccagaat gctacaaaga ctgtgcttga   89340
gttctcccac atctcactca attacacaga agtttcagat tatgtaacag atgctgtgct   89400
gggttaggca gagccatctg acttgttttg ctttatttta gaccatgaga tgggtgagtt   89460
tttcttttta atgccacatt cttttaagaa ttaaaaacct ccacttggct gtcagcattg   89520
gaaatcagag tgatggtgca agccctgatg aggacaatgt ccttgtctat gaaaaggtga   89580
aatcattgct tgaaatcgct aagcaggaca tgcagtccca gatggagggg ggaattcggg   89640
agctggttgg aaaagagtat ttggcacttt gcagccttga gaggtgcaga agagacaccg   89700
aggggttcac caccagagcc accattgtca gagaggcgtc cagctgtgtc cacctgggac   89760
tctgccttca gggcttcttg cctggctggg agctgcacag gcagactcct gggacggtgt   89820
gccgacagct ctgggcaccc ccttctagga tctgattcct gaggaatcac aatgtggatt   89880
tcacaatcac ttccagtgtc ttttgccaac ctctgtgaac agatgtgcaa ttaaaaaaaa   89940
aaaaagaaag gggcccaatt ctcaacactg taagtggaaa ctttttaatg gaaaggata    90000 ggctaatgaa ttgaatttga aatctgagac agaaccgatg catcaaatgt gctggtgttt   90060
acagataata caagggggc tgcatcttat ggtttcaatc cttttttaaa tttttgttct    90120
gagagaccca gccagcagac tgccgccagt cttgtcagag atgtcagtgg tggccactct   90180
gaatggaaag cagcatctct cagcatctct gaggcactgc tcctcagcgg agactgtggt   90240
ggctttgcct ttcagcacgc atcctttcta cgatgcctga cagtgcccag ggaatgggca   90300
gagctgggag ctctgaagcc cttccaccta aaccaccctg ggtcacctga cctagttttc   90360
ctcccaattt taattatgtc aggcacttca caaaggcctc cttggggaca ccatgagctc   90420
actgtcatca gattgctcca atcacagctg tggcttgcac acaaccgcca tctctgcccc   90480
agcagatgct gtgtgtaaac agttgtatta attacatctc aaaaacatgg ttcttgccag   90540
atcctcagga tttgggtgca gcctctgagg tgggtgggag gccctcgagg gagaaatgtc   90600
tgcaggaaat tcttccccta cgagaggtct gttttctaag ttatctaaga gctactgcag   90660
ctgtttactg cagagtgacc ctgctcaaag ctgtggtcac ccaaggcttt gaaagggggac  90720 ctccacttcc gccctgggtg gagcaccgtg ctggagaccc acgcctgcca aggcctcatt   90780
gtcatctcca cacgccgtcc ttggggtggg ccactcctgg gacacgcaga caggaagccg   90840
gccacctgag ccactcggag gctctatcca gagtcagctg ccaagcctca cgtcacacat   90900
cactgttagt cttggagggc tggcggggcc ctgaagtcaa ttgaacactt ggatgacagg   90960
```

-continued

```
gaacttgcca ctgccagagg caatatgctc cattttttttg acagttccaa caattttttct   91020 ttaaactgtc ataaaaaatt gctgctgtga ataccagtgt cggcgtccct gcctcacctt   91080
tacctggtgc ttttccacca cacaaaactg tttctcctcg tgctggcctt gggcttgcag   91140
acagctgatt cttctcctcc cgcggctgag cagcctcctc cgagcaaccc tctgacaact   91200
ctgctccttc tgacaacctc tgcaagggct gccagatgtg aacaaggggc cgggcagaa   91260 ggtatccagg aagactggaa actcgaggaa gcctgccctg tcctgtccac cagactttac   91320
gcttgcgtca ctgggctttg ggacctaagt cctcgtcatt tgttcctttt gcagttccta   91380
ctgttctcag cacttccttc cagcttactg aggtacactc agatgtgata tgccatcggt   91440
acagacacag ttctgctcca gcatttcccc gtgttctttc tgtcgctcta tttactgaat   91500
taccgtgagg atgtggagcg aggctgagtt ctgtattta acaccatttt aattctcacc   91560
tactgagaaa tccatcctct tatcactgtg ctttttttaa cctgtcacga atccatgaaa   91620
tcctatcagc cagcctgcat acttcctttt aaggtgcagt tgaatcagga gaaacttgcc   91680
gcacatgctg cgtccgggca cagcattggc tgaggctgct gccctgacct gtccgctttg   91740
tagtactgcc cagctatgaa acaggttagc cacacatgac ctgcatttag gagtaacaag   91800
tctgtctgta catgcacata cagcaacttt tttaaactgt ctatatttttt tcctgagata   91860 ggtatttata atatctccat cttctttccc attttgaaac ttagaacaag tttgcctgtc   91920
aacagttctc cacagcatac tgtgtattct aggattttct aaggttgagc aacggaggtt   91980
cagcaatttt gacttaattt cttcccatcc cttttccacg cagcccagaa gccttggatc   92040
acgtggtgag gggaagaggt tgtgctatgt cgggaaactc tgtatcgaag ctcggctcag   92100
atcatgacat tctcttgact aaaaccctca gtttccatca aacttgtcac tctggcatta   92160
aagcctgtca ctgtgtggct ctgaaaacct ctctgaacgt gttccctgcc tctgccctgc   92220
aggtccctgt gctccacaga agcccactta tgtgacccac ccccactcat caccaccttc   92280
cctcacccag agcctcagct ccccactccc acctgtaaga cccctactgg aaagattccc   92340
acctgcccct caagattaat ctccaaggac atttccaaat tcctctcccc atctctcagc   92400
cagatggctt tgctccctcc aggaacccca gccaccttcg acctccagca gggcactcca   92460
ctccacattc tcctggtctg tctggctcat cttacctgag ccatgctctc caggtgaagg   92520
actatgtcta actcaactct gctttaaaag cagctaacac attgctcttt gcatattgtt   92580
cactcactaa gttgaactgg acttggacat gcacactgaa ctgcagcgtc tgctgcttct   92640
tggtggccca gctcgtcaaa agaataagat ttcagcaaaa caatgtaaca atttttttta   92700
ccaaaagtaa tgttaacaat atatggtttt cccctgatgt ttgcgtcaaa atgcttttttg   92760 gaaaaaacat ttttcaactc tttagggtca gaattaagca atgaaattta tataccacat   92820
gtataatgtg tatgtttatc taagtatctg ttcatttata tatcttaaat agaaatttta   92880 aaaattttt taaactcct gataaacatt ctcaggaggc acactatgta actgttggtt   92940
gatataccta gctagatggt gaaatcagat tttgtttaaa gcatggagga gagggaaaaa   93000
ttaaatcttg cagattctgc agtccttaac atctttgaaa gaggaacatt tcagacaatg   93060
taataagaag gccacgtgct ttgacttctg tagattttaa aaatactttct gtatagttttc   93120 ttcttccttt gaagaagttt ggggagtttg ggaagatgga gaaagatata agaatagact   93180
ccccatatgg gtcatgaatt atcttttttgc atcagaactc ttagtgcagt ttcagtattt   93240
tcttcctcag gagggtgagc tgcttccgaa tgtcctcccc ttctttgagg catcctctgt   93300
tggtgaactt tgagagcatc catttatgaa gttgatgacc tttcccagtc tctgcaagcc   93360
```

```
cttcagtgtg tgtcctctct gagcaaatct gaattgtgtg cttaatacat ggaaagggat    93420
ttgggagggt tgcttttaa actgatttct taattaatat tatggtttag ttaactagac     93480
agtctcattg cagaagtgca taaccataat atgtcttcaa atatatctcc cttcctaaca    93540
ccctgtaata tacttttgta aagataccct tacagaatgt gatccaccat ttatgaacct    93600
gcagcattgc attcagagac taagtgaaaa gctggcagat tttcatttaa agcacaagct    93660
aaggaagaaa gctggtctag aaggagctac agaagggtaa tgcttaggga gggaatgatg    93720
tgcctgtggg tggtggtagt taaatctaac caaagaatga tgtcgtgggt gtttggatat    93780
tggatggtcc acattgggcc acattctttc aaacataaga gtctgtagaa atatgacctg    93840
taaaagactc ttaaatattc tggaaactgt ttcttccttg tcacatcctt atatatactt    93900
gaacctatgc ctaccagaca tgacatgtga ctattcatac agatttcatc atctctggtt    93960
taagaataaa ggatgctgca tagaaggctc acatctttta attcacaaga ctgaaactgt    94020
tctgaaatga cattgttct aaaaattcat tacttgcatt atattcattt ttatttttcc      94080
atgccagaag ggtagaagtt cctgtgctca tattaagaaa cagcaatgtc aatcgaggcc    94140
caactcaaat ccaatttata ggagttataa agggcgtgtg cctgttttgt ctagaagcag    94200
tgttgggcag cactgagtag gatagaccac ctgttgctac cgataaagga gcagcttctc    94260
gaatgctcct gtctggtagg cactatcccg agtgctttgg cccctcatcc acaatctgtg    94320
tggcaaaagg cattgcaggc aattcagtga ggagaccgag gcatggagag caagtgccat    94380
ggaattccct aaggccgtgc agggagcagg ttgccaagct gggttgaaac cgtcctccgt    94440
aggctcccaa ctccgccgtc gctgctactg tgctggatga tgcctggtag atgcagatgt    94500
ggagccccat ggattctgag acaggccggg tttcagtcct gccctagctg cctattggct    94560
ggatgacctt ggcaagttga ctttcgtgag cctcatttgt ctcatctctc aattaagaaa    94620
acctagagcc tatctgtggg ggttatctga aggattccag ggatgcatat ggcactgtct    94680
accgcatgcg gtaactgttt cacaaatgat gaggagcgat ttatgttctt agtggaaata    94740
tgtcggcgtg tgaagtccca aagctctgcc ctgcctggct tgatccagtg cctaggcact    94800
gcccctcttc ccctctctcc caacccactg taagaggcta ggctgcctca gtaactctga    94860
ggggcattga ctctttcat ccaaaaattc atgttactgc cccacatttt ttctgttgtt      94920
ttacaacgca gtaggaagtg ggcagactgt caggaaaagt gatttatagt catgtattgc    94980
ttgtgctttg gcttcatttg atccaatgca gatcagctgc actcagaaaa ctactcaagt    95040
gaaagagaaa aagtaactga agggggaaat ctggatgagt aagaattcca gggataggaa    95100
tattaatagc aagcttttg cctgatatag tcactttatg ctgcagggt gcccctttat       95160 aaagtgcttg tacaatggat gtttgctttt gattttggat ttggagtcta atgaatgttc    95220
taaattatta ttagaggagc ttgcggttgt tacatgtctg cctttattgc ttattttag     95280 ccatctcccc tgatgtcaaa tgctcaggca agaatgatac attcatttat aatgtggctc    95340
cttcagaaat ataccacata ccttttggtg tggtttgtgg ctgagaagag tggggaatgc    95400
acaagtggaa aactgcagaa agattatgcc ttcatcactt caagtatttg agatgaaact    95460
agatcatttg ctgttgctttt ttattctcat tctaagtgct tttcaaagtc agcgctaaga    95520
ttttaaaatg gttttctgtt gttggcagag agggaattac tctattactt tctgataaaa    95580 cagagtctttt catgatcaaa gagaaccagg ctctagtagt tccagtatcc taacgtggac    95640
actaattgtt tccctccttt tcttcatgaa aacagcttct gcacaaatga tagccttgtg    95700
```

```
aactagccat gggcacaact ggagaagcat ttagggagct ttagtgcaaa ttgagaccac   95760
ctacacatct gactctacag ggtttgacaa catccaggggt gaatcacaaa acatcagtct   95820
aatcagggct tatatagaaa gagtgaaaga actctgattt catcctaaag attatttata   95880
ttaaccattg ttccaaatgc attaactatt ttaatttagt tgttttgatt gttaaaaaaa   95940
acacatctgt ttggtagata agacataatt taagacaaat gttctatttg ataagctttt   96000
agaaacaact tatttttatt ctttcctgtg agataactca gatgtggaga atgtgacaaa   96060 atttaagca taacatgaga agggctgaca cacatagatt tctgtgtgct tacttgaaaa    96120
caacaaaatt taagaatttg gtataggagt tgtatcaggt agtgcagagt ccccaggaga   96180
cctagagacc caggtctggg agcctagcgg caagggctga atgtgggatg acatcagcag   96240
aaactcacag ccactgctat tccaaaaacc cagcagcagc tcagtgcagg gcagtgctga   96300
tagtacagtg cctgcaatcc tggagtggat ttggatgtgt caggtacgca cacgctcact   96360
gctcccccag cagtacgttg aacagtgtgc gtccaggtgt ctgtagggcc cctcgcccta   96420
actcacaaaa ccattctggg tcagaagcca ccaatattgt catcatcctc ccttttctga   96480
gaaccctagt aagtccctcc agtggggcaa gcccaccttt tcccttcatt ctgtggcaat   96540
atgccttcat ttcctaatca gttttgccct gctcattcaa tgcaaaatgg atctgctttc   96600
cttgggcacc aatatgtcca gggattgttt atcaatcttc agttctgttt cctttacata   96660
tccctccaaa aatcaggcct gcactgcctg tgcactccac aatccacagg cctgaaggaa   96720
atgttatctt tgatgtagag acttaaagta aaactcttca aattaattat ttcatgcaaa   96780
aggctagtcc tgactctaat tctaagacat gtctcctaaa ctctggaagt ctgatgtatc   96840
ctattatcaa catttatcct taatgtgatg gtttatcatt tatcctcaaa gctgcattgt   96900
aaaatgtaca ctgtaaagtg tacattttaa agtcggtttt aaaaaatcat atttagagat   96960
cctggtaaaa atctatcaag tcaagacatt accttattac ccatggaatt gtcttcaact   97020
cttacagttc aaatattcct gaattggctt tcacaataaa catcctaaat atgtaagtag   97080
aaacatatat attgccaact ttgtgccttc ccaagcaaaa ttaaaataca ggaaaagtca   97140 gtttgtttttg cccataaata aatatatgtg tgtgtgtatg tgtgtgtata cacatacaca   97200
ctcagaaaag atagaagcag cagcatattt tggcagcatc tggtttattg gaactcaaac   97260
gttctgattg tgcatacaga ctagttaatg tggtaacaat tatgtatttc ttccctgctc   97320
cttgccttct ttccctcccc agttttttttc ttcctgatag taggtgtgta cttttttcct   97380
atttccattg gcaagccaca tgacaagcaa aacgatcact cgaagaatat tgttccctca   97440
atcaagaaaa atgcccattg ggttttgtta tttgatgtta tttgatgaca gagacctatt   97500 gttttttccat ttttctttttt ttgttttccg tggcacctat ggaattaagc aatataaaaa   97560
atctattatt tcagatgttc acgtctaatg aatttcatgt gaaatactgg cagtataacc   97620
ccaaatagag gaaatttgtg aagagtggat gctgcagggc atgagacatc tgcacagagt   97680
tcatctcttc cagcatcttg catgtcccaa gcactgccct gccaggcaga gaatgctgca   97740
gatcacggca gtgaattcca gttgttcaga gcacatttga cttccaaatt ctcaaggcca   97800
cagatttgag gacagaacaa tatttgcatt tgaaattgga agattatttt ttgcacaagt   97860
gcctatatgc tatatagagt ttgcccactc tgcattatct tcccccctgtt ccccgttat   97920 ctggcacaag ctattcaaaa gacacgccta cttgtaaaat aaatgggtttg caaactaagg   97980 aaaatactta aatctcatgt aaatggtact atactatgta taaaaatgtg aagaaacaca   98040
gaacagctca tgaacaccctc cactgctgta taaaagaacc atctttttttc tggctcctat   98100
```

```
tggatgcctt agaaaaatct gtatttcctc tttagttatt gtgtttgaaa gatgaagttg   98160
agacaaaagt tctattcttt ttaagttggc agaacttctg aaaggtgatt tttagctgca   98220
gtgtgactca ttccaaatgc agaaatctct gaccctgagt tagtctattt gtcatgcaag   98280
agcctagaaa agccctgagt gataagaaat ggccataggc cattcccaca gaattttcaa   98340
caaaaataga atcatgctta tgttctagtc atgacttaga acttataact catgttcgga   98400
actgtccatg ttcacgcaca ggggccgtat cactccgcca gagctgccct gggtgccggt   98460
gtgcagaggg gtccgagagt gactgtctct tcctctgttg tcgaatgtgt gggttatctc   98520
cataaatggc tgccatgagc atccttgttc acacattttt aggtacttga gtgagtgtct   98580
gtggaataat tttgggaagt gaaatctgtg gtcagaggtt tgtgagtttt acatgctaca   98640
ttttcagaag ttgagaaata gcagtaggct gaaggcaagt cgccatgcct ggaattcatg   98700
aacactagtt gaaagaactg gcgtgagtta gtcatgacag gagagatggg gaagggagtt   98760
gcaggtagga gggccatctt caaattctca aagtatagtc actccaaacc aaaattcgat   98820
ttaatctgta ggactccatt ctcaaagcac agtcactcca aaccgaaatt cgatttaatc   98880
tgtaggactc caggtggcag aataagaggc aatggatggg tggaagcgaa acagggccaa   98940
agtttgactt catgtgcaac ttcctaagga gtgatttgaa ctccacaaac atgaactaag   99000
cacctcaaca caggctgggc aagttgctgt tcttttggag cttacatctt agtggggaaa   99060
gagaaatgcc tatgtaaaca tataaatcag caggatacat tgtgaggacg gtcattgctc   99120
agtgagactg caatagagtg atacgctgga gggggctgca agggagaagg tgggagggac   99180
agcatttagc agaatgagca gcacagtccc ataggaagaa gaatttattg cctccttagg   99240
caaataaatt cccaaacctt gaacatcaga aaggaaatag attaatgtgc acagaggatt   99300
aaattatgtg atctgcaaag tcatttaaaa tctatttcca cataaaacat attaatgcaa   99360
cctaaacaaa aggggtctgg ataccctcat cttcttccca agcatcaagt ctttctatag   99420
ttaaactgag atgcttttat tcttggaaaa ttttaaggac tatctacagc aatggaagaa   99480
tcgggtgttg ggatgtgttc ccaggtaata atgactgcag gctgatttgg cccttgaggt   99540
gtggcctcat ggccctctcc aaaaaaaatc aaggacctgc tacaaagcac aaagccgact   99600
gcaatgcttg ctgcttactg gttagggcag ctcctctttg ccagcgacca agcagaaagc   99660
aagacaagac aggttctgaa gcagtaattc aaagccttcc tcgctttccc atgtgagtca   99720
ttgctagtca gaatattacc tttgcagaga ggcttaattc caaatttgct cttaaaggga   99780
tatcctctcc tggtttaggt ataaactttt gactcacagg acaaattcta tcattccttt   99840
gggcctagga ttgcatttat ttccatgaca aaagggcctg tctggtgttt cagcaaatga   99900
aaacaaaaat ataagcccca tctccttttg aatgagctct aaaacagttc tccactggac   99960
ttcagaacaa gagggagctc tgggctgctg gctggttgtg catttgctgt gggttccctc  100020
cggcaggcga cctctccgcg ctgagaaggt tatccggata accaagtaag aaagtacatg  100080
aggaggcaca gaaagaaaaa tgtgagagat aacagcataa acacacagtg tatgttgtta  100140
tgaggcatca catgatgaga tactgctggg gagggaagaa gtgaggagat tcctaggaat  100200
cttatgagaa tttccagaga caacaagttt tgagcttttt tttaatttag aaatttacc   100260 ttatttttaa aagaatatgt aacatatccc atgctataaa attctagaca tagtagattt  100320
aaaacagcat aatggaaaat ataaatatct attttctttt cctatttatg tattctgtgc  100380
cagtaggaat gtagccaaaa agagagaaaa ggggtctctg cagacatgga tgtctctgtg  100440
```

```
acttgatcac tgctaaccca agaagataat aaagcagaag catgtatcca ggttgctgca   100500
gccaagcctg cccggtctgc ggggcgtcct cacacatggg gcagctctcc caccccacac   100560
actgggaaag gcggacagag gctgggcaaa gccccaatt ttcgttggca ctgaccccga    100620
tgatttatag gcctttgttt cccatgttaa atgtcttacg atcattaaat tatttatagc   100680
tcaattagca tgtgtccaaa accaggaagt tcataggaga ctgtgtgact gggaattaag   100740
gagcaaagca actttccagt ctgtgattta ctgggtttcc attctgtttc ctgttcggat   100800
ccggaagtag aatttcaaat attgcttttc atgctttatt tgggaccgat tttagccccg   100860
ctctcctttc tcttgccatt cgctggccat tagccaccag cctctgcaca atgaccagct   100920
ggcccctggc agatcttggg cccaggtgtg aagtcgctgg agaagcattt cagggccaag   100980
atgggagtga tttcattttc cattgacact atgcagaaat gaaggggatt caagtgcctt   101040
cagaaaagct tccttccagc gaatggagtt ttggggtttt tccagacttg caactgcttt   101100
tattcttgga agcatcattg ttgctttttc ccccttcca tttatatccc aggaactgat    101160
tcagaaacca tagaaattgg atttggaatc gctgaatgct agcagacagc tgactgcact   101220
cttcccaaga aaccctgcca gctgggttcg ggtatcgcgc ggtgtgtgct ctctctgcct   101280
ggcccgctga gtcctctaac tctaatggat tccttcttac accaaagtgc actagaacta   101340
aagtgttttg cttcattctt tagacatttt gtggtttagg gctcaatcag ccagggtatg   101400
atttgcaatc cacagtaacc ggtttcagag cagctgccca gcgaggcagg tttcatctcg   101460
cttgctagac gttttgtttt ttttttttc taaacctcac accttttatt tattagactt    101520
ggattccagt ttcctgagcc tgtttgtgcc actgattaga caggcttgaa gcagaaccca   101580
ccaggcttcc tgaataaaat gcagcagtga ttgtattagg gggttttaaa ttgctcaaaa   101640
tactgtctaa aaaacactaa aaatcatgtt actttctaga ttgaataaaa tcctatagaa   101700
atgaattcct ggacttgata tgtagcaagc tggcattggc tcgggagtga gtgggctcag   101760
ttaagtgagc taagatgaga tggtgcacag gcgagcaccc acctgaggag tgtttggatg   101820
ttatgatagc cagctcctct gtaaagacct gtccttctat gtcagcagcc cagcagataa   101880
atgacgtgta ataccacat ttaggagggc ttatgatgat gccaattaat ggagaccttt    101940
ttgaaacagg aaggaggtga aacatattcc tttgcttcta catcactgtg tgccaggcac   102000
tgtttacagc atctcgttta accagcagtc accacctgac ggatggctga tgtggggtgg   102060
ggtcccaggg tgggattgcg tgatgggctt ggggtctctg gctgatgggt gccagagctg   102120
ggactggaac tcctggcgtg actgaggcag acacctgggc tacccagcct cacccacgac   102180
gccctcacta agtgacccac aggactcacc ggaagcaggg cagcaaggtc ccctacaga    102240
ggtccccact gcaaaccgat acccagctta gacagcagtt ctgcagtcgg cgtctcaccc   102300
cttcgggtct cattgtgact cactttgata gccacacgat ttaagggtgg ttcagtagtg   102360
atttgatgag tgctgtggct cagggtcatt cccctgccca agcatttcaa attccagaag   102420
ttcatgccct gcatggtggg tgaaaagtct caggccaacc atgagcacac agcagccagg   102480
cgactgaggc agctgcccgg ggtggcacgt tgctcaaacc catcatttgg agtcaaaaca   102540
aacagatgat tagctggggt ggtcactttc aatcaagagt tttcacatcg cctagacatg   102600
gcctcagaat caggcctggt gtggccaggg gctgatctca cagtagacag gaagtgtggc   102660
ccgagggcca tggctgcccc ctcagaaggc cctgtggagt ggctggccga gcctcagcag   102720
cctcctgtga agcgaggaag ggtcttcctg ccggcctctg gagatcagta tgggaatgca   102780
caagtaggaa acgctggatg ggaatccctc tgccctgtga taccaaggca gtgagtttgt   102840
```

```
agactatgga attgctgtcg gagggctctg taaccggcca aggtcacaca ggtagccatt   102900
ggtagagcag ggactggaat cccagacccc caacttccag gactgtgcac ctttctttat   102960
cccatacagc cttacagtca agtgccagtg caacacctga ttcccaggtt ccagcctttg   103020
tcttttataa tgggaatcaa ccttatcttg acgatccaga gatagtcatc aaggaagatt   103080
aaattatccc cttagactca gagtgaccat atcattttcc ctccacacaa ggacactttt   103140
gagaatgaaa aggaggagat gtctgtacca gacgctggat gacaggcacc gacaggctgt   103200
ctgccagggg agcagcgatt cctgtatgtt gtagaaagtt tttcaaaagt caccttggaa   103260
agaggttttg ttccttaacc ttctgttaaa taggaagctc cgtgaatgaa aacaactccc   103320
ttccctaaac attctagtaa tgacccaaca ctgccaagcc tgccagctct gcctcatggt   103380
cgtgttgact gtgtgagact atgtgagtgc ctgctacaca gtacgctttc agtaaacatg   103440
gtattgcctc gataatccca caaaaatgtc ctattcaaat cacctggcac ccaggaaatt   103500
tccttctttt ttttcccagg tgaaatatac agttgaaaac acctgacagc aattcccctc   103560
tcccatgtgt ttgcaggatg gtggttttgg ttcctccatc tttgatgtgt acaagtgtga   103620
tgttttcccc ccacagacaa gtaaaccaca ttctcttcac attcccaatg ttttgtcaat   103680
gtacctcctt caatagagga tcgataagga aaaaaatcat tgacaatctc aattagattc   103740
actatttcat ccaaaagcat agcttagaac tctagttttt gttcaacact cttgccctat   103800
gagtgcacag aactttaatt ctgatacaaa catccctgaa tgtttagctt tgacagagat   103860
tccaaggtga tttgataaga agcagggctg tgtttgggct ctgggagttt ttgatatggt   103920
ttcaagcccc atccaaaacc cacagacctc tagaaagtag gtgcctgcct tcctgcagca   103980
gccctggagc ctgctggggg ctttgagcag ctgctgccaa gccaggcctc acccgacact   104040
ctgatgggca cggccatggt ggcaggggct tggacgctgc caggtgactc taacttgtgg   104100
ccagggtggg aagcactgct ccacagaggt gccaaaacca ggttccttcc tgtgttctca   104160
catttcacag cctcaatgta aaagtaaga catgggcact ctggaatatt acaaaaatat   104220
agaaaagcat gttatagtaa ataaaaggct cacagaattt tgtcatttag gaacaatgat   104280
tattaatata ttagtgtgtg ttttgctca ttaacagtat atcctgagat atttcctata   104340
ccatttaata ttttaaaaga tgtttacact ggccacagta gctcatacct ataatcccaa   104400
cactttagag ggcaaggcag gaggatcact tgaggcttaa aaattagcca ggtgtagtgg   104460
cacatgcctg tagtcccagc tactcaggaa gctgaggctg gaggatcact tgagcccagg   104520
agttcaaggc tgcagtgagc tataattgca ccattgcact ccagcctagg tgacacagtg   104580
agaccctgtt tctaaaataa ataataaata aattaaaaca tttaaaaata catgatgttt   104640
aattattaga ggactcaatt ttatatctat gtatacaata attttaagt ttcttaatat    104700 tggacttta gtacctttt aaaaatacta tttttaaaaa atctgtatt tctaacttt       104760 tataacaaga aacctttggc tttgagatga ctggggaatc cattctttcc tatagtatcc   104820
atgtccaatg gacttaaagt attaatcaat gtgtttatgt tttgttattt ttctggcatt   104880
acaaaaaatt ctaaatatat tgttaccgcc tgtataaata tcagcttttg agagaaggac   104940
attgtgtaga aataatgaaa cactgcaact tgtatttgta ttattctttt tttttttttt   105000 tttttttgaga tggagtctcg ccctgtcacc caggctggag tgcaatggtg cgatctctgc   105060
tcactgcaag ctccgcctcc caggttcaca ccattctcct gcctcagcct cctgagtagc   105120
tgggactaca ggtgcccgcc accgcgccgg gctaatttt tgtattttta gtagagacgg    105180
```

```
ggtttcacca tggtctcgat ctcctgacct catgatctgc ccgcctcagc ctcccaatgc   105240
actgggatta caggcattat attattcttt aaattcacat gagaatttag tatggcttca   105300
aaaaatacca taagttaaaa tatcaccaag actctgttca gacaaaagta tcagaaaagt   105360
gagccaggca ctcacatagt ttatagttta taaaagtgag acaggcatga tctcttaacc   105420
tcactatagt cctgtgaata aggtttattt acatttcatt ttacctgcca ggattattgt   105480
aaaaacgcca agcacattgc ctacacaaac taaatattca gtcaatggct gctattttca   105540
tgagttcgtt ttaacatata tttattgtcc tctactggat ttaagaagtt atatttatta   105600
tcatctaaga ttttagctat tccttctctt aaaaatagat tttataatca atggcagtaa   105660
gggagagtaa ctcgcagttc tctgaatctc aaggggttcc tggaagcctt cctgaaggta   105720
tagtgaaatt tcagcttcac attcccatcc atgagctccc tgcaaatatc ccggtctgct   105780
ctcaggaccc agtgacttac ctatgcagag gctgtagata gcacctggag cttcctgtgt   105840
gccctcctca aactcagcca atgccgtcat acagtagcag gcaggtgtct ttgctgggta   105900
gttggactgg atgtccctgg gattgcagaa ctggaatggg gagtgacatc aggaaactat   105960
aatcatcagg acaacatggt ttgccataac tttaagtttt aagcgaccgc agattatgcg   106020
gagagagatg catgcccaca gccatgcttc ccatgtaact ggagaggggt ctgaagtttg   106080
aaacaagtgt tcctaggcac gggttacagt gtttgttatc atcatacttg atttagaatg   106140
gggcacaaca tgtggattca tggtaactgt tacaacctta ctcattttaa tacctgaaaa   106200
catgctttcc ccatgctggg aatcgaaaga ttctcctagg aaaagaaagg cttgacaaca   106260
tcgattcaaa aagggcatgc attttcctca tttaaataac tctaatgtgc aagtagatcc   106320
cctgacctca agctcagaag agtccaggcc ttcacacctt ctctgcttct gctctggggc   106380
cagctattga gattcctgtg cccacgcaat gcgcacatcc cacccctggc cgctgtccac   106440
aagaaatcca gttgcaccaa gcaccccact ttttgcacct ctcatttatg tactcctaag   106500
agcctcacca caactcccct ctaaaaacat gagttcctga ctgggaattc gatgctgccc   106560
aggcagcttt gctcagaggg agcagccttc tagaaatgtt tcaagtaaac tttcaagtat   106620
aactaaattc aaaaaaaaca catacacaca cacacacaca caagtcaa aggtgtgtaa   106680 tttggccaat atcacaaacc aattagccct ttgtaagtgg cacccagatc aggacagctg   106740
accataccag caccctagaa gcaccccgtg ctgcctcctg ggacagggct accaccatcc   106800
taaggccagc acgatgggcc agctttgcct gctgttgaat tttgcttaca tagaatcctc   106860
cagtaggtac tccttgggt caggttcttt cactcaacat tatgtgttga tatttttcca   106920
tgctgtgctg caaaattgta tttcttgcat tccataactg ggcagttcca tcataggaga   106980
ataccacact gcgttcgtcc attctaccgc caatggacat atgggttctt tctctttctct   107040 tgcagttaca agtttatgaa tattgtccca cgtgtccctg gtgaacttttt gtttgcattt   107100 ctgttgggta cctcagagtg gcgttgctgg gtcagagggt actggtcgct ttagtagctt   107160
tgaaagatat tgccaaaaca ttttccagcg cagttatagc aaaattataca ccaccagcag   107220 tagaaaacat ctcctaattg ctcacagtaa accccccaaag attgccacat acatcttcca   107280
tatcaattac ttaactattc agcaaatttg aagggaaata tatttaatct ttttattcaa   107340
atagtttata aagtggaata gagatgtggg taaaagttgt cttgccaccct tttagatcg    107400 gtaaaagttt gttgaatgca ggcaagaaaa gatgagaaat aatggtaccc aatgaaagac   107460
atagcagtct acaaggaggg gcatttcccg gggtgggggg gacccacact ctgtaactcc   107520
cacattcaat tagcatgtta taggtaagct gcagaaaacg aggcagcttg tcaaagagga   107580
```

```
acggctcttg gccatggttg ctgccctagg aggatatttg atactagcag agctggggca   107640
accctggagg aaaccacctg gaatgatggg agaactcctc cagggaacat ggcccttta    107700 tagatctctg ttataaaaaa taatcccaaa gcagccacca gggcatactg ctgcgatcaa   107760
gtcctaggcg gtattccctt ctgcgccata gaccctgtgc agagtgccct caacgaagga   107820
gcaaggaaga ccaagtctcc cgagggtttg catatgtgta tgtgattctg cagtcatggt   107880
gaatgacaca gtcagggctg cggaaaagca ttggtaaagt gtatatttga ggcttcagaa   107940
gtttgaaaag gctagatttc ctaggccaaa acactgaaaa tttgcaatta gaacttcagt   108000
gctgatgctg ggaagactgg agttagtttg agacatgcac ctgtgcagaa ctgggccccc   108060
agaaaaggag aaggaaggga atccagacca gagtagggcc tgacaccact cagactcggc   108120
gtgtctataa attagaattg cgttacaatt acactttgac attttagtgg tttttaaagt   108180
gcccagcaca agttaatttt tcattaatga atcctttatt cataaaatgc ttagatggag   108240
attacccttt tgagcatttt gccagtgctt ctgaaattaa tggggacctc ctgttggagg   108300
acacagtctg ttgcaatagg tgaccactgc tctgaatcta tgtcacctct ccaggaccac   108360
gggcacaacc atcacctgag gcatgttgga gatgcagatg gtcaggccct cctagaatct   108420
cagaatctgc attttagcaa agtcctgggt aattcctatg tccattggag tttgagaagc   108480
actggtaatc tcaaatactt taaaagatta ctagagtaag ataggctcag taggtacctg   108540
aaggcaccat cccaaagacc agagtggtag aagcaggtgg accagcctct gaacacattt   108600
ctcccccact ccccggctgt gtggaaggtt gccacctttg gggtagtcat tcaacaaaca   108660
cgtgtcaact gtccactatg tgtcaggcca ccactgggca ctggctgtgg ctagctggat   108720
agacaccatt tctgccctcc agaaatgtca tgtccactgg cacatgacaa gtcactaagt   108780
cattcagagc catgggtgac agctccaggg gccgacaaag gagctgtgat ctcacagatc   108840
cacagagaag tgtcccaggg cgggcgggaa ccaggactgc acaggagggg gtgaagtgac   108900
acataagaag tcagcccatc agcctgaaat gctcccccaa atcttcccat tcagtgtttt   108960
ctcagtagca aactcgtggg aaaattggtt attttactta aaaaactcat actagaaagc   109020
tagtttaact ttaaaaataa attttaaaaa catttttatt aacaaatcct acctttcctc   109080
caaagtcaag gagaaaagaa tagaagtgaa caatggacca agtaagccta aaactctgct   109140 cttcccctg ctcattttac agttcaagtg ccattcaatt tatcctggca agaagaggaa   109200
ggcatcatca agaccttaat tttctaatac atctgatctg agaagaatgt gaaagctata   109260
aaattaattt ttgatcaata actacaggcc ttttgagaga gtgccctcct aatgaattga   109320
gtacctattt ctccatacac agtgtctatc atgacctaca aacccttttc ccatgaggtg   109380
taacagagag agattacagc cttggaactg gatgtcagac tctcctggtt taagacaata   109440
agccatgaca tagagcctga aaccaacaca atcttccgag tggttccaga aacatatagg   109500
ggataatgtt ggctctgatg ctgtacatcc ccaacaacca tcaactattt ggaaactaga   109560
atttcagcat aattggagtt ggtgttaccc tagcaaatgc tgtgggaaga gagtctcact   109620
gtgtatcttc tcctgtttaa agcctgaatt tgttcagaat gtaatatctc tgtttagcca   109680
ctctactgaa actgatctag gaaatgttca aaaaaaggta tcccaaggat ccctttgtag   109740
ctacatctgt gggattcccc tcgctctggc gtggcctggc ccctctgcat ttgacaatac   109800
ggtcctatgc ttttgtcttc ctgggctgcg tgaacccacc ctgccctggt tcacctctcc   109860
tcttgaccca tccttatcag tgtcttgaaa ggtccttcta ttggaggaca cattctgttg   109920
```

```
cagcaggtga ccactgcccc aaatctgttt cacctcccca gggccatggg cacaaccatc 109980
cctggagtgt gttagagatg cagttggcca ggtcctccaa aatctcagaa tctgcattt  110040 tgcaaagtcc tgggtaactc ctatgtccat gagagtttga gaagtactgg tctcatgagt 110100
tcctgacata caaatagtgc tgaggccagt atgctgactg ggtagccaga tacaagtgaa 110160
aaccttcctg tttttgcaa  acctggatgg acccgaggcc gctgacgtgg gccaggacaa 110220
gctactcttt ttcagtgttt ctgttgcatc gctgtgtctc tctgtgatca ggtgctgccc 110280
tccctggcag gaggactgca gacaggatga ccaagagcac tctacacagc ctgctctcca 110340
gtgttggggg acgccaccca ccctcgtggt tcctgttcat ctgcctacac gtggagggcc 110400
caagagggct aatatgtgac tatctccact tcctggtacc ctgtgtgaat aacttcactt 110460
actaaaggga tgttgagcaa ctttattaat aatgaagaaa gcactttggt ttgacaaata 110520
atcactccat ttttcattt  gaaagttaac tcttgttagt agagaaagca atgtattaca 110580
accacaagga cgtttacatg gaaatgaacc atctgcaaag catcccccat tttccttta  110640 aatcagccaa tgggtggtgg tgggagaaat attcaccaga gtatttaaca tctatccccc 110700
ttcctagact gtcagctcca tccgggcgga gactgttggt atctccacag cacacacagg 110760
gcctggcaca catccggggc tcagtgagca cttgctgaat ggtgaacaga ttagctctcc 110820
tgggaacgtt gttgacacat ctcataacac tggtttggag tggagggcat tcatcgggct 110880
gcatattcct attttaatt  gtattctcca ctggttacag cacctacagt tataaagaca 110940
ttgttaacat tgcttatagg aagacatttg atggaaatga gtccaaaggc attacggtta 111000
gaaactggcc aggtgtcatt tttgagagat tagataactg ttttccggta gagtgaattg 111060
cctgtttgtt gcaagttggg actttgctgg gctggtttac agggccaagg ggaaagagat 111120
aagtggatct tctagtgaga ggtcatctgt tttgaaagcc tggaagattc catgaactaa 111180
atccaagtct tacaacacag ggaagtgtgt catactgtgc agggatgaag tctccaattt 111240
agcatgaaaa caagagctcc tcacactgtc ctcttcagaa agcccataca atccaaactt 111300
ctgaatgctt agctgcttac aaccatacat agattgaggg ataaaactct gatatggaag 111360
agaaggtaaa catttttgg  cagacattcc caggaaaagg cggctctctt ctctcattgc 111420
tgctgctctt tcagaatcca tttcaacaga ggaggagtca atgggagccc cgtgcctctg 111480
gcagatatca tatggcgttt cagtggcatt gtgtgttacc cttcttaggt aacagctcag 111540
ccattagaag aatgtcctac acaccttctc attttctgtg atgagaggaa tgtgaggtac 111600
tgcccttcga gagctgtcat ttgtcctagt agccagcagc gtgactgtgc tgtcttctgc 111660
tctgtctccc tgtcagcctt ctgcccagcc accaccacta tagttttgtt ctctccattg 111720
gaactcctgg ttcagagaat taccataaaa aacagacccc tagacataca acactctatc 111780
acataatggt gactttgtct tctatttgg  attactgagc tttcttgggt aacttccact 111840
aaatcgaagt taatattaga agaacttcct cttactagaa tcgaaaagca tttaagtgat 111900
gcagtcaagt ttgtaccata agtaattcag tcatttaaca aatatatatg gcctctgtgc 111960
gacagtgacc ttgactggga atgaagctgt cccatgtggg gcctgttctt caaaggcagt 112020
tccctgctgc ccagttcagt ccagtggatc tgggcatctc tctttaatcc gcattagggg 112080
ctctttactg attcttcact atccaaaaag acttggaggg gagacctgag cccacttctg 112140
gaaggaaatg ataacaattt atttagataa tctttgtgca acaagtcaat tcactgaaga 112200
gatctgctct ctaggagcct ctgtgacccc accataactg gaaggctct  acctctccag 112260 tcttcgggcc acatttctct ctggcctgct gtcttcccag cactctcagc cttgctcatg 112320
```

-continued

```
gagcactcta gtcctccgtc gaccttggcc tttggtaacg tgattttttca cctggcagct  112380
cccatctggt ctcactccct cttttttgtcc agtctgcatg acacagcctc acatcgttag  112440
tgttccctca ctccctctt actgcccaac ctgcaaagtc catgcctggg ccagtgcagc   112500
atgtgtcctc aatgggctgc tggtggcagt gggggggaacc gcacagccac gctgtgtgct  112560
gctgaagaaa tgcacagcct cctaccctcg ccctcaagag gcagccatgg ctgcgcattt  112620
ctgcccttct gagctccgct cactttttggc agcagccgtt ccaacctgca tgggatcttc  112680
actctctcac agatgtgctg actcctcctg ctgcctcccc tctctgtgcc ttctcactct   112740
ctgttcccttt tgccctttct cccctttttct cctctgccta cctccaagcc atccatcaca  112800
ggacagctca agcatcagat cctctgggac actttcctta gttgttcagt ctgatgaggt   112860
gtccctcatc ctctcttagc tgaaaatcag cagctgcctc aacttctttt ccagcatgtc  112920
tcatgagtat tgccacaaca gcatctgtca caatgtgggg tagtggctga cttgcttttc  112980
tgccattcaa ctgagttccc tcagtgctgg ggccagcgtg cagtgtcttg tattcagtat  113040
atagctgatt aattgatgaa ttgattaatt aatggttcac actagcacag tgcaaccttc  113100
aatgcaaaga tctcatcaaa ataattcaca tggtgggata ttttagaagg atgaccaggc   113160
tagtttgtag taagaaaaaa tcaacaagac taggtcagga attctttttt tgtctacagg   113220
cttgctatag aagatattga aaatcatcta cctaattacc tttatttttat caggttgtgt   113280
attaaatatc acgtctgggg gaagaaaatg tgatatgtga ttacagacct ttcctggtac   113340
aacatagtac gtttcagatt aactcaaggt attgtggtga tattgcggtc aaagccaggt  113400
gattaaagag tcattctttg aaacaaatat ctgtgcaatc aattaagaaa ttaatttgca  113460
aattttattt gcttagagta attgatatat cattcctttt acaaacaaat ataagaaaa   113520
cttaactaaa aatactgcat atctctttca gattatatat cccagaaagg atatattttt  113580
ctcctttctg gtcttccttt ttggtgtagc atctgtagga aatgcatttc ttcatagcta  113640
agtgtacctc cttgtgaaat atcttcagag tctactggtg cacataagca attgctggca  113700
gcagcttgag ggtctccatc tcacatttat catatgcctt attgcatgag gctttgcaag  113760
aggaggtcta gagctacaat atctcatgga tatgaatgtc aattcaaatc ccagtggcag  113820
tttatgaggg ggaaagccta gaagagaaga aacctagagg aatcaagcag gagggagag  113880
taataaaaga ctagagcagc aggttttttct taactcaaac tagaattaaa tctctgtgtg  113940
tgtgtgcatg tgaatgtgcc cgtatgtgca tgcatgcacg tgtgtaaatg gatgtgtgtg  114000
tgtgtgcatg tgtgtgcaag taagtgtgta tacgtgtgtg ggcatgtatt gtgtacatgt  114060
atgtgtgttt tatgcatctg tttgcaagta tgtgtgtatg cacataaaag tgtgaatgta  114120
catgtgtgct tggtgtatgt gtgtgtatta atgtatgcgt gtagttctag agtctagtta  114180
gagaaagtgc ataagaaat agggaaatta acaagaaagc tatagcttaa attataggaa  114240
aaactttttct ccctatcagt catggtttta aaatgttcag acttgatatg tttcccagtg  114300
ctattgtcag aaaatgtccc tatgacattc catactactt caatcaaatc taaaaccttt  114360
gttccaacat gttttattga tatgagtata tttcaaattt ctaccaggtt tttggagagg  114420
tattttggcc ataaaattga ctaaattatt caaaataaa aatgaataag cctgggccaa   114480
ggcttggaga cttgcttaac tcagttctta aattttcaga ttttcaaaat tacaaattta  114540
agctctaaaa tcatggtgct gtgtatgata ttctttgatt gcaacttatg gttgaaaaac  114600
tatagagggc tttatgctaa gagttgtgga tcttaggatt ttcatgaaat ctgcattatc  114660
```

```
atcatctgca agtttagatg gggcataact gatccaaagg atggatccct cgggggcaat    114720
tcaactggct gattccagcc aagatgacaa cagtcaggat ccgttccctt ctgatcatcc    114780
attgggtgcc ctgatttcct ctacagccct agctgaaaga ccagacacta tctcaggctg    114840
gctgccccac atgccttgct ccacaccaaa ttcacagtct ataaacctga gcctccagtg    114900
ctcctactac catactcact cgaacattcc cgattctgac ctggagatgt caacagctac    114960
ttgatgccac tctcttctat ctttctgtag ctaagccatc cccaagtttg tcgattcacc    115020
ctctttaacc cctgtcgggg tgtccattgt gccccttcac cctgccatct ccctggtgca    115080
ctgttttgca aagttcagca tacatgagcg tcacctggga accttaataa agtgcagatg    115140
ttgattcagc aaatctggga tgccctcggg ctgcatttcc agcaggctcc tggggatgtc    115200
cccgctgctg tgctgcagat gacactctca gtggtgggac tccaggctct gctgtcgcct    115260
cctaggggtt tctccacact ccctggaggc ctaatgggcc cttctccaca tggcagtaag    115320
atctgttttt gtgtttgtgt ttcaagttgg gagaaggaga ttatttaata ctaaaatgtg    115380
caacatggga ttgagaaaac taattattag tcataagttg agtatgcaac attgaaacca    115440
catgctttaa aaaattataa gaaaaaatca tagtatttga agttacaag ctattatggc    115500 taactccatt tatctcagtt agagaagaag agtcacctgt caccagggca ctgccagaag    115560
ccaggctcat ttccaacagc actgggtgct ccagctttgg ggtgccagct cctcccataa    115620
agcaaacaca tacctaggga tgatatttct ttgcaagggc tctgccctac agcttgtaca    115680
tctcaagaag ttatgtaatt aaactgtctg ttttgagaaa attgtagatt cacacatact    115740
agctgtaaga aatgatgcgg ataaatccag cgtaccagct ttccccacgg agacgtcttg    115800
cagcgtcaca gccaggatga ggcattgacc caggcgaagt ccagagcacc tgtgcgctac    115860 agggccccttt gcactgtgct gtcacagaca cgcccacttc cagatgccat ctaggacccc    115920
ctccaaaaag cagaggcatt cttaaaaaca cacatctgca catgttcctc ttcatttgaa    115980
tctgtcagtg gcttctcagt gcctttcaaa tgaaatctaa agtccttaca agccttgcag    116040
caggaacctc tccatcccac ttcccctcac actctcagct tcatctctgc taggctctgt    116100
tcagccaggc agccttttcac agtccctctc ctcctgccct gccaggaagg tcccctgccc    116160
ccaactcttc cccacatgtg gcggggcccc gcttgtcctt agaagcccag ctgaactgct    116220
tcctgaagga acccctccag aacctctcag accaggtcag gtttctgcac tcttagatca    116280
tccccatggc ataatcacag ttgtgatgtt gtgatgattc agtgaatgtc tgtctcccca    116340
ctggatggta agcttcctga gggcaggaac agcattggtt ccagtcaatg ctatgtccca    116400
ggactgttcg ttttttgcaca tactaatcct aaaaggacga tgacaacagc aaccacttac    116460
atgacctaga tgctcttctg ggtgttgtgc aaatattaac aatttaatcc ttgcaacaat    116520
ccacgaggga ggcattcttc tactcccact taacagacaa ggacagtgaa gctagtaaag    116580
agaagtcatt tgcccaaggg gaccccacta ctgttggcag agctgggtgc aaacgcaggc    116640
ttgtgaagcc aggacccatg cattcaaaga ccatgccagg tgcccccact gcacacctca    116700
tccccacata ccagtgaggg ggagagaaat gctcctgcac tgcctctgat taactgcttt    116760
cctagaagtc acacatataa aagggattta attctagtgg gattgaatct caatagtttc    116820
cttattaggt tgatttctgt taatagttta agtactggat atacatgaat tagaaaatct    116880
agattattag caaatgcaaa ctataaagta ttttataaat gttatcttgt ttgtcagggg    116940
atgagtgaga tattccattat acaaaaagta gtgtggattt tgaggtagaa ggtttactaa    117000
ggatcatacc gtagtatgaa atagccacaa acattcagtg aaaccaaaca ccccgctta    117060
```

```
acctcaaact aacactaaat aataaggaat agacttgggg gcagtgcaag tgtatttcta    117120
atggtgaaaa ccattcccca gtgaaaacta atgtaccatc tagttaataa gagctcctct    117180
gacccacgca catcaatact tacatcccaa tggtgatgtg acattttggg ttttgtattt    117240
cttttgcaaa ttgagctagc attttttgatg agtggcaggg ctctgctacc caaccttttgg   117300 acagtttcca agcataaaat cacaattcca gataattctg tcacaaagat ctgggtctca    117360
ttaggaagga gaggaagctg ggagatgatc cagtccaacc tcccccaaac caaacatcac    117420
ggccttctca gttgtttcac caaccatcta aatgttttag taattctaaa aattgatgcg    117480 cttttttccac gaaaggaagt gttaccacat tttccaagtg ggaggcatct atatccttac    117540
tccttcatcc tctccttccc accccctcac ccccaccac ccacacaaca tctgcaattc    117600
ttaaactaaa gcacaaattg ttacaaaagt taattgcact ttcaaaggaa tgcttgtata    117660
gaaactttct cggcttcaag gaaaaataat acgctttgaa tggctgttca acagcataga    117720
aattagctga gtagaaggca ctcatatagc cattaggacc aatcctttct gccgccaaca    117780 cccccttat aaagacttga cagtgggcca gaataaacaa cttcaggatg aattcagttg     117840
agacacaaag tacacacttc cagttttttcc cttctctggt tactggcctc aataaccagg    117900
cagtcaactt aaaaagaaaa acaaaagctt gcttcagatt acagattgca gacttcttat    117960
aatatgtcca tttcaccagg ccccgctctc agccccggga aaggccactg gaaaccacct    118020
cacatggtag ggccttgcgg gagccagtaa taaccttatc tccgtcaaca tgttctgtca    118080
gattgaatgg ggcagccaga gaagccagag ttggcacagg aaccaaaaca aaggcttccc    118140
atcctcctgg agtgagcggt tgagcctgga ttggtgctta gacctataat gggtgcaagc    118200
agcgttcatt catagtggct ttctagaccc agggacttgg ccccagccct gctgctccac    118260
tcctcttctt gcttcattac cacgagtctc ctagaccacc gaacgatgcc tgcatttgaa    118320
agacacttct gctgatcaaa gcagctgatg tgtcccttttg cggttcattt ctaattgtcc    118380
ccaaggagga gaaattcaaa tagtttatta ctgagagtta aagaaatcca ctgaaatatt    118440
ctttggtcta aaattactgt catggcggag cagcttcacc ttagtcattg cccttaaata    118500
tgaaagctat ttaagaaagt ttgcccttaa atatgaaagc tattttaaaa agtttaatga    118560
aagaagagaa tcacaaaaca ttttcaaaaa gcaaaagaaa acctaagaga aaagttgaaa    118620
gtaggaattt tttaaagaat atacgacgtg tgttctgtga ctcaccccctg caagttatttt    118680 gtgtgtattc ccttgcatag taattaataa tgaagcaaag catggcaatg atatcttttc    118740
ttgtctagta ttctagaaga ctccatgttt ttggaaaata tcactctagt tagatctcaa    118800
atatattcaa tcagaaaatg ggttttctac aagattctat atctgtagtc aatagcaaat    118860
ataattctat taagctagta ggatgtgata ggaaactaaa acctagggga gaccaaagca    118920
aggaaaaata cttcctcatc caaacttgag agcaatttac cgtcaggcct actattaata    118980
gatggaatac agattccatt ttcattactc aactgccata ttcattatta cactgtacag    119040
aaaagggaat cacatctgtt gaaaacttat atatgatgtt catgcatgca ttccagtaat    119100
tcaacaattt ttatttatct ttttattgct tgctaatttt tcaaaataat aagctaaaga   119160
aaacaaaatg tttgtgctgt tctcagatga catgttatct cttaaaagga caaaatgtgc    119220
tgtgaaataa tagaatgctt tcagcactca agtgtgagtg agtgctcata catgagagaa    119280
agccgtgggg actacagaag ccaagaagca gatctagctg gggaggcctt tgcagaggat    119340
gtagttgtgt ggagaggcca cacacgtgga attcccagga gggctgtgga ggcggggaat    119400
```

```
ctgcaggaaa gcactggggt gagaaacgtg atgagaaaca attattgtct taaaatatct    119460
gcagggctgt aaggtagaga agcaatacgt tgcatctgtg ttaagtcaaa caaaattatc    119520
aagggactgg tttcagctta acataaggaa caattatgtg atagggttgt caataacaag    119580
agtagactgc ttcttcacac actcctagtc actcagaatg gtccaggagg agtggacaac    119640
catttggtag agtatgggaa ggcagggggcc ctgggtggga gtggtgaggg tagggagtga    119700
gtatcccaat ctagaagtaa attgtgccca gcacggagct gcaacactgc cctgcacaca    119760
aacacacaca aataacaatc cccagcccct gcatttccct ctccggtttc aggaccttgt    119820
atcttacttc aattccttta tttagctgat gatgaaatag gaagagctta gcactaagaa    119880
aatccttttg gagtttggcc ttgggggaaa atgaatcact ccaaccaggt ctgtcttcta    119940
gaaagtatag gatgaaaggg ctcctcatca catacttcct gacctcctgc taggcctttc    120000
cctaaaacag gggctggcaa agcacaacct gtgggtcacg cctagcctgc cacctgtttt    120060
tgcaaataaa gttttattgg agcatgacta tatgtatttg cttacagtct gtggctgcgt    120120
tcacactatc ccagcagagt tgaataattg gacagggac catatgatgg gtgaagctga    120180
aaacatttac tctctggctg tattcagagg aggtttactg agcccttctc tgagacatgg    120240
caagcgctgc ttcaggctca tgcttcacta gattcaggcc tggggcagta aagagccagc    120300
tcaggatagc actcccgact cactcatttt ttcaggcagg ggagccatct aatgtcaagt    120360
gcctacgtgc aggaactggt ctgttaatta gcagctctcc tcatggaagg gataatatat    120420
tctagaaaca ggagtgcggc cctattgcaa gaatgtcctg agccaaaatt aagattcttc    120480
tatggcagaa acttggctgg ggcttctcct gagttaactt ggtagttgtt agtgattttt    120540
gagtcagttt ttccttgtca acgaccccag gaatgagttt gggattacag ggtagccagg    120600
gaaagggaaa gcttcacgcc cgcccccggg acaaggtctg tcttcacact gctacatccc    120660
ttcacccact ttaaaatgaa acttaaaagg aggatttcag ttgagtagga agtgagaaga    120720
gggctcattt taaaacaagc gttaaatgaa accccacaca cactcagagc acacaaatcc    120780
aaccacgctt acaaaaccat cacagagggt caggcgaggc ccttttctaa atgaaaaaga    120840
acaggggtgg agactgttct gagagcatgc tgggttccct gaagggaatt ctcagctgta    120900
tgtgccccgc acaggatccc tgctagacac aaggccagct gccttccttt caagccgcag    120960
acgcatccct gtgtccaggc gggctggtca gctgcggtca gcaccagctt ccccgctcca    121020
tggtgaggtc atcacaacat gtgagcagga gggcaggccg gcaacctctg agtgcttaga    121080
gaaagggacg ggattcctcc tgtgcaaccc ctctagtctc actcagactc aagtctgact    121140
aaggggccag gtgctttgac cagggactct cccctctcac ttccctccca ggagtcacag    121200
gtacatgagt ccttgtttta caaatgaaga aaacagaccc aacatgatta agatgttgcc    121260 ttcataggg tggcaccagg attccaaacc atggactcca ctgagcccag tgcccactga    121320
catgtgccag taacagtgca gctgcctgtg gttctgtcga ctaaactgcc ggcagaggct    121380
ggctttccac cttcttttt tttttttcac tcttcaaaca ctttatgaca tgaacataaa    121440
ctactggctg catcgttctg ctgacaacat gacatgtttc tataacttga aaaagcaag    121500 cagtggactc tcattggta aaattgagtc agtaatcttt taggaaggtt attttcttc    121560 cttttactgc ttctcatctg ttccccgcag taaagaggac aagatgacga cgactcaggg    121620
aacacctcca gcctgaagca gcaccatgcg agcttagacc ttagggtcgg cttagaaacc    121680
acaggcgggg cggcttgggc ccctcggaca ctccctctcg aagctgcttc tccccaagct    121740
accccaaagg cactgagcgc cctctgcccc ccagcaattc aattcactgg ctgtcctgct    121800
```

```
cctgtcagta ctgagagttg catgtttgac cctcggggga aaagtccaga ggccctgggg    121860
tgtccagcat gctctgaggt ccctgctgct gacccctgc gctgtcagca ttcagagaca     121920
ttcacacagc acagcctccc aggctaacag ctgtcatgga acagtggagc agctagacgt    121980
ggccattctg tggcccagtg ctgcagaggt caaaggaca agcgcaggga gcatctttgc     122040
tttcagaaaa aaaaaaaaa aaaagaagca cactggtgca ctgacctgct cctggtgtct    122100
ttgtgattgc tcttttcttt cgattttgg ttgtcttttt tttttgaaa gaggggcttt     122160 tatgctttt tcctaatgtt catgggtaaa ccaatgtaaa tgtgtgtatg tttatagaga    122220
tggctttaaa tcgcaattct gcagtagaga ttgatttttt aaaaaacatg ggtaaaaatt   122280
gaagaaaaat tttaaaagaa catttaaacc atcttgggct aggggtggat atgcaccacc   122340
ccacggaagc caaacaaaat ctctctgcag ataaacattt gcaaaagaa tttccaatcc    122400 caatttttga gtcagagatc tttattcc ttgcaaatta catatctgtt tcaggatttt     122460
tgactataag aagaatgaat gaagatgtgt ttcttacaga taactatgaa caaaccagga   122520
aggataataa cttgtatccc ccaattcgaa tccagaggat gggaaggcat aaaaaaaaga   122580
aatggaagaa actttatttt tagtggtaaa tggtgggact atgtatttta cgtatggtga   122640
agtcaccaag cccaacactt ggcacttgta ggcaaggtag tcttctaatc tgaatgtgaa   122700
gtattatgtt ttcatttgct tggtaatgag gaatattggt gctttcgtcc cagttctcga   122760
gctgactgac ttctctttct gacgtgtgtt cctttagcac acctctacac tgcatggctc   122820
tgagatgtcc tgtgactgtt tcatgtgtaa agttgcctcc ccaaaggact cacatattcc   122880
ttcagggcag tgagtacttc tgattcatcc ttagcagcta ccttcgcgct actttactag   122940
atatgttgta gttgaattaa tgaacaaaag aacaagcaac tttggtgcct ggtgtgcatc   123000
tcagagcagg gtggagtgag cctggccaaa gggtcatcat gcaacctctg tggctgactc   123060
catctggcca cggagcttct cagccatgct tggtattcac atgacttcta gggcgacagc   123120
tcaaccagca aataaacagc ttcatatggg aaatattact cagcctttgt catcaaggag   123180
tgagtcacgg gcctgaactg aatagaagat agaggagaaa aggtgtgtgg actgggtgag   123240
acagcgccca gcgaggtgaa ctcccggcag ccctgcctgt ctttacctgc acatcacctt   123300
gctagggtgc cttcggttgt gagggcctgt ctaggaagag aagagttgca ccctggcagg   123360
cagcactgag ctgtctcatg caaagctgag gaagaaagag tgagctgccc agtgagcctg   123420
ctggggtggt ggaggctggg ctgggctgtg cagtctgcag ccccagcag cccttggcac    123480 cttttctactg cctggtgctc accagctctc cagtaacaaa gagggacgtg aagtcagagg   123540
ggaagggagg tagcacaggg cagtcttgac tttgaacaaa gagctggctt cctgaagtca   123600
gctggccggg ttttgaagcc gattttccag cagtgatctt tgatgccaac cccatttagg   123660
aattctgtat ctccccctac cttctaccag atgtctctga gctcaccttt ggtgataatc   123720
atgcaatctc cgtcatcccc acgtccacac tgccccattc tgtcccaccc cgggttctgt   123780
ggtgctgtcg gctccccagc gagccaggaa gggagaggcc agctctgctg gggctcctgc   123840
cgccctggct ctgcactgcc cttctctggc aggtctgagg cgccactgga ggagccacac   123900
ggccctgaag cagcaaggca gatgccctgg acacagtgga ggcacagagt gcaagcaccg   123960
gcctggccca cagacttttg gaggggaagt ggtattattc agttcaaaag tatgcctgtg   124020
tgtaaagaga gagcccctga acatgagtaa gcaaagtct cagcgcagag attagacaag    124080
tagaatgctg gcccgagagg aggcgtttac tcaccctctg tctaggaagg aaagccaggc   124140
```

```
ccagcacgct cactgctatc tatcctctca cacagaggga ttttgaatcg aagccagcat 124200 cctgtcctttt ctccaatgtc ccctgctcag gagtcaggac tcagcaaggc ccaccccagc 124260
cacacacaga tacagttcca ggactcagaa ctcagcgagg cccaccccag ccacatgcag 124320
gtccagttcc aggattcagg acacagtgag gcccacccga gccacatcca ggtccagttc 124380
caggactcag gattcagtga ggcccacccc agccacacac aggtccagtt ccaggactca 124440
ggactcagcg aggcccaccc cagccacatg caggtccagt tccaggattc aggacacagt 124500
gaggcccacc ccagccatat ccaggttcag ttccaggtaa atcatctgcc ttcctccgtc 124560
caaaagcctt gtttcctgtg tgtccttgtg tttaaaatgg aaacgttatg agaaactgcc 124620
tgccagggca aagggtgctg cccggcacac agtagggact caaaatgaaa ctattgtatt 124680
gaatacataa cagatcaacg ggtattgctt tctgaaatct ttttttagccc aattttgttt 124740 cttatagtcc aataacaggt caaattcatt tctgatttac tagccattca gttgcccata 124800
aaaaatggaa agtgatttaa gattattagt ttaaaaacca atgaaggtaa aacagttatc 124860
attgaaggca cataggcaga aatagattgc aatagttgct gccatgtgaa gcctcagtgt 124920
catgctccat atttagagag atctatgatt tctgaggccc tttcatgtcc atgatctcag 124980
tactgctcac aactgccctg tgaaattcgc cgagctggcc ccatgtcaat cagagtacac 125040
tgagcactga gacccagcat gttgagataa ctggctagag atcatcccat aatggtacca 125100
tcacaatctt cacactgtag aagtttgatg atgtcactgg aagcatattc cacagtccct 125160
tgtgaactgg ccttcctgtg atcagaagca tcagtgaact cccaagaggg tgggaactcc 125220
caagaggtat tctcactcta cttagtgtat attttacaaa tcacaagctt ggctttggat 125280
tcttttaatg gctagaagga gaatcatggg gttggaagtc caccagtttg ggtattctgt 125340
tccctaactc aaaataaaga gatgttattt tcaagtcttc tgcttgttaa cttaattaga 125400
gatacatgag tttgcagctg tgctgggcat gccgcagctt ggcatgttta gtccagaagg 125460
catattataa tgtacatgga agattgtcag aaattcaaaa ggacttttg agtatcacat 125520 gtgtattttc aagttccaat atagattcac attcagtttg acaggtatct ttggatgcct 125580
atcagttaag aactatttat tagttgtgga ataaaatagg gtaaataag gaacaactga 125640 ggaaaaaaca taaaatttgc tttgtgaata aaagttgtct tcaaaattat gactttttcc 125700
atcccacaaa agttttgatt aaacccacaa tgaaaattta aataagtgta tttactttgg 125760
tttaaccact tatttcatta tgactcacaa ctataggttt tctagtttcc attattacaa 125820
actattgtgt ggtttaaatc aatttcatag actagtctag ttctatagtc acaatttata 125880 aaatttttttt atgtggtaaa ttgagtgtct tcatagatgt acatgattat ttctcaattt 125940
ttaaggaatg tattttttaa gatagccttc tttagccttc tttaacactg attttttgtaa 126000 atttttaca gatttttttta aattttttggt aattttttag cataaagtaa tacatggtca 126060
ctatggaaaa cataaaaaca caaaaactat gaagagtaaa taagaaaaac acccagaaat 126120
ttaccattca gaaaaggtca ttgttaacaa cacggtgtat cttcctcctg tcatgcttcc 126180
gtgcatttga gcacatttga gatgtgtata catgttcact ttgagatttt agtatagcaa 126240
aagaaatgac cggtcctgat tcaatgaaac ctctggcaaa ctcgctatat ttccttaca 126300 tatttttaag ttcatcctat aaatgaacta tccattcatc ttatttgaga ttttcttaaa 126360
tctttcagca agaaagcggg aaaaaaatcc tcctctggcc tttaaagcct aattaaatat 126420
atgactaagc tagaaatatt ttataatgac caaccagaaa gtggcaagga ctgtcactct 126480
tcccatacag cccacctcct cctctatctc cctcaggcac acggaaacga gaaaggcaga 126540
```

```
gaaacccagg acaagtcatc caagactttg gtcacatggc catccattgc tttcacaaca    126600
aaaatataaa tccaacatgt gtgtgtgcat ttcataccag taggtccaat aagctatcta    126660
tatatacaca tatgtgtaca cacacacaca cacatcctta cagacactcc ccagcttact    126720
acagtttgac ttaagatttt ttgactttac gatggtgtga aagcaatgca cattcaatgg    126780
aaaccatact tctaatgttg aattttttat cttttcttgg gttagttgat gtctgatatg    126840
ttactttctt gcgatgccag gcaatggctg ggagccagag ctcccagtca gccatgcaat    126900
caagaggcta aacagctgat actatacagt ggactgtgtc accagcattt tggggatatt    126960
gtgttttgtg ttttgaatc ctatcatgtc tacaaaatgc cattttcgac tgctattttc    127020
aatttagggt gggtttatca ggacataacc ctatggaaag ttgaggacca tctgtatatc    127080
tggtagggaa agatggataa caaattcata ggcaaataat aatttcatga ttattattaa    127140
gttattccta cttaataata agtagtgatc actgccaggg agcagagaat gcaggataat    127200
gtgacagatg taatggtggg tacttaagct aatgtagttg cagaacaggc ttttctagag    127260
ggtaggcctt taagcgtacc tcgaagatgc aaaggaagca aagatgcgaa gatctgggct    127320
ggggatggaa gcagagacaa cttggaggcc aaggggagag actgacaaca gcccagctca    127380
tacctcagca gcctttaatg catagctaag aaaacaacaa attaaaacaa ttatagttta    127440
cttagacgat tctaagtgtc taagtggatt tgggcaaatc tggagaaact tgttctaata    127500
ctgtgtctta ataagtaata tagatttgcc caggcttgtg ggcagagtgg tatacacccc    127560
ataatagcag aggaaggcca cagggcctac cctacaaaac cagaggcatt taaaaactta    127620
aaggaggcag attgcttta ttttcagtta aaataaagtg aggagtttct caagaaaaat    127680
aataacgaga ccaccggccc gccctagatg tccaacaaga atgcacagat aacttcgtat    127740
atccactttc ctgaacctgc ccctgacagc caagtggagc acaacaacag atgaaacct    127800 caaaactact gtgctgtgac ataaggcttg ctcaagagga cagtgtggtg tgagtccatc    127860
tatgttctaa agcaagcaaa gctattctgt agtgaaaatg gatcaggaca gcagttgcct    127920
ctggtgtatg ggggcaggga tcgactggga ggggcatgag ggatgacagt tagggtttcg    127980
atcatgacag gaattcagat tactccagca tgtgcatttg ttaaagctca tcaaatgcta    128040
cacttaagat taatcctctc acagtttgtg gatgttacct taaaacaac aatgatgact     128100 gcaaactaat attgaactct ggttagtgat ataccaatgt gaagtatagt gatatctcta    128160
ctttacttta aaatgcatcc aaaggcagac tagaggacca tatctgacag acagaaaaat    128220
agatatgtga taaggtgaat gtagtaaaat gctaacataa ggatgtttgc ggtacaattc    128280
tttcagcttt tctatacatt tataaatcat aataaaattt taggacaaaa agttagtgct    128340
ttgaagtcct aagtcatagg gcctgctgct cttgatgcag tagaatttgt cttcagattt    128400
gcaaagggta aggcaaacca ctagcatttt gtatggaact tgatgcaaat acttttaatt    128460
gtctggtttt caaatgtata gacttaaagt aatatcaact cttctctttga atcaactact    128520 gaaataccta gtcttaaata aatattttta tgtaatcctt aaagtactat gtattcattt    128580
ttctttcttc tttcttttct ggtttgataa atattctata aagtaactgt gtttaatggc    128640
caacatttga gtaagtccat atgcagatcc aaacatctca gttagacaa taacttaaga    128700 caatatagag tggctgacat cccctaacgt gggtccagat gcatgttatg ttatgtttct    128760
gttgcattct caatagttaa ctttaataaa agaaagtcaa aagcttatat attttttcaa    128820
tcttcaaaac atttctggga ggttgtctta gttaattta tgttgctata cccatatcac    128880
```

```
agactgggta atttataaag aaaataaatg tatttggctc atggttctgg tggctgggaa    128940
gtccaagagc atggcattgg catctgcttg gcagctggtg agggccttca tgctgtgtca    129000
atctatggtg gaaggtcaag agagcatgca tgtgaggtgg tggggaagag aaaaagcggg    129060
tttaactcat cctttttatca gggactcact cccgtgatag ctaacccatt cttacatgaa    129120
tggcattaat ccattcctta gggcacagct ctcatgacct aattataata cctcttaaag    129180
tttccacctc tcaacactgt tgcattggtg attaagtttc aataaacgc actttggaaa    129240
acacattcaa accacagcag agatcaacgt tattgtcacc attttcatat ttgaggaaag    129300
catggcacag agagcttgga gaagtacttc aaggtcaccc aatgaggaag tggctaaaca    129360
aaaaccttat cttaaattaa ttaaaaacct cttgctcttt gcagttttgt cttaaatcta    129420
cctaatttgt gactgtaatt tttaagtaat ttactcatat aagtggtctc acattaaatt    129480
ttctcattgc tttatatttc taacatgaga tatttggtat aaggatggaa ccaagatcat    129540
accttgtttt aattagaaaa cctagaccaa gtcattgtga tcctcatcct agatttcagt    129600
taaatgctgc tgtctccttt tgggtatgtg acaggggaaa gcctcagaag aaacaacctt    129660
atgtgttttc ttttgatact ttagtaatta acccaggata gtattcaaga ttgacatgcc    129720
ttatattgaa tcaaatagca tatcaactgc cttcttattc tcaagtatag acatgttggg    129780
taattgggca tttaagtttc tttgcaattt tttccattat taacaaaatt aatgagcaac    129840
attctgcata aggtctgttt cctcagaata cgtttcccaa agtggaatca tcatgacgta    129900
gaatttaagc atacttactt gtttaaacaa attgtccagt tgcttcccaa aatgttttgt    129960
gaattaagat ttcatcaag aatatgtaat gttgttactg tctcccaaat acaggatctt    130020
tttctgaata taaaagttat acatgctaat tgtagacaat gaagggtcat tatcctcata    130080
gataatgaag tgcttctaat acttgtgctt ttattcattt attcaaaaag tgctaaataa    130140
gccctgaagg ggcttttggg gggtcatttg gggcttattt agcactttt gaataaataa    130200
ataaaagcac aagtacagtt tttttaaaat actgttttct ataatagatt aatcttaaat    130260
ggcatgtttt cctttatttt actgacaaaa gttacttact ctgtgattga ataataaaaa    130320
ttctttggtt cagctgagag aaacttgcaa gctgacgtcc ttgattattt aaaatgaaag    130380
cagctgcctg ttttcatctc tctgcatcct gaggaaactc ttctgcaacg tgttccagcc    130440
ctaggttcta gctgaccctg ttcatctgtt tggcacgagg ggcccaacta acacttgcgg    130500
ctacctggac gacagccaat ctagttggaa tgagagttag aggccatagt ctgtcagctg    130560
ggaaagcagc ttttattcca aggtgtgcca accgaaaggc cacatgttat tgtcacaacc    130620
tggtacctac atcagtgctg acatctttaa gaaccttaga attgggaaat cagtttagcc    130680
ctatctgcat gtgtagccga caaccacaca attgttccaa cttgaggttg cattcagagc    130740
aacctcattt cccccatact cctgaggaaa agcagaccag agacgctggg tcaatccaga    130800
gttatggttg gaaaaatgat ggaataattc tgccctggt gataggagag agggactcca    130860
tcttgtcaac tgtcatggtt cccatgtgaa agctatcatt atcactgaaa ttgaatgaga    130920
acacagaagg gaagaacagg gaaatcccca cagagttaaa gaggatgtga agattgcttc    130980
atgtttaatg tttgtgtaag tgctttgggt tggttatgtg ctgtctgaac atgtgctcat    131040
ttccatggct cattgagagg gcagacagtc caatgatact ctttagaatc attcccatgg    131100
ggaaggaaca aagaagcctg taaaatagaa atgcacatgt aaaaagcatt gaagaaagtg    131160
ccagtgtatt gattttggcc atggtttgtg ctctaccacc tggttactgt gattgcagaa    131220
gtgcctttgc agatgaggaa gaacctggcc aaggctcaat ccaacatcca aagccagagg    131280
```

```
ccatatttct tcactcttaa gataatttgg gttcaaatta tagtcccttt acacactctc    131340
tgcctcaaaa ggcccaagac tctcttttgt tatgcttgcc taaacatgcc tttcaaagaa    131400
ctagttctgt aaatacaact ttattataaa cctctccttt gcttttaaaa atggatcacc    131460
acgtccattt ctatggtcca actttgtccc ttaatttaaa attttttctt ggattaagtt    131520
tgatgccttg aaacattagg aactcaagca tacaagattg tatgctggtg gtgagggaag    131580
taactgtgcc tccgcctgtg ctgggtggat caacatggag tgtggacgag catagggatg    131640
tgtgggtttc tcactagctg agagtgtttt taaatgttgt attttgatgt ttgttatttt    131700
ctgaatattc tacagttaga cctttgattt attctttgat gcattcattt gaataatatt    131760
tttaatctcc agccagttag gttttttaatt tacacttttg tccctgattt taggtgtagt    131820
gttgtgtaca ctactgccca gtgtatgtta tgtttgtaaa cattcattgc acgcacaaca    131880
atgtgactca caatatttt gagaagtaaa aagttcatta tatagttatt aactcaaccc    131940
tacagttata ttcgtgaaat accttgtgaa atttattttt tgcctactgg agctcttaca    132000
ggttaatcct gtcttcaaga ttttcataga attttcatct accacccacc cctttaaatt    132060
tcaacatttt tttattttgg cattttaatg caattcaatg cattataggg acaagctatc    132120
tcttattatg aattgcacct tatataaact taaagatctt ttatcacaaa tttctttgct    132180
gtgtccttta gtgagaattt gtattatcag tcactaaagc tcactaagtt agtaagcttt    132240
gcgcccagat gacctgggca ggaatgggtg agtctctgtg tggagagagt gaagaaactg    132300
ctacccttaa tacctggacc ttgagggatt gttttatttt agtttttctg catttctcag    132360
tatttcatgt gatatctgtc tttttcttcc agtttgccaa ggcacgagta acaagctcac    132420
gcagttgggc acttttgaag atcattttct cagcctccag aggatgttca ataactgtga    132480
ggtggtcctt gggaatttgg aaattaccta tgtgcagagg aattatgatc tttccttctt    132540
aaaggttggt gactttgatt ttcctacaca aataaaattg gagaaaatct aagtggagaa    132600
aggcctgggc agaattccac ttgaagtgtg tttatttttg ctatggcaat gacaagtctt    132660
acagagctac aaacgagagt tttatgagaa agccatttta ccagctaatg tcaagtaata    132720
actagaaaag gatatcaaat agaaacaggc taatctggag ttccatgtca tcatagacac    132780
tgacgtttat ccctgaccat tacctcagtc atgatgtgct gccatactcg ctcttaaaaa    132840
ctttttttaa aagccctgct ttgcaccatt tgcctattcc cttagtgtaa atactcctac    132900
tatagctgat ttcaaggtac caagtttcac tcagctggtc acagaattct tatttcacga    132960
taggcgctaa tgaccccata ggagccagct ctgaaggctt cagagtttca ctgaattttg    133020
gatggggttt acttagcctt cttctgtttt tcttttacct ttccttttta aataagaaat    133080
aatgcaagac agatacaaag taattctttt taatttccat tttcactgga gagtgttgaa    133140
ccccgtgagg catgagagca cagtgttcca gaacaatgct tactgctcat tatcacaggg    133200
gtcaaaggct aacgtgcagg gattgttgca gatcgtggac atgctgcctc ctgtgtccat    133260
gactgcaatc gtctacctat tttacagttg ttgagcactc gtgtgcatta gggttcaact    133320
gggcgtccta gggctccctg gacccatttt agacctgag ttcttgagtt cctcaaaaga    133380
gaaatcacgc atttatgttt tctcttctta gaccatccag gaggtggctg gttatgtcct    133440
cattgccctc aacacagtgg agcgaattcc tttggaaaac ctgcagatca tcagaggaaa    133500
tatgtactac gaaaattcct atgccttagc agtcttatct aactatgatg caaataaaac    133560
cggactgaag gagctgccca tgagaaattt acagggtgag aggctgggat gccaaggctg    133620
```

-continued

```
ggggttcata aatgcagaca gcagttccga tggctcccag cgagcttgtc actcaattcc   133680
acctcggaga aggctttat ttttacccag tacacgtgca ctgagtgccg gctgtgtgta    133740
agatactgca ggggaagtta ctgagaagat ggcagatact ggaatgggaa gatttaagcg   133800
gggtaccagt gtttacatgg acatgaaaaa atactgagag atagtaagaa atcgtaaaga   133860
ttctgagtaa aagagagtat gaccaaacaa gctgagcagg aatcgtgaat ctatgtgtgt   133920
aggcagtgaa taaactgcca gtcttattac ctggacctca aggataaaag acatacagta   133980
aaaatcaacc cacattgagg acagtttcga gagtcgcgct gctacacaga aagccctgtg   134040
taagttaagg atagagaatg aggtgttcta gaactttgaa ttttttgtgag caggactcgt   134100
gaggttcctg tgagaggaaa caatgaagga tgatagaaaa gaagggaaat tgattttaaa   134160
aaactggaga tagcagtgat tgtgcctcac tgtgcagtgg gtttggggcc aggaatgtta   134220
aattggtaac ttcatttaac gcccacaacc tttcttcaaa gtaggcactg tacagatgcc   134280
ccttgactta tgatggcatc ctatctggct ggaccccgcc gagggtgaag gcgtcattag   134340
gtcggatttc agggctaatt gaatgtatat tgccttcaca ccatggcaaa gtcgaaaatc   134400
tgtgttaaat catgctaagc cggggactgg ctgtgctctg ccatcgtaca aataaataaa   134460
tggaagtcaa gtaactccct tgagggcccc agctagtgaa tggagaggcc agctatggcc   134520
accactctct gccccagggc gctcaacgcc cctcctgtgc catgcagttc tgacagggag   134580
gcagtgctgg taggaaaggg gtgtgatgaa aggggtgccc agcagaggga gtcatatccg   134640
gagtgacagg agcccaacag gggtgcagcg ctggaaccca agccagcacc tctggtcatg   134700
gctcctcagt tcaccgccta taaaattgtg tggttccccc acaccccttg ctgctcagag   134760
cagccgcgca catgcttgtg ctgtgcgtgc ctcctgtgag atggcctggt acaccggttc   134820
ctacagtgcg cctcacacgc tgtctcggag ggaggcagcc tgtgcgggtg cctggacctc   134880
cgagccagac cctctgggtt cctgcctggc cccgtcctc agcagccaga tggctcggga    134940
gcacattctc caatccctcc gtgtctctgt ttcgtcatct tcaaaaatgt ggatggcata   135000
gctgctaaaa aatggtgaca tacttcctag gtggtgcaga aaattaagtg actgtaggaa   135060
caggcctcag cagctccttc cacttccttg gtatgattgt ttttttaaacc aaggctggga  135120
ttgtatagat gcagattagt taatgtgata ccattaatag ctaacctagt gcctgctgca   135180
gggtgagcct cccctaagcc accgggaagc ggctcctgca gcctcccctca cgtgtgctgg  135240
ccctcctctg gcagtcattg cctgtggtgt gctgaaggcc cagctctgac tgtgcctctg   135300
tgctctcctc gccccgcccc ctgctctctc tcaggtctttt ggtctgttgt ccagctgcc   135360
acagcagcct ggacatccct gttggtgttt ccagccctgt cctctcctga gttccatcca   135420
cctgtgcatg gctttttcat gagtgttttc acggatggtt ctgctgtcat ctccaacctg   135480
ataaacaaag caccacgatt cagcccttat gaccccaagc ttccttcctc agttccttgc   135540
ttctgtgcat ccactgaaga agcctgttcc actgtttccc tgcactgggt ctcctgtctg   135600
caggaagcct tcagccctca cttccacact cctctaagat gtgtgcctgt gcccttctgg   135660
ggaagctcat tttcctagca gcctccagga tcttcagggg tgaatccctc ctttcccacg   135720
ttggtactct gtacacacaa catgcccatt ccctgcctgg ggagctgggc attgcttcat   135780
gaatcagagg tcaatttttt ctctattaaa gtcacagatg ctcattgcac cattgtgaga   135840
atgaatgaag atagtgctta taaatcagcc agcaaggtac ccagcctcac tgtgtcaggg   135900
tctccctggg catgaggtgg ttagagtgtg tgacatgtct gtcccaagc ctgtcagctc    135960
ccagatcgaa gccagtggat ctcattcatc ctcgcagcgc ccacagcact tgcacagggt   136020
```

```
tttgtacaca taagtcattc tgtcaatgtt catgtttaat gtcatcagtg gaacactccc   136080
actttgtaaa gacttgaatg tgttcatccc tgacttttcc acatcttgtt agttcttctt   136140
tggaaacagc tgtacagttt caccatcctg tgcatccctg gagtctacct gtctctgtca   136200
tacattcaga ttcttcttgt ttcgtgtcac tctcatatcc ttttctctaa tgaaaagctc   136260
cgcctgggca tgcaaggtgg agccctggat gccagcccct cacctggcat ccagggctgt   136320
agcactcagg aactgcctcc ctgccctgcc taccccctac atcatgcgac cattccagtc   136380
cagccaatca gccccttggg acccagctta ccacatgcat atcatttatg ctgtgaccac   136440
tgactaaacc attctcttcc ttcctcccca tatttctaaa tttctaatca ttgctcaaag   136500
cccaattcag agaaaaccct agctcctcca tggcaccatc attaacaatt ttatctggcc   136560
gccccccggg aagttcactg ggctaattgc gggactcttg ttcgcaccat ggcatctctt   136620
tagcagaaca taaatgcgaa gagcacatgc atccttcatg ggaatttaaa ggagctggaa   136680
agagtgctca ccgcagttcc attctcccgc agaaatcctg catggcgccg tgcggttcag   136740
caacaaccct gccctgtgca acgtggagag catccagtgg cgggacatag tcagcagtga   136800
cttcctcagc aacatgtcga tggacttcca gaaccacctg ggcagctgta agtgtcgcat   136860
acacactatc tctgcctcca gctcctatgg gggacagctc tacagcactg ggcagggga    136920 gagaagccat gtttagtaag tcacattaat cagaaacaaa aagtagtaag caaaatatct   136980
gaccactaga aaagcatgta tttaccacgg acatagagat cgttttttg tggcgggtgg    137040 cagcccagct ggttggcagt gcaggccacc ggaggcagat cccctgcagg gacagcagag   137100
cacttgtgtc ctgagaagag ctgctgttca tggggctggc agcaccaggg cctctcctag   137160
cctgccctgc tgacactggc cagactccta catgcttctg agtctccaga ggctacccgg   137220
ccctcctgaa gcaccaggggc tgaatccacc cccagctgag ggcatgaaca ctgccacatg   137280
gagtcacaca cacagctggg cactgccatg gagaggaagt ctgtccatgt ttccttgaat   137340
actggtggcc tggtccctgt cccattcccc agtgaggcag cctgtgggga agcctggcag   137400
ggaaccaggc gcaggtcagc gtggcgccct gactcaggcc agcactgatg ggggactctg   137460
agacgcaagc tcacactcac ccagctcccc tgggctgcgc ccgttcctga tcgcttggac   137520
tttctgttct ttagagtaag aagtgatcac catttcctgc ttctttgttt ctccacaact   137580
gtgcagtgga tgcctgtttg ttttctgccc tcagaacaaa aaaaaaaaaa aatagagctg   137640
acgtgaatct tcaaaatcat caactacagg gctttggatt tttgtgtatt tgtttatttt   137700
tcattttatg gatggattgt gatgaaatgc ccgtaataca agattttcca tcttaaccat   137760
tgtaagttac aatgtcagtg gcattataca tccacatggg tgtgtggcca tcaccaccgt   137820
ccacacacag aactctttta tcttgcaaag ctgaaactct acccattaga cagtaactct   137880
ctgctctccc ttccttccca gcctctggcc ctggcaggca acagtccact tgatgtctct   137940
atgaatttga ctgctctggg gctctcatac aggtggaatc atgtagtatc tgtccttttg   138000
tgtctggctt atttcaccta gcaaaatgtc ccgaaggttt atccatgctg tagcacgtgt   138060
taagaatgtc cttcctcttc atggctgaat aatattccat tgtatgttga cactacattt   138120
tgtttgtcca ttcacctatc tacagacact ggggttgctt ccatcttttg actgtttgaa   138180
taatgctgct gtgaacatgg gtattgaggc tctttgtttt atagacatat tattccacca   138240
gatacccatc ctgacaccta ctatgtttgc aagaaactga aagctttatt ttacattgca   138300
aaatttcata ttatgagatc aaggttagca tttcctcagc tgtctggtgg acaatgggga   138360
```

```
ggttaaactg tgcacatttt attttttttt aatgaacctg gaacggttat ggggccagtg   138420
tttgccatgg atcaggtcag gcagcccaca atggcaggtc tccatgttct gtacaacaac   138480
tgtgggaaag acccacagag aaagtgctgg aaagggggaat gatgggtagg ttcatgcagt  138540
aaaaagattc aaatactaca gggcattgaa ctataggcca atatagcatt gctttaagaa   138600
taaacaaaaa ataagacagt aagaataagc ctagcaaaat caaaagtcta taagaactg    138660
acatttcaag ccaataagag aataattcct tattcaataa attgtctgga atgacttaac   138720
tattagggt gaaatatca aagtgagaga actataaagg gttttaaaa aggaattagg       138780
tatgttgggt tagtcgcatt ggagagtgca aattcaccat cgacctgata cctgaaattt   138840
cctccttacc atctagaggc aagttgggaa tgctgccagg ctcctgtggt aaaggaagct   138900
cctctcttga ctggtgcttt atggctacac gttcctgctc agaatggatc tcatttagtc   138960
ttcaccaaaa aaaaaaatct catgagatga tttaagtgtt ttatggacaa gatgtctaaa   139020
actcagaaaa atttcacagt gtgcctagct tttatgttta tgttgaagtt gggcattaga   139080
agttagaatg aatgggttta cttcagagaa aattaaatcc atcacccact ccttgtacta   139140
tgaattccaa atacatatta aatacatata ataaatatt taatatatat gtaagtgcca    139200
gaaggaaaca taaatatgaa tattttgtaa tatcaagttg aagaaaagcc aaaatctgac   139260
atcataaaag aaaactttca agtaaaatat gttaatggct accaggaaaa tattgtgcaa   139320
tgtctgattg ccatgaagag ggttaatatc cttgctatat cactctgtga agtcatcttt   139380
aaaagactaa gaaaaagatg aatctcttaa taaaaacctg gcccagaaca tgagcagcct   139440
ctctctctca ctctcactgt ctctctttct gtcacacaca cacgcaca catacacaca    139500
cacacacaaa tatggccaag aaataaagta aaatgttatt tctaatgtaa taagtaggtc   139560
aaaatagaaa aagaaagcat cacaccttcc tttgcaaagt attgggttc cttttgcttt    139620
taaacacctg ggtcagctgg ggtgtcgaga acagaaatt ctcacgttct gcttgtgggc    139680
atatatgtta ataaaaccaa gcttggcaat atgcctgcaa tatgtatcta aagcttcaaa   139740
gtatgtatag ctttgaccaa tcaatatcac atttcggaat aagagaaaaa gaaataatga   139800
aagtgaaaat cataagagat gtagaaacat attcttatac aagaattcct tgcagcctta   139860
tttataataa atttgtgaa caattatat atctaaaaat aagagattgg ttgaaaaaat     139920
tatgcagcag ccatgctatt gataatcatg ttagatagaa gcatatttaa aggcatggaa   139980
aaattgccat gttttatatg ggttttaag gttataacac aatgtatagt gggattccaa    140040
ttcctgtata tacatagact tatatgtcta tattgattaa ctctggatga gtctcatgtc   140100
ttcttttgc tttcttctat tatccatatt ttatacgatg tgcctgcatt tcttttttgt    140160
aacagatggt caatactaga atcataaaca gatcttgttt gtttattggc aaatgtttcc   140220
cgttagaaaa agatgcattt ttcttttaaa tattttat ttatacaatg attacaagct     140280
tataatagaa atttgaaaat tatatgtgag tacagggtaa aaagttgaaa gaatgggatt   140340
gcacgctaca gatctagctg cttttagcac gcctgcgtag gaccttgctt tctctagacc   140400
tctgttgcag tctctctgcc tacctcctca caacgtccat ccccgcggt cactgtcgtg    140460
atgccagcct ccccggcctt catgtctcta aggagcacca gcgcggcaat tagcgcccctt  140520
tgccttggtg gtattctggc ttcacagtca catgggagat caatcgtcag cttttctgtt   140580
tgaaatctaa attcttcctg actgcagggg acctcgggac ccatgaacac ctctagttta   140640
ctatgtcttc acagtaaaag atatctgcat gactggactc tttaacaaat ttggtggtta   140700
acctactctt tctatataga tatagcactt cgaccttcag acttctcaat actgataaaa   140760
```

```
agaaaacacg acagatgaca ggaaaacctt tgcagctata atttgtaatc ggccaattat   140820
aaaaactgca aaaattgacc agatagctaa ggttttacac agtcatgaaa gtgatctgca   140880
ctgttaacat ttcaccctct gtgcaccatt ctgtgcttct ctctggtttg gagtctagaa   140940
ggttttattt acaggctatg acttaacaat cccagaacgg ctgacacatg cagtcactca   141000
agactggaca cagcaaggaa gtagtgggtc catgccaaag gctcagccag acgagacact   141060
ctagctgtgg caggagatgc cagggaatgc tccaagccta agcagattgt aaacaaggaa   141120
cctcaaattc atgaaaaatt cttgcttatg tggcccatgt cagtaattac tctctgcctc   141180
agtttccgca gctgacatgt aaataaaagc agttcatggt tcatcttctt ttcttatcgg   141240
ggtctcaagt gattctacaa accagccagc caaacaatca gagaataagt tgaaaagatt   141300
gtcttcattt attgaatgtg cttaactcag gcccgggaaa gggcgtcatc agtttctcat   141360
catttcactg agatatgcat ctattacttt tacatttcag gccaaaagtg tgatccaagc   141420
tgtcccaatg ggagctgctg gggtgcagga gaggagaact gccagaaacg taagtcagtg   141480
aacagcctca gacccatgtg tgaccgcccc tctcttcctt cacttgctta ggtgattgga   141540
tttgttttcc ctctgaagac tccaaagagt tactttatta cagggtcaga tgtgaaccag   141600
taggtgaagg acagtcttgc aaatctcacc gcatgcagtt aatccagggt gggctatttt   141660
gggagcttca gcctatcaca ataagtgaa catcagcagg ggctgggcgc ggtggctcac   141720
ccctataatc ccagcacttt gggaggcgga ggcggtcgga tcacgaggtc aggagatcga   141780
gccattctgg ttaacacagt gaaacctcgt ctctactaaa aatacaaaaa attagccggg   141840
cgtggtggcg ggcgcctgta gtcccagcta ctcgggaggc tgaggcagga gaatggcatg   141900
aacctgggag gcggagcttg cagtgagccg agattgtgcc actgcattcc agcctgggcg   141960
acagagcgag actccgtctc aaaacaacaa caacaacaac aacaacaata agtgaacatc   142020
agcaagtacc ccagccctgt cctctgaaca cagcacactt tcccaggaat ggaagacttg   142080
ctcctgttga cagcagtcac cagacttctt gtttcctctc cctccctggc tttctttggt   142140
acccacctac acagaagcct gagcacgggt tctcatgggg acttttccat gtggaccctg   142200
ctttacgatg gagagggcca ttctcctagg tatggttgtc tggctcagcc tctcagtggc   142260
caaggaacct ggggacatga gctcaaaaac ggacactatg tccttaagct gaattgtggg   142320
ggggctgtta ggcccttcta aacactactt cccagcaggt attttttgttc tttgtatgtg   142380
ctttctgcat tgcccaagat gcatctaatt atttagcagg tctcaaagtc tagacttgat   142440
ctcatgagtt ctcttaagtg attaaaaata aatcaggaga aaaagaggc aatcagaaaa   142500
gggcatggtt tgacttagtt tgaatgtggt ttcgttggaa gcaaatgtgt cttcactttt   142560
tcatgaaaaa gtctgcaagt gctctgcgac atccctggga aatgatccta ccctcactct   142620
tcagctcaca gggaaccttt gctctttttc agtgaccaaa atcatctgtg cccagcagtg   142680
ctccgggcgc tgccgtggca agtcccccag tgactgctgc cacaaccagt gtgctgcagg   142740
ctgcacaggc ccccgggaga gcgactgcct ggtaagatgc ccctccagca gcctccctgg   142800
agcaggctgg ggctgcaccc gccccaccca caccaggaca gaagacttcc tgtggggag   142860
ctgtcaatta gcatttgtca taacagacag gatattgccc tctgcctggt gacaaagtat   142920
ctttagtatc ctgcctccac cactcactga gaccttggga aaatgatggg actaccatgc   142980
ctccatttcc ttacctgaca atgatgcata acaaagtctc tcccagttga atgcttaaat   143040
gatgagatgc ctgtgatgtc cgtcattagg acctgggcac agaacaagca ctaaatacta   143100
```

```
catgcaagta tttgtcatga atgtgccttg ttgccagcag cacactctct ttattgtttg   143160
acttcggcta tacctctaga gacttgacac tgtgaggtcc ctaagagacc catggagagc   143220
cacacaggtc ttgctggctg gggctgggtt agggcctcct gacacggatc cctcggctcc   143280
tccaccactg ctcaggcacc tcctgagctg caccctgccc tcaaggggtc ctgaagtact   143340
cactgtcgcc ccattgctcc agaaagtgcc agcagaagcc ttgctgcccc agcgggctct   143400
gagcagcact ggagggtaca ggtcagaagc gtcttggaag tcctggagac gccaaggctg   143460
gtggatgtga ctcctggagt gggagctggt gtgacgaagc ccttcctaag actaaatcca   143520
gagcactctg tggtttcaga gaagattcct aaattccaga gtttggaccc agacccagga   143580
attgtgactt ggttggcctg agctgtttct aatgtgagcc ccaggagaa gactgtgcgt    143640
ggggttggtc ctaggaaaag ccctcgctgt attgggtctg gctcctttac acggcattgt   143700
tctagcaagg ctttctgcca ttcagcaata cattataaaa tatacccctca attgtacttt   143760
ataagggaag cccaatgtcc tttataaggg aaatttaaaca taatttcatt ccatagtcac   143820
cgctataatg tgtgaactcc atcatctata cgttagtaaa cagacgtatt tttatcataa   143880
tccataaatt atgataggtg ggacagtgca cctaagaaaa aaatggactt tttagagaag   143940
ggtctttctg actctgcaga gggcgccagc tgggttttcc cacactagtg gaacactagg   144000
ctgcaaagac agtaacttgg gctttctgac gggagtcaac accgtgctgc gcttcctccg   144060
tgtgtggcgc tgagtgtact tacctcactt gcccagcgtg tcctctctcc tccataggtc   144120
tgccgcaaat tccgagacga agccacgtgc aaggacacct gccccccact catgctctac   144180
aaccccacca cgtaccagat ggatgtgaac cccgagggca aatacagctt tggtgccacc   144240
tgcgtgaaga agtgtcccg tgagtcctcc tctgtgggcc ctctaactgg tcaggcatcc   144300
ttgtcccgct ctgtctcctg ctgagccctg gagtatccca tcttggagag tctttggtgt   144360
gatgtgtttg ccttgcttgg aggaggcgac cctgtgcccg tccaggcaca caggcgaggg   144420
gaggggctgg cttgctaccg aggagcgggc aggtggtggc catctccacc catggggct    144480
gctcagtgca cagggcagat ctgggtggcc aggccacctc acaggagaaa cacctgctgc   144540
tcagccctca ccactcatcc agcagccaca gccgtgggta ttcagttgtc tgctgggcac   144600
aaagccgtgg gcatgccact gtttagtgct tgtgccaagc aggtatttaa tacaccgaaa   144660
tcagagagtc tatcagaaga cctgccttct tgagtggtta aaattctagt gaaagttatg   144720
cctcttagga gtattgcaga ggttttgttt ttgtttttat tttgttttgt tttaatggtt   144780
tgggtttgag ttttgcttgt ttgtacttac atttgtactg gtggctccag ggtttaggga   144840
aattgtgaca taaaataatt cctgacagag aaagcaaaac tttgtctaat gaaagagttt   144900
tagaagccac tcttgatctc tagagggga gattaactga gaaaaaaaat tgaaagaaca    144960
attatgaggg ggagatttta ccctgccaga tttgtgtaca tgaaaaattt tacattccgt   145020
atggaaaaaa aaaacacaaa ataataagcc attataaggt aaatgacaaa caaagctaaa   145080
gaaaaatgtg ccacagtgat gacacagata tatctttgag atagggctta acagagcttt   145140
aaaatccata ggaaaacact tcgagcctga gataccaaga gcagatggtt cacagaagaa   145200
tcatcaatgt cctataaata tttttgagga tcttcttggg gaacttaaaa caggaacagg   145260
ccaggcacag tggctcattg gctcatgcct ttaatcccag cactttggga gactgaaggg   145320
gctggattgt ctgaggtcag gagtttggga ccagcctggc caacagggtg aaacctcgtc   145380
tctactaaaa atacaaaaat tagccgggcg tggtggcgca cgcctgtaat cacagccgct   145440
caggaggctg aggcaggaga attgcttaa cccaggaggc ggaggttgca gtgagctgag   145500
```

```
atcacaccac tgcactccag cctgggtgac agagcaagac tccatctcag acaaacaaaa  145560
aaggaagaca tagagctcct aaaaataacg cagaagtctg ctattaatac aaatgaatta  145620
ctttaaaggt gagagcaggt ggaggagagg gctgaggtgc ctgctgggac gcaaaacagc  145680
tggcccctca agggacccag tgtttcctgc catgatgaaa cacctgtatt gtccacattg  145740
cggcctagaa tgttattaaa ctcttgaacg ggattccttc tctatttgca acctttcatt  145800
ctttgtcctt aaagtaaata aagccaaagg aggatggagc cttccatca ccctcaaga    145860 ggacctggac cgcctgtgtg aggcccgagc acctggtgcc accgtcatca ccttcctttc  145920
atgctctctt ccccaggtaa ttatgtggtg acagatcacg gctcgtgcgt ccgagcctgt  145980
ggggccgaca gctatgagat ggaggaagac ggcgtccgca agtgtaagaa gtgcgaaggg  146040
ccttgccgca aagtaggaa gcccgccggt gtgcggacga ggcttgttct cggctgctga   146100
ggctgggctc tcatgccacc tccaaggaa cacatcttcc tcttctcatt aaaaaacaac    146160
tatacatatc gtttctttaa aacagaagat aaagctgtaa agctaggtta ggcaatggga  146220
aggcactgaa ggttgtgacg gggtgggggg ctctgatgag aacagtcaca gagccagccc  146280
cgctcagcag ctgccaggtg cccagccctg gggagaatcc agggaaggca gagctggaag  146340
cagtgcagct ccaagcggcc catgggaaat aatgaggaga acgcaaggtc agtgtgaggt  146400
gacagggatg gcatctccta caccgccgta gccccaaagt gtactatagg tcctggtgtc  146460
cccccttccc gcctgcactc tccccagccc cttcagtgtt tgttgagtga atgaaggatg  146520
atgtggcagt ggcggttccg gtgaccggaa ttccttcctg cttccctctg cctgtggatc  146580
cctagctatt cttaatccaa caaatgtgaa cggaatacac gtctctctta tctctgcagt  146640
gtgtaacgga ataggtattg gtgaatttaa agactcactc tccataaatg ctacgaatat  146700
taaacacttc aaaaactgca cctccatcag tggcgatctc cacatcctgc cggtggcatt  146760 taggggtga gtcacaggtt cagttgcttg tataaagaaa aacaaaatct gccttttta    146820 ctggtagaga ttggtgatca ataatcaccc tgttgtttgt ttcagtgact ccttcacaca  146880
tactcctcct ctggatccac aggaactgga tattctgaaa accgtaaagg aaatcacagg  146940
tttgagctga attatcacat gaatataaat gggaaatcag tgttttagag agagaacttt   147000
tcgacatatt tcctgttccc ttggaataaa acatttcttt ctgaaatttt accgttaatg  147060
gctgatgttt tgatatttttt caaaagtgca gtttctcctg caggcaaaag gggacacgtt  147120
aagtccaggc ttgggtcatt cactgcggtg taaacacgct ttctccctcc cgcccggccc  147180
cagccagctg ccttggtggc ccataacccc tgagggtaga gggaggggac aggggtaggt  147240
gacaggcagc ctgggcctca ggcttttgaa actggacgcc agagccttgt ggggccacgg  147300
gcaagcctcg ggtctatgac tgccgcctga gctccgcttc cttcctctct aaaatgggaa  147360
gattagacca aaataacaag actgttttaa ggttggaatc aaataaggaa aatttgtaaa  147420
gctccttgta tgtgatacca gatccacaat tggcagataa tcgcagcagg agcctcttcg  147480
gggtaatcag atacgcggcg cagcagggt ctcagggcca cagccagggg ggcggcggga    147540
gacatgcgga atcgcagcgg aaggcggag gcagctgtga actgtggctc ggcctgcgtc    147600
cgccctgcgc atgtacactc agagaagatg ataatgaaaa agaaagcaaa tccaattttc  147660
ccacttactg ttcatataat acagagtccc tgagagtcta gagtaatgtc tcatacaaaa  147720
aagaaactcc tacgtggtgt gtgtctgaag tctttcatct gccttacagg gttttttgctg  147780 attcaggctt ggcctgaaaa caggacggac ctccatgcct ttgagaacct agaaatcata  147840
```

```
cgcggcagga ccaagcaaca gtaagttgac cacagccaaa gcctggtaga ttacatttgc 147900 cttttttagtt ggaaattagg cttaacagga gagttgctaa gatagggcac agagctcctg 147960
catctctcgc cggcattccc aaatgctatc tcacatgagc aggcacaggg agcaagactg 148020
cacgaccact ggcacaggct gtccgctaaa ccacagactt ctcagcgctc gccagtgctt 148080
ctgcttctgt gtccactcca gatcccacat tgcacttagt tgtcaaatct tttcagtcca 148140
tttctaacct atattagctc ctgtgtcttt ccttgtcttt cacggccttg acacttacaa 148200
aacgtgtggg tcaggtactt tgcacactgt ctaaccatgt ctgttcagct ggtgtttttct 148260 caggatgcaa ttgaggttat gcacatctta tcacagggac cagagagact ttttagcacc 148320
actcttcaag aatttccact ttttcagctt tgacagtgga atagacatgc aggtgctcac 148380
acacaagcat ctttaatatg gtaatggtaa tcatcagttt agtggtgtgg aggaggagat 148440
gggaatctct tagtgaaacc cgccttggaa gcagcctcgt tatgagaact gctgcccccta 148500 cttgactctt aaagcactag ataatactgt gcaacattaa agagaataag agtgcgtgaa 148560
atatgcattg cctcccataa actcccttgg ctctgaatct ctgatactaa atatgtggct 148620
accgttgctt cccagaaagg cctttttgct ctgaattctc tggaatgctt tctttgacca 148680
agattcttat aaaaataaga gatttagagc aattttcttg gatggctggt atgagccagt 148740
tggcttagtt gtagggattt aaacaagata agggttactt acttttcaca tttaatgaga 148800
agtctggtga ttccagctcc tactgagaca gggtggccac acgttccagg gtgtgactca 148860
ctgaggcccc agacctgccc tgcaaggaaa acctggctct gccctggtgt cctggcctcc 148920
ctgggcatat gtgggggaga attcctaatg gtattggtta caggctccta tgcgagacca 148980
ctcatctgtg taggagaaag gaaaaagatg ggggaaagaa gagcagcagg gagaggagaa 149040
gcctctggat gatactctaa cccctgcca tccaacaccct gaacatcagt ctcttcatcc 149100
agtgctctca gctggcccag cccccagcct ggggtcagat gagagcttcc tgcaaatgca 149160
gatctctttc ctgtggctcc ttctcaatta cagacagctc ctccacaagg tgcactctgg 149220
ccttgtgctc cctccccaaa ccagcccagc cctcccagcc tgcatcatcg tggtcctgta 149280
ggggctagag gttctcacac ccatcgtggt ctggcagagg ctggtggttc tcacacccat 149340
cgtggtccgg caggggctta gtggttctta tacccatcgt ggttcaggag gggctagtgg 149400
ttctcacacc catcgtggtc tggctggggc tagtggttct catgtccacc gcgtgctttc 149460
ctgctcctcc aggtggctga ggacatcccc ccttcggtct gaatgacttc catccagtca 149520
tctgatatac acattggacc acccaatagc atcctagtgt catgttggat ggtgaagaaa 149580
atgccacagt tactgctttc agggcctcac aaccttgggc atagcttttt ggaggaaggc 149640
cccacttccc aggcatccct cccagacctg gtcagaggcc cctgctcttt gcttccatgt 149700
tgcccacact cactgtgctc ttcacaccgg ctcaaaatga tctgcttacg gggttgtgtc 149760
accaccagat caagcgtcct ggagaggagg aaacatattt aacctgcaca gaatttggga 149820
cagagaacct ctagtgtttg ttcaataaat atatgaatgg atagagggac aggttgggtg 149880
gtggatagat ggatgaaccc acaccttgga agtgtatttg gctgtttgag aggttagaat 149940
atgttctcaa tttccaggca aaatgaaaat ggagaaaata taatgacatt aaggcatttt 150000
attcatcctc cccatctgcc actgggttaa agatactaaa taaacaagga actatctttt 150060
gcctggagga actttaaaaa cacctgcagt tttcaaaagg tgcagtgtgt gcctcccaca 150120
gcatgaccta ccatcattgg aaagcagttt gtagtcaatc aaaggtggtc tggagaaaca 150180
aagttttcag ggatacattg ttttttataat ttttcaccac atgatttttc ttctctccaa 150240
```

```
tgtagtggtc agttttctct tgcagtcgtc agcctgaaca taacatcctt gggattacgc 150300
tccctcaagg agataagtga tggagatgtg ataatttcag gaaacaaaaa tttgtgctat 150360
gcaaatacaa taaactggaa aaaactgttt gggacctccg gtcagaaaac caaaattata 150420
agcaacagag gtgaaaacag ctgcagtaag tcaccgcttt ctgtttagtt tatggagttg 150480
gttctaatgg gtcctttatt tgtatttaga atattgaagg gctattccca tttaaattac 150540
ttttttcagt tccttaagaa gcaaattaaa atcttaagat tcctaactgt gaaattacca 150600
tgtgaattcc attaaaactt tttccagatc attaccattc aatgggatga atttaccctg 150660
aggtttaggc taccaattat ttgtaatgta agtaactaaa tttagtatta gttatattac 150720
cttttagttg taggtcactc tctgctcatt tcagcctgta aagactacag ctacacacat 150780
acacacacag aggaatggaa tgagcacttt acatcaacac ttcctgttct ggctctagag 150840
cctcagcttt tgaagctggt gagagcctgg cctgtgctgg gccttggcca cgggcagcgt 150900
cagctttgag tcaagtgctg gtctggcctc cctagctttg agcctctgtc aattccctta 150960
atctgtttag gctttggctt cctcatccat agaatggaga tatgaatgat tcctacgccg 151020
tagtgctttg agagaattca gtgaaattcc tgtgtgtaaa accttccat ggtgcctagc 151080 acacagcaca cagccaatgg cccaatggct cctatcagct gtgggatttg tcatcagaac 151140
accaccagct ctgctccagg ctgccctggg taccatcaaa acacaccctg tgcccagcag 151200
cacctgctcc tctgcacacc tggttccttc agcaggggca gtggccgtgg gagcacagaa 151260
aacatggagt cccatctggt ttaattgatg ccattgccaa aggggaggac tcacggcacc 151320
ccctctcggg tgccagggtg cctggctccc accaggagga agacctgtcc tccactgtca 151380
ggcacatttc agtcttccca gcagccagca caactacttt gtccttccag tcacggtcgg 151440
cctctgggaa gcccagtctg tgtcctcctc cttcaggggt agccagcatg tctgtgtcac 151500
ccaaggtcat ggagcacagg gcccctcccg ggaaggtgcc gtctcctccg gcccctcggg 151560
tccctgctct gtcactgact gctgtgaccc actctgtctc cgcagaggcc acaggccagg 151620
tctgccatgc cttgtgctcc cccgagggct gctgggccc ggagcccagg gactgcgtct 151680
cttgccggaa tgtcagccga ggcagggaat gcgtggacaa gtgcaaccttt ctggaggggt 151740 aggaggttat ttcttaatc cccttgcgtt gatcaaaaat aaggctccag gttgttgtta 151800
tagctttaca ggcattctgt ttgattttct cttcctttta ttctttgccc ttggcttttg 151860
gaggttttgg gttttctgtg gggagacggg aagttgtttg attgcgttat ttttggcaaa 151920
tttaagcaca ataggaaata agcaagtatt attgcctaat ataatccaat aatttataga 151980
atctcttttc ctggaagtat cttaaatttt tctaagctac aaaaagttcc taagacaaat 152040
gagacagtca tcaatggttc atctagccaa caccgtggcc atttgggctt ttctttgtag 152100
tgcccgattc ctggtgtgtg aaaataaatt aacacaaatt atattgccaa gttaatatct 152160
gttttatgtg cccccagcat gtgttgaaca tcaaacagta ccaggacttt aaatatacc 152220 cacggacaaa gaaataattc ataatgatgt ttgttgaatt tagttgcaat caataaaaag 152280 tgcagttgt gaatgctctg aggttcttga tattgatgta aggctttgaa cgacaaatga 152340
ggacaaaaca taaataggaa agtaaaactg aaggatagag gccaaggcca tgttttagaa 152400
gatttaaaga aaaagggaaa tttggtgagc accataggaa ttacagatgg ctgtaggaat 152460
tcttcctgtt ttactctctg gcatggacc acagcttgga tccagaaata tttaggagca 152520
ggataagagg accaagttca attctatagg aatcctttag ctgataggct cagaacaaat 152580
```

```
cacataattg atagtgctgc ttcaacttca agtaaggaat attgatgcaa tccttacagc 152640
tacaaatgga cagtggtctc atgttttcag ttttcaagtg tttcttaaga ggcaaggtga 152700
tgaaaacgcc cacgtgggga gccccatgtc cttccattag tgtagagaaa cctggtgtcc 152760
agcagcacct gctccctctg caagcccagc cccttcagc aagggcagtg acccagagaa 152820
gaagcacaga agacacaacc ctgtatcaca ttttgtttaa tggtgccatt gaccaaaggg 152880
gaggatgaaa ggcacacact tttttgttgt tttttgagac agagtctcac gccatcaccc 152940
aggctggagt gcagtgatgt gatctcaact cactgcaacc tctgccccct gagttcaggt 153000
gattctcctg cctcagcctc ccaactagct ggaattacag gtgtgcacca ccatgtccag 153060
ctaatttttt gtagttttag tagagacggg gtttcaccac gttggccagg ctggtctcaa 153120
actcctgacc tcaagtgatc tgcccgcctc ggcctcccaa agtgttggga ttataggcat 153180
aagccactgc acctagccaa ggcacacact ttggagaata aacactcctt gttcgctgct 153240
ggagggtaga actatgcttg actactaggc agagtccagt cttactgaca aacagccgta 153300
catctgttct gtcttttcaa tcaaacatca gcttcttgct taacattgat gtgtacatct 153360
tgagggatgt caaaatattg taagctaagt ttttcatacc tgtgttccac actcaccatt 153420
tttagtaata accattgagc gagttcattc tccctccttc cttttctat cacttaatct 153480
aaaattatca ttttccagc ttaattttga taaccatgaa tctggtatta gaggcaggga 153540
acacctcctc aggactatct tttcttttat catttggctt gcttacccaa tatgcaaaaa 153600
ctatgctgta gaaaagcag aaaagatatc ttgattatga atgaagctcc tgtgtttact 153660
cagagagaag atgacccagg attcagttaa caaaatcagc tgattatatt actatatagt 153720
cctggagtcc caactccttg accattacct caagttattt ggaattttga agaggtgatt 153780
tgtgttcctg caataatgtc tcaggggtgg gctgacgggt ttcctcttcc tcctctcagt 153840
gagccaaggg agtttgtgga gaactctgag tgcatacagt gccacccaga gtgcctgcct 153900
caggccatga acatcacctg cacaggacgg gtaagagccc cttgctgcta tccacgtcca 153960
tttcatggga agggccttca cagaagccga acagtgatga tggcccaggg catcctgtgt 154020
gggcaggacg gccatcagag ccacttccca gaggagacgg caggcgctga cagcgctgtc 154080
cgggcagggt gtcggtgaca ttagcacaca cattagcctg cgatgaacat tcactctttc 154140
tgctgacacc cccaacctta tctaagctta tcaaatcctc acatttaacg gaggctgttt 154200
tcacctggtt tcccccatcc ctgacctagt cagcattgct ttatcgcttt catcaaacat 154260
cctcaaattc ttaacattag cttgtaatta attgaagaat tttaaagaa attgctagca 154320
aaacttttta aactgcacaa ctttgtatct atatgttcaa taacatatag atacaatatt 154380
ctttacaata atcttttaaa gaatatgagt gagaattcgg gcccctctca caccaaatgt 154440
cctgatgttg ttaattctca atgttattat atagggagct ctgttttctt gtgagcttca 154500
acagccagtt ctaaatctac taactgaaaa catttttag acattctcta aattgggcag 154560
aagatgacag gactgtgttt tgagggatag gctgccagcg tggctgctta caaagtaaag 154620
acttggttta taggtttgca tggtgttggg ttaaatttct gtcattaaaa taattggcga 154680
tattgacata gtcatctaat tatgctggct ctgggcacac acagcccttg agtgacaaa 154740
accaacatga gagaacttag ccaagggga agccttttcc tgctggtttt atttctgcta 154800
cttctgaagt gtggggcaca caacctgagc agtgctttta tttgagtccc aatgcttta 154860
tttgagtttt gcaaggttat tccaagtttt acaaatagaa ggtagcgtat gactcagtcc 154920
ttgatatgcc aaccactgca cagagacttg ccaccttcct gtcactggag aaacactcat 154980
```

```
gtgggttttc ttaaatttgc ctccctctga gcttcccttt aacttcaact ataatatgca 155040
agaaagacta tctgaccata aatacacatt tgggccaatc aagatggttt tgccaaggaa 155100
agatgcccac aatggttaag cagaatgcaa taatgtagag aatatcattt ctttcatgct 155160
ggtgtatatc atatgcattc aaaaacaggg agaacttcta agcaactaac agtgaccata 155220
tcaagcaggt gcaatcacag ataactggt tttctccttt aagaattttt ctatcatttg 155280
gctttcccca ctcacacaca ctaaatattt taagtaaaaa gttacttcca ttttgaaaga 155340
gaaaagaaag agacatgcat gaacattttt ctccaccttg gtgcagggac cagacaactg 155400
tatccagtgt gcccactaca ttgacggccc ccactgcgtc aagacctgcc cggcaggagt 155460
catgggagaa aacaacaccc tggtctggaa gtacgcagac gccggccatg tgtgccacct 155520
gtgccatcca aactgcacct acgggtgagt ggaaagtgaa ggagaacaga acatttcctc 155580
tcttgcaaat tcagagatca aaaatgtctc ccaagttttc cggcaacaaa ttgccgaggt 155640
ttgtatttga gtcagttact taaggtgttt tggtccccac agccatgcca gtagcaactt 155700
gcttgtgagc aggcctcagt gcagtgggaa tgactctgcc atgcaccgtg tccccggccg 155760
ggcctgtgtt gtgcaatgct gcacatcaca acaggagggt aggggacaa aagagcacag 155820 gtcctggcag ctgccacagt ctccaggggc ttttgcgttt ctctccagat ttctaaggtt 155880
aacatgggga ttagctgttt tgcaatgaat aaaaggtaac attgcctgga atgttgctta 155940
aagacacttt tttaaagcta gttgattgtt aagctgttgc tacttaaatt aaaactactt 156000
tgggccagac gcagtggctc acgcctgtaa ttccagcact ttgggattcc aaggcaggca 156060
gatcacttga ggtcaggagc ttgagaccag gctggccaac atggtgaaac cccacctcta 156120
ctaaaaatac acctgtagtc ccagctactc aggaggctga ggcaggagaa ttgcttgaac 156180
ccgggaggca gaggttgcag tgagccaaga tctcgccact gcactccagc ctgagcacca 156240
agagcgaaac tctgtcgcaa aaacaaaaa caaaaaaaa agctactttg actggaatta 156300
gcagaagcac tctgattgtg tgtatcttat ttactggaat aataaagctg tcaatcaaac 156360
tggatcccac tcaacaatca gaaagagaag ttgagctgtc atatagtagt tcacacttac 156420 ttctgttct caaaatcctc agctttgttt ggaactgtta ctcattcttt ctctgaatcc 156480
atctgtatga gttgtgtgcc cttgggcaag ggtcttacct tctctgtgcc tcactttctt 156540
ttctgtaaat tgggataata atgctgcata gctcacagga tttttatgac catgagttaa 156600
gatatgtcat atacttaaaa tggtgcctgg aaaatggtga atactgagtc aatgatagca 156660
tcattgatgg tgggatggtg atgaggaggt gggagtcaca atggtggtgt tgatggtggt 156720
gatggtggtg aggaggtggg agtcacagtg gtggtggtgt tgatggtggt gaggaggtgg 156780
gagtcacaat ggtggtggtg atggtgttga tggtggtgag gaggtgggag tcacaatggt 156840
ggtagtgatg atggtgttga tggtggtgag gaggtgagag tcacaatgtt ggtggtgttg 156900
gtggtggtgg tggtgaggag gtgggagtca caatggtggc agtgttggtg gtgaggaggt 156960
gggagtcaca atggtggtag tgatgatggt gttgatggtg gtgaggaggt gagagtcaca 157020
atgttggtgg tgttgatggt ggtgatggtg atgaggaggt gggagtcaca atggtggtga 157080
tgagggtggt gatgatgatg aggaggtggg agtcacaatg gtgtcagtgt tgatggtccg 157140
atggtgatga ggaggtggga gtcacaatgt tggtggtgtt gatggtggtg atgatgatga 157200
ggaggtggga gtcacaatgg tgtcagtgtt gatggtggcg atggtgatga ggaggtggga 157260
gtcacaatgg tggtggtgat gacggtgttg acagtggtga cgaggcggga gtcacaatgg 157320
```

```
tgtcggtggt gatggtggtg aggaggtggg agtcacaatg gtggtggtgg tgatggtggt   157380
gatggtggtg aggaggtggg agtcacaatg gtggtggtgt tgatggtggt gatggtggtg   157440
aggaggtggg agtcacaatg gtggtggtgt tgatggtggt gatggtggtg aggaggtggg   157500
agtcacagtg gtggtggtga tgagggtggt gatggtgatg aggaggtggg agtcacaacg   157560
ttggtggtga tgatggtgtt actggtggtg acgaggtggg agtcacaatg gtggtggtgg   157620
tgatggtggt gaggaggtgg gagtcacagt ggtggtggtg ttgatggtgg tgatggtggt   157680
gaggaggtgg gagtcacagt ggtggtggtg ttgatggtgg tgatggtggt gaggaggtga   157740
gagtcacaat ggtagtggcg atgatggtgt tggtggtgag gaggtggaag tcacggtggt   157800
ggcgatgatg gtggtgagga cgtgggagta acaacagtgg cagtgacggt gattgagaca   157860
tgatgatgat ttgtcaactt tctaggaaaa caatcatata atctccaaca gtgatatctt   157920
aatatctttt ccaaaagtat cagatcatat tataagggcc aagtttccag aataatatca   157980
gacataatga cagtggacat cagagcttgg catctaaagg taatgggaat agctctaatg   158040
tctcagcgtg aaaacaaca tttgctatta gtctgagata ctaattatct agttaaggaa   158100
gtactcacct atacctagtt tttaactgtt ttttaaaatc tggaattgat tttgaatttt   158160
aacaaatatt tccctgggaa caatgtaaga ttcttcatat tttcgccttt gggtatacca   158220
acatgccagc tctgttggcc actttgtgag ctcgatgaag catggtataa aagatgcttt   158280
gctagtgttt cacgtaatct atttctataa gcaattttgg agctaagcct ctgaaacaga   158340
attatattat ctgtatagaa taaatgtttt atcttccccc ttttctttct tctggaatag   158400
atgtgcatca gtatctctgc atcaaatatct ctatatcagt atctctgtgt cagtgagcat   158460
atgttgctgg gcttagggga ggtccagaaa gtgattgggt tttggcattt tcaatacact   158520
tactttgtat aagaaatagt ttgccaaata tagaaagagg ggatttagtc aagatttaaa   158580
ttaaaaatgt tagtggtcat ttttctaatg tctttctatt ttttcccagg tcctaataaa   158640
tcttcactgt ctgactttag tctcccacta aaactgcatt tccttctac aatttcaatt    158700 tctcccttg cttcaaataa agtcctgaca ctattcattt gacatatgga attttataaa   158760
tattttcttt agtatgtgtg attacattcc tgattctgag ccttttttaga tgagtatata   158820 gtttgatata atcttgttat tgccacctgt gtcttctccc aaagccatta attatatagg   158880
aattacacga tagaaatggg tttaattttt aaaatacggc caagtgttga tgagagggaa   158940 aatttttta atttctttca ctgagtattt atgacgtgca caacattcct gaatatattg   159000
tctctctcat ttctcagatg ggatgtattg ccttctccat ttctattgtt aaagaaacac   159060
ttacaggggt ttctttaaca acttgtgaac agcagcatca gagcccagac tacagcataa   159120
gcagctgctg attccaaaag ccctaccttc caaccgggca ggtgcagcca cccagacgag   159180
ggggaggaac cctggaggaa tagctatttc tttttttttt ttgtcgagac ggagtcttgt   159240
tctgtcaccc tggctggagt gcagtgccgt gatcttggct cactgcaacc tccacctccc   159300
aggttcaagc aattctcctg cttcagcctc ccgagtagct gggattacag acacctgcca   159360
ccacgcctgg ctaattttg tattttagt acagacaggg tttcaccatg ttggccaggc    159420
ttgtcttgat ctcctgacaa gtgatccaca ccttggcc tcccaaagtg ctgagattac     159480
aggcgtgagc cactgcgccc agcaggaata tctattttta aatggaactg tgtttcata    159540 gtacacggtg aggagaaagt tgctttgaaa tctttatcct aataaaccaa ataatatgaa   159600
aatttgccta ttttaattat atgtaacaaa gtttagttac tgctataatt gcaaatatgt   159660
ataaattcct taccaaaaaa aaaagaatca agtgggagcc agagaataat ttttctgaca   159720
```

```
gaattaaata acatgctata gctgcttgag ttcatactca atagtcattt ctgcagagtt  159780
accgagggcc tcatcagcgt cagcaggagc ccctcgcctt ctgacgctct cacatccttc  159840
tctcctgcag ccccgtcctg ccactgtcct tgtccagctt ctcttcaagg gtcaactggt  159900
ctacctttcc ctacaagtct gtcacagctt cttgttagca atcccatatgg ttgcccaaaa  159960 gcattttcag agcctgcata agactgcatc ttgtagaaaa tttgcagttt caatctgccc  160020
tccctctgcc gggtgttccc attgtattgc attcagcagg cagggagaga ctgctattag  160080
gtctgttcct gagtgactgc tttctgtctc agactgtttg gtgtctgtag gaggtagtgg  160140
ggtgggcagt aacgaggtct cctgtatatt ccacccctac gaagcctgtg tgtttggttt  160200
atgaactaag ctcaaaagca ccacagggg aagactgcag tacatgacac catggaaaag  160260
agggagcacc cagaccccca aattaagaag agcagtgtag agaacagaga cctggagagc  160320
agagatagaa actgttagga tcagattata gtgttacacc agggctcccc aggcctctca  160380
catattgaaa tgtacttgtc catctttctc caggccagga aatgagagtc tcaaagccat  160440
gttattctgc cttttaaac tatcatcctg taatcaaagt aatgatggca gcgtgtccca  160500
ccagagcggg agcccagctg ctcaggagtc atgcttagga tggatccctt ctcttctgcc  160560
gtcagagttt cagctgggtt ggggtggatg cagccacctc catgcctggc cttctgcatc  160620
tgtgatcatc acggcctcct cctgccactg agcctcatgc cttcacgtgt ctgttccccc  160680
cgcttttcct ttctgccacc cctgcacgtg ggccgccagg ttcccaagag tatcctaccc  160740
atttccttcc ttccactccc tttgccagtg cctctcaccc caactagtag ctaaccatca  160800
cccccaggac tgacctcttc ctcctcgctg ccagatgatt gttcaaagca cagaatttgt  160860
cagaaacctg cagggactcc atgctgccag ccttctccgt aattagcatg gccccagtcc  160920
atgcttctag ccttggttcc ttctgcccct ctgtttgaaa ttctagagcc agctgtggga  160980
caattatctg tgtcaaaagc cagatgtgaa aacatctcaa taacaaactg gctgctttgt  161040
tcaatgctag aacaacgcct gtcacagagt agaaactcaa aaatatttgc tgagtgaatg  161100
aacaaatgaa taaatgcata ataaataatt aaccaccaat ccaacatcca gacacatagt  161160
gattttaatt atttaagagt agtttagcat atattgcttt atgatttaat taaaaatctc  161220
caaaatatat gccaaagaag tagaatgaga aaaatgtata tttctctttc acttcctaca  161280
gatgcactgg gccaggtctt gaaggctgtc caacgaatgg gtaagtgttc acagctctgt  161340
gtcacatgga cctcgtcaag aatgaccaca ctgctgtggg tgaagatgct ttcctgcatt  161400
tctgactgtc ctctgtcctg atcaagtttc tatggctctg ggccagccta ccctcagcca  161460
gggtttctgc agagactgcc cagctggttc cacgtggctc cacgtgccaa ctttgtcctc  161520
agtggaggga aagttggaca cacagtgctg gggctgctcc ctgctccgcc gttgctcgat  161580
gcatggcctg cctctgaatt ccttggttcc actggttttg ctgggtcctt ctgtgcctct  161640
agctcctctt ttttctgtc cacttacccc attggtccca tcacaagcct gtgtgtgagt  161700
ggcctttctg ttcgatgaca acctccagca taggggagtg tttctccttg ctttctttcc  161760
cagacacact gcccagcaaa ggcaaaaggg cttccttcaa catcagctct ggccagtttg  161820
ccagagcaaa gccctgagaa aagcaaggtt gaaaagtctt attcaaactc accaggaaag  161880
agtggtgtta ctctcgatgg cgtctagcca ggaatcatgg aattatacac cgagcacctg  161940
tttgccattt tggatgtttc caaacatgaa ccaaacttcc aggcccctct gccatctctg  162000
gtaacattta caaagtccct tcctcaccac tgcccttcct tcattttggc atgctcctcc  162060
```

-continued

```
gcccccgagt tgacagccat agctctctct cctgccacca gtgtcacatg atcgaggaag 162120
aaggcaactt caaaaagact gggtcccctt ccactcccat ctcttcagtg agctgctagg 162180
acacccagca gaacttcccc actccacact gcaatctcag ggatcttagt cacggggctt 162240
tccaccatgt ctccacctgg aaaccagtca tggccattcc ttcttacatc tgctctttc 162300 catctttttc ttctcctcct gttcacccgc ccttactctt gtggcgccct atggatatgc 162360
gctccatagc aaatgattct ttatatctta cggtattcta gtgagctggc acatgtggct 162420
tctggtttcc tctctctgga actagacatg acctctgtgg gagggaggat taaatgcacc 162480
ctacagtctg aggctgcatg atgacatcac tcatcacaat gatgctttct atgtctgaat 162540
cctattcctt tataaccct ttcaagctcg ttcagagagt atttcacaca atccatgtgc 162600
tcatcttaaa agccaaggac ccagaggagt ctcagcattg ccaaaaagtc ccttcaccca 162660
gcctggccag aggcagtgcc tggtccatgt gtatggacta tggcacttca attgcatgga 162720
aatactcttg gaatgaacaa aataccaatc catgaaaaag cattattgaa gtctaagtta 162780 tttttgaat catattttgt taatcaacaa attgaaaaat actcattata tggagaggtc 162840
cagataaagc ctcaattta aaaaatgagg aaaagtgtgc ctggtagggg actggggaga 162900
gcttgagaaa gttgaaacg ttgccttaga agcctgtttt ttctcctttt agaagctaca 162960
tagtgtctca ctttccaaga tcattctaca agatgtcagt gcactgaaac atgcagggc 163020 gtgttgagtg ccaaggccat ggaatctgtc agcaacctca cccttccttg ttcctccacc 163080
tcattccagg cctaagatcc cgtccatcgc cactgggatg gtgggggccc tcctcttgct 163140
gctggtggtg gccctgggga tcggcctctt catgcgaagg cgccacatcg ttcggaagcg 163200
cacgctgcgg aggctgctgc aggagaggga ggtgagtgcc agtcctgggt gggctcagga 163260
gccctcgcac cccgacagga acaagggcca gccccgagaa cgggccatta gcagttgtgt 163320
atgttagata cataattgta ttatgatgca gaaagaatct ctgaatgtgc agttataccc 163380
agttggtgac atgttggtac atccatccga ggaaatggca atgtttctag gctgcaccct 163440
tcaatgtcca caaagctgtg tggcatctgc ttaggacccg gtgcctgtgt gtgcatagga 163500
gggaggccag gaagcctggc tgttgatccc atgctggcac tgtggcgaag gcgagagatt 163560
cctgctttgg aaaacaccat tgtccacaca gtggctttgt ccatgatgga cttcgccaca 163620
gcccagtcct gtgctggaag ccatgttctc tggaaagagc aacccagcgg ctcataagca 163680
taagcgcgtg tgatgtgccc caaccaaacg accgccatgc acaacttccc taccggagtt 163740
ttcaatccag ttaataggcg tggaaacaga catagaaatt gtgtttgttg aaaggtagct 163800
gttcagttaa agaacacctg tatcagagcc tgtgtttcta ccaacttctg tcaagctctg 163860
tagagaaggc gtacatttgt ccttccaaat gagctggcaa gtgccgtgtc ctggcaccca 163920
agcccatgcc gtggctgctg gtcccctgc tgggccatgt ctggcactgc tttccagcat 163980
ggtgagggct gaggtgaccc ttgtctctgt gttcttgtcc cccccagctt gtggagcctc 164040
ttacacccag tggagaagct cccaaccaag ctctcttgag gatcttgaag gaaactgaat 164100
tcaaaaagat caaagtgctg ggctccggtg cgttcggcac ggtgtataag gtaaggtccc 164160
tggcacaggc ctctgggctg ggccgcaggg cctctcatgg tctggtgggg agcccagagt 164220
ccttgcaagc tgtatatttc catcatctac tttactcttt gtttcactga gtgtttggga 164280
aactccagtg ttttttccaa gttattgaga ggaaatcttt tataaccaca gtaatcagtg 164340
gtcctgtgag accaattcac agaccaaagg cattttatg aaaggggcca ttgacctgc 164400 catggggtgc agcacagggc gggaggaggg ccgcctctca ccgcacggca tcagaatgca 164460
```

```
gcccagctga aatgggctca tcttcgtttg cttcttctag atcctctttg catgaaatct 164520
gatttcagtt aggcctagac gcagcatcat taaattctgg atgaaatgat ccacacggac 164580
tttataacag gctttacaag cttgagattc ttttatctaa ataatcagtg tgattcgtgg 164640
agcccaacag ctgcagggct gcggggggcgt cacagccccc agcaatatca gccttaggtg 164700
cggctccaca gccccagtgt ccctcacctt cggggtgcat cgctggtaac atccacccag 164760
atcactgggc agcatgtggc accatctcac aattgccagt taacgtcttc cttctctctc 164820
tgtcataggg actctggatc ccagaaggtg agaaagttaa aattcccgtc gctatcaagg 164880
aattaagaga agcaacatct ccgaaagcca acaaggaaat cctcgatgtg agtttctgct 164940
ttgctgtgtg ggggtccatg gctctgaacc tcaggcccac cttttctcat gtctggcagc 165000
tgctctgctc tagaccctgc tcatctccac atcctaaatg ttcactttct atgtctttcc 165060
cttcctagct ctagtgggta taactccctc cccttagaga cagcactggc ctctcccatg 165120
ctggtatcca ccccaaaagg ctggaaacag gcaattactg gcatctaccc agcactagtt 165180
tcttgacacg catgatgagt gagtgctctt ggtgagcctg gagcatgggt attgttttg 165240 gtattttttg gatgaagaaa tggaggcata aagaaattgg ctgaccctta tatggctggg 165300
atagggttta agccccttgt tatttctgac tctgaaactt gcattcaatt cactccacca 165360
agttatctca tctttgaaat ggctttttt aaaggtgcct agaatatgat ggcgtgcagt 165420
ctataaactg ttgcccacct tctgtacttt ctctcagaat aattcacatt cttctccagt 165480
gtctgttgat tgttactttg tggaataagt tcttggaaaa ttccacaaga ttattgttat 165540
cttcttacta ccaattctat tgaactttct ccaccttctc tgggccttcc ccagccagtg 165600
gtgggaagat gctggctgga gtctgacaga gcctcttcta cactggcctg gcttgctgt 165660 gagttggtgg aaacctttgc tcttgtccca acacagagca agtgaaagag gaggtcaagg 165720
ggctcaggca gcggactagg gaagcagaat cgaggaaaag gaaaaatggc tgacttatta 165780
cctcaaaact ctagagaatt tagttgatct tacagccaag aaggacaaaa gccagagagt 165840
aatatcctcc gcctcatgtc taacccacag aatacatagc aagtaaagag aacatgggcc 165900
tttataaaaa tgtcttaaga tacaatttt taattggagg aaatctacag tttaattttc 165960
tctgggcagc ttttcttcct tttattatag taggggaaat cccatgttga tatacttcta 166020
aatgaaagat gatgaattga tataatacaa taaaaaatct gtaaaattga tgatatactt 166080
atcaagaaaa attagctttc attttaacgg tttacaaatt gagtcaagtc ctagtaacaa 166140
aatgttaagt ctattaacat aaccacaaga aatacaggaa gacgggcaat ctgtgaagcc 166200
tttcacttac aatctctggc ccctcacctg tgctgtgtag gaaaatcttt gtgcacaatt 166260
tgcttcctta attcatttt tattcattca acacattcta ataattata caaaatcatg 166320 ttgaaatgtg aatttcagtg gtatttataa atgcagtgtg aggagggttt ggatgtattc 166380
taagacaata gttgtgcttt gggaaggaag cagtgttcac tgaaaagtgc ccccaggacc 166440
ttttaattgg aggaaatatg cttctgtgga gttggaaatg gggtagaaga tagataaggt 166500
caaggcttaa aagttaagtg cacccaacat ctgaagcgtc catgggcctg catggtggc 166560 tttcgcctgt aatcccagca ctttgggagg ctgaggcagg aggatccctt gagcttagga 166620
gtttgagacc agcctgggca acatactgag acccagtctc tacaaaaaat aaaaaattag 166680
ctgggtgtgg tgtctcatgc ctgtagtccc agccactcag gagatgggaa gatgccttga 166740
gtccaggaga tctaggctgc agtgagctaa aatctcacca ctgcactcca gcctgggtga 166800
```

```
caaagcaaga ccctgctcaa aaaaatagtt agatataaat attaatatag atacctatat  166860
atatctgaat atagatatct atatatactc tgtatatagt tatttagata tataaatata  166920
tatgatatat atttagagag atatatattt agagagatat atatttagag atttatatat  166980
attttatata tatttagaga tatatatctc taaatatata tctctctcta aatatatata  167040
tatctctctc taaatatata tatatcccta aatatattaa ataaataaaa gaaataaaag  167100
aaagctcagt ttggcctcct gcttgtcctg tctcctcatc ccctcttccc cctccatcat  167160
tttatttcct tgccccatgt ttcttcactg cggccatgtc cccctcctc tccaatgatg   167220 gatgtcatgt ctgctgcagt cagagggcga caagcctgga gtgttccctg aagcctgtgg  167280
tttgtggttt gtcctgcagc tcaggctgcc caggcctcac cagcaatcct ggcgggcagg  167340
gcaccacact gggatggaga gggggaagct ggaggaggca ctttctggta aagaaagcaa  167400
aagccagcag tgcccaggcc aatttcaaca gggagttaaa tagcacctta atcctgtggc  167460
aggacagctc atggggccat gtgtgctctt agaaagactc acatgcacgc atgcacggca  167520
gcaatgactc catactcacg ttcccctgca gacaccaggc cccacagcc ggcacacaca   167580 ctgcagcccc agttccatgt tgctagcagt ggcttagtga atgagtaaag ttcttaaaat  167640
gcaggggaca cctgcccttc attcataagg ctggacgtac acctctcctt aaggagttca  167700
agagctagtg gaatcccaat tcatacggta gagccattca cagatgagag agacaagcca  167760
gaaggaagga accaaaagtc atgtcagcag ttaggacaaa ataacaggct ttcaaggtca  167820
caaagcctca gggacactcc tgcggtggga ctgggctagg agccatgggg gctccaactg  167880
tgcgctctgc ctgccagcct gtgggtgctg gggctccacg aagattgttg tggaatacca  167940
agcatgcttg ctgtaggtca cggtgcacgt ttactacttc caagacaaac agccgagaac  168000
aaagctcgct ttagcttctg cgtacaccga acgggacaca cgactgaaca gcgttcccat  168060
tgtgcctgct gggtggggag gaagtgatgg cccagtgggt ctatcagatg ttagtaggat  168120
ggggcctggc ggggctccag gctctgtgtg gccgacaccc acgcccccg ctctgctccc    168180 cattcccagc cccaggtcag ccctgcgagg ccctgcagca gatgggctgc tcaaactgct  168240
ctggtttgca gattttttctt ccctctcaaa tgaatacaat atgttttcaa gtctcaacca  168300
gatcttgaga aaataggaag agccagaggg tttctttggt gttatggttg tacagcttcc  168360
cagactccgg gggagagatg tgatttgtgc tttctggcaa tcccatggcg tattaaattt  168420
tcataggctt tccagtttaa atttagggta ggcaatggaa gggaacgcaa aacagatttc  168480
taggtgtact gtgtgtgtgt ctcccacgtc taaagtctgt taactggagc acccaacagg  168540
ccccacaggc tgccttcaca cagaggacct ggggcgcctc cgacccattg gggtgagcag  168600
tgggccatgg agggagccag ggtcaggaga cctggttgtg ggcctgacct gaccctgctc  168660
agggtggcct caggtgggcc gttcacctcg tcagcctcag cttaccctct gactacagtg  168720
acctcagaca aaatacgctt cctggccctg tccagttctg actttttata aacaagcact  168780
tatccaagtt aaagggatat tttcaatatc tactgagtcc acagatatta aatatctcct  168840
ctcttcttta aaattgtggc attatcttta gaatataaaa ggaaaataac acacactctc  168900
cttgaaaata gagagcctaa acactctgca ggaaatattt aaagctatag tttttgtttg  168960
tttgtcttga atgcaagtgg cctggacttt gacttgcttt gagtctttga ccttcatgac  169020
ttcagtacag ttcaaccctg acagttttga agtaggtatg tgcctagatc tgccctagtc  169080
cctgctggaa tgttgaagaa gcaaaggtcc aggcctcag agcacttgcc acgtacttgc  169140
caacagatac ggggcggaga cttgagtcaa cgtaagagca agtgtgtgcc gggtgatccg  169200
```

```
acactgcaga gcgccagcta gaccctaagc gtgtgctagg ggctgaccaa gccgttcttt  169260
cctcaaaaac ttggtgggga gggtatttt aaaatcacac aaatatttaa gtacagatta  169320
tgatgactgc ctcaaagcag tggctcttca gcttcatcaa gcttcagagt ccagagggtt  169380
tgttcatatg gaaggctagg cctgtctcct gcatttcacc ctcttggcct gggggcggga  169440
cccaagaatg tgtggctcta aaaggttccc aggcaatgct gaggctgctt tctgaaggaa  169500
aaactgcaag ataccaggag agtttcattt agattgaaga gtcgaggaag gctcctctga  169560
gaaagagtct gctaaggaag gaggaggtgg gttctgggga cagaggttct cccgtgggta  169620
agggtggagg gaagctctcc tggggagaag gtgggcagga ggaccagagg ctggaggag  169680 gagggcagtc agcctcgggg cttcccagga acagggacgg ccagggcagg gtttagggca  169740
aggaaagcgt gtgagcatat ttgtatttta gtaaatattt acagtttgcc ctccatgtct  169800
gcagtttcat atccatggat tcaatcaacc acaatgaaaa acgttgggga aaaaaattgc  169860
atcggtactg aacatatacg gactttttt cttgtcatta ttccctaaac aatacagcat  169920
aacaattatt cacatagcat ttgcactgta ttaggtacta taggtaatca ggagatgctg  169980
tagatgggag gatgtctgta ggttacacac aaatgctgtg ccactttata tcaggggctt  170040
gagcatcctc acattttgat atttaaggga ggtcctggaa ccaattcccc agatactgag  170100
ggtccactgt ctgtgtcccc tcgcccacc ttgcctttgt ctcctgtctc ctatctccac  170160
cctgcctccc gccagcctgt tgctcctgac ctgcccgggc accctggagc agcaccctat  170220
ctcagagcct ggctcagtgt gttcacttct gcagagaaac taacttgccc aagtccacac  170280
tcaaaacata ggcattgctg agatgtgaaa agcagctgtg gatgctttct gctacagtct  170340
gtgtgttctt ttccatatct gaataaaagg tcaccaccat ttgtatttta aagagaaaga  170400 gaattatgg gtggaaattg gggattccct cattctcagt cagacagaaa agagggcccc  170460
attgtgtgcc tgattgcaaa taaatttagc ttcctcagcc caagaatagc agaagggtta  170520
aaataaagtc tgtatttatg gctctgtcaa aggaaggccc ctgccttggc agccagccgg  170580
aattagcagg gcagcagatg cctgactcag tgcagcatgg atttcccata gggagcctgg  170640
gggcacagca cagagagacc acttctcttt agaaatgggt cccgggcagc caggcagcct  170700
ttagtcactg tagattgaat gctctgtcca tttcaaaacc tgggactggt ctattgaaag  170760
agcttatcca gctactcttt gcagaggtgc tgtgggcagg gtccccagcc caaatgccca  170820
cccatttccc agagcacagt cagggccaag cctggcctgt ggggaaggga ggcctttctc  170880
cctgctggct cggtgctccc cggatgcctt ctccatcgct tgtcctctgc agcacccaca  170940
gccagcgttc ctgatgtgca gggtcagtca ttacccaggg tgttccggac cccacacaga  171000
ttcctacagg ccctcatgat atttttaaaac acagcatcct caaccttgag gcggaggtct  171060
tcataacaaa gatactatca gttcccaaac tcagagatca ggtgactccg actcctcctt  171120
tatccaatgt gctcctcatg gccactgttg cctgggcctc tctgtcatgg gaatccccca  171180
gatgcaccca ggaggggccc tctcccactg catctgtcac ttcacagccc tgcgtaaacg  171240
tccctgtgct aggtctttg caggcacagc ttttcctcca tgagtacgta ttttgaaact  171300
caagatcgca ttcatgcgtc ttcacctgga aggggtccat gtgcccctcc ttctggccac  171360
catgcgaagc cacactgacg tgcctctccc tccctccagg aagcctacgt gatggccagc  171420
gtggacaacc cccacgtgtg ccgcctgctg ggcatctgcc tcacctccac cgtgcagctc  171480
atcacgcagc tcatgccctt cggctgcctc ctggactatg tccgggaaca caaagacaat  171540
```

```
attggctccc agtacctgct caactggtgt gtgcagatcg caaaggtaat cagggaaggg   171600
agatacgggg aggggagata aggagccagg atcctcacat gcggtctgcg ctcctgggat   171660
agcaagagtt tgccatgggg atatgtgtgt gcgtgcatgc agcacacaca cattccttta   171720
ttttggattc aatcaagttg atcttcttgt gcacaaatca gtgcctgtcc catctgcatg   171780
tggaaactct catcaatcag ctacctttga agaattttct ctttattgag tgctcagtgt   171840
ggtctgatgt ctctgttctt atttctctgg aattctttgt gaatactgtg gtgatttgta   171900
gtggagaagg aatattgctt cccccattca ggacttgata acaaggtaag caagccaggc   171960
caaggccagg aggacccagg tgatagtggt ggagtggagc aggtgccttg caggaggccc   172020
agtgaggagg tgcaaggagc tgacagaggg cgcagctgct gctgctatgt ggctgggcc   172080 ttggctaagt gtcccccttt ccacaggctc gctccagagc cagggcgggg ctgagagagc   172140
agagtggtca ggtagccctg cctgggtgct ggagacaggc acagaacaac aagccaggta   172200
tttcacagct ggtgcggacc cagaaagact tctgcttttg ccccaaaccc ctcccatctc   172260
catcccagtc ttgcatcagt tatttgcact caacttgcta agtcctattt ttttctaaca   172320
atgggtatac atttcatccc attgacttta aaggatttgc aggcaggccc tgtctctgag   172380
aatacgccgt tgcccgtcat ctctctccga cagcagggca gggggtccag agatgtgcca   172440
gggaccagag ggagggagca gacacccacc cggcctgggc aggtcctcct cattgcttgc   172500
atccgcctgg ttagcagtgg cagtcagtcc tgccgagtca ttcgtgaggc gctcacccaa   172560
ctccaggcag atgtaaaagg tgacctacaa gaagacaaac aaaaacatct ggagcgctct   172620
tatgccagca tctgcccttg acaccaccag gcaggctgtt gctgggagcc gtggtgcttg   172680
ggtaagctcc ttcccatggc agagctcctg ggacgcattg tagaagcagg gaccacctcc   172740
caggataacc agatagcagc acaccctgca cagccccttt tactccagca tcatcgggca   172800
ttgatatctc agctgcagcc acaggcggcc cccagcaccc caggaagtgg ggagcgctca   172860
tgcttctctg agcacaaaaa tcactgaata ttttgccat tctcatggtc ataacccggg   172920
ccacagagta gaacactcct atcactgttg ttagacagtg gtcctgggag agggtcttgt   172980
gtgcctcgga tgccagggcc tcttttattt gggaggtgct tgttattct gtgtgtggct   173040 gcatttgttt cccaagactg ccacaacaaa tcatcaccaa cttggtagct caacatagca   173100
cagctttatt ccctcctggc tctggaggcc aggtgtctaa aaggccatgc tcccacaatg   173160
gttctgagga ggatccttcc tgcctctctg gcttctggtg gctccagcat ccctgggctg   173220
tggctgcacc tccccatgtc aacctccgtc ttcacaaggc cttttcctgt gtctctgcaa   173280
ccacaggccc ctctcctttc tcttaataaa gataccagtc attgagtttg aaaattgcta   173340
agagagtctg ttgtaaatct tcttagcaca aaaaaaaatg acagatatgt gaagtggtag   173400
atatattaat tagtttgatt tgatcactcc gctatgtgta taaatgtcaa acaaacatt   173460 gcactccata aatatatata ttaaaaaaga tcccagtcat tgcatttagg cccacccta   173520 aatccaggat gatttcattt caagactttt aactagattt gcaaacccc atttccaaat   173580 aaggtcacat tctgcagttt tgggtagacg tgaaatgtgg agacactgtg caacccactg   173640
tcttggggag ggggtggtca gcctggggca gatgttgctg ggtgtggagc tacatccact   173700
catgccctga cctggaaccc agacctgctt ccccagctct cctcctggtt atctgaagca   173760
gggaatggag agcactgccc tccttgccca ggcagtctct atcacctggt tttagtttct   173820
tcttagcaca tattgcccca gaatatctgg ttggtttatg gcttacttga gtttgtgcct   173880
acctgtccca accgggaggt gagccctggc tattccccaa acccggccct gcatgtggga   173940
```

```
gctgcccttc ctccgttcat cagagggggc aacagtcca cagctgttct taatcatctc 174000
ccagtaaccc ccagctccac aaaggtgact ccttacatgg tggagaggtg gtcgggccat 174060
ccgtgtgaaa tgtgtatgtg accgttttcc ttaaggggca cgtagtcttg gcaggtttcg 174120
ctcaatatag gatgagctca ggactccagt ggactgtgga ttcagatctg gattctggcg 174180
cattcgccgt gtgaacgggg gcacgttgct ggcctgtctg cgcctcgtct cccgactgtg 174240
gagtgtgttc tgccccttgt ctttctggga ggtagggagg gcagtgagcc ccttcgcatc 174300
gcccaccaca ggcccagcac atggctgatc cccactgagt gttcttttcc tcctttgatc 174360
cccctttggct gacctaggtt ggagcagcca ctaaaatata cccagaaaca tcttcctaat 174420
ctacatctgt gccaaccctc attccctggc gcagcatgac catcacatgc ccgccattgt 174480
tcctgatctc tgctgctcat gacctgctct ccagcgctcc ttctcatgct cacattccag 174540
ttggcctgac ctagataagt ggaggtttat ttgaccccaa aaattagcct tctacaaacg 174600
aatataatag tgtccattac agagaataaa cttagtgcgt gtcccattta agcagaagtt 174660
actgaaagcc tgagtttaag tttccagggc ctgaaagttt tccatgacag ttttctgcat 174720
aatattacct acaatttcaa tctgttattt aaagccattc ttgtgtttgt tgtactttga 174780
ttagctttat tttgatttga agtccttta cattacgggc agttaacgct tgtctctgt 174840
tagatttgct tttagttca caagagaaac ctcattcctc tgtatttgaa tagttgcaat 174900
gatggaacag ctgtccctgg agggaaatga aaacagtgat tccccaaatt gtgacaatag 174960
aaatttgctc ttgggttact tacaatgtat ctgagtatta aaaaattttc tttttaaacg 175020
tttgaagtaa aactacccag aaacacttag tggctgacca gaaactaaac tcctggcatc 175080
ctcaaaatgg gatttattgg cttataaatg tcctgtgttg actcacaaag gcacaaacta 175140
tctaggtaag ttttcttcta aatgttgatg ggagagctgg ccactgttat gcaagtttca 175200
ttgtcctgac taaactgcca aagagattac ataaaattat atcaactaga caaaggaaa 175260
aaggaaaaaa aacagaggtg tcttgggagg aatccatatg agaccagtag accatgagag 175320
agacatccct tgccatctac aaggaaaatg gattttgttc tccatatgca aaaccatctc 175380
aggagcttgc ggagacacca cttgcttact agccagaaag agcaggtgcc tcctaaattc 175440
cccacacagg agctcacagt ggctttcatg cactgggatt aagttagact taagaaagcc 175500
tgtctactct tcctgggatt tacaagccag ctagtaaatc ccagaataaa tcacacggca 175560
cagtcatcca aagatcccgt catccgtgcc gtttggaaag ccctgctcct gtgccaccct 175620
ctccccgtgg agcctcccat gcccaggact gcagagtcct gccattcaga ctgcaactca 175680
tctcacattc ttccaaacta tttggacaac agagctttct catcacctaa tgcagattac 175740
agtctcacag aattgagtgt tcaggcagac actgatgtgg ttctgtagta cagcaaacaa 175800
tatcagttta cagtcctgag gccaggcctg gtgaacaacg cacggtagcg gtggggcagg 175860
gttctcagaa tgaaactggc ttacacatgg cactctctga ccacaactgt ataagcacca 175920
aactacactt agttccatct atgaggtaaa atttaatgca gatgaacatc aaagaaaacg 175980
tcaaaggctc cttttttacaa gtacgtgggc tacttaattt ggtccaagtc cattttaaaa 176040
agccctaggt gctttcacgg ctctgctact gacaagaagc cccagtgcct gtgagctgct 176100
aatgggaggg agaggaagat gagctgagtg ggccgggcta tcccgtccac accgggagac 176160
agggaaggag actccaagct ggtggtgcca gcacattcca ggccactcag gcctattcct 176220
aggtgccagg tcacgaaaac cacgctgaca gatcgtgctg tgtgcgtgtc atagcacaca 176280
```

```
agcaggactg tgagagagtg aaagtgacac tgggtggagc actgaggaag ggccacagtg    176340
tgttggtgga gataggctgt catggagaag agaccctggc ttgctctaca ttgcttccaa    176400
tgcaactgca aggcaggtcc cagagggctc cggccttcgt catccaggtt tgctccctcc    176460
cctcatggct ttcccatcct cagatgagga ctcggcagag cctacccctg ctgactaact    176520 gtggcccag ggtggtgact cagccctgca cctcctgatc ccgtctgcac tgggccagag    176580
aggatgactt acccagcacg ttcacatcac acagctttgt ggattcctag gtccaaggac    176640
cagagatttc agttatgtga gttatttttt ttatttgttc ttgcgtattc cacaaagggt    176700
cgcagctaaa cttaacctaa tgatcacttt agtatatcac taaaaagaca aagctcacag    176760
tgctgttgaa gcacattcat catctttaga cattttgact agttatttct taagcattta    176820
cctgctagtg ttaagcatca catgaaatac atatagaagt aagacaaaat ttcttatctc    176880
cccaagtttg ccaacaaata cagagcagga agggaagcag gtcagagcag gaggcgcagc    176940
tatagtgagg ccaccatgca aggcacaggg agggtgagct ccaagtttga atggaatggg    177000
tctgtcagcc aagcccctg gctctgggaa gatagcagtg aacaagccag atggcccctc    177060
accctccaga gccgtgagtc ctgcagacca aacagcgtga caggtccttt ccctgtccag    177120
gaggcctctg tgggtgagag ttggctgcgg acagggcgtg aaggcacttg agggtgggga    177180
agtgactctg actgggagat gctgaggaca gggaggaaac caccagataa gggacactgg    177240
ggaggagggg tggacccctc agggccaagc acatggagcc tcatcacaaa ggcaagatgg    177300
tggccaaatt caaggtcgct gcaaaaggaa tggagaagag agaatagatt tggcatttgg    177360
aggaaatggt gacaatcatg agcacctacc cgggactctc catgggtgct atctctacat    177420
aaactcattc caccctctga ttaatccatt ctacatatgg ggaaacaaag gcatgcggtg    177480
tttacgtcac ttgccaagat ctcaggattt gatccaggtg gcctggttcc atggtgcagc    177540
ctctcagcct gcatggatgc cccagctcag agcatgactc tcaggacagg ggtcccagca    177600
gccctccctc cctgagcagc agggtgcccg tgctgcacca cttctgtcta ggaataggac    177660
attctgacac tttcctgcct cttccgaggt ctagcactta ctctatgcct gcctgggaag    177720
gtggcaagct ggcctgagga acagactctt ccatttttta gggagctcaa ggccacagat    177780
gctctgagat ctggagtcca gagacaggag cggaggcttc tcctggtgac cactctgctt    177840
aaaaacttca tcagatccgt agtttcagag ccccccctgaa ccccatccct tacctctacc    177900
agttgcaggt gggtctctgg ggtggggctg ccctccccac cagcacccca agggctaaaa    177960
ggttgagggg agaacaccat catttgtaca gggggatcct ggaagatgag gcctgagaaa    178020
gccctgcggg gcccctcacc ttctccctag ctgtggccaa gagtgtctgg ccttgcctgc    178080
ctcaggacca gcccaaagtg gaggtgagag gtgagcccca gccccagggg aagggtgat    178140 ggtggtcttg gtctcagcat ggttctggta gaggtgggtt attttgaaga tgatgaacct    178200
taagcctctt tctgatcttg ctttaaataa atacttctga acaacagcaa caacagaata    178260
gtgttgatag gaaagccctc cactccacca gaaccacgcg gccttctcgt cctcccctcc    178320
tccacttcct tcctaagtca ctgctccatg agctcttcca caggagattt acaaaacaga    178380
acacaaacaa tccagttcct gcctctcact ctgaactcct cccaagactc gtggggtgcg    178440
gcagcccctg ggaacaccca gcccttcaag gtcaaacaca gccccgccc ctcactctgg    178500 ggtaccctgc cagaataagc cccgacagcc atgtggagca gagccttctt ttttgtaagt    178560
ggaagttcca ggctggcttt tcaaatcccc ttttaacctc agtgctgtat ttcaaaattc    178620
attccagttt tcctgtagta attaacaaaa ataaatattt taatttcaat taaagtgagg    178680
```

```
gtctcggaga agaagcagga actgagtttc ctgagaggcc ccgctgaggc tttgttgata 178740
tttcttcctg cgacctctgc tcggaccctg ggagctcaca ggccgtatcg cagctcttat 178800
ctttggggac cagttaaagc ataactgcgc caggcacaga gttgtccttt caaatgtgcc 178860
ggcagtggga cggagaccca tgcgtcaagt ctcctctaag ttcacatggg attctctcct 178920
tgtcccaaag ctgtctctga cttaaaaccc tccaactgat tacctgaatt ccagaatatg 178980
tcctgtgctc tctgcccttt cccacgcctt tggtgaagac cggtgttctg aggaaacaga 179040
cactgtgtag aaatggctca ggtcctttaa agccctggtg tgaggagtgg ggaagggctg 179100
ggccagaggt cagctggatt tgttagattg acagagtgac gcggacttcc ccagaggcac 179160
gggaccaagg tgcatgctca cgctgtctca tgctctcaca cataatgtgt gtgtgtgtgt 179220
gtatatatat atacacatat acatatatat atatacacac atatgcatat atataaaacc 179280
ccaagcagcc tctggcttag caggtgcatt tcccagcagg gcaattaaag ccatggtccc 179340
agtagtggtc ttggggtctc agggtatttg gtctgtgcag ccacatgctt cagtctctgg 179400
accccaggtc atctaacgag gtggtcgtgt ggggactggg atagaaaagg tgtctgcacg 179460
gacgtgtgtg aaagggctgg cacatcgcca gtgctcagca ctgtcagctg ctatcaccag 179520
tcattcaatc attcattcat tcattcagtt gttcattctt caacaggccg ttttaaaaat 179580 gtcccagta taccaaaatc tccgctaagc atttaaagag gcagaatgaa agttagcagt 179640
ggtggtgaaa cgaagctggg aatgtgctct gagggcctcc ttgtgggctt aatgaatatg 179700
tagaaaccac gcattttaaa tagagaggga gaaagggaga ggttcctggt cctctgcatg 179760
gggacttgtg tgtggctctt tactgtaggc ctgtgccact cctgctcaac agctaccaca 179820
gaggacgcct tcaacaaatg tgaagaacga acaaaaggta caaatgtgaa gaacgaacag 179880
ggtagaaaga aaggagaaag caagggtgag ggtgagaaat caagggacag agaagagaga 179940
agaggagata gcctgggagt tcacacagcc aagaaggtag acactcagtt gaaccagcaa 180000
gaggctgagc ctaactctcc ctttcgaatg ggcaggagtt catgatattt aataaacaga 180060
ggccttgctc tgtaagagac agggtaccag gcagagagca agtcagcatc gcaggagtca 180120
aacgaggcag acagcggggg cagggagctt gcctctgaag gagacccagg ctgccagagt 180180
agcagggagt ctgggccagt cctcttttgg gaagcgcttc ctcggcttct gccccccctc 180240
tcctctccct ttccacccac catcctgaca taatacttcc taatctggaa gtgttgtcca 180300
gagaagaacc tgctcatttc ctcttaagta ggcagggaag cactaacgtc cagcagcatc 180360
ggaaacccgt aggagcgctc tcggcagtgc agggtgaggg gacagtccat gtagtcatga 180420
gacgtgggtg tcaggcaagc gtctcttttc caaagagaa aaacattaaa ggcctcacaa 180480
acggcgccca aagactaatt ctgcatagca tctttgcgag accctaggtt cttatgatga 180540
ctggttttgc ctgagaaaga aaaaatttta attttgcttt gacatgccaa ttcaacaaat 180600
cattttcaca taatattcat gcaaaaaaaa aacaatttgc cagaaaactt gggaatccat 180660
ccacatctac agcttttccc tgcagtcaca ctacagtggg atccctccat acaggagcgg 180720
cagagtggag caggctagag atgcctgttt gtttctgttt gctgcaccgc agcaagcatt 180780
tctgtcgtgc ccactctgta ctagaaagta catgaacatc agccataaag ggaactagaa 180840
aggtggccca ccctcttggt ggagagagaa gagagtgtgg tagaaacaat aataagaagt 180900
ctgcagaact tgacccctcc cagcctctcc cacctgccag cctggccctt gcagagagat 180960
gcaggctgcc attcttaggc caaagcctgg gacagttggg ctcagcaagg taggcatccg 181020
```

```
tcaagcaagg aggagcaggg gtcagcagtg accccagcag ccagcaggga gaaaggtgca   181080
tgtgacaagg acaccagagg ccgtgggtca ggatcagcca gggtcagggt agcatttcta   181140
ggaattcact ctgttgggcg ctgtgctggc tgcttctcac atattattcc tttcttactc   181200
tcagagcaga gatttcaatt gcagcgagat tgtggaggca gccagggagg tggggagggt   181260
ggtgtcttct aaaagcattt tcagtatcca tgtggtttca gtaataataa taataataaa   181320
ccagtgaaaa gtaaaacagg acaaaaatct tcataggcag tgaaccatat cagagagtcc   181380
aagaaagcac aatgagagtg tggcttaaaa accctgaacg acattccttt gcaccagctt   181440
ggtgaggagg gcatggtccc cgccaccccc caccccact ttgcagataa accacatgca   181500
ggaaggtcag cctggcaagt ccagtaagtt caagcccagg tctcaactgg gcagcagagc   181560
tcctgctctt ctttgtcctc atatacgagc acctctggac ttaaaacttg aggaactgga   181620
tggagaaaag ttaatggtca gcagcgggtt acatcttctt tcatgcgcct ttccattctt   181680
tggatcagta gtcactaacg ttcgccagcc ataagtcctc gacgtggaga ggctcagagc   181740
ctggcatgaa catgaccctg aattcggatg cagagcttct tcccatgatg atctgtccct   181800
cacagcaggg tcttctctgt ttcagggcat gaactacttg gaggaccgtc gcttggtgca   181860
ccgcgacctg gcagccagga acgtactggt gaaaacaccg cagcatgtca agatcacaga   181920
ttttgggctg gccaaactgc tgggtgcgga agagaaagaa taccatgcag aaggaggcaa   181980
agtaaggagg tggctttagg tcagccagca ttttcctgac accagggacc aggctgcctt   182040
cccactagct gtattgttta acacatgcag gggaggatgc tctccagaca ttctgggtga   182100
gctcgcagca gctgctgctg gcagctgggt ccagccaggg tctcctggta gtgtgagcca   182160
gagctgcttt gggaacagta cttgctggga cagtgaatga ggatgttatc cccaggtgat   182220
cattagcaaa tgttaggttt cagtctctcc ctgcaggata tataagtccc cttcaatagc   182280
gcaattggga aaggtcacag ctgccttggt ggtccactgc tgtcaaggac acctaaggaa   182340
caggaaaggc cccatgcgga cccgagctcc cagggctgtc tgtggctcgt ggctgggaca   182400
ggcagcaatg gagtccttct ctcccttcac tggctcggtt tctcttaggg accctcacag   182460
cactaagggg tgcgcgtccc ctgtcaggcc ctcgaatgcc ctcccacagc caggcccctc   182520
tgaggtttca ctctggcctg ctgggctcct agcagccacc aacccatgat gctgggccct   182580
gaaaacacac gcagacctgg atgagtgagg ccactgggca caaccagggc tcccagctca   182640
ccagagcagc ctgggacaca gagggtgctc agaaacctac cagagcagcc ctgaactccg   182700
tcagactgaa atcccctgtt gccgggagga ggcgccgggc ctgggggacg ggtcctgggg   182760
tgatctggct cgtctgtgtg tgtcactcgt aattaggtcc agagtgagtt aacttttttcc   182820
aacagaggga aactaatagt tgtctcactg cctcatctct caccatccca aggtgcctat   182880
caagtggatg gcattggaat caattttaca cagaatctat acccaccaga gtgatgtctg   182940
gagctacggt gagtcataat cctgatgcta atgagtttgt actgaggcca agctggcttt   183000
tattgttagt taatttacat tatatcctct gacatgcaag tattttcttt cgagataatg   183060
actaatgata atgtaatcat tgctgtctat ctattgtact gagaaaacac ggcagaggaa   183120
atcgagtcca gctgccgtcc aaaagtcact ggagattgca atgagctcgt ctggcagggt   183180
gggggtatg ggagggaaag agcttaggaa acggctctcc ctgcaaagtc caaccaaact   183240
ttaacgttaa ccaaaccatt aatgttgcca tgaatttgaa gtgaaccaga gggaggtggc   183300
agaagaagct taatggggaa tagttccggt agagaaatga ggcttaagat gaactaccct   183360
ggcccttatg tgtcagagag aacggcttga caaacacaca ctgaggatgt ctgcagggat   183420
```

```
aaaagaagaa agggagatga cccttgcttc tcgctctcgg gaggaccatc tggtccggcc   183480
ctggggattc tctgtttcct cttctgaatc ccagtgttgc ccagcactgg cctgtaccca   183540
tcctcacgag ggccgctctc ctcacccggc cctaggtccc tgccctgtcc tgagcctaca   183600
ggggcctccc atgttgagaa agtgttgctg acacattgtc tctgaccgct gtgccaggca   183660
ttttctgctg aattaccgca cttggtcctt gaatttcacc cagcaactta ctgaaaggct   183720
ggaacccatg aacctacccc ttcactgagg aaaatcagtt accccagcca tctacagcga   183780
caggagcaag ggaggagtcg cctcacctct ctagaaatgt gtatttgagg agaacactat   183840
tgaaatgaat ttccaagaat aatctagtca gtattacaaa agcaaaatta tttgggatat   183900
cgtccttttt tacttagtat ttttttcttt tcctatagca ttattaactt tctgattttc   183960
caaatacata cacattttta aatttcctga gtctttatct cttctgttaa aatgtaagat   184020
ttatgataca aaggcagaga tttgtgtcca tgaataagtg aagtttggtg tgcacctgtg   184080
agctgagcca cctcaattaa tggaacagat aaggaaataa aggtctgctg atgcattgtt   184140
atttacagcc attttcagaa tgtatctcct ctccacgagg gaactgcagg gtcctgcccc   184200
aagccattta ttttgtcctc aagcagcccg ccctcccac tccaggcaca gcccggtctc   184260
ctgctggtct cccctcttcc cacttgctcc ccctcatcta tgctccagac agaggccaca   184320
tatatttttt aacttttttt tttttttttt tgagacagag tcttgccctg tcacccaggc   184380
tggagtgcag tggtgcagtc tcggctcact gcaacctcca cctcccgggt tcaagtgatt   184440
ctcctgcctc agcctcctga gtagctggga ttacaggcgc acaccaccat gcccagctaa   184500 tttttttgtat ctctagttga gacagggttt cactatgttg gccaggctgg tctcgaactc   184560
ctgacctcat gatctgcccg cctcggcctc ccaaagtgca tatttttaa ctttatcaga   184620 cttttcattc tctgctcaac atctttcttt ggtcctccag gtatgttcag ataaaacctg   184680
agcacctggc catgactgat gggttgctgg gccatctggc cctggcaact ctcccgtcca   184740
ccaggtcccc ctcccgtcac gctccaggca tagcctgtgt gtgccagcgc aatgcccaca   184800
ctccatgcac aagtggaagc cctctcaaag tcagtggctt agtgccttga tgtggtcaca   184860
cccattctca ggaagtccgt tcccactgaa aacattgtgt gttttcaaca tcattgaggc   184920
tgccacggca gattataatc actggcctag gcagcccact ggaactacca gaccatgagc   184980
ctgaattttt tgtttaaaaa tcatatcctg ttttctctac tctctagtct ctagtcaagg   185040
tgaattattc aatttaataa attaggggcc tagtgtgttg taccaaggag ctaaaaagag   185100
agaactcgca acaccttcca gcccattctc cacctaacac tggctatact ggctctcctc   185160
tctctcgctg tttgttccaa aatctaataa cctgtcttcc cactagaatt catcatacat   185220
gtttaaaaac ctagttaaat agtagttaaa ctgactgcat agatctggaa atgagacagt   185280 cttttctttta caaatccata tagactatga gttgggggca ggggatgaca caagaatcta   185340
ttttcttgcc cccaaaccat tgctttcctt ccaatgttaa gcttgtattc tgtgtattaa   185400
ttcaggtggt tccgtttggg aatggcctct gttacccaga gatgggaggg ccatcagaac   185460
tcggggttgt ctgaaaaaac actggttcta aaattatcac tgctttcact tgttttaac   185520 catcatagtt gtttgatttt gaaggaaaaa catgaggggtt tttattctat gcttgttata   185580
tctatattgt ggtttcgtat tttttagatt ttagtacctg acattttttt aactttatt   185640 ttaggttcag gggtacatgt gcaggtttgt tatataggta aatttgtgtc atgggggttt   185700
gttacacaga ttatttttatc acccagggat taagcctagt acccattagt tattttcct   185760
```

```
gatcctctcc ctcctcccat cctccaccgt cctatagacc ccagtgtgtg ttgttcccct    185820
ctaagtgtcc atgtgttctc atcatttagc tcccacttat aagtaagaac atgcggtatt    185880
tgattttctg ttcctgcatt agtttgctag ggatgatggc ctctagctcc atccatgttc    185940
ttgcaaagta catgatctca ttctcttttg tggctgccta gtgttccatg tgtatatgt     186000 accacatttt ctttatccag tctgtcattg atgggcattt aggttgattc catgtctttg    186060
ctattgtaaa tagtgctgca gtgaaaatac gcatgcatat gtctttatgg tagaatgatt    186120
tatattcctt tgagtaatgg gattgccggg tcaaatggta gttctgtttt tagctatctg    186180
agaaattgcc acactctttt ccacaataat tgaactaatt tacattccca ccaacagtgt    186240
aaaagcattc cttttctcc acaacctcac cagcatgtgt tgggattttt ttttttttt      186300 acttttcaat aatagccatc tgactggtat gagatggtat ctcagtgtgg ttttgatttt    186360
tatttcttta atgatcagtg atgttaagct cttttttcata tacttgttgg ctgcatgtat   186420
gtcttcttct aaaagtgtc tgctcatgtc ctttgcccac ttttttaatgg gattgtttaa    186480 ttttttcttg tgaatttact taagttcctt atagatgctg gttattagac ccttctcaga    186540
tttgtagctt gcaaaaatgt tcacccattc tgtgggttgt cttcactctg atgatagttt    186600
cttttgctgt gcagaagatc ttcagtttag ttagatccca tttgtcaatt tttgcttttg    186660
ttgcaattgc ttgatgtgtt ttcatcatga aatcttagcc cattcctata tccagaatgg    186720
tattacctag gttgtcttcc agggttttta tagtttgggg tttacatttt aagtcttaa     186780 tccatgttga gtttattttt gtgtatggtg taaggaagga gtccagtttc aatcttcttc    186840
atggctagct agtcatcatt tattgagtag ggagtccttt attcattgct tttttttttt    186900
tgtcaacttt gtcaacgatc acatggttgt aggtgtgcag ccttatttct gggctctcta    186960
ttctgtttca ttggtctgta tgtctgtttc tgtactagta ccatgctgtt ttggttactg    187020
tatccctgta gtttaaagtc aggtagcatc atgcttccag cttttgttctt tttgcttagg   187080 attgccttgg caattcaggc tctttttggg ttccatgtga attttaaat tgtatttttct    187140 agttctgtga agaatctcat tggtagtgtg ataggagtaa cattgaatct ataaaatact    187200
ttgggcagta tagtcatttt aatgatattg attctttcta tccatgagca tggaatgttt    187260
ttccatttgt ttgtgtcatc tctgatttct ttaagcagtg ttttgtggtt cttattgtag    187320 agatcttttca ctttcctggt ttactgtatt tctaggtatt ttattcttttt tgtggcaatt   187380 gtgaattgaa ttgcattcct gatttggttc tcagcttgac tgttgttggc atattggaat    187440
gctaattatt tttgtacatt gatttttgtac aactgagtct tcactgaagt tgtttatcag   187500
cttaaggggt tttgggcaag actatgggt tttctagata taggatcatg tcatctgcaa     187560
acagagatag ctgttttcct ctcttcctgt ttggatgtcc attatttctt tctctcacct    187620
gatttatctg gccaggactt ccaatactat gttaaatagg agtgttgaga gagggaatcc    187680
ttgtcttgtg tcaattttca aggggaatgt tttcaacttt tgcccattca atatgatgtt    187740
ggctgtgggt ttgccataga tggctattat gttgaggttt gttctttaaa tacctagttt    187800
attgagaatt ttaaacatgt tgaatttat tgagagcctt ttctgcatct attgagatga     187860
tcatgtggct tttgtcctta gttctgtttg tgtggtgaat cacatttatt gatttgcata    187920
tgttgaacca atcttgcatc ccagggatga agccgacttg attgtggtgg cttaagcttt    187980
ttgatgtgct gctggattcg atttgccagt attttgttga ggatttttat gtctatgttc    188040
atcagagata ttggcctgaa gttttctttt tttgtggatc tctgccaagc tttggtatca    188100
ggatgacatt ggcctcatag aatgagttaa ggaagagtcc ctccttctca atttttttgg    188160
```

```
aatagtttca gtaggaatgg taccagcttt ttttgtacat cttgtagaat tggctatga    188220 atccatctag tcttaggctt tgttttggtt ggtaggctat ttattactga ttcaattttg    188280
gagctcatta ttggtctgtt cagggattca gtttcttcct gaggttttta tttttatcaa    188340
atggaactta acctttttca tttccaattt ttttatgatc taaaaatgtg cagtttacag    188400
ccctgttcag aatctgcatc ttcctcattc tgcagataca ggtccctcag agcaggtgac    188460
tgagtgtgta tcctgtctgg agcataatac ttatgctagt agagttactg ttgtctttat    188520
tgttaattac caaagtttac cacttatcag tcacttacta cttgctgggc attgcactaa    188580
gcatttcagt tgtattatct tgttgggtcc ttacagcaat cctgtgaaac agatactgct    188640
attaccccac tttatagaga ggtagactga ggcttccagc attgaagcaa attgcccaag    188700
actacagaaa tgtaggtttc taaacatcaa gaaacagtaa ccagtaatga tgactaaagc    188760
aagggattgt gattgttcat tcatgatccc actgccttct tttcttgctt catcctctca    188820
ggggtgaccg tttgggagtt gatgaccttt ggatccaagc catatgacgg aatccctgcc    188880
agcgagatct cctccatcct ggagaaagga gaacgcctcc ctcagccacc catatgtacc    188940
atcgatgtct acatgatcat ggtcaagtgt gagtgactgg tgggtctgtc cacactgcct    189000
agctgagcct tggtggctgc tcttagccaa acagctgagg cctttgcatc cctggagaaa    189060
tgtcatcaca ttacttaagg caggcacaca aatccagaaa catctgtaaa taccccttca    189120
agcattcttt taaagacact tcttgactca ttgggcagta tgacctgaca tttgcccatg    189180
tttgcaagca aataaataaa actaaagtct tccgcaagcc attacaccaa atatattctat    189240 tcgctgagtt actcaatgaa ataccgagtt gccctatatt ttgaagcctg ttaccagaga    189300
gactgaatgt ttttaaatgc atggcagtga gtaacaacat aaggctaata gagtcaacat    189360
ttctgctttg acttaaacct tttaaaccag tggatttatg tgaagtctct gcagtgtggc    189420
atttaaacat ttcaatctaa ataagagtgt gtaatttgat tgatgctatt attctaccag    189480
attcacgagt gcagtgggct ctggaggtag cattacatgc atgggatgag catttgcaaa    189540
agaaagttgt atagggaata tgacagagcc aagttaatgt aaatattaat gcctttctga    189600
actctaggcc acagagttga tctttttttaa cttccttggt ttgggctaag gaagctgtga    189660
tccagagaag ccacgtgatt tgtctaaggt cacatagcag tctggcctaa aatagcttga    189720
tatgctgtgg atgaaaaata aatgtgatcc ctcaagaggc atgaggattt ccaggcagta    189780
gccatacctc caaattgttt aatctggatt tagattgttg ggtagtcaca tgcagcagca    189840
cagttaacag tgtgtcctcc tgtggaagtg gccagcacag ccagccctct cacttgcatg    189900
catgcccacc agccttctca cttgcatgca tgcccactgg gtatgtgctg tactggagac    189960
gccgggggta ggggcccagt cccaaccccca aattctttaa agcctatttt tctaagttgc    190020
atctggtttc ctacctgaag gaatgctaag ggtggatgtt gagtgaggac cttggtgcag    190080
ggcaccctgc agtcaggata gttcatggag agcaattgta cagacccaca ctgctccatc    190140
ccctcaggcg taacacagga tgctgacccc aggaagagtg ggcgtagaaa aactagaggg    190200
cattattgtt attctgattc aaatgtacag tgctggcatg gtctttaaac agtaaccagt    190260
actagctggc caagacagaa aagtctacca caaagacttg gttctttcat cacttatttg    190320
actggaagtg tcgcatcacc aatgccttct ttaagcaatg ccatctttat catttcttcc    190380
agtgttctaa ttgcactgtt ttttctcatt ccttccccag gctggatgat agacgcagat    190440
agtcgcccaa agttccgtga gttgatcatc gaattctcca aaatggcccg agaccccag    190500
```

```
cgctaccttg tcattcaggt acaaattgca gtctgcgctt ccattgggaa gagtccctct    190560
aatgagcatc tcatgtcact gtgttctgtc acatgccagc ctggcctccc tgtgtcccag    190620
atcgcattat aaaccctcc  agcgcattag agcaagcctc agtaaggcgc aggccacatc    190680
gtgaactaag cagcatccgt gagtgggcc  cacccaactc catctccccc tccccgtctg    190740
aactctcctc tggtgctcgt cctcactgtc cggctagcca aagcctcagc tgggtctaag    190800
agagaagcat ggtctattgg gctttggtgt caggcagacg tggcttcaca cccctgactc    190860
tccacttctt cgcatcaccc aggcagccga tccacctatc tccttccata acacaggaat    190920
accaaaacca agctcacagg attgtctcaa agattcaata aaatatgttg caaaatacgc    190980
tccctaacac ctcacagcaa ggtgcacaaa tcgatgaatg ctgcagcttc ttcccttttct   191040 gtttcctcag aagctatttg aatctcatgt aggggctttc aagcatcaaa ggatggttca    191100
tgttttattt taaggcaccc acatcatgtc atgaggggag gcagctataa tttagagaac    191160
caagggggat ttcattataa caaaattggc aaacacacag gcacctgctg gcaatagacc    191220
cctgctccta tagccaagaa gtggaatagc atctctacgg gccattctaa tagcctcaaa    191280
atctctgcac caggggatg  aaagaatgca tttgccaagt cctacagact ccaacttcta    191340
ccgtgccctg atggatgaag aagacatgga cgacgtggtg gatgccgacg agtacctcat    191400
cccacagcag ggcttcttca gcagcccctc cacgtcacgg actcccctcc tgagctctct    191460
ggtatgaaat ctctgtctct ctctctctca agctgtgtct actcatttga acaaattgaa    191520
ttttagggaa ataaccatc  tagtgaaact cacatggaaa tgaagtcaat tttaaccaaa    191580
tggtaaaatc aaaatcaaaa taaattaagt gtattaatta ttttgttgca ttgcaacaac    191640
ttgattgtaa gccttttagg tccactatgg aatgtaatta aatcaaaact aaacctagtt    191700
gctctaaaac taacgattaa gacaaaaatt aaacaccttc acaatatacc ctccatgagg    191760
cacaccacct gcattcagga aaagtggatg agatgtggta caagcattcc atgggcaatt    191820 ctctgttttct ttttccagag tgcaaccagc aacaattcca ccgtggcttg cattgataga    191880
aatggggtat gtatgaacac cttataagcc agaatttaca gctctccact atggctctat    191940
tttacatgga aaatgcctta acctaaataa ttttaaccca gataatcttg agttttcttc    192000
ctgtgtgggt ttttccctgc acggctgtca cgcctcacag tgccgttcaa agcgtgactc    192060
ctggaccagt agtagcatcg cctggccttg ttagaaacgc cattttttcag gccactgccc   192120 cagtttgacc aaatcaggac ctctgggggt ggcacccagt agtctatgtt tgagccactt    192180
tccaggtgat gctgatgtct gttgaagtgt gaggccgtgg tctagaccgc actgtgccat    192240
gcagaaacca ctagccacat gtggctactt caacttaaat gttaatgagt taaaatgaaa    192300
taaaatataa aattcagttt ctcacacatg tgaagtgtcc agtagccaca cgtggctagt    192360
ggtgaccgta ttgaagagca ccgctcatag cacacctccc tcactgcgga aagttctgct    192420
gtacagcacc cagcaacagc cctgctgccc aaccctgcag cctgtggccc aagtagcacc    192480
agcacccacc agggtgcaag actctcaagg cctgcccaac ctactaatca gaaccagcat    192540
ctcaaggaga tctcgggtga ttttttgcaaa cactgaagtt ggggcagccc tgaccggagt    192600
aaccttccct catttcctcc tgcagctgca aagctgtccc atcaaggaag acagcttctt    192660
gcagcgatac agctcagacc ccacaggcgc cttgactgag gacagcatag acgacacctt    192720
cctcccagtg cctggtgagt ggcttgtctg gaaacagtcc tgctcctcaa cctcctcgac    192780
ccactcagca gcagccagtc tccagtgtcc aagccaggtg ctccctccag catctccaga    192840
gggggaaaca gtggcagatt tgcagacaca gtgaagggcg taaggagcag ataaacacat    192900
```

```
gaccgagcct gcacaagctc tttgttgtgt ctggttgttt gctgtacctc tgttgtaaga 192960
atgaatctgc aaaatttcta gcttatgaag caaatcacgg acatacacat ctgtgtgtgt 193020
gagtgttcat gatgtgtgta catctgtgta tgtgtgtgtg tgtatgtgtg tgtttgtgac 193080
agatttgatc cctgttctct ctgctggctc tatcttgacc tgtgaaacgt atatttaact 193140
aattaaatat tagttaatat taataaattt taagctttat ccagatactc ataacctgct 193200
aacacacaca catatacaca cacatacaca tacacacata tacacacacc acacacatac 193260
acagacacca cacacatacc atacacagac acatacacat gcacacacat atacacacac 193320
acctcaaata catacacacc acacacacat acatgtatac acatacacac acaccacaca 193380
tacaccacaa aaaccccaca cacatacaca tatacacacc acacacacca catacacaca 193440
cgtatacaca catatataca cacatacacc atgcatacat acacaccaca catacataca 193500
gacacaccac acacacgtac acacaacaca caacacagac acacacgtac acacactaca 193560
gacatgtatg cacacataca cacacaccac acatacacat acacagacac atatacacta 193620
cacacaccat tacatacaca cgtacacata caccacacac accacacata cacacaccac 193680
acacacatac acacgccaca cacacaccac aaaaaccgca cacacataca aacatataca 193740
cactacacca cacatacaca cacacaccac acaccacaca cacacataca cacaccacac 193800
acaccacaca tacacgcacc acacatacac acacgtagac acaccacaca caccacagaa 193860
acacacatta acacaccaca tacacatatg tatgtgcata tacacaccca caccccacac 193920
acacatgtat aaagatttag atatatataa aacatacgtt atatatatgt tgatgtaata 193980
tctaatatct atatatctaa tatgtagttt attagctatc taatatctat gtcatatata 194040
tcaaatcttt atatataaaa atatgtagaa atctttatac atatgttata tgtatataaa 194100
gatttagata tataacatat gtaagttata tatatgttag tgtaatatct aatatatagt 194160
ttattggcta tctaatataa tataaacaga ttatcaatat tataagctat tagaaaaatg 194220
caagttaagg cagatgatat acctctttca caccaactca cacaccaact acacacacac 194280
atacacacag acacacacga cacacaccat acacatgtac acacacacca catatacaca 194340
aacgtacaca cacaccacac acacatacac accacacaca caacacacat acatacacat 194400
ccacacacca cacatgtaca cacaccacac acacacatac acaccacata cacatatgta 194460
tgcacacata cacaccaaca ccacacagac accacacatg cataaacata tagacatata 194520
cacaccacac accatatgta cacatgtaca cacaccacac atatacacac aacacacaca 194580
aatacacaca ccacacacac accacaaaaa ccccacacac acaaacatat acccccaca 194640 catacgcata tatacacaca cacatacaca ccacacacat acacaccaca cacacaccac 194700
acatacacac acgtacacac accacacaca caccacagac acacaccaca catacataca 194760
catacacaca ccacacacac gtacacacac cacacacaca cagacacaca tagacacacc 194820
acatacacac ccacaccaca cacacacaac tcataccaca catacataca caatagacac 194880
atacacacca cacacaccat acatacacac gtatacacac accacatata cacacgta 194940 cacacacacc acacacaccc acatgcacac accacacaca catacaaata tacaccacac 195000
acacatacac cacacacacg gtgcacatac acacacatat acacacacca gacacacata 195060
ccacatacac atcacacata tatgtataca tgcatacaca tacacacaca catacacaca 195120
ctctcctcaa ggcagtttat cctctgagaa ctttaaattt acaaaagaca catatgtcca 195180
ttactttgag aaggacagga aagaacccac tttcttttgc agcaacagca agagggccct 195240
```

-continued

```
cccaaggctc ctgctccctg tcataagtct ccttgttgag gacattcaca gggttcagaa   195300
cccagggatc ctgcatggga tggtgctttg ctgattactt cacctctgat ttctttccac   195360
tttcagaata cataaaccag tccgttccca aaaggcccgc tggctctgtg cagaatcctg   195420
tctatcacaa tcagcctctg aaccccgcgc ccagcagaga cccacactac caggaccccc   195480
acagcactgc agtgggcaac cccgagtatc tcaacactgt ccagcccacc tgtgtcaaca   195540
gcacattcga cagccctgcc cactgggccc agaaaggcag ccaccaaatt agcctggaca   195600
accctgacta ccagcaggac ttctttccca aggaagccaa gccaaatggc atctttaagg   195660
gctccacagc tgaaaatgca gaatacctaa gggtcgcgcc acaaagcagt gaatttattg   195720
gagcatgacc acggaggata gtatgagccc taaaaatcca gactctttcg atacccagga   195780
ccaagccaca gcaggtcctc catcccaaca gccatgcccg cattagctct tagacccaca   195840
gactggtttt gcaacgttta caccgactag ccaggaagta cttccacctc gggcacattt   195900
tgggaagttg cattcctttg tcttcaaact gtgaagcatt tacagaaacg catccagcaa   195960
gaatattgtc cctttgagca gaaatttatc tttcaaagag gtatatttga aaaaaaaaaa   196020
aaaagtatat gtgaggattt ttattgattg gggatcttgg agttttttcat tgtcgctatt   196080
gatttttact tcaatgggct cttccaacaa ggaagaagct tgctggtagc acttgctacc   196140
ctgagttcat ccaggcccaa ctgtgagcaa ggagcacaag ccacaagtct tccagaggat   196200
gcttgattcc agtggttctg cttcaaggct tccactgcaa aacactaaag atccaagaag   196260
gccttcatgg ccccagcagg ccggatcggt actgtatcaa gtcatggcag gtacagtagg   196320
ataagccact ctgtcccttc ctgggcaaag aagaaacgga ggggatgaat tcttccttag   196380
acttactttt gtaaaaatgt ccccacggta cttactcccc actgatggac cagtggtttc   196440
cagtcatgag cgttagactg acttgtttgt cttccattcc attgttttga aactcagtat   196500
gccgcccctg tcttgctgtc atgaaatcag caagagagga tgacacatca aataataact   196560
cggattccag cccacattgg attcatcagc atttggacca atagcccaca gctgagaatg   196620
tggaatacct aaggataaca ccgcttttgt tctcgcaaaa acgtatctcc taatttgagg   196680
ctcagatgaa atgcatcagg tccttttgggg catagatcag aagactacaa aaatgaagct   196740
gctctgaaat ctcctttagc catcacccca acccccaaa attagtttgt gttacttatg   196800
gaagatagtt ttctccttt acttcacttc aaaagctttt tactcaaaga gtatatgttc   196860
cctccaggtc agctgccccc aaacccctc cttacgcttt gtcacacaaa aagtgtctct   196920
gccttgagtc atctattcaa gcacttacag ctctggccac aacagggcat tttacaggtg   196980
cgaatgacag tagcattatg agtagtgtga attcaggtag taaatatgaa actagggttt   197040
gaaattgata atgctttcac aacatttgca gatgttttag aaggaaaaaa gttccttcct   197100
aaaataattt ctctacaatt ggaagattgg aagattcagc tagttaggag cccatttttt   197160
cctaatctgt gtgtgccctg taacctgact ggttaacagc agtcctttgt aaacagtgtt   197220
ttaaactctc ctagtcaata tccaccccat ccaatttatc aaggaagaaa tggttcagaa   197280
aatattttca gcctacagtt atgttcagtc acacacacat acaaaatgtt cctttgtctt   197340
ttaaagtaat ttttgactcc cagatcagtc agagccccta cagcattgtt aagaaagtat   197400
ttgattttg tctcaatgaa aataaaacta tattcatttc cactctatta tgctctcaaa   197460
taccoctaag catctatact agcctggtat gggtat                             197496
```

<210> SEQ ID NO 6
<211> LENGTH: 123

```
<212> TYPE: DNA
<213> ORGANISM: Homo sapiens
<220> FEATURE:
<221> NAME/KEY: misc_feature
<223> OTHER INFORMATION: EGFR exon 18

<400> SEQUENCE: 6
cttgtggagc ctcttacacc cagtggagaa gctcccaacc aagctctctt gaggatcttg      60
aaggaaactg aattcaaaaa gatcaaagtg ctgggctccg gtgcgttcgg cacggtgtat     120
aag                                                                  123

<210> SEQ ID NO 7
<211> LENGTH: 99
<212> TYPE: DNA
<213> ORGANISM: Homo sapiens
<220> FEATURE:
<221> NAME/KEY: misc_feature
<223> OTHER INFORMATION: EGFR exon 19

<400> SEQUENCE: 7
ggactctgga tcccagaagg tgagaaagtt aaaattcccg tcgctatcaa ggaattaaga      60
gaagcaacat ctccgaaagc caacaaggaa atcctcgat                            99

<210> SEQ ID NO 8
<211> LENGTH: 186
<212> TYPE: DNA
<213> ORGANISM: Homo sapiens
<220> FEATURE:
<221> NAME/KEY: misc_feature
<223> OTHER INFORMATION: EGFR exon 20

<400> SEQUENCE: 8
gaagcctacg tgatggccag cgtggacaac ccccacgtgt gccgcctgct ggcatctgc       60 ctcacctcca ccgtgcagct catcacgcag ctcatgccct tcggctgcct cctggactat    120
gtccgggaac acaaagacaa tattggctcc cagtacctgc tcaactggtg tgtgcagatc    180
gcaaag                                                               186

<210> SEQ ID NO 9
<211> LENGTH: 156
<212> TYPE: DNA
<213> ORGANISM: Homo sapiens
<220> FEATURE:
<221> NAME/KEY: misc_feature
<223> OTHER INFORMATION: EGFR exon 21

<400> SEQUENCE: 9
ggcatgaact acttggagga ccgtcgcttg gtgcaccgcg acctggcagc caggaacgta      60
ctggtgaaaa caccgcagca tgtcaagatc acagattttg gctggccaa actgctgggt     120 gcggaagaga aagaatacca tgcagaagga ggcaaa                              156

<210> SEQ ID NO 10
<211> LENGTH: 1255
<212> TYPE: PRT
<213> ORGANISM: Homo sapiens
<220> FEATURE:
<221> NAME/KEY: misc_feature
<223> OTHER INFORMATION: human ErbB2, Isoform 1 (canonical, UniProt ID
       P04626-1)

<400> SEQUENCE: 10

Met Glu Leu Ala Ala Leu Cys Arg Trp Gly Leu Leu Leu Ala Leu Leu
1               5                   10                  15
```

```
Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430
```

```
Gly Arg Ile Leu His Asn Gly Ala Tyr Ser Leu Thr Leu Gln Gly Leu
            435                 440                 445

Gly Ile Ser Trp Leu Gly Leu Arg Ser Leu Arg Glu Leu Gly Ser Gly
        450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
        610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Leu Gly Val Val Phe Gly
            660                 665                 670

Ile Leu Ile Lys Arg Arg Gln Gln Lys Ile Arg Lys Tyr Thr Met Arg
        675                 680                 685

Arg Leu Leu Gln Glu Thr Glu Leu Val Glu Pro Leu Thr Pro Ser Gly
690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
        770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
```

```
                850                 855                 860
Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
                900                 905                 910

Trp Glu Leu Met Thr Phe Gly Ala Lys Pro Tyr Asp Gly Ile Pro Ala
            915                 920                 925

Arg Glu Ile Pro Asp Leu Leu Glu Lys Gly Glu Arg Leu Pro Gln Pro
        930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
                980                 985                 990

Asp Leu Gly Pro Ala Ser Pro Leu  Asp Ser Thr Phe Tyr  Arg Ser Leu
            995                 1000                1005

Leu Glu  Asp Asp Asp Met Gly  Asp Leu Val Asp Ala  Glu Glu Tyr
    1010                1015                1020

Leu Val  Pro Gln Gln Gly Phe  Phe Cys Pro Asp Pro  Ala Pro Gly
    1025                1030                1035

Ala Gly  Gly Met Val His  His Arg His Arg Ser  Ser Thr Arg
    1040                1045                1050

Ser Gly  Gly Gly Asp Leu Thr  Leu Gly Leu Glu Pro  Ser Glu Glu
    1055                1060                1065

Glu Ala  Pro Arg Ser Pro  Leu Ala Pro Ser Glu Gly  Ala Gly Ser
    1070                1075                1080

Asp Val  Phe Asp Gly Asp Leu  Gly Met Gly Ala Ala  Lys Gly Leu
    1085                1090                1095

Gln Ser  Leu Pro Thr His Asp  Pro Ser Pro Leu Gln  Arg Tyr Ser
    1100                1105                1110

Glu Asp  Pro Thr Val Pro Leu  Pro Ser Glu Thr Asp  Gly Tyr Val
    1115                1120                1125

Ala Pro  Leu Thr Cys Ser Pro  Gln Pro Glu Tyr Val  Asn Gln Pro
    1130                1135                1140

Asp Val  Arg Pro Gln Pro Pro  Ser Pro Arg Glu Gly  Pro Leu Pro
    1145                1150                1155

Ala Ala  Arg Pro Ala Gly Ala  Thr Leu Glu Arg Pro  Lys Thr Leu
    1160                1165                1170

Ser Pro  Gly Lys Asn Gly Val  Val Lys Asp Val Phe  Ala Phe Gly
    1175                1180                1185

Gly Ala  Val Glu Asn Pro Glu  Tyr Leu Thr Pro Gln  Gly Gly Ala
    1190                1195                1200

Ala Pro  Gln Pro His Pro Pro  Pro Ala Phe Ser Pro  Ala Phe Asp
    1205                1210                1215

Asn Leu  Tyr Tyr Trp Asp Gln  Asp Pro Pro Glu Arg  Gly Ala Pro
    1220                1225                1230

Pro Ser  Thr Phe Lys Gly Thr  Pro Thr Ala Glu Asn  Pro Glu Tyr
    1235                1240                1245

Leu Gly  Leu Asp Val Pro Val
    1250                1255
```

<210> SEQ ID NO 11
<211> LENGTH: 645
<212> TYPE: PRT
<213> ORGANISM: Homo sapiens
<220> FEATURE:
<221> NAME/KEY: misc_feature
<223> OTHER INFORMATION: human ErbB2, Isoform 2 (UniProt ID P04626-2)

<400> SEQUENCE: 11

```
Met Pro Ile Trp Lys Phe Pro Asp Glu Glu Gly Ala Cys Gln Pro Cys
1               5                   10                  15

Pro Ile Asn Cys Thr His Ser Cys Val Asp Leu Asp Asp Lys Gly Cys
            20                  25                  30

Pro Ala Glu Gln Arg Ala Ser Pro Leu Thr Ser Ile Ile Ser Ala Val
        35                  40                  45

Val Gly Ile Leu Leu Val Val Val Leu Gly Val Val Phe Gly Ile Leu
    50                  55                  60

Ile Lys Arg Arg Gln Gln Lys Ile Arg Lys Tyr Thr Met Arg Arg Leu
65                  70                  75                  80

Leu Gln Glu Thr Glu Leu Val Glu Pro Leu Thr Pro Ser Gly Ala Met
                85                  90                  95

Pro Asn Gln Ala Gln Met Arg Ile Leu Lys Glu Thr Glu Leu Arg Lys
            100                 105                 110

Val Lys Val Leu Gly Ser Gly Ala Phe Gly Thr Val Tyr Lys Gly Ile
        115                 120                 125

Trp Ile Pro Asp Gly Glu Asn Val Lys Ile Pro Val Ala Ile Lys Val
    130                 135                 140

Leu Arg Glu Asn Thr Ser Pro Lys Ala Asn Lys Glu Ile Leu Asp Glu
145                 150                 155                 160

Ala Tyr Val Met Ala Gly Val Gly Ser Pro Tyr Val Ser Arg Leu Leu
                165                 170                 175

Gly Ile Cys Leu Thr Ser Thr Val Gln Leu Val Thr Gln Leu Met Pro
            180                 185                 190

Tyr Gly Cys Leu Leu Asp His Val Arg Glu Asn Arg Gly Arg Leu Gly
        195                 200                 205

Ser Gln Asp Leu Leu Asn Trp Cys Met Gln Ile Ala Lys Gly Met Ser
    210                 215                 220

Tyr Leu Glu Asp Val Arg Leu Val His Arg Asp Leu Ala Ala Arg Asn
225                 230                 235                 240

Val Leu Val Lys Ser Pro Asn His Val Lys Ile Thr Asp Phe Gly Leu
                245                 250                 255

Ala Arg Leu Leu Asp Ile Asp Glu Thr Glu Tyr His Ala Asp Gly Gly
            260                 265                 270

Lys Val Pro Ile Lys Trp Met Ala Leu Glu Ser Ile Leu Arg Arg Arg
        275                 280                 285

Phe Thr His Gln Ser Asp Val Trp Ser Tyr Gly Val Thr Val Trp Glu
    290                 295                 300

Leu Met Thr Phe Gly Ala Lys Pro Tyr Asp Gly Ile Pro Ala Arg Glu
305                 310                 315                 320

Ile Pro Asp Leu Leu Glu Lys Gly Glu Arg Leu Pro Gln Pro Pro Ile
                325                 330                 335

Cys Thr Ile Asp Val Tyr Met Ile Met Val Lys Cys Trp Met Ile Asp
            340                 345                 350

Ser Glu Cys Arg Pro Arg Phe Arg Glu Leu Val Ser Glu Phe Ser Arg
```

```
                    355                 360                 365
Met Ala Arg Asp Pro Gln Arg Phe Val Val Ile Gln Asn Glu Asp Leu
    370                 375                 380

Gly Pro Ala Ser Pro Leu Asp Ser Thr Phe Tyr Arg Ser Leu Leu Glu
385                 390                 395                 400

Asp Asp Asp Met Gly Asp Leu Val Asp Ala Glu Glu Tyr Leu Val Pro
                405                 410                 415

Gln Gln Gly Phe Phe Cys Pro Asp Pro Ala Pro Gly Ala Gly Gly Met
                420                 425                 430

Val His His Arg His Arg Ser Ser Thr Arg Ser Gly Gly Gly Asp
                435                 440                 445

Leu Thr Leu Gly Leu Glu Pro Ser Glu Glu Glu Ala Pro Arg Ser Pro
                450                 455                 460

Leu Ala Pro Ser Glu Gly Ala Gly Ser Asp Val Phe Asp Gly Asp Leu
465                 470                 475                 480

Gly Met Gly Ala Ala Lys Gly Leu Gln Ser Leu Pro Thr His Asp Pro
                485                 490                 495

Ser Pro Leu Gln Arg Tyr Ser Glu Asp Pro Thr Val Pro Leu Pro Ser
                500                 505                 510

Glu Thr Asp Gly Tyr Val Ala Pro Leu Thr Cys Ser Pro Gln Pro Glu
                515                 520                 525

Tyr Val Asn Gln Pro Asp Val Arg Pro Gln Pro Pro Ser Pro Arg Glu
                530                 535                 540

Gly Pro Leu Pro Ala Ala Arg Pro Ala Gly Ala Thr Leu Glu Arg Pro
545                 550                 555                 560

Lys Thr Leu Ser Pro Gly Lys Asn Gly Val Val Lys Asp Val Phe Ala
                565                 570                 575

Phe Gly Gly Ala Val Glu Asn Pro Glu Tyr Leu Thr Pro Gln Gly Gly
                580                 585                 590

Ala Ala Pro Gln Pro His Pro Pro Pro Ala Phe Ser Pro Ala Phe Asp
                595                 600                 605

Asn Leu Tyr Tyr Trp Asp Gln Asp Pro Pro Glu Arg Gly Ala Pro Pro
                610                 615                 620

Ser Thr Phe Lys Gly Thr Pro Thr Ala Glu Asn Pro Glu Tyr Leu Gly
625                 630                 635                 640

Leu Asp Val Pro Val
                645

<210> SEQ ID NO 12
<211> LENGTH: 569
<212> TYPE: PRT
<213> ORGANISM: Homo sapiens
<220> FEATURE:
<221> NAME/KEY: misc_feature
<223> OTHER INFORMATION: human ErbB2, Isoform 3 (UniProt ID P04626-3)

<400> SEQUENCE: 12

Met Arg Arg Leu Leu Gln Glu Thr Glu Leu Val Glu Pro Leu Thr Pro
1               5                   10                  15

Ser Gly Ala Met Pro Asn Gln Ala Gln Met Arg Ile Leu Lys Glu Thr
                20                  25                  30

Glu Leu Arg Lys Val Lys Val Leu Gly Ser Gly Ala Phe Gly Thr Val
            35                  40                  45

Tyr Lys Gly Ile Trp Ile Pro Asp Gly Glu Asn Val Lys Ile Pro Val
        50                  55                  60
```

```
Ala Ile Lys Val Leu Arg Glu Asn Thr Ser Pro Lys Ala Asn Lys Glu
 65                  70                  75                  80

Ile Leu Asp Glu Ala Tyr Val Met Ala Gly Val Gly Ser Pro Tyr Val
                 85                  90                  95

Ser Arg Leu Leu Gly Ile Cys Leu Thr Ser Val Gln Leu Val Thr
            100                 105                 110

Gln Leu Met Pro Tyr Gly Cys Leu Leu Asp His Val Arg Glu Asn Arg
            115                 120                 125

Gly Arg Leu Gly Ser Gln Asp Leu Leu Asn Trp Cys Met Gln Ile Ala
            130                 135                 140

Lys Gly Met Ser Tyr Leu Glu Asp Val Arg Leu Val His Arg Asp Leu
145                 150                 155                 160

Ala Ala Arg Asn Val Leu Val Lys Ser Pro Asn His Val Lys Ile Thr
                165                 170                 175

Asp Phe Gly Leu Ala Arg Leu Leu Asp Ile Asp Glu Thr Glu Tyr His
            180                 185                 190

Ala Asp Gly Gly Lys Val Pro Ile Lys Trp Met Ala Leu Glu Ser Ile
            195                 200                 205

Leu Arg Arg Arg Phe Thr His Gln Ser Asp Val Trp Ser Tyr Gly Val
210                 215                 220

Thr Val Trp Glu Leu Met Thr Phe Gly Ala Lys Pro Tyr Asp Gly Ile
225                 230                 235                 240

Pro Ala Arg Glu Ile Pro Asp Leu Leu Glu Lys Gly Glu Arg Leu Pro
                245                 250                 255

Gln Pro Pro Ile Cys Thr Ile Asp Val Tyr Met Ile Met Val Lys Cys
            260                 265                 270

Trp Met Ile Asp Ser Glu Cys Arg Pro Arg Phe Arg Glu Leu Val Ser
            275                 280                 285

Glu Phe Ser Arg Met Ala Arg Asp Pro Gln Arg Phe Val Val Ile Gln
            290                 295                 300

Asn Glu Asp Leu Gly Pro Ala Ser Pro Leu Asp Ser Thr Phe Tyr Arg
305                 310                 315                 320

Ser Leu Leu Glu Asp Asp Met Gly Asp Leu Val Asp Ala Glu Glu
            325                 330                 335

Tyr Leu Val Pro Gln Gln Gly Phe Phe Cys Pro Asp Pro Ala Pro Gly
            340                 345                 350

Ala Gly Gly Met Val His His His Arg Ser Ser Ser Thr Arg Ser
            355                 360                 365

Gly Gly Gly Asp Leu Thr Leu Gly Leu Glu Pro Ser Glu Glu Glu Ala
            370                 375                 380

Pro Arg Ser Pro Leu Ala Pro Ser Glu Gly Ala Gly Ser Asp Val Phe
385                 390                 395                 400

Asp Gly Asp Leu Gly Met Gly Ala Ala Lys Gly Leu Gln Ser Leu Pro
            405                 410                 415

Thr His Asp Pro Ser Pro Leu Gln Arg Tyr Ser Glu Asp Pro Thr Val
            420                 425                 430

Pro Leu Pro Ser Glu Thr Asp Gly Tyr Val Ala Pro Leu Thr Cys Ser
            435                 440                 445

Pro Gln Pro Glu Tyr Val Asn Gln Pro Asp Val Arg Pro Gln Pro Pro
            450                 455                 460

Ser Pro Arg Glu Gly Pro Leu Pro Ala Ala Arg Pro Ala Gly Ala Thr
465                 470                 475                 480

Leu Glu Arg Pro Lys Thr Leu Ser Pro Gly Lys Asn Gly Val Val Lys
```

```
                    485                 490                 495
Asp Val Phe Ala Phe Gly Gly Ala Val Glu Asn Pro Glu Tyr Leu Thr
                500                 505                 510

Pro Gln Gly Gly Ala Ala Pro Gln Pro His Pro Pro Ala Phe Ser
            515                 520                 525

Pro Ala Phe Asp Asn Leu Tyr Tyr Trp Asp Gln Asp Pro Pro Glu Arg
            530                 535                 540

Gly Ala Pro Pro Ser Thr Phe Lys Gly Thr Pro Thr Ala Glu Asn Pro
545                 550                 555                 560

Glu Tyr Leu Gly Leu Asp Val Pro Val
                565

<210> SEQ ID NO 13
<211> LENGTH: 1240
<212> TYPE: PRT
<213> ORGANISM: Homo sapiens
<220> FEATURE:
<221> NAME/KEY: misc_feature
<223> OTHER INFORMATION: human ErbB2, Isoform 4 (UniProt ID P04626-4)

<400> SEQUENCE: 13

Met Pro Arg Gly Ser Trp Lys Pro Gln Val Cys Thr Gly Thr Asp Met
1               5                   10                  15

Lys Leu Arg Leu Pro Ala Ser Pro Glu Thr His Leu Asp Met Leu Arg
            20                  25                  30

His Leu Tyr Gln Gly Cys Gln Val Val Gln Gly Asn Leu Glu Leu Thr
        35                  40                  45

Tyr Leu Pro Thr Asn Ala Ser Leu Ser Phe Leu Gln Asp Ile Gln Glu
    50                  55                  60

Val Gln Gly Tyr Val Leu Ile Ala His Asn Gln Val Arg Gln Val Pro
65                  70                  75                  80

Leu Gln Arg Leu Arg Ile Val Arg Gly Thr Gln Leu Phe Glu Asp Asn
                85                  90                  95

Tyr Ala Leu Ala Val Leu Asp Asn Gly Asp Pro Leu Asn Asn Thr Thr
            100                 105                 110

Pro Val Thr Gly Ala Ser Pro Gly Gly Leu Arg Glu Leu Gln Leu Arg
        115                 120                 125

Ser Leu Thr Glu Ile Leu Lys Gly Gly Val Leu Ile Gln Arg Asn Pro
130                 135                 140

Gln Leu Cys Tyr Gln Asp Thr Ile Leu Trp Lys Asp Ile Phe His Lys
145                 150                 155                 160

Asn Asn Gln Leu Ala Leu Thr Leu Ile Asp Thr Asn Arg Ser Arg Ala
                165                 170                 175

Cys His Pro Cys Ser Pro Met Cys Lys Gly Ser Arg Cys Trp Gly Glu
            180                 185                 190

Ser Ser Glu Asp Cys Gln Ser Leu Thr Arg Thr Val Cys Ala Gly Gly
        195                 200                 205

Cys Ala Arg Cys Lys Gly Pro Leu Pro Thr Asp Cys Cys His Glu Gln
    210                 215                 220

Cys Ala Ala Gly Cys Thr Gly Pro Lys His Ser Asp Cys Leu Ala Cys
225                 230                 235                 240

Leu His Phe Asn His Ser Gly Ile Cys Glu Leu His Cys Pro Ala Leu
                245                 250                 255

Val Thr Tyr Asn Thr Asp Thr Phe Glu Ser Met Pro Asn Pro Glu Gly
            260                 265                 270
```

-continued

```
Arg Tyr Thr Phe Gly Ala Ser Cys Val Thr Ala Cys Pro Tyr Asn Tyr
            275                 280                 285

Leu Ser Thr Asp Val Gly Ser Cys Thr Leu Val Cys Pro Leu His Asn
        290                 295                 300

Gln Glu Val Thr Ala Glu Asp Gly Thr Gln Arg Cys Glu Lys Cys Ser
305                 310                 315                 320

Lys Pro Cys Ala Arg Val Cys Tyr Gly Leu Gly Met Glu His Leu Arg
                325                 330                 335

Glu Val Arg Ala Val Thr Ser Ala Asn Ile Gln Glu Phe Ala Gly Cys
            340                 345                 350

Lys Lys Ile Phe Gly Ser Leu Ala Phe Leu Pro Glu Ser Phe Asp Gly
        355                 360                 365

Asp Pro Ala Ser Asn Thr Ala Pro Leu Gln Pro Glu Gln Leu Gln Val
    370                 375                 380

Phe Glu Thr Leu Glu Glu Ile Thr Gly Tyr Leu Tyr Ile Ser Ala Trp
385                 390                 395                 400

Pro Asp Ser Leu Pro Asp Leu Ser Val Phe Gln Asn Leu Gln Val Ile
                405                 410                 415

Arg Gly Arg Ile Leu His Asn Gly Ala Tyr Ser Leu Thr Leu Gln Gly
            420                 425                 430

Leu Gly Ile Ser Trp Leu Gly Leu Arg Ser Leu Arg Glu Leu Gly Ser
        435                 440                 445

Gly Leu Ala Leu Ile His His Asn Thr His Leu Cys Phe Val His Thr
    450                 455                 460

Val Pro Trp Asp Gln Leu Phe Arg Asn Pro His Gln Ala Leu Leu His
465                 470                 475                 480

Thr Ala Asn Arg Pro Glu Asp Glu Cys Val Gly Glu Gly Leu Ala Cys
                485                 490                 495

His Gln Leu Cys Ala Arg Gly His Cys Trp Gly Pro Gly Pro Thr Gln
            500                 505                 510

Cys Val Asn Cys Ser Gln Phe Leu Arg Gly Gln Glu Cys Val Glu Glu
        515                 520                 525

Cys Arg Val Leu Gln Gly Leu Pro Arg Glu Tyr Val Asn Ala Arg His
    530                 535                 540

Cys Leu Pro Cys His Pro Glu Cys Gln Pro Gln Asn Gly Ser Val Thr
545                 550                 555                 560

Cys Phe Gly Pro Glu Ala Asp Gln Cys Val Ala Cys Ala His Tyr Lys
                565                 570                 575

Asp Pro Pro Phe Cys Val Ala Arg Cys Pro Ser Gly Val Lys Pro Asp
            580                 585                 590

Leu Ser Tyr Met Pro Ile Trp Lys Phe Pro Asp Glu Glu Gly Ala Cys
        595                 600                 605

Gln Pro Cys Pro Ile Asn Cys Thr His Ser Cys Val Asp Leu Asp Asp
    610                 615                 620

Lys Gly Cys Pro Ala Glu Gln Arg Ala Ser Pro Leu Thr Ser Ile Ile
625                 630                 635                 640

Ser Ala Val Val Gly Ile Leu Leu Val Val Val Leu Gly Val Val Phe
                645                 650                 655

Gly Ile Leu Ile Lys Arg Arg Gln Gln Lys Ile Arg Lys Tyr Thr Met
            660                 665                 670

Arg Arg Leu Leu Gln Glu Thr Glu Leu Val Glu Pro Leu Thr Pro Ser
        675                 680                 685

Gly Ala Met Pro Asn Gln Ala Gln Met Arg Ile Leu Lys Glu Thr Glu
```

```
            690             695             700
Leu Arg Lys Val Lys Val Leu Gly Ser Gly Ala Phe Gly Thr Val Tyr
705             710             715             720

Lys Gly Ile Trp Ile Pro Asp Gly Glu Asn Val Lys Ile Pro Val Ala
            725             730             735

Ile Lys Val Leu Arg Glu Asn Thr Ser Pro Lys Ala Asn Lys Glu Ile
            740             745             750

Leu Asp Glu Ala Tyr Val Met Ala Gly Val Gly Ser Pro Tyr Val Ser
755             760             765

Arg Leu Leu Gly Ile Cys Leu Thr Ser Thr Val Gln Leu Val Thr Gln
770             775             780

Leu Met Pro Tyr Gly Cys Leu Leu Asp His Val Arg Glu Asn Arg Gly
785             790             795             800

Arg Leu Gly Ser Gln Asp Leu Leu Asn Trp Cys Met Gln Ile Ala Lys
            805             810             815

Gly Met Ser Tyr Leu Glu Asp Val Arg Leu Val His Arg Asp Leu Ala
            820             825             830

Ala Arg Asn Val Leu Val Lys Ser Pro Asn His Val Lys Ile Thr Asp
            835             840             845

Phe Gly Leu Ala Arg Leu Leu Asp Ile Asp Glu Thr Glu Tyr His Ala
850             855             860

Asp Gly Gly Lys Val Pro Ile Lys Trp Met Ala Leu Glu Ser Ile Leu
865             870             875             880

Arg Arg Arg Phe Thr His Gln Ser Asp Val Trp Ser Tyr Gly Val Thr
            885             890             895

Val Trp Glu Leu Met Thr Phe Gly Ala Lys Pro Tyr Asp Gly Ile Pro
            900             905             910

Ala Arg Glu Ile Pro Asp Leu Leu Glu Lys Gly Glu Arg Leu Pro Gln
            915             920             925

Pro Pro Ile Cys Thr Ile Asp Val Tyr Met Ile Met Val Lys Cys Trp
930             935             940

Met Ile Asp Ser Glu Cys Arg Pro Arg Phe Arg Glu Leu Val Ser Glu
945             950             955             960

Phe Ser Arg Met Ala Arg Asp Pro Gln Arg Phe Val Val Ile Gln Asn
            965             970             975

Glu Asp Leu Gly Pro Ala Ser Pro Leu Asp Ser Thr Phe Tyr Arg Ser
            980             985             990

Leu Leu Glu Asp Asp Asp Met Gly Asp Leu Val Asp Ala Glu Glu Tyr
            995             1000            1005

Leu Val Pro Gln Gln Gly Phe Phe Cys Pro Asp Pro Ala Pro Gly
    1010            1015            1020

Ala Gly Gly Met Val His His Arg His Arg Ser Ser Ser Thr Arg
    1025            1030            1035

Ser Gly Gly Gly Asp Leu Thr Leu Gly Leu Glu Pro Ser Glu Glu
    1040            1045            1050

Glu Ala Pro Arg Ser Pro Leu Ala Pro Ser Glu Gly Ala Gly Ser
    1055            1060            1065

Asp Val Phe Asp Gly Asp Leu Gly Met Gly Ala Ala Lys Gly Leu
    1070            1075            1080

Gln Ser Leu Pro Thr His Asp Pro Ser Pro Leu Gln Arg Tyr Ser
    1085            1090            1095

Glu Asp Pro Thr Val Pro Leu Pro Ser Glu Thr Asp Gly Tyr Val
    1100            1105            1110
```

```
Ala Pro Leu Thr Cys Ser Pro Gln Pro Glu Tyr Val Asn Gln Pro
    1115                1120                1125

Asp Val Arg Pro Gln Pro Ser Pro Arg Glu Gly Pro Leu Pro
    1130                1135                1140

Ala Ala Arg Pro Ala Gly Ala Thr Leu Glu Arg Pro Lys Thr Leu
    1145                1150                1155

Ser Pro Gly Lys Asn Gly Val Val Lys Asp Val Phe Ala Phe Gly
    1160                1165                1170

Gly Ala Val Glu Asn Pro Glu Tyr Leu Thr Pro Gln Gly Gly Ala
    1175                1180                1185

Ala Pro Gln Pro His Pro Pro Pro Ala Phe Ser Pro Ala Phe Asp
    1190                1195                1200

Asn Leu Tyr Tyr Trp Asp Gln Asp Pro Pro Glu Arg Gly Ala Pro
    1205                1210                1215

Pro Ser Thr Phe Lys Gly Thr Pro Thr Ala Glu Asn Pro Glu Tyr
    1220                1225                1230

Leu Gly Leu Asp Val Pro Val
    1235                1240

<210> SEQ ID NO 14
<211> LENGTH: 1225
<212> TYPE: PRT
<213> ORGANISM: Homo sapiens
<220> FEATURE:
<221> NAME/KEY: misc_feature
<223> OTHER INFORMATION: human ErbB2, Isoform 5 (UniProt ID P04626-5)

<400> SEQUENCE: 14

Met Lys Leu Arg Leu Pro Ala Ser Pro Glu Thr His Leu Asp Met Leu
1               5                   10                  15

Arg His Leu Tyr Gln Gly Cys Gln Val Val Gln Gly Asn Leu Glu Leu
            20                  25                  30

Thr Tyr Leu Pro Thr Asn Ala Ser Leu Ser Phe Leu Gln Asp Ile Gln
        35                  40                  45

Glu Val Gln Gly Tyr Val Leu Ile Ala His Asn Gln Val Arg Gln Val
    50                  55                  60

Pro Leu Gln Arg Leu Arg Ile Val Arg Gly Thr Gln Leu Phe Glu Asp
65                  70                  75                  80

Asn Tyr Ala Leu Ala Val Leu Asp Asn Gly Asp Pro Leu Asn Asn Thr
                85                  90                  95

Thr Pro Val Thr Gly Ala Ser Pro Gly Gly Leu Arg Glu Leu Gln Leu
            100                 105                 110

Arg Ser Leu Thr Glu Ile Leu Lys Gly Gly Val Leu Ile Gln Arg Asn
        115                 120                 125

Pro Gln Leu Cys Tyr Gln Asp Thr Ile Leu Trp Lys Asp Ile Phe His
    130                 135                 140

Lys Asn Asn Gln Leu Ala Leu Thr Leu Ile Asp Thr Asn Arg Ser Arg
145                 150                 155                 160

Ala Cys His Pro Cys Ser Pro Met Cys Lys Gly Ser Arg Cys Trp Gly
                165                 170                 175

Glu Ser Ser Glu Asp Cys Gln Ser Leu Thr Arg Thr Val Cys Ala Gly
            180                 185                 190

Gly Cys Ala Arg Cys Lys Gly Pro Leu Pro Thr Asp Cys Cys His Glu
        195                 200                 205

Gln Cys Ala Ala Gly Cys Thr Gly Pro Lys His Ser Asp Cys Leu Ala
```

```
            210                 215                 220
Cys Leu His Phe Asn His Ser Gly Ile Cys Glu Leu His Cys Pro Ala
225                 230                 235                 240

Leu Val Thr Tyr Asn Thr Asp Thr Phe Glu Ser Met Pro Asn Pro Glu
                245                 250                 255

Gly Arg Tyr Thr Phe Gly Ala Ser Cys Val Thr Ala Cys Pro Tyr Asn
                260                 265                 270

Tyr Leu Ser Thr Asp Val Gly Ser Cys Thr Leu Val Cys Pro Leu His
                275                 280                 285

Asn Gln Glu Val Thr Ala Glu Asp Gly Thr Gln Arg Cys Glu Lys Cys
                290                 295                 300

Ser Lys Pro Cys Ala Arg Val Cys Tyr Gly Leu Gly Met Glu His Leu
305                 310                 315                 320

Arg Glu Val Arg Ala Val Thr Ser Ala Asn Ile Gln Glu Phe Ala Gly
                325                 330                 335

Cys Lys Lys Ile Phe Gly Ser Leu Ala Phe Leu Pro Glu Ser Phe Asp
                340                 345                 350

Gly Asp Pro Ala Ser Asn Thr Ala Pro Leu Gln Pro Glu Gln Leu Gln
                355                 360                 365

Val Phe Glu Thr Leu Glu Glu Ile Thr Gly Tyr Leu Tyr Ile Ser Ala
                370                 375                 380

Trp Pro Asp Ser Leu Pro Asp Leu Ser Val Phe Gln Asn Leu Gln Val
385                 390                 395                 400

Ile Arg Gly Arg Ile Leu His Asn Gly Ala Tyr Ser Leu Thr Leu Gln
                405                 410                 415

Gly Leu Gly Ile Ser Trp Leu Gly Leu Arg Ser Leu Arg Glu Leu Gly
                420                 425                 430

Ser Gly Leu Ala Leu Ile His His Asn Thr His Leu Cys Phe Val His
                435                 440                 445

Thr Val Pro Trp Asp Gln Leu Phe Arg Asn Pro His Gln Ala Leu Leu
450                 455                 460

His Thr Ala Asn Arg Pro Glu Asp Glu Cys Val Gly Glu Gly Leu Ala
465                 470                 475                 480

Cys His Gln Leu Cys Ala Arg Gly His Cys Trp Gly Pro Gly Pro Thr
                485                 490                 495

Gln Cys Val Asn Cys Ser Gln Phe Leu Arg Gly Gln Glu Cys Val Glu
                500                 505                 510

Glu Cys Arg Val Leu Gln Gly Leu Pro Arg Glu Tyr Val Asn Ala Arg
                515                 520                 525

His Cys Leu Pro Cys His Pro Glu Cys Gln Pro Gln Asn Gly Ser Val
                530                 535                 540

Thr Cys Phe Gly Pro Glu Ala Asp Gln Cys Val Ala Cys Ala His Tyr
545                 550                 555                 560

Lys Asp Pro Pro Phe Cys Val Ala Arg Cys Pro Ser Gly Val Lys Pro
                565                 570                 575

Asp Leu Ser Tyr Met Pro Ile Trp Lys Phe Pro Asp Glu Glu Gly Ala
                580                 585                 590

Cys Gln Pro Cys Pro Ile Asn Cys Thr His Ser Cys Val Asp Leu Asp
                595                 600                 605

Asp Lys Gly Cys Pro Ala Glu Gln Arg Ala Ser Pro Leu Thr Ser Ile
                610                 615                 620

Ile Ser Ala Val Val Gly Ile Leu Leu Val Val Val Leu Gly Val Val
625                 630                 635                 640
```

```
Phe Gly Ile Leu Ile Lys Arg Gln Gln Lys Ile Arg Lys Tyr Thr
                645                 650                 655

Met Arg Arg Leu Leu Gln Glu Thr Glu Leu Val Glu Pro Leu Thr Pro
            660                 665                 670

Ser Gly Ala Met Pro Asn Gln Ala Gln Met Arg Ile Leu Lys Glu Thr
            675                 680                 685

Glu Leu Arg Lys Val Lys Val Leu Gly Ser Gly Ala Phe Gly Thr Val
        690                 695                 700

Tyr Lys Gly Ile Trp Ile Pro Asp Gly Glu Asn Val Lys Ile Pro Val
705                 710                 715                 720

Ala Ile Lys Val Leu Arg Glu Asn Thr Ser Pro Lys Ala Asn Lys Glu
                725                 730                 735

Ile Leu Asp Glu Ala Tyr Val Met Ala Gly Val Gly Ser Pro Tyr Val
            740                 745                 750

Ser Arg Leu Leu Gly Ile Cys Leu Thr Ser Thr Val Gln Leu Val Thr
        755                 760                 765

Gln Leu Met Pro Tyr Gly Cys Leu Leu Asp His Val Arg Glu Asn Arg
    770                 775                 780

Gly Arg Leu Gly Ser Gln Asp Leu Leu Asn Trp Cys Met Gln Ile Ala
785                 790                 795                 800

Lys Gly Met Ser Tyr Leu Glu Asp Val Arg Leu Val His Arg Asp Leu
                805                 810                 815

Ala Ala Arg Asn Val Leu Val Lys Ser Pro Asn His Val Lys Ile Thr
            820                 825                 830

Asp Phe Gly Leu Ala Arg Leu Leu Asp Ile Asp Glu Thr Glu Tyr His
        835                 840                 845

Ala Asp Gly Gly Lys Val Pro Ile Lys Trp Met Ala Leu Glu Ser Ile
    850                 855                 860

Leu Arg Arg Arg Phe Thr His Gln Ser Asp Val Trp Ser Tyr Gly Val
865                 870                 875                 880

Thr Val Trp Glu Leu Met Thr Phe Gly Ala Lys Pro Tyr Asp Gly Ile
                885                 890                 895

Pro Ala Arg Glu Ile Pro Asp Leu Leu Glu Lys Gly Glu Arg Leu Pro
            900                 905                 910

Gln Pro Pro Ile Cys Thr Ile Asp Val Tyr Met Ile Met Val Lys Cys
        915                 920                 925

Trp Met Ile Asp Ser Glu Cys Arg Pro Arg Phe Arg Glu Leu Val Ser
    930                 935                 940

Glu Phe Ser Arg Met Ala Arg Asp Pro Gln Arg Phe Val Val Ile Gln
945                 950                 955                 960

Asn Glu Asp Leu Gly Pro Ala Ser Pro Leu Asp Ser Thr Phe Tyr Arg
                965                 970                 975

Ser Leu Leu Glu Asp Asp Asp Met Gly Asp Leu Val Asp Ala Glu Glu
            980                 985                 990

Tyr Leu Val Pro Gln Gln Gly Phe Phe Cys Pro Asp Pro Ala Pro Gly
        995                 1000                1005

Ala Gly Gly Met Val His His Arg His Arg Ser Ser Ser Thr Arg
    1010                1015                1020

Ser Gly Gly Gly Asp Leu Thr Leu Gly Leu Glu Pro Ser Glu Glu
    1025                1030                1035

Glu Ala Pro Arg Ser Pro Leu Ala Pro Ser Glu Gly Ala Gly Ser
    1040                1045                1050
```

Asp Val Phe Asp Gly Asp Leu Gly Met Gly Ala Ala Lys Gly Leu
1055             1060                 1065

Gln Ser Leu Pro Thr His Asp Pro Ser Pro Leu Gln Arg Tyr Ser
1070             1075                 1080

Glu Asp Pro Thr Val Pro Leu Pro Ser Glu Thr Asp Gly Tyr Val
1085             1090                 1095

Ala Pro Leu Thr Cys Ser Pro Gln Pro Glu Tyr Val Asn Gln Pro
1100             1105                 1110

Asp Val Arg Pro Gln Pro Pro Ser Pro Arg Glu Gly Pro Leu Pro
1115             1120                 1125

Ala Ala Arg Pro Ala Gly Ala Thr Leu Glu Arg Pro Lys Thr Leu
1130             1135                 1140

Ser Pro Gly Lys Asn Gly Val Val Lys Asp Val Phe Ala Phe Gly
1145             1150                 1155

Gly Ala Val Glu Asn Pro Glu Tyr Leu Thr Pro Gln Gly Gly Ala
1160             1165                 1170

Ala Pro Gln Pro His Pro Pro Pro Ala Phe Ser Pro Ala Phe Asp
1175             1180                 1185

Asn Leu Tyr Tyr Trp Asp Gln Asp Pro Pro Glu Arg Gly Ala Pro
1190             1195                 1200

Pro Ser Thr Phe Lys Gly Thr Pro Thr Ala Glu Asn Pro Glu Tyr
1205             1210                 1215

Leu Gly Leu Asp Val Pro Val
1220             1225

<210> SEQ ID NO 15
<211> LENGTH: 888
<212> TYPE: PRT
<213> ORGANISM: Homo sapiens
<220> FEATURE:
<221> NAME/KEY: misc_feature
<223> OTHER INFORMATION: human ErbB2, Isoform 6 (UniProt ID P04626-6)

<400> SEQUENCE: 15

Met Glu Leu Ala Ala Leu Cys Arg Trp Gly Leu Leu Ala Leu Leu
1               5                   10                  15

Pro Pro Gly Ala Ala Ser Thr Gln Val Cys Thr Gly Thr Asp Met Lys
                20                  25                  30

Leu Arg Leu Pro Ala Ser Pro Glu Thr His Leu Asp Met Leu Arg His
                35                  40                  45

Leu Tyr Gln Gly Cys Gln Val Val Gln Gly Asn Leu Glu Leu Thr Tyr
    50                  55                      60

Leu Pro Thr Asn Ala Ser Leu Ser Phe Leu Gln Asp Ile Gln Glu Val
65              70                  75                      80

Gln Gly Tyr Val Leu Ile Ala His Asn Gln Val Arg Gln Val Pro Leu
                85                  90                      95

Gln Arg Leu Arg Ile Val Arg Gly Thr Gln Leu Phe Glu Asp Asn Tyr
                100                 105                 110

Ala Leu Ala Val Leu Asp Asn Gly Asp Pro Leu Asn Asn Thr Thr Pro
            115                 120                 125

Val Thr Gly Ala Ser Pro Gly Gly Leu Arg Glu Leu Gln Leu Arg Ser
            130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

```
Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590
```

Pro Pro Phe Cys Val Ala Arg Cys Pro Ser Gly Val Lys Pro Asp Leu
            595                 600                 605

Ser Tyr Met Pro Ile Trp Lys Phe Pro Asp Glu Glu Gly Ala Cys Gln
610                 615                 620

Pro Cys Pro Ile Asn Cys Thr His Ser Pro Leu Thr Ser Ile Ile Ser
625                 630                 635                 640

Ala Val Val Gly Ile Leu Leu Val Val Val Leu Gly Val Val Phe Gly
            645                 650                 655

Ile Leu Ile Lys Arg Arg Gln Gln Lys Ile Arg Lys Tyr Thr Met Arg
            660                 665                 670

Arg Leu Leu Gln Glu Thr Glu Leu Val Glu Pro Leu Thr Pro Ser Gly
            675                 680                 685

Ala Met Pro Asn Gln Ala Gln Met Arg Ile Leu Lys Glu Thr Glu Leu
            690                 695                 700

Arg Lys Val Lys Val Leu Gly Ser Gly Ala Phe Gly Thr Val Tyr Lys
705                 710                 715                 720

Gly Ile Trp Ile Pro Asp Gly Glu Asn Val Lys Ile Pro Val Ala Ile
            725                 730                 735

Lys Val Leu Arg Glu Asn Thr Ser Pro Lys Ala Asn Lys Glu Ile Leu
            740                 745                 750

Asp Glu Thr Ile Ser Asn Leu Phe Ser Asn Phe Ala Pro Arg Gly Pro
            755                 760                 765

Ser Ala Cys Cys Glu Pro Thr Cys Trp Cys His Ser Gly Lys Gly Gln
770                 775                 780

Asp Ser Leu Pro Arg Glu Glu Trp Gly Arg Gln Arg Phe Cys Leu
785                 790                 795                 800

Trp Gly Cys Arg Gly Glu Pro Arg Val Leu Asp Thr Pro Gly Arg Ser
            805                 810                 815

Cys Pro Ser Ala Pro Pro Ser Ser Cys Leu Gln Pro Ser Leu Arg Gln
            820                 825                 830

Pro Leu Leu Leu Gly Pro Gly Pro Thr Arg Ala Gly Gly Ser Thr Gln
            835                 840                 845

His Leu Gln Arg Asp Thr Tyr Gly Arg Glu Pro Arg Val Pro Gly Ser
850                 855                 860

Gly Arg Ala Ser Val Asn Gln Lys Ala Lys Ser Ala Glu Ala Leu Met
865                 870                 875                 880

Cys Pro Gln Gly Ala Gly Lys Ala
            885

<210> SEQ ID NO 16
<211> LENGTH: 1342
<212> TYPE: PRT
<213> ORGANISM: Homo sapiens
<220> FEATURE:
<221> NAME/KEY: misc_feature
<223> OTHER INFORMATION: human ErbB3, Isoform 1 (canonical; UniProt ID
      P21860-1)

<400> SEQUENCE: 16

Met Arg Ala Asn Asp Ala Leu Gln Val Leu Gly Leu Leu Phe Ser Leu
1               5                   10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
            35                  40                  45

Leu Tyr Lys Leu Tyr Glu Arg Cys Glu Val Val Met Gly Asn Leu Glu

```
            50                  55                  60
Ile Val Leu Thr Gly His Asn Ala Asp Leu Ser Phe Leu Gln Trp Ile
 65                  70                  75                  80
Arg Glu Val Thr Gly Tyr Val Leu Val Ala Met Asn Glu Phe Ser Thr
                     85                  90                  95
Leu Pro Leu Pro Asn Leu Arg Val Arg Gly Thr Gln Val Tyr Asp
                100                 105                 110
Gly Lys Phe Ala Ile Phe Val Met Leu Asn Tyr Asn Thr Asn Ser Ser
                115                 120                 125
His Ala Leu Arg Gln Leu Arg Leu Thr Gln Leu Thr Glu Ile Leu Ser
                130                 135                 140
Gly Gly Val Tyr Ile Glu Lys Asn Asp Lys Leu Cys His Met Asp Thr
145                 150                 155                 160
Ile Asp Trp Arg Asp Ile Val Arg Asp Arg Asp Ala Glu Ile Val Val
                    165                 170                 175
Lys Asp Asn Gly Arg Ser Cys Pro Pro Cys His Glu Val Cys Lys Gly
                180                 185                 190
Arg Cys Trp Gly Pro Gly Ser Glu Asp Cys Gln Thr Leu Thr Lys Thr
                    195                 200                 205
Ile Cys Ala Pro Gln Cys Asn Gly His Cys Phe Gly Pro Asn Pro Asn
210                 215                     220
Gln Cys Cys His Asp Glu Cys Ala Gly Gly Cys Ser Gly Pro Gln Asp
225                     230                 235                 240
Thr Asp Cys Phe Ala Cys Arg His Phe Asn Asp Ser Gly Ala Cys Val
                    245                 250                 255
Pro Arg Cys Pro Gln Pro Leu Val Tyr Asn Lys Leu Thr Phe Gln Leu
                260                 265                 270
Glu Pro Asn Pro His Thr Lys Tyr Gln Tyr Gly Gly Val Cys Val Ala
                275                 280                 285
Ser Cys Pro His Asn Phe Val Val Asp Gln Thr Ser Cys Val Arg Ala
                290                 295                 300
Cys Pro Pro Asp Lys Met Glu Val Asp Lys Asn Gly Leu Lys Met Cys
305                 310                 315                 320
Glu Pro Cys Gly Gly Leu Cys Pro Lys Ala Cys Glu Gly Thr Gly Ser
                    325                 330                 335
Gly Ser Arg Phe Gln Thr Val Asp Ser Ser Asn Ile Asp Gly Phe Val
                340                 345                 350
Asn Cys Thr Lys Ile Leu Gly Asn Leu Asp Phe Leu Ile Thr Gly Leu
                355                 360                 365
Asn Gly Asp Pro Trp His Lys Ile Pro Ala Leu Asp Pro Glu Lys Leu
370                 375                 380
Asn Val Phe Arg Thr Val Arg Glu Ile Thr Gly Tyr Leu Asn Ile Gln
385                 390                 395                 400
Ser Trp Pro Pro His Met His Asn Phe Ser Val Phe Ser Asn Leu Thr
                    405                 410                 415
Thr Ile Gly Gly Arg Ser Leu Tyr Asn Arg Gly Phe Ser Leu Leu Ile
                420                 425                 430
Met Lys Asn Leu Asn Val Thr Ser Leu Gly Phe Arg Ser Leu Lys Glu
                435                 440                 445
Ile Ser Ala Gly Arg Ile Tyr Ile Ser Ala Asn Arg Gln Leu Cys Tyr
                450                 455                 460
His His Ser Leu Asn Trp Thr Lys Val Leu Arg Gly Pro Thr Glu Glu
465                 470                 475                 480
```

```
Arg Leu Asp Ile Lys His Asn Arg Pro Arg Asp Cys Val Ala Glu
            485                 490                 495

Gly Lys Val Cys Asp Pro Leu Cys Ser Ser Gly Cys Trp Gly Pro
            500                 505                 510

Gly Pro Gly Gln Cys Leu Ser Cys Arg Asn Tyr Ser Arg Gly Val
            515                 520                 525

Cys Val Thr His Cys Asn Phe Leu Asn Gly Glu Pro Arg Glu Phe Ala
            530                 535                 540

His Glu Ala Glu Cys Phe Ser Cys His Pro Glu Cys Gln Pro Met Glu
545                 550                 555                 560

Gly Thr Ala Thr Cys Asn Gly Ser Gly Ser Asp Thr Cys Ala Gln Cys
            565                 570                 575

Ala His Phe Arg Asp Gly Pro His Cys Val Ser Ser Cys Pro His Gly
            580                 585                 590

Val Leu Gly Ala Lys Gly Pro Ile Tyr Lys Tyr Pro Asp Val Gln Asn
            595                 600                 605

Glu Cys Arg Pro Cys His Glu Asn Cys Thr Gln Gly Cys Lys Gly Pro
            610                 615                 620

Glu Leu Gln Asp Cys Leu Gly Gln Thr Leu Val Leu Ile Gly Lys Thr
625                 630                 635                 640

His Leu Thr Met Ala Leu Thr Val Ile Ala Gly Leu Val Val Ile Phe
            645                 650                 655

Met Met Leu Gly Gly Thr Phe Leu Tyr Trp Arg Gly Arg Arg Ile Gln
            660                 665                 670

Asn Lys Arg Ala Met Arg Arg Tyr Leu Glu Arg Gly Glu Ser Ile Glu
            675                 680                 685

Pro Leu Asp Pro Ser Glu Lys Ala Asn Lys Val Leu Ala Arg Ile Phe
            690                 695                 700

Lys Glu Thr Glu Leu Arg Lys Leu Lys Val Leu Gly Ser Gly Val Phe
705                 710                 715                 720

Gly Thr Val His Lys Gly Val Trp Ile Pro Glu Gly Glu Ser Ile Lys
            725                 730                 735

Ile Pro Val Cys Ile Lys Val Ile Glu Asp Lys Ser Gly Arg Gln Ser
            740                 745                 750

Phe Gln Ala Val Thr Asp His Met Leu Ala Ile Gly Ser Leu Asp His
            755                 760                 765

Ala His Ile Val Arg Leu Leu Gly Leu Cys Pro Gly Ser Ser Leu Gln
            770                 775                 780

Leu Val Thr Gln Tyr Leu Pro Leu Gly Ser Leu Leu Asp His Val Arg
785                 790                 795                 800

Gln His Arg Gly Ala Leu Gly Pro Gln Leu Leu Leu Asn Trp Gly Val
            805                 810                 815

Gln Ile Ala Lys Gly Met Tyr Tyr Leu Glu Glu His Gly Met Val His
            820                 825                 830

Arg Asn Leu Ala Ala Arg Asn Val Leu Leu Lys Ser Pro Ser Gln Val
            835                 840                 845

Gln Val Ala Asp Phe Gly Val Ala Asp Leu Leu Pro Pro Asp Lys
            850                 855                 860

Gln Leu Leu Tyr Ser Glu Ala Lys Thr Pro Ile Lys Trp Met Ala Leu
865                 870                 875                 880

Glu Ser Ile His Phe Gly Lys Tyr Thr His Gln Ser Asp Val Trp Ser
            885                 890                 895
```

```
Tyr Gly Val Thr Val Trp Glu Leu Met Thr Phe Gly Ala Glu Pro Tyr
                900             905             910

Ala Gly Leu Arg Leu Ala Glu Val Pro Asp Leu Leu Glu Lys Gly Glu
        915             920             925

Arg Leu Ala Gln Pro Gln Ile Cys Thr Ile Asp Val Tyr Met Val Met
    930             935             940

Val Lys Cys Trp Met Ile Asp Glu Asn Ile Arg Pro Thr Phe Lys Glu
945             950             955             960

Leu Ala Asn Glu Phe Thr Arg Met Ala Arg Asp Pro Pro Arg Tyr Leu
            965             970             975

Val Ile Lys Arg Glu Ser Gly Pro Gly Ile Ala Pro Gly Pro Glu Pro
        980             985             990

His Gly Leu Thr Asn Lys Lys Leu Glu Glu Val Glu Leu Glu Pro Glu
        995             1000            1005

Leu Asp Leu Asp Leu Asp Leu Glu Ala Glu Glu Asp Asn Leu Ala
    1010            1015            1020

Thr Thr Thr Leu Gly Ser Ala Leu Ser Leu Pro Val Gly Thr Leu
    1025            1030            1035

Asn Arg Pro Arg Gly Ser Gln Ser Leu Leu Ser Pro Ser Ser Gly
    1040            1045            1050

Tyr Met Pro Met Asn Gln Gly Asn Leu Gly Glu Ser Cys Gln Glu
    1055            1060            1065

Ser Ala Val Ser Gly Ser Ser Glu Arg Cys Pro Arg Pro Val Ser
    1070            1075            1080

Leu His Pro Met Pro Arg Gly Cys Leu Ala Ser Glu Ser Ser Glu
    1085            1090            1095

Gly His Val Thr Gly Ser Glu Ala Glu Leu Gln Glu Lys Val Ser
    1100            1105            1110

Met Cys Arg Ser Arg Ser Arg Ser Arg Ser Pro Arg Pro Arg Gly
    1115            1120            1125

Asp Ser Ala Tyr His Ser Gln Arg His Ser Leu Leu Thr Pro Val
    1130            1135            1140

Thr Pro Leu Ser Pro Pro Gly Leu Glu Glu Glu Asp Val Asn Gly
    1145            1150            1155

Tyr Val Met Pro Asp Thr His Leu Lys Gly Thr Pro Ser Ser Arg
    1160            1165            1170

Glu Gly Thr Leu Ser Ser Val Gly Leu Ser Ser Val Leu Gly Thr
    1175            1180            1185

Glu Glu Glu Asp Glu Asp Glu Glu Tyr Glu Tyr Met Asn Arg Arg
    1190            1195            1200

Arg Arg His Ser Pro Pro His Pro Pro Arg Pro Ser Ser Leu Glu
    1205            1210            1215

Glu Leu Gly Tyr Glu Tyr Met Asp Val Gly Ser Asp Leu Ser Ala
    1220            1225            1230

Ser Leu Gly Ser Thr Gln Ser Cys Pro Leu His Pro Val Pro Ile
    1235            1240            1245

Met Pro Thr Ala Gly Thr Thr Pro Asp Glu Asp Tyr Glu Tyr Met
    1250            1255            1260

Asn Arg Gln Arg Asp Gly Gly Gly Pro Gly Gly Asp Tyr Ala Ala
    1265            1270            1275

Met Gly Ala Cys Pro Ala Ser Glu Gln Gly Tyr Glu Glu Met Arg
    1280            1285            1290

Ala Phe Gln Gly Pro Gly His Gln Ala Pro His Val His Tyr Ala
```

```
                1295                1300                1305

Arg Leu Lys Thr Leu Arg Ser Leu Glu Ala Thr Asp Ser Ala Phe
        1310                1315                1320

Asp Asn Pro Asp Tyr Trp His Ser Arg Leu Phe Pro Lys Ala Asn
    1325                1330                1335

Ala Gln Arg Thr
    1340

<210> SEQ ID NO 17
<211> LENGTH: 183
<212> TYPE: PRT
<213> ORGANISM: Homo sapiens
<220> FEATURE:
<221> NAME/KEY: misc_feature
<223> OTHER INFORMATION: human ErbB3, Isoform 2 (UniProt ID P21860-2)

<400> SEQUENCE: 17

Met Arg Ala Asn Asp Ala Leu Gln Val Leu Gly Leu Leu Phe Ser Leu
1               5                  10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
        115                 120                 125

His Ala Leu Arg Gln Leu Arg Leu Thr Gln Leu Thr Gly Gln Phe Pro
    130                 135                 140

Met Val Pro Ser Gly Leu Thr Pro Gln Pro Ala Gln Asp Trp Tyr Leu
145                 150                 155                 160

Leu Asp Asp Asp Pro Arg Leu Leu Thr Leu Ser Ala Ser Ser Lys Val
                165                 170                 175

Pro Val Thr Leu Ala Ala Val
            180

<210> SEQ ID NO 18
<211> LENGTH: 331
<212> TYPE: PRT
<213> ORGANISM: Homo sapiens
<220> FEATURE:
<221> NAME/KEY: misc_feature
<223> OTHER INFORMATION: human ErbB3, Isoform 3 (UniProt ID P21860-3)

<400> SEQUENCE: 18

Met Arg Ala Asn Asp Ala Leu Gln Val Leu Gly Leu Leu Phe Ser Leu
1               5                  10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
        35                  40                  45

Leu Tyr Lys Leu Tyr Glu Arg Cys Glu Val Val Met Gly Asn Leu Glu
```

```
                      50                  55                  60
Ile Val Leu Thr Gly His Asn Ala Asp Leu Ser Phe Leu Gln Trp Ile
 65                  70                  75                  80

Arg Glu Val Thr Gly Tyr Val Leu Val Ala Met Asn Glu Phe Ser Thr
                     85                  90                  95

Leu Pro Leu Pro Asn Leu Arg Val Val Arg Gly Thr Gln Val Tyr Asp
                100                 105                 110

Gly Lys Phe Ala Ile Phe Val Met Leu Asn Tyr Asn Thr Asn Ser Ser
                115                 120                 125

His Ala Leu Arg Gln Leu Arg Leu Thr Gln Leu Thr Glu Ile Leu Ser
130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
                180                 185                 190

Arg Cys Trp Gly Pro Gly Ser Glu Asp Cys Gln Thr Leu Thr Lys Thr
                195                 200                 205

Ile Cys Ala Pro Gln Cys Asn Gly His Cys Phe Gly Pro Asn Pro Asn
210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Gln Pro Leu Val Tyr Asn Lys Leu Thr Phe Gln Leu
                260                 265                 270

Glu Pro Asn Pro His Thr Lys Tyr Gln Tyr Gly Gly Val Cys Val Ala
                275                 280                 285

Ser Cys Pro His Asn Phe Val Val Asp Gln Thr Ser Cys Val Arg Ala
                290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Phe
                325                 330

<210> SEQ ID NO 19
<211> LENGTH: 1283
<212> TYPE: PRT
<213> ORGANISM: Homo sapiens
<220> FEATURE:
<221> NAME/KEY: misc_feature
<223> OTHER INFORMATION: human ErbB3, Isoform 4 (UniProt ID P21860-4)

<400> SEQUENCE: 19

Met Gly Asn Leu Glu Ile Val Leu Thr Gly His Asn Ala Asp Leu Ser
  1               5                  10                  15

Phe Leu Gln Trp Ile Arg Glu Val Thr Gly Tyr Val Leu Val Ala Met
                 20                  25                  30

Asn Glu Phe Ser Thr Leu Pro Leu Pro Asn Leu Arg Val Val Arg Gly
             35                  40                  45

Thr Gln Val Tyr Asp Gly Lys Phe Ala Ile Phe Val Met Leu Asn Tyr
         50                  55                  60

Asn Thr Asn Ser Ser His Ala Leu Arg Gln Leu Arg Leu Thr Gln Leu
 65                  70                  75                  80
```

```
Thr Glu Ile Leu Ser Gly Gly Val Tyr Ile Glu Lys Asn Asp Lys Leu
                85                  90                  95

Cys His Met Asp Thr Ile Asp Trp Arg Asp Ile Val Arg Asp Arg Asp
        100                 105                 110

Ala Glu Ile Val Val Lys Asp Asn Gly Arg Ser Cys Pro Pro Cys His
        115                 120                 125

Glu Val Cys Lys Gly Arg Cys Trp Gly Pro Gly Ser Glu Asp Cys Gln
    130                 135                 140

Thr Leu Thr Lys Thr Ile Cys Ala Pro Gln Cys Asn Gly His Cys Phe
145                 150                 155                 160

Gly Pro Asn Pro Asn Gln Cys Cys His Asp Glu Cys Ala Gly Gly Cys
                165                 170                 175

Ser Gly Pro Gln Asp Thr Asp Cys Phe Ala Cys Arg His Phe Asn Asp
            180                 185                 190

Ser Gly Ala Cys Val Pro Arg Cys Pro Gln Pro Leu Val Tyr Asn Lys
        195                 200                 205

Leu Thr Phe Gln Leu Glu Pro Asn Pro His Thr Lys Tyr Gln Tyr Gly
    210                 215                 220

Gly Val Cys Val Ala Ser Cys Pro His Asn Phe Val Val Asp Gln Thr
225                 230                 235                 240

Ser Cys Val Arg Ala Cys Pro Pro Asp Lys Met Glu Val Asp Lys Asn
                245                 250                 255

Gly Leu Lys Met Cys Glu Pro Cys Gly Gly Leu Cys Pro Lys Ala Cys
            260                 265                 270

Glu Gly Thr Gly Ser Gly Ser Arg Phe Gln Thr Val Asp Ser Ser Asn
        275                 280                 285

Ile Asp Gly Phe Val Asn Cys Thr Lys Ile Leu Gly Asn Leu Asp Phe
    290                 295                 300

Leu Ile Thr Gly Leu Asn Gly Asp Pro Trp His Lys Ile Pro Ala Leu
305                 310                 315                 320

Asp Pro Glu Lys Leu Asn Val Phe Arg Thr Val Arg Glu Ile Thr Gly
                325                 330                 335

Tyr Leu Asn Ile Gln Ser Trp Pro Pro His Met His Asn Phe Ser Val
            340                 345                 350

Phe Ser Asn Leu Thr Thr Ile Gly Gly Arg Ser Leu Tyr Asn Arg Gly
        355                 360                 365

Phe Ser Leu Leu Ile Met Lys Asn Leu Asn Val Thr Ser Leu Gly Phe
    370                 375                 380

Arg Ser Leu Lys Glu Ile Ser Ala Gly Arg Ile Tyr Ile Ser Ala Asn
385                 390                 395                 400

Arg Gln Leu Cys Tyr His His Ser Leu Asn Trp Thr Lys Val Leu Arg
                405                 410                 415

Gly Pro Thr Glu Glu Arg Leu Asp Ile Lys His Asn Arg Pro Arg Arg
            420                 425                 430

Asp Cys Val Ala Glu Gly Lys Val Cys Asp Pro Leu Cys Ser Ser Gly
        435                 440                 445

Gly Cys Trp Gly Pro Gly Pro Gly Gln Cys Leu Ser Cys Arg Asn Tyr
    450                 455                 460

Ser Arg Gly Gly Val Cys Val Thr His Cys Asn Phe Leu Asn Gly Glu
465                 470                 475                 480

Pro Arg Glu Phe Ala His Glu Ala Glu Cys Phe Ser Cys His Pro Glu
                485                 490                 495

Cys Gln Pro Met Glu Gly Thr Ala Thr Cys Asn Gly Ser Gly Ser Asp
```

```
                500             505             510
Thr Cys Ala Gln Cys Ala His Phe Arg Asp Gly Pro His Cys Val Ser
            515                 520                 525

Ser Cys Pro His Gly Val Leu Gly Ala Lys Gly Pro Ile Tyr Lys Tyr
    530                 535                 540

Pro Asp Val Gln Asn Glu Cys Arg Pro Cys His Glu Asn Cys Thr Gln
545                 550                 555                 560

Gly Cys Lys Gly Pro Glu Leu Gln Asp Cys Leu Gly Gln Thr Leu Val
                565                 570                 575

Leu Ile Gly Lys Thr His Leu Thr Met Ala Leu Thr Val Ile Ala Gly
            580                 585                 590

Leu Val Val Ile Phe Met Met Leu Gly Gly Thr Phe Leu Tyr Trp Arg
        595                 600                 605

Gly Arg Arg Ile Gln Asn Lys Arg Ala Met Arg Arg Tyr Leu Glu Arg
    610                 615                 620

Gly Glu Ser Ile Glu Pro Leu Asp Pro Ser Glu Lys Ala Asn Lys Val
625                 630                 635                 640

Leu Ala Arg Ile Phe Lys Glu Thr Glu Leu Arg Lys Leu Lys Val Leu
                645                 650                 655

Gly Ser Gly Val Phe Gly Thr Val His Lys Gly Val Trp Ile Pro Glu
            660                 665                 670

Gly Glu Ser Ile Lys Ile Pro Val Cys Ile Lys Val Ile Glu Asp Lys
        675                 680                 685

Ser Gly Arg Gln Ser Phe Gln Ala Val Thr Asp His Met Leu Ala Ile
    690                 695                 700

Gly Ser Leu Asp His Ala His Ile Val Arg Leu Leu Gly Leu Cys Pro
705                 710                 715                 720

Gly Ser Ser Leu Gln Leu Val Thr Gln Tyr Leu Pro Leu Gly Ser Leu
                725                 730                 735

Leu Asp His Val Arg Gln His Arg Gly Ala Leu Gly Pro Gln Leu Leu
            740                 745                 750

Leu Asn Trp Gly Val Gln Ile Ala Lys Gly Met Tyr Tyr Leu Glu Glu
        755                 760                 765

His Gly Met Val His Arg Asn Leu Ala Ala Arg Asn Val Leu Leu Lys
    770                 775                 780

Ser Pro Ser Gln Val Gln Val Ala Asp Phe Gly Val Ala Asp Leu Leu
785                 790                 795                 800

Pro Pro Asp Asp Lys Gln Leu Leu Tyr Ser Glu Ala Lys Thr Pro Ile
                805                 810                 815

Lys Trp Met Ala Leu Glu Ser Ile His Phe Gly Lys Tyr Thr His Gln
            820                 825                 830

Ser Asp Val Trp Ser Tyr Gly Val Thr Val Trp Glu Leu Met Thr Phe
        835                 840                 845

Gly Ala Glu Pro Tyr Ala Gly Leu Arg Leu Ala Glu Val Pro Asp Leu
    850                 855                 860

Leu Glu Lys Gly Glu Arg Leu Ala Gln Pro Gln Ile Cys Thr Ile Asp
865                 870                 875                 880

Val Tyr Met Val Met Val Lys Cys Trp Met Ile Asp Glu Asn Ile Arg
                885                 890                 895

Pro Thr Phe Lys Glu Leu Ala Asn Glu Phe Thr Arg Met Ala Arg Asp
            900                 905                 910

Pro Pro Arg Tyr Leu Val Ile Lys Arg Glu Ser Gly Pro Gly Ile Ala
        915                 920                 925
```

-continued

Pro Gly Pro Glu Pro His Gly Leu Thr Asn Lys Lys Leu Glu Glu Val
            930                 935                 940

Glu Leu Glu Pro Glu Leu Asp Leu Asp Leu Asp Leu Glu Ala Glu Glu
945                 950                 955                 960

Asp Asn Leu Ala Thr Thr Thr Leu Gly Ser Ala Leu Ser Leu Pro Val
                965                 970                 975

Gly Thr Leu Asn Arg Pro Arg Gly Ser Gln Ser Leu Leu Ser Pro Ser
            980                 985                 990

Ser Gly Tyr Met Pro Met Asn Gln Gly Asn Leu Gly Glu Ser Cys Gln
        995                 1000                1005

Glu Ser Ala Val Ser Gly Ser Ser Glu Arg Cys Pro Arg Pro Val
    1010                1015                1020

Ser Leu His Pro Met Pro Arg Gly Cys Leu Ala Ser Glu Ser Ser
    1025                1030                1035

Glu Gly His Val Thr Gly Ser Glu Ala Glu Leu Gln Glu Lys Val
    1040                1045                1050

Ser Met Cys Arg Ser Arg Ser Arg Ser Arg Ser Pro Arg Pro Arg
    1055                1060                1065

Gly Asp Ser Ala Tyr His Ser Gln Arg His Ser Leu Leu Thr Pro
    1070                1075                1080

Val Thr Pro Leu Ser Pro Pro Gly Leu Glu Glu Glu Asp Val Asn
    1085                1090                1095

Gly Tyr Val Met Pro Asp Thr His Leu Lys Gly Thr Pro Ser Ser
    1100                1105                1110

Arg Glu Gly Thr Leu Ser Ser Val Gly Leu Ser Ser Val Leu Gly
    1115                1120                1125

Thr Glu Glu Glu Asp Glu Asp Glu Glu Tyr Glu Tyr Met Asn Arg
    1130                1135                1140

Arg Arg Arg His Ser Pro Pro His Pro Pro Arg Pro Ser Ser Leu
    1145                1150                1155

Glu Glu Leu Gly Tyr Glu Tyr Met Asp Val Gly Ser Asp Leu Ser
    1160                1165                1170

Ala Ser Leu Gly Ser Thr Gln Ser Cys Pro Leu His Pro Val Pro
    1175                1180                1185

Ile Met Pro Thr Ala Gly Thr Thr Pro Asp Glu Asp Tyr Glu Tyr
    1190                1195                1200

Met Asn Arg Gln Arg Asp Gly Gly Pro Gly Gly Asp Tyr Ala
    1205                1210                1215

Ala Met Gly Ala Cys Pro Ala Ser Glu Gln Gly Tyr Glu Glu Met
    1220                1225                1230

Arg Ala Phe Gln Gly Pro Gly His Gln Ala Pro His Val His Tyr
    1235                1240                1245

Ala Arg Leu Lys Thr Leu Arg Ser Leu Glu Ala Thr Asp Ser Ala
    1250                1255                1260

Phe Asp Asn Pro Asp Tyr Trp His Ser Arg Leu Phe Pro Lys Ala
    1265                1270                1275

Asn Ala Gln Arg Thr
    1280

<210> SEQ ID NO 20
<211> LENGTH: 699
<212> TYPE: PRT
<213> ORGANISM: Homo sapiens
<220> FEATURE:

<221> NAME/KEY: misc_feature
<223> OTHER INFORMATION: human ErbB3, Isoform 5 (UniProt ID P21860-5)

<400> SEQUENCE: 20

| | | | | | | | | | | | | | | | |
|---|---|---|---|---|---|---|---|---|---|---|---|---|---|---|---|
| Met | Ala | Leu | Thr | Val | Ile | Ala | Gly | Leu | Val | Val | Ile | Phe | Met | Met | Leu |
| 1 | | | | 5 | | | | | 10 | | | | | 15 | |
| Gly | Gly | Thr | Phe | Leu | Tyr | Trp | Arg | Gly | Arg | Arg | Ile | Gln | Asn | Lys | Arg |
| | | | 20 | | | | | 25 | | | | | 30 | | |
| Ala | Met | Arg | Arg | Tyr | Leu | Glu | Arg | Gly | Glu | Ser | Ile | Glu | Pro | Leu | Asp |
| | | 35 | | | | | 40 | | | | | 45 | | | |
| Pro | Ser | Glu | Lys | Ala | Asn | Lys | Val | Leu | Ala | Arg | Ile | Phe | Lys | Glu | Thr |
| 50 | | | | | 55 | | | | | 60 | | | | | |
| Glu | Leu | Arg | Lys | Leu | Lys | Val | Leu | Gly | Ser | Gly | Val | Phe | Gly | Thr | Val |
| 65 | | | | | 70 | | | | 75 | | | | | 80 | |
| His | Lys | Gly | Val | Trp | Ile | Pro | Glu | Gly | Glu | Ser | Ile | Lys | Ile | Pro | Val |
| | | | | 85 | | | | | 90 | | | | | 95 | |
| Cys | Ile | Lys | Val | Ile | Glu | Asp | Lys | Ser | Gly | Arg | Gln | Ser | Phe | Gln | Ala |
| | | | 100 | | | | | 105 | | | | | 110 | | |
| Val | Thr | Asp | His | Met | Leu | Ala | Ile | Gly | Ser | Leu | Asp | His | Ala | His | Ile |
| | | | 115 | | | | | 120 | | | | | 125 | | |
| Val | Arg | Leu | Leu | Gly | Leu | Cys | Pro | Gly | Ser | Ser | Leu | Gln | Leu | Val | Thr |
| | 130 | | | | | 135 | | | | | 140 | | | | |
| Gln | Tyr | Leu | Pro | Leu | Gly | Ser | Leu | Leu | Asp | His | Val | Arg | Gln | His | Arg |
| 145 | | | | | 150 | | | | | 155 | | | | | 160 |
| Gly | Ala | Leu | Gly | Pro | Gln | Leu | Leu | Leu | Asn | Trp | Gly | Val | Gln | Ile | Ala |
| | | | | 165 | | | | | 170 | | | | | 175 | |
| Lys | Gly | Met | Tyr | Tyr | Leu | Glu | Glu | His | Gly | Met | Val | His | Arg | Asn | Leu |
| | | | | 180 | | | | | 185 | | | | | 190 | |
| Ala | Ala | Arg | Asn | Val | Leu | Leu | Lys | Ser | Pro | Ser | Gln | Val | Gln | Val | Ala |
| | | | 195 | | | | | 200 | | | | | 205 | | |
| Asp | Phe | Gly | Val | Ala | Asp | Leu | Leu | Pro | Pro | Asp | Lys | Gln | Leu | Leu |
| | | 210 | | | | | 215 | | | | | 220 | | | |
| Tyr | Ser | Glu | Ala | Lys | Thr | Pro | Ile | Lys | Trp | Met | Ala | Leu | Glu | Ser | Ile |
| 225 | | | | | 230 | | | | | 235 | | | | | 240 |
| His | Phe | Gly | Lys | Tyr | Thr | His | Gln | Ser | Asp | Val | Trp | Ser | Tyr | Gly | Val |
| | | | | 245 | | | | | 250 | | | | | 255 | |
| Thr | Val | Trp | Glu | Leu | Met | Thr | Phe | Gly | Ala | Glu | Pro | Tyr | Ala | Gly | Leu |
| | | | | 260 | | | | | 265 | | | | | 270 | |
| Arg | Leu | Ala | Glu | Val | Pro | Asp | Leu | Leu | Glu | Lys | Gly | Glu | Arg | Leu | Ala |
| | | | 275 | | | | | 280 | | | | | 285 | | |
| Gln | Pro | Gln | Ile | Cys | Thr | Ile | Asp | Val | Tyr | Met | Val | Met | Val | Lys | Cys |
| | | 290 | | | | | 295 | | | | | 300 | | | |
| Trp | Met | Ile | Asp | Glu | Asn | Ile | Arg | Pro | Thr | Phe | Lys | Glu | Leu | Ala | Asn |
| 305 | | | | | 310 | | | | | 315 | | | | | 320 |
| Glu | Phe | Thr | Arg | Met | Ala | Arg | Asp | Pro | Arg | Tyr | Leu | Val | Ile | Lys |
| | | | 325 | | | | | 330 | | | | | 335 | | |
| Arg | Glu | Ser | Gly | Pro | Gly | Ile | Ala | Pro | Gly | Pro | Glu | Pro | His | Gly | Leu |
| | | | 340 | | | | | 345 | | | | | 350 | | |
| Thr | Asn | Lys | Lys | Leu | Glu | Glu | Val | Glu | Leu | Glu | Pro | Glu | Leu | Asp | Leu |
| | | | 355 | | | | | 360 | | | | | 365 | | |
| Asp | Leu | Asp | Leu | Glu | Ala | Glu | Glu | Asp | Asn | Leu | Ala | Thr | Thr | Thr | Leu |
| | | | 370 | | | | | 375 | | | | | 380 | | |
| Gly | Ser | Ala | Leu | Ser | Leu | Pro | Val | Gly | Thr | Leu | Asn | Arg | Pro | Arg | Gly |
| 385 | | | | | 390 | | | | | 395 | | | | | 400 |

```
Ser Gln Ser Leu Leu Ser Pro Ser Ser Gly Tyr Met Pro Met Asn Gln
            405                 410                 415

Gly Asn Leu Gly Glu Ser Cys Gln Glu Ser Ala Val Ser Gly Ser Ser
        420                 425                 430

Glu Arg Cys Pro Arg Pro Val Ser Leu His Pro Met Pro Arg Gly Cys
        435                 440                 445

Leu Ala Ser Glu Ser Ser Glu Gly His Val Thr Gly Ser Glu Ala Glu
    450                 455                 460

Leu Gln Glu Lys Val Ser Met Cys Arg Ser Arg Ser Arg Ser Arg Ser
465                 470                 475                 480

Pro Arg Pro Arg Gly Asp Ser Ala Tyr His Ser Gln Arg His Ser Leu
                485                 490                 495

Leu Thr Pro Val Thr Pro Leu Ser Pro Pro Gly Leu Glu Glu Glu Asp
            500                 505                 510

Val Asn Gly Tyr Val Met Pro Asp Thr His Leu Lys Gly Thr Pro Ser
            515                 520                 525

Ser Arg Glu Gly Thr Leu Ser Ser Val Gly Leu Ser Ser Val Leu Gly
        530                 535                 540

Thr Glu Glu Glu Asp Glu Asp Glu Glu Tyr Glu Tyr Met Asn Arg Arg
545                 550                 555                 560

Arg Arg His Ser Pro Pro His Pro Pro Arg Pro Ser Ser Leu Glu Glu
                565                 570                 575

Leu Gly Tyr Glu Tyr Met Asp Val Gly Ser Asp Leu Ser Ala Ser Leu
            580                 585                 590

Gly Ser Thr Gln Ser Cys Pro Leu His Pro Val Pro Ile Met Pro Thr
        595                 600                 605

Ala Gly Thr Thr Pro Asp Glu Asp Tyr Glu Tyr Met Asn Arg Gln Arg
    610                 615                 620

Asp Gly Gly Gly Pro Gly Gly Asp Tyr Ala Ala Met Gly Ala Cys Pro
625                 630                 635                 640

Ala Ser Glu Gln Gly Tyr Glu Glu Met Arg Ala Phe Gln Gly Pro Gly
                645                 650                 655

His Gln Ala Pro His Val His Tyr Ala Arg Leu Lys Thr Leu Arg Ser
            660                 665                 670

Leu Glu Ala Thr Asp Ser Ala Phe Asp Asn Pro Asp Tyr Trp His Ser
        675                 680                 685

Arg Leu Phe Pro Lys Ala Asn Ala Gln Arg Thr
    690                 695

<210> SEQ ID NO 21
<211> LENGTH: 1308
<212> TYPE: PRT
<213> ORGANISM: Homo sapiens
<220> FEATURE:
<221> NAME/KEY: misc_feature
<223> OTHER INFORMATION: human ErbB4, Isoform JM-A CYT-1 (canonical;
      UniProt ID Q15303-1)

<400> SEQUENCE: 21

Met Lys Pro Ala Thr Gly Leu Trp Val Trp Val Ser Leu Leu Val Ala
1               5                   10                  15

Ala Gly Thr Val Gln Pro Ser Asp Ser Gln Ser Val Cys Ala Gly Thr
            20                  25                  30

Glu Asn Lys Leu Ser Ser Leu Ser Asp Leu Glu Gln Gln Tyr Arg Ala
        35                  40                  45
```

```
Leu Arg Lys Tyr Tyr Glu Asn Cys Glu Val Val Met Gly Asn Leu Glu
 50                  55                  60

Ile Thr Ser Ile Glu His Asn Arg Asp Leu Ser Phe Leu Arg Ser Val
 65                  70                  75                  80

Arg Glu Val Thr Gly Tyr Val Leu Val Ala Leu Asn Gln Phe Arg Tyr
                 85                  90                  95

Leu Pro Leu Glu Asn Leu Arg Ile Ile Arg Gly Thr Lys Leu Tyr Glu
                100                 105                 110

Asp Arg Tyr Ala Leu Ala Ile Phe Leu Asn Tyr Arg Lys Asp Gly Asn
                115                 120                 125

Phe Gly Leu Gln Glu Leu Gly Leu Lys Asn Leu Thr Glu Ile Leu Asn
130                 135                 140

Gly Val Tyr Val Asp Gln Asn Lys Phe Leu Cys Tyr Ala Asp Thr
145                 150                 155                 160

Ile His Trp Gln Asp Ile Val Arg Asn Pro Trp Pro Ser Asn Leu Thr
                165                 170                 175

Leu Val Ser Thr Asn Gly Ser Ser Gly Cys Gly Arg Cys His Lys Ser
                180                 185                 190

Cys Thr Gly Arg Cys Trp Gly Pro Thr Glu Asn His Cys Gln Thr Leu
                195                 200                 205

Thr Arg Thr Val Cys Ala Glu Gln Cys Asp Gly Arg Cys Tyr Gly Pro
210                 215                 220

Tyr Val Ser Asp Cys Cys His Arg Glu Cys Ala Gly Gly Cys Ser Gly
225                 230                 235                 240

Pro Lys Asp Thr Asp Cys Phe Ala Cys Met Asn Phe Asn Asp Ser Gly
                245                 250                 255

Ala Cys Val Thr Gln Cys Pro Gln Thr Phe Val Tyr Asn Pro Thr Thr
                260                 265                 270

Phe Gln Leu Glu His Asn Phe Asn Ala Lys Tyr Thr Tyr Gly Ala Phe
                275                 280                 285

Cys Val Lys Lys Cys Pro His Asn Phe Val Val Asp Ser Ser Ser Cys
                290                 295                 300

Val Arg Ala Cys Pro Ser Ser Lys Met Glu Val Glu Glu Asn Gly Ile
305                 310                 315                 320

Lys Met Cys Lys Pro Cys Thr Asp Ile Cys Pro Lys Ala Cys Asp Gly
                325                 330                 335

Ile Gly Thr Gly Ser Leu Met Ser Ala Gln Thr Val Asp Ser Ser Asn
                340                 345                 350

Ile Asp Lys Phe Ile Asn Cys Thr Lys Ile Asn Gly Asn Leu Ile Phe
                355                 360                 365

Leu Val Thr Gly Ile His Gly Asp Pro Tyr Asn Ala Ile Glu Ala Ile
370                 375                 380

Asp Pro Glu Lys Leu Asn Val Phe Arg Thr Val Arg Glu Ile Thr Gly
385                 390                 395                 400

Phe Leu Asn Ile Gln Ser Trp Pro Pro Asn Met Thr Asp Phe Ser Val
                405                 410                 415

Phe Ser Asn Leu Val Thr Ile Gly Gly Arg Val Leu Tyr Ser Gly Leu
                420                 425                 430

Ser Leu Leu Ile Leu Lys Gln Gln Gly Ile Thr Ser Leu Gln Phe Gln
                435                 440                 445

Ser Leu Lys Glu Ile Ser Ala Gly Asn Ile Tyr Ile Thr Asp Asn Ser
450                 455                 460

Asn Leu Cys Tyr Tyr His Thr Ile Asn Trp Thr Thr Leu Phe Ser Thr
```

```
              465                 470                 475                 480
        Ile Asn Gln Arg Ile Val Ile Arg Asp Asn Arg Lys Ala Glu Asn Cys
                            485                 490                 495

Thr Ala Glu Gly Met Val Cys Asn His Leu Cys Ser Ser Asp Gly Cys
                            500                 505                 510

Trp Gly Pro Gly Pro Asp Gln Cys Leu Ser Cys Arg Arg Phe Ser Arg
                            515                 520                 525

Gly Arg Ile Cys Ile Glu Ser Cys Asn Leu Tyr Asp Gly Glu Phe Arg
                            530                 535                 540

Glu Phe Glu Asn Gly Ser Ile Cys Val Glu Cys Asp Pro Gln Cys Glu
        545                 550                 555                 560

Lys Met Glu Asp Gly Leu Leu Thr Cys His Gly Pro Gly Pro Asp Asn
                            565                 570                 575

Cys Thr Lys Cys Ser His Phe Lys Asp Gly Pro Asn Cys Val Glu Lys
                            580                 585                 590

Cys Pro Asp Gly Leu Gln Gly Ala Asn Ser Phe Ile Phe Lys Tyr Ala
                            595                 600                 605

Asp Pro Asp Arg Glu Cys His Pro Cys His Pro Asn Cys Thr Gln Gly
                            610                 615                 620

Cys Asn Gly Pro Thr Ser His Asp Cys Ile Tyr Tyr Pro Trp Thr Gly
        625                 630                 635                 640

His Ser Thr Leu Pro Gln His Ala Arg Thr Pro Leu Ile Ala Ala Gly
                            645                 650                 655

Val Ile Gly Gly Leu Phe Ile Leu Val Ile Val Gly Leu Thr Phe Ala
                            660                 665                 670

Val Tyr Val Arg Arg Lys Ser Ile Lys Lys Lys Arg Ala Leu Arg Arg
                            675                 680                 685

Phe Leu Glu Thr Glu Leu Val Glu Pro Leu Thr Pro Ser Gly Thr Ala
                            690                 695                 700

Pro Asn Gln Ala Gln Leu Arg Ile Leu Lys Glu Thr Glu Leu Lys Arg
        705                 710                 715                 720

Val Lys Val Leu Gly Ser Gly Ala Phe Gly Thr Val Tyr Lys Gly Ile
                            725                 730                 735

Trp Val Pro Glu Gly Glu Thr Val Lys Ile Pro Val Ala Ile Lys Ile
                            740                 745                 750

Leu Asn Glu Thr Thr Gly Pro Lys Ala Asn Val Glu Phe Met Asp Glu
                            755                 760                 765

Ala Leu Ile Met Ala Ser Met Asp His Pro His Leu Val Arg Leu Leu
                            770                 775                 780

Gly Val Cys Leu Ser Pro Thr Ile Gln Leu Val Thr Gln Leu Met Pro
        785                 790                 795                 800

His Gly Cys Leu Leu Glu Tyr Val His Glu His Lys Asp Asn Ile Gly
                            805                 810                 815

Ser Gln Leu Leu Leu Asn Trp Cys Val Gln Ile Ala Lys Gly Met Met
                            820                 825                 830

Tyr Leu Glu Glu Arg Arg Leu Val His Arg Asp Leu Ala Ala Arg Asn
                            835                 840                 845

Val Leu Val Lys Ser Pro Asn His Val Lys Ile Thr Asp Phe Gly Leu
                            850                 855                 860

Ala Arg Leu Leu Glu Gly Asp Glu Lys Glu Tyr Asn Ala Asp Gly Gly
        865                 870                 875                 880

Lys Met Pro Ile Lys Trp Met Ala Leu Glu Cys Ile His Tyr Arg Lys
                            885                 890                 895
```

```
Phe Thr His Gln Ser Asp Val Trp Ser Tyr Gly Val Thr Ile Trp Glu
            900                 905                 910

Leu Met Thr Phe Gly Gly Lys Pro Tyr Asp Gly Ile Pro Thr Arg Glu
            915                 920                 925

Ile Pro Asp Leu Leu Glu Lys Gly Glu Arg Leu Pro Gln Pro Pro Ile
            930                 935                 940

Cys Thr Ile Asp Val Tyr Met Val Met Val Lys Cys Trp Met Ile Asp
945                 950                 955                 960

Ala Asp Ser Arg Pro Lys Phe Lys Glu Leu Ala Ala Glu Phe Ser Arg
                965                 970                 975

Met Ala Arg Asp Pro Gln Arg Tyr Leu Val Ile Gln Gly Asp Asp Arg
            980                 985                 990

Met Lys Leu Pro Ser Pro Asn Asp Ser Lys Phe Phe Gln Asn Leu Leu
            995                 1000                1005

Asp Glu Glu Asp Leu Glu Asp Met Met Asp Ala Glu Glu Tyr Leu
        1010                1015                1020

Val Pro Gln Ala Phe Asn Ile Pro Pro Pro Ile Tyr Thr Ser Arg
        1025                1030                1035

Ala Arg Ile Asp Ser Asn Arg Ser Glu Ile Gly His Ser Pro Pro
        1040                1045                1050

Pro Ala Tyr Thr Pro Met Ser Gly Asn Gln Phe Val Tyr Arg Asp
        1055                1060                1065

Gly Gly Phe Ala Ala Glu Gln Gly Val Ser Val Pro Tyr Arg Ala
        1070                1075                1080

Pro Thr Ser Thr Ile Pro Glu Ala Pro Val Ala Gln Gly Ala Thr
        1085                1090                1095

Ala Glu Ile Phe Asp Asp Ser Cys Cys Asn Gly Thr Leu Arg Lys
        1100                1105                1110

Pro Val Ala Pro His Val Gln Glu Asp Ser Ser Thr Gln Arg Tyr
        1115                1120                1125

Ser Ala Asp Pro Thr Val Phe Ala Pro Glu Arg Ser Pro Arg Gly
        1130                1135                1140

Glu Leu Asp Glu Glu Gly Tyr Met Thr Pro Met Arg Asp Lys Pro
        1145                1150                1155

Lys Gln Glu Tyr Leu Asn Pro Val Glu Glu Asn Pro Phe Val Ser
        1160                1165                1170

Arg Arg Lys Asn Gly Asp Leu Gln Ala Leu Asp Asn Pro Glu Tyr
        1175                1180                1185

His Asn Ala Ser Asn Gly Pro Pro Lys Ala Glu Asp Glu Tyr Val
        1190                1195                1200

Asn Glu Pro Leu Tyr Leu Asn Thr Phe Ala Asn Thr Leu Gly Lys
        1205                1210                1215

Ala Glu Tyr Leu Lys Asn Asn Ile Leu Ser Met Pro Glu Lys Ala
        1220                1225                1230

Lys Lys Ala Phe Asp Asn Pro Asp Tyr Trp Asn His Ser Leu Pro
        1235                1240                1245

Pro Arg Ser Thr Leu Gln His Pro Asp Tyr Leu Gln Glu Tyr Ser
        1250                1255                1260

Thr Lys Tyr Phe Tyr Lys Gln Asn Gly Arg Ile Arg Pro Ile Val
        1265                1270                1275

Ala Glu Asn Pro Glu Tyr Leu Ser Glu Phe Ser Leu Lys Pro Gly
        1280                1285                1290
```

```
Thr Val Leu Pro Pro Pro Pro Tyr Arg His Arg Asn Thr Val Val
    1295                1300                1305
```

<210> SEQ ID NO 22
<211> LENGTH: 1298
<212> TYPE: PRT
<213> ORGANISM: Homo sapiens
<220> FEATURE:
<221> NAME/KEY: misc_feature
<223> OTHER INFORMATION: human ErbB4, Isoform JM-B CYT-1 (UniProt ID
      Q15303-2)

<400> SEQUENCE: 22

```
Met Lys Pro Ala Thr Gly Leu Trp Val Trp Val Ser Leu Leu Val Ala
1               5                   10                  15

Ala Gly Thr Val Gln Pro Ser Asp Ser Gln Ser Val Cys Ala Gly Thr
            20                  25                  30

Glu Asn Lys Leu Ser Ser Leu Ser Asp Leu Glu Gln Gln Tyr Arg Ala
        35                  40                  45

Leu Arg Lys Tyr Tyr Glu Asn Cys Glu Val Val Met Gly Asn Leu Glu
    50                  55                  60

Ile Thr Ser Ile Glu His Asn Arg Asp Leu Ser Phe Leu Arg Ser Val
65                  70                  75                  80

Arg Glu Val Thr Gly Tyr Val Leu Val Ala Leu Asn Gln Phe Arg Tyr
                85                  90                  95

Leu Pro Leu Glu Asn Leu Arg Ile Ile Arg Gly Thr Lys Leu Tyr Glu
            100                 105                 110

Asp Arg Tyr Ala Leu Ala Ile Phe Leu Asn Tyr Arg Lys Asp Gly Asn
        115                 120                 125

Phe Gly Leu Gln Glu Leu Gly Leu Lys Asn Leu Thr Glu Ile Leu Asn
    130                 135                 140

Gly Gly Val Tyr Val Asp Gln Asn Lys Phe Leu Cys Tyr Ala Asp Thr
145                 150                 155                 160

Ile His Trp Gln Asp Ile Val Arg Asn Pro Trp Pro Ser Asn Leu Thr
                165                 170                 175

Leu Val Ser Thr Asn Gly Ser Ser Gly Cys Gly Arg Cys His Lys Ser
            180                 185                 190

Cys Thr Gly Arg Cys Trp Gly Pro Thr Glu Asn His Cys Gln Thr Leu
        195                 200                 205

Thr Arg Thr Val Cys Ala Glu Gln Cys Asp Gly Arg Cys Tyr Gly Pro
    210                 215                 220

Tyr Val Ser Asp Cys Cys His Arg Glu Cys Ala Gly Gly Cys Ser Gly
225                 230                 235                 240

Pro Lys Asp Thr Asp Cys Phe Ala Cys Met Asn Phe Asn Asp Ser Gly
                245                 250                 255

Ala Cys Val Thr Gln Cys Pro Gln Thr Phe Val Tyr Asn Pro Thr Thr
            260                 265                 270

Phe Gln Leu Glu His Asn Phe Asn Ala Lys Tyr Thr Tyr Gly Ala Phe
        275                 280                 285

Cys Val Lys Lys Cys Pro His Asn Phe Val Val Asp Ser Ser Ser Cys
    290                 295                 300

Val Arg Ala Cys Pro Ser Ser Lys Met Glu Val Glu Glu Asn Gly Ile
305                 310                 315                 320

Lys Met Cys Lys Pro Cys Thr Asp Ile Cys Pro Lys Ala Cys Asp Gly
                325                 330                 335

Ile Gly Thr Gly Ser Leu Met Ser Ala Gln Thr Val Asp Ser Ser Asn
```

```
                340               345               350
Ile Asp Lys Phe Ile Asn Cys Thr Lys Ile Asn Gly Asn Leu Ile Phe
            355                   360                   365

Leu Val Thr Gly Ile His Gly Asp Pro Tyr Asn Ala Ile Glu Ala Ile
            370                   375                   380

Asp Pro Glu Lys Leu Asn Val Phe Arg Thr Val Arg Glu Ile Thr Gly
385                     390                   395                   400

Phe Leu Asn Ile Gln Ser Trp Pro Pro Asn Met Thr Asp Phe Ser Val
                405                   410                   415

Phe Ser Asn Leu Val Thr Ile Gly Gly Arg Val Leu Tyr Ser Gly Leu
            420                   425                   430

Ser Leu Leu Ile Leu Lys Gln Gln Gly Ile Thr Ser Leu Gln Phe Gln
            435                   440                   445

Ser Leu Lys Glu Ile Ser Ala Gly Asn Ile Tyr Ile Thr Asp Asn Ser
            450                   455                   460

Asn Leu Cys Tyr Tyr His Thr Ile Asn Trp Thr Thr Leu Phe Ser Thr
465                   470                   475                   480

Ile Asn Gln Arg Ile Val Ile Arg Asp Asn Arg Lys Ala Glu Asn Cys
                485                   490                   495

Thr Ala Glu Gly Met Val Cys Asn His Leu Cys Ser Ser Asp Gly Cys
            500                   505                   510

Trp Gly Pro Gly Pro Asp Gln Cys Leu Ser Cys Arg Arg Phe Ser Arg
            515                   520                   525

Gly Arg Ile Cys Ile Glu Ser Cys Asn Leu Tyr Asp Gly Glu Phe Arg
            530                   535                   540

Glu Phe Glu Asn Gly Ser Ile Cys Val Glu Cys Asp Pro Gln Cys Glu
545                   550                   555                   560

Lys Met Glu Asp Gly Leu Leu Thr Cys His Gly Pro Gly Pro Asp Asn
                565                   570                   575

Cys Thr Lys Cys Ser His Phe Lys Asp Gly Pro Asn Cys Val Glu Lys
            580                   585                   590

Cys Pro Asp Gly Leu Gln Gly Ala Asn Ser Phe Ile Phe Lys Tyr Ala
            595                   600                   605

Asp Pro Asp Arg Glu Cys His Pro Cys His Pro Asn Cys Thr Gln Gly
            610                   615                   620

Cys Ile Gly Ser Ser Ile Glu Asp Cys Ile Gly Leu Met Asp Arg Thr
625                   630                   635                   640

Pro Leu Ile Ala Ala Gly Val Ile Gly Gly Leu Phe Ile Leu Val Ile
                645                   650                   655

Val Gly Leu Thr Phe Ala Val Tyr Val Arg Arg Lys Ser Ile Lys Lys
            660                   665                   670

Lys Arg Ala Leu Arg Arg Phe Leu Glu Thr Glu Leu Val Glu Pro Leu
            675                   680                   685

Thr Pro Ser Gly Thr Ala Pro Asn Gln Ala Gln Leu Arg Ile Leu Lys
            690                   695                   700

Glu Thr Glu Leu Lys Arg Val Lys Val Leu Gly Ser Gly Ala Phe Gly
705                   710                   715                   720

Thr Val Tyr Lys Gly Ile Trp Val Pro Glu Gly Glu Thr Val Lys Ile
                725                   730                   735

Pro Val Ala Ile Lys Ile Leu Asn Glu Thr Thr Gly Pro Lys Ala Asn
            740                   745                   750

Val Glu Phe Met Asp Glu Ala Leu Ile Met Ala Ser Met Asp His Pro
            755                   760                   765
```

-continued

His Leu Val Arg Leu Leu Gly Val Cys Leu Ser Pro Thr Ile Gln Leu
    770             775             780

Val Thr Gln Leu Met Pro His Gly Cys Leu Leu Glu Tyr Val His Glu
785             790             795             800

His Lys Asp Asn Ile Gly Ser Gln Leu Leu Leu Asn Trp Cys Val Gln
            805             810             815

Ile Ala Lys Gly Met Met Tyr Leu Glu Glu Arg Arg Leu Val His Arg
        820             825             830

Asp Leu Ala Ala Arg Asn Val Leu Val Lys Ser Pro Asn His Val Lys
    835             840             845

Ile Thr Asp Phe Gly Leu Ala Arg Leu Leu Glu Gly Asp Glu Lys Glu
    850             855             860

Tyr Asn Ala Asp Gly Gly Lys Met Pro Ile Lys Trp Met Ala Leu Glu
865             870             875             880

Cys Ile His Tyr Arg Lys Phe Thr His Gln Ser Asp Val Trp Ser Tyr
            885             890             895

Gly Val Thr Ile Trp Glu Leu Met Thr Phe Gly Gly Lys Pro Tyr Asp
        900             905             910

Gly Ile Pro Thr Arg Glu Ile Pro Asp Leu Leu Glu Lys Gly Glu Arg
    915             920             925

Leu Pro Gln Pro Pro Ile Cys Thr Ile Asp Val Tyr Met Val Met Val
    930             935             940

Lys Cys Trp Met Ile Asp Ala Asp Ser Arg Pro Lys Phe Lys Glu Leu
945             950             955             960

Ala Ala Glu Phe Ser Arg Met Ala Arg Asp Pro Gln Arg Tyr Leu Val
            965             970             975

Ile Gln Gly Asp Asp Arg Met Lys Leu Pro Ser Pro Asn Asp Ser Lys
        980             985             990

Phe Phe Gln Asn Leu Leu Asp Glu Glu Asp Leu Glu Asp Met Met Asp
    995             1000            1005

Ala Glu Glu Tyr Leu Val Pro Gln Ala Phe Asn Ile Pro Pro Pro
    1010            1015            1020

Ile Tyr Thr Ser Arg Ala Arg Ile Asp Ser Asn Arg Ser Glu Ile
    1025            1030            1035

Gly His Ser Pro Pro Ala Tyr Thr Pro Met Ser Gly Asn Gln
    1040            1045            1050

Phe Val Tyr Arg Asp Gly Gly Phe Ala Ala Glu Gln Gly Val Ser
    1055            1060            1065

Val Pro Tyr Arg Ala Pro Thr Ser Thr Ile Pro Glu Ala Pro Val
    1070            1075            1080

Ala Gln Gly Ala Thr Ala Glu Ile Phe Asp Asp Ser Cys Cys Asn
    1085            1090            1095

Gly Thr Leu Arg Lys Pro Val Ala Pro His Val Gln Glu Asp Ser
    1100            1105            1110

Ser Thr Gln Arg Tyr Ser Ala Asp Pro Thr Val Phe Ala Pro Glu
    1115            1120            1125

Arg Ser Pro Arg Gly Glu Leu Asp Glu Glu Gly Tyr Met Thr Pro
    1130            1135            1140

Met Arg Asp Lys Pro Lys Gln Glu Tyr Leu Asn Pro Val Glu Glu
    1145            1150            1155

Asn Pro Phe Val Ser Arg Arg Lys Asn Gly Asp Leu Gln Ala Leu
    1160            1165            1170

```
Asp Asn Pro Glu Tyr His Asn Ala Ser Asn Gly Pro Pro Lys Ala
    1175                1180                1185

Glu Asp Glu Tyr Val Asn Glu Pro Leu Tyr Leu Asn Thr Phe Ala
    1190                1195                1200

Asn Thr Leu Gly Lys Ala Glu Tyr Leu Lys Asn Asn Ile Leu Ser
    1205                1210                1215

Met Pro Glu Lys Ala Lys Lys Ala Phe Asp Asn Pro Asp Tyr Trp
    1220                1225                1230

Asn His Ser Leu Pro Pro Arg Ser Thr Leu Gln His Pro Asp Tyr
    1235                1240                1245

Leu Gln Glu Tyr Ser Thr Lys Tyr Phe Tyr Lys Gln Asn Gly Arg
    1250                1255                1260

Ile Arg Pro Ile Val Ala Glu Asn Pro Glu Tyr Leu Ser Glu Phe
    1265                1270                1275

Ser Leu Lys Pro Gly Thr Val Leu Pro Pro Pro Tyr Arg His
    1280                1285                1290

Arg Asn Thr Val Val
    1295

<210> SEQ ID NO 23
<211> LENGTH: 1292
<212> TYPE: PRT
<213> ORGANISM: Homo sapiens
<220> FEATURE:
<221> NAME/KEY: misc_feature
<223> OTHER INFORMATION: human ErbB4, Isoform JM-A CYT-2 (UniProt ID
      Q15303-3)

<400> SEQUENCE: 23

Met Lys Pro Ala Thr Gly Leu Trp Val Trp Val Ser Leu Leu Val Ala
1               5                   10                  15

Ala Gly Thr Val Gln Pro Ser Asp Ser Gln Ser Val Cys Ala Gly Thr
                20                  25                  30

Glu Asn Lys Leu Ser Ser Leu Ser Asp Leu Glu Gln Gln Tyr Arg Ala
            35                  40                  45

Leu Arg Lys Tyr Tyr Glu Asn Cys Glu Val Val Met Gly Asn Leu Glu
        50                  55                  60

Ile Thr Ser Ile Glu His Asn Arg Asp Leu Ser Phe Leu Arg Ser Val
65                  70                  75                  80

Arg Glu Val Thr Gly Tyr Val Leu Val Ala Leu Asn Gln Phe Arg Tyr
                85                  90                  95

Leu Pro Leu Glu Asn Leu Arg Ile Ile Arg Gly Thr Lys Leu Tyr Glu
                100                 105                 110

Asp Arg Tyr Ala Leu Ala Ile Phe Leu Asn Tyr Arg Lys Asp Gly Asn
            115                 120                 125

Phe Gly Leu Gln Glu Leu Gly Leu Lys Asn Leu Thr Glu Ile Leu Asn
        130                 135                 140

Gly Gly Val Tyr Val Asp Gln Asn Lys Phe Leu Cys Tyr Ala Asp Thr
145                 150                 155                 160

Ile His Trp Gln Asp Ile Val Arg Asn Pro Trp Pro Ser Asn Leu Thr
                165                 170                 175

Leu Val Ser Thr Asn Gly Ser Ser Gly Cys Gly Arg Cys His Lys Ser
                180                 185                 190

Cys Thr Gly Arg Cys Trp Gly Pro Thr Glu Asn His Cys Gln Thr Leu
            195                 200                 205

Thr Arg Thr Val Cys Ala Glu Gln Cys Asp Gly Arg Cys Tyr Gly Pro
```

```
                210                 215                 220
Tyr Val Ser Asp Cys Cys His Arg Glu Cys Ala Gly Gly Cys Ser Gly
225                 230                 235                 240

Pro Lys Asp Thr Asp Cys Phe Ala Cys Met Asn Phe Asn Asp Ser Gly
                245                 250                 255

Ala Cys Val Thr Gln Cys Pro Gln Thr Phe Val Tyr Asn Pro Thr Thr
                260                 265                 270

Phe Gln Leu Glu His Asn Phe Asn Ala Lys Tyr Thr Tyr Gly Ala Phe
            275                 280                 285

Cys Val Lys Lys Cys Pro His Asn Phe Val Val Asp Ser Ser Ser Cys
        290                 295                 300

Val Arg Ala Cys Pro Ser Ser Lys Met Glu Val Glu Glu Asn Gly Ile
305                 310                 315                 320

Lys Met Cys Lys Pro Cys Thr Asp Ile Cys Pro Lys Ala Cys Asp Gly
                325                 330                 335

Ile Gly Thr Gly Ser Leu Met Ser Ala Gln Thr Val Asp Ser Ser Asn
                340                 345                 350

Ile Asp Lys Phe Ile Asn Cys Thr Lys Ile Asn Gly Asn Leu Ile Phe
            355                 360                 365

Leu Val Thr Gly Ile His Gly Asp Pro Tyr Asn Ala Ile Glu Ala Ile
        370                 375                 380

Asp Pro Glu Lys Leu Asn Val Phe Arg Thr Val Arg Glu Ile Thr Gly
385                 390                 395                 400

Phe Leu Asn Ile Gln Ser Trp Pro Pro Asn Met Thr Asp Phe Ser Val
                405                 410                 415

Phe Ser Asn Leu Val Thr Ile Gly Gly Arg Val Leu Tyr Ser Gly Leu
                420                 425                 430

Ser Leu Leu Ile Leu Lys Gln Gln Gly Ile Thr Ser Leu Gln Phe Gln
            435                 440                 445

Ser Leu Lys Glu Ile Ser Ala Gly Asn Ile Tyr Ile Thr Asp Asn Ser
        450                 455                 460

Asn Leu Cys Tyr Tyr His Thr Ile Asn Trp Thr Thr Leu Phe Ser Thr
465                 470                 475                 480

Ile Asn Gln Arg Ile Val Ile Arg Asp Asn Arg Lys Ala Glu Asn Cys
                485                 490                 495

Thr Ala Glu Gly Met Val Cys Asn His Leu Cys Ser Ser Asp Gly Cys
                500                 505                 510

Trp Gly Pro Gly Pro Asp Gln Cys Leu Ser Cys Arg Arg Phe Ser Arg
            515                 520                 525

Gly Arg Ile Cys Ile Glu Ser Cys Asn Leu Tyr Asp Gly Glu Phe Arg
        530                 535                 540

Glu Phe Glu Asn Gly Ser Ile Cys Val Glu Cys Asp Pro Gln Cys Glu
545                 550                 555                 560

Lys Met Glu Asp Gly Leu Leu Thr Cys His Gly Pro Gly Pro Asp Asn
                565                 570                 575

Cys Thr Lys Cys Ser His Phe Lys Asp Gly Pro Asn Cys Val Glu Lys
                580                 585                 590

Cys Pro Asp Gly Leu Gln Gly Ala Asn Ser Phe Ile Phe Lys Tyr Ala
            595                 600                 605

Asp Pro Asp Arg Glu Cys His Pro Cys His Pro Asn Cys Thr Gln Gly
        610                 615                 620

Cys Asn Gly Pro Thr Ser His Asp Cys Ile Tyr Tyr Pro Trp Thr Gly
625                 630                 635                 640
```

-continued

```
His Ser Thr Leu Pro Gln His Ala Arg Thr Pro Leu Ile Ala Ala Gly
                645                 650                 655

Val Ile Gly Gly Leu Phe Ile Leu Val Ile Val Gly Leu Thr Phe Ala
            660                 665                 670

Val Tyr Val Arg Arg Lys Ser Ile Lys Lys Arg Ala Leu Arg Arg
        675                 680                 685

Phe Leu Glu Thr Glu Leu Val Glu Pro Leu Thr Pro Ser Gly Thr Ala
    690                 695                 700

Pro Asn Gln Ala Gln Leu Arg Ile Leu Lys Glu Thr Glu Leu Lys Arg
705                 710                 715                 720

Val Lys Val Leu Gly Ser Gly Ala Phe Gly Thr Val Tyr Lys Gly Ile
                725                 730                 735

Trp Val Pro Glu Gly Glu Thr Val Lys Ile Pro Val Ala Ile Lys Ile
            740                 745                 750

Leu Asn Glu Thr Thr Gly Pro Lys Ala Asn Val Glu Phe Met Asp Glu
        755                 760                 765

Ala Leu Ile Met Ala Ser Met Asp His Pro His Leu Val Arg Leu Leu
    770                 775                 780

Gly Val Cys Leu Ser Pro Thr Ile Gln Leu Val Thr Gln Leu Met Pro
785                 790                 795                 800

His Gly Cys Leu Leu Glu Tyr Val His Glu His Lys Asp Asn Ile Gly
                805                 810                 815

Ser Gln Leu Leu Leu Asn Trp Cys Val Gln Ile Ala Lys Gly Met Met
            820                 825                 830

Tyr Leu Glu Glu Arg Arg Leu Val His Arg Asp Leu Ala Ala Arg Asn
        835                 840                 845

Val Leu Val Lys Ser Pro Asn His Val Lys Ile Thr Asp Phe Gly Leu
    850                 855                 860

Ala Arg Leu Leu Glu Gly Asp Glu Lys Glu Tyr Asn Ala Asp Gly Gly
865                 870                 875                 880

Lys Met Pro Ile Lys Trp Met Ala Leu Glu Cys Ile His Tyr Arg Lys
                885                 890                 895

Phe Thr His Gln Ser Asp Val Trp Ser Tyr Gly Val Thr Ile Trp Glu
            900                 905                 910

Leu Met Thr Phe Gly Gly Lys Pro Tyr Asp Gly Ile Pro Thr Arg Glu
        915                 920                 925

Ile Pro Asp Leu Leu Glu Lys Gly Glu Arg Leu Pro Gln Pro Pro Ile
    930                 935                 940

Cys Thr Ile Asp Val Tyr Met Val Met Val Lys Cys Trp Met Ile Asp
945                 950                 955                 960

Ala Asp Ser Arg Pro Lys Phe Lys Glu Leu Ala Ala Glu Phe Ser Arg
                965                 970                 975

Met Ala Arg Asp Pro Gln Arg Tyr Leu Val Ile Gln Gly Asp Asp Arg
            980                 985                 990

Met Lys Leu Pro Ser Pro Asn Asp Ser Lys Phe Phe Gln Asn Leu Leu
        995                 1000                1005

Asp Glu Glu Asp Leu Glu Asp Met Met Asp Ala Glu Glu Tyr Leu
    1010                1015                1020

Val Pro Gln Ala Phe Asn Ile Pro Pro Pro Ile Tyr Thr Ser Arg
    1025                1030                1035

Ala Arg Ile Asp Ser Asn Arg Asn Gln Phe Val Tyr Arg Asp Gly
    1040                1045                1050
```

-continued

Gly Phe Ala Ala Glu Gln Gly Val Ser Val Pro Tyr Arg Ala Pro
    1055                1060                1065

Thr Ser Thr Ile Pro Glu Ala Pro Val Ala Gln Gly Ala Thr Ala
    1070                1075                1080

Glu Ile Phe Asp Asp Ser Cys Cys Asn Gly Thr Leu Arg Lys Pro
    1085                1090                1095

Val Ala Pro His Val Gln Glu Asp Ser Ser Thr Gln Arg Tyr Ser
    1100                1105                1110

Ala Asp Pro Thr Val Phe Ala Pro Glu Arg Ser Pro Arg Gly Glu
    1115                1120                1125

Leu Asp Glu Glu Gly Tyr Met Thr Pro Met Arg Asp Lys Pro Lys
    1130                1135                1140

Gln Glu Tyr Leu Asn Pro Val Glu Glu Asn Pro Phe Val Ser Arg
    1145                1150                1155

Arg Lys Asn Gly Asp Leu Gln Ala Leu Asp Asn Pro Glu Tyr His
    1160                1165                1170

Asn Ala Ser Asn Gly Pro Pro Lys Ala Glu Asp Glu Tyr Val Asn
    1175                1180                1185

Glu Pro Leu Tyr Leu Asn Thr Phe Ala Asn Thr Leu Gly Lys Ala
    1190                1195                1200

Glu Tyr Leu Lys Asn Asn Ile Leu Ser Met Pro Glu Lys Ala Lys
    1205                1210                1215

Lys Ala Phe Asp Asn Pro Asp Tyr Trp Asn His Ser Leu Pro Pro
    1220                1225                1230

Arg Ser Thr Leu Gln His Pro Asp Tyr Leu Gln Glu Tyr Ser Thr
    1235                1240                1245

Lys Tyr Phe Tyr Lys Gln Asn Gly Arg Ile Arg Pro Ile Val Ala
    1250                1255                1260

Glu Asn Pro Glu Tyr Leu Ser Glu Phe Ser Leu Lys Pro Gly Thr
    1265                1270                1275

Val Leu Pro Pro Pro Pro Tyr Arg His Arg Asn Thr Val Val
    1280                1285                1290

<210> SEQ ID NO 24
<211> LENGTH: 1282
<212> TYPE: PRT
<213> ORGANISM: Homo sapiens
<220> FEATURE:
<221> NAME/KEY: misc_feature
<223> OTHER INFORMATION: human ErbB4, Isoform JM-B CYT-2 (UniProt ID
      Q15303-4)

<400> SEQUENCE: 24

Met Lys Pro Ala Thr Gly Leu Trp Val Trp Val Ser Leu Leu Val Ala
1               5                   10                  15

Ala Gly Thr Val Gln Pro Ser Asp Ser Gln Ser Val Cys Ala Gly Thr
                20                  25                  30

Glu Asn Lys Leu Ser Ser Leu Ser Asp Leu Glu Gln Gln Tyr Arg Ala
            35                  40                  45

Leu Arg Lys Tyr Tyr Glu Asn Cys Glu Val Val Met Gly Asn Leu Glu
        50                  55                  60

Ile Thr Ser Ile Glu His Asn Arg Asp Leu Ser Phe Leu Arg Ser Val
65                  70                  75                  80

Arg Glu Val Thr Gly Tyr Val Leu Val Ala Leu Asn Gln Phe Arg Tyr
                85                  90                  95

Leu Pro Leu Glu Asn Leu Arg Ile Ile Arg Gly Thr Lys Leu Tyr Glu

```
                100                 105                 110
Asp Arg Tyr Ala Leu Ala Ile Phe Leu Asn Tyr Arg Lys Asp Gly Asn
            115                 120                 125
Phe Gly Leu Gln Glu Leu Gly Leu Lys Asn Leu Thr Glu Ile Leu Asn
            130                 135                 140
Gly Gly Val Tyr Val Asp Gln Asn Lys Phe Leu Cys Tyr Ala Asp Thr
145                 150                 155                 160
Ile His Trp Gln Asp Ile Val Arg Asn Pro Trp Pro Ser Asn Leu Thr
                165                 170                 175
Leu Val Ser Thr Asn Gly Ser Ser Gly Cys Gly Arg Cys His Lys Ser
                180                 185                 190
Cys Thr Gly Arg Cys Trp Gly Pro Thr Glu Asn His Cys Gln Thr Leu
                195                 200                 205
Thr Arg Thr Val Cys Ala Glu Gln Cys Asp Gly Arg Cys Tyr Gly Pro
            210                 215                 220
Tyr Val Ser Asp Cys Cys His Arg Glu Cys Ala Gly Gly Cys Ser Gly
225                 230                 235                 240
Pro Lys Asp Thr Asp Cys Phe Ala Cys Met Asn Phe Asn Asp Ser Gly
                245                 250                 255
Ala Cys Val Thr Gln Cys Pro Gln Thr Phe Val Tyr Asn Pro Thr Thr
                260                 265                 270
Phe Gln Leu Glu His Asn Phe Asn Ala Lys Tyr Thr Tyr Gly Ala Phe
                275                 280                 285
Cys Val Lys Lys Cys Pro His Asn Phe Val Val Asp Ser Ser Ser Cys
            290                 295                 300
Val Arg Ala Cys Pro Ser Ser Lys Met Glu Val Glu Glu Asn Gly Ile
305                 310                 315                 320
Lys Met Cys Lys Pro Cys Thr Asp Ile Cys Pro Lys Ala Cys Asp Gly
                325                 330                 335
Ile Gly Thr Gly Ser Leu Met Ser Ala Gln Thr Val Asp Ser Ser Asn
                340                 345                 350
Ile Asp Lys Phe Ile Asn Cys Thr Lys Ile Asn Gly Asn Leu Ile Phe
                355                 360                 365
Leu Val Thr Gly Ile His Gly Asp Pro Tyr Asn Ala Ile Glu Ala Ile
            370                 375                 380
Asp Pro Glu Lys Leu Asn Val Phe Arg Thr Val Arg Glu Ile Thr Gly
385                 390                 395                 400
Phe Leu Asn Ile Gln Ser Trp Pro Pro Asn Met Thr Asp Phe Ser Val
                405                 410                 415
Phe Ser Asn Leu Val Thr Ile Gly Gly Arg Val Leu Tyr Ser Gly Leu
                420                 425                 430
Ser Leu Leu Ile Leu Lys Gln Gln Gly Ile Thr Ser Leu Gln Phe Gln
            435                 440                 445
Ser Leu Lys Glu Ile Ser Ala Gly Asn Ile Tyr Ile Thr Asp Asn Ser
            450                 455                 460
Asn Leu Cys Tyr Tyr His Thr Ile Asn Trp Thr Thr Leu Phe Ser Thr
465                 470                 475                 480
Ile Asn Gln Arg Ile Val Ile Arg Asp Asn Arg Lys Ala Glu Asn Cys
                485                 490                 495
Thr Ala Glu Gly Met Val Cys Asn His Leu Cys Ser Ser Asp Gly Cys
            500                 505                 510
Trp Gly Pro Gly Pro Asp Gln Cys Leu Ser Cys Arg Arg Phe Ser Arg
            515                 520                 525
```

```
Gly Arg Ile Cys Ile Glu Ser Cys Asn Leu Tyr Asp Gly Glu Phe Arg
    530                 535                 540

Glu Phe Glu Asn Gly Ser Ile Cys Val Glu Cys Asp Pro Gln Cys Glu
545                 550                 555                 560

Lys Met Glu Asp Gly Leu Leu Thr Cys His Gly Pro Gly Pro Asp Asn
                565                 570                 575

Cys Thr Lys Cys Ser His Phe Lys Asp Gly Pro Asn Cys Val Glu Lys
            580                 585                 590

Cys Pro Asp Gly Leu Gln Gly Ala Asn Ser Phe Ile Phe Lys Tyr Ala
        595                 600                 605

Asp Pro Asp Arg Glu Cys His Pro Cys His Pro Asn Cys Thr Gln Gly
    610                 615                 620

Cys Ile Gly Ser Ser Ile Glu Asp Cys Ile Gly Leu Met Asp Arg Thr
625                 630                 635                 640

Pro Leu Ile Ala Ala Gly Val Ile Gly Gly Leu Phe Ile Leu Val Ile
                645                 650                 655

Val Gly Leu Thr Phe Ala Val Tyr Val Arg Arg Lys Ser Ile Lys Lys
            660                 665                 670

Lys Arg Ala Leu Arg Arg Phe Leu Glu Thr Glu Leu Val Glu Pro Leu
        675                 680                 685

Thr Pro Ser Gly Thr Ala Pro Asn Gln Ala Gln Leu Arg Ile Leu Lys
    690                 695                 700

Glu Thr Glu Leu Lys Arg Val Lys Val Leu Gly Ser Gly Ala Phe Gly
705                 710                 715                 720

Thr Val Tyr Lys Gly Ile Trp Val Pro Glu Gly Glu Thr Val Lys Ile
                725                 730                 735

Pro Val Ala Ile Lys Ile Leu Asn Glu Thr Thr Gly Pro Lys Ala Asn
            740                 745                 750

Val Glu Phe Met Asp Glu Ala Leu Ile Met Ala Ser Met Asp His Pro
        755                 760                 765

His Leu Val Arg Leu Leu Gly Val Cys Leu Ser Pro Thr Ile Gln Leu
    770                 775                 780

Val Thr Gln Leu Met Pro His Gly Cys Leu Leu Glu Tyr Val His Glu
785                 790                 795                 800

His Lys Asp Asn Ile Gly Ser Gln Leu Leu Leu Asn Trp Cys Val Gln
                805                 810                 815

Ile Ala Lys Gly Met Met Tyr Leu Glu Glu Arg Arg Leu Val His Arg
            820                 825                 830

Asp Leu Ala Ala Arg Asn Val Leu Val Lys Ser Pro Asn His Val Lys
        835                 840                 845

Ile Thr Asp Phe Gly Leu Ala Arg Leu Leu Glu Gly Asp Glu Lys Glu
    850                 855                 860

Tyr Asn Ala Asp Gly Gly Lys Met Pro Ile Lys Trp Met Ala Leu Glu
865                 870                 875                 880

Cys Ile His Tyr Arg Lys Phe Thr His Gln Ser Asp Val Trp Ser Tyr
                885                 890                 895

Gly Val Thr Ile Trp Glu Leu Met Thr Phe Gly Gly Lys Pro Tyr Asp
            900                 905                 910

Gly Ile Pro Thr Arg Glu Ile Pro Asp Leu Leu Glu Lys Gly Glu Arg
        915                 920                 925

Leu Pro Gln Pro Pro Ile Cys Thr Ile Asp Val Tyr Met Val Met Val
    930                 935                 940
```

Lys Cys Trp Met Ile Asp Ala Asp Ser Arg Pro Lys Phe Lys Glu Leu
945                 950                 955                 960

Ala Ala Glu Phe Ser Arg Met Ala Arg Asp Pro Gln Arg Tyr Leu Val
            965                 970                 975

Ile Gln Gly Asp Asp Arg Met Lys Leu Pro Ser Pro Asn Asp Ser Lys
        980                 985                 990

Phe Phe Gln Asn Leu Leu Asp Glu Glu Asp Leu Glu Asp Met Met Asp
    995                 1000                1005

Ala Glu Glu Tyr Leu Val Pro Gln Ala Phe Asn Ile Pro Pro Pro
    1010                1015                1020

Ile Tyr Thr Ser Arg Ala Arg Ile Asp Ser Asn Arg Asn Gln Phe
    1025                1030                1035

Val Tyr Arg Asp Gly Gly Phe Ala Ala Glu Gln Gly Val Ser Val
    1040                1045                1050

Pro Tyr Arg Ala Pro Thr Ser Thr Ile Pro Glu Ala Pro Val Ala
    1055                1060                1065

Gln Gly Ala Thr Ala Glu Ile Phe Asp Asp Ser Cys Cys Asn Gly
    1070                1075                1080

Thr Leu Arg Lys Pro Val Ala Pro His Val Gln Glu Asp Ser Ser
    1085                1090                1095

Thr Gln Arg Tyr Ser Ala Asp Pro Thr Val Phe Ala Pro Glu Arg
    1100                1105                1110

Ser Pro Arg Gly Glu Leu Asp Glu Glu Gly Tyr Met Thr Pro Met
    1115                1120                1125

Arg Asp Lys Pro Lys Gln Glu Tyr Leu Asn Pro Val Glu Glu Asn
    1130                1135                1140

Pro Phe Val Ser Arg Arg Lys Asn Gly Asp Leu Gln Ala Leu Asp
    1145                1150                1155

Asn Pro Glu Tyr His Asn Ala Ser Asn Gly Pro Pro Lys Ala Glu
    1160                1165                1170

Asp Glu Tyr Val Asn Glu Pro Leu Tyr Leu Asn Thr Phe Ala Asn
    1175                1180                1185

Thr Leu Gly Lys Ala Glu Tyr Leu Lys Asn Asn Ile Leu Ser Met
    1190                1195                1200

Pro Glu Lys Ala Lys Lys Ala Phe Asp Asn Pro Asp Tyr Trp Asn
    1205                1210                1215

His Ser Leu Pro Pro Arg Ser Thr Leu Gln His Pro Asp Tyr Leu
    1220                1225                1230

Gln Glu Tyr Ser Thr Lys Tyr Phe Tyr Lys Gln Asn Gly Arg Ile
    1235                1240                1245

Arg Pro Ile Val Ala Glu Asn Pro Glu Tyr Leu Ser Glu Phe Ser
    1250                1255                1260

Leu Lys Pro Gly Thr Val Leu Pro Pro Pro Tyr Arg His Arg
    1265                1270                1275

Asn Thr Val Val
    1280

<210> SEQ ID NO 25
<211> LENGTH: 640
<212> TYPE: PRT
<213> ORGANISM: Homo sapiens
<220> FEATURE:
<221> NAME/KEY: misc_feature
<223> OTHER INFORMATION: human NRG1, Isoform 1 (canonical; UniProt ID
      Q02297-1)

```
<400> SEQUENCE: 25

Met Ser Glu Arg Lys Glu Gly Arg Gly Lys Gly Lys Lys Lys
1               5                   10                  15

Glu Arg Gly Ser Gly Lys Lys Pro Glu Ser Ala Ala Gly Ser Gln Ser
                20                  25                  30

Pro Ala Leu Pro Pro Arg Leu Lys Glu Met Lys Ser Gln Glu Ser Ala
            35                  40                  45

Ala Gly Ser Lys Leu Val Leu Arg Cys Glu Thr Ser Ser Glu Tyr Ser
        50                  55                  60

Ser Leu Arg Phe Lys Trp Phe Lys Asn Gly Asn Glu Leu Asn Arg Lys
65                  70                  75                  80

Asn Lys Pro Gln Asn Ile Lys Ile Gln Lys Pro Gly Lys Ser Glu
                85                  90                  95

Leu Arg Ile Asn Lys Ala Ser Leu Ala Asp Ser Gly Glu Tyr Met Cys
                100                 105                 110

Lys Val Ile Ser Lys Leu Gly Asn Asp Ser Ala Ser Ala Asn Ile Thr
                115                 120                 125

Ile Val Glu Ser Asn Glu Ile Ile Thr Gly Met Pro Ala Ser Thr Glu
            130                 135                 140

Gly Ala Tyr Val Ser Ser Glu Ser Pro Ile Arg Ile Ser Val Ser Thr
145                 150                 155                 160

Glu Gly Ala Asn Thr Ser Ser Ser Thr Ser Thr Ser Thr Thr Gly Thr
                165                 170                 175

Ser His Leu Val Lys Cys Ala Glu Lys Glu Lys Thr Phe Cys Val Asn
                180                 185                 190

Gly Gly Glu Cys Phe Met Val Lys Asp Leu Ser Asn Pro Ser Arg Tyr
            195                 200                 205

Leu Cys Lys Cys Gln Pro Gly Phe Thr Gly Ala Arg Cys Thr Glu Asn
        210                 215                 220

Val Pro Met Lys Val Gln Asn Gln Glu Lys Ala Glu Glu Leu Tyr Gln
225                 230                 235                 240

Lys Arg Val Leu Thr Ile Thr Gly Ile Cys Ile Ala Leu Leu Val Val
                245                 250                 255

Gly Ile Met Cys Val Val Ala Tyr Cys Lys Thr Lys Lys Gln Arg Lys
            260                 265                 270

Lys Leu His Asp Arg Leu Arg Gln Ser Leu Arg Ser Glu Arg Asn Asn
        275                 280                 285

Met Met Asn Ile Ala Asn Gly Pro His His Pro Asn Pro Pro Glu
290                 295                 300

Asn Val Gln Leu Val Asn Gln Tyr Val Ser Lys Asn Val Ile Ser Ser
305                 310                 315                 320

Glu His Ile Val Glu Arg Glu Ala Glu Thr Ser Phe Ser Thr Ser His
                325                 330                 335

Tyr Thr Ser Thr Ala His His Ser Thr Thr Val Thr Gln Thr Pro Ser
                340                 345                 350

His Ser Trp Ser Asn Gly His Thr Glu Ser Ile Leu Ser Glu Ser His
            355                 360                 365

Ser Val Ile Val Met Ser Ser Val Glu Asn Ser Arg His Ser Ser Pro
370                 375                 380

Thr Gly Gly Pro Arg Gly Arg Leu Asn Gly Thr Gly Gly Pro Arg Glu
385                 390                 395                 400

Cys Asn Ser Phe Leu Arg His Ala Arg Glu Thr Pro Asp Ser Tyr Arg
                405                 410                 415
```

```
Asp Ser Pro His Ser Glu Arg Tyr Val Ser Ala Met Thr Thr Pro Ala
            420                 425                 430

Arg Met Ser Pro Val Asp Phe His Thr Pro Ser Ser Pro Lys Ser Pro
        435                 440                 445

Pro Ser Glu Met Ser Pro Val Ser Ser Met Thr Val Ser Met Pro
450                 455                 460

Ser Met Ala Val Ser Pro Phe Met Glu Glu Arg Pro Leu Leu Leu
465                 470                 475                 480

Val Thr Pro Pro Arg Leu Arg Glu Lys Lys Phe Asp His His Pro Gln
                485                 490                 495

Gln Phe Ser Ser Phe His His Asn Pro Ala His Asp Ser Asn Ser Leu
            500                 505                 510

Pro Ala Ser Pro Leu Arg Ile Val Glu Asp Glu Glu Tyr Glu Thr Thr
            515                 520                 525

Gln Glu Tyr Glu Pro Ala Gln Glu Pro Val Lys Lys Leu Ala Asn Ser
530                 535                 540

Arg Arg Ala Lys Arg Thr Lys Pro Asn Gly His Ile Ala Asn Arg Leu
545                 550                 555                 560

Glu Val Asp Ser Asn Thr Ser Ser Gln Ser Ser Asn Ser Glu Ser Glu
                565                 570                 575

Thr Glu Asp Glu Arg Val Gly Glu Asp Thr Pro Phe Leu Gly Ile Gln
            580                 585                 590

Asn Pro Leu Ala Ala Ser Leu Glu Ala Thr Pro Ala Phe Arg Leu Ala
            595                 600                 605

Asp Ser Arg Thr Asn Pro Ala Gly Arg Phe Ser Thr Gln Glu Glu Ile
            610                 615                 620

Gln Ala Arg Leu Ser Ser Val Ile Ala Asn Gln Asp Pro Ile Ala Val
625                 630                 635                 640

<210> SEQ ID NO 26
<211> LENGTH: 648
<212> TYPE: PRT
<213> ORGANISM: Homo sapiens
<220> FEATURE:
<221> NAME/KEY: misc_feature
<223> OTHER INFORMATION: human NRG1, Isoform 2 (UniProt ID Q02297-2)

<400> SEQUENCE: 26

Met Ser Glu Arg Lys Glu Gly Arg Gly Lys Gly Lys Gly Lys Lys Lys
1               5                   10                  15

Glu Arg Gly Ser Gly Lys Lys Pro Glu Ser Ala Ala Gly Ser Gln Ser
            20                  25                  30

Pro Ala Leu Pro Pro Arg Leu Lys Glu Met Lys Ser Gln Glu Ser Ala
        35                  40                  45

Ala Gly Ser Lys Leu Val Leu Arg Cys Glu Thr Ser Ser Glu Tyr Ser
    50                  55                  60

Ser Leu Arg Phe Lys Trp Phe Lys Asn Gly Asn Glu Leu Asn Arg Lys
65                  70                  75                  80

Asn Lys Pro Gln Asn Ile Lys Ile Gln Lys Lys Pro Gly Lys Ser Glu
                85                  90                  95

Leu Arg Ile Asn Lys Ala Ser Leu Ala Asp Ser Gly Glu Tyr Met Cys
            100                 105                 110

Lys Val Ile Ser Lys Leu Gly Asn Asp Ser Ala Ser Ala Asn Ile Thr
        115                 120                 125

Ile Val Glu Ser Asn Glu Ile Ile Thr Gly Met Pro Ala Ser Thr Glu
```

```
              130                 135                 140
Gly Ala Tyr Val Ser Ser Glu Ser Pro Ile Arg Ile Ser Val Ser Thr
145                 150                 155                 160

Glu Gly Ala Asn Thr Ser Ser Thr Ser Thr Ser Thr Thr Gly Thr
                    165                 170                 175

Ser His Leu Val Lys Cys Ala Glu Lys Thr Phe Cys Val Asn
                180                 185                 190

Gly Gly Glu Cys Phe Met Val Lys Asp Leu Ser Asn Pro Ser Arg Tyr
            195                 200                 205

Leu Cys Lys Cys Gln Pro Gly Phe Thr Gly Ala Arg Cys Thr Glu Asn
        210                 215                 220

Val Pro Met Lys Val Gln Asn Gln Glu Lys His Leu Gly Ile Glu Phe
225                 230                 235                 240

Ile Glu Ala Glu Glu Leu Tyr Gln Lys Arg Val Leu Thr Ile Thr Gly
                245                 250                 255

Ile Cys Ile Ala Leu Leu Val Val Gly Ile Met Cys Val Val Ala Tyr
                260                 265                 270

Cys Lys Thr Lys Lys Gln Arg Lys Lys Leu His Asp Arg Leu Arg Gln
            275                 280                 285

Ser Leu Arg Ser Glu Arg Asn Asn Met Met Asn Ile Ala Asn Gly Pro
290                 295                 300

His His Pro Asn Pro Pro Pro Glu Asn Val Gln Leu Val Asn Gln Tyr
305                 310                 315                 320

Val Ser Lys Asn Val Ile Ser Ser Glu His Ile Val Glu Arg Glu Ala
                325                 330                 335

Glu Thr Ser Phe Ser Thr Ser His Tyr Thr Ser Thr Ala His His Ser
                340                 345                 350

Thr Thr Val Thr Gln Thr Pro Ser His Ser Trp Ser Asn Gly His Thr
            355                 360                 365

Glu Ser Ile Leu Ser Glu Ser His Ser Val Ile Val Met Ser Ser Val
        370                 375                 380

Glu Asn Ser Arg His Ser Ser Pro Thr Gly Gly Pro Arg Gly Arg Leu
385                 390                 395                 400

Asn Gly Thr Gly Gly Pro Arg Glu Cys Asn Ser Phe Leu Arg His Ala
                405                 410                 415

Arg Glu Thr Pro Asp Ser Tyr Arg Asp Ser Pro His Ser Glu Arg Tyr
                420                 425                 430

Val Ser Ala Met Thr Thr Pro Ala Arg Met Ser Pro Val Asp Phe His
            435                 440                 445

Thr Pro Ser Ser Pro Lys Ser Pro Pro Ser Glu Met Ser Pro Pro Val
450                 455                 460

Ser Ser Met Thr Val Ser Met Pro Ser Met Ala Val Ser Pro Phe Met
465                 470                 475                 480

Glu Glu Glu Arg Pro Leu Leu Leu Val Thr Pro Pro Arg Leu Arg Glu
                485                 490                 495

Lys Lys Phe Asp His His Pro Gln Gln Phe Ser Ser Phe His His Asn
                500                 505                 510

Pro Ala His Asp Ser Asn Ser Leu Pro Ala Ser Pro Leu Arg Ile Val
            515                 520                 525

Glu Asp Glu Glu Tyr Glu Thr Thr Gln Glu Tyr Glu Pro Ala Gln Glu
        530                 535                 540

Pro Val Lys Lys Leu Ala Asn Ser Arg Arg Ala Lys Arg Thr Lys Pro
545                 550                 555                 560
```

```
Asn Gly His Ile Ala Asn Arg Leu Glu Val Asp Ser Asn Thr Ser Ser
                565                 570                 575

Gln Ser Ser Asn Ser Glu Ser Glu Thr Glu Asp Glu Arg Val Gly Glu
            580                 585                 590

Asp Thr Pro Phe Leu Gly Ile Gln Asn Pro Leu Ala Ala Ser Leu Glu
        595                 600                 605

Ala Thr Pro Ala Phe Arg Leu Ala Asp Ser Arg Thr Asn Pro Ala Gly
    610                 615                 620

Arg Phe Ser Thr Gln Glu Glu Ile Gln Ala Arg Leu Ser Ser Val Ile
625                 630                 635                 640

Ala Asn Gln Asp Pro Ile Ala Val
                645

<210> SEQ ID NO 27
<211> LENGTH: 462
<212> TYPE: PRT
<213> ORGANISM: Homo sapiens
<220> FEATURE:
<221> NAME/KEY: misc_feature
<223> OTHER INFORMATION: human NRG1, Isoform 3 (UniProt ID Q02297-3)

<400> SEQUENCE: 27

Met Ser Glu Arg Lys Glu Gly Arg Gly Lys Gly Lys Gly Lys Lys Lys
1               5                   10                  15

Glu Arg Gly Ser Gly Lys Lys Pro Glu Ser Ala Ala Gly Ser Gln Ser
            20                  25                  30

Pro Ala Leu Pro Pro Arg Leu Lys Glu Met Lys Ser Gln Glu Ser Ala
        35                  40                  45

Ala Gly Ser Lys Leu Val Leu Arg Cys Glu Thr Ser Ser Glu Tyr Ser
    50                  55                  60

Ser Leu Arg Phe Lys Trp Phe Lys Asn Gly Asn Glu Leu Asn Arg Lys
65                  70                  75                  80

Asn Lys Pro Gln Asn Ile Lys Ile Gln Lys Lys Pro Gly Lys Ser Glu
                85                  90                  95

Leu Arg Ile Asn Lys Ala Ser Leu Ala Asp Ser Gly Glu Tyr Met Cys
            100                 105                 110

Lys Val Ile Ser Lys Leu Gly Asn Asp Ser Ala Ser Ala Asn Ile Thr
        115                 120                 125

Ile Val Glu Ser Asn Glu Ile Ile Thr Gly Met Pro Ala Ser Thr Glu
    130                 135                 140

Gly Ala Tyr Val Ser Ser Glu Ser Pro Ile Arg Ile Ser Val Ser Thr
145                 150                 155                 160

Glu Gly Ala Asn Thr Ser Ser Ser Thr Ser Thr Ser Thr Thr Gly Thr
                165                 170                 175

Ser His Leu Val Lys Cys Ala Glu Lys Glu Lys Thr Phe Cys Val Asn
            180                 185                 190

Gly Gly Glu Cys Phe Met Val Lys Asp Leu Ser Asn Pro Ser Arg Tyr
        195                 200                 205

Leu Cys Lys Cys Gln Pro Gly Phe Thr Gly Ala Arg Cys Thr Glu Asn
    210                 215                 220

Val Pro Met Lys Val Gln Asn Gln Glu Lys Ala Glu Glu Leu Tyr Gln
225                 230                 235                 240

Lys Arg Val Leu Thr Ile Thr Gly Ile Cys Ile Ala Leu Leu Val Val
                245                 250                 255

Gly Ile Met Cys Val Val Ala Tyr Cys Lys Thr Lys Lys Gln Arg Lys
```

```
            260                 265                 270
Lys Leu His Asp Arg Leu Arg Gln Ser Leu Arg Ser Glu Arg Asn Asn
        275                 280                 285

Met Met Asn Ile Ala Asn Gly Pro His His Pro Asn Pro Pro Pro Glu
        290                 295                 300

Asn Val Gln Leu Val Asn Gln Tyr Val Ser Lys Asn Val Ile Ser Ser
305                 310                 315                 320

Glu His Ile Val Glu Arg Glu Ala Glu Thr Ser Phe Ser Thr Ser His
                325                 330                 335

Tyr Thr Ser Thr Ala His His Ser Thr Thr Val Thr Gln Thr Pro Ser
                340                 345                 350

His Ser Trp Ser Asn Gly His Thr Glu Ser Ile Leu Ser Glu Ser His
            355                 360                 365

Ser Val Ile Val Met Ser Ser Val Glu Asn Ser Arg His Ser Ser Pro
        370                 375                 380

Thr Gly Gly Pro Arg Gly Arg Leu Asn Gly Thr Gly Gly Pro Arg Glu
385                 390                 395                 400

Cys Asn Ser Phe Leu Arg His Ala Arg Glu Thr Pro Asp Ser Tyr Arg
                405                 410                 415

Asp Ser Pro His Ser Glu Arg His Asn Leu Ile Ala Glu Leu Arg Arg
                420                 425                 430

Asn Lys Ala His Arg Ser Lys Cys Met Gln Ile Gln Leu Ser Ala Thr
            435                 440                 445

His Leu Arg Ser Ser Ser Ile Pro His Leu Gly Phe Ile Leu
        450                 455                 460

<210> SEQ ID NO 28
<211> LENGTH: 247
<212> TYPE: PRT
<213> ORGANISM: Homo sapiens
<220> FEATURE:
<221> NAME/KEY: misc_feature
<223> OTHER INFORMATION: human NRG1, Isoform 4 (UniProt ID Q02297-4)

<400> SEQUENCE: 28

Met Ser Glu Arg Lys Glu Gly Arg Gly Lys Gly Lys Gly Lys Lys Lys
1               5                   10                  15

Glu Arg Gly Ser Gly Lys Lys Pro Glu Ser Ala Ala Gly Ser Gln Ser
            20                  25                  30

Pro Ala Leu Pro Pro Arg Leu Lys Glu Met Lys Ser Gln Glu Ser Ala
        35                  40                  45

Ala Gly Ser Lys Leu Val Leu Arg Cys Glu Thr Ser Ser Glu Tyr Ser
    50                  55                  60

Ser Leu Arg Phe Lys Trp Phe Lys Asn Gly Asn Glu Leu Asn Arg Lys
65                  70                  75                  80

Asn Lys Pro Gln Asn Ile Lys Ile Gln Lys Lys Pro Gly Lys Ser Glu
                85                  90                  95

Leu Arg Ile Asn Lys Ala Ser Leu Ala Asp Ser Gly Glu Tyr Met Cys
            100                 105                 110

Lys Val Ile Ser Lys Leu Gly Asn Asp Ser Ala Ser Ala Asn Ile Thr
        115                 120                 125

Ile Val Glu Ser Asn Glu Ile Ile Thr Gly Met Pro Ala Ser Thr Glu
    130                 135                 140

Gly Ala Tyr Val Ser Ser Glu Ser Pro Ile Arg Ile Ser Val Ser Thr
145                 150                 155                 160
```

Glu Gly Ala Asn Thr Ser Ser Ser Thr Ser Thr Thr Gly Thr
              165                 170                 175

Ser His Leu Val Lys Cys Ala Glu Lys Glu Lys Thr Phe Cys Val Asn
                180                 185                 190

Gly Gly Glu Cys Phe Met Val Lys Asp Leu Ser Asn Pro Ser Arg Tyr
              195                 200                 205

Leu Cys Lys Cys Gln Pro Gly Phe Thr Gly Ala Arg Cys Thr Glu Asn
              210                 215                 220

Val Pro Met Lys Val Gln Asn Gln Glu Ser Ala Gln Met Ser Leu Leu
225                 230                 235                 240

Val Ile Ala Ala Lys Thr Thr
              245

<210> SEQ ID NO 29
<211> LENGTH: 645
<212> TYPE: PRT
<213> ORGANISM: Homo sapiens
<220> FEATURE:
<221> NAME/KEY: misc_feature
<223> OTHER INFORMATION: human NRG1, Isoform 6 (UniProt ID Q02297-6)

<400> SEQUENCE: 29

Met Ser Glu Arg Lys Glu Gly Arg Gly Lys Gly Lys Gly Lys Lys Lys
1               5                   10                  15

Glu Arg Gly Ser Gly Lys Lys Pro Glu Ser Ala Ala Gly Ser Gln Ser
              20                  25                  30

Pro Ala Leu Pro Pro Arg Leu Lys Glu Met Lys Ser Gln Glu Ser Ala
              35                  40                  45

Ala Gly Ser Lys Leu Val Leu Arg Cys Glu Thr Ser Ser Glu Tyr Ser
50                  55                  60

Ser Leu Arg Phe Lys Trp Phe Lys Asn Gly Asn Glu Leu Asn Arg Lys
65                  70                  75                  80

Asn Lys Pro Gln Asn Ile Lys Ile Gln Lys Lys Pro Gly Lys Ser Glu
              85                  90                  95

Leu Arg Ile Asn Lys Ala Ser Leu Ala Asp Ser Gly Glu Tyr Met Cys
              100                 105                 110

Lys Val Ile Ser Lys Leu Gly Asn Asp Ser Ala Ser Ala Asn Ile Thr
              115                 120                 125

Ile Val Glu Ser Asn Glu Ile Ile Thr Gly Met Pro Ala Ser Thr Glu
              130                 135                 140

Gly Ala Tyr Val Ser Ser Glu Ser Pro Ile Arg Ile Ser Val Ser Thr
145                 150                 155                 160

Glu Gly Ala Asn Thr Ser Ser Ser Thr Ser Thr Ser Thr Thr Gly Thr
              165                 170                 175

Ser His Leu Val Lys Cys Ala Glu Lys Glu Lys Thr Phe Cys Val Asn
              180                 185                 190

Gly Gly Glu Cys Phe Met Val Lys Asp Leu Ser Asn Pro Ser Arg Tyr
              195                 200                 205

Leu Cys Lys Cys Pro Asn Glu Phe Thr Gly Asp Arg Cys Gln Asn Tyr
              210                 215                 220

Val Met Ala Ser Phe Tyr Lys His Leu Gly Ile Glu Phe Met Glu Ala
225                 230                 235                 240

Glu Glu Leu Tyr Gln Lys Arg Val Leu Thr Ile Thr Gly Ile Cys Ile
              245                 250                 255

Ala Leu Leu Val Val Gly Ile Met Cys Val Val Ala Tyr Cys Lys Thr
              260                 265                 270

```
Lys Lys Gln Arg Lys Lys Leu His Asp Arg Leu Arg Gln Ser Leu Arg
            275                 280                 285

Ser Glu Arg Asn Asn Met Met Asn Ile Ala Asn Gly Pro His His Pro
290                 295                 300

Asn Pro Pro Glu Asn Val Gln Leu Val Asn Gln Tyr Val Ser Lys
305                 310                 315                 320

Asn Val Ile Ser Ser Glu His Ile Val Glu Arg Glu Ala Glu Thr Ser
                325                 330                 335

Phe Ser Thr Ser His Tyr Thr Ser Thr Ala His His Ser Thr Thr Val
                340                 345                 350

Thr Gln Thr Pro Ser His Ser Trp Ser Asn Gly His Thr Glu Ser Ile
            355                 360                 365

Leu Ser Glu Ser His Ser Val Ile Val Met Ser Ser Val Glu Asn Ser
370                 375                 380

Arg His Ser Ser Pro Thr Gly Gly Pro Arg Gly Arg Leu Asn Gly Thr
385                 390                 395                 400

Gly Gly Pro Arg Glu Cys Asn Ser Phe Leu Arg His Ala Arg Glu Thr
                405                 410                 415

Pro Asp Ser Tyr Arg Asp Ser Pro His Ser Glu Arg Tyr Val Ser Ala
            420                 425                 430

Met Thr Thr Pro Ala Arg Met Ser Pro Val Asp Phe His Thr Pro Ser
            435                 440                 445

Ser Pro Lys Ser Pro Pro Ser Glu Met Ser Pro Pro Val Ser Ser Met
450                 455                 460

Thr Val Ser Met Pro Ser Met Ala Val Ser Pro Phe Met Glu Glu Glu
465                 470                 475                 480

Arg Pro Leu Leu Leu Val Thr Pro Pro Arg Leu Arg Glu Lys Lys Phe
                485                 490                 495

Asp His His Pro Gln Gln Phe Ser Ser Phe His His Asn Pro Ala His
            500                 505                 510

Asp Ser Asn Ser Leu Pro Ala Ser Pro Leu Arg Ile Val Glu Asp Glu
            515                 520                 525

Glu Tyr Glu Thr Thr Gln Glu Tyr Glu Pro Ala Gln Glu Pro Val Lys
            530                 535                 540

Lys Leu Ala Asn Ser Arg Arg Ala Lys Arg Thr Lys Pro Asn Gly His
545                 550                 555                 560

Ile Ala Asn Arg Leu Glu Val Asp Ser Asn Thr Ser Ser Gln Ser Ser
                565                 570                 575

Asn Ser Glu Ser Glu Thr Glu Asp Glu Arg Val Gly Glu Asp Thr Pro
            580                 585                 590

Phe Leu Gly Ile Gln Asn Pro Leu Ala Ala Ser Leu Glu Ala Thr Pro
            595                 600                 605

Ala Phe Arg Leu Ala Asp Ser Arg Thr Asn Pro Ala Gly Arg Phe Ser
610                 615                 620

Thr Gln Glu Glu Ile Gln Ala Arg Leu Ser Ser Val Ile Ala Asn Gln
625                 630                 635                 640

Asp Pro Ile Ala Val
                645

<210> SEQ ID NO 30
<211> LENGTH: 637
<212> TYPE: PRT
<213> ORGANISM: Homo sapiens
<220> FEATURE:
```

```
<221> NAME/KEY: misc_feature
<223> OTHER INFORMATION: human NRG1, Isoform 7 (UniProt ID Q02297-7)

<400> SEQUENCE: 30

Met Ser Glu Arg Lys Glu Gly Arg Gly Lys Gly Lys Gly Lys Lys
1               5                   10                  15

Glu Arg Gly Ser Gly Lys Lys Pro Glu Ser Ala Ala Gly Ser Gln Ser
                20                  25                  30

Pro Ala Leu Pro Pro Arg Leu Lys Glu Met Lys Ser Gln Glu Ser Ala
            35                  40                  45

Ala Gly Ser Lys Leu Val Leu Arg Cys Glu Thr Ser Ser Glu Tyr Ser
    50                  55                  60

Ser Leu Arg Phe Lys Trp Phe Lys Asn Gly Asn Glu Leu Asn Arg Lys
65                  70                  75                  80

Asn Lys Pro Gln Asn Ile Lys Ile Gln Lys Lys Pro Gly Lys Ser Glu
                85                  90                  95

Leu Arg Ile Asn Lys Ala Ser Leu Ala Asp Ser Gly Glu Tyr Met Cys
            100                 105                 110

Lys Val Ile Ser Lys Leu Gly Asn Asp Ser Ala Ser Ala Asn Ile Thr
            115                 120                 125

Ile Val Glu Ser Asn Glu Ile Ile Thr Gly Met Pro Ala Ser Thr Glu
130                 135                 140

Gly Ala Tyr Val Ser Ser Glu Ser Pro Ile Arg Ile Ser Val Ser Thr
145                 150                 155                 160

Glu Gly Ala Asn Thr Ser Ser Ser Thr Ser Thr Ser Thr Thr Gly Thr
                165                 170                 175

Ser His Leu Val Lys Cys Ala Glu Lys Glu Lys Thr Phe Cys Val Asn
            180                 185                 190

Gly Gly Glu Cys Phe Met Val Lys Asp Leu Ser Asn Pro Ser Arg Tyr
            195                 200                 205

Leu Cys Lys Cys Pro Asn Glu Phe Thr Gly Asp Arg Cys Gln Asn Tyr
            210                 215                 220

Val Met Ala Ser Phe Tyr Lys Ala Glu Glu Leu Tyr Gln Lys Arg Val
225                 230                 235                 240

Leu Thr Ile Thr Gly Ile Cys Ile Ala Leu Leu Val Val Gly Ile Met
                245                 250                 255

Cys Val Val Ala Tyr Cys Lys Thr Lys Lys Gln Arg Lys Lys Leu His
            260                 265                 270

Asp Arg Leu Arg Gln Ser Leu Arg Ser Glu Arg Asn Asn Met Met Asn
            275                 280                 285

Ile Ala Asn Gly Pro His His Pro Asn Pro Pro Pro Glu Asn Val Gln
290                 295                 300

Leu Val Asn Gln Tyr Val Ser Lys Asn Val Ile Ser Ser Glu His Ile
305                 310                 315                 320

Val Glu Arg Glu Ala Glu Thr Ser Phe Ser Thr Ser His Tyr Thr Ser
                325                 330                 335

Thr Ala His His Ser Thr Thr Val Thr Gln Thr Pro Ser His Ser Trp
            340                 345                 350

Ser Asn Gly His Thr Glu Ser Ile Leu Ser Glu Ser His Ser Val Ile
            355                 360                 365

Val Met Ser Ser Val Glu Asn Ser Arg His Ser Ser Pro Thr Gly Gly
370                 375                 380

Pro Arg Gly Arg Leu Asn Gly Thr Gly Gly Pro Arg Glu Cys Asn Ser
385                 390                 395                 400
```

```
Phe Leu Arg His Ala Arg Glu Thr Pro Asp Ser Tyr Arg Asp Ser Pro
                405                 410                 415

His Ser Glu Arg Tyr Val Ser Ala Met Thr Thr Pro Ala Arg Met Ser
            420                 425                 430

Pro Val Asp Phe His Thr Pro Ser Ser Pro Lys Ser Pro Pro Ser Glu
        435                 440                 445

Met Ser Pro Pro Val Ser Ser Met Thr Val Ser Met Pro Ser Met Ala
    450                 455                 460

Val Ser Pro Phe Met Glu Glu Glu Arg Pro Leu Leu Leu Val Thr Pro
465                 470                 475                 480

Pro Arg Leu Arg Glu Lys Lys Phe Asp His His Pro Gln Gln Phe Ser
                485                 490                 495

Ser Phe His His Asn Pro Ala His Asp Ser Asn Ser Leu Pro Ala Ser
            500                 505                 510

Pro Leu Arg Ile Val Glu Asp Glu Glu Tyr Glu Thr Thr Gln Glu Tyr
        515                 520                 525

Glu Pro Ala Gln Glu Pro Val Lys Lys Leu Ala Asn Ser Arg Arg Ala
    530                 535                 540

Lys Arg Thr Lys Pro Asn Gly His Ile Ala Asn Arg Leu Glu Val Asp
545                 550                 555                 560

Ser Asn Thr Ser Ser Gln Ser Ser Asn Ser Glu Ser Glu Thr Glu Asp
                565                 570                 575

Glu Arg Val Gly Glu Asp Thr Pro Phe Leu Gly Ile Gln Asn Pro Leu
            580                 585                 590

Ala Ala Ser Leu Glu Ala Thr Pro Ala Phe Arg Leu Ala Asp Ser Arg
        595                 600                 605

Thr Asn Pro Ala Gly Arg Phe Ser Thr Gln Glu Glu Ile Gln Ala Arg
    610                 615                 620

Leu Ser Ser Val Ile Ala Asn Gln Asp Pro Ile Ala Val
625                 630                 635

<210> SEQ ID NO 31
<211> LENGTH: 241
<212> TYPE: PRT
<213> ORGANISM: Homo sapiens
<220> FEATURE:
<221> NAME/KEY: MISC_FEATURE
<223> OTHER INFORMATION: human NRG1, Isoform 8 (UniProt ID Q02297-8)

<400> SEQUENCE: 31

Met Ser Glu Arg Lys Glu Gly Arg Gly Lys Gly Lys Gly Lys Lys Lys
1               5                   10                  15

Glu Arg Gly Ser Gly Lys Lys Pro Glu Ser Ala Ala Gly Ser Gln Ser
            20                  25                  30

Pro Ala Leu Pro Pro Arg Leu Lys Glu Met Lys Ser Gln Glu Ser Ala
        35                  40                  45

Ala Gly Ser Lys Leu Val Leu Arg Cys Glu Thr Ser Ser Glu Tyr Ser
    50                  55                  60

Ser Leu Arg Phe Lys Trp Phe Lys Asn Gly Asn Glu Leu Asn Arg Lys
65                  70                  75                  80

Asn Lys Pro Gln Asn Ile Lys Ile Gln Lys Lys Pro Gly Lys Ser Glu
                85                  90                  95

Leu Arg Ile Asn Lys Ala Ser Leu Ala Asp Ser Gly Glu Tyr Met Cys
            100                 105                 110

Lys Val Ile Ser Lys Leu Gly Asn Asp Ser Ala Ser Ala Asn Ile Thr
```

|   |   | 115 |   |   | 120 |   |   | 125 |   |   |   |

Ile Val Glu Ser Asn Glu Ile Ile Thr Gly Met Pro Ala Ser Thr Glu
    130              135              140

Gly Ala Tyr Val Ser Ser Glu Ser Pro Ile Arg Ile Ser Val Ser Thr
145              150              155              160

Glu Gly Ala Asn Thr Ser Ser Thr Ser Thr Ser Thr Thr Gly Thr
              165              170              175

Ser His Leu Val Lys Cys Ala Glu Lys Glu Lys Thr Phe Cys Val Asn
            180              185              190

Gly Gly Glu Cys Phe Met Val Lys Asp Leu Ser Asn Pro Ser Arg Tyr
        195              200              205

Leu Cys Lys Cys Pro Asn Glu Phe Thr Gly Asp Arg Cys Gln Asn Tyr
        210              215              220

Val Met Ala Ser Phe Tyr Ser Thr Ser Thr Pro Phe Leu Ser Leu Pro
225              230              235              240

Glu

<210> SEQ ID NO 32
<211> LENGTH: 422
<212> TYPE: PRT
<213> ORGANISM: Homo sapiens
<220> FEATURE:
<221> NAME/KEY: misc_feature
<223> OTHER INFORMATION: human NRG1, Isoform 9 (UniProt ID Q02297-9)

<400> SEQUENCE: 32

Met Arg Trp Arg Arg Ala Pro Arg Arg Ser Gly Arg Pro Gly Pro Arg
1                5                  10                15

Ala Gln Arg Pro Gly Ser Ala Ala Arg Ser Ser Pro Pro Leu Pro Leu
            20              25              30

Leu Pro Leu Leu Leu Leu Leu Gly Thr Ala Ala Leu Ala Pro Gly Ala
              35              40              45

Ala Ala Gly Asn Glu Ala Ala Pro Ala Gly Ala Ser Val Cys Tyr Ser
    50              55              60

Ser Pro Pro Ser Val Gly Ser Val Gln Glu Leu Ala Gln Arg Ala Ala
65              70              75              80

Val Val Ile Glu Gly Lys Val His Pro Gln Arg Arg Gln Gln Gly Ala
            85              90              95

Leu Asp Arg Lys Ala Ala Ala Ala Gly Glu Ala Gly Ala Trp Gly
              100              105              110

Gly Asp Arg Glu Pro Pro Ala Ala Gly Pro Arg Ala Leu Gly Pro Pro
        115              120              125

Ala Glu Glu Pro Leu Leu Ala Ala Asn Gly Thr Val Pro Ser Trp Pro
    130              135              140

Thr Ala Pro Val Pro Ser Ala Gly Glu Pro Gly Glu Glu Ala Pro Tyr
145              150              155              160

Leu Val Lys Val His Gln Val Trp Ala Val Lys Ala Gly Gly Leu Lys
            165              170              175

Lys Asp Ser Leu Leu Thr Val Arg Leu Gly Thr Trp Gly His Pro Ala
        180              185              190

Phe Pro Ser Cys Gly Arg Leu Lys Glu Asp Ser Arg Tyr Ile Phe Phe
        195              200              205

Met Glu Pro Asp Ala Asn Ser Thr Ser Arg Ala Pro Ala Ala Phe Arg
    210              215              220

Ala Ser Phe Pro Pro Leu Glu Thr Gly Arg Asn Leu Lys Lys Glu Val

```
                      225                 230                 235                 240

Ser Arg Val Leu Cys Lys Arg Cys Ala Leu Pro Pro Arg Leu Lys Glu
                      245                 250                 255

Met Lys Ser Gln Glu Ser Ala Ala Gly Ser Lys Leu Val Leu Arg Cys
                      260                 265                 270

Glu Thr Ser Ser Glu Tyr Ser Ser Leu Arg Phe Lys Trp Phe Lys Asn
                      275                 280                 285

Gly Asn Glu Leu Asn Arg Lys Asn Lys Pro Gln Asn Ile Lys Ile Gln
                      290                 295                 300

Lys Lys Pro Gly Lys Ser Glu Leu Arg Ile Asn Lys Ala Ser Leu Ala
      305                 310                 315                 320

Asp Ser Gly Glu Tyr Met Cys Lys Val Ile Ser Lys Leu Gly Asn Asp
                      325                 330                 335

Ser Ala Ser Ala Asn Ile Thr Ile Val Glu Ser Asn Ala Thr Ser Thr
                      340                 345                 350

Ser Thr Thr Gly Thr Ser His Leu Val Lys Cys Ala Glu Lys Glu Lys
                      355                 360                 365

Thr Phe Cys Val Asn Gly Gly Glu Cys Phe Met Val Lys Asp Leu Ser
                      370                 375                 380

Asn Pro Ser Arg Tyr Leu Cys Lys Cys Pro Asn Glu Phe Thr Gly Asp
      385                 390                 395                 400

Arg Cys Gln Asn Tyr Val Met Ala Ser Phe Tyr Ser Thr Ser Thr Pro
                      405                 410                 415

Phe Leu Ser Leu Pro Glu
                      420

<210> SEQ ID NO 33
<211> LENGTH: 296
<212> TYPE: PRT
<213> ORGANISM: Homo sapiens
<220> FEATURE:
<221> NAME/KEY: misc_feature
<223> OTHER INFORMATION: human NRG1, Isoform 10 (UniProt ID Q02297-10)

<400> SEQUENCE: 33

Met Glu Ile Tyr Ser Pro Asp Met Ser Glu Val Ala Ala Glu Arg Ser
      1               5                   10                  15

Ser Ser Pro Ser Thr Gln Leu Ser Ala Asp Pro Ser Leu Asp Gly Leu
                      20                  25                  30

Pro Ala Ala Glu Asp Met Pro Glu Pro Gln Thr Glu Asp Gly Arg Thr
                      35                  40                  45

Pro Gly Leu Val Gly Leu Ala Val Pro Cys Cys Ala Cys Leu Glu Ala
          50                  55                  60

Glu Arg Leu Arg Gly Cys Leu Asn Ser Glu Lys Ile Cys Ile Val Pro
      65                  70                  75                  80

Ile Leu Ala Cys Leu Val Ser Leu Cys Leu Cys Ile Ala Gly Leu Lys
                      85                  90                  95

Trp Val Phe Val Asp Lys Ile Phe Glu Tyr Asp Ser Pro Thr His Leu
                      100                 105                 110

Asp Pro Gly Gly Leu Gly Gln Asp Pro Ile Ile Ser Leu Asp Ala Thr
                      115                 120                 125

Ala Ala Ser Ala Val Trp Val Ser Ser Glu Ala Tyr Thr Ser Pro Val
                      130                 135                 140

Ser Arg Ala Gln Ser Glu Ser Glu Val Gln Val Thr Val Gln Gly Asp
      145                 150                 155                 160
```

```
Lys Ala Val Val Ser Phe Glu Pro Ser Ala Pro Thr Pro Lys Asn
                165                 170                 175

Arg Ile Phe Ala Phe Ser Phe Leu Pro Ser Thr Ala Pro Ser Phe Pro
            180                 185                 190

Ser Pro Thr Arg Asn Pro Glu Val Arg Thr Pro Lys Ser Ala Thr Gln
            195                 200                 205

Pro Gln Thr Thr Glu Thr Asn Leu Gln Thr Ala Pro Lys Leu Ser Thr
            210                 215                 220

Ser Thr Ser Thr Thr Gly Thr Ser His Leu Val Lys Cys Ala Glu Lys
225                 230                 235                 240

Glu Lys Thr Phe Cys Val Asn Gly Gly Glu Cys Phe Met Val Lys Asp
            245                 250                 255

Leu Ser Asn Pro Ser Arg Tyr Leu Cys Lys Cys Pro Asn Glu Phe Thr
            260                 265                 270

Gly Asp Arg Cys Gln Asn Tyr Val Met Ala Ser Phe Tyr Ser Thr Ser
            275                 280                 285

Thr Pro Phe Leu Ser Leu Pro Glu
            290                 295

<210> SEQ ID NO 34
<211> LENGTH: 590
<212> TYPE: PRT
<213> ORGANISM: Homo sapiens
<220> FEATURE:
<221> NAME/KEY: misc_feature
<223> OTHER INFORMATION: human NRG1, Isoform 11 (UniProt ID Q02297-11)

<400> SEQUENCE: 34

Met Gly Lys Gly Arg Ala Gly Arg Val Gly Thr Thr Ala Leu Pro Pro
1               5                   10                  15

Arg Leu Lys Glu Met Lys Ser Gln Glu Ser Ala Ala Gly Ser Lys Leu
                20                  25                  30

Val Leu Arg Cys Glu Thr Ser Ser Glu Tyr Ser Ser Leu Arg Phe Lys
            35                  40                  45

Trp Phe Lys Asn Gly Asn Glu Leu Asn Arg Lys Asn Lys Pro Gln Asn
    50                  55                  60

Ile Lys Ile Gln Lys Lys Pro Gly Lys Ser Glu Leu Arg Ile Asn Lys
65                  70                  75                  80

Ala Ser Leu Ala Asp Ser Gly Glu Tyr Met Cys Lys Val Ile Ser Lys
                85                  90                  95

Leu Gly Asn Asp Ser Ala Ser Ala Asn Ile Thr Ile Val Glu Ser Asn
            100                 105                 110

Ala Thr Ser Thr Ser Thr Thr Gly Thr Ser His Leu Val Lys Cys Ala
            115                 120                 125

Glu Lys Glu Lys Thr Phe Cys Val Asn Gly Gly Glu Cys Phe Met Val
            130                 135                 140

Lys Asp Leu Ser Asn Pro Ser Arg Tyr Leu Cys Lys Cys Pro Asn Glu
145                 150                 155                 160

Phe Thr Gly Asp Arg Cys Gln Asn Tyr Val Met Ala Ser Phe Tyr Lys
                165                 170                 175

His Leu Gly Ile Glu Phe Met Glu Ala Glu Leu Tyr Gln Lys Arg
            180                 185                 190

Val Leu Thr Ile Thr Gly Ile Cys Ile Ala Leu Leu Val Val Gly Ile
            195                 200                 205

Met Cys Val Val Ala Tyr Cys Lys Thr Lys Lys Gln Arg Lys Lys Leu
            210                 215                 220
```

His Asp Arg Leu Arg Gln Ser Leu Arg Ser Glu Arg Asn Asn Met Met
225                 230                 235                 240

Asn Ile Ala Asn Gly Pro His His Pro Asn Pro Pro Glu Asn Val
            245                 250                 255

Gln Leu Val Asn Gln Tyr Val Ser Lys Asn Val Ile Ser Ser Glu His
        260                 265                 270

Ile Val Glu Arg Glu Ala Glu Thr Ser Phe Ser Thr Ser His Tyr Thr
            275                 280                 285

Ser Thr Ala His His Ser Thr Thr Val Thr Gln Thr Pro Ser His Ser
        290                 295                 300

Trp Ser Asn Gly His Thr Glu Ser Ile Leu Ser Glu Ser His Ser Val
305                 310                 315                 320

Ile Val Met Ser Ser Val Glu Asn Ser Arg His Ser Ser Pro Thr Gly
            325                 330                 335

Gly Pro Arg Gly Arg Leu Asn Gly Thr Gly Gly Pro Arg Glu Cys Asn
        340                 345                 350

Ser Phe Leu Arg His Ala Arg Glu Thr Pro Asp Ser Tyr Arg Asp Ser
            355                 360                 365

Pro His Ser Glu Arg Tyr Val Ser Ala Met Thr Thr Pro Ala Arg Met
        370                 375                 380

Ser Pro Val Asp Phe His Thr Pro Ser Ser Pro Lys Ser Pro Pro Ser
385                 390                 395                 400

Glu Met Ser Pro Pro Val Ser Ser Met Thr Val Ser Met Pro Ser Met
            405                 410                 415

Ala Val Ser Pro Phe Met Glu Glu Glu Arg Pro Leu Leu Leu Val Thr
        420                 425                 430

Pro Pro Arg Leu Arg Glu Lys Lys Phe Asp His His Pro Gln Gln Phe
        435                 440                 445

Ser Ser Phe His His Asn Pro Ala His Asp Ser Asn Ser Leu Pro Ala
    450                 455                 460

Ser Pro Leu Arg Ile Val Glu Asp Glu Glu Tyr Glu Thr Thr Gln Glu
465                 470                 475                 480

Tyr Glu Pro Ala Gln Glu Pro Val Lys Lys Leu Ala Asn Ser Arg Arg
            485                 490                 495

Ala Lys Arg Thr Lys Pro Asn Gly His Ile Ala Asn Arg Leu Glu Val
        500                 505                 510

Asp Ser Asn Thr Ser Ser Gln Ser Ser Asn Ser Glu Ser Glu Thr Glu
    515                 520                 525

Asp Glu Arg Val Gly Glu Asp Thr Pro Phe Leu Gly Ile Gln Asn Pro
        530                 535                 540

Leu Ala Ala Ser Leu Glu Ala Thr Pro Ala Phe Arg Leu Ala Asp Ser
545                 550                 555                 560

Arg Thr Asn Pro Ala Gly Arg Phe Ser Thr Gln Glu Glu Ile Gln Ala
            565                 570                 575

Arg Leu Ser Ser Val Ile Ala Asn Gln Asp Pro Ile Ala Val
        580                 585                 590

<210> SEQ ID NO 35
<211> LENGTH: 420
<212> TYPE: PRT
<213> ORGANISM: Homo sapiens
<220> FEATURE:
<221> NAME/KEY: MISC_FEATURE
<223> OTHER INFORMATION: human NRG1, Isoform 12 (UniProt ID Q02297-12)

<400> SEQUENCE: 35

```
Met Ser Glu Arg Lys Glu Gly Arg Gly Lys Gly Lys Lys Lys
1               5                   10                  15

Glu Arg Gly Ser Gly Lys Lys Pro Glu Ser Ala Ala Gly Ser Gln Ser
            20                  25                  30

Pro Ala Leu Pro Pro Arg Leu Lys Glu Met Lys Ser Gln Glu Ser Ala
            35                  40                  45

Ala Gly Ser Lys Leu Val Leu Arg Cys Glu Thr Ser Ser Glu Tyr Ser
    50                  55                  60

Ser Leu Arg Phe Lys Trp Phe Lys Asn Gly Asn Glu Leu Asn Arg Lys
65                  70                  75                  80

Asn Lys Pro Gln Asn Ile Lys Ile Gln Lys Lys Pro Gly Lys Ser Glu
                85                  90                  95

Leu Arg Ile Asn Lys Ala Ser Leu Ala Asp Ser Gly Glu Tyr Met Cys
            100                 105                 110

Lys Val Ile Ser Lys Leu Gly Asn Asp Ser Ala Ser Ala Asn Ile Thr
            115                 120                 125

Ile Val Glu Ser Asn Glu Ile Ile Thr Gly Met Pro Ala Ser Thr Glu
    130                 135                 140

Gly Ala Tyr Val Ser Ser Glu Ser Pro Ile Arg Ile Ser Val Ser Thr
145                 150                 155                 160

Glu Gly Ala Asn Thr Ser Ser Ser Thr Ser Thr Ser Thr Thr Gly Thr
                165                 170                 175

Ser His Leu Val Lys Cys Ala Glu Lys Glu Lys Thr Phe Cys Val Asn
            180                 185                 190

Gly Gly Glu Cys Phe Met Val Lys Asp Leu Ser Asn Pro Ser Arg Tyr
            195                 200                 205

Leu Cys Lys Cys Pro Asn Glu Phe Thr Gly Asp Arg Cys Gln Asn Tyr
    210                 215                 220

Val Met Ala Ser Phe Tyr Lys Ala Glu Glu Leu Tyr Gln Lys Arg Val
225                 230                 235                 240

Leu Thr Ile Thr Gly Ile Cys Ile Ala Leu Leu Val Val Gly Ile Met
                245                 250                 255

Cys Val Val Ala Tyr Cys Lys Thr Lys Lys Gln Arg Lys Lys Leu His
            260                 265                 270

Asp Arg Leu Arg Gln Ser Leu Arg Ser Glu Arg Asn Asn Met Met Asn
    275                 280                 285

Ile Ala Asn Gly Pro His His Pro Asn Pro Pro Pro Glu Asn Val Gln
290                 295                 300

Leu Val Asn Gln Tyr Val Ser Lys Asn Val Ile Ser Ser Glu His Ile
305                 310                 315                 320

Val Glu Arg Glu Ala Glu Thr Ser Phe Ser Thr Ser His Tyr Thr Ser
                325                 330                 335

Thr Ala His His Ser Thr Thr Val Thr Gln Thr Pro Ser His Ser Trp
            340                 345                 350

Ser Asn Gly His Thr Glu Ser Ile Leu Ser Glu Ser His Ser Val Ile
            355                 360                 365

Val Met Ser Ser Val Glu Asn Ser Arg His Ser Ser Pro Thr Gly Gly
    370                 375                 380

Pro Arg Gly Arg Leu Asn Gly Thr Gly Gly Pro Arg Glu Cys Asn Ser
385                 390                 395                 400

Phe Leu Arg His Ala Arg Glu Thr Pro Asp Ser Tyr Arg Asp Ser Pro
                405                 410                 415
```

-continued

```
His Ser Glu Arg
            420

<210> SEQ ID NO 36
<211> LENGTH: 17
<212> TYPE: PRT
<213> ORGANISM: Homo sapiens

<400> SEQUENCE: 36

Glu Ala Tyr Met Ala Ser Val Asp Asn Pro His Val Cys Arg Leu Leu
1               5                   10                  15

Gly

<210> SEQ ID NO 37
<211> LENGTH: 15
<212> TYPE: PRT
<213> ORGANISM: Homo sapiens

<400> SEQUENCE: 37

Asp Glu Ala Tyr Val Met Ala Ser Val Asp Asn Pro His Val Cys
1               5                   10                  15
```